US011492361B2

(12) United States Patent
Dunham et al.

(10) Patent No.: US 11,492,361 B2
(45) Date of Patent: Nov. 8, 2022

(54) COMPOUNDS USEFUL IN HIV THERAPY

(71) Applicants: GlaxoSmithKline Intellectual Property Development Limited, Middlesex (GB); The University of North Carolina at Chapel Hill, Chapel Hill, NC (US); ViiV Healthcare Company, Wilmington, DE (US)

(72) Inventors: Richard M. Dunham, Research Triangle Park, NC (US); David Margolis, Chapel Hill, NC (US); Vincent Wing-Fai Tai, Research Triangle Park, NC (US); Jun Tang, Research Triangle Park, NC (US)

(73) Assignees: GlaxoSmithKline Intellectual Property Development Limited, Middlesex (GB); The University of North Carolina at Chapel Hill, Chapel Hill, NC (US); ViiV Healthcare Company, Wilmington, DE (US)

( * ) Notice: Subject to any disclaimer, the term of this patent is extended or adjusted under 35 U.S.C. 154(b) by 15 days.

(21) Appl. No.: 16/948,873

(22) Filed: Oct. 5, 2020

(65) Prior Publication Data
US 2021/0009609 A1   Jan. 14, 2021

Related U.S. Application Data

(63) Continuation of application No. 16/897,351, filed on Jun. 10, 2020, now Pat. No. 10,870,663, which is a continuation of application No. 16/621,312, filed as application No. PCT/IB2019/060267 on Nov. 28, 2019, now abandoned.

(60) Provisional application No. 62/773,563, filed on Nov. 30, 2018.

(51) Int. Cl.
 *C07D 519/00* (2006.01)
 *A61P 31/18* (2006.01)

(52) U.S. Cl.
 CPC ............ *C07D 519/00* (2013.01); *A61P 31/18* (2018.01)

(58) Field of Classification Search
 CPC ............................... C07D 519/00; A61P 31/18
 See application file for complete search history.

(56) References Cited

U.S. PATENT DOCUMENTS

| | | | |
|---|---|---|---|
| 7,932,382 B2 | 4/2011 | Wang et al. |
| 7,960,372 B2 | 6/2011 | Wang et al. |
| 8,278,293 B2 | 10/2012 | Wang et al. |
| 8,815,927 B2 | 8/2014 | Wang et al. |
| 9,546,174 B2 | 1/2017 | Wang et al. |
| 2011/0003877 A1 | 1/2011 | Condon et al. |
| 2015/0307499 A1 | 10/2015 | Cosford et al. |
| 2019/0135861 A1 | 5/2019 | Cosford et al. |

FOREIGN PATENT DOCUMENTS

| | | |
|---|---|---|
| EP | 2058312 | 5/2009 |
| WO | 2005/069894 A2 | 8/2005 |
| WO | 2006/010118 A2 | 1/2006 |
| WO | 2007/130626 A2 | 11/2007 |
| WO | 2008/128171 A2 | 10/2008 |
| WO | 2009/126947 A2 | 10/2009 |
| WO | 2010/014994 A1 | 2/2010 |
| WO | 2010/142994 A1 | 12/2010 |
| WO | 11/002684 A1 | 1/2011 |
| WO | 2011/050068 A2 | 4/2011 |
| WO | 2014/031487 A1 | 2/2014 |
| WO | 2014/085489 A1 | 6/2014 |
| WO | 2015/187998 A2 | 12/2015 |

OTHER PUBLICATIONS

Byakwaga, et al., "The Kynurenine Pathway of Tryptophan Catabolism, CD4+ T-Cell Recovery, and Mortality Among HIV-Infected Ugandans Initialing Antiretroviral Therapy." J Infect Dis; 2014; pp. 383-391; vol. 210 (3).
Campbell, et al., "SMAC Mimetics Induce Autophagy-Dependent Apoptosis of HIV-1-Infecled Resting Memory CD4+ T Cells." Cell Host Microbe; 2018; pp. 689-702; vol. 24(5).
Deeks, "HIV Infection, Inflammation, Immunosenescence, and Aging." Annu Rev Med.; 2011; pp. 141-155; vol. 62.
Ebert, et al., "Cellular inhibitor of apoptosis proteins prevent cleamace of hepatitis B virus." PNAS; 2015; pp. 5797-5802; vol. 112(18).
Henrich, et al., "Antiretroviral-Free HIV-1 Remission and Viral Rebound After Allogeneic Stem Cell Transplantation." Annal of Internal Medicine; 2014; pp. 319-327; vol. 161(5).
Henrich, et al., "Long-term reduction in peripheral blood HIV Type 1 reservoirs following reduced-intensity conditioning allogeneic stem cell transplantation." J Infect Dis; 2013; pp. 1694-1702; vol. 2017(11).
Hunt, et al., "Gut spithelial barrier dysfunction and innate immune activation predict mortality in treated HIV infection." J Infect Dis; 2014; pp. 1228-1238; vol. 210(8).
Hutter, et al, "Long-term control of HIV by CCR5 Delta32/Delta32 stem-cell transplantation." N Engl J Med; 2009; pp. 692-698; vol. 360(7).
Lohse, et al., "Survival of persons with and without HIV infection in Denmark, 1995-2005." Ann Intern Med; 2007; pp. 87-95; vol. 146(2).
Sampey, et al., "The SMAC Mimetic AZD5582 is a Potent HOV Latency Reversing Agent." bioRxiv; 2018.
Shalaby, et al., "Thiopeptide Synthesis. alpha-Amino Thionoacid Derivatives of Nitrobenzotriazole as Thioacylating Agents." J Org Chem; 1996; pp. 9045-9048; vol. 61(25).

(Continued)

*Primary Examiner* — Paul V Ward
(74) *Attorney, Agent, or Firm* — Robert J. Smith

(57) ABSTRACT

The invention relates to compounds of Formula (I), salts thereof, combinations, pharmaceutical compositions thereof, as well as therapeutic methods of treatment and prevention.

24 Claims, 1 Drawing Sheet
Specification includes a Sequence Listing.

(56) References Cited

OTHER PUBLICATIONS

Tenorio, et al., "Soluble markers of inflammation and coagulation but not T-cell activation predict non-AIDS-defining morbid events during suppressive antiretroviral treatment." J Infect Dis; 2014; pp. 1248-1259; vol. 210(8).

Zhang, et al. "Asymmetric phosphoric acid-catalyzed four-component Ugi reaction." Science; 2018; vol. 361(6407).

Pache, et al., "BIRC2/cIAP1 Suppresses HIV-1 Transcription and Can Be Targeted by Smac Mimetics to Promote Reversal of Viral Latency." Cell Host Microbe; 2015; pp. 345-353; vol. 18(3).

Sun, et al., "Structure-Based Design, Synthesis, Evaluation, and Crystallographic Studies of Conformationally Constrained Smac Mimetics as Inhibitors of the X-linked Inhibitor of Apoptosis Protein (XIAP)." J. Med. Chem; 2008; pp. 7169-7180; vol. 51.

Tamanini, et al., "Discovery of a Potent Nonbpeptidomimetic, Small-Molecule Antagonist of Cellular Inhibitor of Apoptosis Protein 1 (cIAP1) and X-Linked Inhibitor of Apoptosis Protein (XIAP)." J Med Chem.; 2017; pp. 4611-4625.

Vamos, et al., "Expedient Synthesis of Highly Potent Antagonists of Inhibitor of Apoptosis Proteins (IAPs) with Unique Selectivity for ML-IAP." ACS Chem Biology; 2013; pp. 725-732; vol. 8.

PCT/IB2019/060267, International Search Report and Written Opinion, dated Feb. 6, 2020.

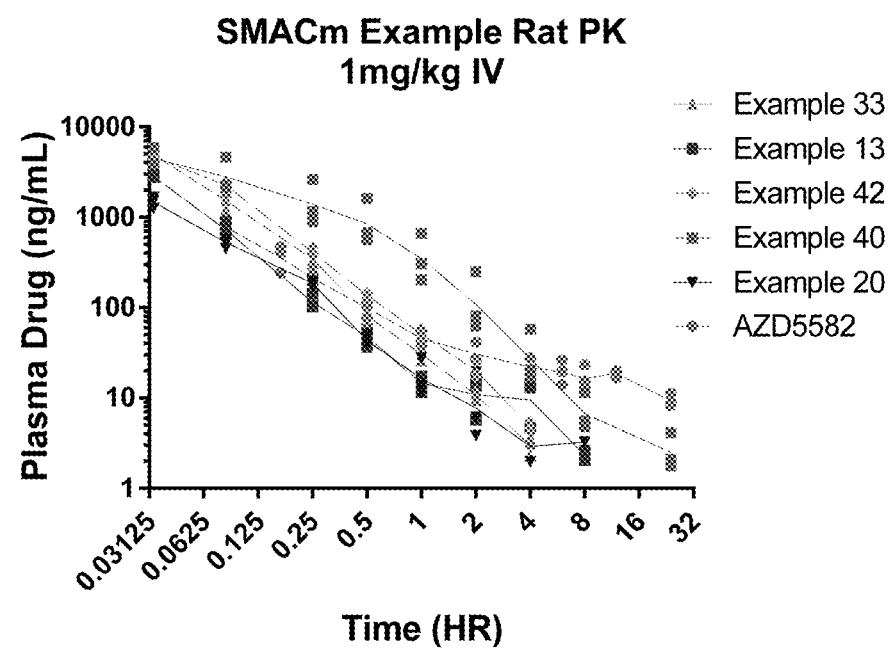

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: synthetic primer

<400> SEQUENCE: 1
atcaagcagc tatgcaaatg tt                                              22

<210> SEQ ID NO 2
<211> LENGTH: 30
<212> TYPE: DNA
<213> ORGANISM: Artificial Sequence
<220> FEATURE:
<223> OTHER INFORMATION: synthetic primer

<400> SEQUENCE: 2
ctgaagggta ctagtagttc ctgctatgtc                                      30

<210> SEQ ID NO 3
<211> LENGTH: 29
<212> TYPE: DNA
<213> ORGANISM: Artificial Sequence
<220> FEATURE:
<223> OTHER INFORMATION: synthetic probe

<400> SEQUENCE: 3
accatcaatg aggaagctgc agaatggga                                       29

<210> SEQ ID NO 4
<211> LENGTH: 152
<212> TYPE: DNA
<213> ORGANISM: Artificial Sequence
<220> FEATURE:
<223> OTHER INFORMATION: synthetic standard control

<400> SEQUENCE: 4
atcaagcagc catgcaaatg ttaaaagaga ccatcaatga ggaagctgca gaatgggata     60
gattgcatcc agtgcatgca gggcctattg caccaggcca gatgagagaa ccaagggaa     120 gtgacatagc aggaactact agtacccttc ag                                  152
```

COMPOUNDS USEFUL IN HIV THERAPY

CROSS-REFERENCE TO RELATED APPLICATIONS

This application is a continuation application of Ser. No. 16/897,351 filed Jul. 20, 2020, now allowed, which is a continuation application of Ser. No. 16/621,312 filed Dec. 11, 2019, pending, which is filed pursuant to 35 U.S.C. § 371 as a United States National Phase Application of International Application No. PCT/IB2019/060267 filed Nov. 28, 2019 which claims priority from U.S. Provisional Application No. 62/773,563 filed Nov. 30, 2018.

FIELD OF THE INVENTION

The present invention relates to compounds, pharmaceutical compositions, and methods of use thereof in connection with individuals infected with HIV, HBV or cancer.

SEQUENCE LISTING

This application contains sequences, listed in an electronic Sequence Listing entitled PR66692_Seq_List, 2 KB in size, created using Patent-In 3.5 on Nov. 12, 2010, the contents and sequences of which are hereby incorporated by reference herein.

BACKGROUND OF THE INVENTION

Human immunodeficiency virus type 1 (HIV-1) infection leads to the contraction of acquired immune deficiency disease (AIDS). The number of cases of HIV continues to rise, and currently an estimated over thirty-five million individuals worldwide suffer from HIV infection e.g., http://www.sciencedirect.com/science/article/pii/S235230181630087X?via%3Dihub Presently, long-term suppression of viral replication with antiretroviral drugs is the only option for treating HIV-1 infection. Indeed, the U.S. Food and Drug Administration has approved twenty-five drugs over six different inhibitor classes, which have been shown to greatly increase patient survival and quality of life. However, additional therapies are still believed to be required due to a number of issues including, but not limited to undesirable drug-drug interactions; drug-food interactions; non-adherence to therapy; drug resistance due to mutation of the enzyme target; and inflammation related to the immunologic damage caused by the HIV infection.

Currently, almost all HIV positive patients are treated with therapeutic regimens of antiretroviral drug combinations termed, highly active antiretroviral therapy ("HAART"). However, HAART therapies are often complex because a combination of different drugs must be administered often daily to the patient to avoid the rapid emergence of drug-resistant HIV-1 variants. Despite the positive impact of HAART on patient survival, drug resistance can still occur and the survival and quality of life are not normalized as compared to uninfected persons [Lohse Ann Intern Med 2007 146; 87-95], Indeed, the incidence of several non-AIDS morbidities and mortalities, such as cardiovascular disease, frailty, and neurocognitive impairment, are increased in HAART-suppressed, HIV-infected subjects [Deeks Annu Rev Med 2011; 62:141-155], This increased incidence of non-AIDS morbidity/mortality occurs in the context of, and is potentially caused by, elevated systemic inflammation related to the immunologic damage caused by HIV infection and residual HIV infection [Hunt J Infect Dis 2014][Byakagwa J Infect Dis 2014][Tenorio J Infect Dis 2014].

Modern antiretroviral therapy (ART) has the ability to effectively suppress HIV replication and improve health outcomes for HIV-infected persons, but is believed to not be capable of completely eliminating HIV viral reservoirs within the individual. HIV genomes can remain latent within mostly immune cells in the infected individual and may reactivate at any time, such that after interruption of ART, virus replication typically resumes within weeks. In a handful of individuals, the size of this viral reservoir has been significantly reduced and upon cessation of ART, the rebound of viral replication has been delayed [Henrich T J J Infect Dis 2013][Henrich T J Ann Intern Med 2014], In one case, the viral reservoir was eliminated during treatment of leukemia and no viral rebound was observed during several years of follow-up [Hutter G N Engl J Med 2009], These examples suggest the concept that reduction or elimination of the viral reservoir may be possible and can lead to viral remission or cure. As such, ways have been pursued to eliminate the viral reservoir, by direct molecular means, including excision of viral genomes with CRISPR/Cas9 systems, or to induce reactivation of the latent reservoir during ART so that the latent cells are eliminated. It is believed that reversal of latency is required to make latently infected cells vulnerable to clearance.

SMACm (Second Mitochondrial-derived Activator of Caspases) mimetics are a class of compounds that have recently entered clinical trials as potential cancer treatments. The drugs deplete and/or inhibit cellular inhibitor of apoptosis proteins (cIAP) that act as anti-apoptotic proteins, thereby promoting the cell death of cancer cells. Antagonism and/or depletion of cIAP also leads to activation of the non-canonical NF-kB signaling pathway, that may induce HIV expression and may enable elimination of HIV infected cells. In addition, SMAC mimetics may selectively promote the cell death of cells infected by HIV [Campbell Cell Host Microbe 2018] or HBV [Ebert Proc Nat Acad Sci 2013] by antagonizing anti-apoptotic proteins.

Recently, the targeting of the non-canonical NF-kB (ncNF-κB) pathway to reverse latency in cell line models was reported. The ncNF-κB pathway is typically activated by ligation of a subset of TNF receptor family members. In the steady state, a multimolecular complex with ubiquitin ligase activity consisting of TNF receptor-associated factor 2 (TRAF2), TRAF3, and cellular inhibitor of apoptosis protein-1 (cIAP1) associates with the cytoplasmic portion of the unligated receptor and constitutively ubiquitinylates and degrades the NF-κB-inducing kinase (NIK). Upon receptor ligation, cIAP1 ubiquitinylates TRAF3 and auto-ubiquitinylates, leading to proteasomal degradation of TRAF3 and cIAP1, thereby disinhibiting NIK accumulation. NIK is constitutively active and, once accumulated, phosphorylates the inhibitor of κB kinase-α (IKKα) homodimer. The activated IKKα/IKKα homodimer then phosphorylates the inactive p100 form of NFκB2 leading to ubiquitinylation by Skp1-Cul1-F-box ubiquitin ligase (SCFβTrCP) and proteasomal cleavage of p100, releasing the active p52 subunit. p52 associates with RelB, and this heterodimer translocates into the nucleus to drive transcription from κB promoter elements. In addition to receptor ligation, ncNF-κB can be activated by signaling intermediates of the apoptosis cascade. Cleavage of the second mitochondrial activator of caspases (SMAC) from the mitochondrial membrane exposes the N-terminal motif Ala-Val-Pro-Ile, which binds specifically to the baculovirus intermediate repeat (BIR)

domains of the IAP proteins. Such BIR binding in cIAP1/2 activates the ubiquitin ligase activity of the TRAF2:TRAF3:cIAP complex, inducing autoubiquitinylation and degradation of cIAP1/2, NIK accumulation, and activation of the ncNF-κB pathway. Binding of SMAC to the BIR domains of XIAP and ML-IAP antagonizes the caspase inhibition activities of these molecules, often overexpressed in tumor cells, leading to potentiation of apoptosis. As such the Ala-Val-Pro-Ile motif of SMAC has been the subject of significant attention in oncology, leading to discovery of a class of peptide mimetics that have SMAC-like activity, referred to as SMAC mimetics (SMACm). SMACm potently activate the ncNF-κB pathway and do not induce apoptosis in non-tumor cells, and as such are of interest to reverse HIV latency. See e.g., Richard Dunham et. al., The SMAC Mimetic AZD5582 is a Potent HIV Latency Reversing Agent, bioRxiv, May 2, 2018; doi: http://dx.doi.org/10.1101/312447.

U.S. Pat. No. 7,960,372 relates to bivalent diazo bicyclic SMAC mimetics that inhibit the activity of IAP.

SUMMARY OF THE INVENTION

In one aspect, the invention provides a compound of the structure according to Formula (I):

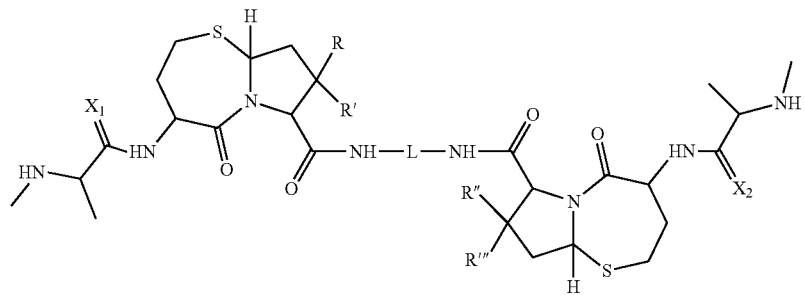

(I)

or a pharmaceutically acceptable salt or stereoisomer thereof, wherein:

R, R', R" and R'" are independently selected from H and CH$_3$;

X$_1$ and X$_2$ are independently selected from the group consisting of O and S; and L is a linker selected from the group consisting of:

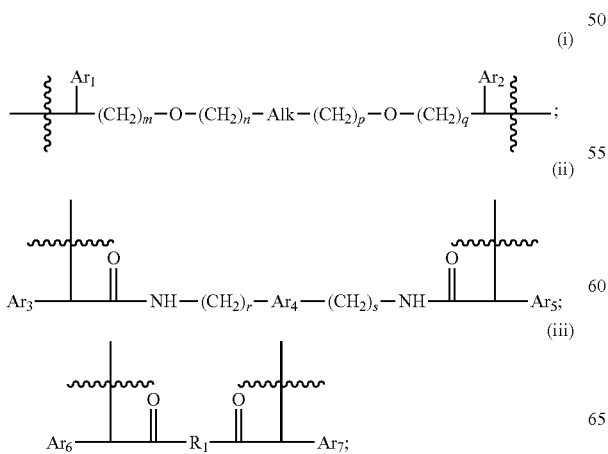

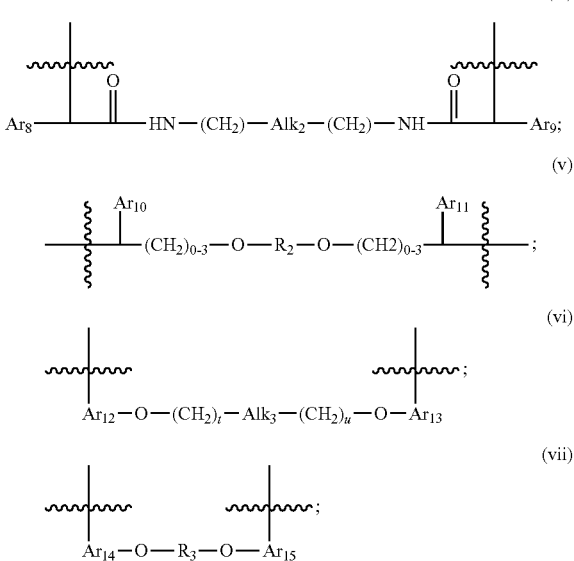

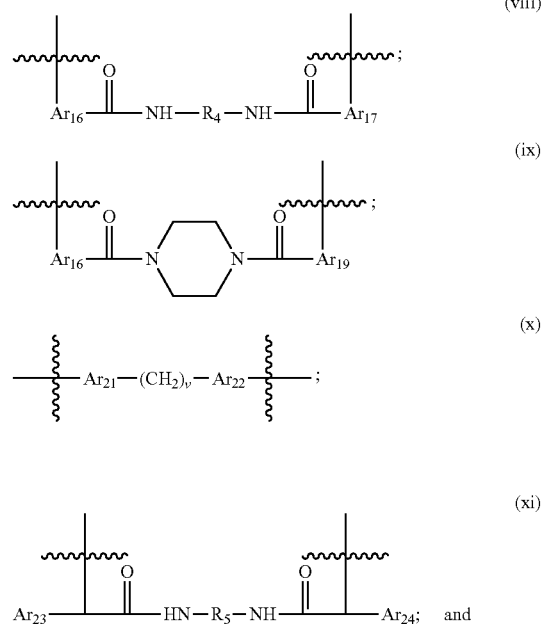

-continued (xii)

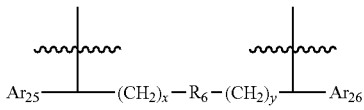

-continued

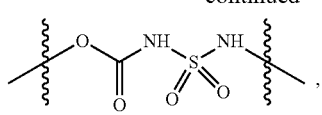

wherein:

Ar$_1$, Ar$_2$, Ar$_3$, Ar$_4$, Ar$_5$, Ar$_6$, Ar$_7$, Ar$_8$, Ar$_9$, Ar$_{10}$, Ar$_{11}$, Ar$_{12}$, Ar$_{13}$, Ar$_{14}$, Ar$_{15}$, Ar$_{16}$, Ar$_{17}$, Ar$_{18}$, Ar$_{19}$, Ar$_{21}$, Ar$_{22}$, Ar$_{23}$, Ar$_{24}$, Ar$_{25}$ and Ar$_{26}$ are each independently selected from (C$_6$-C$_{14}$)aryl;

Alk, Alk$_2$ and Alk$_3$ are each independently selected from:

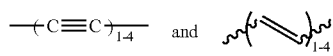

R$_1$, is C$_3$-C$_6$ cycloalkyl or C$_1$-C$_6$ heterocycle;

R$_2$ is selected from the group consisting of —(CH$_2$)$_a$—, —(CH$_2$)$_b$—O—(CH$_2$)$_c$—, —(CH$_2$)$_d$—(C$_6$-C$_{14}$)aryl-(CH$_2$)$_e$— and —(CH$_2$)$_f$—(C$_1$-C$_6$)heteroaryl-(CH$_2$)$_g$—;

R$_3$ is selected from the group consisting of —(CH$_2$)$_h$—; —(CH$_2$)$_i$—O—(CH$_2$)$_j$—, —(CH$_2$)$_k$—(C$_6$-C$_{14}$)aryl-(CH$_2$)$_l$— and —(CH$_2$)$_{m'}$—(C$_1$-C$_6$)heteroaryl-(CH$_2$)$_{m''}$—;

R$_4$ is C$_3$-C$_6$ cycloalkyl, (C$_6$-C$_{14}$)aryl or (CH$_2$)$_n$—(C$_6$-C$_{14}$)aryl-(CH$_2$)$_{n'}$, (CH$_2$)$_{n''}$-Alk-(CH$_2$)$_{n'''}$, wherein n', n'', n''' and n'''' are independently selected from 1 to 8

R$_5$ is C$_3$-C$_6$ cycloalkyl;

R$_6$ is selected from the group consisting of (CH$_2$)$_z$,

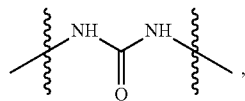

a, b, c, d, e, f, g, h, i, j, k, l, m, m', m'', n, p, q, r, s, t, u, v, x, y and z are each independently selected from 1 to 12.

In another aspect, the invention relates to a compound of Formula (Ia):

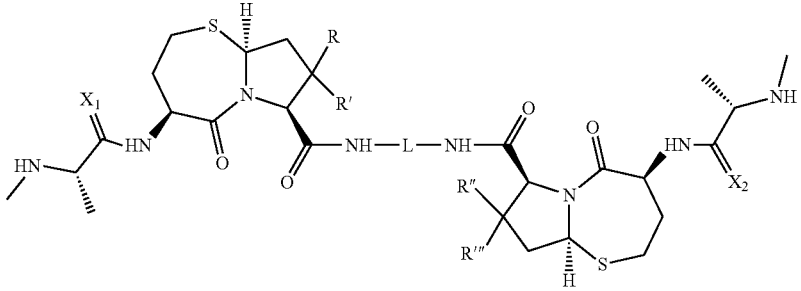

(Ia)

or a pharmaceutically acceptable salt or stereoisomer thereof, wherein:

R, R', R'' and R''' are independently selected from H and CH$_3$;

X$_1$ and X$_2$ are independently selected from the group consisting of O and S; and L is a linker selected from the group consisting of:

(i)
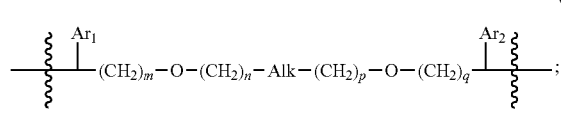

(ii)

(iii)
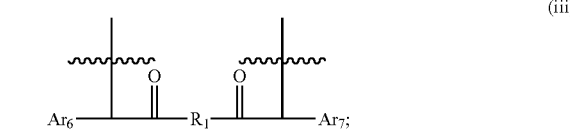

(iv)
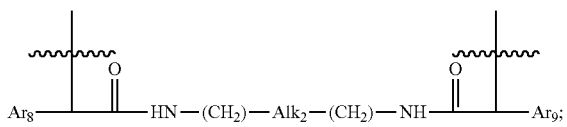

(v)
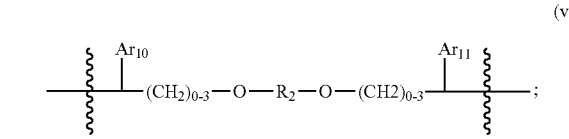

(vi)
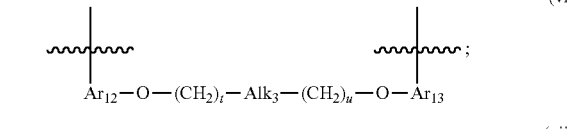

(vii)
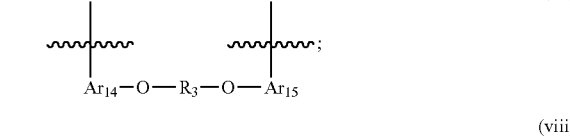

(viii)
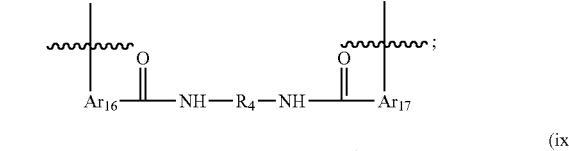

(ix)
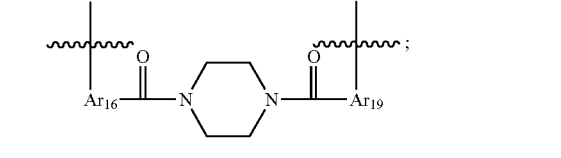

(x)
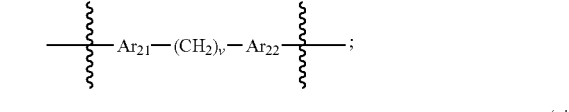

(xi)
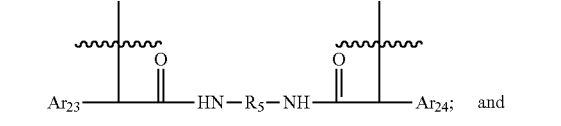

-continued (xii)
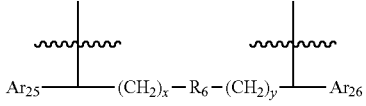

wherein:

$Ar_1$, $Ar_2$, $Ar_3$, $Ar_4$, $Ar_5$, $Ar_6$, $Ar_7$, $Ar_8$, $Ar_9$, $Ar_{10}$, $Ar_{11}$, $Ar_{12}$, $Ar_{13}$, $Ar_{14}$, $Ar_{15}$, $Ar_{16}$, $Ar_{17}$, $Ar_{18}$, $Ar_{19}$, $Ar_{21}$, $Ar_{22}$, $Ar_{23}$, $Ar_{24}$, $Ar_{25}$ and $Ar_{26}$ are each independently selected from $(C_6\text{-}C_{14})$aryl;

Alk, $Alk_2$ and $Alk_3$ are each independently selected from:

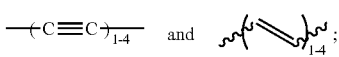

$R_1$, is $C_3\text{-}C_6$ cycloalkyl or $C_1\text{-}C_6$ heterocycle;

$R_2$ is selected from the group consisting of $-(CH_2)_a-$, $-(CH_2)_b-O-(CH_2)_c-$, $-(CH_2)_d-(C_6\text{-}C_{14})$aryl-$(CH_2)_e-$ and $-(CH_2)_f-(C_1\text{-}C_6)$heteroaryl-$(CH_2)_g-$;

$R_3$ is selected from the group consisting of $-(CH_2)_h-$; $-(CH_2)_iO-(CH_2)_j-$, $-(CH_2)_k-(C_6\text{-}C_{14})$aryl-$(CH_2)_l-$ and $-(CH_2)_{m'}-(C_1\text{-}C_6)$heteroaryl-$(CH_2)_{m''}-$;

$R_4$ is $C_3\text{-}C_6$ cycloalkyl, $(C_6\text{-}C_{14})$aryl or $(CH_2)_{n'}-(C_6\text{-}C_{14})$aryl-$(CH_2)_{n''}$, $(CH_2)_{n'''}$-Alk-$(CH_2)_{n''''}$, wherein n', n'', n''' and n'''' are independently selected from 1 to 8

$R_5$ is $C_3\text{-}C_6$ cycloalkyl;

$R_6$ is selected from the group consisting of $(CH_2)_z$,

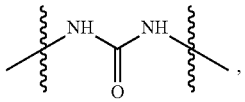

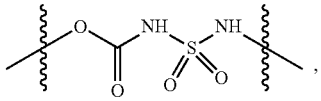

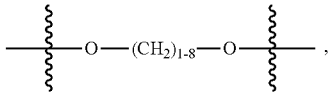

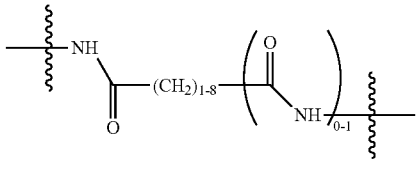, and

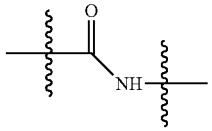

a, b, c, d, e, f, g, h, i, j, k, l, m, m', m'', n, p, q, r, s, t, u, v, x, y and z are each independently selected from 1 to 12.

In another aspect, the invention relates to a compound of Formula (Ib):

(Ib)

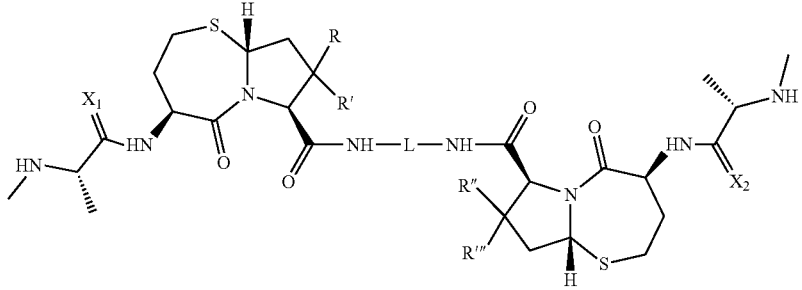

or a pharmaceutically acceptable salt or stereoisomer thereof, wherein:

R, R', R" and R"' are independently selected from H and CH$_3$;

X$_1$ and X$_2$ are independently selected from the group consisting of O and S; and L is a linker selected from the group consisting of:

(i)

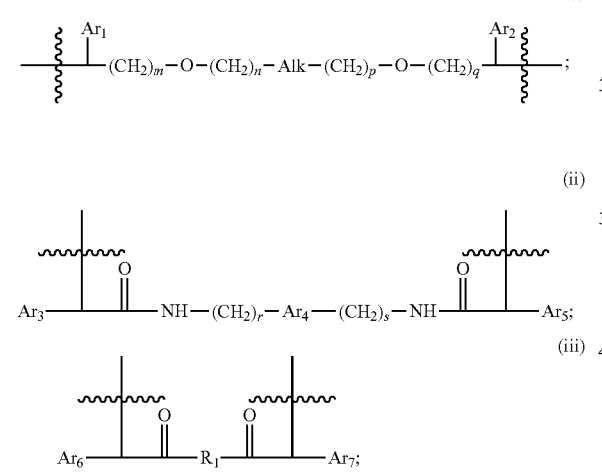

(ii)

(iii)

(iv)

(v)

(vi)

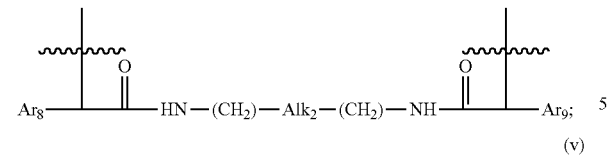

(vii)

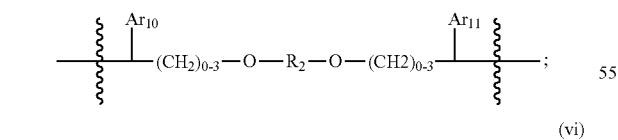

-continued (viii)

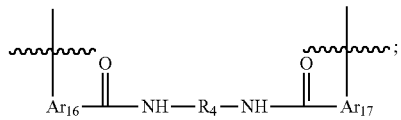

(ix)

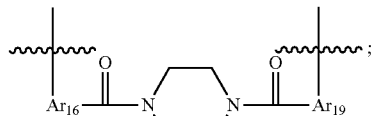

(x)

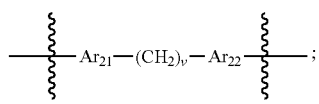

(xi)

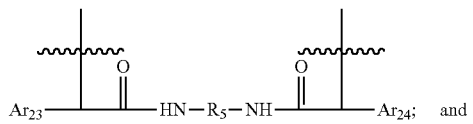

and (xii)

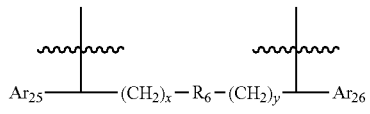

wherein:

Ar$_1$, Ar$_2$, Ar$_3$, Ar$_4$, Ar$_5$, Ar$_6$, Ar$_7$, Ar$_8$, Ar$_9$, Ar$_{10}$, Ar$_{11}$, Ar$_{12}$, Ar$_{13}$, Ar$_{14}$, Ar$_{15}$, Ar$_{16}$, Ar$_{17}$, Ar$_{18}$, Ar$_{19}$, Ar$_{21}$, Ar$_{22}$, Ar$_{23}$, Ar$_{24}$, Ar$_{25}$ and Ar$_{26}$ are each independently selected from (C$_6$-C$_{14}$)aryl;

Alk, Alk$_2$ and Alk$_3$ are each independently selected from:

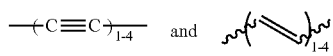

R$_1$, is C$_3$-C$_6$ cycloalkyl or C$_1$-C$_6$ heterocycle;
R$_2$ is selected from the group consisting of —(CH$_2$)$_a$—, —(CH$_2$)$_b$—O—(CH$_2$)$_c$—, —(CH$_2$)$_d$—(C$_6$-C$_{14}$)aryl-(CH$_2$)$_e$— and —(CH$_2$)$_f$—(C$_1$-C$_6$)heteroaryl-(CH$_2$)$_g$—;
R$_3$ is selected from the group consisting of —(CH$_2$)$_h$—; —(CH$_2$)$_i$—O—(CH$_2$)$_j$—, —(CH$_2$)$_k$—(C$_6$-C$_{14}$)aryl-(CH$_2$)$_l$— and —(CH$_2$)$_m$—(C$_1$-C$_6$)heteroaryl-(CH$_2$)$_{m'}$—;
R$_4$ is C$_3$-C$_6$ cycloalkyl, (C$_6$-C$_{14}$)aryl or (CH$_2$)$_{n'}$—(C$_6$-C$_{14}$)aryl-(CH$_2$)$_{n''}$, (CH$_2$)$_{n'''}$-Alk-(CH$_2$)$_{n''''}$, wherein n', n", n'" and n"" are independently selected from 1 to 8
R$_5$ is C$_3$-C$_6$ cycloalkyl;
R$_6$ is selected from the group consisting of (CH$_2$)$_z$,

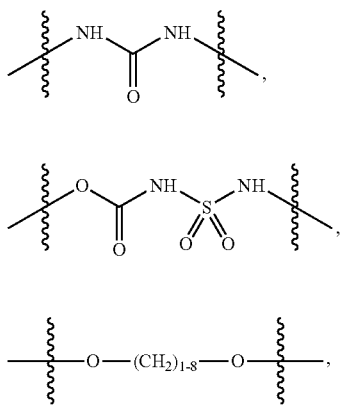

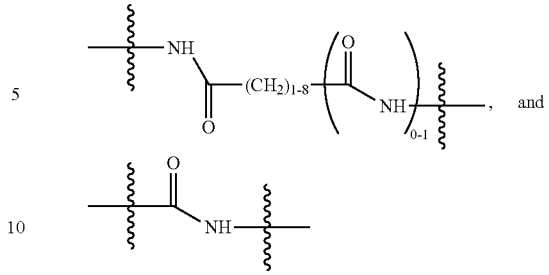

a, b, c, d, e, f, g, h, i, j, k, l, m, m', m". n, p, q, r, s, t, u, v, x, y and z are each independently selected from 1 to 12.

In another aspect, the invention relates to a compound represented by the Formula (II):

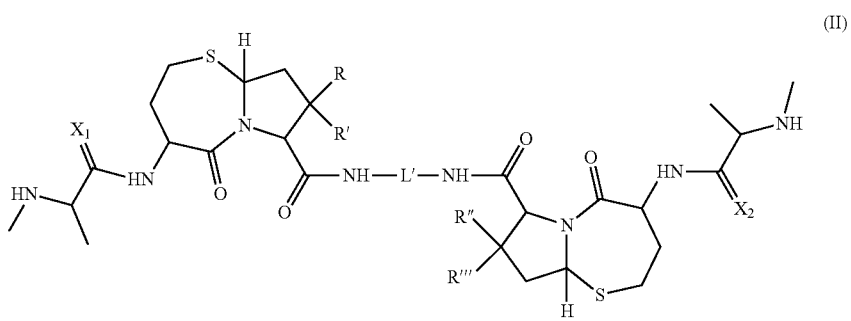

wherein
R, R', R" and R'" are independently selected from H and $CH_3$;

$X_1$ and $X_2$ are independently selected from the group consisting of O and S; and L' is a linker of the formula:

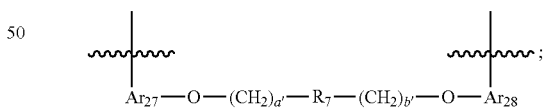

wherein:
$Ar_{27}$ and $Ar_{28}$ are each independently selected from $C_6$-$C_{14}$ aryl, $R_7$ is selected from the group consisting of

$C_6$ aryl and —$(CH_2)_{4-15}$—; and a' and b' are independently selected from 0 to 6.

In another aspect, the invention relates to a compound represented by the formula (III):

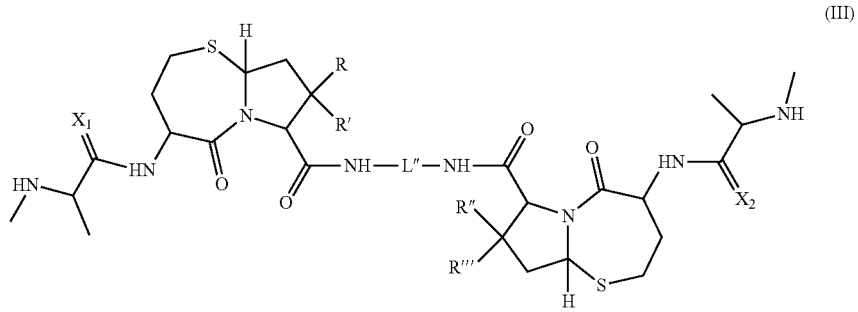

(III)

wherein

R, R', R" and R'" are independently selected from H and CH$_3$;

X$_1$ and X$_2$ are independently selected from the group consisting of O and S; and L" is a linker of the formula:

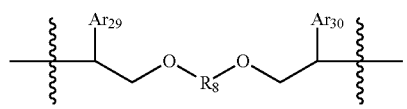

wherein Ar$_{29}$ and Ar$_{30}$ are independently selected from C$_6$-C$_{10}$ aryl and R$_8$ is selected from the group consisting of:

—(C≡C)$_{14}$—,

—(CH$_2$)$_{6-15}$—, '- and —(CH$_2$)$_{d'}$—(C$_6$-C$_{10}$)aryl-(CH$_2$)$_{e'}$—; wherein d' and e' are independently selected and ranging from 1 to 6.

In another aspect, the invention provides a pharmaceutical composition comprising a compound according to Formula (I), (Ia), (Ib), (II), (III) or a pharmaceutically acceptable salt thereof and a pharmaceutically acceptable excipient.

In another aspect, the invention provides a method of treating or curing an HIV infection in a subject comprising administering to the subject a compound of Formula (I), (Ia), (Ib), (II), (III) or a pharmaceutically acceptable salt thereof.

In another aspect, the invention provides a method of depleting HIV infected cells comprising administering to a subject a compound of Formula (I), (Ia), (Ib), (II), (III) or a pharmaceutically acceptable salt thereof.

In another aspect, the invention provides a method of depleting HIV infected cells comprising administering to a subject a compound of Formula (I), (Ia), (Ib), (II), (III) or a pharmaceutically acceptable salt thereof and one or more additional agents active against HIV. In certain aspects, these agents active against HIV are selected from the group consisting of anti-retroviral agents, latency reversing agents, and agents for clearance therapy.

These and other aspects are encompassed by the invention as set forth herein.

BRIEF DESCRIPTION OF THE FIGURES

FIG. 1 is a graph comparing rodent pharmacokinetic (PK) data of several compounds of Formula I with that of SMACm AZD5582 PK data.

DETAILED DESCRIPTION

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers all alternatives, modifications, and equivalents. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in this field. All publications, patent applications, patents, and other references mentioned herein are incorporated by reference in their entirety.

Apoptosis, a type of programmed cell death, plays an important role in maintaining homeostasis and regulating the number of cells in higher organisms. Abnormal apoptosis is involved in a number of diseases, including autoimmune disorders, degenerative diseases of the Central Nervous System, cancer, and viral infections, such as HIV. The family of Inhibitor of Apoptosis Proteins (IAPs) plays a key role in the suppression of proapoptotic signaling in mammalian cells. SMACm, which mimic a critical tetrapeptide sequence from the second mitochondria-derived activator of caspase, have been shown to disrupt the binding of IAPs with their functional partner and restore apoptotic response to proapoptotic stimuli in cells. Since the early 2000s, great effort has focused on the design and preparation of SMAC mimetics as IAP antagonists, particularly in promoting cell death in tumor cells and more recently in reversing HIV latency. Such investigations have explored the activation of the non-canonical NF-kB pathway (ncNF-kB) as a potential method by which SMAC mimics selectively deplete latent HIV cells. An example of an early SMAC mimetic is monomeric SBI-0637142, prepared by researchers at the Sanford-Burnham Medical Research Institute. In HIV depletion tests, SBI-0637142 was found to be potent in cell line assays, but did not exhibit activity in p100-p52 conversion or HIV caRNA induction in primary cells. Much work has also been directed to the development of bivalent mimetics, which are covalently linked momomeric SMAC mimetics. AstraZeneca's AZD5582 and Medivir's Birinapant TL32711 are examples of dimeric SMAC mimetics. In HIV latency reversal studies, Birinapant TL32711 was not potent in Jurkat, p100-p52 conversion, or HIV caRNA induction. Conversely, AZD5582 exhibited an increase in cell-associated HIV RNA expression in resting CD4+ T cells through Jurkat assay experiments, p100-p52 conversion studies, and HIV and CaRNA induction (Sampey et al. bioRxiv 312447). However, AZD5582 can also demonstrate tolerability issues.

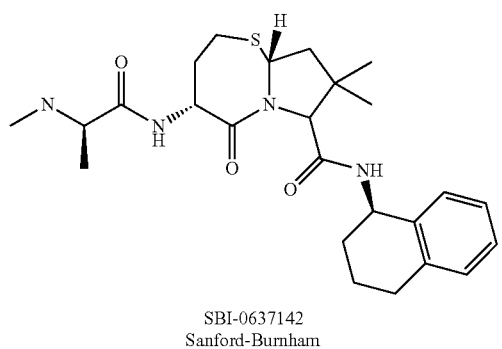

SBI-0637142
Sanford-Burnham

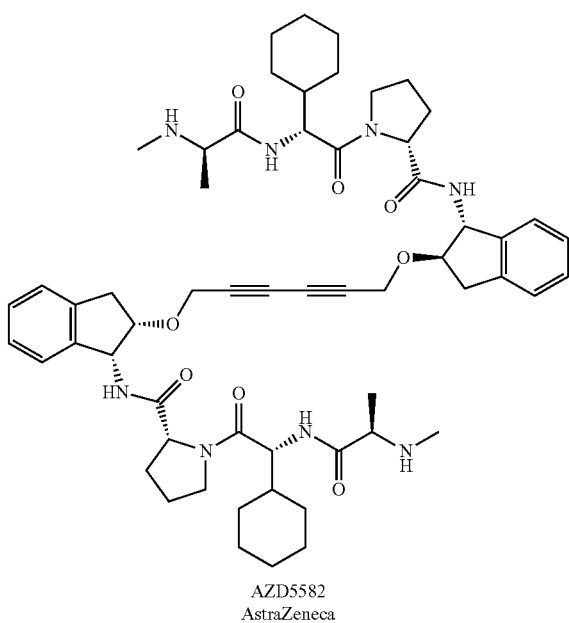

AZD5582
AstraZeneca

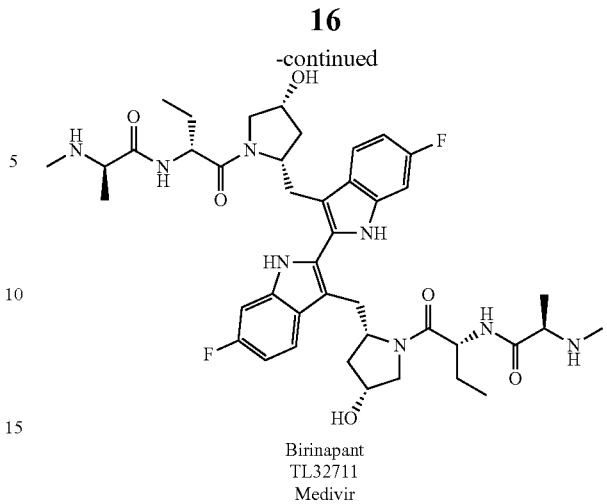

Birinapant
TL32711
Medivir

Disclosed herein are dimeric SMACm believed to be sufficiently potent and effective enough to activate ncNF-kB, reverse HIV latency in primary, unmodified human cells as single agents, and may have less off-target toxicity relative to other dimeric SMACm such as AZD5582, making them suitable for consideration for further development. In particular, the dimeric SMACm of the invention are capable of inducing HIV RNA expression in unstimulated, resting primary CD4+ T cells from HIV-infected donors whose viremia is completely suppressed by standard therapy. Other SMACm, specifically monomeric molecules or dimeric molecules with unoptimized linkers, are not believed to have this effect in these cells, the primary latent reservoir of persistent infection. Moreover, the dimeric SMACm of the invention are capable of a clinically measurable reversal of latency in two animal models (SIV-infected, antiretroviral suppressed rhesus macaques and HIV-infected ART-suppressed humanized mouse) as evidenced by intermittent plasma viremia that transiently emerges despite successful ongoing antiviral therapy It is to be understood that the terminology used herein is for the purpose of describing particular embodiments only and is not intended to limit the scope of the present invention. In this specification and in the claims that follow, reference will be made to a number of terms that shall be defined to have the following meanings As used herein unless otherwise specified, "alkyl" refers to a monovalent saturated aliphatic hydrocarbyl group having from 1 to 14 carbon atoms and, in some embodiments, from 1 to 8 carbon atoms or 1 to 6 carbon atoms. "(Cx-Cy) alkyl" refers to alkyl groups having from x to y carbon atoms. The term "alkyl" includes, by way of example, linear and branched hydrocarbyl groups such as methyl ($CH_3$), ethyl ($CH_3CH_2$), n-propyl ($CH_3CH_2CH_2$), isopropyl (($CH_3)_2$ CH), n-butyl ($CH_3CH_2CH_2CH_2$), isobutyl (($CH_3)_2$ $CHCH_2$), sec-butyl (($CH_3$)($CH_3CH_2$)CH), t-butyl (($CH_3)_3$ C), n-pentyl ($CH_3CH_2CH_2CH_2CH_2$), and neopentyl (($CH_3)_3$ $CCH_2$). It should be noted that the recitation of e.g., ($C_1$-$C_{12}$) alkyl also encompasses ranges within this group e.g., ($C_1$—C)alkyl.

"Alkylene" or "alkylene" refers to divalent saturated aliphatic hydrocarbyl groups having from 1 to 10 carbon atoms and, in some embodiments, from 1 to 6 carbon atoms. "($C_u$$C_v$)alkylene" refers to alkylene groups having from u to v carbon atoms. The alkylene groups include branched and straight chain hydrocarbyl groups. For example, "($C_1$-$C_6$) alkylene" is meant to include methylene, ethylene, propylene, 2-methypropylene, dimethylethylene, pentylene, and so forth. As such, the term "propylene" could be exemplified by the following structure:

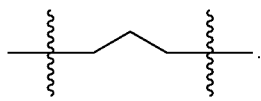 [SMILES: *CCC*]

Likewise, the term "dimethylbutylene" could be exemplified by any of the following three structures or more:

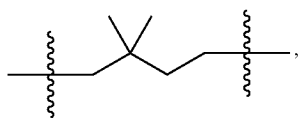 [SMILES: *CCC(C)(C)C*]

p, or

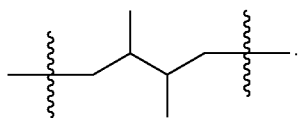 [SMILES: *CC(C)C(C)C*]

Furthermore, the term "$(C_1-C_6)$alkylene" is meant to include such branched chain hydrocarbyl groups as cyclopropylmethylene, which could be exemplified by the following structure:

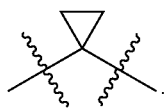 [SMILES: *C1(*)CC1]

"Alkynyl", or "alkyne" refers to a linear monovalent hydrocarbon radical or a branched monovalent hydrocarbon radical containing at least one triple bond. The term "alkynyl" is also meant to include those hydrocarbyl groups having one triple bond and one double bond. For example, $(C_2-C_6)$ alkynyl is meant to include ethynyl, propynyl, and the like.

"Aryl" refers to an aromatic group of from 6 to 14 carbon atoms and no ring heteroatoms and having a single ring (e.g., phenyl) or multiple condensed (fused) rings (e.g., naphthyl or anthryl). For multiple ring systems, including fused, bridged, and spiro ring systems having aromatic and non-aromatic rings that have no ring heteroatoms, the term "Aryl" or "Ar" applies when the point of attachment is at an aromatic carbon atom (e.g., 5,6,7,8 tetrahydronaphthalene-2-yl is an aryl group as its point of attachment is at the 2-position of the aromatic phenyl ring). In one embodiment, a preferred bicyclic aryl system may be represented by the formula:

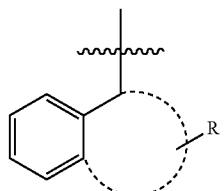

wherein the size of the ring fused to the $C_6$ aryl group ranges from 4 to 8

For the purposes of clarity, other points of attachment are encompassed by "Aryl" or "Ar", e.g., the point of attachment being at a non-aromatic carbon atom.

"Cycloalkyl" refers to a saturated or partially saturated cyclic group of from 3 to 14 carbon atoms and no ring heteroatoms and having a single ring or multiple rings including fused, bridged, and spiro ring systems. For multiple ring systems having aromatic and non-aromatic rings that have no ring heteroatoms, the term "cycloalkyl" applies when the point of attachment is at a non-aromatic carbon atom (e.g. 5,6,7,8,-tetrahydronaphthalene-5-yl). The term "Cycloalkyl" includes cycloalkenyl groups, such as cyclohexenyl. Examples of cycloalkyl groups include, for instance, adamantyl, cyclopropyl, cyclobutyl, cyclohexyl, cyclopentyl, cyclooctyl, cyclopentenyl, and cyclohexenyl. Examples of cycloalkyl groups that include multiple bicycloalkyl ring systems are bicyclohexyl, bicyclopentyl, bicyclooctyl, and the like. Two such bicycloalkyl multiple ring structures are exemplified and named below: bicyclohexyl, and bicyclohexyl.

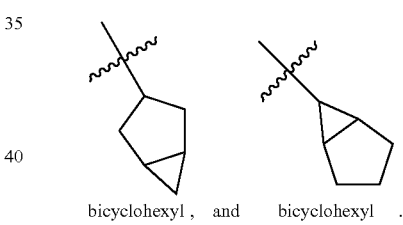

bicyclohexyl, and bicyclohexyl .

"$(C_u-C_v)$cycloalkyl" refers to cycloalkyl groups having u to v carbon atoms.

"Spiro cycloalkyl" refers to a 3 to 10 member cyclic substituent formed by replacement of two hydrogen atoms at a common carbon atom in a cyclic ring structure or in an alkylene group having 2 to 9 carbon atoms, as exemplified by the following structure wherein the group shown here attached to bonds marked with wavy lines is substituted with a spiro cycloalkyl group:

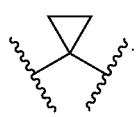 [SMILES: *C1(*)CC1]

"Fused cycloalkyl" refers to a 3 to 10 member cyclic substituent formed by the replacement of two hydrogen atoms at different carbon atoms in a cycloalkyl ring structure, as exemplified by the following structure wherein the cycloalkyl group shown here contains bonds marked with wavy lines which are bonded to carbon atoms that are substituted with a fused cycloalkyl group:

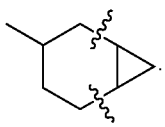

"AUC" refers to the area under the plot of plasma concentration of drug (not logarithm of the concentration) against time after drug administration.

"$EC_{50}$" refers to the concentration of a drug that gives half-maximal response. Sometimes, it is also converted to the $pEC_{50}$ scale ($-\log IC_{50}$), in which higher values indicate exponentially greater potency.

"$IC_{50}$" refers to the half-maximal inhibitory concentration of a drug. Sometimes, it is also converted to the $pIC_{50}$ scale ($-\log IC_{50}$), in which higher values indicate exponentially greater potency.

"Heteroaryl" refers to an aromatic group of from e.g., and unless otherwise noted 1 to 14 carbon atoms (preferably 1 to 12 carbon atoms, and more preferably 2 to 12 carbon atoms) and 1 to 6 heteroatoms (more preferably 1 to 3 heteroatoms) selected from oxygen, nitrogen, and sulfur and includes single ring (e.g. imidazolyl) and multiple ring systems (e.g. benzimidazol-2-yl and benzimidazol-6-yl). For multiple ring systems, including fused, bridged, and spiro ring systems having aromatic and non-aromatic rings, the term "heteroaryl" applies if there is at least one ring heteroatom and the point of attachment is at an atom of an aromatic ring (e.g. 1,2,3,4-tetrahydroquinolin-6-yl and 5,6,7,8-tetrahydroquinolin-3-yl). In some embodiments, the nitrogen and/or the sulfur ring atom(s) of the heteroaryl group are optionally oxidized to provide for the Noxide (N→O), sulfinyl, or sulfonyl moieties. A prefix indicating the number of carbon atoms (e.g., $C_x$-$C_y$) refers to the total number of carbon atoms in the portion of the heteroaryl group exclusive of the number of heteroatoms. Also encompassed by this group are all ranges between x and y, e.g., $C_1$-$C_{14}$ encompasses $C_2$-$C_{14}$, $C_2$-$C_9$ etc. More specifically the term heteroaryl includes, but is not limited to, pyridyl, furanyl, thienyl, thiazolyl, isothiazolyl, triazolyl, imidazolyl, imidazolinyl, isoxazolyl, pyrrolyl, pyrazolyl, pyridazinyl, pyrimidinyl, purinyl, phthalazyl, naphthylpryidyl, benzofuranyl, tetrahydrobenzofuranyl, isobenzofuranyl, benzothiazolyl, benzoisothiazolyl, benzotriazolyl, indolyl, isoindolyl, indolizinyl, dihydroindolyl, indazolyl, indolinyl, benzoxazolyl, quinolyl, isoquinolyl, quinolizyl, quianazolyl, quinoxalyl, tetrahydroquinolinyl, isoquinolyl, quinazolinonyl, benzimidazolyl, benzisoxazolyl, benzothienyl, benzopyridazinyl, pteridinyl, carbazolyl, carbolinyl, phenanthridinyl, acridinyl, phenanthrolinyl, phenazinyl, phenoxazinyl, phenothiazinyl, phthalimidyl, and tetrazole. In one embodiment, for example, a ($C_3$-$C_9$) heteroaryl spiro ring fused system is present, more preferably, ($C_4$-$C_6$) heteroaryl.

"Heterocyclic" or "heterocycle" or "heterocycloalkyl" or "heterocyclyl" refers to a saturated or partially saturated cyclic group having from e.g., and unless otherwise noted 1 to 14 carbon atoms (preferably 1 to 12 carbon atoms, and more preferably 2 to 12 carbon atoms) and from 1 to 6 heteroatoms (more preferably 1 to 3 heteroatoms) selected from nitrogen, sulfur, phosphorus or oxygen and includes single ring and multiple ring systems including fused, bridged, and spiro ring systems. For multiple ring systems having aromatic and/or non-aromatic rings, the terms "heterocyclic", "heterocycle", "heterocycloalkyl", or "heterocyclyl" apply when there is at least one ring heteroatom and the point of attachment is at an atom of a non-aromatic ring (e.g. 1,2,3,4-tetrahydroquinoline-3-yl, 5,6,7,8-tetrahydroquinoline-6-yl, and decahydroquinolin-6-yl). In one embodiment, the nitrogen, phosphorus and/or sulfur atom(s) of the heterocyclic group are optionally oxidized to provide for the N-oxide, phosphinane oxide, sulfinyl, sulfonyl moieties. More specifically the heterocyclyl includes, but is not limited to, tetrahydropyranyl, piperidinyl, piperazinyl, 3-pyrrolidinyl, 2-pyrrolidon-1-yl, morpholinyl, and pyrrolidinyl. A prefix indicating the number of carbon atoms (e.g., $C_x$-$C_y$) refers to the total number of carbon atoms in the portion of the heterocyclyl group exclusive of the number of heteroatoms. Also encompassed by this group are all ranges between x and y, e.g., $C_1$-$C_{12}$ encompasses $C_2$-$C_{12}$, $C_2$-$C_9$ etc. In one embodiment, for example, a ($C_3$-$C_9$) heterocyclic spiro ring fused system is present, more preferably, ($C_4$-$C_6$) heterocycle.

Examples of heterocycle and heteroaryl groups include, but are not limited to, azetidine, pyrrole, imidazole, pyrazole, pyridine, pyrazine, pyrimidine, pyridazine, pyridone, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4tetrahydroisoquinoline, 4,5,6,7tetrahydrobenzo[b]thiophene, thiazole, thiazolidine, thiophene, benzo[b]thiophene, morpholine, thiomorpholine (also referred to as thiamorpholine), piperidine, pyrrolidine, and tetrahydrofuranyl.

In addition to the above embodiments set forth herein, "Fused heterocyclic" or "fused heterocycle" refer to a 3 to 9 member cyclic substituent (more preferably 4 to 6 member) formed by the replacement of two hydrogen atoms at different carbon atoms in a cycloalkyl ring structure, as exemplified by the following structure wherein the cycloalkyl group shown here contains bonds marked with wavy lines which are bonded to carbon atoms that are substituted with a fused heterocyclic group:

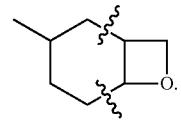

An embodiment of spiro ring system (e.g., without limitation, formed from $R^2$ and $R^3$) in Formula (I), (Ia), (Ib), (II) or (III) includes, without limitation:

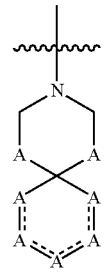

wherein A can be selected from e.g., C(O), O, N, B, B(OH), Si or P, P(O)R

"Compound", "compounds", "chemical entity", and "chemical entities" as used herein refers to a compound encompassed by the generic formulae disclosed herein, any subgenus of those generic formulae, and any forms of the compounds within the generic and subgeneric formulae, including the racemates, stereoisomers, and tautomers of the compound or compounds.

The term "heteroatom" means nitrogen, oxygen, or sulfur and includes any oxidized form of nitrogen, such as N(O) {$N^+$—$O^-$} and sulfur such as S(O) and S(O)$_2$, and the quaternized form of any basic nitrogen.

"Linker" ("L") refers to a substance (e.g., molecule) that binds the two portions of the molecule.

"Polymorphism" refers to when two or more clearly different phenotypes exist in the same population of a species where the occurrence of more than one form or morph. In order to be classified as such, morphs must occupy the same habitat at the same time and belong to a panmictic population (one with random mating).

"Protein binding" refers to the binding of a drug to proteins in blood plasma, tissue membranes, red blood cells and other components of blood.

"Protein shift" refers to determining a binding shift by comparing the $EC_{50}$ values determined in the absence and presence of human serum.

"Racemates" refers to a mixture of enantiomers. In an embodiment of the invention, the compounds of Formula I, Ia, Ib, II and III, or pharmaceutically acceptable salts thereof, are enantiomerically enriched with one enantiomer wherein all of the chiral carbons referred to are in one configuration. In general, reference to an enantiomerically enriched compound or salt, is meant to indicate that the specified enantiomer will comprise more than 50% by weight of the total weight of all enantiomers of the compound or salt.

"Solvate" or "solvates" of a compound refer to those compounds, as defined above, which are bound to a stoichiometric or nonstoichiometric amount of a solvent. Solvates of a compound includes solvates of all forms of the compound. In certain embodiments, solvents are volatile, nontoxic, and/or acceptable for administration to humans in trace amounts. Suitable solvates include water.

"Stereoisomer" or "stereoisomers" refer to compounds that differ in the chirality of one or more stereocenters. Stereoisomers include enantiomers and diastereomers, including the compounds of Formula (I), (Ia), (Ib), (II) and (III) and linkers (L) of Formulas (I) through (xiii) set forth herein, as well as linkers set forth in Formulas (II) and (III).

"Tautomer" refer to alternate forms of a compound that differ in the position of a proton, such as enol/keto and imine/enamine tautomers, or the tautomeric forms of heteroaryl groups containing a ring atom attached to both a ring NH moiety and a ring =N moiety such as pyrazoles, imidazoles, benzimidazoles, triazoles, and tetrazoles.

The term 'atropisomer' refers to a stereoisomer resulting from an axis of asymmetry. This can result from restricted rotation about a single bond where the rotational barrier is high enough to allow differentiation of the isomeric species up to and including complete isolation of stable non-interconverting diastereomer or enantiomeric species. One skilled in the art will recognize that upon installing a nonsymmetrical $R^x$ to core, the formation of atropisomers is possible. In addition, once a second chiral center is installed in a given molecule containing an atropisomer, the two chiral elements taken together can create diastereomeric and enantiomeric stereochemical species. Depending upon the substitution about the Cx axis, interconversion between the atropisomers may or may not be possible and may depend on temperature. In some instances, the atropisomers may interconvert rapidly at room temperature and not resolve under ambient conditions. Other situations may allow for resolution and isolation but interconversion can occur over a period of seconds to hours or even days or months such that optical purity is degraded measurably over time. Yet other species may be completely restricted from interconversion under ambient and/or elevated temperatures such that resolution and isolation is possible and yields stable species. When known, the resolved atropisomers were named using the helical nomenclature. For this designation, only the two ligands of highest priority in front and behind the axis are considered. When the turn priority from the front ligand 1 to the rear ligand 1 is clockwise, the configuration is P, if counterclockwise it is M.

"Pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use; 2002.

"Patient" or "subject" refers to mammals and includes humans and nonhuman mammals.

Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease.

As indicated above, "treatment" of a disorder includes prevention of the disorder. A person of ordinary skill in the art will appreciate that "prevention" is not an absolute term. In medicine, "prevention" is understood to refer to the prophylactic administration of a drug to substantially diminish the likelihood or severity of a disorder or biological manifestation thereof, or to delay the onset of such disorder or biological manifestation thereof.

The terms "intermittent" or "intermittently" as used herein means stopping and starting at either regular or irregular intervals. As used herein, the term "viral infection" describes a diseased state in which a virus invades healthy cells, uses the cell's reproductive machinery to multiply or replicate and ultimately lyse the cell resulting in cell death, release of viral particles and the infection of other cells by the newly produced progeny viruses. Latent infection by certain viruses is also a possible result of viral infection.

As used herein, the term "treating viral infections" means to inhibit the replication of the particular virus, to inhibit viral transmission, and to ameliorate or alleviate the symptoms of the disease caused by the viral infection. The treatment is considered "therapeutic" if there is a reduction in viral load, decrease in mortality and/or morbidity. "Preventing viral infections" means to prevent the virus from establishing itself in the host. A treatment is considered "prophylactic" if the subject is exposed to the virus, but does not become infected with the virus as a result of treatment.

As used herein "latency" means a concept describing 1) the dormant state of viral activity within a population of cells, wherein viral production, viral packaging, and host cell lysis does not occur, or occurs at a very low frequency, or 2) the down-regulation or absence of gene expression within an infected cell.

As used herein, "reversing latent HIV infection" refers to a treatment that upregulates the expression of integrated HIV genomes within latently infected cells, such as the agent that activates the non-canonical NF-kB pathway, leading to susceptibility of the infected cell to virally-induced cell death or immunologic clearance. As used herein, "depleting latent HIV infection" refers to the clearance of latently HIV-infected cells that may follow the reversal of HIV latency by reagents such as those that activate the non-canonical NF-kB pathway.

In certain embodiments, the latent HIV infected cells are resting CD4+ T cells.

Wherever dashed lines occur adjacent to single bonds denoted by solid lines, then the dashed line represents an optional double bond at that position. Likewise, wherever dashed circles appear within ring structures denoted by solid lines or solid circles, then the dashed circles represent one to three optional double bonds arranged according to their proper valence taking into account whether the ring has any optional substitutions around the ring as will be known by one of skill in the art. For example, the dashed line in the structure below could either indicate a double bond at that position or a single bond at that position:

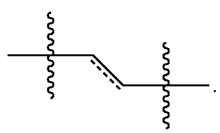

Where specific compounds or generic formulas are drawn that have aromatic rings, such as aryl or heteroaryl rings, then it will understood by one of still in the art that the particular aromatic location of any double bonds are a blend of equivalent positions even if they are drawn in different locations from compound to compound or from formula to formula. For example, in the two pyridine rings (A and B) below, the double bonds are drawn in different locations, however, they are known to be the same structure and compound:

A

B

The present invention includes compounds as well as their pharmaceutically acceptable salts. Accordingly, the word "or" in the context of "a compound or a pharmaceutically acceptable salt thereof" is understood to refer to either: 1) a compound alone or a compound and a pharmaceutically acceptable salt thereof (alternative), or 2) a compound and a pharmaceutically acceptable salt thereof (in combination).

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)(alkyl)OC(O). In a term such as "—C(R$^x$)$_2$—", it should be understood that the two R$^x$ groups can be the same, or they can be different if R$^x$ is defined as having more than one possible identity. In addition, certain substituents are drawn as —R$^x$R$^y$, where the "—" indicates a bond adjacent to the parent molecule and R$^y$ being the terminal portion of the functionality. Similarly, it is understood that the above definitions are not intended to include impermissible substitution patterns (e.g., methyl substituted with 5 fluoro groups). Such impermissible substitution patterns are well known to the skilled artisan.

The invention provides compounds of Formulas (I), (Ia), (Ib), (II) and (III), as well as various forms of these compounds set forth herein (e.g., pharmaceutically acceptable salts). It should be appreciated that any reference to the compounds of Formulas (I), (Ia), (Ib), (II) and (III) herein is clearly meant to also include, without limitation, those compounds set forth in Table 1.

In one aspect, the invention provides a compound of the structure according to Formula (I):

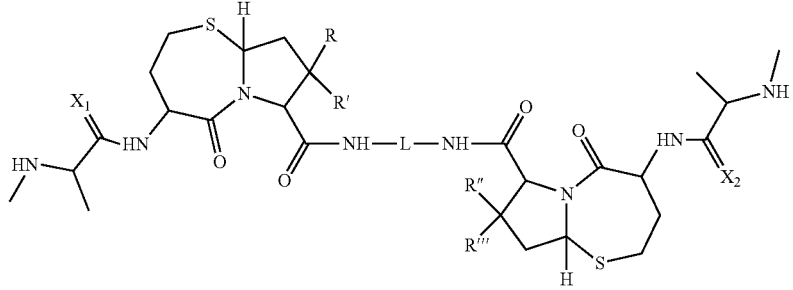

(I)

or a pharmaceutically acceptable salt or stereoisomer thereof, wherein:

R, R', R" and R'" are independently selected from H and CH$_3$;

X$_1$ and X$_2$ are independently selected from the group consisting of O and S; and L is a linker selected from the group consisting of:

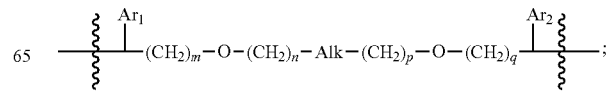

(i)

(ii)
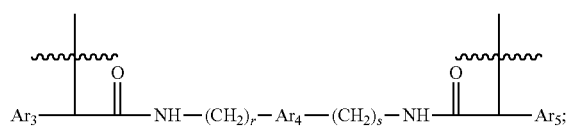

(iii)
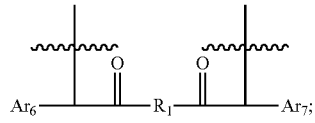

(iv)
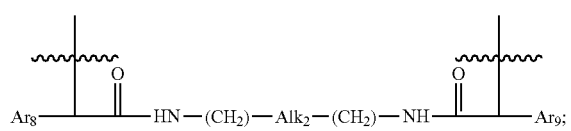

(v)
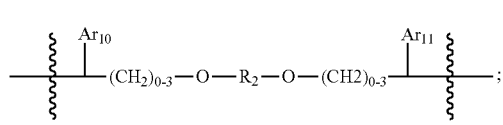

(vi)
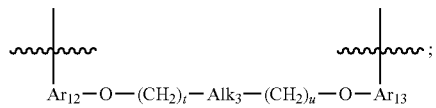

(vii)
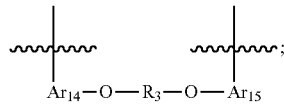

(viii)
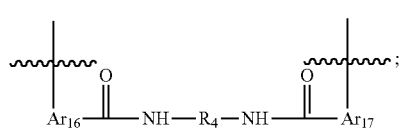

(ix)
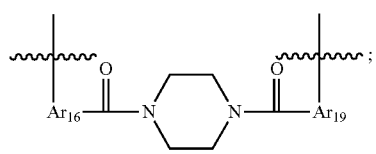

(x)
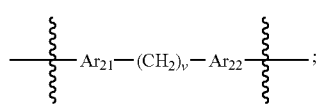

(xi)
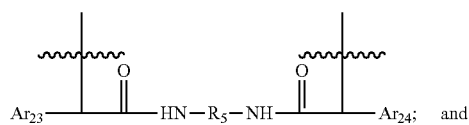

(xii)
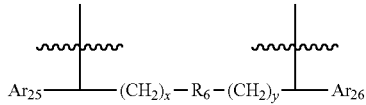

wherein:

$Ar_1$, $Ar_2$, $Ar_3$, $Ar_4$, $Ar_5$, $Ar_6$, $Ar_7$, $Ar_8$, $Ar_9$, $Ar_{10}$, $Ar_{11}$, $Ar_{12}$, $Ar_{13}$, $Ar_{14}$, $Ar_{15}$, $Ar_{16}$, $Ar_{17}$, $Ar_{18}$, $Ar_{19}$, $Ar_{21}$, $Ar_{22}$, $Ar_{23}$, $Ar_{24}$, $Ar_{25}$ and $Ar_{26}$ are each independently selected from ($C_6$-$C_{14}$)aryl;

Alk, $Alk_2$ and $Alk_3$ are each independently selected from:

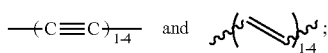

$R_1$, is $C_3$-$C_6$ cycloalkyl or $C_1$-$C_6$ heterocycle;

$R_2$ is selected from the group consisting of —$(CH_2)_a$—, —$(CH_2)_b$—O—$(CH_2)_c$—, —$(CH_2)_d$—($C_6$-$C_{14}$)aryl-$(CH_2)_e$— and —$(CH_2)_f$—($C_1$-$C_6$)heteroaryl-$(CH_2)_g$—; more preferably $C_2$ heteroaryl $R_3$ is selected from the group consisting of —$(CH_2)_h$—; —$(CH_2)_i$—O—$(CH_2)_j$, —$(CH_2)_k$—($C_6$-$C_{14}$)aryl-$(CH_2)_l$— and —$(CH_2)_{m'}$—($C_1$-$C_6$)heteroaryl-$(CH_2)_{m''}$—;

$R_4$ is $C_3$-$C_6$ cycloalkyl, ($C_6$-$C_{14}$)aryl or $(CH_2)_{n'}$—($C_6$-$C_4$)aryl-$(CH_2)_{n''}$, $(CH_2)_{n'''}$-Alk-$(CH_2)_{n''''}$, wherein n', n'', n''' and n'''' are independently selected from 1 to 8

$R_5$ is $C_3$-$C_6$ cycloalkyl;

$R_6$ is selected from the group consisting of $(CH_2)_z$,

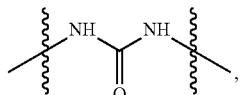

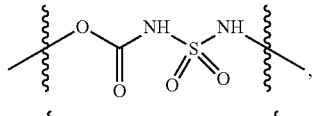

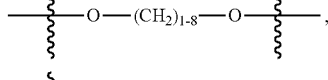

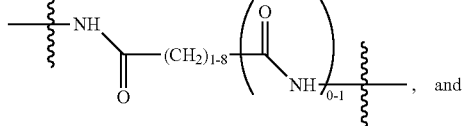

a, b, c, d, e, f, g, h, i, j, k, l, m, m', m''. n, p, q, r, s, t, u, v, x, y and z are each independently selected from 1 to 12.

In another aspect, the invention relates to a compound of Formula (Ia):

(Ia)

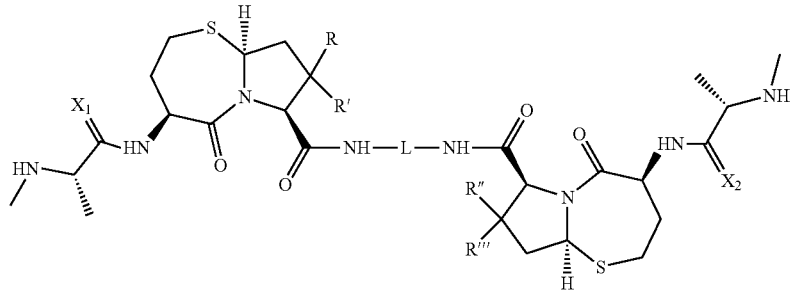

or a pharmaceutically acceptable salt or stereoisomer thereof, wherein:

R, R', R" and R'" are independently selected from H and $CH_3$;

$X_1$ and $X_2$ are independently selected from the group consisting of O and S; and L is a linker selected from the group consisting of:

(i)

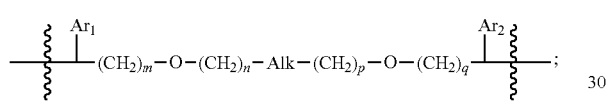

(ii)

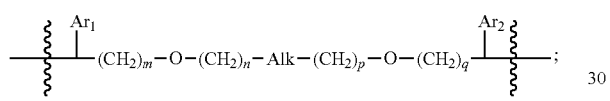

(iii)

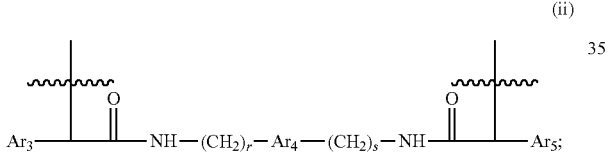

(iv)

(v)

(vi)

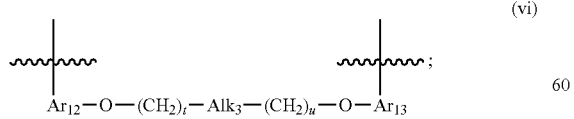

(vii)

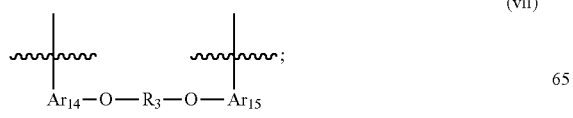

(viii)

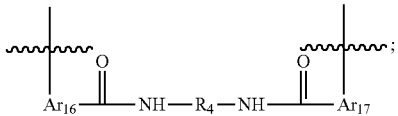

(ix)

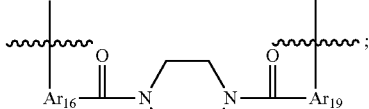

(x)

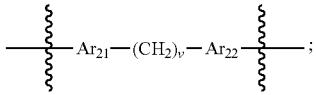

(xi)

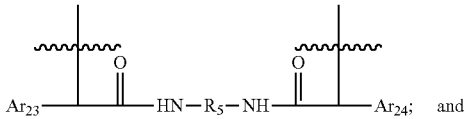

and (xii)

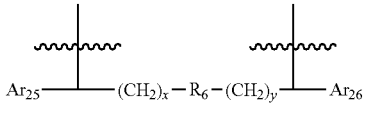

wherein:

$Ar_1$, $Ar_2$, $Ar_3$, $Ar_4$, $Ar_5$, $Ar_6$, $Ar_7$, $Ar_8$, $Ar_9$, $Ar_{10}$, $Ar_{11}$, $Ar_{12}$, $Ar_{13}$, $Ar_{14}$, $Ar_{15}$, $Ar_{16}$, $Ar_{17}$, $Ar_{18}$, $Ar_{19}$, $Ar_{21}$, $Ar_{22}$, $Ar_{23}$, $Ar_{24}$, $Ar_{25}$ and $Ar_{26}$ are each independently selected from $(C_6-C_{14})$aryl;

Alk, $Alk_2$ and $Alk_3$ are each independently selected from:

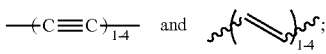

$R_1$, is $C_3-C_6$ cycloalkyl or $C_1-C_6$ heterocycle;

$R_2$ is selected from the group consisting of $-(CH_2)_a-$, $-(CH_2)_b-O-(CH_2)_c-$, $-(CH_2)_d-(C_6-C_{14})$aryl-$(CH_2)_e-$ and $-(CH_2)_f-(C_1-C_6)$heteroaryl-$(CH_2)_g-$;

$R_3$ is selected from the group consisting of $-(CH_2)_h-$; $-(CH_2)_i-O-(CH_2)_j-$, $-(CH_2)_k-(C_6-C_{14})$aryl-$(CH_2)_l-$ and $-(CH_2)_m-(C_1-C_6)$heteroaryl-$(CH_2)_{m'}-$;

$R_4$ is $C_3-C_6$ cycloalkyl, $(C_6-C_{14})$aryl or $(CH_2)_{n'}-(C_6-C_{14})$aryl-$(CH_2)_{n''}$, $(CH_2)_{n'''}$-Alk-$(CH_2)_{n''''}$, wherein n', n", n'" and n"" are independently selected from 1 to 8

$R_5$ is $C_3-C_6$ cycloalkyl;

$R_6$ is selected from the group consisting of $(CH_2)_z$,

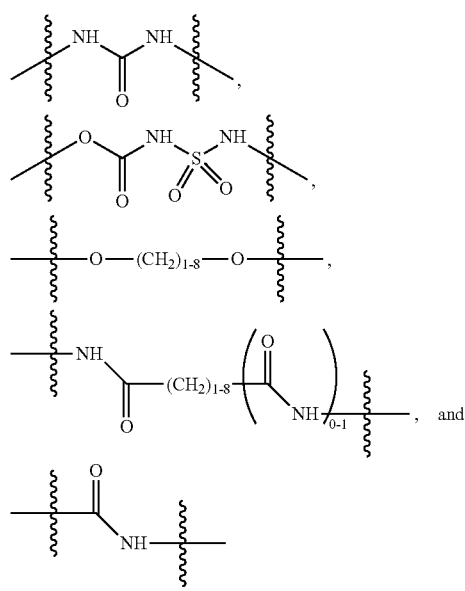

a, b, c, d, e, f, g, h, i, j, k, l, m, m', m". n, p, q, r, s, t, u, v, x, y and z are each independently selected from 1 to 12.

In another aspect, the invention relates to a compound of Formula (Ib):

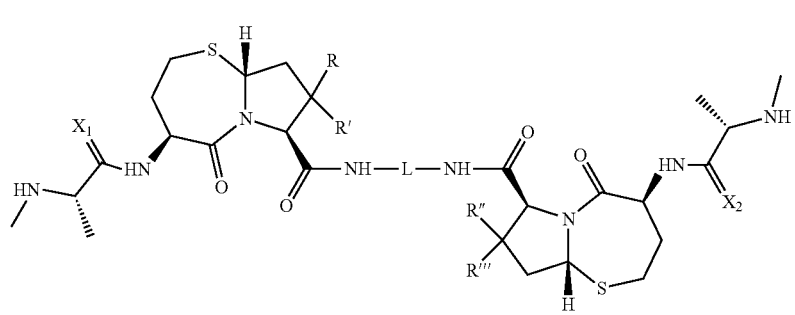

(Ib)

or a pharmaceutically acceptable salt or stereoisomer thereof, wherein:

R, R', R" and R'" are independently selected from H and CH$_3$;

X$_1$ and X$_2$ are independently selected from the group consisting of O and S; and L is a linker selected from the group consisting of:

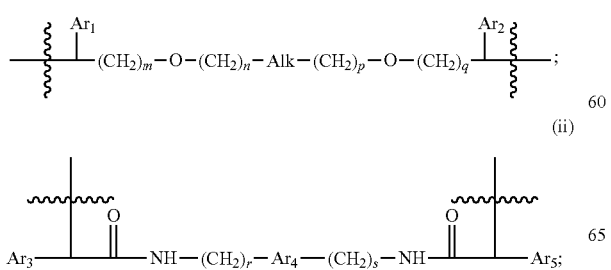

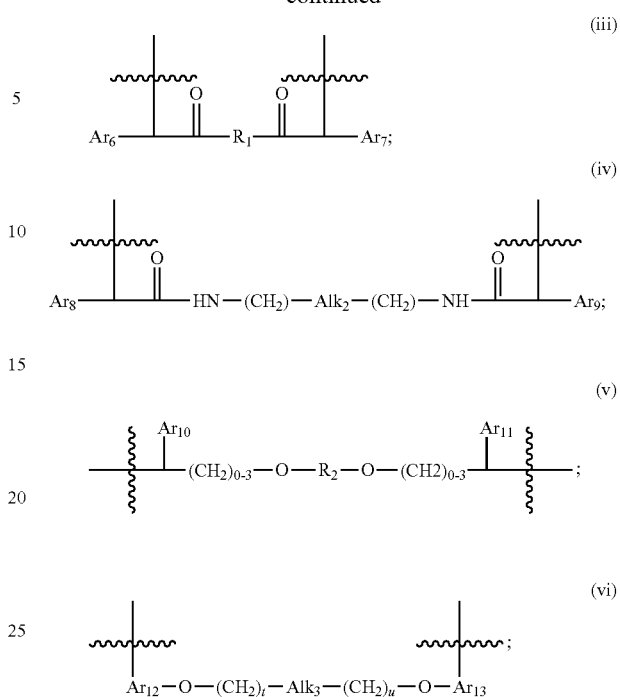

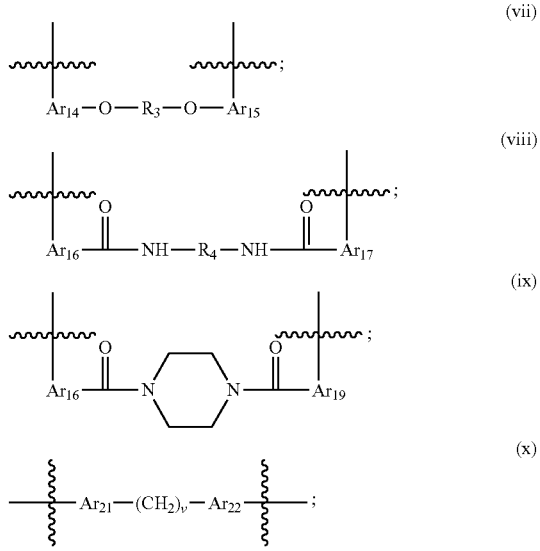

-continued (xi)

Ar$_{23}$—[structure]—HN—R$_5$—NH—[structure]—Ar$_{24}$; and (xii)

Ar$_{25}$—[structure]—(CH$_2$)$_x$—R$_6$—(CH$_2$)$_y$—[structure]—Ar$_{26}$ wherein:

Ar$_1$, Ar$_2$, Ar$_3$, Ar$_4$, Ar$_5$, Ar$_6$, Ar$_7$, Ar$_8$, Ar$_9$, Ar$_{10}$, Ar$_{11}$, Ar$_{12}$, Ar$_{13}$, Ar$_{14}$, Ar$_{15}$, Ar$_{16}$, Ar$_{17}$, Ar$_{18}$, Ar$_{19}$, Ar$_{21}$, Ar$_{22}$, Ar$_{23}$, Ar$_{24}$, Ar$_{25}$ and Ar$_{26}$ are each independently selected from (C$_6$-C$_{14}$)aryl;

Alk, Alk$_2$ and Alk$_3$ are each independently selected from:

—(C≡C)$_{1-4}$—  and  [alkenyl structure]$_{1-4}$;

R$_1$, is C$_3$-C$_6$ cycloalkyl or C$_1$-C$_6$ heterocycle;

R$_2$ is selected from the group consisting of —(CH$_2$)$_a$—, —(CH$_2$)$_b$—O—(CH$_2$)$_c$—, —(CH$_2$)$_d$—(C$_6$-C$_{14}$)aryl-(CH$_2$)$_e$— and —(CH$_2$)$_f$—(C$_1$-C$_6$)heteroaryl-(CH$_2$)$_g$—;

R$_3$ is selected from the group consisting of —(CH$_2$)$_h$—; —(CH$_2$)$_i$—O—(CH$_2$)$_j$—, —(CH$_2$)$_k$—(C$_6$-C$_{14}$)aryl-(CH$_2$)$_l$— and —(CH$_2$)$_m$—(C$_1$-C$_6$)heteroaryl-(CH$_2$)$_{m'}$—;

R$_4$ is C$_3$-C$_6$ cycloalkyl, (C$_6$-C$_{14}$)aryl or (CH$_2$)$_{n'}$—(C$_6$-C$_{14}$)aryl-(CH$_2$)$_{n''}$, (CH$_2$)$_{n'''}$-Alk-(CH$_2$)$_{n''''}$, wherein n', n'', n''' and n'''' are independently selected from 1 to 8

R$_5$ is C$_3$-C$_6$ cycloalkyl;

R$_6$ is selected from the group consisting of (CH$_2$)$_z$,

[urea structure with NH-C(O)-NH]

[carbamate-sulfonamide structure O-C(O)-NH-S(O)$_2$-NH]

—O—(CH$_2$)$_{1-8}$—O—,

—NH—C(O)—(CH$_2$)$_{1-8}$—(C(O)—NH)$_{0-1}$—, and

—C(O)—NH— a, b, c, d, e, f, g, h, i, j, k, l, m, m', m''. n, p, q, r, s, t, u, v, x, y and z are each independently selected from 1 to 12.

In various embodiments, and in addition to the above, the variables a, b, c, d, e, f, g, h, i, j, k, l, m, m', m''. n, p, q, r, s, t, u, v, x, y and z for Formulas (I), (Ia), (Ib), (II) and (III) may each be independently selected from 1 to 8

In various embodiments, at least one of R'' and R''' is CH$_3$. Preferably, both R'' and R' are each CH$_3$.

Most preferably, each of R, R', R'' and R''' is CH$_3$.

In various embodiments, both X$_1$ and X$_2$ are O.

In various embodiments, both X$_1$ and X$_2$ are S.

In various embodiments, X$_1$ is O and X$_2$ is S.

In various embodiments, X$_1$ is S and X$_2$ is O.

In various embodiments, each of Alk, Alk$_2$ and Alk$_3$ is preferably:

[structure showing —C≡C—C≡C—]

In various embodiments, each of Ar$_1$, Ar$_2$, Ar$_3$, Ar$_4$, Ar$_5$, Ar$_6$, Ar$_7$, Ar$_8$, Ar$_9$, Ar$_{10}$, Ar$_{11}$, Ar$_{21}$, Ar$_{22}$, Ar$_{23}$, Ar$_{24}$, Ar$_{25}$ and Ar$_{26}$ may be C$_6$ aryl.

In various embodiments, each of Ar$_{12}$, Ar$_{13}$, Ar$_{14}$, Ar$_{15}$ Ar$_{16}$, Ar$_{17}$, Ar$_{18}$ and Ar$_{19}$ may be C$_9$ aryl. In preferred embodiments, C$_9$ aryl is represented by

[indane structure with NH and R substituent]

wherein the nitrogen in NH connects through the amide bond to the compound bicyclic system(s) and R denotes attachment to the linker.

In various embodiments, each of Ar$_{16}$, Ar$_{17}$, Ar$_{18}$ and Ar$_{19}$ is C$_{10}$ aryl. In preferred embodiments, C$_{10}$ aryl is represented by

[tetrahydronaphthalene structure with NH and R substituent]

wherein the nitrogen in NH connects through the amide bond to the compound bicyclic system(s) and R denotes attachment to the linker.

In various embodiments, the linker is of the Formula (i):

(i)

[structure] —[Ar$_1$]—(CH$_2$)$_m$—O—(CH$_2$)$_n$-Alk-(CH$_2$)$_p$—O—(CH$_2$)$_q$—[Ar$_2$]— [structure]

Each of Ar$_1$ and Ar$_2$ may be independently selected from C$_8$-C$_9$ aryl Preferably, with respect to the Formula (i), Ar$_1$ is C$_8$ aryl. Alk is:

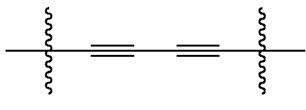 [SMILES: *C#CC#C*]

$Ar_2$ is $C_6$ aryl, m is 1, n is 1, p is 1 and q is 1. In one embodiment, $X_1$ is S and $X_2$ is S. In one embodiment, $X_1$ is S and $X_2$ is O.

In various embodiments, the linker is of the formula (ii):

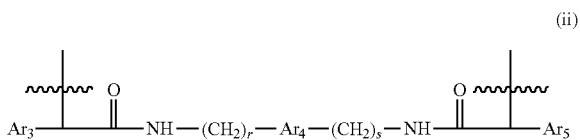

(ii)

Each of $Ar_3$, $Ar_2$ and $Ar_5$ may be independently selected from $C_6$-$C_9$ aryl Preferably, with respect to the formula (ii), $Ar_3$ is $C_6$ aryl, $Ar_4$ is $C_6$ aryl, r is 1, $Ar_4$ is $C_6$ aryl, s is 1 and $Ar_5$ is $C_6$ aryl. In one embodiment, $X_1$ is O and $X_2$ is O. In one embodiment, $X_1$ is S and $X_2$ is S.

In various embodiments, the linker is of the formula (iii):

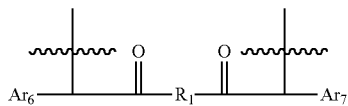

(iii)

wherein $Ar_6$ and $Ar_7$ are each independently $C_6$-$C_9$ aryl, most preferably each are $C_6$ aryl;

wherein $R_1$ is preferably $C_1$-$C_6$ heterocycle (e.g., $C_4$ heterocycle), most preferably:

In various embodiments, the linker is of the formula (iv):

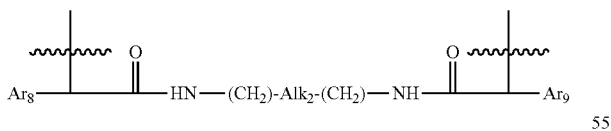

(iv)

Preferably, with respect to the formula (iv), $Ar_8$ is $C_{6-9}$ aryl, more preferably $C_6$ aryl, and $Alk_2$ is:

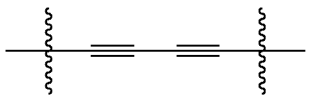 [SMILES: *C#CC#C*]

and $Ar_9$ is $C_6$ aryl; $C_{6-9}$ aryl, more preferably $C_6$ aryl.

In various embodiments, the linker is of the formula (v):

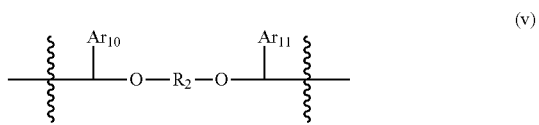

(v)

Preferably, with respect to the formula (v), $Ar_{10}$ is $C_{6-9}$ aryl, more preferably $C_6$ aryl, $Ar_{11}$ is preferably $C_{6-9}$ aryl, more preferably $C_6$ aryl and $R_2$ is selected from —(CH$_2$)— $C_{6-9}$ aryl-(CH$_2$)—, (more preferably, —(CH$_2$)—$C_6$ aryl-(CH$_2$)—), —(CH$_2$)$_{1-8}$— (more preferably —(CH$_2$)$_4$—, —(CH$_2$)$_3$—, or —(CH$_2$)$_6$—) and —(CH$_2$)$_{2-6}$—O—(CH$_2$)$_{2-6}$— (more preferably —(CH$_2$)$_{2-4}$—O—(CH$_2$)$_{2-4}$). In one embodiment, $R_2$ is —(CH$_2$)$_2$—O—(CH$_2$)$_2$—. When $R_2$ is heteroaryl, it is preferably $C_2$ heteroaryl.

In various embodiments, the linker is of the formula (vi):

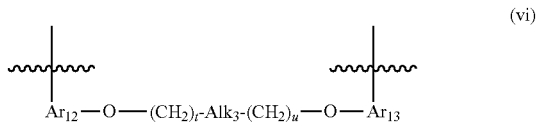

(vi)

Preferably, with respect to the formula (vi), $Ar_{12}$ is $C_{6-9}$ aryl, t is 1-4 (more preferably, t is 1), $Alk_3$ is:

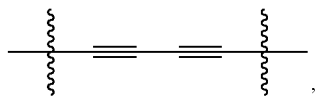

, u is 1-4 (more preferably, u is 1) and $Ar_{13}$ is $C_{6-9}$ aryl. Most preferably, $Ar_{12}$ and $Ar_{13}$ are each $C_9$aryl, and most preferably, $C_9$ aryl is represented as follows:

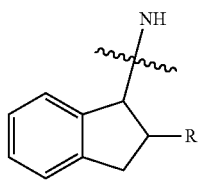

wherein the nitrogen in NH connects through the amide bond to the compound bicyclic system(s) and R denotes attachment to the linker.

In various embodiments, the linker is of the formula (vii):

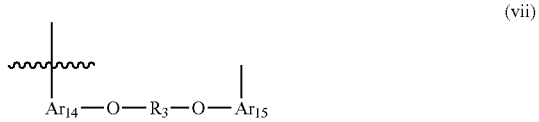

(vii)

Preferably, with respect to the formula (vii), $Ar_{14}$ is $C_{6-9}$ aryl (more preferably, $C_9$ aryl), $R_3$ is selected from the group consisting of (CH$_2$)$_{1-12}$ (e.g., (CH$_2$)$_{4-6}$); —(CH$_2$)$_{1-6}$—O—(CH$_2$)$_{1-6}$— (e.g., —(CH$_2$)$_{2-4}$—O—(CH$_2$)$_{2-4}$—), and $Ar_{15}$ is $C_9$ aryl. More preferably, with respect to the formula (vii), $Ar_{14}$ is $C_9$ aryl, $R_3$ is selected from the group consisting of —(CH$_2$)$_{4-12}$—, —(CH$_2$)$_{2-4}$—O—(CH$_2$)$_{2-4}$—, In preferred embodiments, $Ar_{14}$ and $Ar_{15}$ are each $C_9$ aryl as follows:

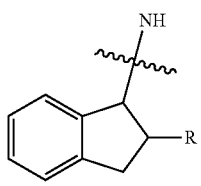

wherein the nitrogen in NH connects through the amide bond to the compound bicyclic system(s) and R denotes attachment to the linker.

In various embodiments, the linker is of the formula (viii):

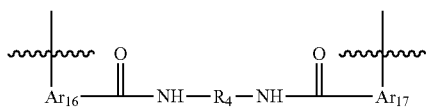

(viii)

Preferably, $Ar_{16}$ is $C_{6-10}$ aryl, more preferably, $C_9$ aryl or $C_{10}$ aryl, $R_4$ is selected from the group consisting of $C_3$-$C_6$ cycloalkyl or $(C_6$-$C_{14})$aryl and $Ar_{17}$ is $C_{6-10}$ aryl, more preferably, $C_9$ aryl or $C_{10}$ aryl. More preferably, $R_4$ is $C_6$ cycloalkyl, $C_6$ aryl, —CH$_2$—$C_6$ aryl-CH$_2$—, or

In various embodiments, the linker is of the formula (ix):

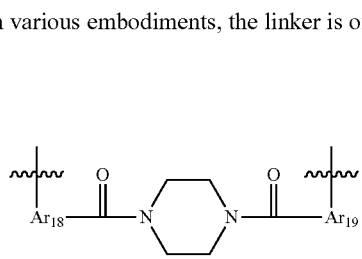

(ix)

Preferably, $Ar_{18}$ is $C_{6-10}$ aryl, more preferably, $C_9$ aryl or $C_{10}$ aryl and $Ar_{19}$ is $C_{6-10}$ aryl, more preferably, $C_9$ aryl or $C_{10}$ aryl.

In various embodiments, the linker is of the formula (x):

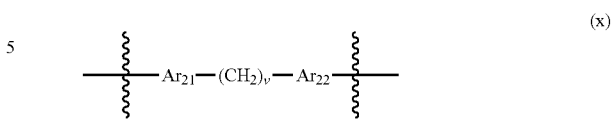

(x)

Preferably, $A_{21}$ and $A_{22}$ are independently selected from $C_{6-9}$aryl, and v ranges from 1 to 6. More preferably in one embodiment, $Ar_{21}$ is $C_6$ aryl, v is 1 and $Ar_{22}$ is $C_6$ aryl. More preferably in one embodiment, $Ar_{21}$ is $C_6$ aryl, v is 2 and $Ar_{22}$ is $C_6$ aryl.

In various embodiments, the linker is of the formula (xi):

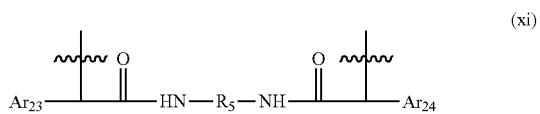

(xi)

Preferably, $Ar_{23}$ is $C_{6-9}$ aryl, more preferably $C_6$aryl, $R_5$ is $C_3$-$C_6$ cycloalkyl and $Ar_{24}$ is preferably $C_{6-9}$ aryl, more preferably $C_6$aryl. Most preferably, $R_5$ is $C_6$ cycloalkyl.

In another aspect, the invention provides a compound of Formula (II):

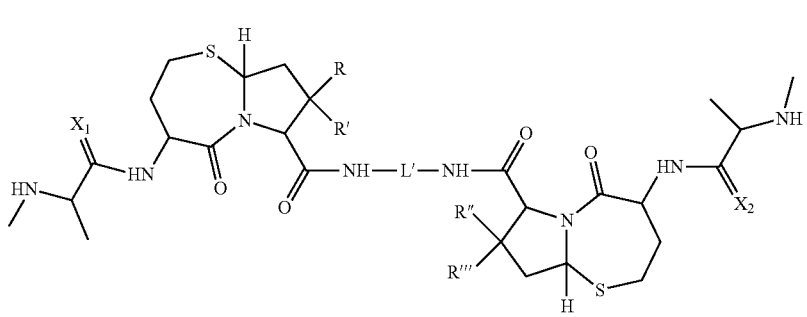

(II)

wherein
R, R', R" and R'" are independently selected from H and CH$_3$;
$X_1$ and $X_2$ are independently selected from the group consisting of O and S; and
L' is a linker of the formula:

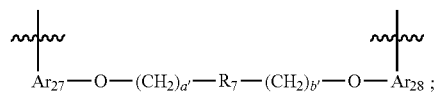

wherein:
$Ar_{27}$ and $Ar_{28}$ are each independently selected from $C_6$-$C_{14}$ aryl,
$R_7$ is selected from the group consisting of
and

—(C≡C)—.

$C_6$ aryl and $-(CH_2)_{4-15}-$ (more preferably, $-(CH_2)_{6-10}-$);

a' and b' are independently selected from 0 to 6.

In various embodiments, R, R', R" and R'" are each $CH_3$.

In various embodiments, $X_1$ and $X_2$ are each O;

In various embodiments, $Ar_{27}$ and $Ar_{28}$ are each selected from $C_8$-$C_{10}$ aryl, and are each more preferably $C_9$ aryl. In various embodiments, $C_9$ aryl may be represented by the formula

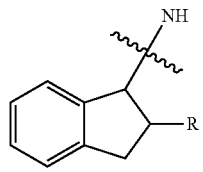

wherein the nitrogen in NH connects through the amide bond to the compound bicyclic system(s) and R denotes attachment to the linker. Most preferably, $C_9$ aryl is of the formula:

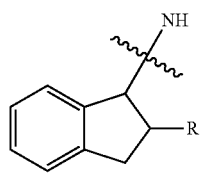

In one embodiment, R, R', R" and R'" are each $CH_3$, $X_1$ and $X_2$ are each O; a' is 1, b' is 1, $R_7$ is:

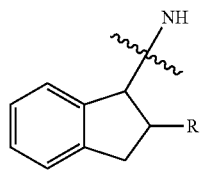

$Ar_{27}$ and $Ar_{28}$ are each of the formula:

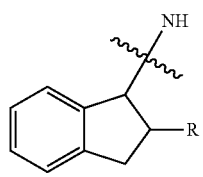

In one embodiment, the invention provides a compound of formula (II), with the proviso that when R, R', R" and R'" are each $CH_3$, $X_1$ and $X_2$ are each O, $Ar_{27}$ and $Ar_{28}$ are each of the formula:

and a' is 1, and b' is 1, $R_7$ is not:

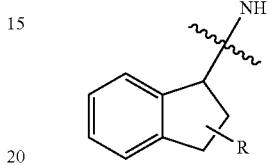

In various embodiments, the compound of Formula (II) is encompassed, wherein a' is 0, b' is 0 and $R_7$ is $-(CH_2)_{6-15}-$, (more preferably-$(CH_2)_{6-10}-$), R, R', R" and R'" are each $CH_3$, $X_1$ and $X_2$ are each O, and $Ar_{27}$ and $Ar_{28}$ are each $C_9$ aryl. Preferably, $C_9$ aryl is represented by the formula

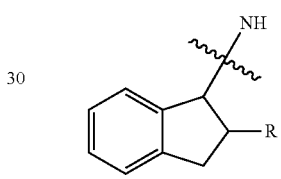

wherein the nitrogen in NH connects through the amide bond to the compound bicyclic system(s) and R denotes attachment to the linker. Most preferably, $C_9$ aryl is of the formula:

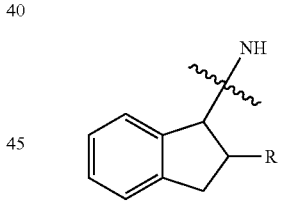

In one embodiment, the invention provides a compound of Formula (II), wherein a' is 0, b' is 0, $R_7$ is $-(CH_2)_6-$, R, R', R" and R'" are each $CH_3$, $X_1$ and $X_2$ are each O, and $Ar_{27}$ and $Ar_{28}$ are each $C_9$ aryl represented by the formula:

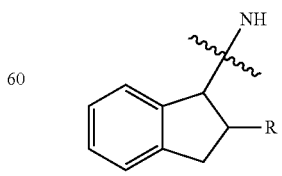

wherein the nitrogen in NH connects through the amide bond to the compound bicyclic system(s) and R denotes attachment to the linker.

In one aspect, the invention provides a compound of formula (II), with the provisio that when R, R', R" and R'" are each $CH_3$, $X_1$ and $X_2$ are each O, $Ar_{27}$ and $Ar_{28}$ are each of the formula:

and a' is 0, b' is 0, $R_7$ is not $-(CH_2)_6-$:

In another aspect, the invention provides a compound of the structure according to Formula (III):

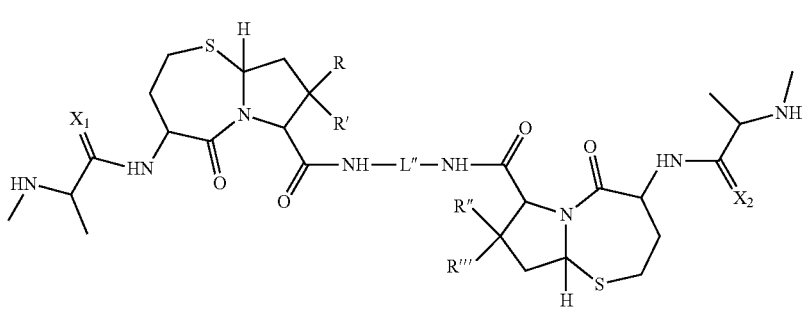

(III)

wherein

R, R', R" and R'" are independently selected from H and CH$_3$;

X$_1$ and X$_2$ are independently selected from the group consisting of O and S; and L" is a linker of the formula:

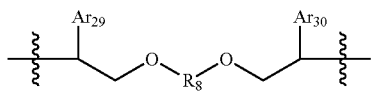

wherein Ar$_{29}$ and Ar$_{30}$ are independently selected from C$_6$-C$_{10}$ aryl and R$_8$ is selected from the group consisting of:

—(CH$_2$)$_{6-15}$—, '- and —(CH$_2$)$_{d'}$—(C$_6$-C$_{10}$)aryl-(CH$_2$)$_{e'}$—; wherein d' and e' are independently selected and ranging from 1 to 6.

In one embodiment of the compound of formula (III), R, R', R" and R'" are each CH$_3$; X$_1$ and X$_2$ are each O, Ar$_{29}$ and Ar$_{30}$ are each C$_6$ aryl, and R$_8$ is:

In one embodiment of the compound of formula (III), R, R', R" and R'" are each CH$_3$; X$_1$ and X$_2$ are each O, Ar$_{29}$ and Ar$_{30}$ are each C$_8$ aryl, and R$_8$ is —(CH$_2$)—(C$_6$)aryl-(CH$_2$)—.

In one embodiment of the compound of formula (III), R, R', R" and R'" are each CH$_3$; X$_1$ and X$_2$ are each O, Ar$_{29}$ and Ar$_{30}$ are each C$_6$ aryl, and R$_8$ is —(CH$_2$)$_6$—.

In the above formulae (II) and (III) any of the aryl groups may be optionally substituted by any one of the following, without limitation: (C$_1$-C$_6$)alkyl, (C$_1$-C$_6$)alkoxy, halo, oxo, haloalkyl, bihaloalkyl, trihaloalkyl, haloalkoxy, bihaloalkoxy, trihaloalkoxy, hydroxyl, amino, and amide. Additionally, any of the aryl groups in formulas (I), (Ia) and (Ib) may also be optionally substituted with the above.

Exemplary compounds encompassed by the present invention include, without limitation, those in the following Table 1:

TABLE 1

| Compound No | Compound structure | Compound name |
|---|---|---|
| 1 | 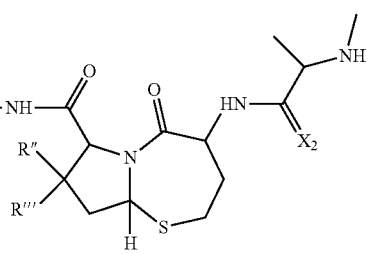 | (4S,4'S,7S,7'S,9aS,9a'S)-N,N'-(methylenebis(4,1-phenylene))bis(8,8-dimethyl-4-((S)-2-(methylamino)propanamido)-5-oxooctahydropyrrolo[2,1-b][1,3]thiazepine-7-carboxamide) |

TABLE 1-continued

| Compound No | Compound structure | Compound name |
|---|---|---|
| 2 | 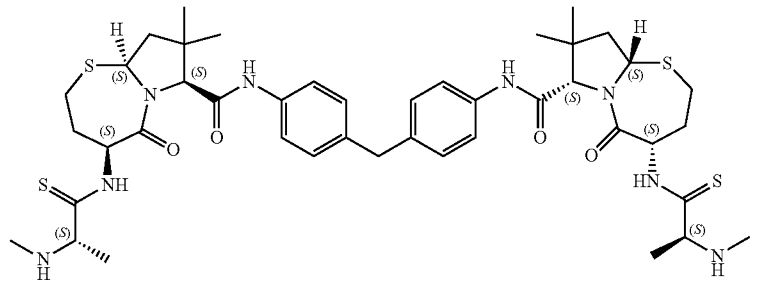 | (4S,4'S,7S,7'S,9aS,9a'S)-N,N'-(methylenebis(4,1-phenylene))bis(8,8-dimethyl-4-((S)-2-(methylamino)propanethioamido)-5-oxooctahydropyrrolo[2,1-b][1,3]thiazepine-7-carboxamide) |
| 3 | 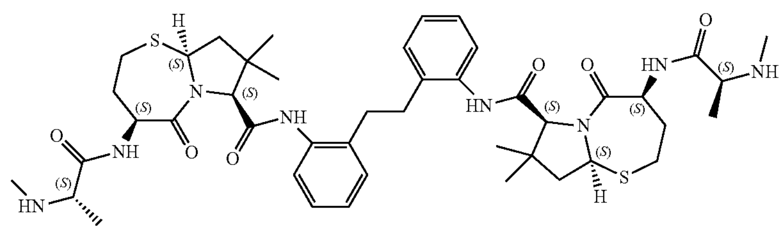 | (4S,4'S,7S,7'S,9aS,9a'S)-N,N'-(ethane-1,2-diylbis(2,1-phenylene))bis(8,8-dimethyl-4-((S)-2-(methylamino)propanamido)-5-oxooctahydropyrrolo[2,1-b][1,3]thiazepine-7-carboxamide) |
| 4 | 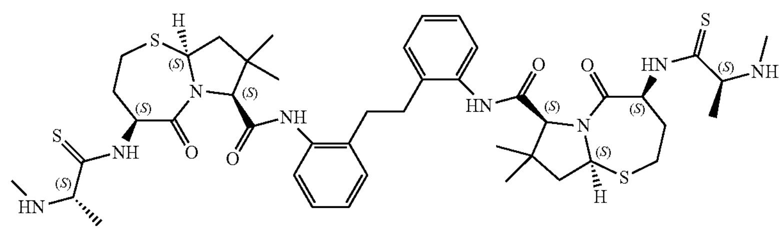 | (4S,4'S,7S,7'S,9aS,9a'S)-N,N'-(ethane-1,2-diylbis(2,1-phenylene))bis(8,8-dimethyl-4-((S)-2-(methylamino)propanethioamido)-5-oxooctahydropyrrolo[2,1-b][1,3]thiazepine-7-carboxamide) |
| 5 | 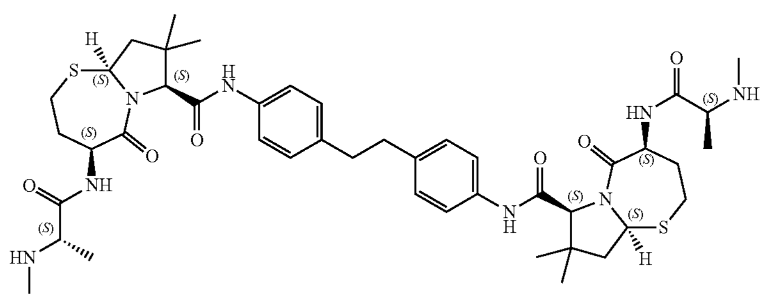 | (4S,4'S,7S,7'S,9aS,9a'S)-N,N'-(ethane-1,2-diylbis(4,1-phenylene))bis(8,8-dimethyl-4-((S)-2-(methylamino)propanamido)-5-oxooctahydropyrrolo[2,1-b][1,3]thiazepine-7-carboxamide) |
| 6 | 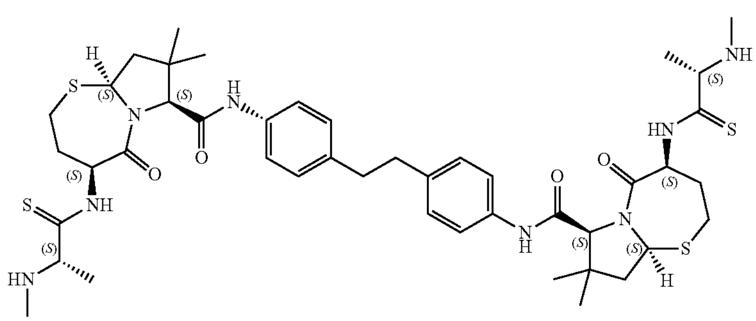 | (4S,4'S,7S,7'S,9aS,9a'S)-N,N'-(ethane-1,2-diylbis(4,1-phenylene))bis(8,8-dimethyl-4-((S)-2-(methylamino)propanethioamido)-5-oxooctahydropyrrolo[2,1-b][1,3]thiazepine-7-carboxamide) |

TABLE 1-continued

| Compound No | Compound structure | Compound name |
|---|---|---|
| 7 | 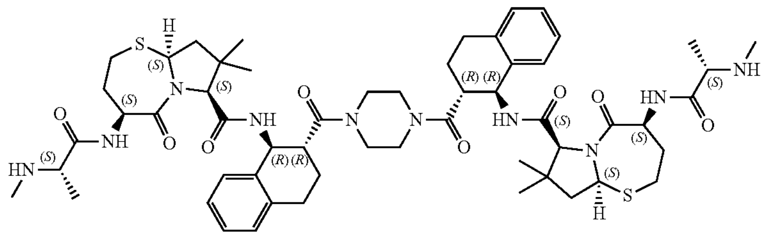 | (4S,4'S,7S,7'S,9aS,9a'S)-N,N'-((1R,1'R,2R,2'R)-(piperazine-1,4-dicarbonyl)bis(1,2,3,4-tetrahydronaphthalene-2,1-diyl))bis(8,8-dimethyl-4-((S)-2-(methylamino)propanamido)-5-oxooctahydropyrrolo[2,1-b][1,3]thiazepine-7-carboxamide) |
| 8 | 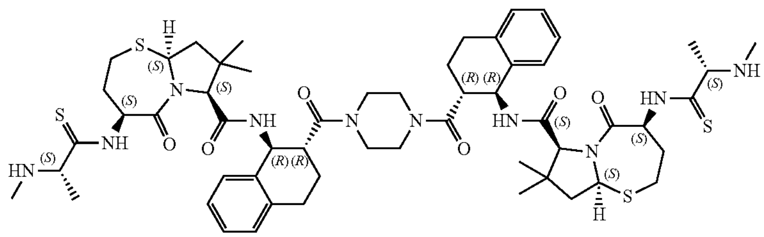 | (4S,4'S,7S,7'S,9aS,9a'S)-N,N'-((1R,1'R,2R,2'R)-(piperazine-1,4-dicarbonyl)bis(1,2,3,4-tetrahydronaphthalene-2,1-diyl))bis(8,8-dimethyl-4-((S)-2-(methylamino)propanethioamido)-5-oxooctahydropyrrolo[2,1-b][1,3]thiazepine-7-carboxamide) |
| 9 | 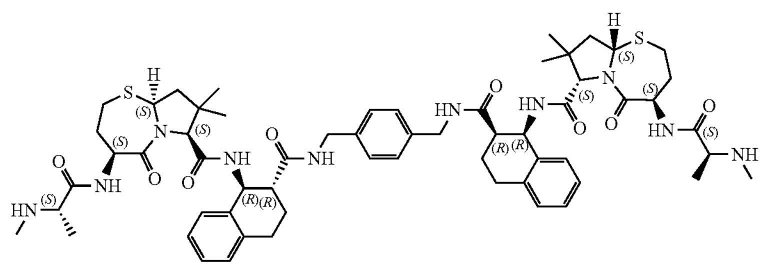 | (4S,4'S,7S,7'S,9aS,9a'S)-N,N'-((1R,1'R,2R,2'R)-(((1,4-phenylenebis(methylene))bis(azanediyl))bis(carbonyl))bis(1,2,3,4-tetrahydronaphthalene-2,1-diyl))bis(8,8-dimethyl-4-((S)-2-(methylamino)propanamido)-5-oxooctahydropyrrolo[2,1-b][1,3]thiazepine-7-carboxamide) |
| 10 | 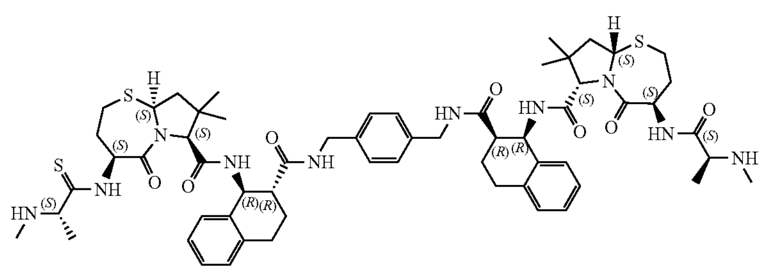 | (4S,4'S,7S,7'S,9aS,9a'S)-N,N'-((1R,1'R,2R,2'R)-(((1,4-phenylenebis(methylene))bis(azanediyl))bis(carbonyl))bis(1,2,3,4-tetrahydronaphthalene-2,1-diyl))bis(8,8-dimethyl-4-((S)-2-(methylamino)propanethioamido)-5-oxooctahydropyrrolo[2,1-b][1,3]thiazepine-7-carboxamide) |
| 11 | 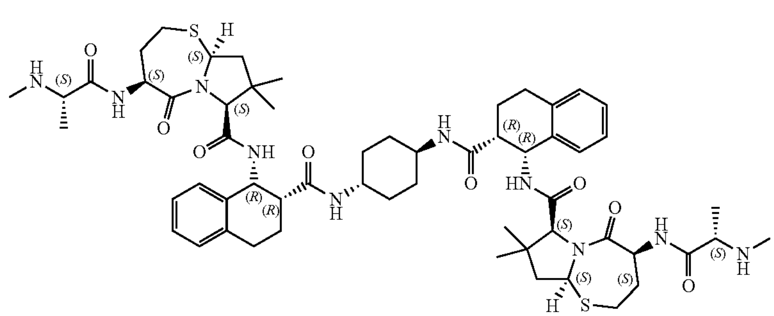 | (4S,7S,9aS)-8,8-dimethyl-4-[(2S)-2-(methylamino)propanamido]-5-oxo-N-[(1R,2R)-2-{[(1rs,4rs)-4-[(1R,2R)-1-[(4S,7S,9aS)-8,8-dimethyl-4-[(2S)-2-(methylamino)propanamido]-5-oxo-octahydropyrrolo[2,1-b][1,3]thiazepine-7-amido]-1,2,3,4-tetrahydronaphthalene-2-amido]cyclohexyl]carbamoyl}-1,2,3,4-tetrahydronaphthalen-1-yl]-octahydropyrrolo[2,1-b][1,3]thiazepine-7-carboxamide |

TABLE 1-continued

| Compound No | Compound structure | Compound name |
|---|---|---|
| 12 | 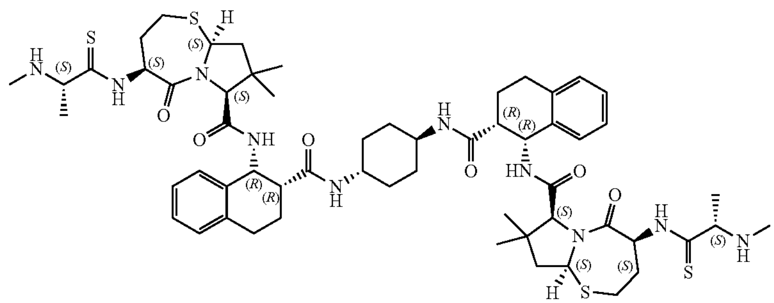 | (4S,7S,9aS)-8,8-dimethyl-4-[(2S)-2-(methylamino)propanethioamido]-5-oxo-N-[(1R,2R)-2-{[(1rs,4rs)-4-[(1R,2R)-1-[(4S,7S,9aS)-8,8-dimethyl-4-[(2S)-2-(methylamino)propanethioamido]-5-oxo-octahydropyrrolo[2,1-b][1,3]thiazepine-7-amido]-1,2,3,4-tetrahydronaphthalene-2-amido]cyclohexyl]carbamoyl}-1,2,3,4-tetrahydronaphthalen-1-yl]-octahydropyrrolo[2,1-b][1,3]thiazepine-7-carboxamide |
| 13 | 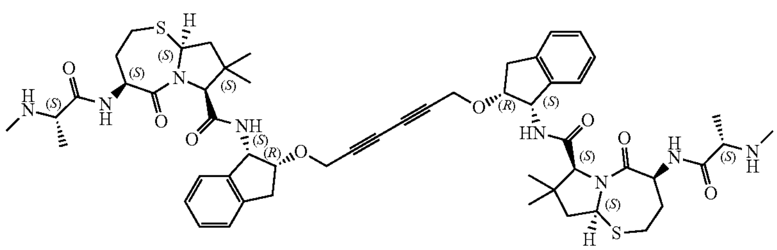 | (4S,4'S,7S,7'S,9aS,9a'S)-N,N'-((1S,1'S,2R,2'R)-(hexa-2,4-diyne-1,6-diylbis(oxy))bis(2,3-dihydro-1H-indene-2,1-diyl))bis(8,8-dimethyl-4-((S)-2-(methylamino)propanamido)-5-oxooctahydropyrrolo[2,1-b][1,3]thiazepine-7-carboxamide) |
| 14 | 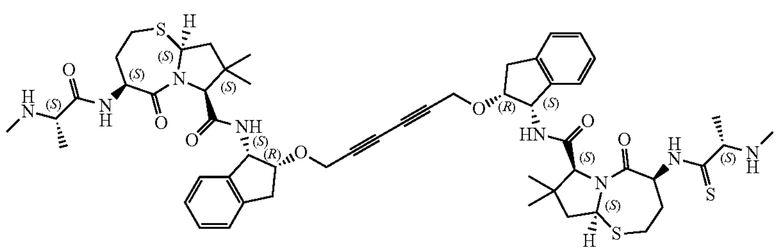 | (4S,7S,9aS)-N-((1S,2R)-2-((6-((((1S,2R)-1-((4S,7S,9aS)-8,8-dimethyl-4-((S)-2-(methylamino)propanamido)-5-oxooctahydropyrrolo[2,1-b][1,3]thiazepine-7-carboxamido)-2,3-dihydro-1H-inden-2-yl)oxy)hexa-2,4-diyn-1-yl)oxy)-2,3-dihydro-1H-inden-1-yl)-8,8-dimethyl-4-((S)-2-(methylamino)propanethioamido)-5-oxooctahydropyrrolo[2,1-b][1,3]thiazepine-7-carboxamide |
| 15 | 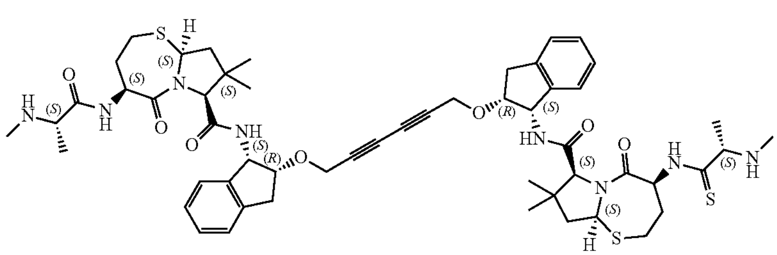 | (4S,4'S,7S,7'S,9aS,9a'S)-N,N'-((1S,1'S,2R,2'R)-(hexa-2,4-diyne-1,6-diylbis(oxy))bis(2,3-dihydro-1H-indene-2,1-diyl))bis(8,8-dimethyl-4-((S)-2-(methylamino)propanethioamido)-5-oxooctahydropyrrolo[2,1-b][1,3]thiazepine-7-carboxamide) |
| 16 | 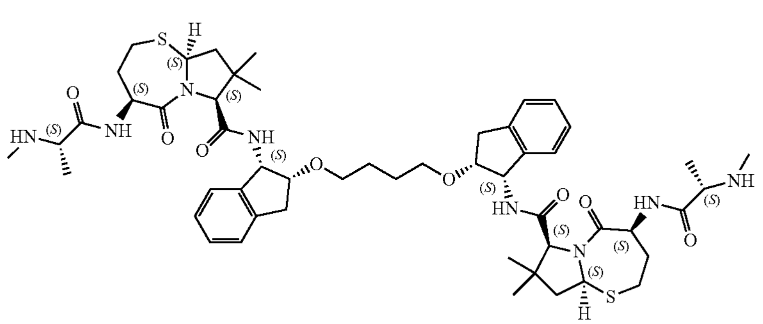 | (4S,4'S,7S,7'S,9aS,9a'S)-N,N'-((1S,1'S,2R,2'R)-(butane-1,4-diylbis(oxy))bis(2,3-dihydro-1H-indene-2,1-diyl))bis(8,8-dimethyl-4-((S)-2-(methylamino)propanamido)-5-oxooctahydropyrrolo[2,1-b][1,3]thiazepine-7-carboxamide) |

TABLE 1-continued

| Compound No | Compound structure | Compound name |
|---|---|---|
| 17 | 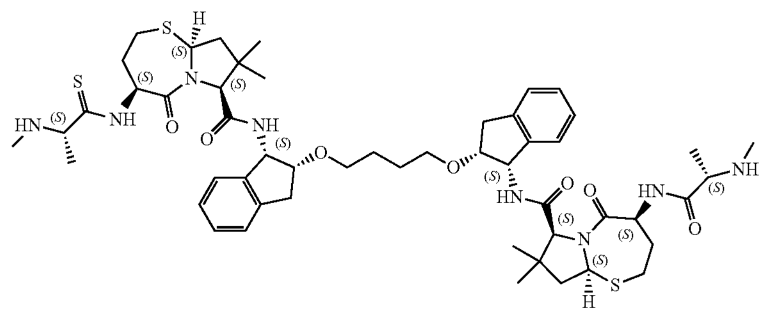 | (4S,4'S,7S,7'S,9aS,9a'S)-N,N'-((1S,1'S,2R,2'R)-(butane-1,4-diylbis(oxy))bis(2,3-dihydro-1H-indene-2,1-diyl))bis(8,8-dimethyl-4-((S)-2-(methylamino)propanethioamido)-5-oxooctahydropyrrolo[2,1-b][1,3]thiazepine-7-carboxamide) |
| 18 | 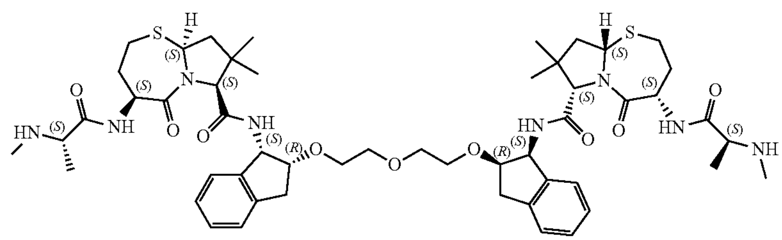 | (4S,4'S,7S,7'S,9aS,9a'S)-N,N'-((1S,1'S,2R,2'R)-((oxybis(ethane-2,1-diyl))bis(oxy))bis(2,3-dihydro-1H-indene-2,1-diyl))bis(8,8-dimethyl-4-((S)-2-(methylamino)propanamido)-5-oxooctahydropyrrolo[2,1-b][1,3]thiazepine-7-carboxamide) |
| 19 | 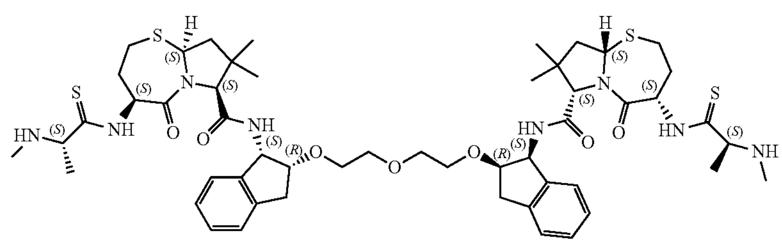 | (4S,4'S,7S,7'S,9aS,9a'S)-N,N'-((1S,1'S,2R,2'R)-((oxybis(ethane-2,1-diyl))bis(oxy))bis(2,3-dihydro-1H-indene-2,1-diyl))bis(8,8-dimethyl-4-((S)-2-(methylamino)propanethioamido)-5-oxooctahydropyrrolo[2,1-b][1,3]thiazepine-7-carboxamide) |
| 20 | 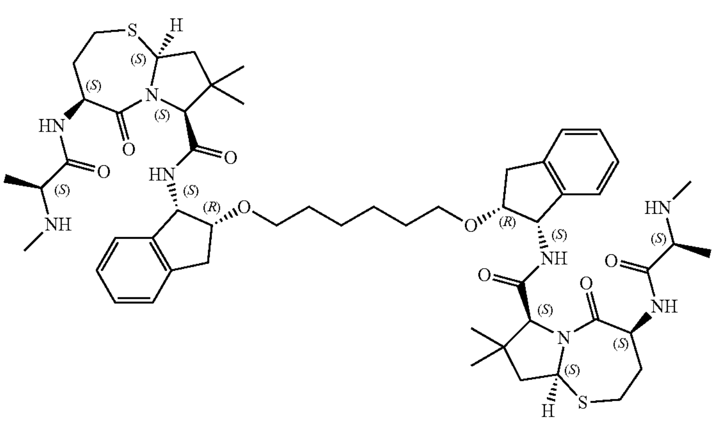 | (4S,4'S,7S,7'S,9aS,9a'S)-N,N'-((1S,1'S,2R,2'R)-(hexane-1,6-diylbis(oxy))bis(2,3-dihydro-1H-indene-2,1-diyl))bis(8,8-dimethyl-4-((S)-2-(methylamino)propanamido)-5-oxooctahydropyrrolo[2,1-b][1,3]thiazepine-7-carboxamide) |

TABLE 1-continued

| Compound No | Compound structure | Compound name |
|---|---|---|
| 21 | 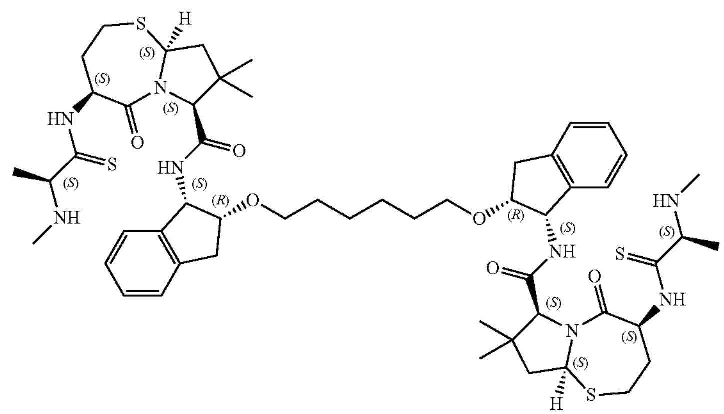 | (4S,4'S,7S,7'S,9aS,9a'S)-N,N'-((1S,1'S,2R,2'R)-(hexane-1,6-diylbis(oxy))bis(2,3-dihydro-1H-indene-2,1-diyl))bis(8,8-dimethyl-4-((S)-2-(methylamino)propanethioamido)-5-oxooctahydropyrrolo[2,1-b][1,3]thiazepine-7-carboxamide) |
| 22 | 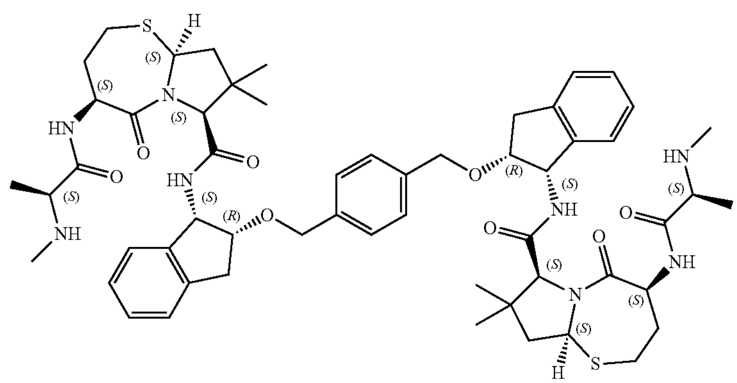 | (4S,4'S,7S,7'S,9aS,9a'S)-N,N'-((1S,1'S,2R,2'R)-((1,4-phenylenebis(methylene))bis(oxy))bis(2,3-dihydro-1H-indene-2,1-diyl))bis(8,8-dimethyl-4-((S)-2-(methylamino)propanamido)-5-oxooctahydropyrrolo[2,1-b][1,3]thiazepine-7-carboxamide) |
| 23 | 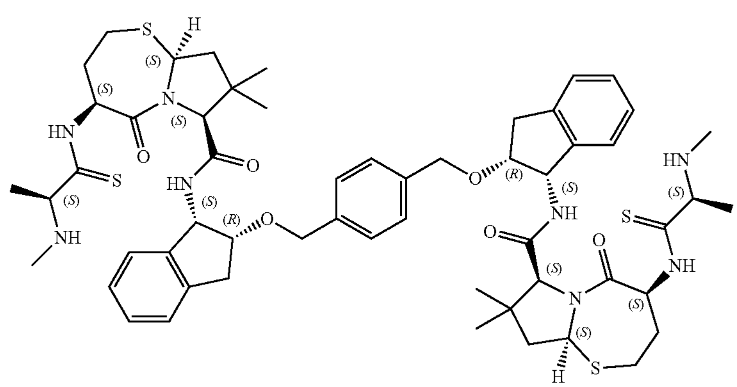 | (4S,4'S,7S,7'S,9aS,9a'S)-N,N'-((1S,1'S,2R,2'R)-((1,4-phenylenebis(methylene))bis(oxy))bis(2,3-dihydro-1H-indene-2,1-diyl))bis(8,8-dimethyl-4-((S)-2-(methylamino)propanethioamido)-5-oxooctahydropyrrolo[2,1-b][1,3]thiazepine-7-carboxamide) |
| 24 | 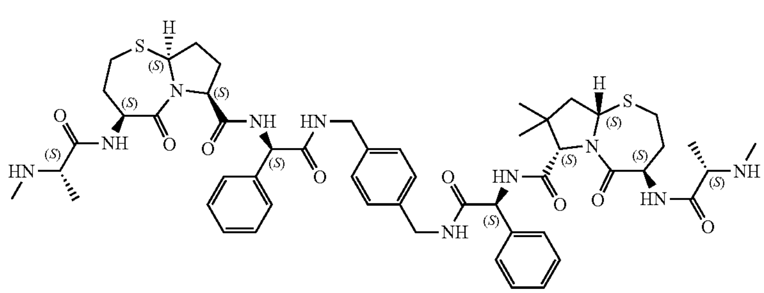 | (4S,4'S,7S,7'S,9aS,9a'S)-N,N'-((1S,1'S)-((1,4-phenylenebis(methylene))bis(azanediyl))bis(2-oxo-1-phenylethane-2,1-diyl))bis(8,8-dimethyl-4-((S)-2-(methylamino)propanamido)-5-oxooctahydropyrrolo[2,1-b][1,3]thiazepine-7-carboxamide) |

TABLE 1-continued

| Compound No | Compound structure | Compound name |
|---|---|---|
| 25 | 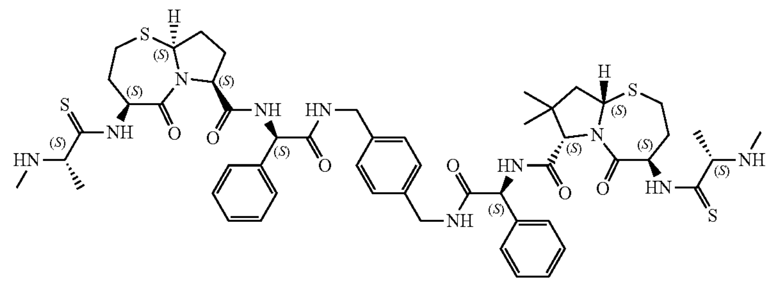 | (4S,4'S,7S,7'S,9aS,9a'S)-N,N'-((1S,1'S)-((1,4-phenylenebis(methylene))bis(azanediyl))bis(2-oxo-1-phenylethane-2,1-diyl))bis(8,8-dimethyl-4-((S)-2-(methylamino)propanethioamido)-5-oxooctahydropyrrolo[2,1-b][1,3]thiazepine-7-carboxamide) |
| 26 | 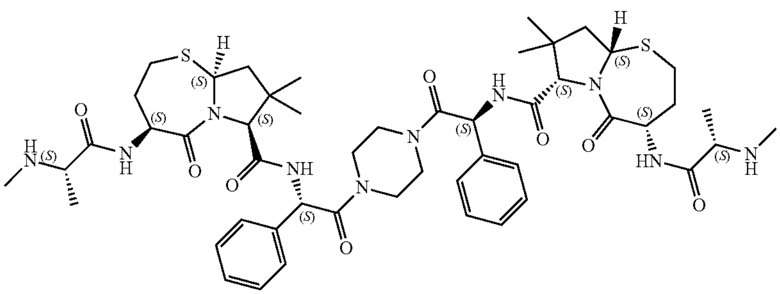 | (4S,4'S,7S,7'S,9aS,9a'S)-N,N'-((1S,1'S)-piperazine-1,4-diylbis(2-oxo-1-phenylethane-2,1-diyl))bis(8,8-dimethyl-4-((S)-2-(methylamino)propanamido)-5-oxooctahydropyrrolo[2,1-b][1,3]thiazepine-7-carboxamide) |
| 27 | 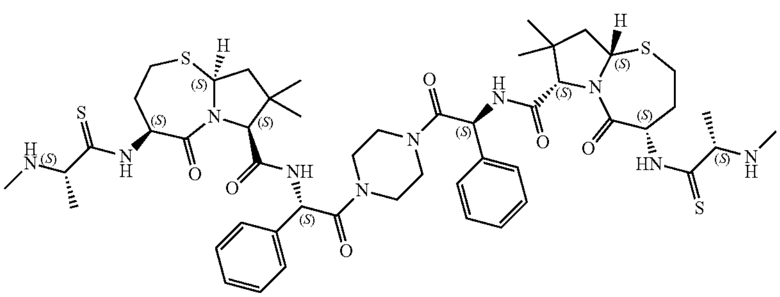 | (4S,4'S,7S,7'S,9aS,9a'S)-N,N'-((1S,1'S)-piperazine-1,4-diylbis(2-oxo-1-phenylethane-2,1-diyl))bis(8,8-dimethyl-4-((S)-2-(methylamino)propanethioamido)-5-oxooctahydropyrrolo[2,1-b][1,3]thiazepine-7-carboxamide) |
| 28 | 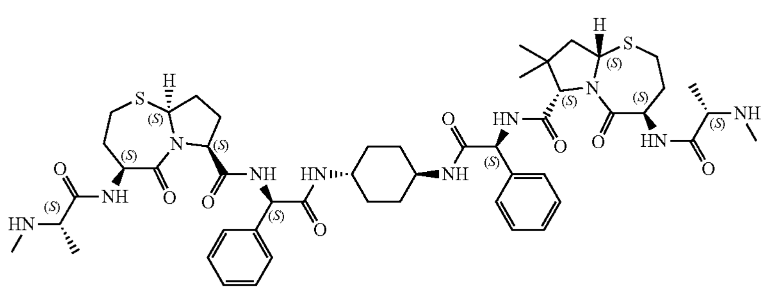 | (2S)-N-[(4S,7S,9aS)-8,8-dimethyl-5-oxo-7-{[(S)-phenyl({[(1rs,4rs)-4-[(2S)-2-{[(4S,7S,9aS)-8,8-dimethyl-4-[(2S)-2-(methylamino)propanamido]-5-oxo-octahydropyrrolo[2,1-b][1,3]thiazepin-7-yl]formamido}-2-phenylacetamido]cyclohexyl]carbamoyl})methyl]carbamoyl}-octahydropyrrolo[2,1-b][1,3]thiazepin-4-yl]-2-(methylamino)propanamide |
| 29 | 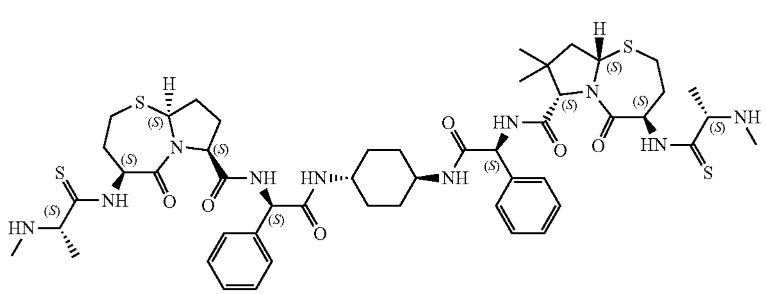 | (2S)-2-{[(4S,7S,9aS)-8,8-dimethyl-4-[(2S)-2-(methylamino)propanethioamido]-5-oxo-octahydropyrrolo[2,1-b][1,3]thiazepin-7-yl]formamido}-2-phenyl-N-[(1rs,4rs)-4-[(2S)-2-{[(4S,7S,9aS)-8,8-dimethyl-4-[(2S)-2-(methylamino)propanethioamido]-5-oxo-octahydropyrrolo[2,1-b][1,3]thiazepin-7-yl]formamido}-2-phenylacetamido]cyclohexyl]acetamide |

TABLE 1-continued

| Compound No | Compound structure | Compound name |
|---|---|---|
| 30 | 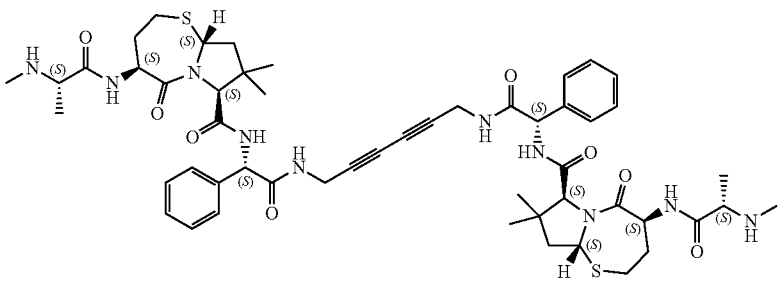 | (4S,4'S,7S,7'S,9aS,9a'S)-N,N'-((1S,1'S)-(hexa-2,4-diyne-1,6-diylbis(azanediyl))bis(2-oxo-1-phenylethane-2,1-diyl))bis(8,8-dimethyl-4-((S)-2-(methylamino)propanamido)-5-oxooctahydropyrrolo[2,1-b][1,3]thiazepine-7-carboxamide) |
| 31 | 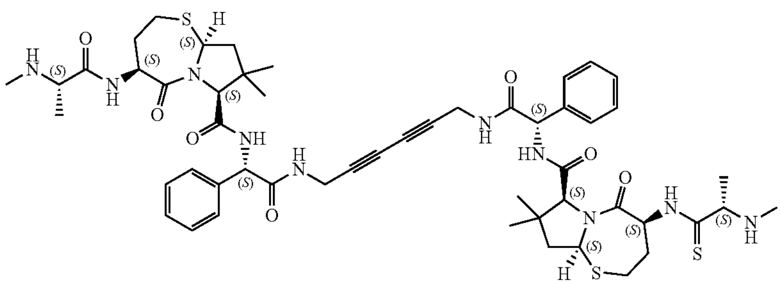 | (4S,7S,9aS)-N-((S)-2-((6-((S)-2-((4S,7S,9aS)-8,8-dimethyl-4-((S)-2-(methylamino)propanamido)-5-oxooctahydropyrrolo[2,1-b][1,3]thiazepine-7-carboxamido)-2-phenylacetamido)hexa-2,4-diyn-1-yl)amino)-2-oxo-1-phenylethyl)-8,8-dimethyl-4-((S)-2-(methylamino)propanethioamido)-5-oxooctahydropyrrolo[2,1-b][1,3]thiazepine-7-carboxamide |
| 32 | 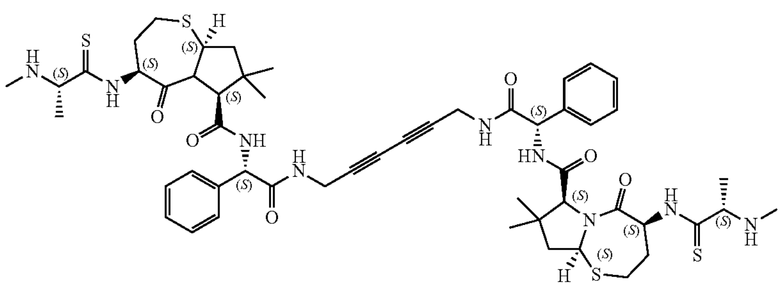 | (4S,4'S,7S,7'S,9aS,9a'S)-N,N'-((1S,1'S)-(hexa-2,4-diyne-1,6-diylbis(azanediyl))bis(2-oxo-1-phenylethane-2,1-diyl))bis(8,8-dimethyl-4-((S)-2-(methylamino)propanethioamido)-5-oxooctahydropyrrolo[2,1-b][1,3]thiazepine-7-carboxamide) |
| 33 | 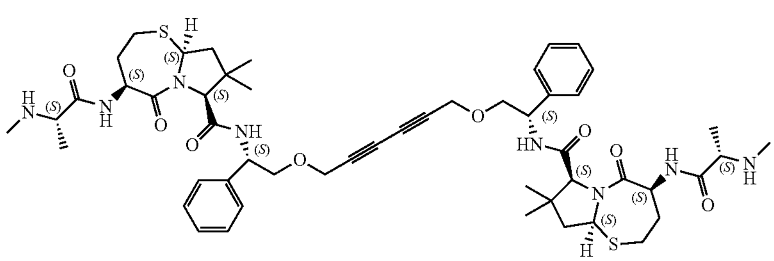 | (4S,4'S,7S,7'S,9aS,9a'S)-N,N'-((1S,1'S)-(hexa-2,4-diyne-1,6-diylbis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide) |
| 34 | 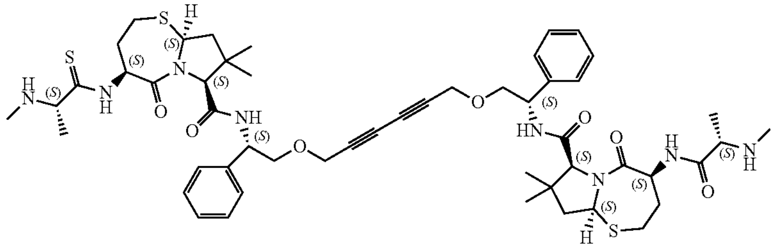 | (4S,7S,9aS)-N-((S)-2-((6-((S)-2-((4S,7S,9aS)-8,8-dimethyl-4-((S)-2-(methylamino)propanamido)-5-oxooctahydropyrrolo[2,1-b][1,3]thiazepine-7-carboxamido)-2-phenylethoxy)hexa-2,4-diyn-1-yl)oxy)-1-phenylethyl)-8,8-dimethyl-4-((S)-2-(methylamino)propanethioamido)-5-oxooctahydropyrrolo[2,1-b][1,3]thiazepine-7-carboxamide |

TABLE 1-continued

| Compound No | Compound structure | Compound name |
|---|---|---|
| 35 | 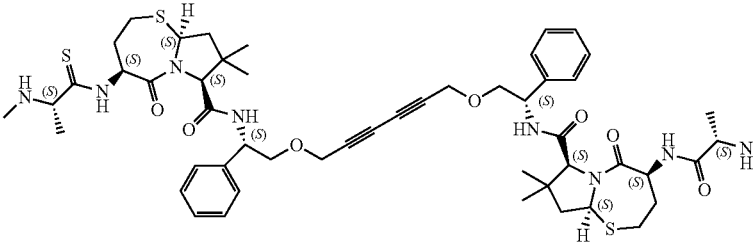 | (4S,4'S,7S,7'S,9aS,9a'S)-N,N'-((1S,1'S)-(hexa-2,4-diyne-1,6-diylbis(oxy))bis(1-phenylethane-2,1-diyl))bis(8,8-dimethyl-4-((S)-2-(methylamino)propanethioamido)-5-oxooctahydropyrrolo[2,1-b][1,3]thiazepine-7-carboxamide) |
| 36 | 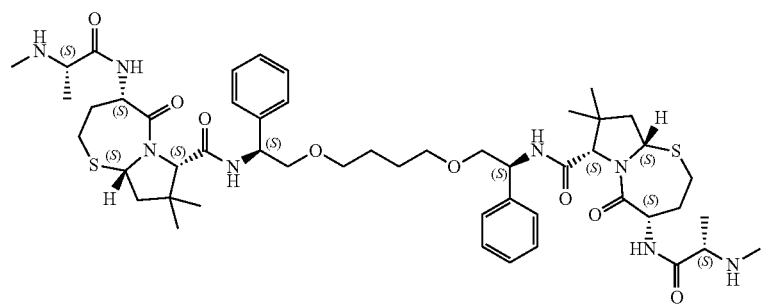 | (4S,4'S,7S,7'S,9aS,9a'S)-N,N'-((1S,1'S)-(butane-1,4-diylbis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide) |
| 37 | 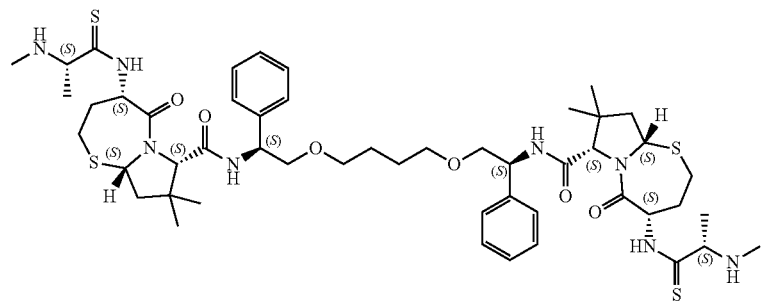 | (4S,4'S,7S,7'S,9aS,9a'S)-N,N'-((1S,1'S)-(butane-1,4-diylbis(oxy))bis(1-phenylethane-2,1-diyl))bis(8,8-dimethyl-4-((S)-2-(methylamino)propanethioamido)-5-oxooctahydropyrrolo[2,1-b][1,3]thiazepine-7-carboxamide) |
| 38 | 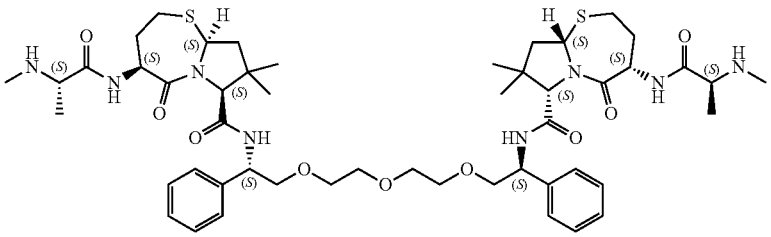 | (4S,4'S,7S,7'S,9aS,9a'S)-N,N'-((1S,1'S)-((oxybis(ethane-2,1-diyl))bis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide) |
| 39 | 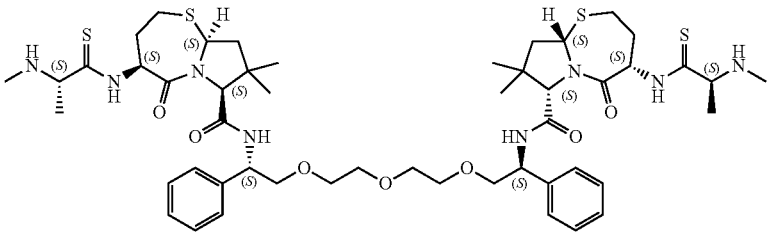 | (4S,4'S,7S,7'S,9aS,9a'S)-N,N'-((1S,1'S)-((oxybis(ethane-2,1-diyl))bis(oxy))bis(1-phenylethane-2,1-diyl))bis(8,8-dimethyl-4-((S)-2-(methylamino)propanethioamido)-5-oxooctahydropyrrolo[2,1-b][1,3]thiazepine-7-carboxamide) |

TABLE 1-continued

| Compound No | Compound structure | Compound name |
|---|---|---|
| 40 | 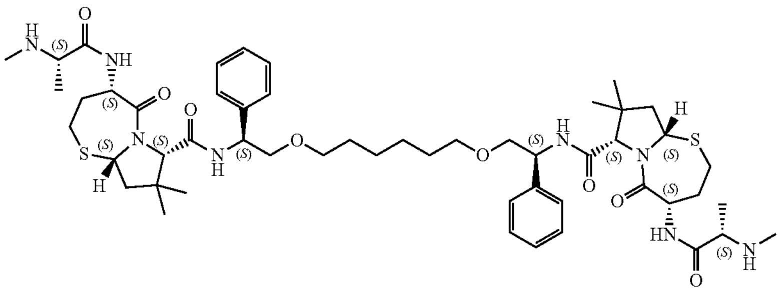 | (4S,4'S,7S,7'S,9aS,9a'S)-N,N'-((1S,1'S)-(hexane-1,6-diylbis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide) |
| 41 | 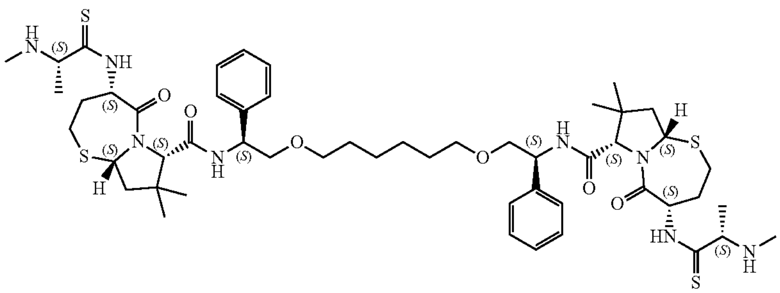 | (4S,4'S,7S,7'S,9aS,9a'S)-N,N'-((1S,1'S)-(hexane-1,6-diylbis(oxy))bis(1-phenylethane-2,1-diyl))bis(8,8-dimethyl-4-((S)-2-(methylamino)propanethioamido)-5-oxooctahydropyrrolo[2,1-b][1,3]thiazepine-7-carboxamide) |
| 42 | 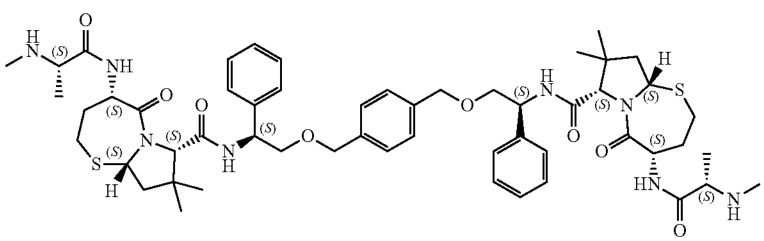 | (4S,4'S,7S,7'S,9aS,9a'S)-N,N'-((1S,1'S)-((1,4-phenylenebis(methylene))bis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide) |
| 43 | 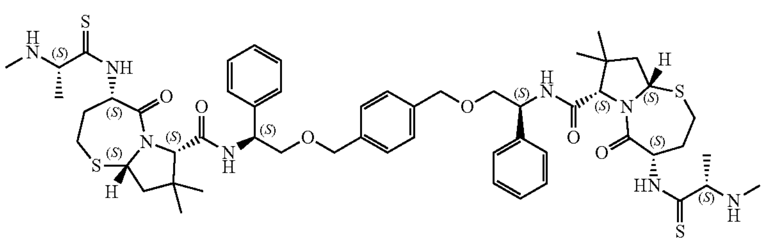 | (4S,4'S,7S,7'S,9aS,9a'S)-N,N'-((1S,1'S)-((1,4-phenylenebis(methylene))bis(oxy))bis(1-phenylethane-2,1-diyl))bis(8,8-dimethyl-4-((S)-2-(methylamino)propanethioamido)-5-oxooctahydropyrrolo[2,1-b][1,3]thiazepine-7-carboxamide) |
| 44 | 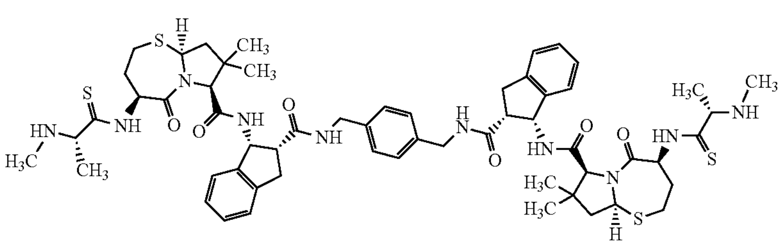 | (4S,7S,9aS)-N-[(1R,2R)-2-({[4-({[(1R,2R)-1-[(4S,7S,9aS)-8,8-dimethyl-4-[(2S)-2-(methylamino)propanethioamido]-5-oxo-octahydropyrrolo[2,1-b][1,3-2,3-dihydro-1H-inden-2-yl]formamido}methyl)phenyl]methyl}carbamoyl)-2,3-dihydro-1H-inden-1-yl]-8,8-dimethyl-4-[(2S)-2-(methylamino)propanethioamido]-5-oxo-octahydropyrrolo[2,1-b][1,3]thiazepine-7-carboxamide |

TABLE 1-continued

| Compound No | Compound structure | Compound name |
|---|---|---|
| 45 | 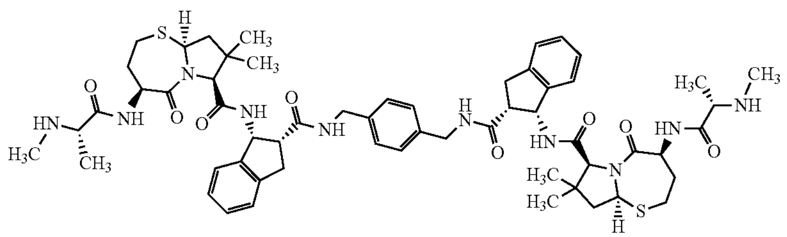 | (4S,7S,9aS)-N-[(1R,2R)-2-({[4-({[(1R,2R)-1-[(4S,7S,9aS)-8,8-dimethyl-4-[(2S)-2-(methylamino)propanamido]-5-oxo-octahydropyrrolo[2,1-b][1,3]thiazepine-7-amido]-2,3-dihydro-1H-inden-2-yl]formamido}methyl)phenyl]methyl}carbamoyl)-2,3-dihydro-1H-inden-1-yl]-8,8-dimethyl-4-[(2S)-2-(methylamino)propanamido]-5-oxo-octahydropyrrolo[2,1-b][1,3]thiazepine-7-carboxamide |
| 46 | 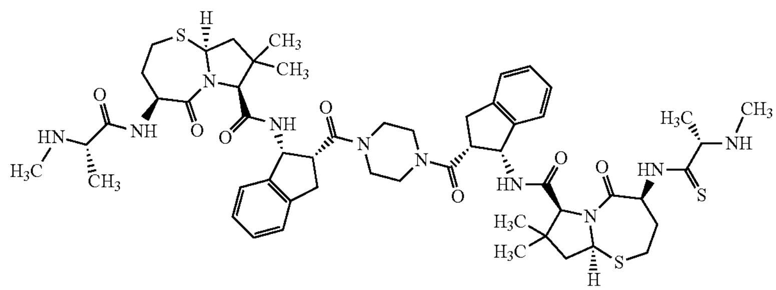 | (4S,7S,9aS)-N-[(1R,2R)-2-{4-[(1R,2R)-1-[(4S,7S,9aS)-8,8-dimethyl-4-[(2S)-2-(methylamino)propanamido]-5-oxo-octahydropyrrolo[2,1-b][1,3]thiazepine-7-amido]-2,3-dihydro-1H-indene-2-carbonyl]piperazine-1-carbonyl}-2,3-dihydro-1H-inden-1-yl]-8,8-dimethyl-4-[(2S)-2-(methylamino)propanamido]-5-oxo-octahydropyrrolo[2,1-b][1,3]thiazepine-7-carboxamide |
| 47 | 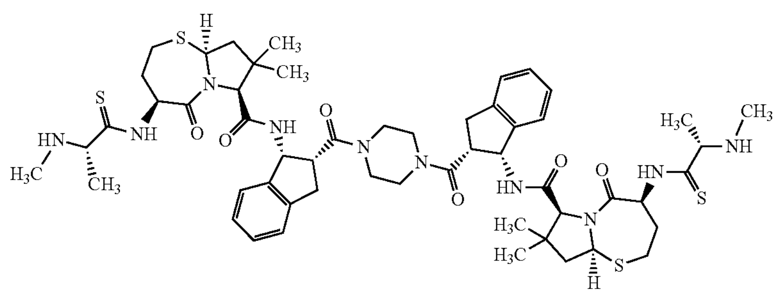 | (4S,7S,9aS)-N-[(1R,2R)-2-{4-[(1R,2R)-1-[(4S,7S,9aS)-8,8-dimethyl-4-[(2S)-2-(methylamino)propanethioamido]-5-oxo-octahydropyrrolo[2,1-b][1,3]thiazepine-7-amido]-2,3-dihydro-1H-indene-2-carbonyl]piperazine-1-carbonyl}-2,3-dihydro-1H-inden-1-yl]-8,8-dimethyl-4-[(2S)-2-(methylamino)propanethioamido]-5-oxo-octahydropyrrolo[2,1-b][1,3]thiazepine-7-carboxamide |
| 48 | 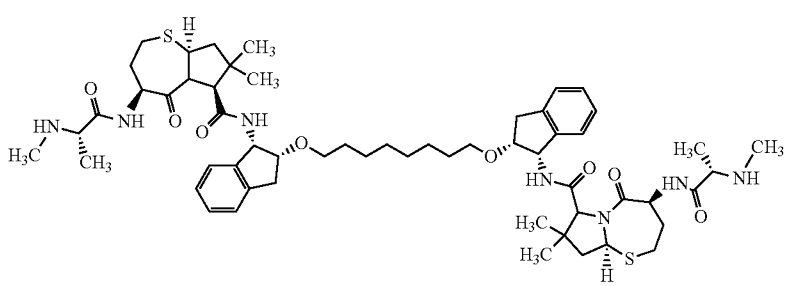 | (4S,7S,9aS)-N-[(1S,2R)-2-[(8-{[(1S,2R)-1-[(4S,7S,9aS)-8,8-dimethyl-4-[(2S)-2-(methylamino)propanamido]-5-oxo-octahydropyrrolo[2,1-b][1,3]thiazepine-7-amido]-2,3-dihydro-1H-inden-2-yl]oxy}octyl)oxy]-2,3-dihydro-1H-inden-1-yl]-8,8-dimethyl-4-[(2S)-2-(methylamino)propanamido]-5-oxo-octahydropyrrolo[2,1-b][1,3]thiazepine-7-carboxamide |
| 49 | 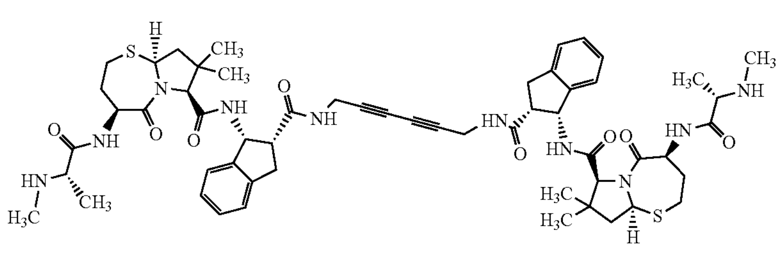 | (4S,7S,9aS)-N-[(1R,2R)-2-[(6-{[(1R,2R)-1-[(4S,7S,9aS)-8,8-dimethyl-4-[(2S)-2-(methylamino)propanamido]-5-oxo-octahydropyrrolo[2,1-b][1,3]thiazepine-7-amido]-2,3-dihydro-1H-inden-2-yl]formamido}hexa-2,4-diyn-1-yl)carbamoyl]-2,3-dihydro-1H-inden-1-yl]-8,8-dimethyl-4-[(2S)-2-(methylamino)propanamido]-5-oxo-octahydropyrrolo[2,1-b][1,3]thiazepine-7-carboxamide |

TABLE 1-continued

| Compound No | Compound structure | Compound name |
|---|---|---|
| 50 | 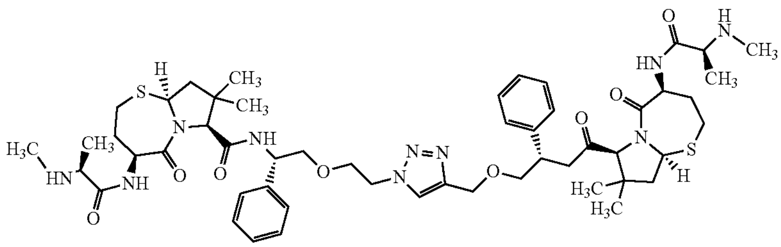 | (4S,7S,9aS)-N-[(1S)-2-[2-(4-{[(2S)-2-{[(4S,7S,9aS)-8,8-dimethyl-4-[(2S)-2-(methylamino)propanamido]-5-oxo-octahydropyrrolo[2,1-b][1,3]thiazepin-7-yl]formamido}-2-phenylethoxy]methyl}-1H-1,2,3-triazol-1-yl)ethoxy]-1-phenylethyl]-8,8-dimethyl-4-[(2S)-2-(methylamino)propanamido]-5-oxo-octahydropyrrolo[2,1-b][1,3]thiazepine-7-carboxamide |
| 51 | 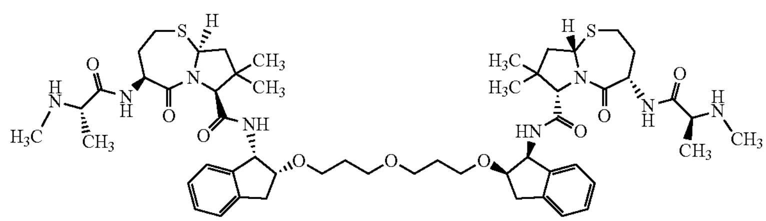 | (4S,7S,9aS)-N-[(1S,2R)-2-[3-(3-{[(1S,2R)-1-[(4S,7S,9aS)-8,8-dimethyl-4-[(2S)-2-(methylamino)propanamido]-5-oxo-octahydropyrrolo[2,1-b][1,3]thiazepine-7-amido]-2,3-dihydro-1H-inden-2-yl]oxy}propoxy)propoxy]-2,3-dihydro-1H-inden-1-yl]-8,8-dimethyl-4-[(2S)-2-(methylamino)propanamido]-5-oxo-octahydropyrrolo[2,1-b][1,3]thiazepine-7-carboxamide |
| 52 | 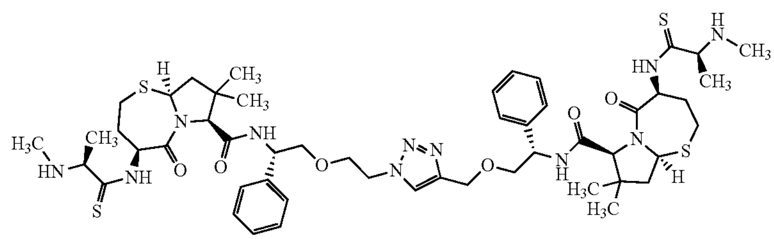 | (4S,7S,9aS)-N-[(1S)-2-42-(4-{[(2S)-2-{[(4S,7S,9aS)-8,8-dimethyl-4-[(2S)-2-(methylamino)propanethioamido]-5-oxo-octahydropyrrolo[2,1-b][1,3]thiazepin-7-yl]formamido}-2-phenylethoxy]methyl}-1H-1,2,3-triazol-1-yl)ethoxy]-1-phenylethyl]-8,8-dimethyl-4-[(2S)-2-(methylamino)propanethioamido]-5-oxo-octahydropyrrolo[2,1-b][1,3]thiazepine-7-carboxamide |
| 53 | 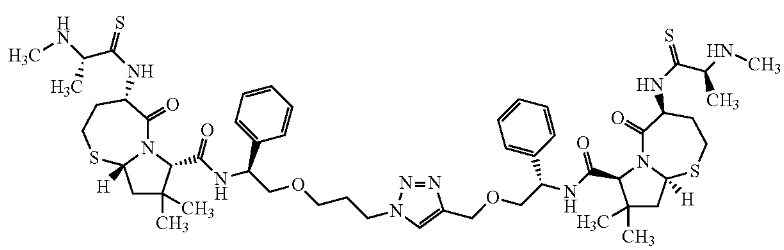 | (4S,7S,9aS)-N-[(1S)-2-43-(4-{[(2S)-2-{[(4S,7S,9aS)-8,8-dimethyl-4-[(2S)-2-(methylamino)propanethioamido]-5-oxo-octahydropyrrolo[2,1-b][1,3]thiazepin-7-yl]formamido}-2-phenylethoxy]methyl}-1H-1,2,3-triazol-1-yl)propoxy]-1-phenylethyl]-8,8-dimethyl-4-[(2S)-2-(methylamino)propanethioamido]-5-oxo-octahydropyrrolo[2,1-b][1,3]thiazepine-7-carboxamide |
| 54 | 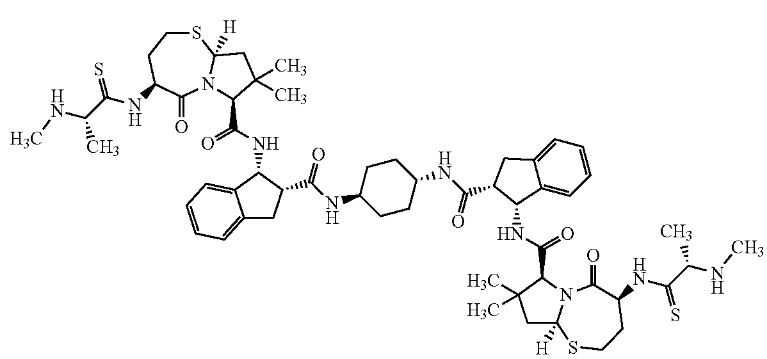 | (4S,7S,9aS)-8,8-dimethyl-4-[(2S)-2-(methylamino)propanethioamido]-5-oxo-N-[(1R,2R)-2-{[(1rs,4rs)-4-[(1R,2R)-1-[(4S,7S,9aS)-8,8-dimethyl-4-[(2S)-2-(methylamino)propanethioamido]-5-oxo-octahydropyrrolo[2,1-b][1,3]thiazepine-7-amido]-2,3-dihydro-1H-indene-2-amido]cyclohexyl]carbamoyl}-2,3-dihydro-1H-inden-1-yl]-octahydropyrrolo[2,1-b][1,3]thiazepine-7-carboxamide |

TABLE 1-continued

| Compound No | Compound structure | Compound name |
|---|---|---|
| 55 | 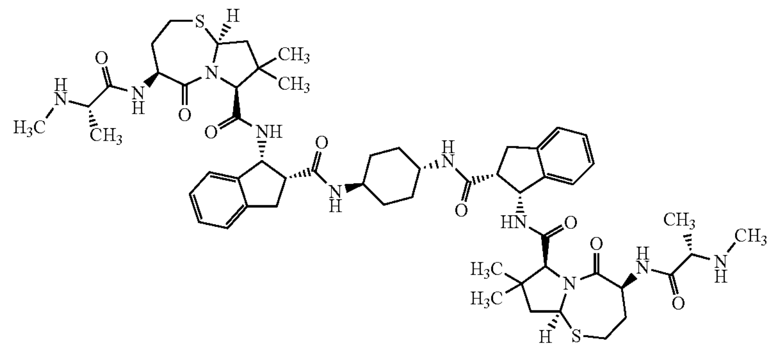 | (4S,7S,9aS)-8,8-dimethyl-4-[(2S)-2-(methylamino)propanamido]-5-oxo-N-[(1R,2R)-2-{[(1rs,4rs)-4-[(1R,2R)-1-[(4S,7S,9aS)-8,8-dimethyl-4-[(2S)-2-(methylamino)propanamido]-5-oxo-octahydropyrrolo[2,1-b][1,3]thiazepine-7-amido]-2,3-dihydro-1H-indene-2-amido]cyclohexyl]carbamoyl}-2,3-dihydro-1H-inden-1-yl]-octahydropyrrolo[2,1-b][1,3]thiazepine-7-carboxamide |
| 56 | 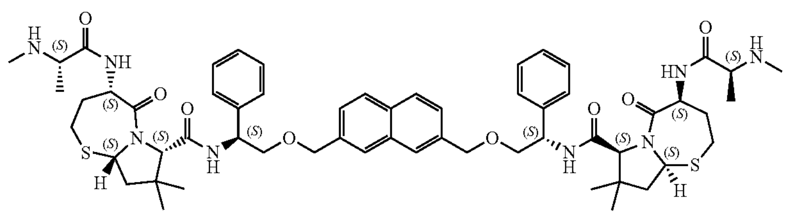 | (4S,4'S,7S,7'S,9aS,9a'S)-N,N'-((1S,1'S)-((naphthalene-2,7-diylbis(methylene))bis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide |
| 57 | 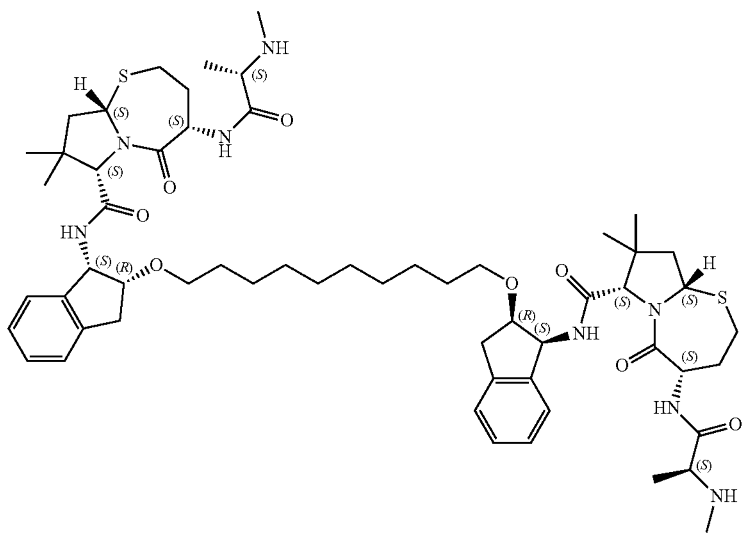 | (4S,4'S,7S,7'S,9aS,9a'S)-N,N'-((1S,1'S,2R,2'R)-(decane-1,10-diylbis(oxy))bis(2,3-dihydro-1H-indene-2,1-diyl))bis(8,8-dimethyl-4-((S)-2-(methylamino)propanamido)-5-oxooctahydropyrrolo[2,1-b][1,3]thiazepine-7-carboxamide) |
| 58 | 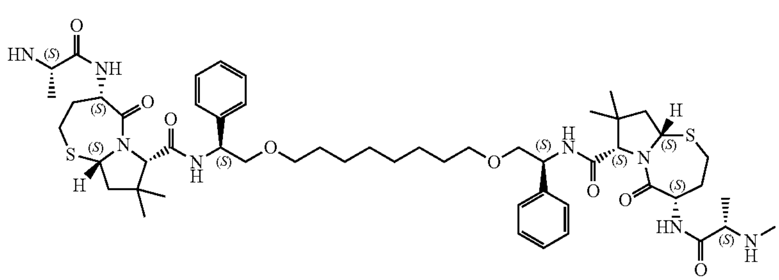 | (4S,4'S,7S,7'S,9aS,9a'S)-N,N'-((1S,1'S)-(octane-1,8-diylbis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide) |

TABLE 1-continued

| Compound No | Compound structure | Compound name |
|---|---|---|
| 59 | 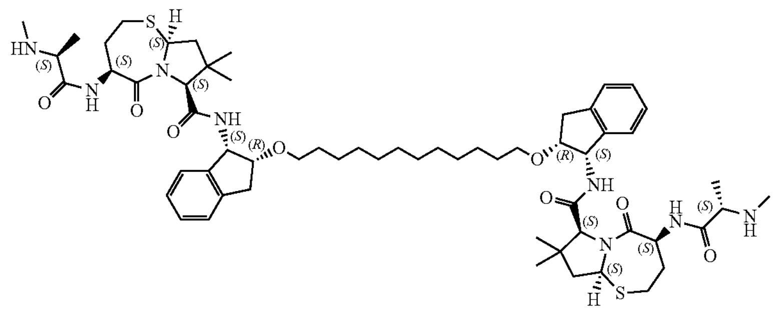 | (4S,4'S,7S,7'S,9aS,9a'S)-N,N'-((1S,1'S,2R,2'R)-(dodecane-1,12-diylbis(oxy))bis(2,3-dihydro-1H-indene-2,1-diyl))bis(8,8-dimethyl-4-((S)-2-(methylamino)propanamido)-5-oxooctahydropyrrolo[2,1-b][1,3]thiazepine-7-carboxamide) |
| 60 | 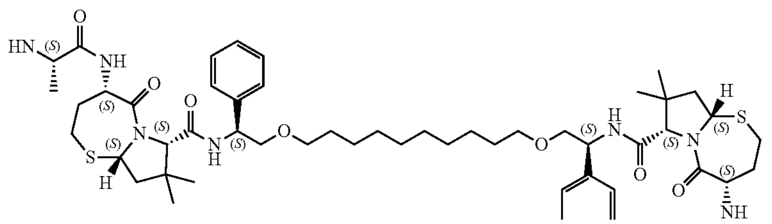 | (4S,4'S,7S,7'S,9aS,9a'S)-N,N'-((1S,1'S)-(decane-1,10-diylbis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide) |
| 61 | 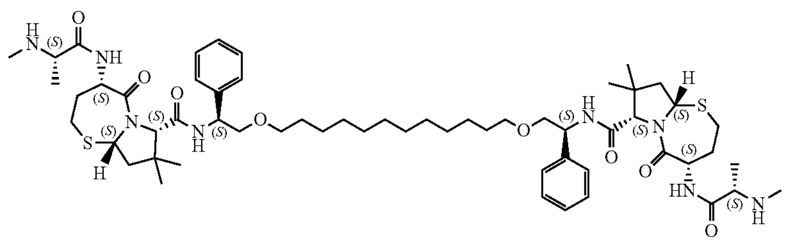 | (4S,4'S,7S,7'S,9aS,9a'S)-N,N'-((1S,1'S)-(dodecane-1,12-diylbis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide) |
| 62 | 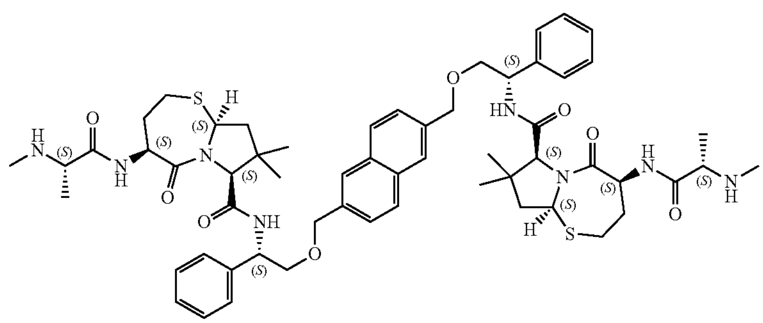 | 4S,4'S,7S,7'S,9aS,9a'S)-N,N'-((1S,1'S)-((naphthalene-2,6-diylbis(methylene))bis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide) |
| 63 | 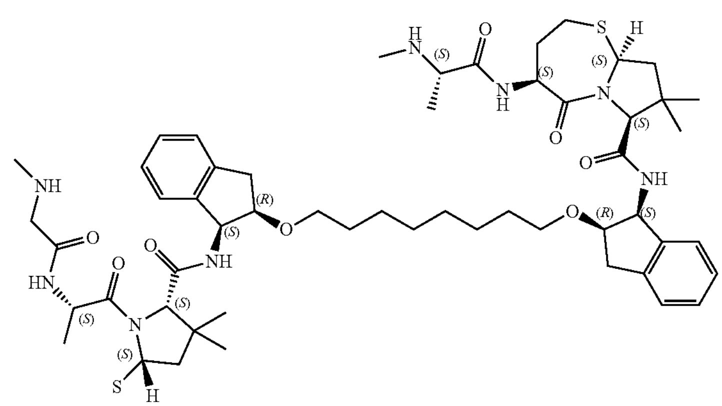 | (4S,4'S,7S,7'S,9aS,9a'S)-N,N'-((1S,1'S,2R,2'R)-(octane-1,8-diylbis(oxy))bis(2,3-dihydro-1H-indene-2,1-diyl))bis(8,8-dimethyl-4-((S)-2-(methylamino)propanamido)-5-oxooctahydropyrrolo[2,1-b][1,3]thiazepine-7-carboxamide) |

In one aspect, the invention relates to a compound selected from the group consisting of:
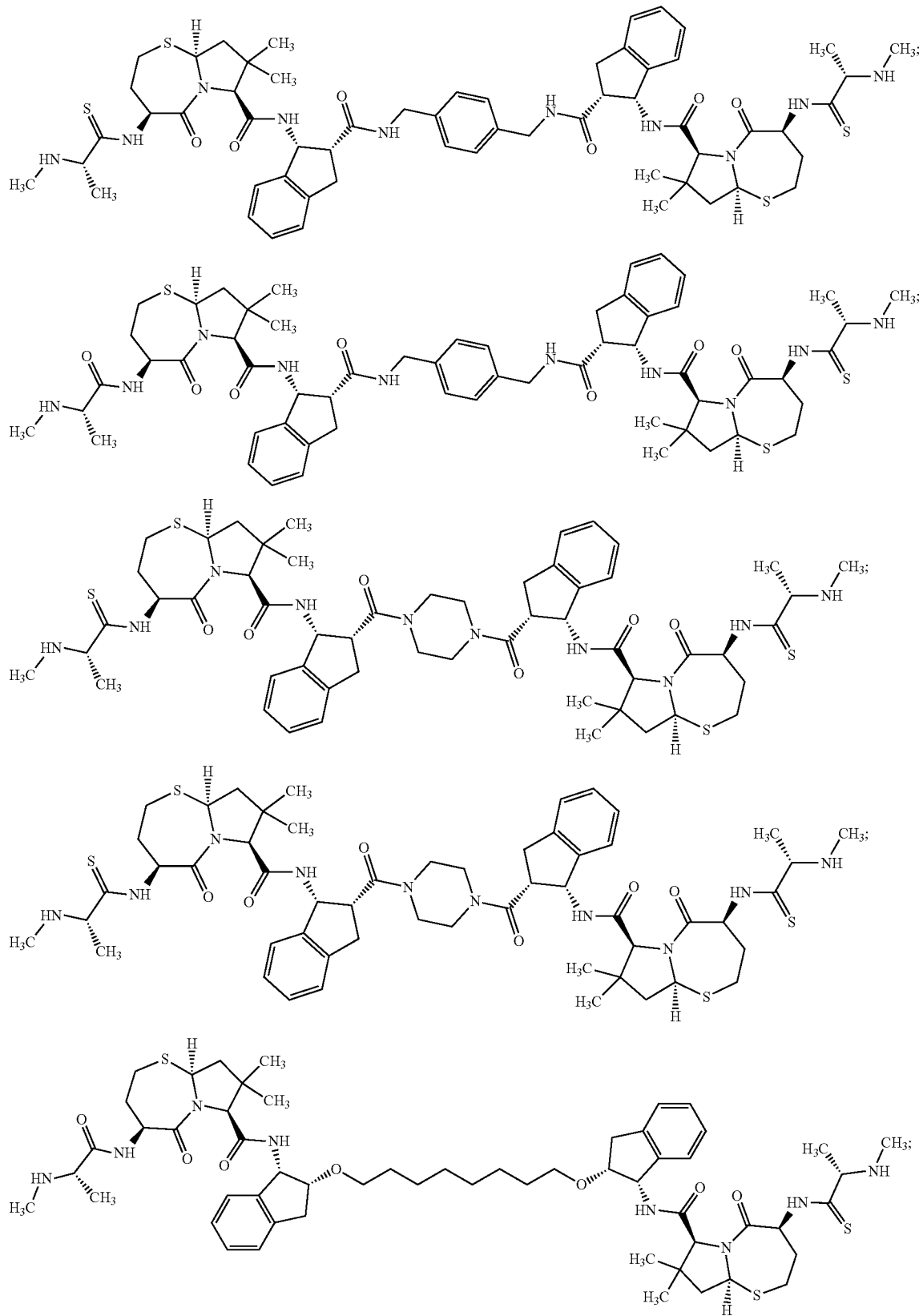

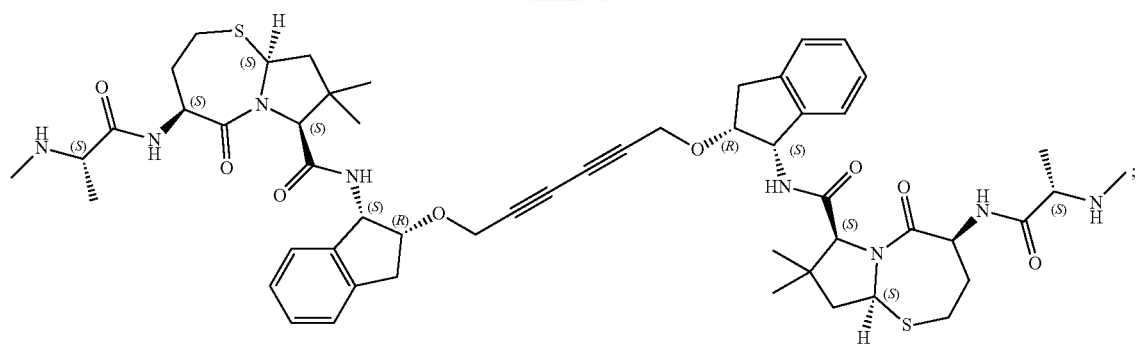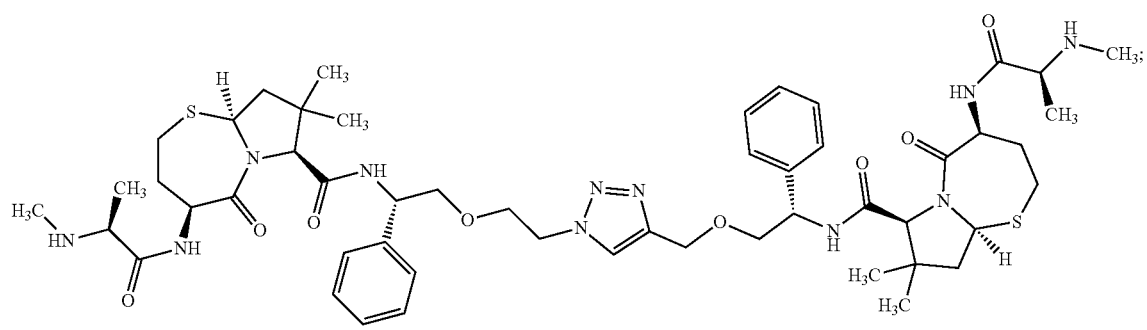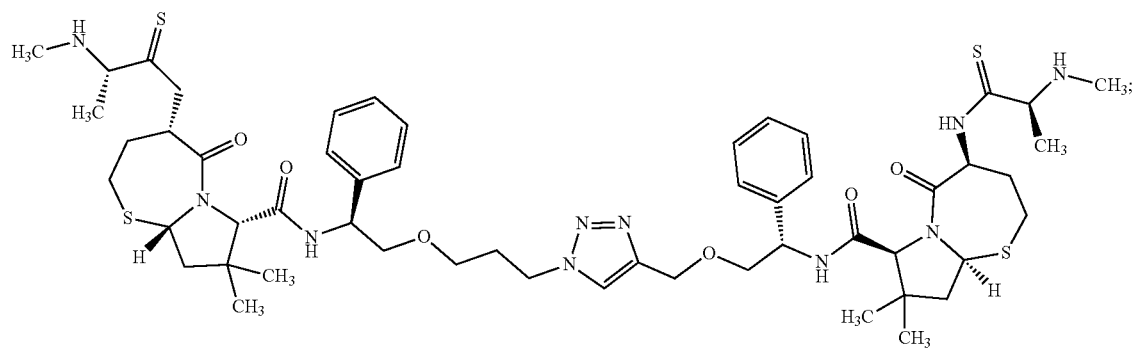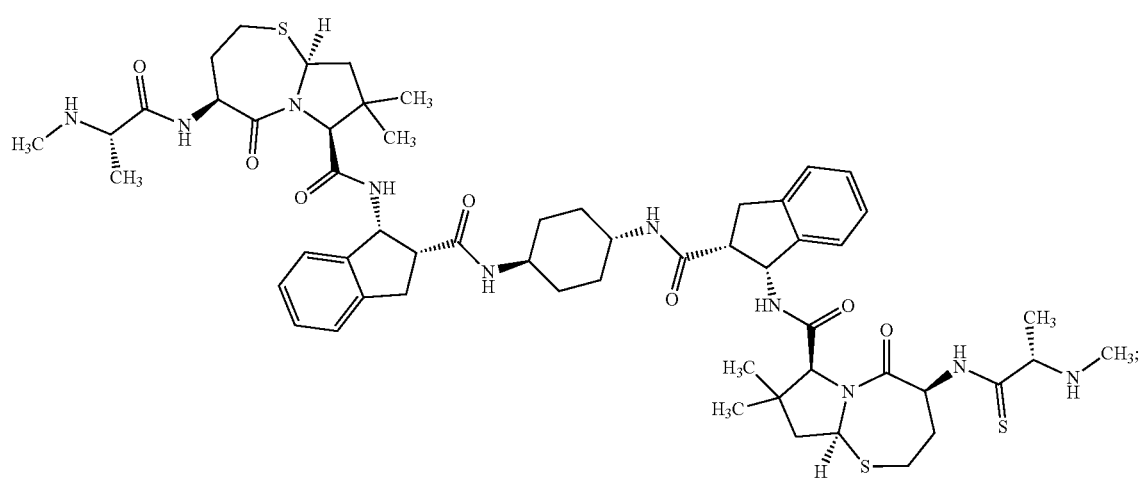

-continued
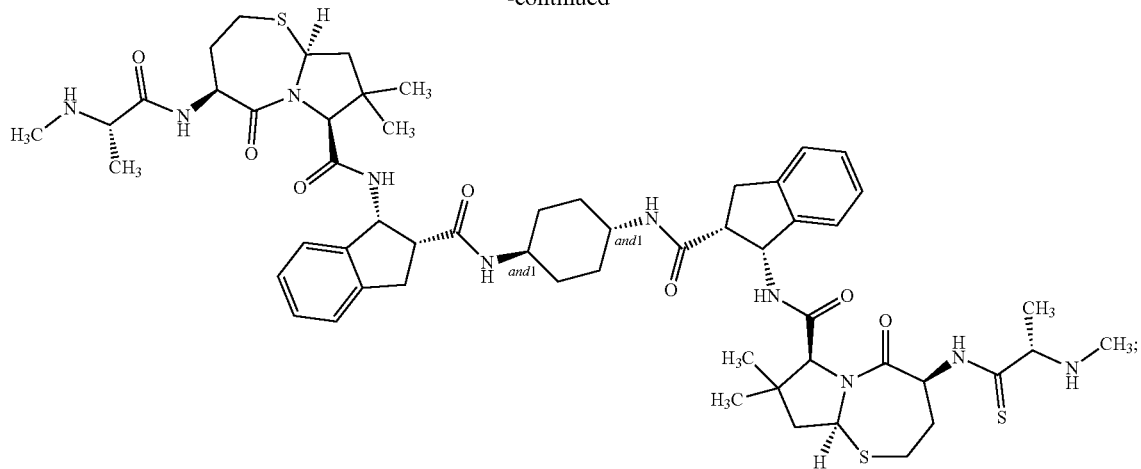
and pharmaceutically acceptable salts thereof.
In one aspect, the invention provides a compound selected from the group consisting of:
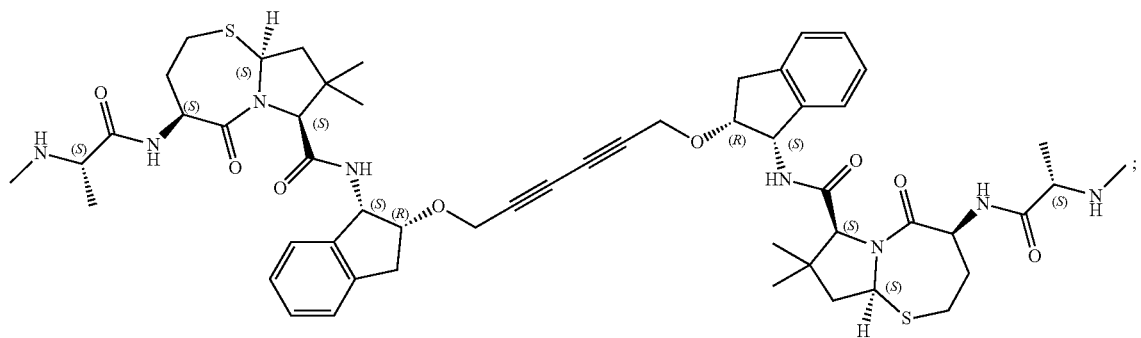
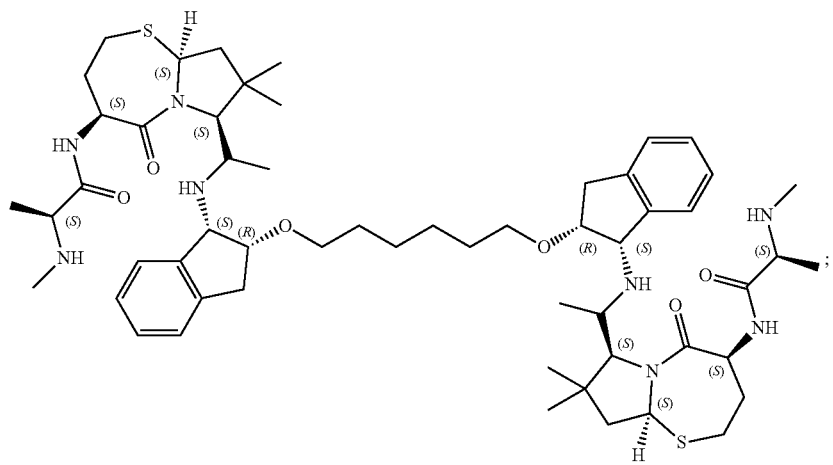
and pharmaceutically acceptable salts thereof.

Pharmaceutically acceptable salts are also within the scope of the invention with respect to all compounds 1-63 set forth herein. Most preferably, each of compounds 1-63 may be present generically as hydrochloride (i.e., HCl salts), e.g., more specifically a dihydrochloride, (2 HCl) salt. Also within the scope of the invention are any of compounds 1-63 present as a single species, including pharmaceutically acceptable salts thereof, as well as any of these compounds in free base form.

Specific examples of linkers (L) that can be used in accordance with the present invention include those selected from the group consisting of:

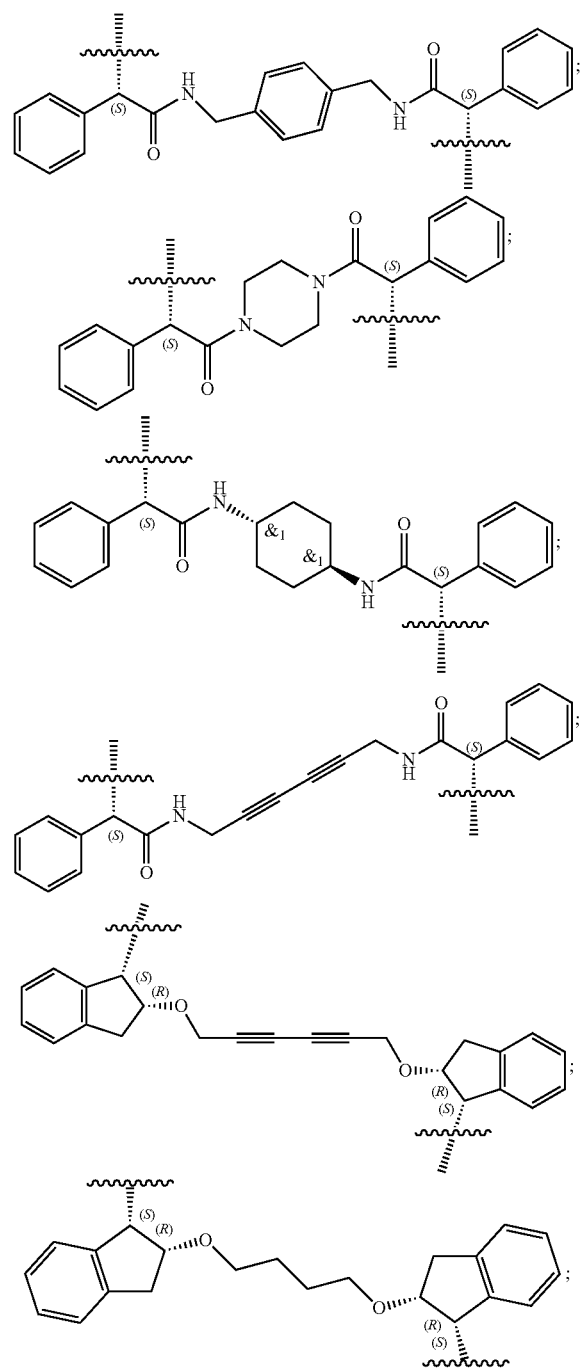

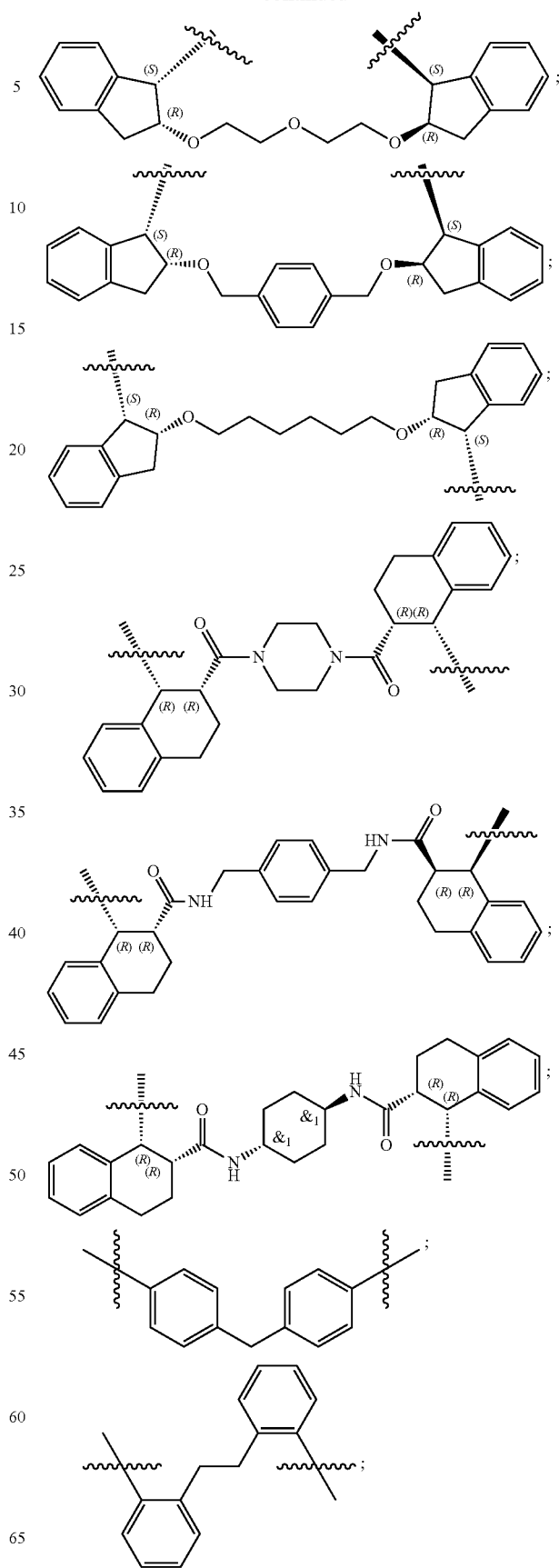

-continued

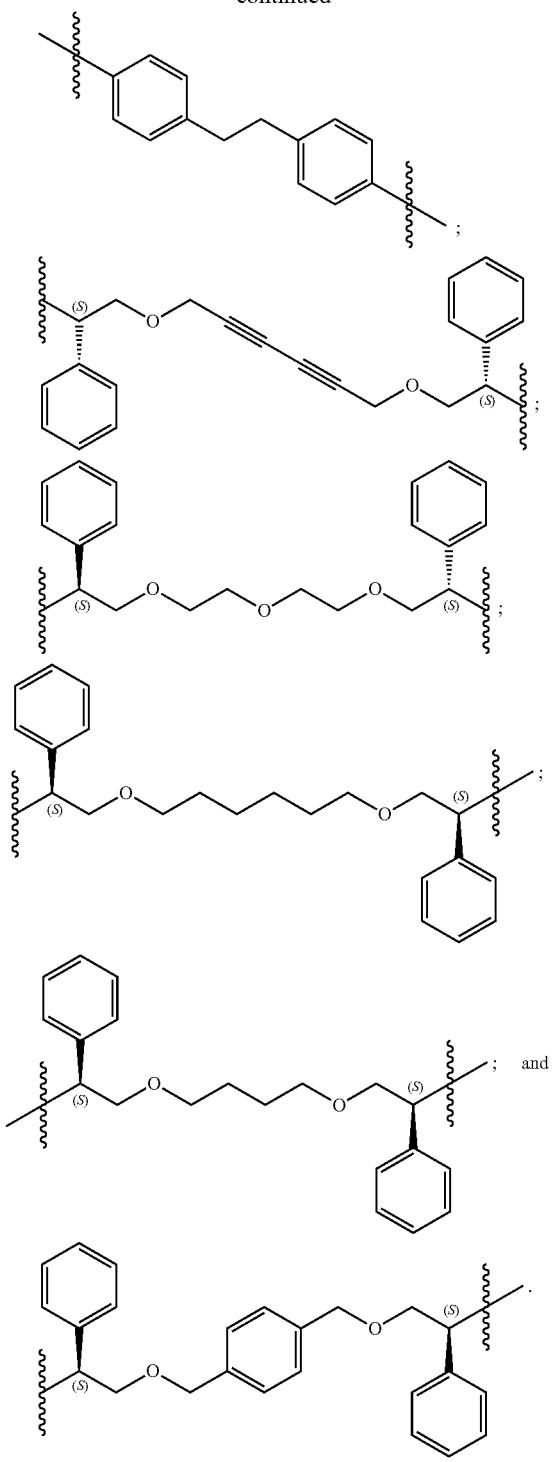

In accordance with one embodiment of the present invention, there is provided a pharmaceutical composition comprising a compound of Formula (I), (Ia), (Ib), (II) or (III) or a pharmaceutically acceptable salt thereof, and a pharmaceutically acceptable excipient. In a further embodiment, the compound is present in amorphous form. In a further embodiment, the pharmaceutical composition is in a tablet form. In a further embodiment, the compound is present as a spray dried dispersion. In a further embodiment, the composition is present in nanoparticulate form, e.g., particles between 1 and 100 nanometers in size.

In accordance with one embodiment of the present invention, there is provided a method of treating an HIV infection in a subject comprising administering to the subject a compound of Formula (I), (Ia), (Ib), (II) or (III) or a pharmaceutically acceptable salt thereof.

In accordance with one embodiment of the present invention, there is provided a method of treating an HIV infection in a subject comprising administering to the subject a pharmaceutical composition as described herein.

Furthermore, the compounds of the invention, as well as linkers (L), can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and l isomers can be prepared using chiral synthons or chiral reagents, or resolved using conventional techniques. If, for instance, a particular enantiomer of a compound of the present invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

In another embodiment of the present invention, there is provided a compound of Formula I, Ia, Ib, II or III, or a pharmaceutically acceptable salt thereof for use in medical therapy.

In another embodiment of the present invention, there is provided a compound of Formula I, Ia, Ib, II or III, or a pharmaceutically acceptable salt thereof for use in treating an HIV infection.

In another embodiment of the invention, there is provided a compound of Formula I, Ia, Ib, II or III, wherein the compound or salt of the compound is used in the manufacture of a medicament for use in the treatment of an HIV infection in a human.

In one aspect, the invention provides a method of curing an HIV infection in a subject comprising administering to the subject a compound of Formulas I, Ia, Ib, II and III, as well as any compound of Table 1, along with pharmaceutically salts thereof. "Cure" or "Curing" a disease in a patient refer to is used to denote the eradication, stoppage, halt or end of the human immunodeficiency virus or symptoms, or the progression of the symptoms or virus, for a defined period. As an example, in one embodiment, "cure" or "curing" refers to a therapeutic administration or a combination of administrations that alone or in combination with one or more other compounds induces and maintains sustained viral control (undetectable levels of plasma viremia by, e.g., a polymerase chain reaction (PCR) test, a bDNA (branched chain DNA) test or a NASBA (nucleic acid sequence based amplification) test,) of human immunodeficiency virus after a minimum of two years without any other therapeutic intervention. The above PCR, bDNA and NASBA tests are carried out using techniques known and familiar to one skilled in the art. As an example, the eradication, stoppage, halt or end of the human immunodeficiency virus or symptoms, or the progression of the symptoms or virus, may be sustained for a minimum of two years.

In one aspect, the invention provides a method of curing an HIV infection in a subject comprising administering to the subject a pharmaceutical composition comprising a compound of Formulas I, Ia, Ib, II and III, along with pharmaceutically salts thereof.

In one aspect, the invention provides the use of a compound of Formulas I, Ia, Ib, II and III, or a pharmaceutically acceptable salt thereof in the manufacture of a medicament for use in curing an HIV infection.

In one aspect, the invention provides a compound of Formulas I, Ia, Ib, II and III, or a pharmaceutically acceptable salt thereof for use in curing an HIV infection.

Combinations of compounds of Formulas I, Ia, Ib, II and III, and one or more agents useful in HIV therapy may also be used in methods of curing an HIV infection.

In one embodiment, the pharmaceutical formulation containing a compound of Formula I, Ia, Ib, II or III, or a salt thereof is a formulation adapted for parenteral administration. In another embodiment, the formulation is a long-acting parenteral formulation. In a further embodiment, the formulation is a nano-particle formulation.

The compounds of the present invention and their salts, solvates, or other pharmaceutically acceptable derivatives thereof, may be employed alone or in combination with other therapeutic agents. Therefore, in other embodiments, the methods of treating and/or preventing an HIV infection in a subject may in addition to administration of a compound of Formula I, Ia, Ib, II or III further comprising administration of one or more additional pharmaceutical agents active against HIV.

In such embodiments, the one or more additional agents active against HIV is selected from the group consisting of anti-retroviral agents, latency reversing agents, and agents for clearance therapy.

In other embodiments, the one or more additional agents active against HIV is selected from the group consisting of nucleotide reverse transcriptase inhibitors, non-nucleotide reverse transcriptase inhibitors, protease inhibitors, entry inhibitors, attachment and fusion inhibitors, integrase inhibitors, maturation inhibitors, CXCR4 and/or CCR5 inhibitors, histone deacetylase inhibitors, histone crotonyl transferase inhibitors, protein kinase C agonists, proteasome inhibitors, TLR7 agonists, bromodomain inhibitors, and neutralizing antibodies, and combinations thereof.

In certain embodiments, the one or more additional agents active against HIV is selected from the group consisting of zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine, efavirenz, loviride, immunocal, oltipraz, capravirine, lersivirine, GSK2248761, TMC-278, TMC-125, etravirine, saquinavir, ritonavir, indinavir, nelfinavir, amprenavir, fosamprenavir, brecanavir, darunavir, atazanavir, tipranavir, palinavir, lasinavir, enfuvirtide, T-20, T-1249, PRO-542, PRO-140, TNX-355, BMS-806, BMS-663068 and BMS-626529, 5-Helix, raltegravir, elvitegravir, dolutegravir, cabotegravir, bictegravir, vicriviroc (Sch-C), Sch-D, TAK779, maraviroc, TAK449, didanosine, tenofovir, lopinavir, darunavir, vorinostat, panobinostat, romidepin, valpronic acid, mocetinostat, sodium corotonate, bryostatin, ingenol B, disulforam, GS-9620, JQ1, iBET151, bortezomib, epigallocatechin gallate, salinosporamide A, carfilzomib, broadly neutralizing antibodies (bNAb), eCD4-Ig, CD4-Ig, and dual-affinity re-targeting (DART) proteins.

As such, the compounds of the present invention of Formula (I), (Ia), (Ib), (II) or (III) and any other pharmaceutically active agent(s) may be administered together or separately and, when administered separately, administration may occur simultaneously or sequentially, in any order. The amounts of the compounds of Formula (I), (Ia), (Ib), (II) or (III) of the present invention and the other pharmaceutically active agent(s) and the relative timings of administration will be selected in order to achieve the desired combined therapeutic effect. The administration in combination of a compound of the present invention of Formula (I), (Ia), (Ib), (II) or (III) and salts, solvates, or other pharmaceutically acceptable derivatives thereof with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time. The amounts of the compound(s) of Formula I, Ia, Ib, II or III or salts thereof and the other pharmaceutically active agent(s) and the relative timings of administration will be selected in order to achieve the desired combined therapeutic effect.

In addition, the compounds of the present invention of Formula (I), (Ia), (Ib), (II) or (III) may be used in combination with one or more other agents that may be useful in the treatment of HIV. They agents may include anti-retroviral agents, latency reversing agents, and agents for clearance therapy. Several examples of anti-retroviral agents are provided below:

Nucleotide reverse transcriptase inhibitors such as zidovudine, didanosine, lamivudine, zalcitabine, abacavir, stavudine, adefovir, adefovir dipivoxil, fozivudine, todoxil, emtricitabine, alovudine, amdoxovir, elvucitabine, and similar agents;

Non-nucleotide reverse transcriptase inhibitors (including an agent having anti-oxidation activity such as immunocal, oltipraz, etc.) such as nevirapine, delavirdine, efavirenz, loviride, immunocal, oltipraz, capravirine, lersivirine, GSK2248761, TMC-278, TMC-125, etravirine, and similar agents;

Protease inhibitors such as saquinavir, ritonavir, indinavir, nelfinavir, amprenavir, fosamprenavir, brecanavir, darunavir, atazanavir, tipranavir, palinavir, lasinavir, and similar agents;

Entry, attachment and fusion inhibitors such as enfuvirtide (T-20), T-1249, PRO-542, PRO-140, TNX-355, BMS-806, BMS-663068 and BMS-626529, 5-Helix and similar agents;

Integrase inhibitors such as raltegravir, elvitegravir, dolutegravir, cabotegravir, bictegravir and N similar agents;

Maturation inhibitors such as PA-344 and PA-457, and similar agents; and

CXCR4 and/or CCR5 inhibitors such as vicriviroc (Sch-C), Sch-D, TAK779, maraviroc (UK 427,857), TAK449, as well as those disclosed in WO 02/74769, PCT/US03/39644, PCT/US03/39975, PCT/US03/39619, PCT/US03/39618, PCT/US03/39740, and PCT/US03/39732, and similar agents.

Further examples where the compounds of the present invention may be used in combination with one or more agents useful in the prevention or treatment of HIV are found in Table 2.

TABLE 2

| FDA Approval | Brand Name | Generic Name | Manufacturer |
| --- | --- | --- | --- |
| Nucleoside Reverse Transcriptase Inhibitors (NRTIs) | | | |
| 1987 | Retrovir | zidovudine, azidothymidine, AZT, ZDV | GlaxoSmithKline |
| 1991 | Videx | didanosine, dideoxyinosine, ddI | Bristol-Myers Squibb |
| 1992 | Hivid | zalcitabine, dideoxycytidine, ddC | Roche Pharmaceuticals |
| 1994 | Zerit | stavudine, d4T | Bristol-Myers Squibb |
| 1995 | Epivir | lamivudine, 3TC | GlaxoSmithKline |
| 1997 | Combivir | lamivudine + zidovudine | GlaxoSmithKline |
| 1998 | Ziagen | abacavir sulfate, ABC | GlaxoSmithKline |
| 2000 | Trizivir | abacavir + lamivudine + zidovudine | GlaxoSmithKline |
| 2000 | Videx EC | enteric coated didanosine, ddI EC | Bristol-Myers Squibb |
| 2001 | Viread | tenofovir disoproxil fumarate, TDF | Gilead Sciences |
| 2003 | Emtriva | emtricitabine, FTC | Gilead Sciences |
| 2004 | Epzicom | abacavir + lamivudine | GlaxoSmithKline |
| 2004 | Truvada | emtricitabine + tenofovir disoproxil fumarate | Gilead Sciences |
| Non-Nucleosides Reverse Transcriptase Inhibitors (NNRTIs) | | | |
| 1996 | Viramune | nevirapine, NVP | Boehringer Ingelheim |
| 1997 | Rescriptor | delavirdine, DLV | Pfizer |
| 1998 | Sustiva | efavirenz, EFV | Bristol-Myers Squibb |
| 2008 | Intelence | Etravirine | Tibotec Therapeutics |
| Protease Inhibitors (PIs) | | | |
| 1995 | Invirase | saquinavir mesylate, SQV | Roche Pharmaceuticals |
| 1996 | Norvir | ritonavir, RTV | Abbott Laboratories |
| 1996 | Crixivan | indinavir, IDV | Merck |
| 1997 | Viracept | nelfinavir mesylate, NFV | Pfizer |
| 1997 | Fortovase | saquinavir (no longer marketed) | Roche Pharmaceuticals |
| 1999 | Agenerase | amprenavir, APV | GlaxoSmithKline |
| 2000 | Kaletra | lopinavir + ritonavir, LPV/RTV | Abbott Laboratories |
| 2003 | Reyataz | atazanavir sulfate, ATV | Bristol-Myers Squibb |
| 2003 | Lexiva | fosamprenavir calcium, FOS-APV | GlaxoSmithKline |

TABLE 2-continued

| FDA Approval | Brand Name | Generic Name | Manufacturer |
| --- | --- | --- | --- |
| 2005 | Aptivus | tripranavir, TPV | Boehringer Ingelheim |
| 2006 | Prezista | Darunavir | Tibotec Therapeutics |
| Fusion Inhibitors | | | |
| 2003 | Fuzeon | Enfuvirtide, T-20 | Roche Pharmaceuticals & Trimeris |
| Entry Inhibitors | | | |
| 2007 | Selzentry | Maraviroc | Pfizer |
| Integrase Inhibitors | | | |
| 2007 | Isentress | Raltegravir | Merck |
| 2013 | Tivicay | Dolutegravir | ViiV Healthcare |
| — | — | Cabotegravir | |

The present invention may be used in combination with other agents that induce HIV expression, such as latency reversing agents. Several latency reversing agents include, but are not limited to, the following: histone deacetylase inhibitors (e.g., vorinostat, panobinostat, romidepin), histone crotonyl transferase inhibitors (sodium corotonate), protein kinase C agonists (e.g., bryostatin, ingenol B), disulfiram, TLR7 agonists (e.g., GS-9620), bromodomain inhibitors (e.g., JQ1, iBET151). Many of these agents are described in further detail below.

The present invention may be used in combination with other agents that induce HIV expression, such as agents for clearance therapy. Several examples of agents for clearance therapy, or of immunological combinations for clearance, include, but are not limited to, the following: neutralizing and broadly neutralizing antibodies (bNAb), eCD4-Ig, CD4-Ig, and dual-affinity re-targeting (DART) proteins.

The scope of combinations of compounds of this invention with HIV agents is not limited to those mentioned above, but includes in principle any combination with any pharmaceutical composition useful for the treatment and/or prevention of HIV. As noted, in such combinations the compounds of the present invention and other HIV agents may be administered separately or in conjunction. In addition, one agent may be prior to, concurrent to, or subsequent to the administration of other agent(s).

The present invention may be used in combination with one or more agents useful as pharmacological enhancers as well as with or without additional compounds for the prevention or treatment of HIV. Examples of such pharmacological enhancers (or pharmakinetic boosters) include, but are not limited to, ritonavir, GS-9350 (cobicistat), and SPI-452.

Ritonavir is 10-hydroxy-2-methyl-5-(1-methyethyl)-1-1[2-(1-methylethyl)-4-thiazolyl]-3,6-dioxo-8,11-bis(phenyl-methyl)-2,4,7,12-tetraazatridecan-13-oic acid, 5-thiazolylm-ethyl ester, [5S-(5S*,8R*,10R*,11R*)] and is available from Abbott Laboratories of Abbott park, Illinois, as Norvir. Ritonavir is an HIV protease inhibitor indicated with other antiretroviral agents for the treatment of HIV infection. Ritonavir also inhibits P450 mediated drug metabolism as well as the P-gycoprotein (Pgp) cell transport system, thereby resulting in increased concentrations of active compound within the organism.

GS-9350 (cobicistat) is a compound being developed by Gilead Sciences of Foster City Calif. as a pharmacological enhancer.

SPI-452 is a compound being developed by *Sequoia* Pharmaceuticals of Gaithersburg, Md., as a pharmacological enhancer.

In one embodiment of the present invention, a compound of Formula I, Ia, Ib, II or III is used in combination with ritonavir. In one embodiment, the combination is an oral fixed dose combination. In another embodiment, the compound of Formula I, Ia, Ib, II or III is formulated as a long acting parenteral injection and ritonavir is formulated as an oral composition. In one embodiment, a kit containing the compound of Formula I, Ia, Ib, II or III is formulated as a long acting parenteral injection and ritonavir formulated as an oral composition. In another embodiment, the compound of Formula I, Ia, Ib, II or III is formulated as a long acting parenteral injection and ritonavir is formulated as an injectable composition. In one embodiment, a kit containing the compound of Formula I, Ia, Ib, II or III is formulated as a long acting parenteral injection and ritonavir formulated as an injectable composition.

In another embodiment of the present invention, a compound of Formula I, Ia, Ib, II or III is used in combination with GS-9350. In one embodiment, the combination is an oral fixed dose combination. In another embodiment, the compound of Formula I, Ia, Ib, II or III is formulated as a long acting parenteral injection and GS-9350 is formulated as an oral composition. In one embodiment, there is provided a kit containing the compound of Formula I, Ia, Ib, II or III is formulated as a long acting parenteral injection and GS-9350 formulated as an oral composition. In another embodiment, the compound of Formula I, Ia, Ib, II or III is formulated as a long acting parenteral injection and GS-9350 is formulated as an injectable composition. In one embodiment, is a kit containing the compound of Formula I, Ia, Ib, II or III is formulated as a long acting parenteral injection and GS-9350 formulated as an injectable composition.

In one embodiment of the present invention, a compound of Formula I, Ia, Ib, II or III is used in combination with SPI-452. In one embodiment, the combination is an oral fixed dose combination. In another embodiment, the compound of Formula I, Ia, Ib, II or III is formulated as a long acting parenteral injection and SPI-452 is formulated as an oral composition. In one embodiment, there is provided a kit containing the compound of Formula I, Ia, Ib, II or III is formulated as a long acting parenteral injection and SPI-452 formulated as an oral composition. In another embodiment, the compound of Formula I, Ia, Ib, II or III is formulated as a long acting parenteral injection and SPI-452 is formulated as an injectable composition. In one embodiment, there is provided a kit containing the compound of Formula I, Ia, Ib, II or III is formulated as a long acting parenteral injection and SPI-452 formulated as an injectable composition.

In one embodiment of the present invention, a compound of Formula I, Ia, Ib, II or III is used in combination with compounds which are found in previously filed PCT/CN2011/0013021, which is herein incorporated by reference.

The above other therapeutic agents, when employed in combination with the chemical entities described herein, may be used, for example, in those amounts indicated in the Physicians' Desk Reference (PDR) or as otherwise determined by one of ordinary skill in the art.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formula I, Ia, Ib, II or III.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formula I, Ia, Ib, II or III, wherein said virus is an HIV virus. In some embodiments, the HIV virus is the HIV-1 virus.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formula I, Ia, Ib, II or III, further comprising administration of a therapeutically effective amount of one or more agents active against an HIV virus.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formula I, Ia, Ib, II or III, further comprising administration of a therapeutically effective amount of one or more agents active against the HIV virus, wherein said agent active against HIV virus is selected from Nucleotide reverse transcriptase inhibitors; Non-nucleotide reverse transcriptase inhibitors; Protease inhibitors; Entry, attachment and fusion inhibitors; Integrase inhibitors; Maturation inhibitors; CXCR4 inhibitors; and CCR5 inhibitors.

In another aspect, the invention provides a method of depleting latent HIV infected cells comprising administering to a subject a compound of Formula (I), (Ia), (Ib), (II) or (III) or a pharmaceutically acceptable salt thereof.

In various embodiments of the above method, each of $Alk$, $Alk_2$ and $Alk_3$ is represented by the formula:

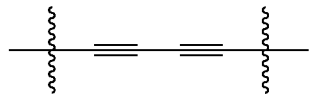 [SMILES: *C#CC#C*]

In various embodiments of the above method, each of $Ar_1$, $Ar_2$, $Ar_3$, $Ar_4$, $Ar_5$, $Ar_6$, $Ar_7$, $Ar_8$, $Ar_9$, $Ar_{10}$, $Ar_{11}$, $Ar_{21}$, $Ar_{22}$, $Ar_{23}$, $Ar_{24}$, $Ar_{25}$ and $Ar_{26}$ is $C_6$ aryl.

In various embodiments of the above invention, each of $Ar_{12}$, $Ar_{13}$, $Ar_{14}$ and $Ar_{15}$, $Ar_{16}$, $Ar_{17}$, $Ar_{18}$, and $Ar_{19}$ is $C_9$ aryl.

In various embodiments of the above invention, each of $Ar_{16}$, $Ar_{17}$, $Ar_{18}$ and $Ar_{19}$ is $C_{10}$ aryl.

In various embodiments of the above invention, the linker (L) is selected from the group consisting of:

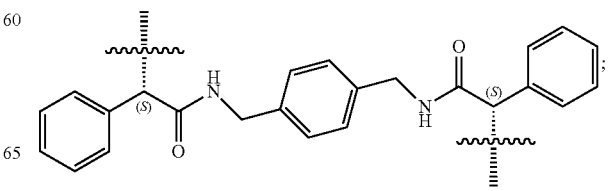

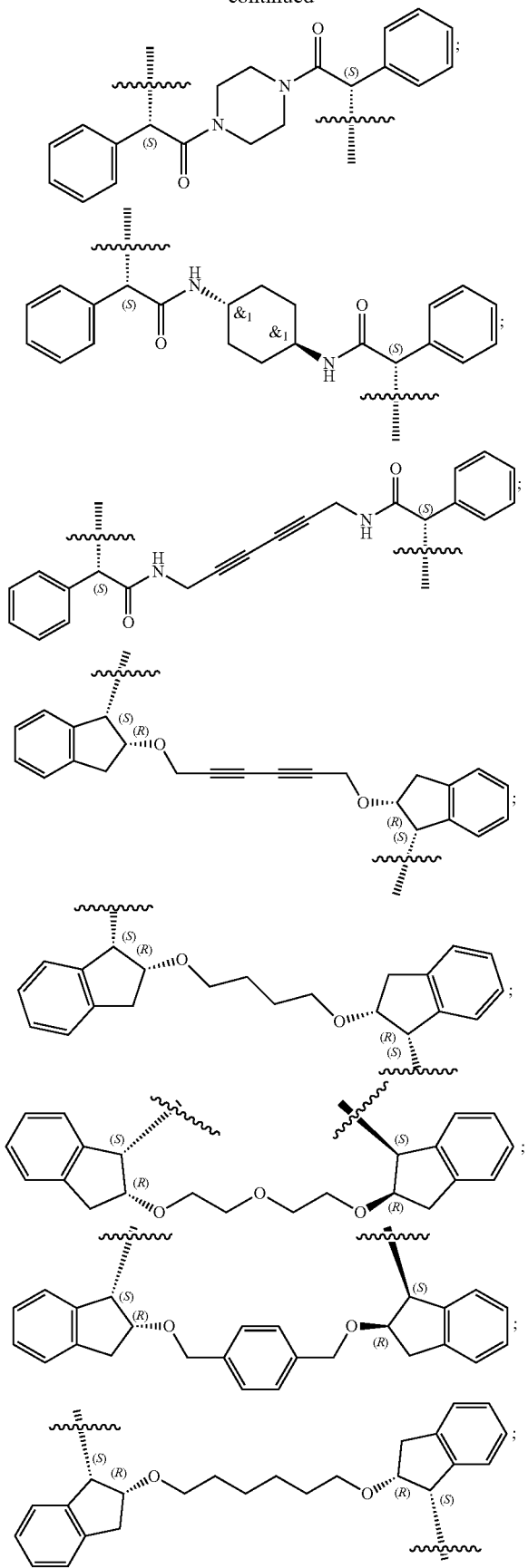
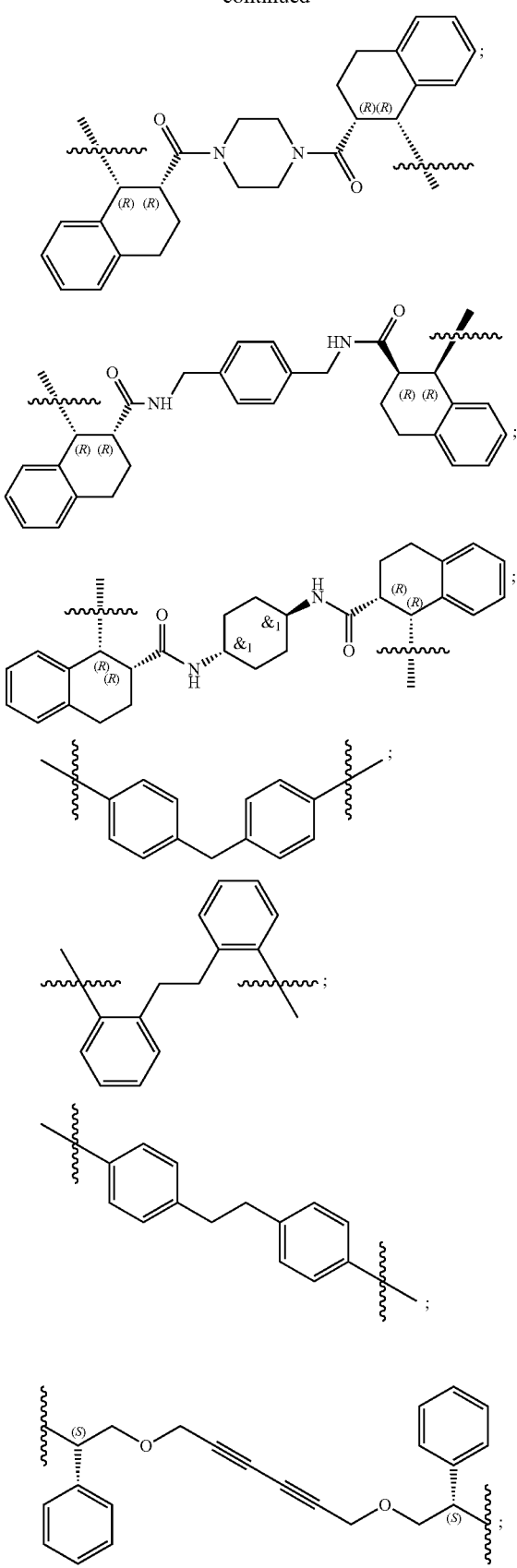

85
-continued

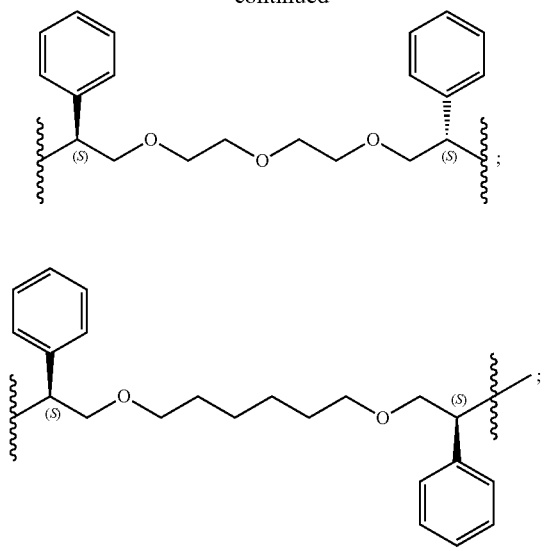

86
-continued

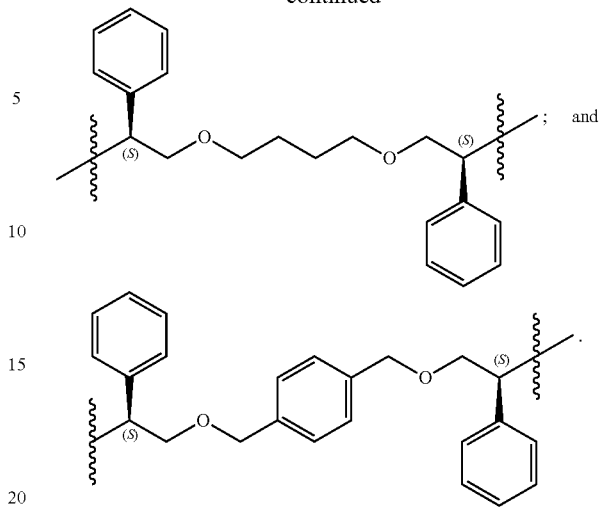

In various embodiments of the above invention, the compound is selected from the group consisting of:

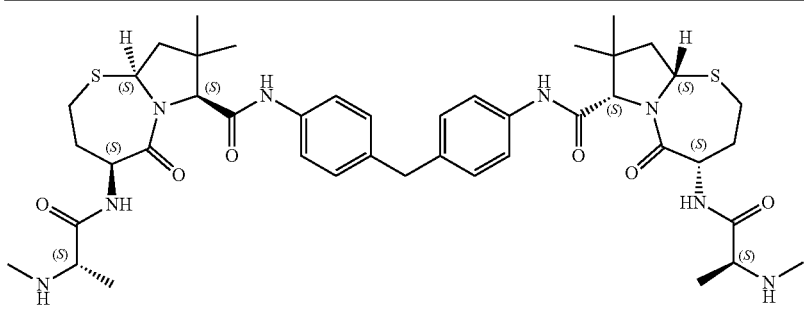

(S,4S,4'S,7S,7'S,9aS,9a'S)-N,N'-(methylenebis(4,1-phenylene))bis(8,8-dimethyl-4-((S)-2-(methylamino) propanamido)-5-oxooctahydropyrrolo[2,1-b][1,3]thiazepine-7-carboxamide)

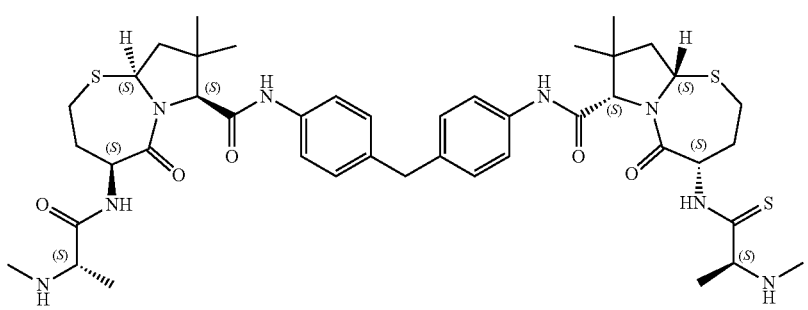

(S,4S,4'S,7S,7'S,9aS,9a'S)-N,N'-(methylenebis(4,1-phenylene))bis(8,8-dimethyl-4-((S)-2-(methylamino) propanethioamido)-5-oxooctahydropyrrolo[2,1-b][1,3]thiazepine-7-carboxamide)

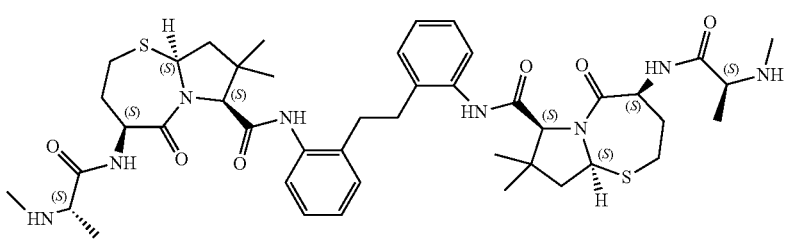

(S,4S,4'S,7S,7'S,9aS,9a'S)-N,N'-(ethane-1,2-diylbis(2,1-phenylene))bis(8,8-dimethyl-4-((S)-2-(methylamino) propanamido)-5-oxooctahydropyrrolo[2,1-b][1,3]thiazepine-7-carboxamide)

-continued

| | |
|---|---|
| 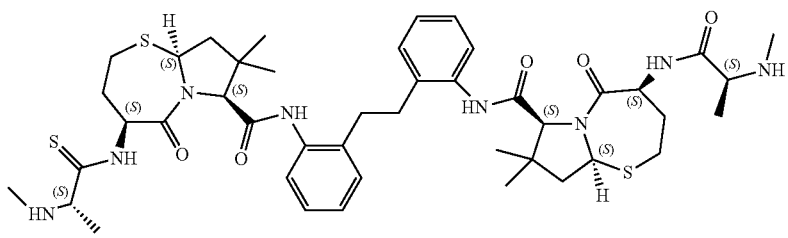 | (S,4S,4'S,7S,7'S,9aS,9a'S)-N,N'-(ethane-1,2-diylbis(2,1-phenylene))bis(8,8-dimethyl-4-((S)-2-(methylamino) propanethioamido)-5-oxooctahydropyrrolo[2,1-b][1,3]thiazepine-7-carboxamide) |
| 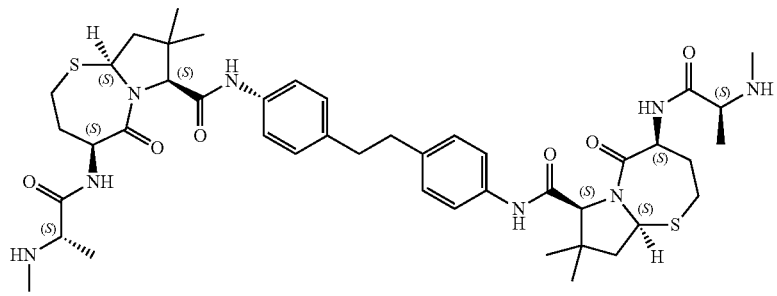 | (S,4S,4'S,7S,7'S,9aS,9a'S)-N,N'-(ethane-1,2-diylbis(4,1-phenylene))bis(8,8-dimethyl-4-((S)-2-(methylamino)propanamido)-5-oxooctahydropyrrolo[2,1-b][1,3]thiazepine-7-carboxamide) |
| 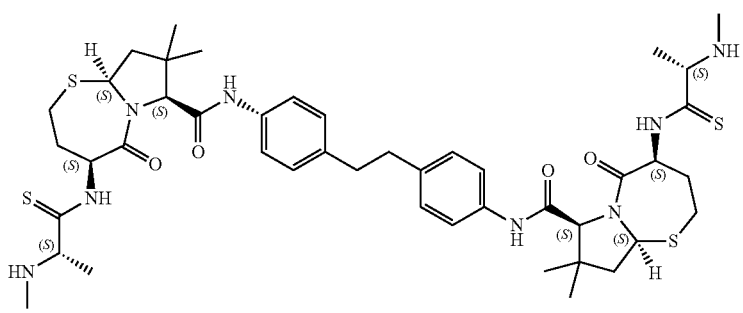 | (S,4S,4'S,7S,7'S,9aS,9a'S)-N,N'-(ethane-1,2-diylbis(4,1-phenylene))bis(8,8-dimethyl-4-((S)-2-(methylamino)propanethioamido)-5-oxooctahydropyrrolo[2,1-b][1,3]thiazepine-7-carboxamide) |
| 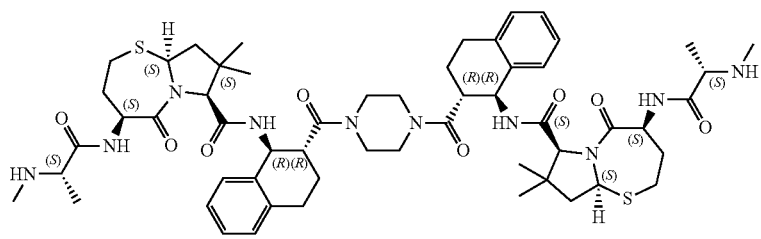 | (S,4S,4'S,7S,7'S,9aS,9a'S)-N,N'-((1R,1'R,2R,2'R)-(piperazine-1,4-dicarbonyl)bis(1,2,3,4-tetrahydronaphthalene-2,1-diyl))bis(8,8-dimethyl-((4(S)-2-(methylamino)propanamido)-5-oxooctahydropyrrolo[2,1-b][1,3]thiazepine-7-carboxamide) |
| 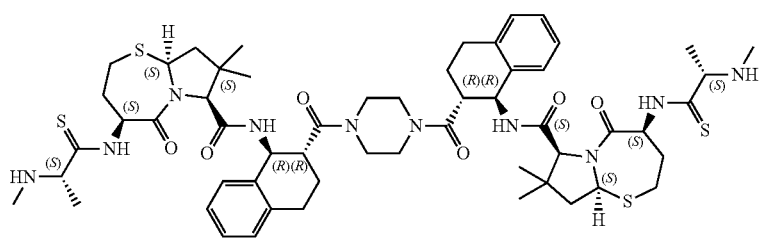 | (S,4S,4'S,7S,7'S,9aS,9a'S)-N,N'-((1R,1'R,2R,2'R)-(piperazine-1,4-dicarbonyl)bis(1,2,3,4-tetrahydronaphthalene-2,1-diyl))bis(8,8-dimethyl-4-((S)-2-(methylamino)propanethioamido)-5-oxooctahydropyrrolo[2,1-b][1,3]thiazepine-7-carboxamide) |
| 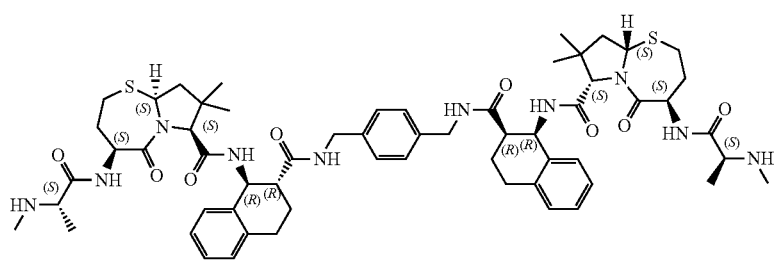 | (S,4S,4'S,7S,7'S,9aS,9a'S)-N,N'-((1R,1'R,2R,2'R)-(((1,4-phenylenebis(methylene))bis(azanediyl))bis(carbonyl))bis(1,2,3,4-tetrahydronaphthalene-2,1-diyl))bis(8,8-dimethyl-4-((S)-2-(methylamino)propanamido)-5-oxooctahydropyrrolo[2,1-b][1,3]thiazepine-7-carboxamide) |

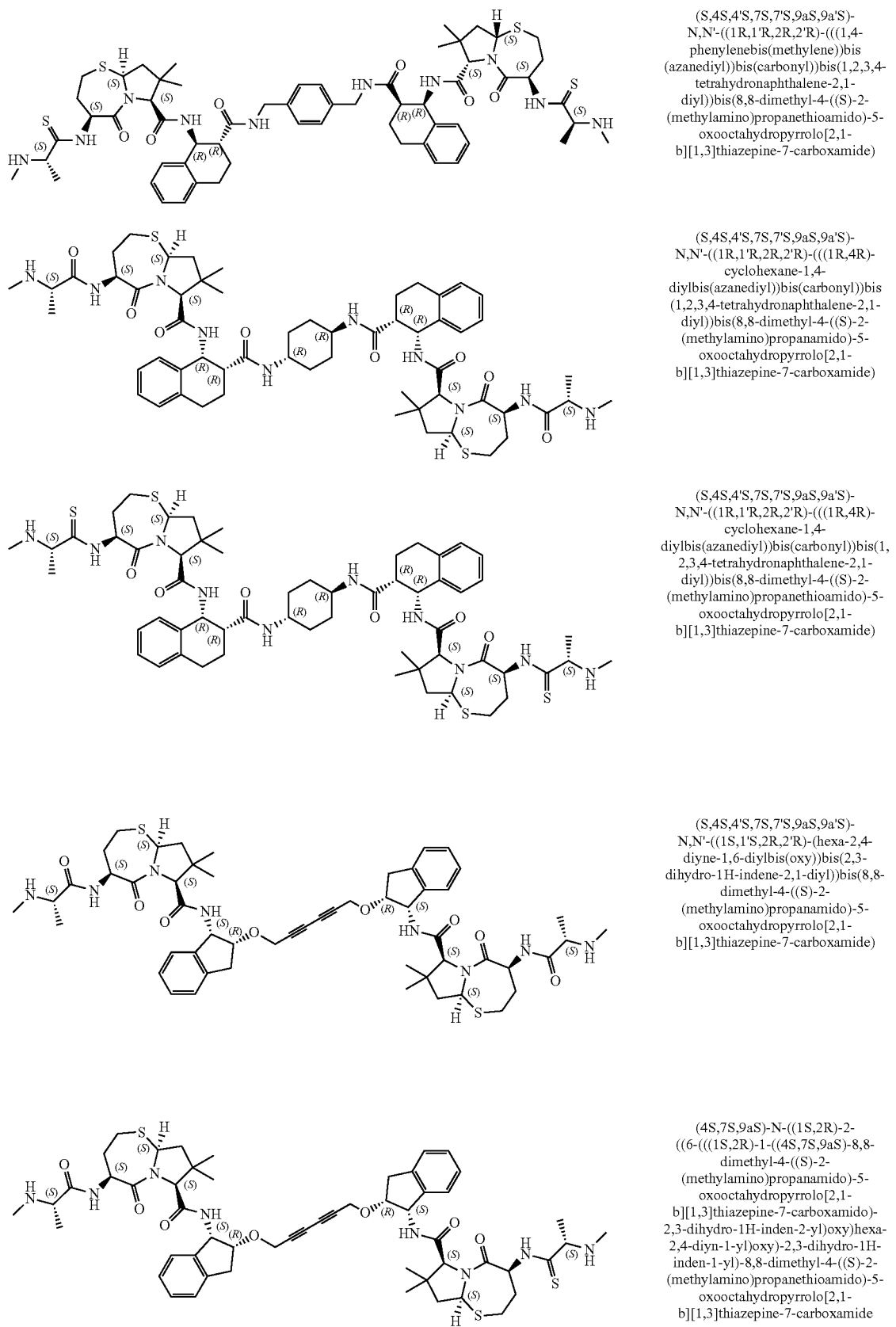

(S,4S,4'S,7S,7'S,9aS,9a'S)-N,N'-((1R,1'R,2R,2'R)-(((1,4-phenylenebis(methylene))bis(azanediyl))bis(carbonyl))bis(1,2,3,4-tetrahydronaphthalene-2,1-diyl))bis(8,8-dimethyl-4-((S)-2-(methylamino)propanethioamido)-5-oxooctahydropyrrolo[2,1-b][1,3]thiazepine-7-carboxamide)

(S,4S,4'S,7S,7'S,9aS,9a'S)-N,N'-((1R,1'R,2R,2'R)-(((1R,4R)-cyclohexane-1,4-diylbis(azanediyl))bis(carbonyl))bis(1,2,3,4-tetrahydronaphthalene-2,1-diyl))bis(8,8-dimethyl-4-((S)-2-(methylamino)propanamido)-5-oxooctahydropyrrolo[2,1-b][1,3]thiazepine-7-carboxamide)

(S,4S,4'S,7S,7'S,9aS,9a'S)-N,N'-((1R,1'R,2R,2'R)-(((1R,4R)-cyclohexane-1,4-diylbis(azanediyl))bis(carbonyl))bis(1,2,3,4-tetrahydronaphthalene-2,1-diyl))bis(8,8-dimethyl-4-((S)-2-(methylamino)propanethioamido)-5-oxooctahydropyrrolo[2,1-b][1,3]thiazepine-7-carboxamide)

(S,4S,4'S,7S,7'S,9aS,9a'S)-N,N'-((1S,1'S,2R,2'R)-(hexa-2,4-diyne-1,6-diylbis(oxy))bis(2,3-dihydro-1H-indene-2,1-diyl))bis(8,8-dimethyl-4-((S)-2-(methylamino)propanamido)-5-oxooctahydropyrrolo[2,1-b][1,3]thiazepine-7-carboxamide)

(4S,7S,9aS)-N-((1S,2R)-2-((6-(((1S,2R)-1-((4S,7S,9aS)-8,8-dimethyl-4-((S)-2-(methylamino)propanamido)-5-oxooctahydropyrrolo[2,1-b][1,3]thiazepine-7-carboxamido)-2,3-dihydro-1H-inden-2-yl)oxy)hexa-2,4-diyn-1-yl)oxy)-2,3-dihydro-1H-inden-1-yl)-8,8-dimethyl-4-((S)-2-(methylamino)propanethioamido)-5-oxooctahydropyrrolo[2,1-b][1,3]thiazepine-7-carboxamide

| | |
|---|---|
| 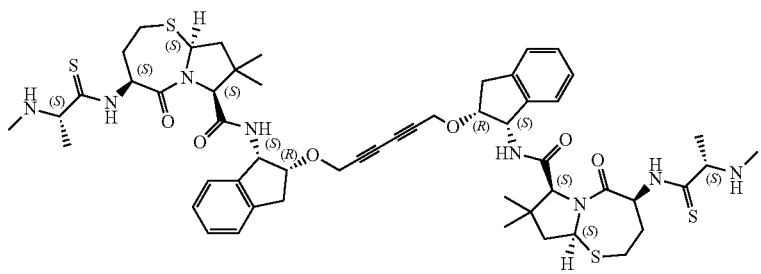 | (S,4S,4'S,7S,7'S,9aS,9a'S)-N,N'-((1S,1'S,2R,2'R)-(hexa-2,4-diyne-1,6-diylbis(oxy))bis(2,3-dihydro-1H-indene-2,1-diyl))bis(8,8-dimethyl-4-((S)-2-(methylamino)propanethioamido)-5-oxooctahydropyrrolo[2,1-b][1,3]thiazepine-7-carboxamide) |
| 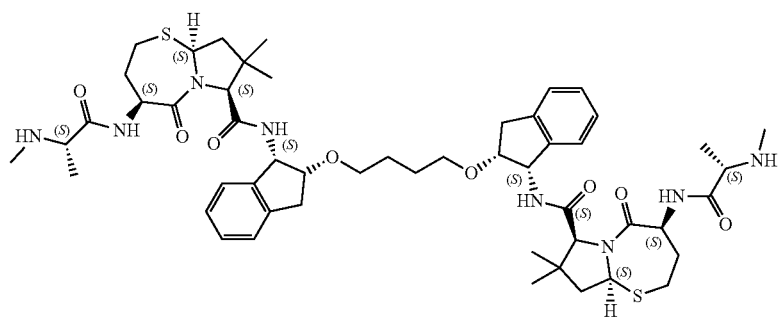 | (S,4S,4'S,7S,7'S,9aS,9a'S)-N,N'-((1S,1'S,2R,2'R)-(butane-1,4-diylbis(oxy))bis(2,3-dihydro-1H-indene-2,1-diylbis(8,8-dimethyl-4-((S)-2-(methylamino)propanamido)-5-oxooctahydropyrrolo[2,1-b][1,3]thiazepine-7-carboxamide) |
| 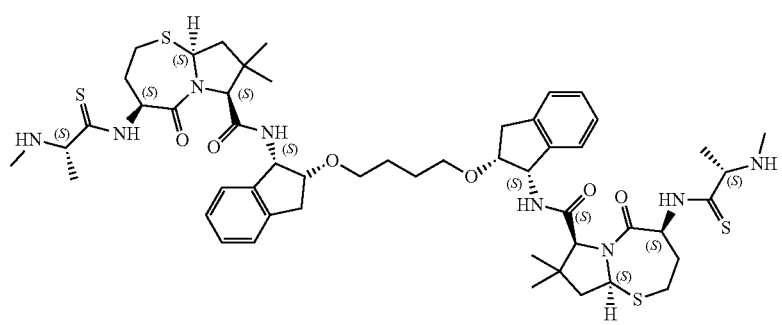 | (S,4S,4'S,7S,7'S,9aS,9a'S)-N,N'-((1S,1'S,2R,2'R)-(butane-1,4-diylbis(oxy))bis(2,3-dihydro-1H-indene-2,1-diyl))bis(8,8-dimethyl-4-((S)-2-(methylamino)propanethioamido)-5-oxooctahydropyrrolo[2,1-b][1,3]thiazepine-7-carboxamide) |
| 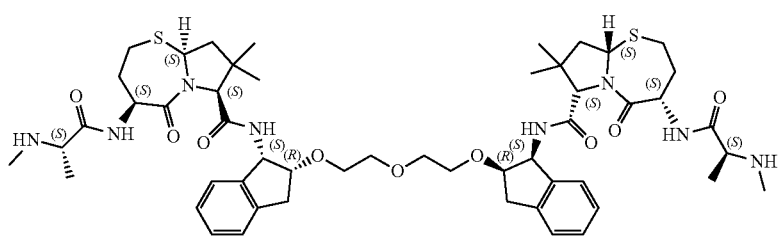 | (S,4S,4'S,7S,7'S,9aS,9a'S)-N,N'-((1S,1'S,2R,2'R)-((oxybis(ethane-2,1-diyl))bis(oxy))bis(2,3-dihydro-1H-indene-2,1-diyl))bis(8,8-dimethyl-4-((S)-2-(methylamino)propanamido)-5-oxooctahydropyrrolo[2,1-b][1,3]thiazepine-7-carboxamide) |
| 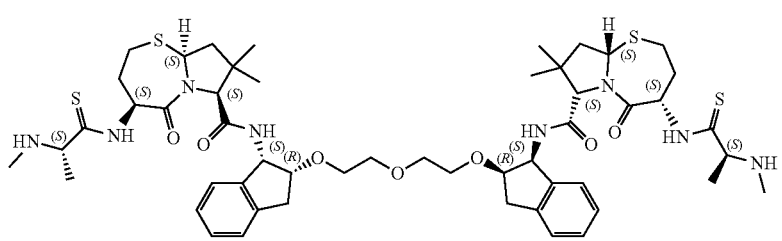 | (S,4S,4'S,7S,7'S,9aS,9a'S)-N,N'-((1S,1'S,2R,2'R)-((oxybis(ethane-2,1-diyl)bis(oxy))bis(2,3-dihydro-1H-indene-2,1-diyl))bis(8,8-dimethyl-4-((S)-2-(methylamino)propanethioamido)-5-oxooctahydropyrrolo[2,1-b][1,3]thiazepine-7-carboxamide) |

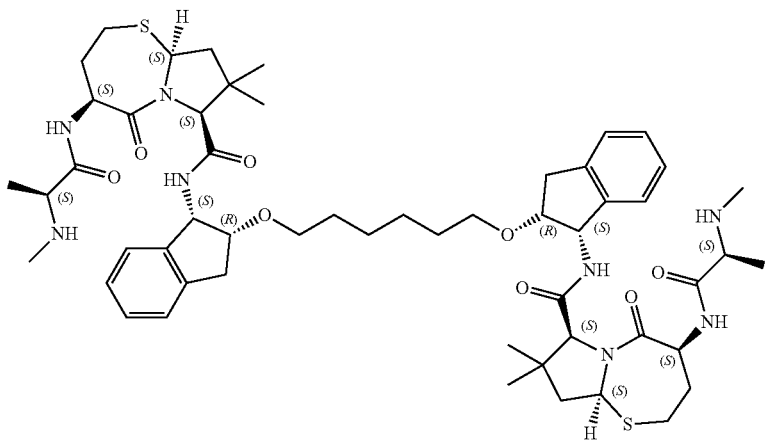

(S,4S,4'S,7S,7'S,9aS,9a'S)-N,N'-((1S,1'S,2R,2'R)-(hexane-1,6-diylbis(oxy))bis(2,3-dihydro-1H-indene-2,1-diyl))bis(8,8-dimethyl-4-((S)-2-(methylamino)propanamido)-5-oxooctahydropyrrolo[2,1-b][1,3]thiazepine-7-carboxamide)

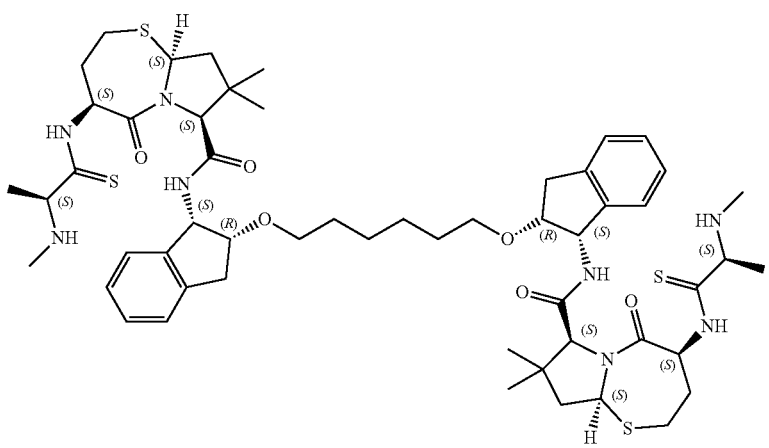

(S,4S,4'S,7S,7'S,9aS,9a'S)-N,N'-((1S,1'S,2R,2'R)-(hexane-1,6-diylbis(oxy))bis(2,3-dihydro-1H-indene-2,1-diyl))bis(8,8-dimethyl-4-((S)-2-(methylamino)propanethioamido)-5-oxooctahydropyrrolo[2,1-b][1,3]thiazepine-7-carboxamide)

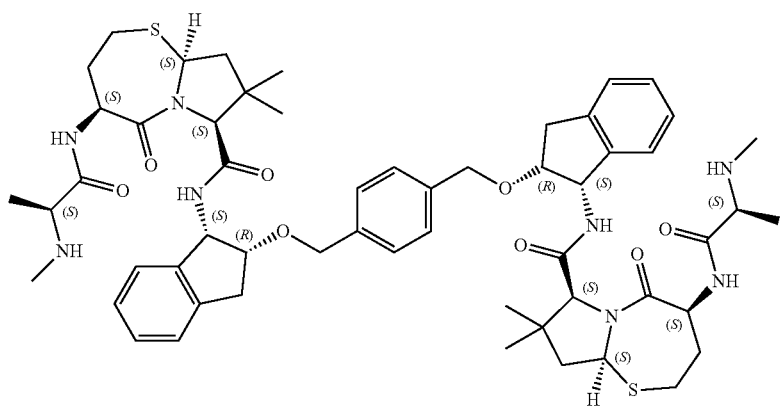

(S,4S,4'S,7S,7'S,9aS,9a'S)-N,N'-((1S,1'S,2R,2'R)-((1,4-phenylenebis(methylene))bis(oxy))bis(2,3-dihydro-1H-indene-2,1-diyl))bis(8,8-dimethyl-4-((S)-2-(methylamino)propanamido)-5-oxooctahydropyrrolo[2,1-b][1,3]thiazepine-7-carboxamide)

-continued

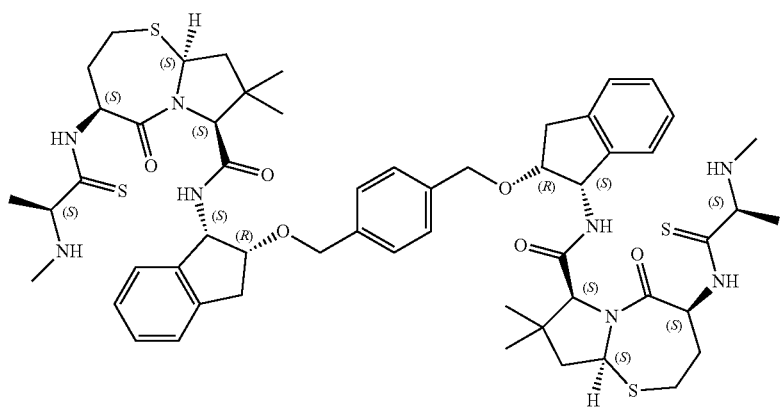

(S,4S,4'S,7S,7'S,9aS,9a'S)-
N,N'-((1S,1'S,2R,2'R)-((1,4-
phenylenebis(methylene))bis(oxy))
bis(2,3-dihydro-1H-indene-2,1-
diyl))bis(8,8-dimethyl-4-((S)-2-
(methylamino)propanethioamido)-5-
oxooctahydropyrrolo[2,1-
b][1,3]thiazepine-7-carboxamide)

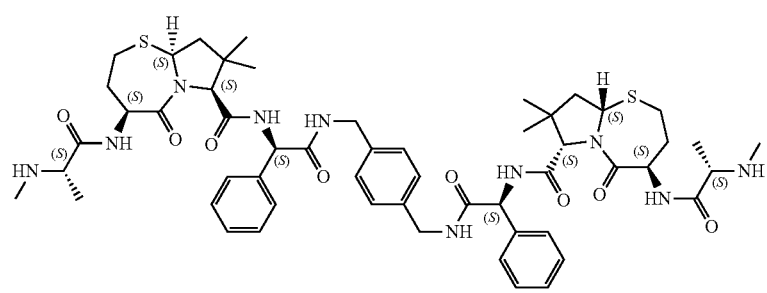

(S,4S,4'S,7S,7'S,9aS,9a'S)-
N,N'-((1S,1'S)-((1,4-
phenylenebis(methylene))bis
(azanediyl))bis(2-oxo-1-phenylethane-2,1-
diyl))bis(8,8-dimethyl-4-((S)-2-
(methylamino)propanamido)-5-
oxooctahydropyrrolo[2,1-
b][1,3]thiazepine-7-carboxamide)

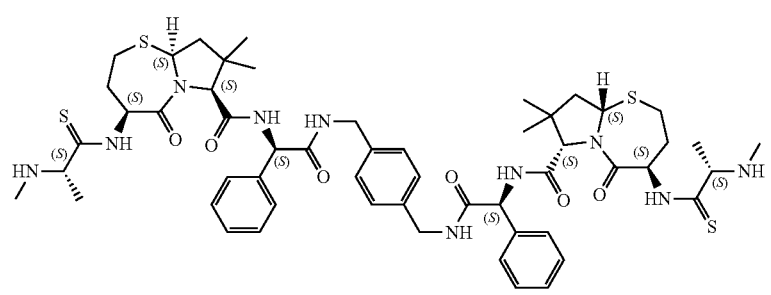

(S,4S,4'S,7S,7'S,9aS,9a'S)-
N,N'-((1S,1'S)-((1,4-
phenylenebis(methylene))bis
(azanediyl))bis(2-oxo-1-phenylethane-2,1-
diyl))bis(8,8-dimethyl-4-((S)-2-
(methylamino)propanethioamido)-5-
oxooctahydropyrrolo[2,1-
b][1,3]thiazepine-7-carboxamide)

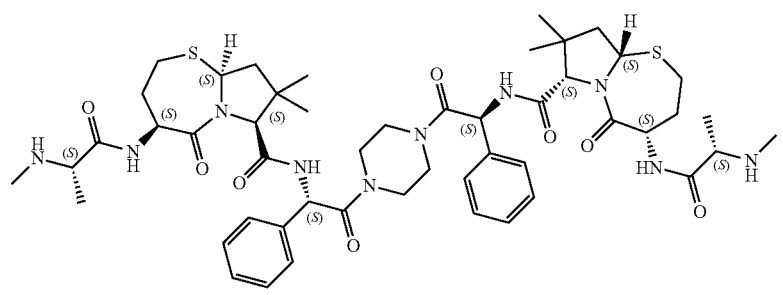

(S,4S,4'S,7S,7'S,9aS,9a'S)-
N,N'-((1S,1'S)-piperazine-1,4-
diylbis(2-oxo-1-phenylethane-2,1-
diyl))bis(8,8-dimethyl-4-((S)-2-
(methylamino)propanamido)-5-
oxooctahydropyrrolo[2,1-
b][1,3]thiazepine-7-carboxamide)

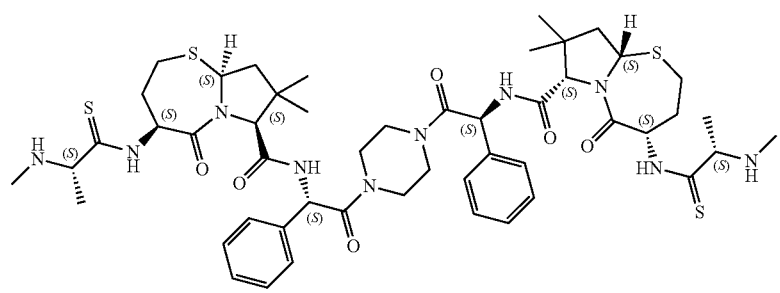

(S,4S,4'S,7S,7'S,9aS,9a'S)-
N,N'-((1S,1'S)-piperazine-1,4-
diylbis(2-oxo-1-phenylethane-2,1-
diyl))bis(8,8-dimethyl-4-((S)-2-
(methylamino)propanethioamido)-5-
oxooctahydropyrrolo[2,1-
b][1,3]thiazepine-7-carboxamide)

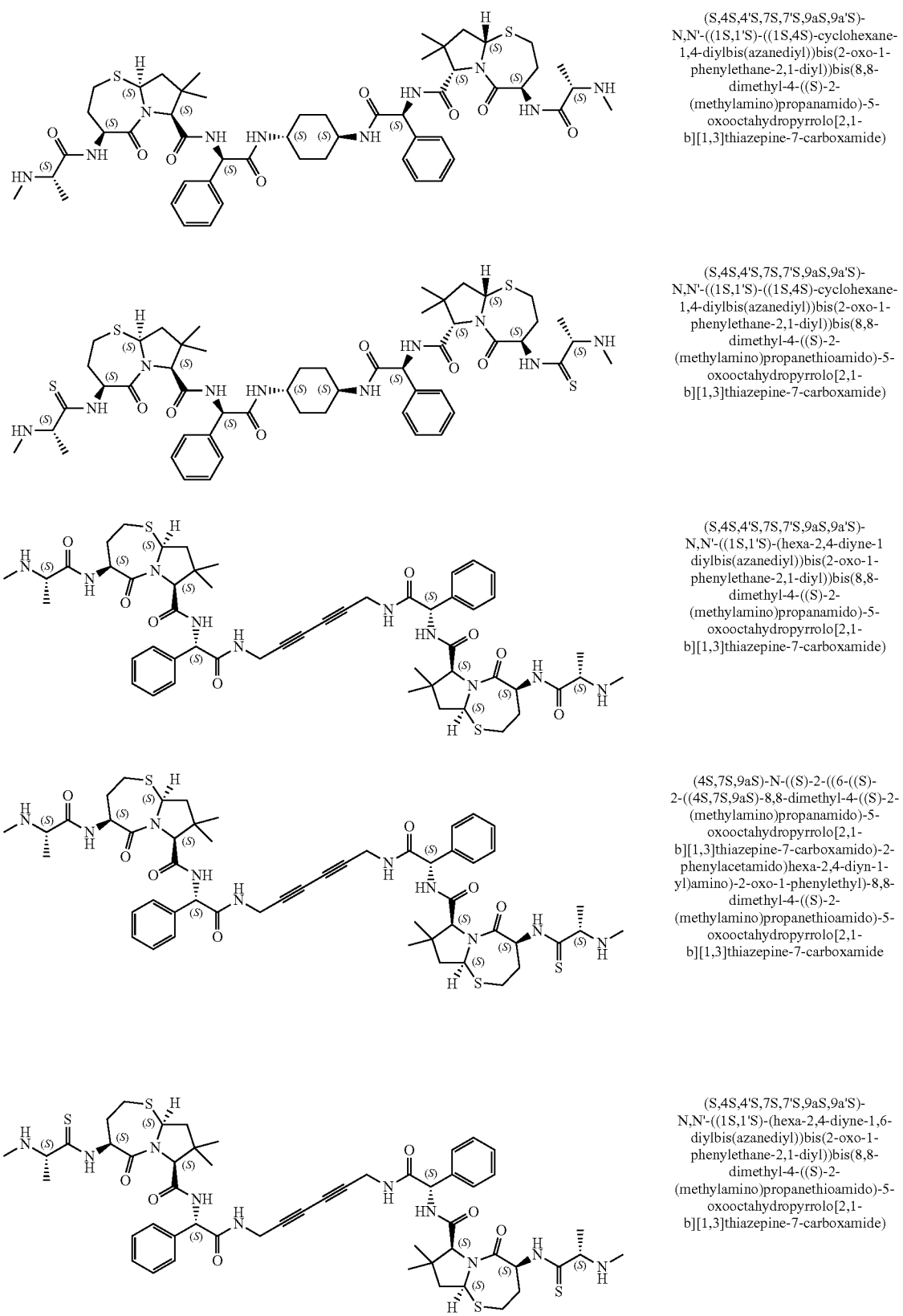

(S,4S,4'S,7S,7'S,9aS,9a'S)-
N,N'-((1S,1'S)-((1S,4S)-cyclohexane-
1,4-diylbis(azanediyl))bis(2-oxo-1-
phenylethane-2,1-diyl))bis(8,8-
dimethyl-4-((S)-2-
(methylamino)propanamido)-5-
oxooctahydropyrrolo[2,1-
b][1,3]thiazepine-7-carboxamide)

(S,4S,4'S,7S,7'S,9aS,9a'S)-
N,N'-((1S,1'S)-((1S,4S)-cyclohexane-
1,4-diylbis(azanediyl))bis(2-oxo-1-
phenylethane-2,1-diyl))bis(8,8-
dimethyl-4-((S)-2-
(methylamino)propanethioamido)-5-
oxooctahydropyrrolo[2,1-
b][1,3]thiazepine-7-carboxamide)

(S,4S,4'S,7S,7'S,9aS,9a'S)-
N,N'-((1S,1'S)-(hexa-2,4-diyne-1
diylbis(azanediyl))bis(2-oxo-1-
phenylethane-2,1-diyl))bis(8,8-
dimethyl-4-((S)-2-
(methylamino)propanamido)-5-
oxooctahydropyrrolo[2,1-
b][1,3]thiazepine-7-carboxamide)

(4S,7S,9aS)-N-((S)-2-((6-((S)-
2-((4S,7S,9aS)-8,8-dimethyl-4-((S)-2-
(methylamino)propanamido)-5-
oxooctahydropyrrolo[2,1-
b][1,3]thiazepine-7-carboxamido)-2-
phenylacetamido)hexa-2,4-diyn-1-
yl)amino)-2-oxo-1-phenylethyl)-8,8-
dimethyl-4-((S)-2-
(methylamino)propanethioamido)-5-
oxooctahydropyrrolo[2,1-
b][1,3]thiazepine-7-carboxamide (S,4S,4'S,7S,7'S,9aS,9a'S)-
N,N'-((1S,1'S)-(hexa-2,4-diyne-1,6-
diylbis(azanediyl))bis(2-oxo-1-
phenylethane-2,1-diyl))bis(8,8-
dimethyl-4-((S)-2-
(methylamino)propanethioamido)-5-
oxooctahydropyrrolo[2,1-
b][1,3]thiazepine-7-carboxamide)

-continued

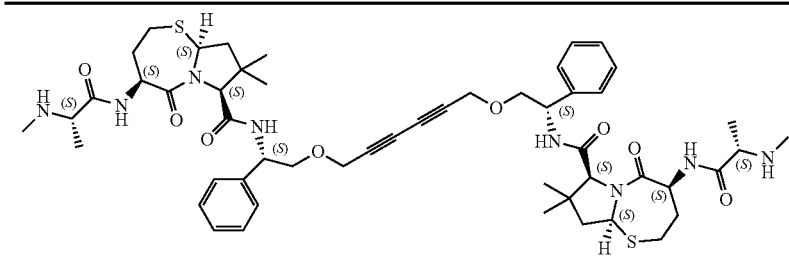

(S,4S,4'S,7S,7'S,9aS,9a'S)-N,N'-((1S,1'S)-(hexa-2,4-diyn-1,6-diylbis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide)

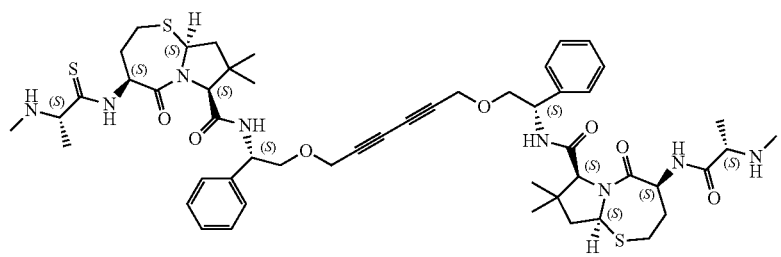

(4S,7S,9aS)-N-((S)-2-((6-((S)-2-((4S,7S,9aS)-8,8-dimethyl-4-((S)-2-(methylamino)propanamido)-5-oxooctahydropyrrolo[2,1-b][1,3]thiazepine-7-carboxamido)-2-phenylethoxy)hexa-2,4-diyn-1-yl)oxy)-1-phenylethyl)-8,8-dimethyl-4-((S)-2-(methylamino)propanethioamido)-5-oxooctahydropyrrolo[2,1-b][1,3]thiazepine-7-carboxamide

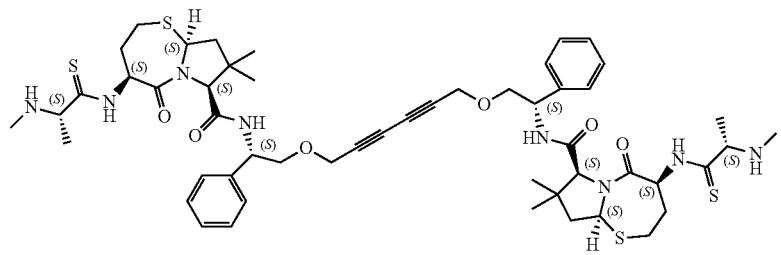

(S,4S,4'S,7S,7'S,9aS,9a'S)-N,N'-((1S,1'S)-(hexa-2,4-diyn-1,6-diylbis(oxy))bis(1-phenylethane-2,1-diyl))bis(8,8-dimethyl-4-((S)-2-(methylamino)propanethioamido)-5-oxooctahydropyrrolo[2,1-b][1,3]thiazepine-7-carboxamide)

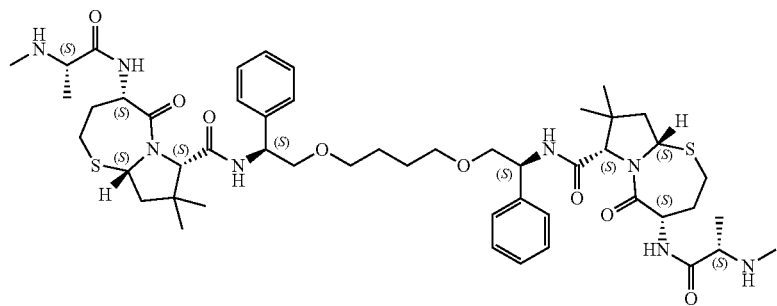

(S,4S,4'S,7S,7'S,9aS,9a'S)-N,N'-((1S,1'S)-(butane-1,4-diylbis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide)

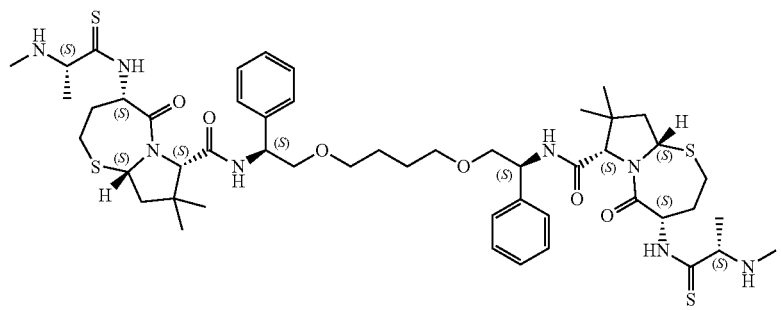

(S,4S,4'S,7S,7'S,9aS,9a'S)-N,N'-((1S,1'S)-(butane-1,4-diylbis(oxy))bis(1-phenylethane-2,1-diyl))bis(8,8-dimethyl-4-((S)-2-(methylamino)propanethioamido)-5-oxooctahydropyrrolo[2,1-b][1,3]thiazepine-7-carboxamide)

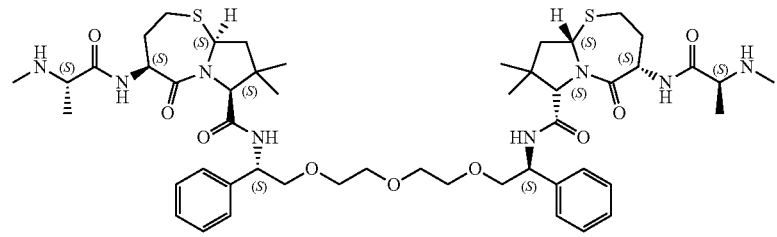

(S,4S,4'S,7S,7'S,9aS,9a'S)-N,N'-((1S,1'S)-((oxybis(ethane-2,1-diyl))bis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide)

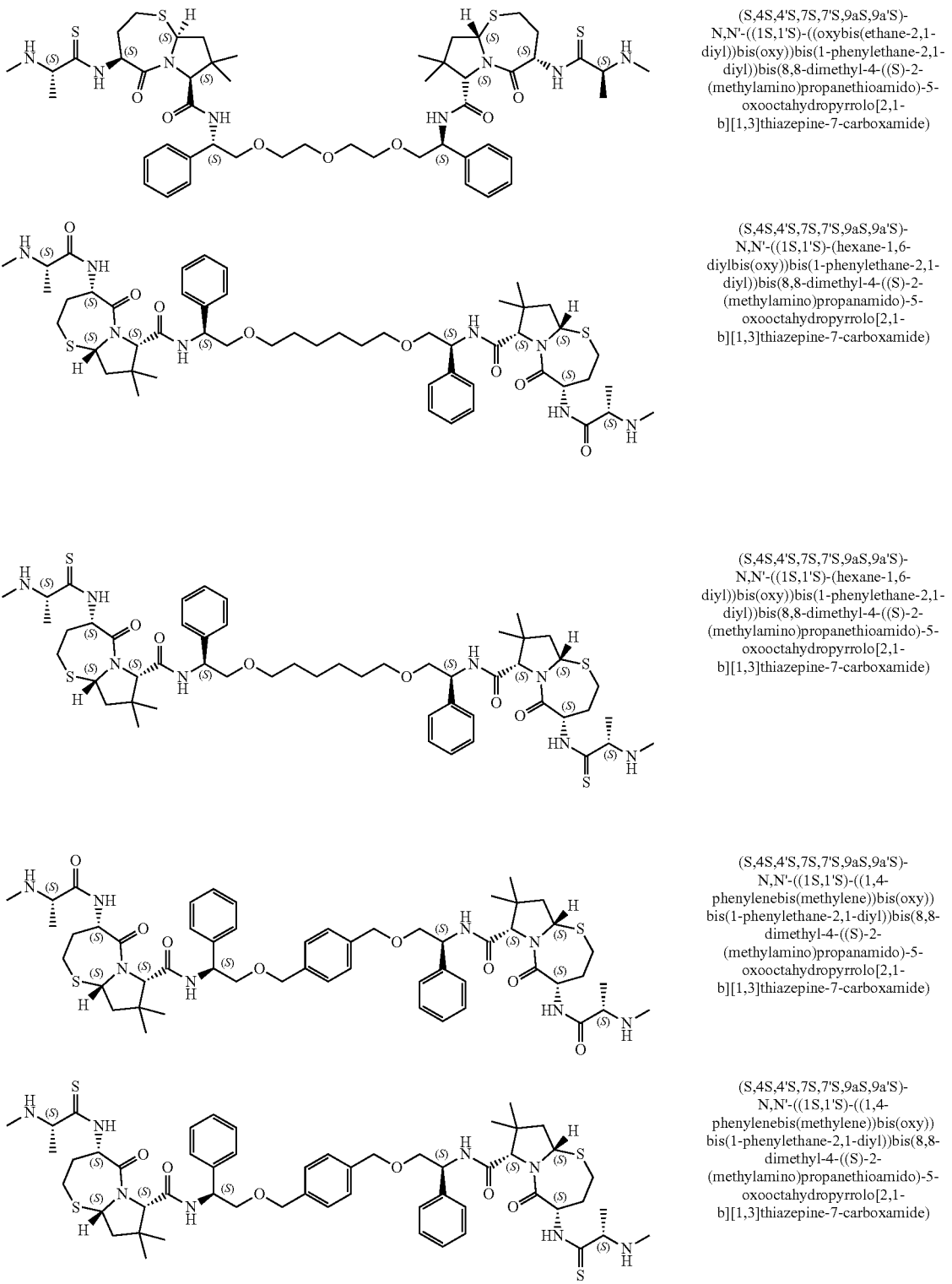

In various embodiments of the above method, $X_1$ and $X_2$ are each O, preferably for the Formulas (Ia) and (Ib).

In various embodiments of the above method, in the linker (L), each of $Ar_1$, $Ar_2$, $Ar_3$, $Ar_4$, $Ar_5$, $Ar_6$, $Ar_7$, $Ar_8$, $Ar_9$, $Ar_{10}$, $Ar_{11}$, $Ar_{20}$, $Ar_{21}$, $Ar_{22}$, $Ar_{23}$, and $Ar_{24}$ is $C_6$ aryl.

In various embodiments of the above method, the linker (L) is selected from the group consisting of (i) and (v).

In various embodiments of the above method, each of m, n, p, and q is 1 and each $(CH_2)_{0-3}$ group in formula (v) is represented by $(CH_2)$.

In various embodiments of the above method, as well as compounds, the linker (L) is selected from the group consisting of:

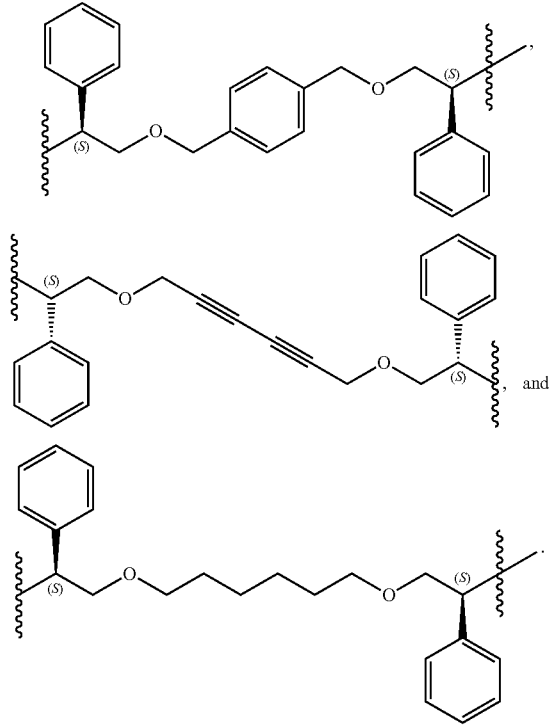

In various embodiments of the above method, the linker (L) is selected from the group consisting of (vi) and (vii), and each of $Ar_{12}$, $Ar_{13}$, $Ar_{14}$ and $Ar_{15}$ is $C_9$ aryl.

In various embodiments of the above method, each of $Ar_{12}$ and $Ar_{14}$ is

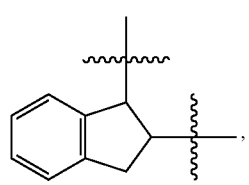 [SMILES: *C1Cc2ccccc2C1*]

and each of $Ar_{13}$ and $Ar_{15}$ is

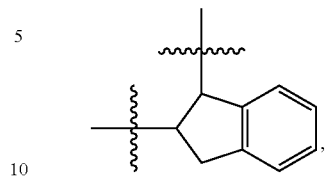

where the wavy lines represent points of attachment.

In various embodiments of the above method, the linker (L) is selected from the group consisting of:

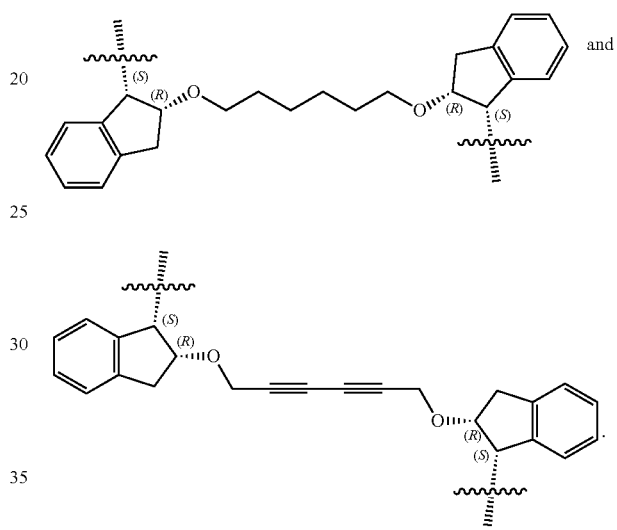

In one embodiment of the invention, the invention relates to a compound (compound 13) of the formula:

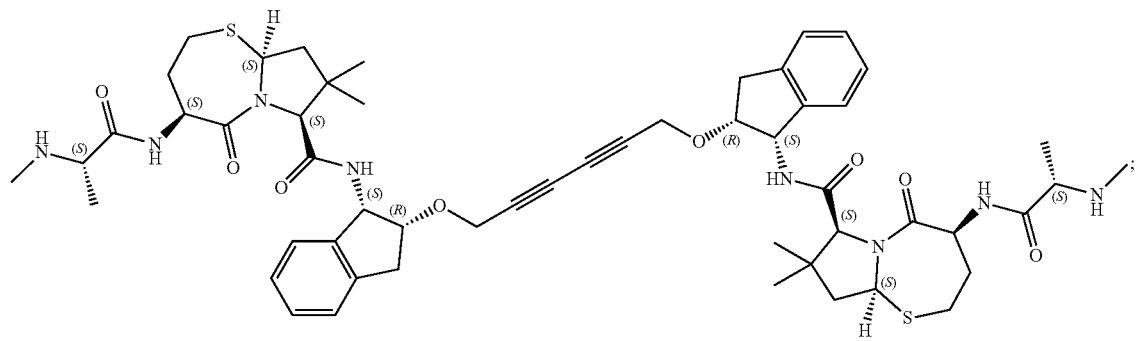

or a pharmaceutically acceptable salt thereof. The invention also includes a pharmaceutical composition comprising this compound, or a pharmaceutically acceptable salt thereof, and a pharmaceutically acceptable excipient including e.g., those set forth herein. The invention also includes a method of treating an HIV infection in a subject comprising administering to the subject this compound or a pharmaceutically acceptable salt thereof, as well as combinations. The invention also includes this compound, or a pharmaceutically acceptable salt thereof, for use in treating an HIV infection.

The invention also includes use of this compound, in the manufacture of a medicament for treating an HIV infection. The invention also includes a method of depleting latent HIV infected cells comprising administering to a subject this compound or a pharmaceutically acceptable salt thereof, as well as combinations thereof.

In one embodiment of the invention, the invention relates to a compound (compound 20) of the formula:

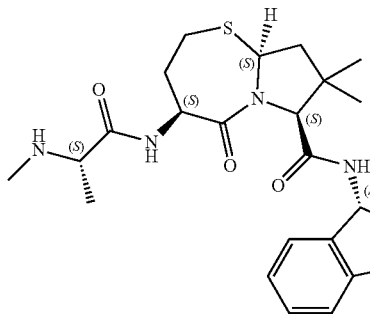
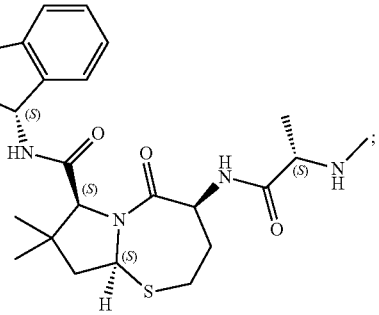

or a pharmaceutically acceptable salt thereof. The invention also includes a pharmaceutical composition comprising this compound, or a pharmaceutically acceptable salt thereof, and a pharmaceutically acceptable excipient. including e.g., those set forth herein. The invention also includes a method of treating an HIV infection in a subject comprising administering to the subject this compound or a pharmaceutically acceptable salt thereof, as well as combinations. The invention also includes this compound, or a pharmaceutically acceptable salt thereof, for use in treating an HIV infection. The invention also includes use of this compound, in the manufacture of a medicament for treating an HIV infection. The invention also includes a method of depleting latent HIV infected cells comprising administering to a subject this compound or a pharmaceutically acceptable salt thereof, as well as combinations thereof.

In various embodiments, the method of depleting latent HIV infection further comprises administering to the subject one or more additional agents active against HIV as disclosed hereinabove. As an example, in various embodiments, the one or more additional agents is selected from the group consisting of nucleotide reverse transcriptase inhibitors, non-nucleotide reverse transcriptase inhibitors, protease inhibitors, entry inhibitors, attachment and fusion inhibitors, integrase inhibitors, maturation inhibitors, CXCR4 and/or CCR5 inhibitors, histone deacetylase inhibitors, histone crotonyl transferase inhibitors, protein kinase C agonists, proteasome inhibitors, TLR7 agonists, bromodomain inhibitors, and antibodies for clearance therapy, and combinations thereof. In various embodiments, the one or more additional agents active against HIV is selected from the group consisting of zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine e, efavirenz, loviride, immunocal, oltipraz, capravirine, lersivirine, GSK2248761, TMC-278, TMC-125, etravirine, saquinavir, ritonavir, indinavir, nelfinavir, amprenavir, fosamprenavir, brecanavir, darunavir, atazanavir, tipranavir, palinavir, lasinavir, enfuvirtide, T-20, T-1249, PRO-542, PRO-140, TNX-355, BMS-806, BMS-663068 and BMS-626529, 5-Helix, raltegravir, elvitegravir, dolutegravir, cabotegravir, bictegravir, vicriviroc (Sch-C), Sch-D, TAK779, maraviroc, TAK449, didanosine, tenofovir, lopinavir, darunavir, vorinostat, panobinostat, romidepin, valpronic acid, mocetinostat, sodium corotonate, bryostatin, ingenol B, disulforam, GS-9620, JQ1, iBET151, bortezomib, epigallocatechin gallate, salinosporamide A, carfilzomib, and neutralizing antibodies, eCD4-Ig, CD4-g, bNAb, DARTS and IgA.

The compounds according to Formula I, Ia, Ib, II and III and pharmaceutically acceptable salts thereof may be useful in the treatment of cancer, pre-cancerous syndromes. Suitably the present invention relates to a method for treating cancers selected from the group consisting of brain (gliomas), glioblastomas, astrocytomas, glioblastoma multiforme, Bannayan-Zonana syndrome, Cowden disease, Lhermitte-Duclos disease, Wilm's tumor, Ewing's sarcoma, Rhabdomyosarcoma, ependymoma, medulloblastoma, head and neck, kidney, liver, melanoma, ovarian, pancreatic, adenocarcinoma, ductal adenocarcinoma, adenosquamous carcinoma, acinar cell carcinoma, glucagonoma, insulinoma, prostate, sarcoma, osteosarcoma, giant cell tumor of bone, thyroid, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, Immunoblastic large cell leukemia, mantle cell leukemia, multiple myeloma, megakaryoblastic leukemia, multiple myeloma, acute megakaryocytic leukemia, promyelocytic leukemia, erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

Suitably the present invention relates to a method for treating pre-cancerous syndromes in a mammal, including a human, wherein the pre-cancerous syndrome is selected from: cervical intraepithelial neoplasia, monoclonal gammapathy of unknown significance (MGUS), myelodysplastic syndrome, aplastic anemia, cervical lesions, skin nevi (pre-melanoma), prostatic intraepithleial (intraductal) neoplasia (PIN), Ductal Carcinoma in situ (DCIS), colon polyps and severe hepatitis or cirrhosis.

The compounds of Formulas (I), (Ia), (Ib), (II), (III) and pharmaceutically acceptable salts thereof may be co-administered with at least one other active agent known to be useful in the treatment of cancer or pre-cancerous syndromes.

By the term "co-administration" as used herein is meant either simultaneous administration or any manner of separate sequential administration of a c-MYC inhibiting compound, as described herein, and a further active agent or agents, known to be useful in the treatment of cancer, including chemotherapy and radiation treatment. The term further active agent or agents, as used herein, includes any compound or therapeutic agent known to or that demonstrates advantageous properties when administered to a patient in need of treatment for cancer. Preferably, if the administration is not simultaneous, the compounds are administered in a close time proximity to each other. Furthermore, it does not matter if the compounds are administered in the same dosage form, e.g. one compound may be administered by injection and another compound may be administered orally.

Examples of a further active ingredient or ingredients (anti-neoplastic agent) for use in combination or co-administered with the presently invented combinations are indicated below. This list is non-limiting. Additional anti-neoplastic agents are contemplated for use with the presently invented compounds.

Typically, any anti-neoplastic agent that has activity versus a susceptible tumor being treated may be co-administered in the treatment of cancer in the present invention. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and *vinca* alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; cell cycle signaling inhibitors; proteasome inhibitors; and inhibitors of cancer metabolism.

Examples of a further active ingredient or ingredients (anti-neoplastic agent) for use in combination or co-administered with the presently invented compounds are chemotherapeutic agents.

Anti-microtubule or anti-mitotic agents are phase specific agents active against the microtubules of tumor cells during M or the mitosis phase of the cell cycle. Examples of anti-microtubule agents include, but are not limited to, diterpenoids and *vinca* alkaloids.

Diterpenoids, which are derived from natural sources, are phase specific anti-cancer agents that operate at the $G_2/M$ phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate β-ester with (2R,3S)—N-benzoyl-3-phenylisoserine; is a natural diterpene product isolated from the Pacific yew tree *Taxus brevifolia* and is commercially available as an injectable solution TAXOL. It is a member of the taxane family of terpenes. It was first isolated in 1971 by Wani et al. J. Am. Chem. Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Intern, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine, N-tert-butyl ester, 13-ester with 5β-20-epoxy-1,2α,4,7β, 10β,13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine [R—(R*,R*)-2,3-dihydroxybutanedioate (1:2) (salt)], commercially available as an injectable solution of vinorelbine tartrate (NAVELBINE®), is a semisynthetic *vinca* alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine [1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids, leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S, 10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2(1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2', 2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl) methyl] methylamino] benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I: DNA: irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b] quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681, 835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagagonists such as goserelin acetate and luprolide.

Signal transduction pathway inhibitors are those inhibitors, which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3 domain blockers, serine/threonine kinases, phosphotidylinositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases. Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6): 803-818; Shawver et al DDT Vol 2, No. 2 Feb. 1997; and Lofts, F. J. et al, "Growth factor receptors as targets", New Molecular Targets for Cancer Chemotherapy, ed. Workman, Paul and Kerr, David, CRC press 1994, London.

Suitably, the pharmaceutically active compounds of the invention are used in combination with a VEGFR inhibitor, suitably 5-[[4-[(2,3-dimethyl-2H-indazol-6-yl)methylamino]-2-pyrimidinyl]amino]-2-methylbenzenesulfonamide, or a pharmaceutically acceptable salt, suitably the monohydrochloride salt thereof, which is disclosed and claimed in International Application No. PCT/US01/49367, having an International filing date of Dec. 19, 2001, International Publication Number WO02/059110 and an International Publication date of Aug. 1, 2002, the entire disclosure of which is hereby incorporated by reference, and which is the compound of Example 69. 5-[[4-[(2,3-dimethyl-2H-indazol-6-yl)methylamino]-2-pyrimidinyl] amino]-2-methylbenzenesulfonamide can be prepared as described in International Application No. PCT/US01/49367.

Suitably, 5-[[4-[(2,3-dimethyl-2H-indazol-6-yl)methylamino]-2-pyrimidinyl]amino]-2-methylbenzenesulfonamide is in the form of a monohydrochloride salt. This salt form can be prepared by one of skill in the art from the description in International Application No. PCT/US01/49367, having an International filing date of Dec. 19, 2001.

5-[[4-[(2,3-dimethyl-2H-indazol-6-yl)methylamino]-2-pyrimidinyl]amino]-2-methylbenzenesulfonamide is sold commercially as the monohydrochloride salt and is known by the generic name pazopanib and the trade name Votrient®.

Pazopanib is implicated in the treatment of cancer and ocular diseases/angiogenesis. Suitably the present invention relates to the treatment of cancer and ocular diseases/angiogenesis, suitably age-related macular degeneration, which method comprises the administration of a compound of Formula (I) alone or in combination with pazopanib.

Tyrosine kinases, which are not growth factor receptor kinases are termed non-receptor tyrosine kinases. Non-receptor tyrosine kinases for use in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual review of Immunology. 15:371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, akt kinase family members, PDK1 and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; Pearce, L. R et al. Nature Reviews Molecular Cell Biology (2010) 11, 9-22. and Martinez-Iacaci, L., et al, Int. J. Cancer (2000), 88(1), 44-52.

Suitably, the pharmaceutically active compounds of the invention are used in combination with a MEK inhibitor. Suitably, N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide, or a pharmaceutically acceptable salt or solvate, suitably the dimethyl sulfoxide solvate, thereof, which is disclosed and claimed in International Application No. PCT/JP2005/011082, having an International filing date of Jun. 10, 2005; International Publication Number WO 2005/121142 and an International Publication date of Dec. 22, 2005, the entire disclosure of which is hereby incorporated by reference. N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide, can be prepared as described in United States Patent Publication No. US 2006/0014768, Published Jan. 19, 2006, the entire disclosure of which is hereby incorporated by reference.

Suitably, the pharmaceutically active compounds of the invention are used in combination with a B-Raf inhibitor. Suitably, N-{3-[5-(2-Amino-4-pyrimidinyl)-2-(1,1-dimethylethyl)-1,3-thiazol-4-yl]-2-fluorophenyl}-2,6-difluorobenzenesulfonamide, or a pharmaceutically acceptable salt thereof, which is disclosed and claimed, in International Application No. PCT/US2009/042682, having an International filing date of May 4, 2009, the entire disclosure of which is hereby incorporated by reference. N-{3-[5-(2-Amino-4-pyrimidinyl)-2-(1,1-dimethylethyl)-1,3-thiazol-4-yl]-2-fluorophenyl}-2,6-difluorobenzenesulfonamide can be prepared as described in International Application No. PCT/US2009/042682.

Suitably, the pharmaceutically active compounds of the invention are used in combination with an Akt inhibitor. Suitably, N-{(1S)-2-amino-1-[(3,4-difluorophenyl)methyl]ethyl}-5-chloro-4-(4-chloro-1-methyl-1H-pyrazol-5-yl)-2-furancarboxamide or a pharmaceutically acceptable salt thereof, which is disclosed and claimed in International Application No. PCT/US2008/053269, having an International filing date of Feb. 7, 2008; International Publication Number WO 2008/098104 and an International Publication date of Aug. 14, 2008, the entire disclosure of which is hereby incorporated by reference. N-{(1S)-2-amino-1-[(3,4-difluorophenyl)methyl]ethyl}-5-chloro-4-(4-chloro-1-methyl-1H-pyrazol-5-yl)-2-furancarboxamide is the compound of example 224 and can be prepared as described in International Application No. PCT/US2008/053269.

Suitably, the pharmaceutically active compounds of the invention are used in combination with an Akt inhibitor. Suitably, N-{(1S)-2-amino-1-[(3-fluorophenyl)methyl]ethyl}-5-chloro-4-(4-chloro-1-methyl-1H-pyrazol-5-yl)-2-thiophenecarboxamide or a pharmaceutically acceptable salt thereof, which is disclosed and claimed in International Application No. PCT/US2008/053269, having an International filing date of Feb. 7, 2008; International Publication Number WO 2008/098104 and an International Publication date of Aug. 14, 2008, the entire disclosure of which is hereby incorporated by reference. N-{(1S)-2-amino-1-[(3-fluorophenyl)methyl]ethyl}-5-chloro-4-(4-chloro-1-methyl-1H-pyrazol-5-yl)-2-thiophenecarboxamide is the compound of example 96 and can be prepared as described in International Application No. PCT/US2008/053269. Suitably, N-{(1S)-2-amino-1-[(3-fluorophenyl)methyl]ethyl}-5-chloro-4-(4-chloro-1-methyl-1H-pyrazol-5-yl)-2-thiophenecarboxamide is in the form of a hydrochloride salt. The salt form can be prepared by one of skill in the art from the description in International Application No. PCT/US2010/022323, having an International filing date of Jan. 28, 2010.

Inhibitors of Phosphotidylinositol-3 Kinase family members including blockers of PI3-kinase, ATM, DNA-PK, and Ku may also be useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also of interest in the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer:erbB Family Receptor Tyrosine Kniases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Non-receptor kinase angiogenesis inhibitors may also be useful in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Accordingly, non-receptor tyrosine kinase inhibitors may be used in combination with the compounds of the present invention. For example, anti-VEGF antibodies, which do not recognize VEGFR (the receptor tyrosine kinase), but bind to the ligand; small molecule inhibitors of integrin (alpha, betas) that will inhibit angiogenesis; endostatin and angiostatin (non-RTK) may also prove useful in combination with the disclosed compounds. (See Bruns C J et al (2000), Cancer Res., 60: 2926-2935; Schreiber A B, Winkler M E, and Derynck R. (1986), Science, 232: 1250-1253; Yen L et al. (2000), Oncogene 19: 3460-3469).

Agents used in immunotherapeutic regimens may also be useful in combination with the compounds of Formula (I). There are a number of immunologic strategies to generate an immune response. These strategies are generally in the realm of tumor vaccinations. The efficacy of immunologic approaches may be greatly enhanced through combined inhibition of signaling pathways using a small molecule inhibitor. Discussion of the immunologic/tumor vaccine approach against erbB2/EGFR are found in Reilly R T et al. (2000), Cancer Res. 60: 3569-3576; and Chen Y, Hu D, Eling D J, Robbins J, and Kipps T J. (1998), Cancer Res. 58: 1965-1971.

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812-1823; and Kitada S et al. (1994), Antisense Res. Dev. 4: 71-79.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230. Further, p21WAF1/CIP1 has been described as a potent and universal inhibitor of cyclin-dependent kinases (Cdks) (Ball et al., Progress in Cell Cycle Res., 3: 125 (1997)). Compounds that are known to induce expression of p21WAF1/CIP1 have been implicated in the suppression of cell proliferation and as having tumor suppressing activity (Richon et al., Proc. Nat Acad. Sci. U.S.A. 97(18): 10014-10019 (2000)), and are included as cell cycle signaling inhibitors. Histone deacetylase (HDAC) inhibitors are implicated in the transcriptional activation of p21WAF1/CIP1 (Vigushin et al., Anticancer Drugs, 13(1): 1-13 (January 2002)), and are suitable cell cycle signaling inhibitors for use in combination herein.

Examples of such HDAC inhibitors include:

1. Vorinostat, including pharmaceutically acceptable salts thereof. Marks et al., Nature Biotechnology 25, 84 to 90 (2007); Stenger, Community Oncology 4, 384-386 (2007).

Vorinostat has the following chemical structure and name:

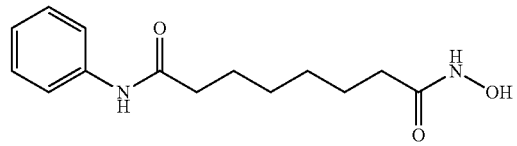

N-hydroxy-N'-phenyl-octanediamide

2. Romidepsin, including pharmaceutically acceptable salts thereof.
Vinodhkumar et al., Biomedicine & Pharmacotherapy 62 (2008) 85-93.
Romidepsin, has the following chemical structure and name:

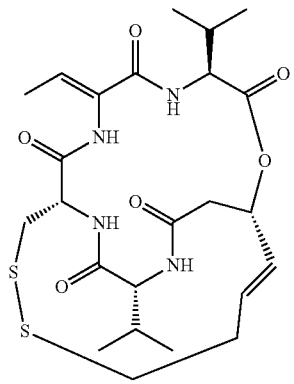

(1S,4S,7Z,10S,16E,21R)-7-ethylidene-4,21-di(propan-2-yl)-2-oxa-12,13-oxa,130 dithia-5,8,20,23-tetrazabicyclo[8.7.6]tricos-16-ene-3,6,9,19,22-pentone 3. Panobinostat, including pharmaceutically acceptable salts thereof. Drugs of the Future 32(4): 315-322 (2007).
Panobinostat, has the following chemical structure and name:

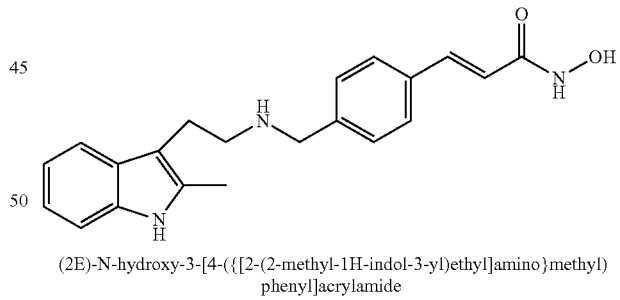

(2E)-N-hydroxy-3-[4-({[2-(2-methyl-1H-indol-3-yl)ethyl]amino}methyl)phenyl]acrylamide 4. Valproic acid, including pharmaceutically acceptable salts thereof. Gottlicher, et al., EMBO J. 20(24): 6969-6978 (2001).
Valproic acid, has the following chemical structure and name:

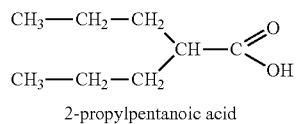

2-propylpentanoic acid

5. Mocetinostat (MGCD0103), including pharmaceutically acceptable salts thereof. Balasubramanian et al., Cancer Letters 280: 211-221 (2009).

Mocetinostat, has the following chemical structure and name:

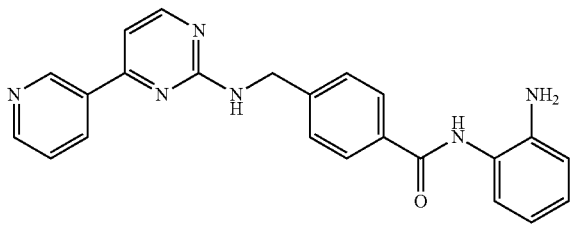

N-(2-Aminophenyl)-4-[[(4-pyridin-3-ylpyrimidin-2-yl)amino]methyl]benzamide

Further examples of such HDAC inhibitors are included in Bertrand European Journal of Medicinal Chemistry 45, (2010) 2095-2116, particularly the compounds of table 3 therein as indicated below.

Hydroxamic acids

1

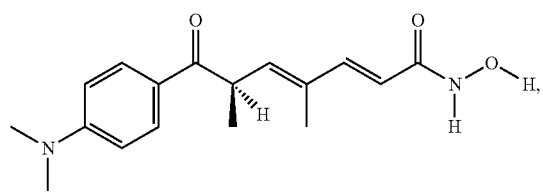

Trichostatine A (TSA)

2

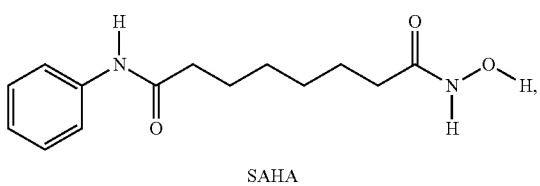

SAHA

3

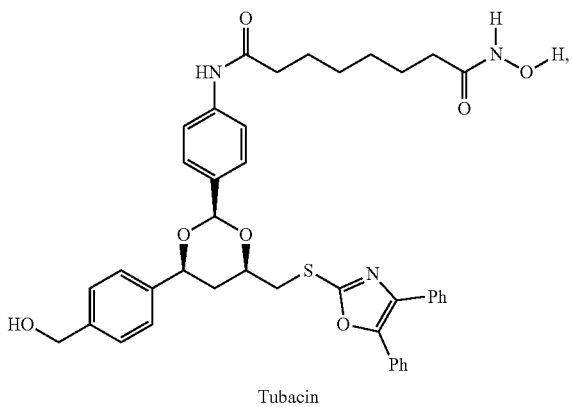

Tubacin

4

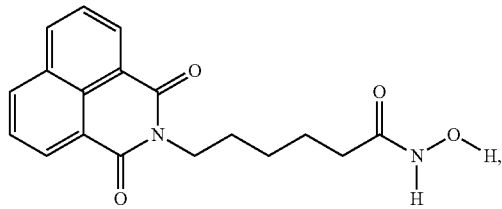

LAQ824

5

Sulfonamide

6

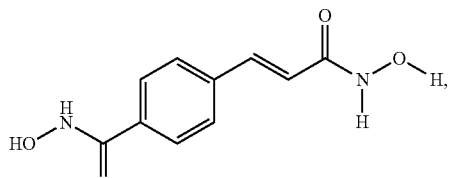

Scriptaid

7

CBHA

8

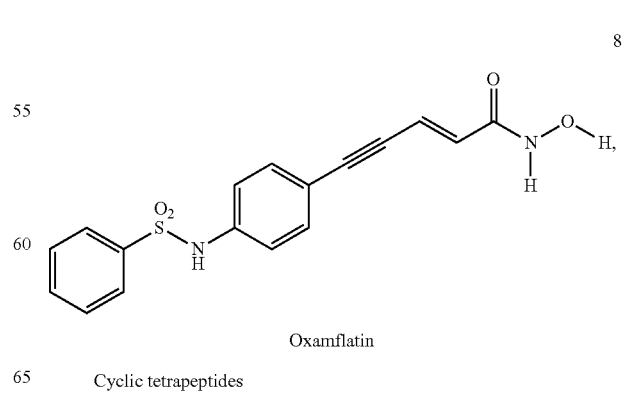

Oxamflatin

Cyclic tetrapeptides

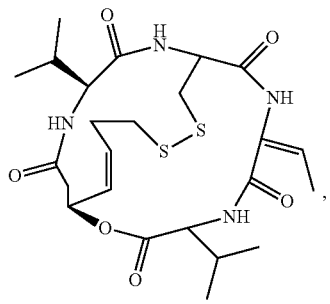

FK228

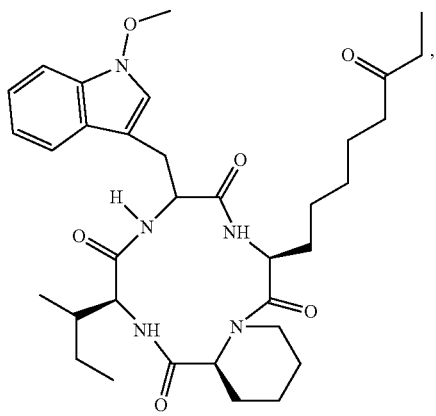

Apicidin

Short chain carboxylic acids

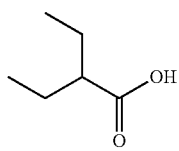

Valproic acid

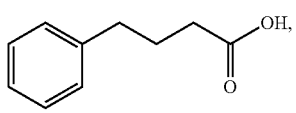

Phenylbutyric acid

Benzamides

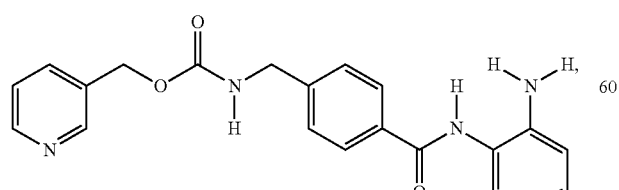

MS-275

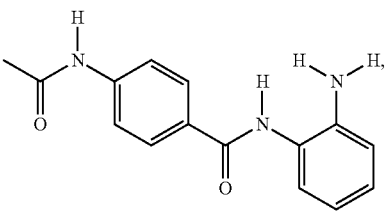

Cl-994

Keto derivatives

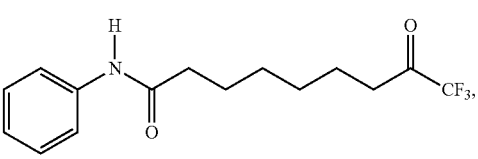

Trifluorométhyl cétone

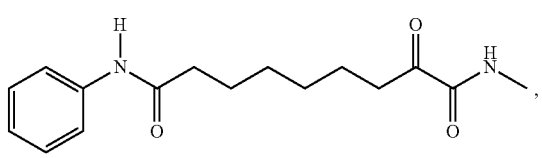

alpha-cétoamide

Proteasome inhibitors are drugs that block the action of proteasomes, cellular complexes that break down proteins, like the p53 protein. Several proteasome inhibitors are marketed or are being studied in the treatment of cancer. Suitable proteasome inhibitors for use in combination herein include:

1. Bortezomib (Velcade®), including pharmaceutically acceptable salts thereof. Adams J, Kauffman M (2004), *Cancer Invest* 22 (2): 304-11.

Bortezomib has the following chemical structure and name.

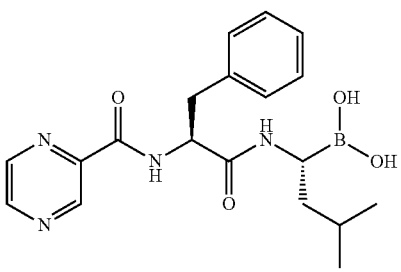

[(1R)-3-methyl-1-({(2S)-3-phenyl-2-[(pyrazin-2-ylcarbonyl)amino]propanoyl}amino)butyl]boronic acid 2. Disulfiram, including pharmaceutically acceptable salts thereof.

Bouma et al. (1998). *J. Antimicrob. Chemother.* 42 (6): 817-20.

Disulfiram has the following chemical structure and name.

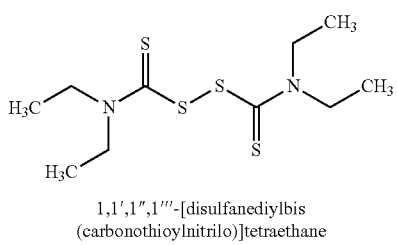 [SMILES: CCN(CC)C(=S)SSC(=S)N(CC)CC]

1,1',1'',1'''-[disulfanediylbis
(carbonothioylnitrilo)]tetraethane

3. Epigallocatechin gallate (EGCG), including pharmaceutically acceptable salts thereof. Williamson et al., (December 2006), *The Journal of Allergy and Clinical Immunology* 118 (6): 1369-74.

Epigallocatechin gallate has the following chemical structure and name.

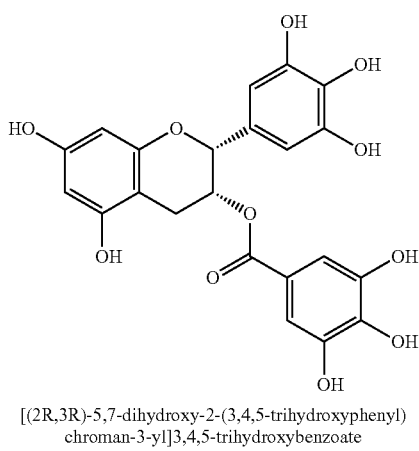 [SMILES: O=C(O[C@@H]1Cc2c(O)cc(O)cc2O[C@@H]1c1cc(O)c(O)c(O)c1)c1cc(O)c(O)c(O)c1]

[(2R,3R)-5,7-dihydroxy-2-(3,4,5-trihydroxyphenyl)
chroman-3-yl]3,4,5-trihydroxybenzoate 4. Salinosporamide A, including pharmaceutically acceptable salts thereof.

Feling et at., (2003), *Angew. Chem. Int. Ed. Engl.* 42 (3): 355-7.

Salinosporamide A has the following chemical structure and name.

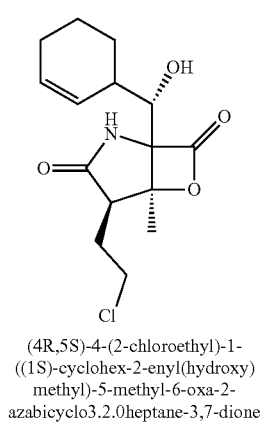 [SMILES: C[C@@]12OC(=O)C1([C@@H](O)C1C=CCCC1)NC(=O)[C@@H]2CCCl]

(4R,5S)-4-(2-chloroethyl)-1-
((1S)-cyclohex-2-enyl(hydroxy)
methyl)-5-methyl-6-oxa-2-
azabicyclo3.2.0heptane-3,7-dione 5. Carfilzomib, including pharmaceutically acceptable salts thereof. Kuhn D J, et al, Blood, 2007, 110:3281-3290.

Carfilzomib has the following chemical structure and name.

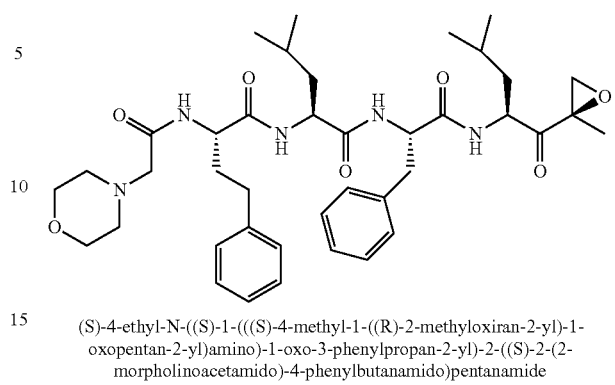

(S)-4-ethyl-N-((S)-1-(((S)-4-methyl-1-((R)-2-methyloxiran-2-yl)-1-
oxopentan-2-yl)amino)-1-oxo-3-phenylpropan-2-yl)-2-((S)-2-(2-
morpholinoacetamido)-4-phenylbutanamido)pentanamide The 70 kilodalton heat shock proteins (Hsp70s) and 90 kilodalton heat shock proteins (Hsp90s) are a families of ubiquitously expressed heat shock proteins. Hsp70s and Hsp90s are over expressed certain cancer types. Several Hsp70s and Hsp90s inhibitors are being studied in the treatment of cancer. Suitable Hsp70s and Hsp90s inhibitors for use in combination herein include:

1. 17-AAG (Geldanamycin), including pharmaceutically acceptable salts thereof. Jia W et al. *Blood*. 2003 Sep. 1; 102(5):1824-32.

17-AAG (Geldanamycin) has the following chemical structure and name.

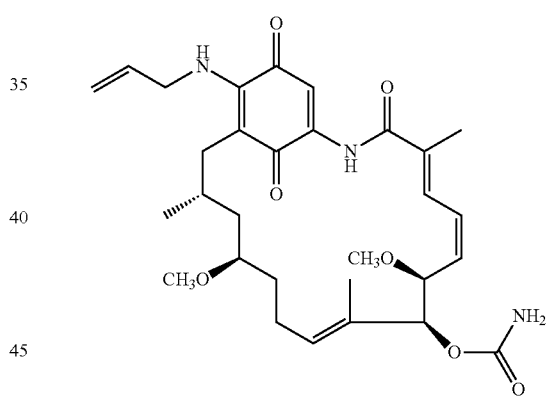

17-(Allylamino)-17-demethoxygeldanamycin

2. Radicicol, including pharmaceutically acceptable salts thereof. (Lee et al., Mol Cell Endocrinol. 2002, 188, 47-54)

Radicicol has the following chemical structure and name.

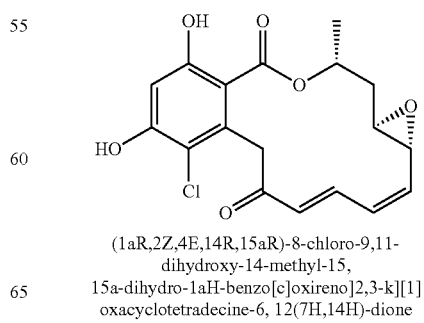

(1aR,2Z,4E,14R,15aR)-8-chloro-9,11-
dihydroxy-14-methyl-15,
15a-dihydro-1aH-benzo[c]oxireno]2,3-k][1]
oxacyclotetradecine-6, 12(7H,14H)-dione Inhibitors of cancer metabolism—Many tumor cells show a markedly different metabolism from that of normal tissues. For example, the rate of glycolysis, the metabolic process that converts glucose to pyruvate, is increased, and the pyruvate generated is reduced to lactate, rather than being further oxidized in the mitochondria via the tricarboxylic acid (TCA) cycle. This effect is often seen even under aerobic conditions and is known as the Warburg Effect.

Lactate dehydrogenase A (LDH-A), an isoform of lactate dehydrogenase expressed in muscle cells, plays a pivotal role in tumor cell metabolism by performing the reduction of pyruvate to lactate, which can then be exported out of the cell. The enzyme has been shown to be upregulated in many tumor types. The alteration of glucose metabolism described in the Warburg effect is critical for growth and proliferation of cancer cells and knocking down LDH-A using RNA-i has been shown to lead to a reduction in cell proliferation and tumor growth in xenograft models.

D. A. Tennant et. al., Nature Reviews, 2010, 267.

P. Leder, et. al., Cancer Cell, 2006, 9, 425.

High levels of fatty acid synthase (FAS) have been found in cancer precursor lesions. Pharmacological inhibition of FAS affects the expression of key oncogenes involved in both cancer development and maintenance.

Alli et al. Oncogene (2005) 24, 39-46. doi:10.1038

Inhibitors of cancer metabolism, including inhibitors of LDH-A and inhibitors of fatty acid biosynthesis (or FAS inhibitors), are suitable for use in combination with the compounds of this invention.

In one embodiment, the cancer treatment method of the claimed invention includes the co-administration a compound of Formula I, Ia, Ib, II or III and/or a pharmaceutically acceptable salt thereof and at least one anti-neoplastic agent, such as one selected from the group consisting of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, cell cycle signaling inhibitors; proteasome inhibitors; and inhibitors of cancer metabolism.

In one embodiment, a compound of Formula, Ia and Ib is used as a chemosensitizer to enhance tumor cell killing.

In one embodiment, a compound of Formula I, Ia, Ib, II or III is used in combination as a chemosensitizer to enhance tumor cell killing.

In one embodiment, a compound of Formula I, Ia, Ib, II or III is used in combination with a compound that inhibits the activity of protein kinase R (PKR)-like ER kinase, PERK (PERK inhibitor).

Suitably, the compounds of Formula I, Ia, Ib, II, III and pharmaceutically acceptable salts thereof may be co-administered with at least one other active agent known to be inhibitors of PERK kinase (EIF2K3) for treating or lessening the severity of neurodegenerative diseases/injury, such as Alzheimer's disease, spinal cord injury, traumatic brain injury, ischemic stroke, stroke, diabetes, Parkinson disease, Huntington's disease, Creutzfeldt-Jakob Disease, and related prion diseases, progressive supranuclear palsy, amyotrophic lateral sclerosis, myocardial infarction, cardiovascular disease, inflammation, fibrosis, chronic and acute diseases of the liver, chronic and acute diseases of the lung, chronic and acute diseases of the kidney, chronic traumatic encephalopathy (CTE), neurodegeneration, dementia, traumatic brain injury, cognitive impairment, atherosclerosis, ocular diseases, arrhythmias, in organ transplantation and in the transportation of organs for transplantation.

"Chemotherapeutic" or "chemotherapeutic agent" is used in accordance with its plain ordinary meaning and refers to a chemical composition or compound having antineoplastic properties or the ability to inhibit the growth or proliferation of cells.

Additionally, the compounds described herein can be co-administered with conventional immunotherapeutic agents including, but not limited to, immunostimulants (e.g., Bacillus Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), and radioimmunotherapy (e.g., anti-CD20 monoclonal antibody conjugated to $^{111}$In, $^{90}$Y, or $^{131}$I, etc.).

In a further embodiment, the compounds described herein can be co-administered with conventional radiotherapeutic agents including, but not limited to, radionuclides such as $^{47}$Sc, $^{64}$C, $^{67}$C, $^{89}$Sr, $^{86}$Y, $^{87}$Y, and $^{212}$Bi, optionally conjugated to antibodies directed against tumor antigens.

Additional examples of a further active ingredient or ingredients (anti-neoplastic agent) for use in combination or co-administered with the compounds are anti-PD-L1 agents.

Anti-PD-L1 antibodies and methods of making the same are known in the art.

Such antibodies to PD-L1 may be polyclonal or monoclonal, and/or recombinant, and/or humanized.

Exemplary PD-L1 antibodies are disclosed in:

U.S. Pat. No. 8,217,149; Ser. No. 12/633,339;

U.S. Pat. No. 8,383,796; Ser. No. 13/091,936;

U.S. Pat. No. 8,552,154; Ser. No. 13/120,406;

US patent publication No. 20110280877; Ser. No. 13/068,337;

US Patent Publication No. 20130309250; Ser. No. 13/892,671;

WO2013019906;

WO2013079174;

U.S. application Ser. No. 13/511,538 (filed Aug. 7, 2012), which is the US National Phase of International Application No. PCT/US10/58007 (filed 2010);

and

U.S. application Ser. No. 13/478,511 (filed May 23, 2012).

Additional exemplary antibodies to PD-L1 (also referred to as CD274 or B7-H1) and methods for use are disclosed in U.S. Pat. No. 7,943,743; US20130034559, WO2014055897, U.S. Pat. Nos. 8,168,179; and 7,595,048. PD-L1 antibodies are in development as immuno-modulatory agents for the treatment of cancer.

In one embodiment, the antibody to PD-L1 is an antibody disclosed in U.S. Pat. No. 8,217,149. In another embodiment, the anti-PD-1 antibody comprises the CDRs of an antibody disclosed in U.S. Pat. No. 8,217,149.

In another embodiment, the antibody to PD-L1 is an antibody disclosed in U.S. application Ser. No. 13/511,538. In another embodiment, the anti-PD-1 antibody comprises the CDRs of an antibody disclosed in U.S. application Ser. No. 13/511,538.

In another embodiment, the antibody to PD-L1 is an antibody disclosed in application Ser. No. 13/478,511. In another embodiment, the anti-PD-1 antibody comprises the CDRs of an antibody disclosed in U.S. application Ser. No. 13/478,511.

In one embodiment, the anti-PD-1 antibody is BMS-936559 (MDX-1105). In another embodiment, the anti-PD-1 antibody is MPDL3280A (RG7446). In another embodiment, the anti-PD-1 antibody is MEDI4736.

Additional examples of a further active ingredient or ingredients (anti-neoplastic agent) for use in combination or co-administered with the presently invented ATF4 pathway inhibiting compounds are PD-1 antagonist.

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any embodiments of the aspects or embodiments of the present invention in which a human individual is to be treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in the any of the aspects of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments, the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments.

Examples of mAbs that bind to human PD-1, and useful in the various aspects and embodiments of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Specific anti-human PD-1 mAbs useful as the PD-1 antagonist in any of the aspects and embodiments of the present invention include: MK-3475, a humanized IgG4 mAb with the structure described in *WHO Drug Information*, Vol. 27, No. 2, pages 161-162 (2013) and which comprises the heavy and light chain amino acid sequences shown in FIG. 6; nivolumab, a human IgG4 mAb with the structure described in *WHO Drug Information*, Vol. 27, No. 1, pages 68-69 (2013) and which comprises the heavy and light chain amino acid sequences shown in FIG. 7; the humanized antibodies h409A11, h409A16 and h409A17, which are described in WO2008/156712, and AMP-514, which is being developed by Medimmune.

Other PD-1 antagonists useful in the any of the aspects and embodiments of the present invention include an immunoadhesin that specifically binds to PD-1, and preferably specifically binds to human PD-1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Other examples of mAbs that bind to human PD-L1, and useful in the treatment method, medicaments and uses of the present invention, are described in WO2013/019906, WO2010/077634 A and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C.

KEYTRUDA/pembrolizumab is an anti-PD-1 antibody marketed for the treatment of lung cancer by Merck. The amino acid sequence of pembrolizumab and methods of using are disclosed in U.S. Pat. No. 8,168,757.

Opdivo/nivolumab is a fully human monoclonal antibody marketed by Bristol Myers Squibb directed against the negative immunoregulatory human cell surface receptor PD-1 (programmed death-1 or programmed cell death-1/PCD-1) with immunopotentiation activity. Nivolumab binds to and blocks the activation of PD-1, an Ig superfamily transmembrane protein, by its ligands PD-L1 and PD-L2, resulting in the activation of T-cells and cell-mediated immune responses against tumor cells or pathogens. Activated PD-1 negatively regulates T-cell activation and effector function through the suppression of P13k/Akt pathway activation. Other names for nivolumab include: BMS-936558, MDX-1106, and ONO-4538. The amino acid sequence for nivolumab and methods of using and making are disclosed in U.S. Pat. No. 8,008,449.

Additional examples of a further active ingredient or ingredients (anti-neoplastic agent) for use in combination or co-administered with the compounds of the invention are immuno-modulators.

As used herein "immuno-modulators" refer to any substance including monoclonal antibodies that affects the immune system. The ICOS binding proteins of the present invention can be considered immune-modulators. Immuno-modulators can be used as anti-neoplastic agents for the treatment of cancer. For example, immune-modulators include, but are not limited to, anti-CTLA-4 antibodies such as ipilimumab (YERVOY) and anti-PD-1 antibodies (Opdivo/nivolumab and Keytruda/pembrolizumab). Other immuno-modulators include, but are not limited to, OX-40 antibodies, PD-L1 antibodies, LAG3 antibodies, TIM-3 antibodies, 41BB antibodies and GITR antibodies.

Yervoy (ipilimumab) is a fully human CTLA-4 antibody marketed by Bristol Myers Squibb. The protein structure of ipilimumab and methods are using are described in U.S. Pat. Nos. 6,984,720 and 7,605,238.

In another embodiment, this invention provides a compound of Table 1 described herein or a Formula (I), (Ia), (Ib), (II) or (III), or a pharmaceutically acceptable salt or prodrug thereof, for use in the treatment of a hepatitis B virus-related disease, condition or disorder. This invention provides a compound of Table 1 or a pharmaceutically acceptable salt or prodrug thereof, for use in the treatment of a hepatitis B virus-related disease, condition or disorder. wherein the hepatitis B virus-related disease, condition or disorder may be jaundice, liver cancer, liver inflammation, liver fibrosis, liver cirrhosis, liver failure, diffuse hepatocellular inflammatory disease, hemophagocytic syndrome or serum hepatitis).

In further embodiments, the compound of the present invention of Formula (I), (Ia), (Ib), (II) or (III), or pharmaceutically acceptable salts thereof, is selected from the group of compounds set forth in Table 1. Additionally, the present invention also encompasses each of these compounds individually and pharmaceutically acceptable salts thereof.

In another embodiment, there is provided a pharmaceutical composition comprising a pharmaceutically acceptable diluent and a therapeutically effective amount of a compound of Formula I, Ia, Ib, II or III or a pharmaceutically acceptable salt thereof.

In certain embodiments, the compound(s) of the present invention, or a pharmaceutically acceptable salt thereof, is chosen from the compounds set forth in Table 1. The compounds of the present invention can be supplied in the form of a pharmaceutically acceptable salt. The terms "pharmaceutically acceptable salt" refer to salts prepared from pharmaceutically acceptable inorganic and organic acids and bases. Accordingly, the word "or" in the context of "a compound or a pharmaceutically acceptable salt thereof" is understood to refer to either a compound or a pharmaceutically acceptable salt thereof (alternative), or a compound and a pharmaceutically acceptable salt thereof (in combination).

As used herein, the term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication. The skilled artisan will appreciate that pharmaceutically acceptable salts of compounds according to Formula I, Ia, Ib, II or III may be prepared. These pharmaceutically acceptable salts may be prepared in situ during the final isolation and purification of the compound, or by separately reacting the purified compound in its free acid or free base form with a suitable base or acid, respectively.

Illustrative pharmaceutically acceptable acid salts of the compounds of the present invention can be prepared from the following acids, including, without limitation formic, acetic, propionic, benzoic, succinic, glycolic, gluconic, lactic, maleic, malic, tartaric, citric, nitic, ascorbic, glucuronic, maleic, fumaric, pyruvic, aspartic, glutamic, benzoic, hydrochloric, hydrobromic, hydroiodic, isocitric, trifluoroacetic, pamoic, propionic, anthranilic, mesylic, oxalacetic, oleic, stearic, salicylic, p-hydroxybenzoic, nicotinic, phenylacetic, mandelic, embonic (pamoic), methanesulfonic, phosphoric, phosphonic, ethanesulfonic, benzenesulfonic, pantothenic, toluenesulfonic, 2-hydroxyethanesulfonic, sulfanilic, sulfuric, salicylic, cyclohexylaminosulfonic, algenic, -hydroxybutyric, galactaric and galacturonic acids. Preferred pharmaceutically acceptable salts include the salts of hydrochloric acid and trifluoroacetic acid.

Illustrative pharmaceutically acceptable inorganic base salts of the compounds of the present invention include metallic ions. More preferred metallic ions include, but are not limited to, appropriate alkali metal salts, alkaline earth metal salts and other physiological acceptable metal ions. Salts derived from inorganic bases include aluminum, ammonium, calcium, copper, ferric, ferrous, lithium, magnesium, manganic salts, manganous, potassium, sodium, zinc, and the like and in their usual valences. Exemplary base salts include aluminum, calcium, lithium, magnesium, potassium, sodium and zinc. Other exemplary base salts include the ammonium, calcium, magnesium, potassium, and sodium salts. Still other exemplary base salts include, for example, hydroxides, carbonates, hydrides, and alkoxides including NaOH, KOH, $Na_2CO_3$, $K_2CO_3$, NaH, and potassium-t-butoxide.

Salts derived from pharmaceutically acceptable organic non-toxic bases include salts of primary, secondary, and tertiary amines, including in part, trimethylamine, diethylamine, N, N'-dibenzylethylenediamine, chloroprocaine, choline, diethanolamine, ethylenediamine, meglumine (N-methylglucamine) and procaine; substituted amines including naturally occurring substituted amines; cyclic amines; quaternary ammonium cations; and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

All of the above salts can be prepared by those skilled in the art by conventional means from the corresponding compound of the present invention. For example, the pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. The salt may precipitate from solution and be collected by filtration or may be recovered by evaporation of the solvent. The degree of ionisation in the salt may vary from completely ionised to almost non-ionised. Lists of suitable salts are found in *Remington's Pharmaceutical Sciences*, 17th ed., Mack Publishing Company, Easton, Pa., 1985, p. 1418, as well as in Berge, J. Pharm. Sci., 1977, 66, 1-19, or those listed in P H Stahl and C G Wermuth, editors, *Handbook of Pharmaceutical Salts; Properties, Selection and Use, Second Edition* Stahl/Wermuth: Wiley-VCH/VHCA, 2011 (see http://www.wiley.com/WileyCDA/WileyTitle/productCd-3906390519.html, the disclosures of which are hereby incorporated by reference only with regards to the lists of suitable salts.

The compounds of Formula (I), (Ia), (Ib), (II) or (III) of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water. Pharmaceutically acceptable solvates include hydrates and other solvates wherein the solvent of crystallization may be isotopically substituted, e.g. $D_2O$, $d_6$-acetone, $d_6$-DMSO.

Compounds of Formula (I), (Ia), (Ib), (II) or (III) containing one or more asymmetric carbon atoms can exist as two or more stereoisomers. Where a compound of Formula (I), (Ia), (Ib), (II) or (III) contains an alkenyl or alkenylene group or a cycloalkyl group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism.

Included within the scope of the claimed compounds of present invention are all stereoisomers, geometric isomers and tautomeric forms of the compounds of Formula I, Ia, Ib, II or III, including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of Formula I, Ia, Ib, II or III contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person. Chiral compounds of the invention (and chiral precursors thereof) may be obtained in enantiomerically-enriched form using chromatography, typically HPLC, on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Mixtures of stereoisomers may be separated by conventional techniques known to those skilled in the art. [see, for example, "Stereochemistry of Organic Compounds" by E L Eliel (Wiley, New York, 1994).]

The present invention includes all pharmaceutically acceptable isotopically-labelled compounds of Formula (I), (Ia), (Ib), (II) or (III) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S. Certain isotopically-labelled compounds of Formula (I), (Ia), (Ib), (II) or (III), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Isotopically-labelled compounds of Formula (I), (Ia), (Ib), (II) or (III) can generally be prepared by conventional techniques known to those skilled in the art or by processes analogous to those described in the accompanying Examples and Preparations using an appropriate isotopically-labelled reagents in place of the non-labelled reagent previously employed.

The compounds of the present invention may be administered as prodrugs. Thus, certain derivatives of compounds of Formula (I), (Ia), (Ib), (II) or (III), which may have little or no pharmacological activity themselves can, when administered into or onto the body, be converted into compounds of Formula (I), (Ia), (Ib), (II) or (III) as 'prodrugs'.

Administration of the chemical entities described herein can be via any of the accepted modes of administration for agents that serve similar utilities including, but not limited to, orally, sublingually, subcutaneously, intravenously, intranasally, topically, transdermally, intraperitoneally, intramuscularly, intrapulmonarilly, vaginally, rectally, or intraocularly. In some embodiments, oral or parenteral administration is used.

Pharmaceutical compositions or formulations include solid, semi-solid, liquid and aerosol dosage forms, such as, e.g., tablets, capsules, powders, liquids, suspensions, suppositories, aerosols or the like. The chemical entities can also be administered in sustained or controlled release dosage forms, including depot injections, or implant preparation, osmotic pumps, pills, transdermal (including electrotransport) patches, and the like, for prolonged and/or timed, pulsed administration at a predetermined rate. In certain embodiments, the compositions are provided in unit dosage forms suitable for single administration of a precise dose. The active ingredient can be compressed into pellets or small cylinders and implanted subcutaneously or intramuscularly as depot injections or implants. Implants may employ inert materials such as biodegradable polymers or synthetic silicones, for example, Silastic or silicone rubber.

The chemical entities can also be administered in the form of liposome delivery systems, such as small unilamellar vesicles, large unilamellar vesicles and multilamellar vesicles. Liposomes can be formed from a variety of phospholipids, such as cholesterol, stearylamine, or phosphatidylcholines. Liposomal preparations of tyrosine kinase inhibitors may also be used in the methods of the invention. Liposome versions of tyrosine kinase inhibitors may be used to increase tolerance to the inhibitors.

The chemical entities can also be delivered by the use of monoclonal antibodies as individual carriers to which the compound molecules are coupled.

The chemical entities can also be prepared with soluble polymers as targetable drug carriers. Such polymers can include polyvinyl pyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the chemical entities can be prepared with biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The chemical entities described herein can be administered either alone or more typically in combination with a conventional pharmaceutical carrier, excipient or the like (e.g., mannitol, lactose, starch, magnesium stearate, sodium saccharine, talcum, cellulose, sodium crosscarmellose, glucose, gelatin, sucrose, magnesium carbonate, and the like). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like). Generally, depending on the intended mode of administration, the pharmaceutical composition will contain about 0.005% to 95%; in certain embodiments, about 0.5% to 50% by weight of a chemical entity. Actual methods of preparing such dosage forms are known, or will be apparent, to those skilled in this art; for example, see Remington's Pharmaceutical Sciences, Mack Publishing Company, Easton, Pa.

In certain embodiments, the compositions will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils or triglycerides) is encapsulated in a gelatin capsule.

Liquid pharmaceutically administrable compositions can, for example, be prepared by dissolving, dispersing, etc. at least one chemical entity and optional pharmaceutical adjuvants in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of chemical entities contained in such parenteral compositions is highly dependent on the specific nature thereof, as well as the activity of the chemical entities and the needs of the subject. However, percentages of active ingredient of 0.01% to 10% in solution are employable, and will be higher if the composition is a solid which will be subsequently diluted to the above percentages. In certain embodiments, the composition will comprise from about 0.2 to 2% of the active agent in solution.

Pharmaceutical compositions of the chemical entities described herein may also be administered to the respiratory tract as an aerosol or solution for a nebulizer, or as a microfine powder for insufflation, alone or in combination with an inert carrier such as lactose. In such a case, the particles of the pharmaceutical composition have diameters of less than 50 microns, in certain embodiments, less than 10 microns.

In general, the chemical entities provided will be administered in a therapeutically effective amount by any of the accepted modes of administration for agents that serve similar utilities. The dosage regimen utilizing the chemical entities described herein can be selected in accordance with a variety of factors including type, species, age, weight, sex and the type of disease being treated; the severity (i.e., stage) of the disease to be treated; the route of administration; the renal and hepatic function of the patient; and the particular compound or salt thereof employed. A dosage regimen can be used, for example, to prevent, inhibit (fully or partially), or arrest the progress of the disease. The drug can be administered more than once a day, such as once or twice a day.

Intravenously or subcutaneously, the patient would receive the chemical entities described herein in therapeutically effective amounts sufficient to deliver between about 0.001 to 200 mg per kilogram body weight of the recipient per day; such as about 0.005-100 mg/kg/day, for example, from about 0.005 to 1 mg/kg/day. Thus, for administration to a 70 kg person, the dosage range may be about 0.35-70 mg per day. Such quantities may be administered in a number of suitable ways, e.g. large volumes of low concentrations of the chemical entities during one extended period of time or several times a day. The quantities can be administered for one or more consecutive days, intermittent days or a combination thereof per week (7-day period). Alternatively, low volumes of high concentrations of the chemical entities during a short period of time, e.g. once a day for one or more days either consecutively, intermittently or a combination thereof per week (7-day period).

In accordance with the invention, the chemical entities described herein can be administered by continuous or intermittent dosages. For example, intermittent administration of the chemical entity may be administration one to six days per week or it may mean administration in cycles (e.g. daily administration for two to eight consecutive weeks, then a rest period with no administration for up to one week) or it may mean administration on alternate days. The compositions may be administered in cycles, with rest periods in between the cycles (e.g. treatment for two to eight weeks with a rest period of up to a week between treatments).

Subcutaneous formulations can be prepared according to procedures well known in the art at a pH in the range between about 5 and about 12, which include suitable buffers and isotonicity agents.

In general, the chemical entities will be administered as pharmaceutical compositions by any one of the following routes: oral, systemic (e.g., transdermal, intranasal or by suppository), or parenteral (e.g., intramuscular, intravenous or subcutaneous) administration. In certain embodiments, oral administration with a convenient daily dosage regimen that can be adjusted according to the degree of affliction may be used. Compositions can take the form of tablets, pills, capsules, semisolids, powders, sustained release formulations, solutions, suspensions, elixirs, aerosols, or any other appropriate compositions. Another manner for administering the provided chemical entities is inhalation.

The choice of formulation depends on various factors such as the mode of drug administration and bioavailability of the drug substance. For delivery via inhalation the chemical entity can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDIs typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical compositions have been developed for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a cross-linked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, at least one chemical entity described herein in combination with at least one pharmaceutically acceptable excipient. Acceptable excipients are non-toxic, aid administration, and do not adversely affect the therapeutic benefit of the at least one chemical entity described herein. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, for injectable solutions, include water, saline, aqueous dextrose, and glycols.

Compressed gases may be used to disperse a chemical entity described herein in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the chemical entity in a composition can vary within the full range employed by those skilled in the art. Typically, the composition will contain, on a weight percent (wt %) basis, from about 0.01-99.99 wt % of at least one chemical entity described herein based on the total composition, with the balance being one or more suitable pharmaceutical excipients. In certain embodiments, the at least one chemical entity described herein is present at a level of about 1-80 wt %.

In various embodiments, pharmaceutical compositions of the present invention encompass compounds of Formula (I), (Ia), (Ib), (II) or (III), salts thereof, and combinations of the above.

The various modes of administration, dosages, and dosing schedules described herein merely set forth specific embodiments and should not be construed as limiting the broad scope of the invention. Any permutations, variations, and combinations of the dosages and dosing schedules are included within the scope of the present invention.

Compounds of the invention may be made according to various schemes described below Synthetic Methods The methods of synthesis for the provided chemical entities employ readily available starting materials using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

Additionally, the methods of this invention may employ protecting groups which prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, Protecting Groups in Organic Synthesis, Third Edition, Wiley, New York, 1999, and references cited therein.

Furthermore, the provided chemical entities may contain one or more chiral centers and such compounds can be prepared or isolated as pure stereoisomers, i.e., as individual enantiomers or diastereomers, or as stereoisomer-enriched mixtures. All such stereoisomers (and enriched mixtures) are included within the scope of this specification, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplementals (Elsevier Science Publishers, 1989), Organic Reactions, Volumes 1-40 (John Wiley and Sons, 1991), March's Advanced Organic Chemistry, (John Wiley and Sons, 4th Edition), and Larock's Comprehensive Organic Transformations (VCH Publishers Inc., 1989).

Unless specified to the contrary, the reactions described herein take place at atmospheric pressure, generally within a temperature range from −78 C to 200 C. Further, except as employed in the Examples or as otherwise specified, reaction times and conditions are intended to be approximate, e.g., taking place at about atmospheric pressure within a temperature range of about −78 C to about 110 C over a period of about 1 to about 24 hours; reactions left to run overnight average a period of about 16 hours.

The terms "solvent," "organic solvent," and "inert solvent" each mean a solvent inert under the conditions of the reaction being described in conjunction therewith, including, for example, benzene, toluene, acetonitrile, tetrahydrofuranyl ("THF"), dimethylformamide ("DMF"), chloroform, methylene chloride (or dichloromethane), diethyl ether, methanol, N-methylpyrrolidone ("NMP"), pyridine and the like.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples herein below. However, other equivalent separation or isolation procedures can also be used.

When desired, the (R)- and (S)-isomers may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

EXAMPLES

The following examples serve to more fully describe the manner of making and using the above-described invention. It is understood that these examples in no way serve to limit the true scope of the invention, but rather are presented for illustrative purposes. In the examples below and the synthetic schemes above, the following abbreviations have the following meanings. If an abbreviation is not defined, it has its generally accepted meaning.

aq.=Aqueous
μL=Microliters
μM=Micromolar
NMR=nuclear magnetic resonance
Boc=tert-butoxycarbonyl
Br=Broad
Cbz=Benzyloxycarbonyl
d=Doublet
Δ=chemical shift
° C.=degrees celcius
DCM=Dichloromethane
dd=doublet of doublets
DMAP=4-(Dimethylamino)pyridine
DMEM=Dulbeco's Modified Eagle's Medium
DMF=N,N-dimethylformamide
DMP=2,2-dimethoxypropane
DMSO=Dimethylsulfoxide
EtOAc=ethyl acetate
ESI=electrospray ionization
G or g=Gram
h or hr=Hours
HCV=hepatitis C virus
HPLC=high performance liquid chromatography
Hz=Hertz
IU=International Units
$IC_{50}$=inhibitory concentration at 50% inhibition
J=coupling constant (given in Hz unless otherwise indicated)
LHMDS=Lithium bis(trimethylsilyl)amide
M=Multiplet
M=Molar
$M+H^+$=parent mass spectrum peak plus $H^+$
Mg or mg=Milligram
Min=Minutes
mL=Milliliter
mM=Millimolar
Mmol=Millimole
MS=mass spectrum
Nm=Nanomolar
ppm=parts per million
p-TsOH=p-Toluenesulfonic acid
q.s.=sufficient amount
S=Singlet
RT=room temperature
sat.=Saturated
T=Triplet
TBS-Cl=tert-Butyldimethylsilyl chloride
TFA=trifluoroacetic acid Equipment Description $^1$H NMR spectra were recorded on a Varian spectrometer. Chemical shifts are expressed in parts per million (ppm, units). Coupling constants are in units of hertz (Hz). Splitting patterns describe apparent multiplicities and are designated as s (singlet), d (doublet), t (triplet), q (quartet), quint (quintet), m (multiplet), br (broad).

The analytical low-resolution mass spectra (MS) were recorded on Waters (Acquity). The following conditions were employed described below.
Instrument: Agilent 1200-6100
Scan Mode: Alternating Positive/Negative Electrospray
Scan Range: 100-1000 amu
LC Conditions:
The LCMS analysis was conducted on a HALO C-18, 4.6*50 mm, 2.7 μm, C18 column at 45° C.
1.0 uL of sample was injected
The gradient employed was:
Mobile Phase A: Water+0.1% v/v Formic Acid
Mobile Phase B: Acetonitrile+0.1% v/v Formic Acid

| Time | % A | % B | Flow Rate |
| --- | --- | --- | --- |
| 0.00 min | 95 | 5 | 1.8 ml/min |
| 1.0 min | 5 | 95 | 1.8 ml/min |
| 2.0 min | 5 | 95 | 1.8 ml/min |
| 2.5 min | 95 | 5 | 1.8 ml/min |

UV detection provided by summed absorbance signal at 214 nm and 254 nm scanning
Instrument: Shimadzu LCMS-2020
Scan Mode: Alternating Positive/Negative Electrospray
Scan Range: 100-2000 amu
LC Conditions:
The LCMS analysis was conducted on a HALO C-18, 4.6*50 mm, 2.7 μm, C18 column at 45° C.
1.0 uL of sample was injected
The gradient employed was:
Mobile Phase A: Water+0.1% v/v Formic Acid
Mobile Phase B: Acetonitrile+0.1% v/v Formic Acid

| Time | % A | % B | Flow Rate |
| --- | --- | --- | --- |
| 0.00 min | 95 | 5 | 1.5 ml/min |
| 1.0 min | 5 | 95 | 1.5 ml/min |
| 2.0 min | 5 | 95 | 1.5 ml/min |
| 2.5 min | 95 | 5 | 1.5 ml/min |
| 3.0 min | 95 | 5 | 1.5 ml/min |

UV detection provided by summed absorbance signal at 214 nm and 254 nm scanning

Schemes and Experimental Procedures

The following schemes and procedures illustrate how compounds of the present invention can be prepared. The specific solvents and reaction conditions referred to are also illustrative and are not intended to be limiting. Compounds not described are either commercially available or are readily prepared by one skilled in the art using available starting materials. The Examples disclosed herein are for illustrative purposes only and are not intended to limit the compounds of the scope of the invention.

Additional examples contained within were determined to have the shown configuration by spectroscopic methods well known to those skilled in the art including, but not limited to, 1D and 2D NMR methods. Compounds of Formula (I), (Ia), (Ib), (II) or (III) can for example be synthesized according to Schemes 1-6.

In one embodiment, the compound of Formula 1.12 may be prepared as shown in Scheme 1. The bicyclic ring system in Formulas 1.5 and 1.6 can be formed using the 4 component Ugi reaction of carboxylic acid 1.1, isocyanide 1.2, aldehyde 1.3 and ammonia to give a dipeptide 1.4 followed by acid deprotection and cyclization. Compounds of Formulas 1.5 and 1.6 can be synthesized using asymmetric Ugi syntheses with the addition of chiral reagents such as chiral phosphoric acids (Jian Zhang, et al, Science, 2018, 361, 1087). Isocyanides (Isocyanide Chemistry: Application in Synthesis and Material Science, Edited by V. Nenajdenko, Wiley-VCH, 1$^{st}$ Ed) can be synthesized by dehydration of formamides using for example phosphorus oxychloride, phosgene, diphosgene, toluenesulfonyl chloride, etc. Formamides can in turn be prepared by formylation of the amine by ethyl formate, mixed formic-acetic anhydride, formic acid/carbodiimides, activated formic acid ester. Aldehyde with Formula 1.3 (M. Vamos, et al, ACS Chem. Biol., 2013, 8, 725-732) can be prepared from the di-methylation of 4,4-dimethoxybutanenitrile followed by reduction with DIBAL-H. The compound of formula 1.8 can be prepared by coupling of Boc-N-Methyl-L-Ala-OH 1.7 with the desired diastereoisomer 1.5 using standard amide coupling reagents such as T3P, HATU, HBTU, EDC/HOBt, TBTU, and the like in the presence of a base such as Hunig's base, N-methyl morpholine and the like in an appropriate solvent such as DMF, DCM, and the like. The alkyne in Formula 1.8 can be selectively reduced through hydrogenation in the presence of Lindlar's catalyst, or alternative methods to give the alkene of Formula 1.9. The alkene of Formula 1.9 can be dimerized using Grubbs olefin metathesis to give the compound of Formula 1.10. The olefin of Formula 1.10 can be reduced using hydrogenation in the presence of a metal catalyst such as palladium on carbon, platinum to yield the compound of Formula 1.11 in which the Boc protecting groups can be removed under acidic conditions such as HCl, TFA or the like.

Scheme 1

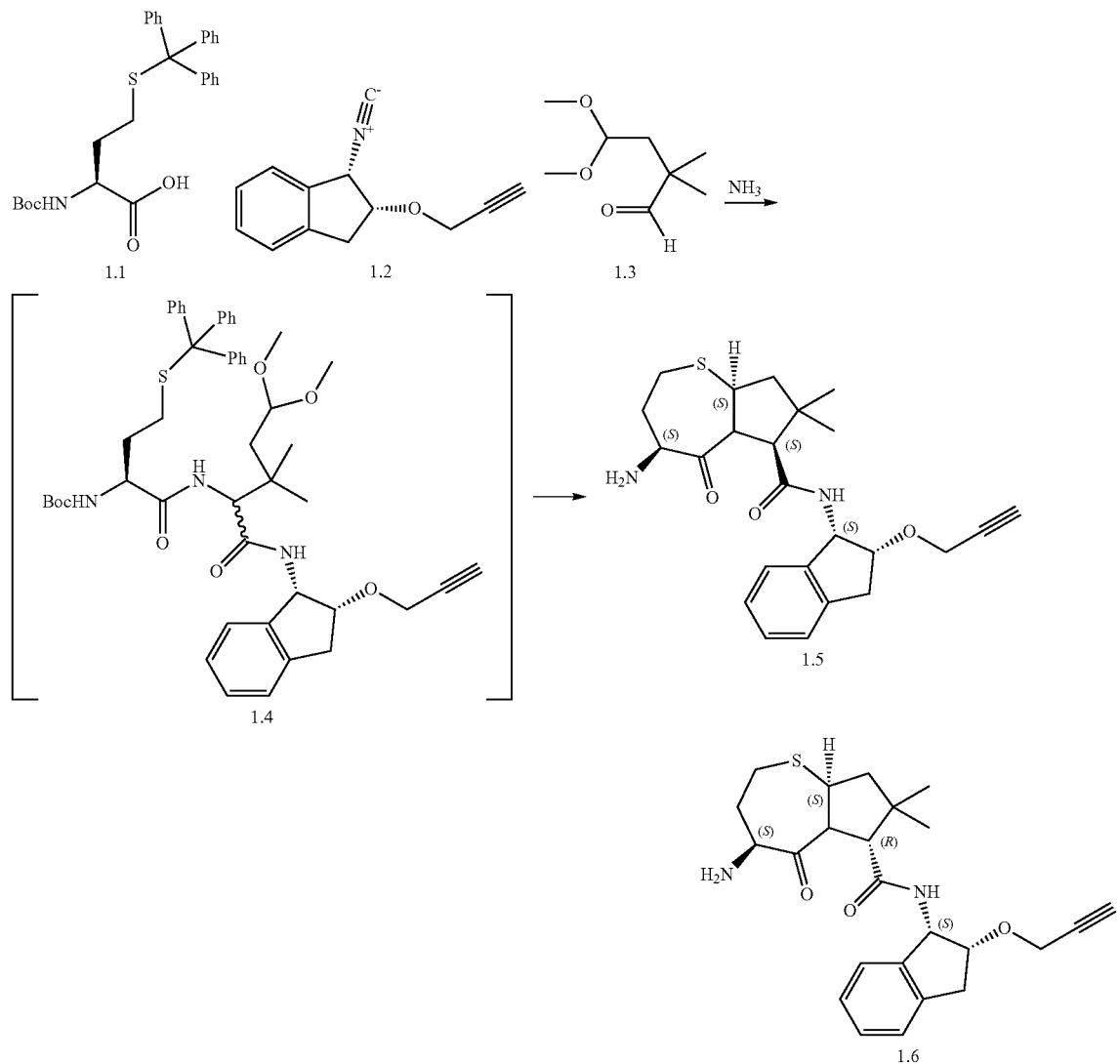

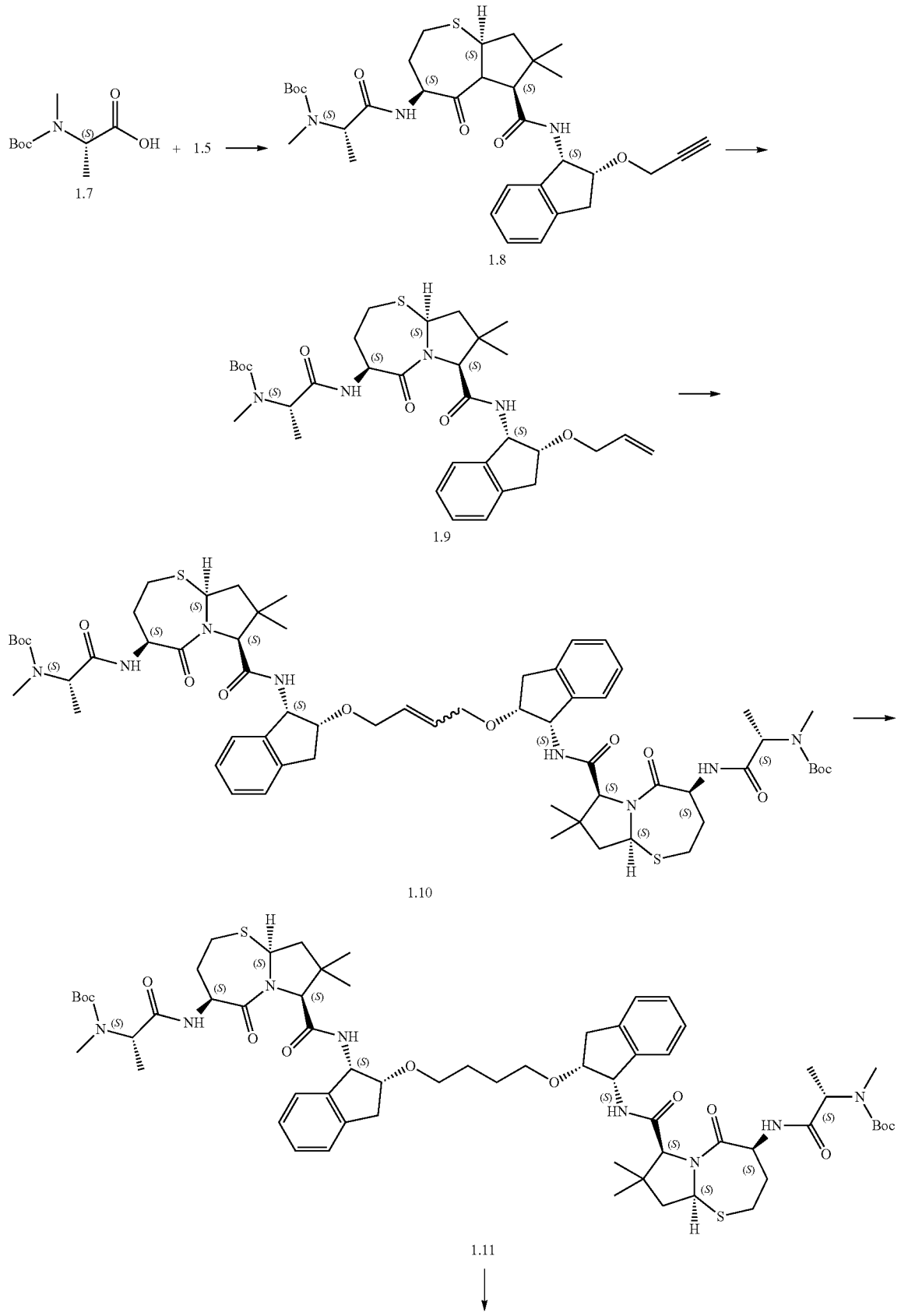

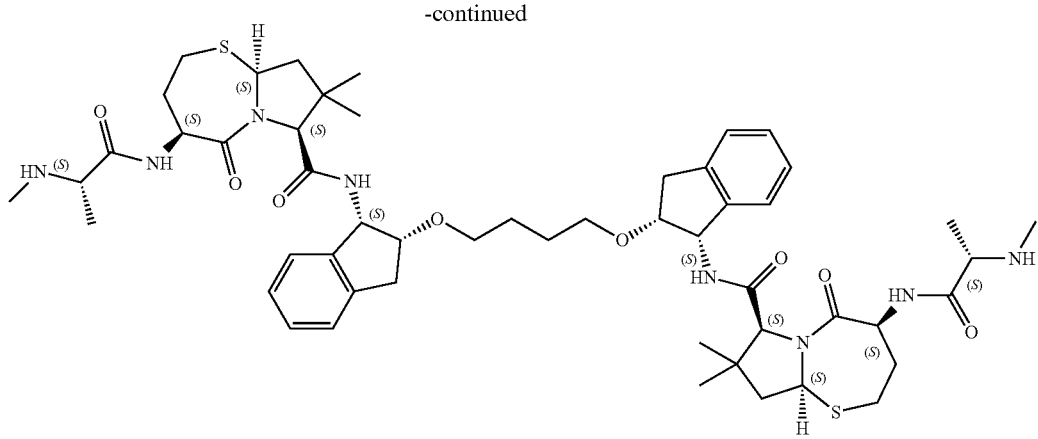

1.12

In another embodiment, the intermediate of Formula 2.8 can be prepared according to Scheme 2. Intermediate 2.8 is a versatile intermediate in regards to Formula I, Ia, Ib, II or III by coupling with various diamines that are skilled in the art. The Bicyclic compound of Formula 2.5 can be prepared by using the 4 component Ugi reaction of acid 2.1, isocyanide 2.2, aldehyde 2.3 and ammonia to give the dipeptide of Formula 2.4. The compound of Formula 2.5 can be prepared by treatment of dipeptide 2.4 with acid which can result in the formation of the bicyclic ring structure as well as the indole amide (O. Kreye, et al, SYNLETT, 2007, p 3188-3192). Compound of formula 2.6 and 2.7 can be prepared by coupling of Boc-N-Methyl-L-Ala-OH 1.7 with compound 2.5 using standard amide coupling reagents such as T3P, HATU, HBTU, EDC/HOBt, TBTU, and the like in the presence of a base such as Hunig's base, N-methyl morpholine and the like in an appropriate solvent such as DMF, DCM, and the like. The acid of Formula 2.8 can be prepared through the basic hydrolysis of the indole amide of Formula 2.6 in the presence of sodium hydroxide or the like in solvents such as water, methanol.

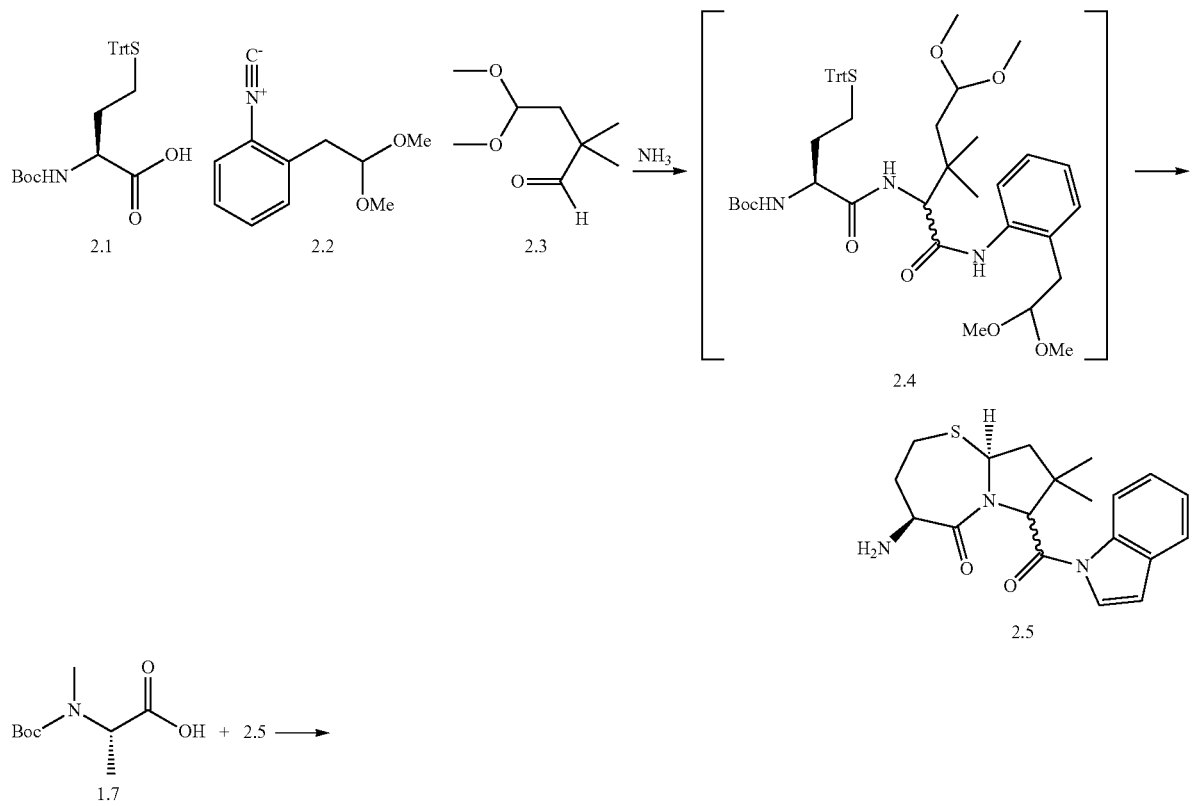

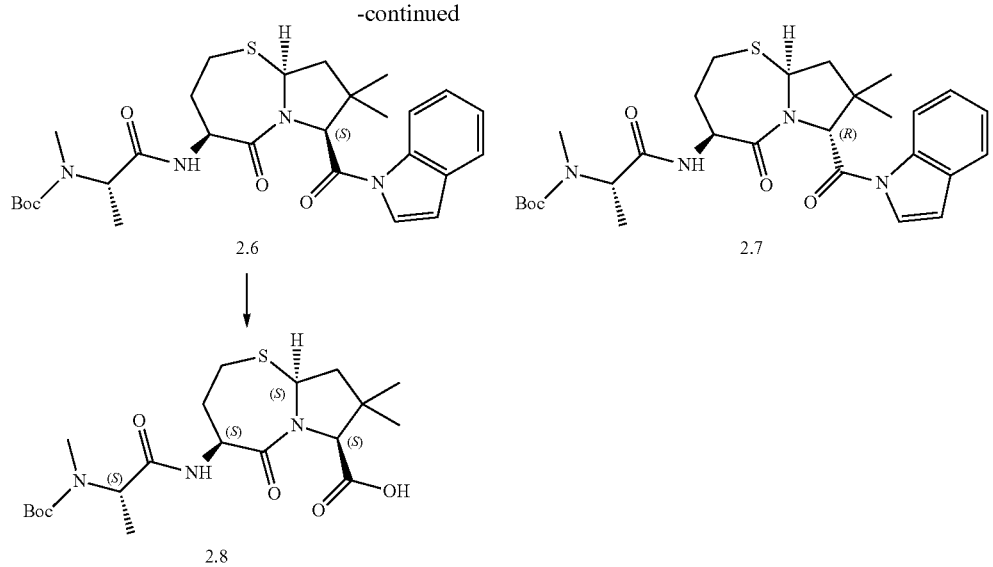

In another embodiment, the intermediate of Formula 3.7 can be prepared according to Scheme 3. Intermediate 3.7 is a versatile intermediate with respect to the compounds of Formula I, Ia, Ib, II or III by coupling with various diamines that are skilled in the art.

Scheme 3. An activated thioamidation reagent of Formula 3.4 can be prepared as follows. Amid coupling of Boc-N-Methyl-L-Ala-OH 1.7 with diamine of formula 3.1 using mixed anhydride coupling condition or alternative amide coupling conditions can provide the compound of Formula 3.2. The thionation of amide 3.2 using phosphorous pentasulfide in the presence of abase such as sodium carbonate or the like in solvent such as THF may yield the thioamide of Formula 3.3. The nitrobenzotriazole reagent of Formula 3.4 can be prepared by treating the thiomaide 3.3 with sodium nitrite in acetic acid in solvents such as THF and the like (M. Ashraf Shalaby, et al, J. Org. Chem. 1996, 61, p9045-9048).

The compound of Formulas 3.5 and 3.6 can be prepared by reacting indole amide 2.5 and activated thioacylating reagent of formula 3.4 in the presence of abase such as Hunig's base, triethylamine or the like in solvents such as DCM, DMF or the like. The separated diastereoiosmer of Formula 3.5 can be treated with aqueous base such as sodium hydroxide in an alcohol solvent such as methanol to give the intermediate of Formula 3.7.

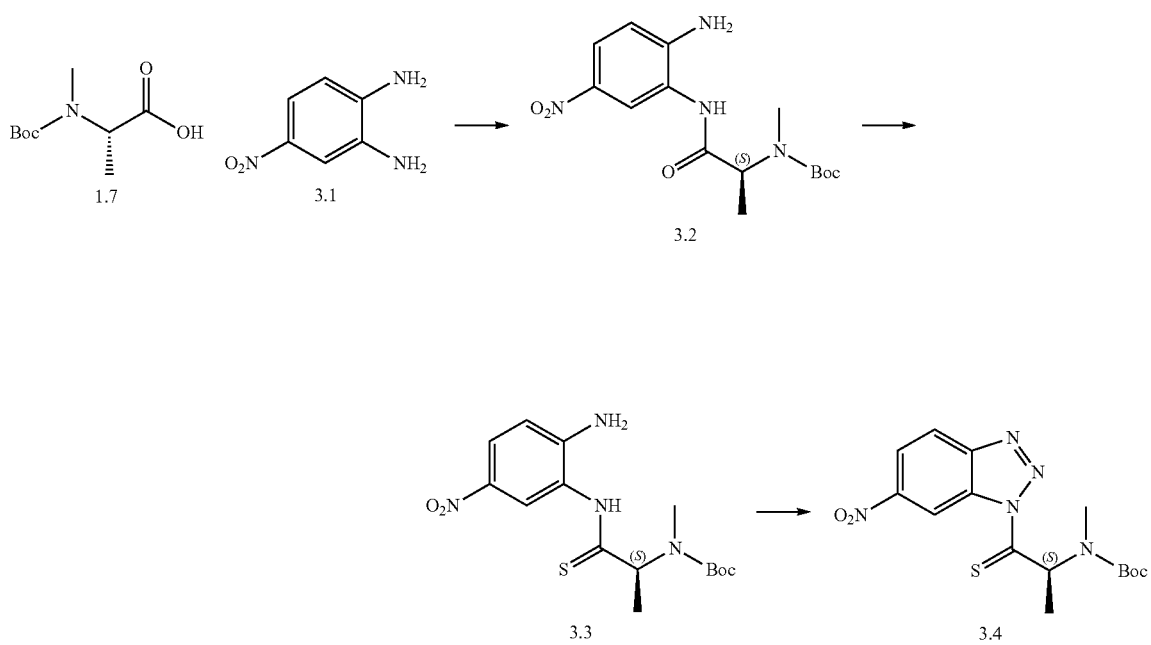

3.4 + 2.5 →

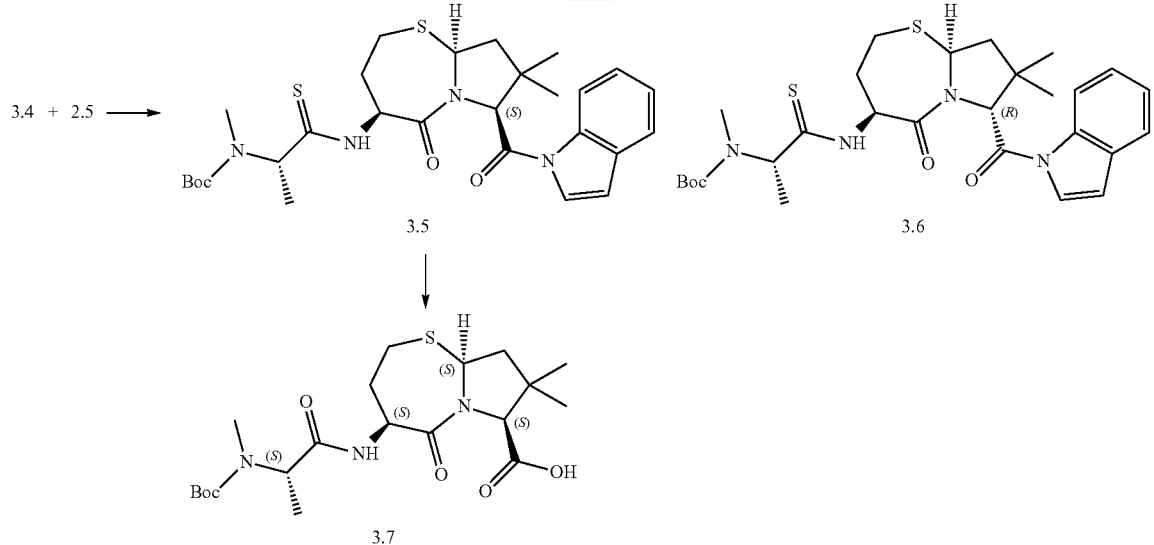

In another embodiment, compounds of formula 4.3 and 4.5 can be prepared according to Scheme 4. Compounds of formula 4.2 and 4.4 can be prepared by coupling of the intermediates 2.8 or 3.7 with a diamine 4.1 in the presence of a coupling reagent or through activated esters in the presence of a base such as Hunig's base, triethylamie or the like and in solvents such as DMF, THF, DCM or the like.

Coupling reagents such as HATU, TBTU, BOP, PyBOP, DEPBT, EDC/HOBt, EEDQ but not limited to the list can be used in the coupling reactions. The compounds of Formulas 4.3 and 4.5 can be prepared by Boc deprotection of the compounds 4.2 and 4.4 under acidic conditions such as HCl, TFA or the like.

Scheme 4

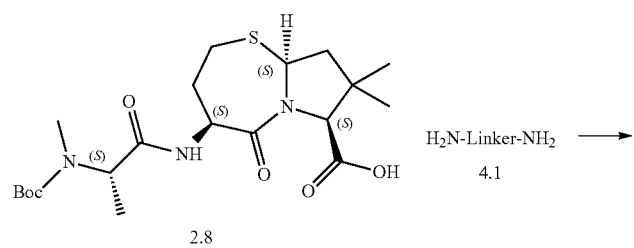

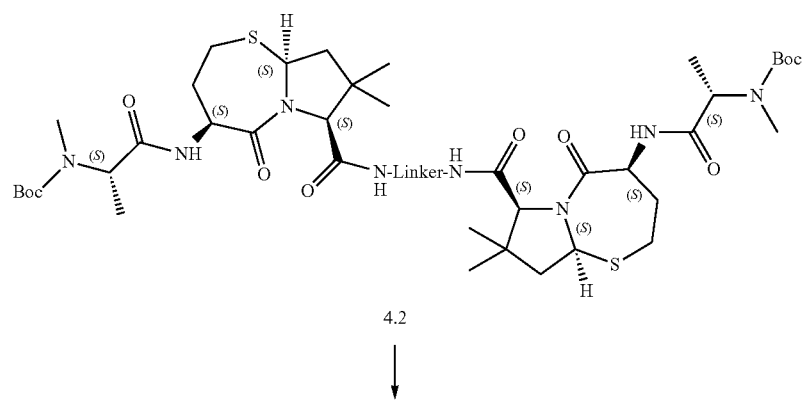

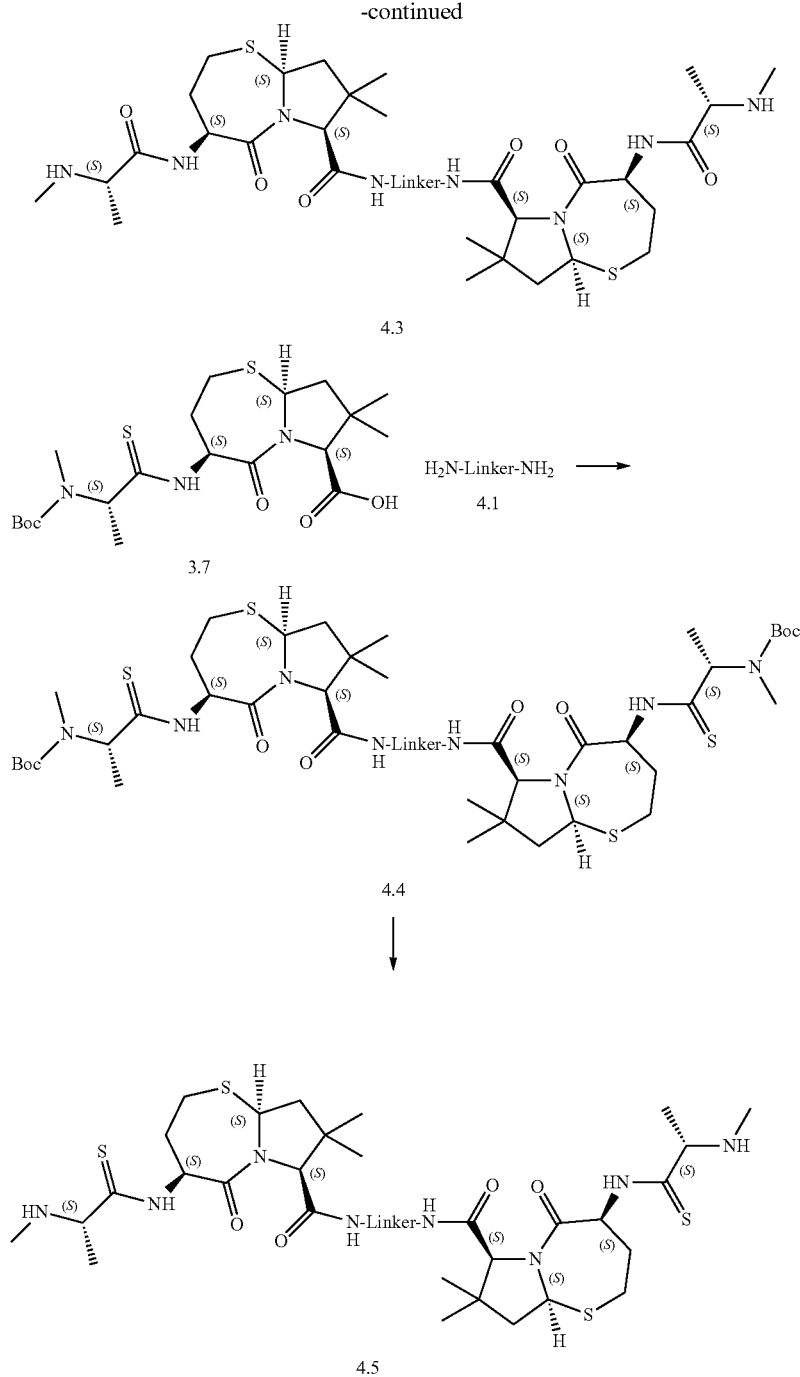

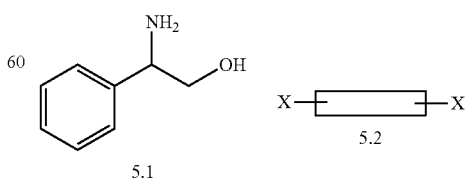

Scheme 5

The diamines for the coupling of Intermediates 2.8 and 3.7 are readily available from commercial suppliers or can be made within the skill of the art. Various examples are illustrated in Scheme 5 but not limited to the type of chemistry or functional groups used for the linkers. The diamines of Formulas 5.3 and 5.5 can be prepared by the bis-alkylation of amino alcohols 5.1 or 5.4 where X is a leaving group such as a halide, tosylate, mesylate or the like in the presence of a base such as sodium hydride, or the like in solvents such as DMF, THF or the like. Compounds of formula 5.8 and 5.10 can be prepared by coupling of protected amino acids 5.6 and 5.9 under amide coupling conditions followed by acid deprotection.

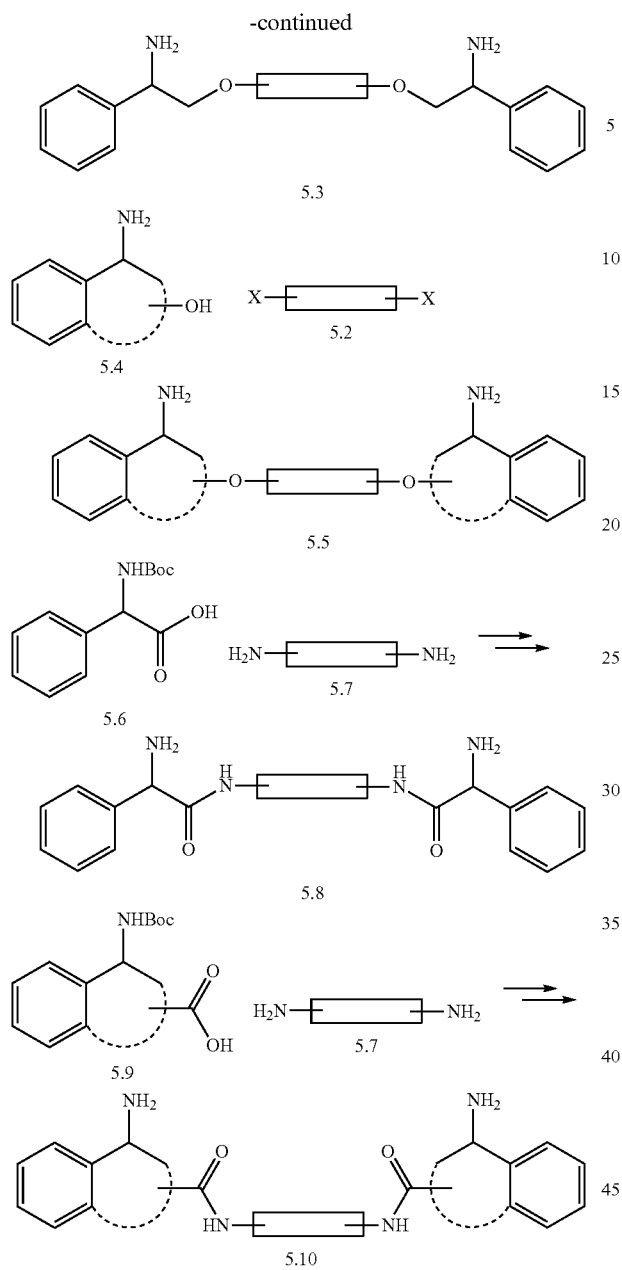

Wherein the rectangular box ▭ is a linker.

In another embodiment, the dimers of Formulas 6.7, 6.8, 6.9, 6.10 and 6.11 can be prepared according to Scheme 6. The compounds of Formulas 6.3, 6.4, 6.5 and 6.6 can be prepared by amide bond coupling Intermediates 2.8 and 3.7 with the amines of Formulas 6.1 and 6.2 where X and Y are linkers with functional groups at the termini that can be used for further reaction. Examples of function groups but not limited to the following lists are protected amine, protected carboxylic acid, protected thiols, alkyne, alkene, sulfonyl chloride, azide, hydroxyl, halides, nitriles, isocyanates. The monomers of Formulas 6.3 and 6.5 can dimerize to form dimers of Formulas 6.7 and 6.11, for example when X contains an alkyne, alkene, amines or alternative functional groups that can further react to form homodimers through copper-mediated alkyne coupling, olefin metathesis, urea or sulfamide formation. The monomers of Formulas 6.3, 6.4, 6.5 and 6.6 can react with each other to form heterodimers of Formulas of 6.8, 6.9 and 6.10, for example when X contains an amine and Y contained a carboxylic acid, sulfonyl chloride, isocyanate which can form an amdie, sulfonamide, or urea; or for example when X is an alkyne and Y is an azide which can form a triazol; or when X contains a hydroxy and Y contains a halogen which can form an ether. The chemistry is not limited to the list above but other combinations for those skilled in the art.

Intermediate I (4S,7S,9aS)-4-((S)-2-((tert-butoxycarbonyl)(methyl)amino)propanamido)-8,8-dimethyl-5-oxooctahydro-pyrrolo[2,1-b][1,3]thiazepine-7-carboxylic Acid

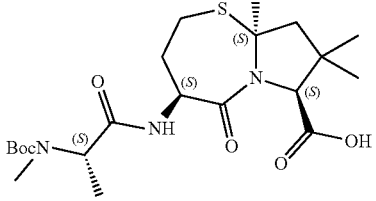

Step 1: (E)-1-(2-nitrostyryl)pyrrolidine

To a solution of 1-methyl-2-nitrobenzene (50 g, 365 mmol) in N,N-dimethylformamide (200 mL) was added pyrrolidine (31.1 g, 438 mmol) and 1,1-dimethoxy-N,N-dimethylmethanamine (52.2 g, 438 mmol). The resulting mixture was stirred at 60° C. After 5 h, the temperature was increased to 80° C. and stirred for 17 h. Upon cooling to room temperature, the mixture was partitioned between methyl tert-butyl ether (500 mL) and water (1 L). The aqueous phase was separated and extracted with methyl tert-butyl ether (500 mL). The combined organic layers were washed with brine, dried over anhydrous sodium sulfate, filtered and concentrated to give (E)-1-(2-nitrostyryl)pyrrolidine (80 g, crude) as dark red oil. This was used for the next step without further purification.

Step 2: 1-(2,2-dimethoxyethyl)-2-nitrobenzene

To a solution of (E)-1-(2-nitrostyryl)pyrrolidine (80 g, crude) in methanol (600 mL) was added trimethylchlorosilane (59.5 g, 550 mmol) slowly. The mixture was heated to reflux for 24 h. At which time the solution was allowed to cool to room temperature and concentrated in vacuo to get the residue. It was partitioned between ethyl acetate (500 mL) and 5% aqueous citric acid (800 mL). The aqueous layer was extracted with ethyl acetate (2×300 mL). The combined organic layers were washed with 5% aqueous sodium bicarbonate (300 mL) followed by brine. The crude was dried over anhydrous sodium sulfate, filtered and concentrated to give 1-(2,2-dimethoxyethyl)-2-nitrobenzene (79 g, crude) as dark red oil which was used for the next step without further purification.

Step 3: 2-(2,2-dimethoxyethyl)aniline

To a solution of 1-(2,2-dimethoxyethyl)-2-nitrobenzene (79 g, 374.4 mmol) in methanol (1 L) was added palladium on activated carbon (17.6 g). The mixture was stirred under hydrogen at 50 psi at room temperature for 17 h. The mixture was filtered through diatomite and rinsed with methanol. The filtrate was concentrated to give the crude product. The crude was dissolved in methyl tert-butyl ether (500 mL) and filtered. The filtrate was concentrated to give 2-(2,2-dimethoxyethyl)aniline (60 g, 331.5 mmol, 88.5% yield) as dark red oil. This was used for the next step without further purification. $^1$H NMR (400 MHz, DMSO-d$_6$) δ ppm 6.98-6.89 (m, 2H), 6.63 (dd, J=7.9, 1.1 Hz, 1H), 6.51 (td, J=7.4, 1.2 Hz, 1H), 4.80 (s, 2H), 4.55 (t, J=5.6 Hz, 1H), 3.25 (s, 6H), 2.72 (d, J=5.6 Hz, 2H).

Step 4:
N-(2-(2,2-dimethoxyethyl)phenyl)formamide

To a solution of 2-(2,2-dimethoxyethyl)aniline (60 g, 331.5 mmol) and ethyl formate (36.8 g, 497.2 mmol) in dry tetrahydrofuran (400 mL) was added a solution of 1 M lithium bis(trimethylsilyl)amide (597 mL, 597 mmol) slowly. The mixture was stirred at room temperature for 12 h and then refluxed for 18 h. At which time saturated ammonium chloride (200 mL) was added and the mixture was extracted with ethyl acetate (3×200 mL). The organic phases were combined, dried over anhydrous sodium sulfate, filtered and concentrated. The crude was purified by silica gel chromatography [petroleum ether/ethyl acetate (6:1 v/v)] to afford N-(2-(2,2 dimethoxyethyl)phenyl)formamide (58 g, 277.5 mmol, 83.7% yield) as dark red oil.

LCMS (2.5 min formic acid): Rt=1.354 min, m/z: 209.1 [M+1]$^+$, 231.9 [M+Na]$^+$.

Step 5: 1-(2,2-dimethoxyethyl)-2-isocyanobenzene

To a solution of N-(2-(2,2 dimethoxyethyl)phenyl)formamide (58 g, 277.5 mmol) in dichloromethane (500 mL) at 0° C. was added triethylamine (143 g, 1415.3 mmol) followed by phosphorus oxychloride (63.9 g, 416.3 mmol). The mixture was warmed to room temperature and stirred for 2 h. At which time it was poured into saturated aqueous sodium bicarbonate (300 mL) and extracted with dichloromethane (3×200 mL). The organic layers were dried over anhydrous sodium sulfate, filtered and concentrated. The crude was purified by silica gel chromatography [petroleum ether/ethyl acetate (20:1 v/v)] to afford 1-(2,2-dimethoxy-ethyl)-2-isocyanobenzene (42 g, 218.5 mmol, 79.2% yield) as a pale brown oil. $^1$H NMR (400 MHz, DMSO-d$_6$) δ ppm 7.57-7.27 (m, 4H), 4.61 (t, J=5.6 Hz, 1H), 3.27 (s, 6H), 3.00 (d, J=5.6 Hz, 2H). LCMS (2.5 min formic acid): Rt=1.455 min, m/z: 192.0 (M+1)$^+$.

Step 6: 4,4-dimethoxy-2,2-dimethylbutanenitrile

To a solution of diisopropylamine (89.4 mL, 682 mmol) in tetrahydrofuran (1 L) at −10° C. under nitrogen was added a solution of 2.4 M n-butyl lithium in hexane (288 mL, 682 mmol). After 30 min, the mixture was cooled to −78° C. and a solution of 4,4-dimethoxybutanenitrile (40 g, 310 mmol) in tetrahydrofuran (30 mL) was added. After 1 h methyl iodide (42.4 mL, 682 mmol) was added very slowly. The mixture was allowed to warm to room temperature and stirred overnight. At which time it was quenched with saturated aqueous ammonium chloride and extracted with ethyl acetate (3×400 mL). The organic layers were dried over anhydrous sodium sulfate, filtered and concentrated. The crude was purified by silica gel chromatography [petroleum ether/ethyl acetate (30:1 v/v)] to afford 4,4-dimethoxy-2,2-dimethylbutanenitrile (35 g, 223 mmol, 71.9% yield) as pale yellow oil. $^1$H-NMR (400 MHz, CDCl$_3$) δ ppm 4.60 (t, J=5.4 Hz, 1H), 3.36 (s, 6H), 1.83 (d, J=5.4 Hz, 2H), 1.39 (s, 6H).

Step 7: 4,4-dimethoxy-2,2-dimethylbutanal

To a solution of 4,4-dimethoxy-2,2-dimethylbutanenitrile (27 g, 172 mmol) in dichloromethane (800 mL) was added a solution of 1 M diisobutylaluminium hydride in hexane (189 mL, 189 mmol) slowly at −78° C. for 3.5 h. At which time it was warmed to room temperature and quenched with saturated aqueous ammonium chloride (400 mL) and Rochelle salt (400 mL). The aqueous phase was extracted with dichloromethane (2×400 mL). The combined organic layers were washed with brine (400 mL), dried over anhydrous sodium sulfate, filtered and concentrated. The crude was purified by silica gel chromatography [petroleum ether/ethyl acetate (30:1 v/v)] to afford 4,4-dimethoxy-2,2-dimethylbutanal (13 g, 81.1 mmol, 47.1% yield) as a colorless oil. LCMS (2.5 min formic acid): Rt=1.453 min, m/z: 182.9 (M+Na)$^+$.

Step 8: (4S,9aS)-4-amino-7-(1H-indole-1-carbonyl)-8,8-dimethylhexahydropyrrolo[2,1-b][1,3]thiazepin-5(2H)-one a. A mixture of N-(tert-butoxycarbonyl)-S-trityl-L-homo-cysteine (11.8 g, 24.7 mmol), 1-(2,2-dimethoxyethyl)-2-isocyanobenzene (from Step 5) (4.5 g, 23.5 mmol), 4,4-dimethoxy-2,2-dimethylbutanal (from Step 7) (4.5 g, 28.2 mmol) and 7 M ammonia in methanol (10 mL) in 2,2,2-trifluoroethanol (150 mL) was stirred at 100° C. for 2 h. At which time it was quenched with 1 M aq. sodium hydroxide solution (200 mL) and extracted with ethyl acetate (3×150 mL). The combined organic phases were dried over anhydrous sodium sulfate, filtered and concentrated to give crude tert-butyl ((2S)-1-((1-((2-(2,2-dimethoxyethyl)phenyl) amino)-5,5-dimethoxy-3,3-dimethyl-1-oxopentan-2-yl) amino)-1-oxo-4-(tritylthio)butan-2-yl)carbamate (26 g, crude) as brown solid. It was used for the next step without any further purification.

b. Further to step a, to a solution of crude tert-butyl ((2S)-1-((1-((2-(2,2-dimethoxyethyl)phenyl)amino)-5,5-di-methoxy-3,3-dimethyl-1-oxopentan-2-yl)amino)-1-oxo-4-(tritylthio)butan-2-yl)carbamate (26 g, crude) in dichloromethane (200 mL) was added trifluoroacetic acid (20 mL) slowly. The mixture was stirred at 40° C. for 2 h. The solvent was concentrated and the crude was purified by silica gel chromatography [dichloromethane/methanol (25:1 v/v)] to afford (4S,9aS)-4-amino-7-(1H-indole-1-carbonyl)-8,8-di-methylhexahydropyrrolo[2,1-b][1,3]thiazepin-5(2H)-one (7.5 g, 21.0 mmol) as a sandy solid. LCMS (2.5 min formic acid): Rt=1.361 min, m/z: 357.9 (M+1)$^+$.

Step 9: tert-butyl ((S)-1-(((4S,7S,9aS)-7-(1H-indole-1-carbonyl)-8,8-dimethyl-5-oxooctahydropyrrolo[2,1-b][1,3]thiazepin-4-yl)amino)-1-oxopropan-2-yl)(methyl)carbamate To a solution of (4S,9aS)-4-amino-7-(1H-indole-1-carbo-nyl)-8,8-dimethylhexahydropyrrolo[2,1-b][1,3]thiazepin-5(2H)-one (14 g, 39.2 mmol), N-(tert-butoxycarbonyl)-N-methyl-L-alanine (8.76 g, 43.1 mmol), 1-hydroxybenzotriazole (5.82 g, 43.1 mmol) and 4-methyl-morpholine (11.88 g, 117.6 mmol) in tetrahydrofuran (400 mL) was added N-(3-dimethylaminopropyl)-N'-ethylcarbodiimide hydrochloride (8.27 g, 43.1 mmol). The mixture was stirred at room temperature for 3 h. At which time it was quenched with saturated aqueous sodium bicarbonate solution (300 mL) and extracted with ethyl acetate (3×150 mL). The combined organic layers were washed with brine (200 mL), dried over anhydrous sodium sulfate, filtered and concentrated. The crude was purified by silica gel chromatography [petroleum ether/ethyl acetate (2:1 v/v to 1:1 v/v)] to afford tert-butyl ((S)-1-(((4S,7R,9aS)-7-(1H-indole-1-carbonyl)-8,8-dimethyl-5-oxooctahydropyrrolo[2,1-b][1,3]thiazepin-4-yl)amino)-1-oxopropan-2-yl)(methyl)carbamate (5.2 g, 9.6 mmol, 24.5% yield) as sandy solid and the desired product tert-butyl ((S)-1-(((4S,7S,9aS)-7-(1H-indole-1-carbonyl)-8,8-dimethyl-5-oxooctahydropyrrolo[2,1-b][1,3]thiazepin-4-yl)amino)-1-oxopropan-2-yl)(methyl)carbamate (5.0 g, 9.2 mmol, 23.5% yield) as pale yellow solid. LCMS (2.5 min formic acid): Rt=1.740 min, m/z: 564.8 (M+1)⁺.

Step 10: (4S,7S,9aS)-4-((S)-2-((tert-butoxycarbonyl)(methyl)amino)propanamido)-8,8-dimethyl-5-oxooctahydropyrrolo[2,1-b][1,3]thiazepine-7-carboxylic Acid To a solution of tert-butyl ((S)-1-(((4S,7S,9aS)-7-(1H-indole-1-carbonyl)-8,8-dimethyl-5-oxooctahydropyrrolo[2,1-b][1,3]thiazepin-4-yl)amino)-1-oxopropan-2-yl)(methyl)carbamate (3.9 g, 7.19 mmol) in methanol (60 mL) was added 1 M aqueous sodium hydroxide solution (60 mL). The mixture was stirred at room temperature for 24 h. The volatile solvent was removed under reduced pressure. The remaining aqueous phase was washed with ethyl acetate (50 mL) and the pH of the aqueous phase was adjusted with citric acid to pH 3. The aqueous phase was extracted with ethyl acetate (3×60 mL). The combined organic phases were washed with brine (100 mL), dried over anhydrous sodium sulfate, filtered and concentrated. The crude was purified by silica gel chromatography [petroleum ether/ethyl acetate (1:2 v/v)] to afford (4S,7S,9aS)-4-((S)-2-((tert-butoxycarbonyl)(methyl)amino)propanamido)-8,8-dimethyl-5-oxooctahydropyrrolo[2,1-b][1,3]thiazepine-7-carboxylic acid (2 g, 4.51 mmol, 62.7% yield) as a white solid. LCMS (2.5 min formic acid): Rt=1.493 min, m/z: 443.9 (M+1). ¹H NMR (400 MHz, CDCl₃) δ ppm 12.57 (s, 1H), 7.75 (d, J=6.6 Hz, 1H), 5.46 (t, J=7.2 Hz, 1H), 4.64-4.60 (m, 1H), 4.43 (s, 1H), 3.98 (s, 1H), 3.17-3.11 (m, 1H), 2.88 (dd, J=14.6, 3.0 Hz, 1H), 2.74 (s, 3H), 2.27 (dd, J=12.9, 7.5 Hz, 1H), 2.12-2.10 (m, 1H), 1.80 (dd, J=13.0, 7.1 Hz, 1H), 1.74-1.68 (m, J=11.2 Hz, 1H), 1.40 (s, 9H), 1.25 (d, J=7.1 Hz, 3H), 1.09 (d, J=10.6 Hz, 6H).

Intermediate II (4S,7S,9aS)-4-((S)-2-((tert-butoxycarbonyl)(methyl)amino)propanethioamido)-8,8,9a-trimethyl-5-oxooctahydropyrrolo[2,1-b][1,3]thiazepine-7-carboxylic Acid

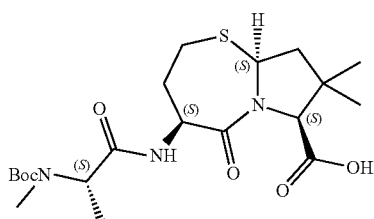

Step 1: tert-butyl (S)-(1-((2-amino-5-nitrophenyl)amino)-1-oxopropan-2-yl)(methyl)carbamate To a solution of N-(tert-butoxycarbonyl)-N-methyl-L-alanine (20.3 g, 100 mmol) in dry tetrahydrofuran (1.2 L) was added 4-methylmorpholine (20.2 g, 200 mmol). The mixture was stirred at −20° C. for 10 min followed by the addition of isobutyl carbonochloridate (13.6 g, 100 mmol) dropwise. The mixture was stirred at −15° C. for 2 h and warmed to room temperature overnight. The mixture was diluted with ethyl acetate (1.6 L) and washed successively with 1 M aq. disodium hydrogen phosphate solution (1 L), 5% aq. sodium bicarbonate solution (1 L) and brine (1 L). The organic phase was dried over anhydrous sodium sulfate, filtered and concentrated to give (S)-tert-butyl (1-((2-amino-5-nitrophenyl)amino)-1-oxopropan-2-yl)(methyl)carbamate (30 g, 88.7 mmol, 88.7% yield) as dark red oil. LCMS (2.5 min formic acid): Rt=1.537 min, m/z: 360.9 (M+Na)⁺.

Step 2: tert-butyl (S)-(1-((2-amino-5-nitrophenyl)amino)-1-thioxopropan-2-yl)(methyl)carbamate To a solution of phosphorus (V) sulfide (24.4 g, 110 mmol) in dry tetrahydrofuran (1.6 L) was added sodium carbonate (5.8 g, 55 mmol). The mixture was stirred for 1 h at room temperature which was then cooled to 0° C. Tert-butyl (S)-(1-((2-amino-5-nitrophenyl)amino)-1-oxopropan-2-yl)(methyl)carbamate (40 g, 110 mmol) was added to the reaction. The mixture was stirred at room temperature for 3 h. The solvent was concentrated in vacuo and diluted with ethyl acetate (1 L) which was washed with 5% aq. sodium bicarbonate solution (500 mL) and brine (500 mL). The organic layer was dried over anhydrous sodium sulfate, filtered and concentrated to give tert-butyl (S)-(1-((2-amino-5-nitrophenyl)amino)-1-thioxopropan-2-yl)(methyl)carbamate (33 g, 93.2 mmol, 84.7% yield) product as an orange solid. LCMS (2.5 min formic acid): Rt=1.602 min, m/z: 376.8 (M+Na)⁺.

Step 3: tert-butyl (S)-methyl(1-(6-nitro-1H-benzo[d][1,2,3]triazol-1-yl)-1-thioxopropan-2-yl)carbamate To a solution of tert-butyl (S)-(1-((2-amino-5-nitrophenyl)amino)-1-thioxopropan-2-yl)(methyl)carbamate (30 g, 84.6 mmol) in dry tetrahydrofuran (250 mL) and acetic acid (250 mL) was added sodium nitrite (9 g, 130.4 mmol). The mixture was stirred at 0° C. for 1.5 h. It was washed successively with water (3×500 mL), 5% aq. sodium bicarbonate solution (2×500 mL) and brine (500 mL). The organic layer was dried over anhydrous sodium sulfate, filtered and concentrated to give tert-butyl (S)-methyl(1-(6-nitro-1H-benzo[d][1,2,3]triazol-1-yl)-1-thioxopropan-2-yl)carbamate (20 g, 54.8 mmol, 64.8% yield) as brown oil which was used for the next step without further purification.

Step 4: tert-butyl ((S)-1-(((4S,7S,9aS)-7-(1H-indole-1-carbonyl)-8,8-dimethyl-5-oxooctahydropyrrolo[2,1-b][1,3]thiazepin-4-yl)amino)-1-thioxopropan-2-yl)(methyl)carbamate To a solution of (4S,9aS)-4-amino-7-(1H-indole-1-carbonyl)-8,8-dimethylhexahydropyrrolo[2,1-b][1,3]thiazepin-5(2H)-one (15 g, 42 mmol) and tert-butyl (S)-methyl(1-(6-nitro-1H-benzo[d][1,2,3]triazol-1-yl)-1-thioxopropan-2-yl) carbamate (20 g, 54.7 mmol) in dichloromethane (400 mL) was added triethylamine (8.6 g, 84.6 mmol) at 0° C. The mixture was stirred at room temperature overnight. The mixture was concentrated under reduced pressure to give the crude. The crude was purified by silica gel chromatography (ethyl acetate/Petroleum ether=1/15) to give tert-butyl ((S)-1-(((4S,7R,9aS)-7-(1H-indole-1-carbonyl)-8,8-dimethyl-5-oxooctahydropyrrolo[2,1-b][1,3]thiazepin-4-yl)amino)-1-thioxopropan-2-yl)(methyl)carbamate (3.0 g, 5.37 mmol, 25.5% yield) as yellow oil and the desired diastereoisomer tert-butyl ((S)-1-(((4S,7S,9aS)-7-(1H-indole-1-carbonyl)-8,8-dimethyl-5-oxooctahydropyrrolo[2,1-b][1,3]thiazepin-4-yl)amino)-1-thioxopropan-2-yl)(methyl)carbamate (3.9 g, 6.98 mmol, 29.4% yield) as a yellow oil. LCMS (2.5 min formic acid): Rt=1.905 min, m/z: 580.8 (M+Na)$^+$.

Step 5: (4S,7S,9aS)-4-(2-((tert-butoxycarbonyl) (methyl)amino)ethanethioamido)-8,8,9a-trimethyl-5-oxooctahydropyrrolo[2,1-b][1,3]thiazepine-7-carboxylic Acid To a solution of tert-butyl (2-(((4S,7S,9aS)-7-(1H-indole-1-carbonyl)-8,8-dimethyl-5-oxooctahydropyrrolo[2,1-b][1,3]thiazepin-4-yl)amino)-2-thioxoethyl)(methyl)carbamate (1.5 g, 2.69 mmol) in methanol was added 1 M aq. sodium hydroxide solution (60 mL) slowly. The mixture was stirred at room temperature overnight. The volatile solvent was removed under reduced pressure and the remaining solution was extracted with ethyl acetate (50 mL). The pH of the aqueous layer was adjusted with 20% aqueous citric acid solution to pH 4 which was then extracted with ethyl acetate (3×100 mL). The organic layers were combined, washed with brine (100 mL), dried over anhydrous sodium sulfate, filtered and concentrated to give (4S,7S,9aS)-4-(2-((tert-butoxycarbonyl)(methyl)amino)ethanethioamido)-8,8,9a-trimethyl-5-oxooctahydropyrrolo[2,1-b][1,3]thiazepine-7-carboxylic acid (1 g, 21.8 mmol, 81% yield) as brown oil. LCMS (2.5 min formic acid): Rt=1.632 min, m/z: 481.8 (M+Na)$^+$.

Example 1

(4S,4'S,7S,7'S,9aS,9a'S)—N,N'-(methylenebis(4,1-phenylene))bis(8,8-dimethyl-4-((S)-2-(methylamino) propanamido)-5-oxooctahydropyrrolo[2,1-b][1,3]thiazepine-7-carboxamide)dihydrochloride

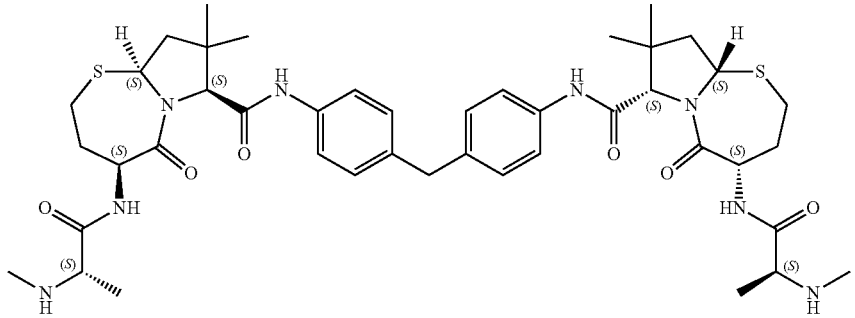

Step 1: N, N'-(methylenebis (4,1-phenylene)) diformamide

To a solution of 4,4'-methylenedianiline (5 g, 25.2 mmol) in toluene (40 mL) was added formic acid (4.64 g, 100.8 mmol). The mixture was stirred at 110° C. for 2 h. The reaction was concentrated. The crude was washed with dichloromethane and filtered to get the desired product N, N'-(methylenebis (4,1-phenylene)) diformamide (4.7 g, 18.5 mmol, 73.4% yield) as white solid. LCMS (2.5 min formic acid): Rt=1.165 min, m/z: 255.1 (M+1)$^+$.

Step 2: bis (4-isocyanophenyl)methane

To a solution of N, N'-(methylenebis (4,1-phenylene)) diformamide (4.7 g, 18.5 mmol) in dichloromethane (150 mL) at 0° C. was added triethylamine (19 g, 188.7 mmol) followed by the addition of phosphorus oxychloride (8.5 g, 55.4 mmol). The mixture was warmed to room temperature and stirred for 2 h. The reaction was poured into saturated aqueous sodium bicarbonate (100 mL) and extracted with dichloromethane (3×60 mL). The organics were dried over anhydrous sodium sulfate, filtered and concentrated. The crude was purified by silica gel chromatography [dichloromethane/methanol (25:1 v/v)] to afford bis (4-isocyanophenyl) methane (1.6 g, 7.3 mmol, 39.6% yield) as a white solid. LCMS (2.5 min formic acid): Rt=1.715 min, m/z: 218.9 (M+1)$^+$.

Step 3: (4S,4'S,9aS,9a'S)—N,N'-(methylenebis(4,1-phenylene))bis(4-amino-8,8-dimethyl-5-oxooctahydropyrrolo[2,1-b][1,3]thiazepine-7-carboxamide A mixture of N-(tert-butoxycarbonyl)-S-trityl-L-homocysteine (2.4 g, 5.04 mmol), bis(4-isocyanophenyl)methane (500 mg, 2.29 mmol), 4,4-dimethoxy-2,2-dimethylbutanal (954 mg, 5.95 mmol) and 7 M ammonia in methanol (2 mL, 14 mmol) in 2,2,2-trifluoroethanol (10 mL) was stirred at 80° C. for 30 min under microwave conditions. The mixture was quenched with 1 M aqueous sodium hydroxide (20 mL) and extracted with ethyl acetate (3×15 mL). The organic phases were combined, dried over anhydrous sodium sulfate, filtered and concentrated to give crude di-tert-butyl ((2S,2'S)-((((methylenebis(4,1-phenylene))bis(azanediyl)) bis(5,5-dimethoxy-3,3-dimethyl-1-oxopentane-1,2-diyl))bis (azanediyl))bis(1-oxo-4-(tritylthio)butane-1,2-diyl))dicarbamate (2.0 g, crude) as a brown solid. It was used to next step without any further purification. To a solution of crude di-tert-butyl ((2S,2'S)-((((methylenebis(4,1-phenylene))bis (azanediyl))bis(5,5-dimethoxy-3,3-dimethyl-1-oxopentane-1,2-diyl))bis(azanediyl))bis(1-oxo-4-(tritylthio)butane-1,2-diyl))dicarbamate (2 g, crude) in dichloromethane (20 mL) was added trifluoroacetic acid (5 mL) slowly. The mixture was stirred at 40° C. for 2 h. The reaction was concentrated and purified by silica gel chromatography [dichloromethane/methanol (6:1 v/v)] to afford (4S,4'S,9aS,9a'S)—N,N'-(methylenebis(4,1-phenylene))bis(4-amino-8,8-dimethyl-5-oxooctahydropyrrolo[2,1-b][1,3]thiazepine-7-carboxamide)

(500 mg, 0.74 mmol) as a sandy solid. LCMS (2.5 min formic acid): Rt=1.263 min, m/z: 678.8 (M+1)$^+$.

Step 4: di-tert-butyl ((2S,2'S)-(((4S,4'S,7S,7'S,9aS, 9a'S)-(((methylenebis(4,1-phenylene))bis (azanediyl))bis(carbonyl))bis(8,8-dimethyl-5-oxooctahydropyrrolo[2,1-b][1,3]thiazepine-7,4-diyl))bis (azanediyl))bis(1-oxopropane-1,2-diyl))bis (methylcarbamate)

To a solution of (4S,4'S,9aS,9a'S)—N,N'-(methylenebis (4,1-phenylene))bis(4-amino-8,8-dimethyl-5-oxooctahydropyrrolo[2,1-b][1,3]thiazepine-7-carboxamide) (550 mg, 0.810 mmol), N-(tert-butoxycarbonyl)-N-methyl-L-alanine (362 mg, 1.782 mmol), 1-hydroxybenzotriazole (241 mg, 1.782 mmol) and 4-methylmorpholine (491 mg, 4.860 mmol) in tetrahydrofuran (30 mL) was added N-(3-dimethylaminopropyl)-N'-ethylcarbodiimide hydrochloride (342 mg, 1.782 mmol). The mixture was stirred at room temperature for 3 h. The mixture was quenched with saturated aq. sodium bicarbonate (25 mL) and extracted with ethyl acetate (3×15 mL). The combined organic phases were washed with brine (20 mL), dried over anhydrous sodium sulfate, filtered and concentrated. The crude was purified by silica gel chromatography [dichloromethane/methanol (25:1 v/v)] give impure product which was further purified by chiral-HPLC to afford the desired product di-tert-butyl ((2S,2'S)-(((4S,4'S,7S,7'S,9aS,9a'S)-(((methylenebis(4,1-phenylene)) bis(azanediyl))bis(carbonyl))bis(8,8-dimethyl-5-oxooctahydropyrrolo[2,1-b][1,3]thiazepine-7,4-diyl))bis (azanediyl))bis(1-oxopropane-1,2-diyl))bis (methylcarbamate) (55 mg, 0.052 mmol, 6.4% yield) as a white solid. LCMS (2.5 min formic acid): Rt=1.828 min, m/z: 425 [(M-2Boc)+2]$^+$/2.

Step 5: (4S,4'S,7S,7'S,9aS,9a'S)—N,N'-(methylenebis(4,1-phenylene))bis(8,8-dimethyl-4-((S)-2-(methylamino)propanamido)-5-oxooctahydropyrrolo [2,1-b][1,3]thiazepine-7-carboxamide) dihydrochloride To a solution of di-tert-butyl ((2S,2'S)-(((4S,4'S,7S,7'S, 9aS,9a'S)-(((methylenebis(4,1-phenylene))bis(azanediyl)) bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (55 mg, 0.052 mmol) in dichloromethane (6 mL) was added 4 N hydrogen chloride in 1,4-dioxane (1.5 mL). The mixture was stirred at room temperature for 2 h. The solvent was removed under reduced pressure and the solid was dried under high vacuum to give (4S,4'S,7S,7'S,9aS,9a'S)—N,N'-(methylenebis(4,1-phenylene))bis(8,8-dimethyl-4-((S)-2-(methylamino)propanamido)-5-oxooctahydropyrrolo[2,1-b][1,3]thiazepine-7-carboxamide) dihydrochloride (43 mg, 0.046 mmol, 88.5% yield) as white solid. $^1$H NMR (400 MHz, DMSO-d$_6$) δ ppm 10.08 (s, 2H), 9.27-9.24 (m, 2H), 8.87-8.84 (m, 2H), 8.80 (d, J=6.8 Hz, 2H), 7.52 (d, J=8.0 Hz, 2H), 7.14 (d, J=8.0 Hz, 2H), 5.47 (t, J=7.8 Hz, 2H), 4.71 (t, J=9.4 Hz, 2H), 4.26 (s, 2H), 3.84 (s, 2H), 3.71-3.65 (m, 2H), 3.17 (t, J=12.4 Hz, 2H), 2.95-2.91 (m, 2H), 2.48-2.47 (m, 6H), 2.23-2.18 (m, 2H), 2.14-2.10 (m, 2H), 1.96-1.90 (m, 2H), 1.85-1.76 (m, 2H), 1.42 (s, 4H), 1.39 (d, J=7.2 Hz, 6H), 1.09 (m, 6H), 1.02 (m, 6H). LCMS (2.5 min formic acid): Rt=1.268 min, m/z: 848.9 (M+1)$^+$.

Example 2

(4S,4'S,7S,7'S,9aS,9a'S)—N,N'-(methylenebis(4,1-phenylene))bis(8,8-dimethyl-4-((S)-2-(methylamino) propanethioamido)-5-oxooctahydropyrrolo[2,1-b][1, 3]thiazepine-7-carboxamide)dihydrochloride

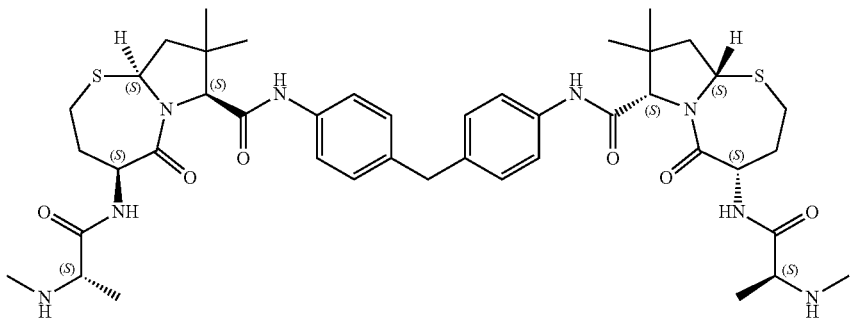

Step 1: di-tert-butyl ((2S,2'S)-(((4S,4'S,7S,7'S,9aS, 9a'S)-(((methylenebis(4,1-phenylene))bis (azanediyl))bis(carbonyl))bis(8,8-dimethyl-5-oxooctahydropyrrolo[2,1-b][1,3]thiazepine-7,4-diyl))bis (azanediyl))bis(1-thioxopropane-1,2diyl))bis (methylcarbamate)

To a solution of (4S,4'S,9aS,9a'S)—N,N'-(methylenebis (4,1-phenylene))bis(4-amino-8,8-dimethyl-5-oxooctahydropyrrolo[2,1-b][1,3]thiazepine-7-carboxamide) (Example 1, Step 3) (260 mg, 0.38 mmol) in dichloromethane (10 mL) at 0° C. was added triethylamine (116.3 mg, 1.15 mmol). After 10 min, a solution of tert-butyl (S)-methyl(1-(6-nitro-1H-benzo[d][1,2,3]triazol-1-yl)-1-thioxopropan-2-yl)carbamate (321.9 mg, 0.88 mmol) in dichloromethane (5 mL) was added. The mixture was stirred at room temperature for another 2 h. The solvent was removed under reduced pressure to give a yellow syrup. The residue was purified by thin layer chromatography [ethyl acetate/petroleum ether (1:4 v/v)] to give yellow oil (200 mg, 0.18 mmol) which was purified further by chiral-HPLC to give title product (45 mg, 0.04 mmol, 10.9% yield). LCMS (2.5 min formic acid): Rt=1.998 min, m/z: 980.6 (M-Boc+1)$^+$.

Step 2: (4S,4'S,7S,7'S,9aS,9a'S)—N,N'-(methylenebis(4,1-phenylene))bis(8,8-dimethyl-4-((S)-2-(methylamino)propanethioamido)-5-oxooctahydropyrrolo[2,1-b][1,3]thiazepine-7-carboxamide) dihydrochloride To a solution of di-tert-butyl ((2S,2'S)-(((4S,4'S,7S,7'S, 9aS,9a'S)-(((methylenebis(4,1-phenylene))bis(azanediyl)) bis(carbonyl))bis(8,8-dimethyl-5-oxooctahydropyrrolo[2,1-b][1,3]thiazepine-7,4-diyl))bis(azanediyl))bis(1- thioxopropane-1,2-diyl))bis(methylcarbamate) (45 mg, 0.042 mmol) in diethyl ether (2 mL) was added hydrogen chloride (4 N in 1,4-dioxane, 1 mL). The reaction was stirred at room temperature for 6 h. The mixture was concentrated under reduced pressure and dried under high vacuum to afford (4S,4'S,7S,7'S,9aS,9a'S)—N,N'-(methylenebis(4,1-phenylene))bis(8,8-dimethyl-4-((S)-2-(methylamino)propanethioamido)-5-oxooctahydropyrrolo[2,1-b][1,3]thiazepine-7-carboxamide) dihydrochloride (22 mg, 0.025 mmol, 55% yield) as light yellow solid. $^1$H NMR (400 MHz, DMSO-d$_6$) δ ppm 11.08-11.96 (m, 2H), 10.15 (s, 1H), 9.89 (s, 1H), 9.64 (s, 1H), 8.66 (s, 1H), 8.42 (s, 1H), 7.52 (d, J=8.0 Hz, 2H), 7.14 (d, J=8.0 Hz, 2H), 5.43 (t, J=7.6 Hz, 2H), 5.16-5.08 (m, 2H), 4.29-4.20 (m, 4H), 3.84 (s, 2H), 3.72-3.67 (m, 2H), 3.22-3.16 (m, 2H), 3.01-2.98 (m, 2H), 2.49 (s, 6H), 2.25-2.21 (m, 4H), 2.00-1.92 (m, 4H), 1.46-1.43 (m, 6H), 1.11 (m, 6H), 1.02 (m, 6H). LCMS (2.5 min formic acid): Rt=1.298 min, m/z: 880.6 (M+1)$^+$.

Example 3

(4S,4'S,7S,7'S,9aS,9a'S)—N,N'-(ethane-1,2-diylbis(2,1-phenylene))bis(8,8-dimethyl-4-((S)-2-(methylamino)propanamido)-5-oxooctahydropyrrolo[2,1-b][1,3]thiazepine-7-carboxamide) dihydrochloride

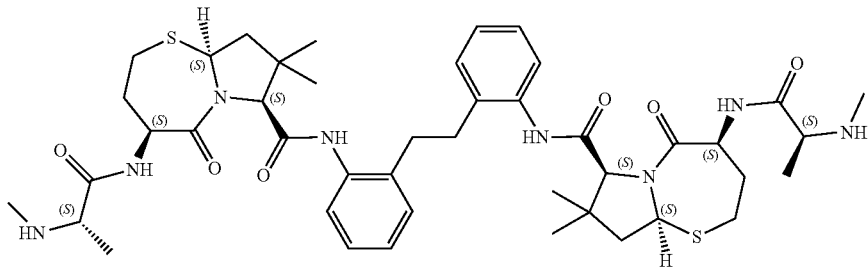

Step 1: 22'-(ethane-1,2-diyl)dianiline

To a solution of 1,2-bis(2-nitrophenyl)ethane (9.5 g, 34.9 mmol) in ethanol (200 mL) was added palladium on activated carbon (1 g). The mixture was stirred under hydrogen (1 atm) at room temperature for 5 h. The catalyst was filtered and the filtrate was concentrated under reduced pressure. The crude was purified by silica gel chromatography [petroleum ether/ethyl acetate (1:1 v/v)] to afford 2,2'-(ethane-1,2-diyl)dianiline (5 g, 23.6 mmol, 67.6% yield) as yellow solid. LCMS (2.5 min formic acid): Rt=1.336 min, 212.9 (M+1)$^+$.

Step 2: N,N'-(ethane-1,2-diylbis(2,1-phenylene)) diformamide

To a solution of 2,2'-(ethane-1,2-diyl)dianiline (5 g, 23.6 mmol) in toluene (100 mL) was added formic acid (4.3 g, 94.4 mmol). The mixture was stirred under reflux overnight. The mixture was concentrated under reduced pressure to give the crude which was washed with petroleum ether to give N,N'-(ethane-1,2-diylbis(2,1-phenylene))diformamide (5 g, 18.7 mmol, 79.2% yield) as white solid.

Step 3: 1,2-bis(2-isocyanophenyl)ethane

To a solution of N,N'-(ethane-1,2-diylbis(2,1-phenylene)) diformamide (2 g, 7.46 mmol) in dichloromethane 50 mL) at 0° C. was added triethylamine (7.5 g, 74.6 mmol) followed by the addition of phosphorus oxychloride (3.4 g, 22.4 mmol). The mixture was warmed to room temperature and stirred for 4 h. The reaction was then poured into saturated aq. sodium bicarbonate solution (50 mL) and extracted with dichloromethane (3×30 mL). The combined organic phases were dried over anhydrous sodium sulfate, filtered and concentrated. The crude was purified by silica gel chromatography [petroleum ether/ethyl acetate (4:1 v/v)] to afford 1,2-bis(2-isocyanophenyl)ethane (1.5 g, 6.47 mmol, 86.7% yield) as white solid. LCMS (2.5 min formic acid): Rt=1.763 min, m/z: 233.0 (M+1)$^+$.

Step 4: (4S,4'S,9aS,9a'S)—N,N'-(ethane-1,2-diylbis(2,1-phenylene))bis(4-amino-8,8-dimethyl-5-oxooctahydropyrrolo[2,1-b][1,3]thiazepine-7-carboxamide)

A mixture of N-(tert-butoxycarbonyl)-S-trityl-L-homocysteine (4.1 g, 8.6 mmol), bis(4-isocyanophenyl)methane (1 g, 4.3 mmol), 4,4-dimethoxy-2,2-dimethylbutanal (1.45 g, 9.0 mmol) and 7 M ammonia in methanol (2.4 mL, 16.8 mmol) in 2,2,2-trifluoroethanol (20 mL) was stirred at 80° C. for 30 min under microwave conditions. The reaction was quenched with 1 M sodium hydroxide solution (40 mL) and extracted with ethyl acetate (3×30 mL). The combined organic layers were dried over anhydrous sodium sulfate, filtered and concentrated to get crude di-tert-butyl ((2S,2'S)-((((ethane-1,2-diylbis(2,1-phenylene))bis(azanediyl))bis(5,5-dimethoxy-3,3-dimethyl-1-oxopentane-1,2-diyl))bis(azanediyl))bis(1-oxo-4-(tritylthio)butane-1,2-diyl)) dicarbamate (4.0 g, crude) as brown solid. To the solution of crude di-tert-butyl ((2S,2'S)-((((ethane-1,2-diylbis(2,1-phenylene))bis(azanediyl))bis(5,5-dimethoxy-3,3-dimethyl-1-oxopentane-1,2-diyl))bis(azanediyl))bis(1-oxo-4-(tritylthio) butane-1,2-diyl))dicarbamate (4 g, crude) in dichloromethane (50 mL) was added trifluoroacetic acid (10 mL) slowly. The mixture was stirred at 40° C. for 2 h. The reaction was concentrated and purified by silica gel chromatography [dichloromethane/methanol (6:1 v/v)] to afford (4S,4'S,9aS,9a'S)—N,N'-(ethane-1,2-diylbis(2,1-phenylene))bis(4-amino-8,8-dimethyl-5-oxooctahydropyrrolo[2,1-b][1,3]thiazepine-7-carboxamide) (2.3 g, 3.32 mmol, 77.2% yield) as yellow solid. LCMS (2.5 min formic acid): Rt=1.317 min, m/z: 692.9 (M+1)$^+$.

Step 5: di-tert-butyl ((2S,2'S)-(((4S,4'S,7S,7'S,9aS, 9a'S)-(((ethane-1,2-diylbis(2,1-phenylene))bis (azanediyl))bis(carbonyl))bis(8,8-dimethyl-5-oxooctahydropyrrolo[2,1-b][1,3]thiazepine-7,4-diyl))bis (azanediyl))bis(1-oxopropane-1,2-diyl))bis (methylcarbamate)

To a solution of (4S,4'S,9aS,9a'S)—N,N'-(ethane-1,2-diylbis(2,1-phenylene))bis(4-amino-8,8-dimethyl-5-oxooctahydropyrrolo[2,1-b][1,3]thiazepine-7-carboxamide) (1 g, 1.44 mmol), N-(tert-butoxycarbonyl)-N-methyl-L-alanine (580 mg, 2.88 mmol), 1-hydroxybenzotriazole (430 mg, 3.17 mmol) and 4-methylmorpholine (580 mg, 5.76 mmol) in tetrahydrofuran (30 mL) was added N-(3-dimethylaminopropyl)-N'-ethylcarbodiimide hydrochloride (580 mg, 3.04 mmol). The mixture was stirred at room temperature for 3 h. The reaction was quenched with saturated aq. sodium bicarbonate solution (25 mL) and extracted with ethyl acetate (3×15 mL). The combined organic layers were washed with brine (20 mL), dried over anhydrous sodium sulfate, filtered and concentrated. The crude was purified by silica gel chromatography [petroleum ether/ethyl acetate (1:1 v/v)] to afford di-tert-butyl ((2S,2'S)-(((4S,4'S,7S,7'S,9aS,9a'S)-(((ethane-1,2-diylbis(2,1-phenylene))bis (azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (1.2 g, 1.13 mmol, 78.5% yield) as beige solid. LCMS (2.5 min formic acid): Rt=1.910 min, m/z: 431.9 [(M-2Boc)+2]$^+$/2.

Step 6: (4S,4'S,7S,7'S,9aS,9a'S)—N,N'-(ethane-1,2-diylbis(2,1-phenylene))bis(8,8-dimethyl-4-((S)-2-(methylamino)propanamido)-5-oxooctahydropyrrolo[2,1-b][1,3]thiazepine-7-carboxamide) dihydrochloride To a solution of di-tert-butyl ((2S,2'S)-(((4S,4'S,7S,7'S,9aS,9a'S)-(((ethane-1,2-diylbis(2,1-phenylene))bis (azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (90 mg, 0.085 mmol) in methanol (10 mL) was added 4 N hydrogen chloride in 1,4-dioxane (5 mL). The mixture was stirred at room temperature for 4 h. The mixture was then concentrated and crystallized from ether and methanol to afford (4S,4'S,7S,7'S,9aS,9a'S)—N,N'-(ethane-1,2-diylbis(2,1-phenylene))bis(8,8-dimethyl-4-((S)-2-(methylamino)propanamido)-5-oxooctahydropyrrolo[2,1-b][1,3]thiazepine-7-carboxamide) dihydrochloride (15 mg, 0.016 mmol, 18.8% yield) as white solid. $^1$H NMR (400 MHz, DMSO-d$_6$) δ ppm 9.51 (s, 2H), 9.15 (s, 2H), 8.83-8.77 (m, 4H), 7.39-7.53 (m, 4H), 7.21-7.12 (m, 4H), 5.50 (t, J=8.0 Hz, 2H), 4.74 (t, J=9.6 Hz, 2H), 4.38 (s, 2H), 3.90-3.82 (m, 2H), 3.17-3.11 (m, 2H), 2.99-2.82 (m, 6H), 2.48 (m, 6H), 2.26-2.21 (m, 2H), 2.04-1.95 (m, 4H), 1.72-1.63 (m, 2H), 1.36 (d, J=6.4 Hz, 6H), 1.14 (m, 6H), 1.12 (m, 6H). LCMS (2.5 min formic acid): Rt=1.293 min, m/z: 862.9 (M+1)$^+$.

Example 4

(4S,4'S,7S,7'S,9aS,9a'S)—N,N'-(ethane-1,2-diylbis(2,1-phenylene))bis(8,8-dimethyl-4-((S)-2-(methylamino)propanethioamido)-5-oxooctahydropyrrolo[2,1-b][1,3]thiazepine-7-carboxamide) dihydrochloride

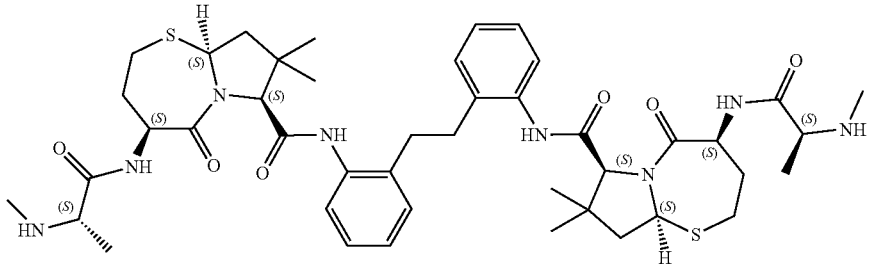

Step 1: di-tert-butyl ((2S,2'S)-(((4S,4'S,7S,7'S,9aS,9a'S)-(((ethane-1,2-diylbis(2,1-phenylene)) bis (azanediyl))bis(carbonyl))bis(8,8-dimethyl-5-oxooctahydropyrrolo[2,1-b][1,3]thiazepine-7,4-diyl))bis (azanediyl))bis(1-thioxopropane-1,2-diyl))bis (methylcarbamate)

To a solution of (4S,4'S,9aS,9a'S)—N,N'-(ethane-1,2-diylbis(2,1-phenylene))bis(4-amino-8,8-dimethyl-5-oxooctahydropyrrolo[2,1-b][1,3]thiazepine-7-carboxamide) (300 mg, 0.44 mmol) in dichloromethane (20 mL) at 0° C. was added triethylamine (132 mg, 1.31 mmol) and tert-butyl (S)-methyl(1-(6-nitro-1H-benzo[d][1,2,3]triazol-1-yl)-1-thioxopropan-2-yl)carbamate (400 mg, 1.09 mmol). The mixture was warmed to room temperature and stirred overnight. The mixture was washed with saturated aq. sodium bicarbonate solution (15 mL) and brine (15 mL). The organic layer was dried over anhydrous sodium sulfate, filtered and concentrated. The crude was purified by Prep-HPLC to give di-tert-butyl ((2S,2'S)-(((4S,4'S,7S,7'S,9aS,9a'S)-(((ethane-1,2-diylbis(2,1-phenylene)) bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate) (50 mg, 0.046 mmol, 10.5% yield) as white solid. LCMS (2.5 min formic acid): Rt=2.173 min, m/z: 1116.6 (M+Na)$^+$.

Step 2: (4S,4'S,7S,7'S,9aS,9a'S)—N,N'-(ethane-1,2-diylbis(2,1-phenylene))bis(8,8-dimethyl-4-((S)-2-(methylamino)propanethioamido)-5-oxooctahydropyrrolo[2,1-b][1,3]thiazepine-7-carboxamide) dihydrochloride To a solution of di-tert-butyl ((2S,2'S)-(((4S,47'S,9aS,9a'S)-(((ethane-1,2-diylbis(2,1-phenylene))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate) (50 mg, 0.046 mmol) in dichloromethane (5 mL) was added 4 N hydrogen chloride in 1,4-dioxane (4 mL). The mixture was stirred at room temperature for 4 h. The mixture was concentrated and dried under high vacuum to give (4S,4'S,7S,7'S,9aS,9a'S)—N,N'-(ethane-1,2-diylbis(2,1-phenylene))bis(8,8-dimethyl-4-((S)-2-(methylamino)propanethioamido)-5-oxooctahydropyrrolo[2,1-b][1,3]thiazepine-7-carboxamide) dihydrochloride (35 mg, 0.036 mmol, 78.3% yield) as yellow solid. $^1$H NMR (400 MHz, DMSO-$d_6$) δ ppm 10.85 (d, J=6.8 Hz, 2H), 9.59 (s, 2H), 9.49 (s, 2H), 8.59 (s, 2H), 7.39-7.33 (m, 4H), 7.21-7.11 (m, 4H), 5.45 (t, J=8.0 Hz, 2H), 5.18 (t, J=8.2 Hz, 2H), 4.41 (s, 2H), 4.25-4.23 (m, 2H), 3.72-3.65 (m, 2H), 3.51-3.47 (m, 2H), 3.16 (t, J=12.4 Hz, 2H), 2.93-2.88 (m, 2H), 2.50 (s, 6H), 2.28-2.16 (m, 4H), 2.06-2.00 (m, 2H), 1.84-1.75 (m, 2H), 1.41 (d, J=6.4 Hz, 6H), 1.14 (m, 12H). LCMS (2.5 min formic acid): Rt=1.389 min, m/z: 894.8 (M+1)$^+$.

Example 5

(4S,4'S,7S,7'S,9aS,9a'S)—N,N'-(ethane-1,2-diylbis(4,1-phenylene))bis(8,8-dimethyl-4-((S)-2-(methylamino)propanamido)-5-oxooctahydropyrrolo[2,1-b][1,3]thiazepine-7-carboxamide) ditrifluoroacetate

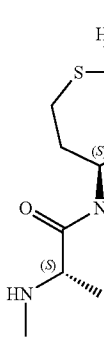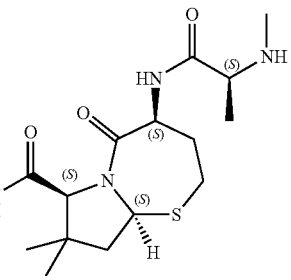

Step 1: di-tert-butyl ((2S,2'S)-(((4S,4'S,7S,7'S,9aS,9a'S)-(((ethane-1,2-diylbis(4,1-phenylene))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate)

To a solution of (4S,7S,9aS)-4-((S)-2-((tert-butoxycarbonyl)(methyl)amino)propanamido)-8,8-dimethyl-5-oxooctahydropyrrolo[2,1-b][1,3]thiazepine-7-carboxylic acid (Intermediate I) (230 mg, 0.519 mmol) in 1,2-dichloroethane (20 mL) was added N-ethoxycarbonyl-2-ethoxy-1,2-dihydroquinoline (EEDQ) (175 mg, 0.709 mmol), N,N-diisopropylethylamine (120 mg, 0.930 mmol) and 4,4'-(ethane-1,2-diyl)dianiline (50 mg, 0.236 mmol). The mixture was stirred at 50° C. overnight. The solvent was removed under reduced pressure followed by purification with silica gel chromatography [petroleum ether/ethyl acetate (2:1 v/v)] to afford the desired product di-tert-butyl ((2S,2'S)-(((4S,4'S,7S,7'S,9aS,9a'S)-(((ethane-1,2-diylbis(4,1-phenylene))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (100 mg, 0.094 mmol, 39.8% yield) as yellow solid. LCMS (2.5 min formic acid): Rt=1.828 min, m/z: 432.0 {[(M-2Boc)+2]/2}$^+$.

Step 2: (4S,4'S,7S,7'S,9aS,9a'S)—N,N'-(ethane-1,2-diylbis(4,1-phenylene))bis(8,8-dimethyl-4-((S)-2-(methylamino)propanamido)-5-oxooctahydropyrrolo[2,1-b][1,3]thiazepine-7-carboxamide) ditrifluoroacetate To a solution of di-tert-butyl ((2S,2'S)-(((4S,4'S,7S,7'S,9aS,9a'S)-(((ethane-1,2-diylbis(4,1-phenylene))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (100 mg, 0.094 mmol) in methanol (5 mL) was added 4 N hydrogen chloride in methanol (5 mL). The mixture was stirred at room temperature for 6 h. The mixture was concentrated and purified by Prep-HPLC to afford (4S,4'S,7S,7'S,9aS,9a'S)—N,N'-(ethane-1,2-diylbis(4,1-phenylene))bis(8,8-dimethyl-4-((S)-2-(methylamino)propanamido)-5-oxooctahydropyrrolo[2,1-b][1,3]thiazepine-7-carboxamide) ditrifluoroacetate (64 mg, 0.059 mmol, 62.8% yield) as white solid. $^1$H NMR (400 MHz, DMSO-$d_6$) δ ppm 9.99 (s, 2H), 8.94 (s, 2H), 8.80-8.78 (m, 4H), 7.50 (d, J=8.0 Hz, 4H), 7.17 (d, J=8.0 Hz, 4H), 5.49 (t, J=7.6 Hz, 2H), 4.73 (t, J=9.0 Hz, 2H), 4.24 (s, 2H), 3.89-3.83 (m, 2H), 3.21-3.15 (m, 2H), 3.12-3.09 (m, 2H), 2.80 (m, 2H), 2.50 (s, 6H), 2.24-2.20 (m, 2H), 2.13-2.11 (m, 2H), 1.98-1.93 (m, 2H), 1.85-1.76 (m, 2H), 1.38 (d, J=6.8 Hz, 6H), 1.10 (m, 6H), 1.03 (m, 6H). LCMS (2.5 min formic acid): Rt=1.284 min, m/z: 862.9 (M+1)$^+$.

Example 6

(4S,4'S,7S,7'S,9aS,9a'S)—N,N'-(ethane-1,2-diylbis(4,1-phenylene))bis(8,8-dimethyl-4-((S)-2-(methylamino)propanethioamido)-5-oxooctahydropyrrolo[2,1-b][1,3]thiazepine-7-carboxamide) dihydrochloride

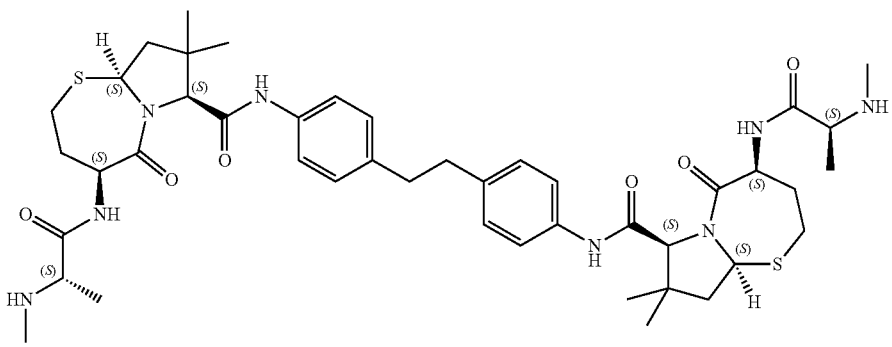

Step 1: di-tert-butyl ((2S,2'S)-(((4S,4'S,7S,7'S,9aS,9a'S)-(((ethane-1,2-diylbis(4,1-phenylene))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate)

To a solution of (4S,7S,9aS)-4-((S)-2-(((tert-butoxycarbonyl)(methyl)amino)propanethioamido)-8,8-dimethyl-5-oxooctahydropyrrolo[2,1-b][1,3]thiazepine-7-carboxylic acid (Intermediate II) (141 mg, 0.312 mmol) in 1,2-dichloroethane (20 mL) was added N-ethoxycarbonyl-2-ethoxy-1,2-dihydroquinoline (EEDQ) (105 mg, 0.423 mmol), N,N-diisopropylethylamine (72 mg, 0.564 mmol) and 4,4'-(ethane-1,2-diyl)dianiline (30 mg, 0.141 mmol). The mixture was stirred at 50° C. overnight. The solvent was removed under reduced pressure. The crude was purified by silica gel chromatography [petroleum ether/ethyl acetate (2:1 v/v)] followed by Prep-HPLC to afford di-tert-butyl ((2S,2'S)-(((4S,4'S,7S,7'S,9aS,9a'S)-(((ethane-1,2-diylbis(4,1-phenylene))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate) (60 mg, 0.055 mmol, 39.0% yield) as white solid. LCMS (2.5 min formic acid): Rt=2.059 min.

Step 2: (4S,4'S,7S,7'S,9aS,9a'S)—N,N'-(ethane-1,2-diylbis(4,1-phenylene))bis(8,8-dimethyl-4-((S)-2-(methylamino)propanethioamido)-5-oxooctahydropyrrolo[2,1-b][1,3]thiazepine-7-carboxamide) dihydrochloride To a solution of di-tert-butyl ((2S,2'S)-(((4S,4'S,7S,7'S,9aS,9a'S)-(((ethane-1,2-diylbis(4,1-phenylene))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate) (70 mg, 0.064 mmol) in methanol (5 mL) was added 4 N hydrogen chloride in methanol (3 mL). The mixture was stirred at room temperature overnight. The solvent was removed under reduced pressure to give (4S,4'S,7S,7'S,9aS,9a'S)—N,N'-(ethane-1,2-diylbis(4,1-phenylene))bis(8,8-dimethyl-4-((S)-2-(methylamino)propanethioamido)-5-oxooctahydropyrrolo[2,1-b][1,3]thiazepine-7-carboxamide) dihydrochloride (43 mg, 0.044 mmol, 68.8% yield) as yellow solid. $^1$H NMR (400 MHz, DMSO-$d_6$) δ ppm 11.04 (d, J=6.0 Hz, 2H), 10.95 (d, J=6.8 Hz, 2H), 10.11-10.10 (m, 2H), 9.80 (s, 1H), 9.56 (s, 1H), 8.64 (s, 1H), 8.43 (s, 1H), 7.51 (d, J=8.0 Hz, 4H), 7.15 (d, J=8.4 Hz, 4H), 5.45 (q, J=5.6 Hz, 2H), 5.18-5.09 (m, 2H), 4.29 (s, 2H), 4.24-4.21 (m, 2H), 3.22-3.17 (m, 2H), 3.02-2.99 (m, 2H), 2.80 (s, 2H), 2.50 (s, 6H), 2.26-2.22 (m, 4H), 2.02-1.91 (m, 4H), 1.46-1.43 (m, 6H), 1.12 (s, 6H), 1.04 (m, 12H). LCMS (2.5 min formic acid): Rt=1.326 min, m/z: 895.1 (M+1)$^+$.

Example 7

(4S,4'S,7S,7'S,9aS,9a'S)—N,N'-((1R,1'R,2R,2'R)-(piperazine-1,4-dicarbonyl)bis(1,2,3,4-tetrahydronaphthalene-2,1-diyl))bis(8,8-dimethyl-4-((S)-2-(methylamino)propanamido)-5-oxooctahydropyrrolo[2,1-b][1,3]thiazepine-7-carboxamide) dihydrochloride

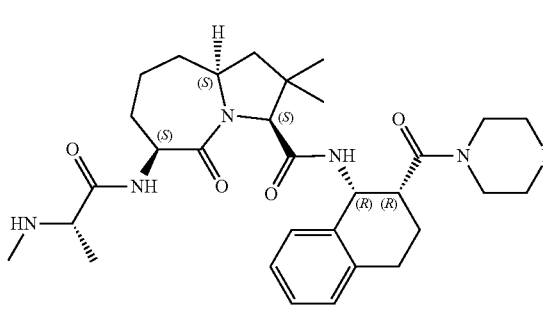
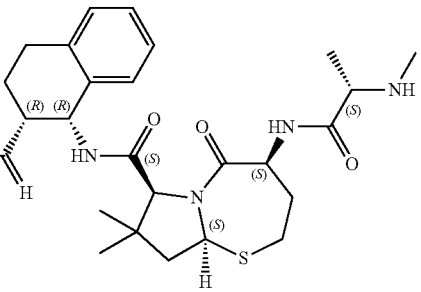

Step 1: (1R,2R)-1-((tert-butoxycarbonyl)amino)-1,2,3,4-tetrahydronaphthalene-2-carboxylic Acid Sodium carbonate was added to a solution of (1R,2R)-1-amino-1,2,3,4-tetrahydronaphthalene-2-carboxylic acid hydrochloride (1.3 g, 5.71 mmol) in dioxane/water (1:1 v/v, 100 mL) to adjust the pH to 8. Di-tert-butyl dicarbonate (1.62 g, 7.42 mmol) was then added. The mixture was stirred at room temperature overnight. Upon completion of reaction, the pH of the mixture was adjusted with 20% citric acid solution to pH 4. The mixture was extracted with ethyl acetate (3×100 mL). The combined organic layers were washed with brine, dried over anhydrous sodium sulfate, filtered and concentrated. The crude was purified by silica gel chromatography [petroleum ether/ethyl acetate (3/2 v/v)] to give (1R,2R)-1-((tert-butoxycarbonyl)amino)-1,2,3,4-tetrahydronaphthalene-2-carboxylic acid (1.3 g, 4.46 mmol, 78.1% yield) as white solid. LCMS (2.5 min formic acid): Rt=1.519 min, m/z: 289.9 (M-1)⁻.

Step 2: di-tert-butyl ((1R,1'R,2R,2'R)-(piperazine-1,4-dicarbonyl)bis(1,2,3,4-tetrahydronaphthalene-2,1-diyl))dicarbamate To a solution of (1R,2R)-1-((tert-butoxycarbonyl)amino)-1,2,3,4-tetrahydronaphthalene-2-carboxylic acid (270 mg, 0.90 mmol) and piperazine (39.9 mg, 0.46 mmol) in N,N-dimethylformamide (12 mL) at −10° C. was added triethylamine (187.5 mg, 1.85 mmol) and diethyl cyanophosphonate (226.7 mg, 1.38 mmol) slowly. The mixture was stirred for 20 min. The mixture was allowed to warm to room temperature and stirred for 3 h. The reaction was quenched with ice water (50 mL) to give a precipitate which was filtered and dried to give di-tert-butyl ((1R,1'R,2R,2'R)-(piperazine-1,4-dicarbonyl)bis(1,2,3,4-tetrahydronaphthalene-2,1-diyl))dicarbamate (435 mg, 0.69 mmol, 68.7% yield) as white solid. LCMS (2.5 min formic acid): Rt=1.74 min, m/z: 532.7 (M-Boc+1)⁺.

Step 3: piperazine-1,4-diylbis(((1R,2R)-1-amino-1,2,3,4-tetrahydronaphthalen-2-yl)methanone) dihydrochloride To a solution of di-tert-butyl ((1R,1'R,2R,2'R)-(piperazine-1,4-dicarbonyl)bis(1,2,3,4-tetrahydronaphthalene-2,1-diyl))dicarbamate (435 mg, 1.0 mmol) in dichloromethane (20 mL) was added 4 N hydrogen chloride in 1,4-dioxane (2 mL) slowly. The mixture was stirred at room temperature overnight. The solvent was concentrated under reduced pressure to give crude piperazine-1,4-diylbis(((1R,2R)-1-amino-1,2,3,4-tetrahydronaphthalen-2-yl)methanone) dihydrochloride (402 mg) as white solid. This was used for reaction without further purification. LCMS (2.5 min formic acid): Rt=1.07 min, m/z: 432.9 (M+1)⁺.

Step 4: di-tert-butyl ((2S,2'S)-(((4S,4'S,7S,7'S,9aS,9a'S)-((((1R,1'R,2R,2'R)-(piperazine-1,4-dicarbonyl)bis(1,2,3,4-tetrahydronaphthalene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate)

A solution of piperazine-1,4-diylbis(((1R,2R)-1-amino-1,2,3,4-tetrahydronaphthalen-2-yl)methanone) dihydrochloride (150 mg, 0.297 mmol), (4S,7S,9aS)-4-((S)-2-((tert-butoxycarbonyl)(methyl)amino)propanamido)-8,8-dimethyl-5-oxooctahydropyrrolo[2,1-b][1,3]thiazepine-7-carboxylic acid (Intermediate I) (319 mg, 0.68 mmol), 1-(3-dimethylaminopropyl)-3-ethylcarbodiimide methiodide (200 mg, 1.02 mmol), 1-hydroxybenzotriazole (187 mg, 1.36 mmol) and N,N-diisopropyl ethylamine (269 mg, 2.04 mmol) in dichloromethane (10 mL) was stirred at room temperature overnight. The reaction was quenched with water (30 mL) and extracted with dichloromethane (3×30 mL). The combined organic layers were washed with brine, dried, filtered and concentrated. The residue was purified by thin layer chromatography [ethyl acetate/petroleum ether (2/1 v/v)] to give impure product (93 mg) as yellow oil. This material was further purified by Prep-HPLC to give di-tert-butyl ((2S,2'S)-(((4S,4'S,7S,7'S,9aS,9a'S)-((((1R,1'R,2R,2'R)-(piperazine-1,4-dicarbonyl)bis(1,2,3,4-tetrahydronaphthalene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (64 mg, 0.05 mmol, 13.9% yield) as white solid. LCMS (3.0 min formic acid): Rt=2.51 min, m/z: 1282.6 (M+1)⁺, 642.5 {[(M-2Boc)+2]/2}⁺.

Step 5: (4S,4'S,7S,7'S,9aS,9a'S)—N,N'-((1R,1'R,2R,2'R)-(piperazine-1,4-dicarbonyl)bis(1,2,3,4-tetrahydronaphthalene-2,1-diyl))bis(8,8-dimethyl-4-((S)-2-(methylamino)propanamido)-5-oxooctahydropyrrolo[2,1-b][1,3]thiazepine-7-carboxamide) dihydrochloride To a solution of di-tert-butyl ((2S,2'S)-(((4S,4'S,7S,7'S,9aS,9a'S)-((((1R,1'R,2R,2'R)-(piperazine-1,4-dicarbonyl)

bis(1,2,3,4-tetrahydronaphthalene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (64 mg, 0.05 mmol) in dichloromethane (5 mL) was added hydrogen chloride (4 N in 1,4-dioxane, 1 mL). The reaction was stirred at room temperature overnight. The solvent was removed under vacuum to give (4S,4'S,7S,7'S,9aS,9a'S)—N,N'-((1R,1'R,2R,2'R)-(piperazine-1,4-dicarbonyl)bis(1,2,3,4-tetrahydronaphthalene-2,1-diyl))bis(8,8-dimethyl-4-((S)-2-(methylamino)propanamido)-5-oxooctahydropyrrolo[2,1-b][1,3]thiazepine-7-carboxamide) dihydrochloride (50 mg, 0.043 mmol, 84.3% yield) as white solid. $^1$H NMR (400 MHz, DMSO-$d_6$) δ ppm 8.64 (s, 2H), 8.00 (d, J=8.8 Hz, 1H), 7.87 (d, J=8.4 Hz, 1H), 7.31-7.25 (m, 2H), 7.19-7.07 (m, 6H), 5.50-5.45 (m, 2H), 5.40-5.34 (m, 2H), 4.70-4.64 (m, 2H), 3.78-3.65 (m, 6H), 3.62-3.59 (m, 2H), 3.49-3.47 (m, 2H), 3.22-3.11 (m, 4H), 3.08-3.03 (m, 4H), 2.93-2.91 (m, 2H), 2.76 (s, 4H), 2.43 (m, 6H), 2.17-2.20 (m, 2H), 2.10-2.01 (m, 4H), 1.94-1.88 (m, 2H), 1.76-1.58 (m, 2H), 1.35-1.32 (m, 6H), 1.03-1.00 (m, 12H). LCMS (2.5 min formic acid): Rt=1.407 min, m/z: 1082.8 (M+1)$^+$.

Example 8

(4S,4'S,7S,7'S,9aS,9a'S)—N,N'-((1R,1'R,2R,2'R)-(piperazine-1,4-dicarbonyl)bis(1,2,3,4-tetrahydronaphthalene-2,1-diyl))bis(8,8-dimethyl-4-((S)-2-(methylamino)propanethioamido)-5-oxooctahydropyrrolo[2,1-b][1,3]thiazepine-7-carboxamide) dihydrochloride Step 1: di-tert-butyl ((2S,2'S)-(((4S,4'S,7S,7'S,9aS,9a'S)-((((1R,1'R,2R,2'R)-(piperazine-1,4-dicarbonyl)bis(1,2,3,4-tetrahydronaphthalene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate)

A solution of piperazine-1,4-diylbis(((1R,2R)-1-amino-1,2,3,4-tetrahydronaphthalen-2-yl)methanone) dihydrochloride (Example 7, Step 3) (150 mg, 0.297 mmol), (4S,7S,9aS)-4-((S)-2-((tert-butoxycarbonyl)(methyl)amino)propanethioamido)-8,8-dimethyl-5-oxooctahydropyrrolo[2,1-b][1,3]thiazepine-7-carboxylic acid (Intermediate II) (272.8 mg, 0.593 mmol), 1-(3-dimethylaminopropyl)-3-ethylcarbodiimide methiodide (170.7 mg, 0.89 mmol), 1-hydroxybenzotriazole (160.5 mg, 1.188 mmol) and N,N-diisopropyl ethylamine (230.2 mg, 1.782 mmol) in dichloromethane (10 mL) was stirred at room temperature overnight. The reaction was quenched with water (30 mL) and extracted with dichloromethane (3×30 mL). The combined organic layers were washed with brine, dried, filtered and concentrated. The residue was purified by thin layer chromatography [ethyl acetate/petroleum ether (2/1 v/v)] to give impure product (170 mg) as yellow oil. This material was further purified by Prep-HPLC to give di-tert-butyl ((2S,2'S)-(((4S,4'S,7S,7'S,9aS,9a'S)-((((1R,1'R,2R,2'R)-(piperazine-1,4-dicarbonyl)bis(1,2,3,4-tetrahydronaphthalene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate) (90 mg, 0.07 mmol, 23.6% yield) as white solid. LCMS (3.0 min formic acid): Rt=2.75 min, m/z: 1315.6 (M+1)$^+$.

Step 2: (4S,4'S,7S,7'S,9aS,9a'S)—N,N'-((1R,1'R,2R,2'R)-(piperazine-1,4-dicarbonyl)bis(1,2,3,4-tetrahydronaphthalene-2,1-diyl))bis(8,8-dimethyl-4-((S)-2-(methylamino)propanethioamido)-5-oxooctahydropyrrolo[2,1-b][1,3]thiazepine-7-carboxamide) dihydrochloride To a solution of di-tert-butyl ((2S,2'S)-(((4S,4'S,7S,7'S,9aS,9a'S)-((((1R,1'R,2R,2'R)-(piperazine-1,4-dicarbonyl)bis(1,2,3,4-tetrahydronaphthalene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate) (96 mg, 0.073 mmol) in dichloromethane (10 mL) was added hydrogen chloride (4 N in 1,4-dioxane, 1 mL). The mixture was stirred at room temperature overnight. The solvent was removed under reduced pressure to give (4S,4'S,7S,7'S,9aS,9a'S)—N,N'-((1R,1'R,2R,2'R)-(piperazine-1,4-dicarbonyl)bis(1,2,3,4-tetrahydronaphthalene-2,1-diyl))bis(8,8-dimethyl-4-((S)-2-(methylamino)propanethioamido)-5-oxooctahydropyrrolo[2,1-b][1,3]thiazepine-7-carboxamide) dihydrochloride (60 mg, 0.05 mmol, 68.8% yield) as white solid. $^1$H NMR (400 MHz, DMSO-$d_6$) δ ppm 11.12-10.98 (m, 1H), 10.89-10.87 (m, 1H), 9.81 (s, 1H), 9.62 (s, 1H), 8.67 (s, 1H), 8.44-8.36 (m, 1H), 8.15-8.07 (m, 1H), 7.95-7.88 (m, 1H), 7.26-7.25 (m, 2H), 7.15-7.09 (m, 6H), 5.47-5.41 (m, 2H), 5.36-5.35 (m, 2H), 5.17-5.03 (m, 2H), 4.41-4.32 (m, 2H), 3.78-3.65 (m, 4H), 3.60-3.47 (m, 4H), 3.39 (s, 2H), 3.25-3.09 (m, 4H), 3.03-2.96 (m, 2H), 2.75 (s, 4H), 2.51 (s, 6H), 2.30-2.19 (m, 6H), 2.02 (s, 2H), 1.91 (s, 2H), 1.66-1.62 (m, 2H), 1.45-1.41 (m, 6H), 1.04 (s, 6H), 1.00 (s, 6H). LCMS (2.5 min formic acid): Rt=1.246 min, m/z: 1114.4 (M+1)$^+$.

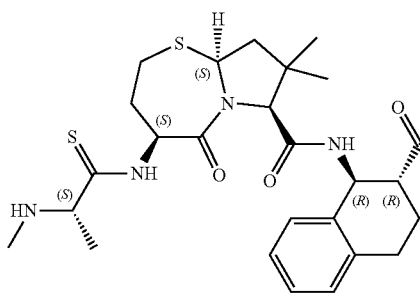
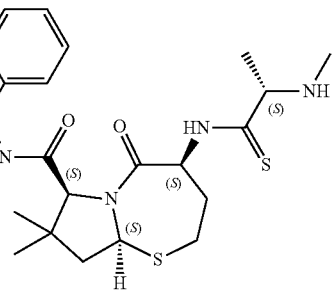

Example 9

(4S,4'S,7S,7'S,9aS,9a'S)—N,N'-((1R,1'R,2R,2'R)-
(((1,4-phenylenebis(methylene))bis(azanediyl))bis
(carbonyl))bis(1,2,3,4-tetrahydronaphthalene-2,1-
diyl))bis(8,8-dimethyl-4-((S)-2-(methylamino)
propanamido)-5-oxooctahydropyrrolo[2,1-b][1,3]
thiazepine-7-carboxamide) dihydrochloride

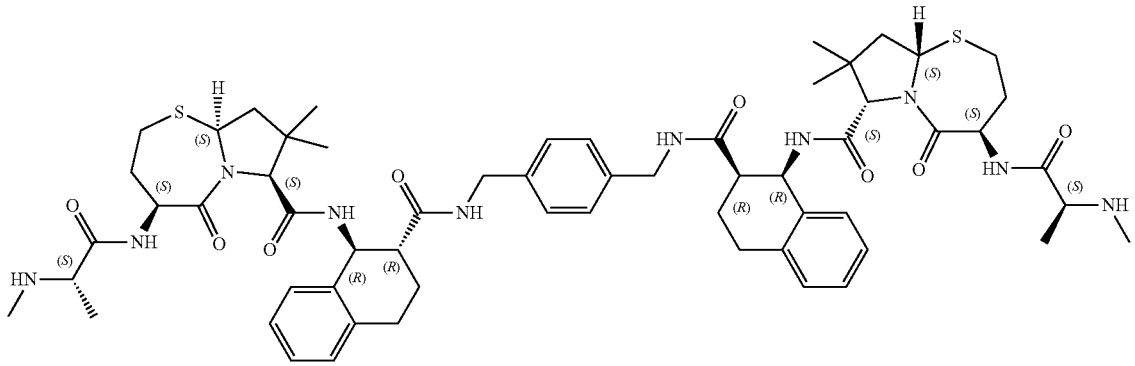

Step 1: di-tert-butyl ((1R,1'R,2R,2'R)-(((1,4-phenylenebis(methylene))bis(azanediyl))bis(carbonyl))bis(1,2,3,4-tetrahydronaphthalene-2,1-diyl))dicarbamate To a solution of (1R,2R)-1-((tert-butoxycarbonyl)amino)-1,2,3,4-tetrahydronaphthalene-2-carboxylic acid (114 mg, 0.39 mmol) and 1,4-phenylenedimethanamine (26 mg, 0.19 mmol) in N,N-dimethylformamide (5 mL) at −10° C. was added triethylamine (79 mg, 0.78 mmol) and diethyl cyanophosphonate (96 mg, 0.59 mmol) slowly. The mixture was stirred for 20 min. The mixture was allowed to warm to room temperature and stirred for 3 h. The reaction was quenched with ice water (50 mL) to give a precipitate which was filtered and dried to give di-tert-butyl ((1R,1'R,2R,2'R)-(((1,4-phenylenebis(methylene))bis(azanediyl))bis(carbonyl))bis(1,2,3,4-tetrahydronaphthalene-2,1-diyl))dicarbamate (180 mg, 0.26 mmol, 67.4% yield) as white solid. LCMS (2.5 min formic acid): Rt=1.736 min, m/z: 704.8 (M+Na)$^+$.

Step 2: (1R,1'R,2R,2'R)—N,N'-(1,4-phenylenebis(methylene))bis(1-amino-1,2,3,4-tetrahydronaphthalene-2-carboxamide) dihydrochloride To a solution of di-tert-butyl ((1R,1'R,2R,2'R)-(((1,4-phenylenebis(methylene))bis(azanediyl))bis(carbonyl))bis(1,2,3,4-tetrahydronaphthalene-2,1-diyl))dicarbamate (180 mg, 0.26 mmol) in dichloromethane (10 mL) was added 4 N hydrogen chloride in 1,4-dioxane (1 mL) slowly. The mixture was stirred at room temperature for 4 h and the solvent was removed under reduced pressure to give (1R,1',2R,2'R)—N,N'-(1,4-phenylenebis(methylene))bis(1-amino-1,2,3,4-tetrahydronaphthalene-2-carboxamide) dihydrochloride (150 mg) as white solid. This was used for the next step without further purification. LCMS (2.5 min formic acid): Rt=1.085 min, m/z: 482.9 (M+1)$^+$.

Step 3: di-tert-butyl ((2S,2'S)-(((4S,4'S,7S,7'S,9aS,9a'S)-((((1R,1'R,2R,2'R)-(((1,4-phenylenebis(methylene))bis(azanediyl))bis(carbonyl))bis(1,2,3,4-tetrahydronaphthalene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate)

A solution of (1R,1'R,2R,2'R)—N,N'-(1,4-phenylenebis(methylene))bis(1-amino-1,2,3,4-tetrahydronaphthalene-2-carboxamide) dihydrochloride (150 mg, 0.27 mmol), (4S,7S,9aS)-4-((S)-2-((tert-butoxycarbonyl)(methyl)amino)propanamido)-8,8-dimethyl-5-oxooctahydropyrrolo[2,1-b][1,3]thiazepine-7-carboxylic acid (Intermediate I) (240 mg, 0.54 mmol), 1-(3-dimethylaminopropyl)-3-ethylcarbodiimide methiodide (155.3 mg, 0.81 mmol), 1-hydroxybenzotriazole (146 mg, 1.08 mmol) and N,N-diisopropyl ethylamine (209.3 mg, 1.62 mmol) in dichloromethane (10 mL) was stirred at room temperature overnight. The reaction was quenched with water (30 mL) and extracted with dichloromethane (3×30 mL). The combined organic layers were washed with brine, dried, filtered and concentrated. The residue was purified by thin layer chromatography [ethyl acetate/petroleum ether (2:1 v/v)] to give crude product (170 mg) as yellow oil. This material was further purified by Prep-HPLC to give di-tert-butyl ((2S,2'S)-(((4S,4'S,7S,7'S,9aS,9a'S)-((((1R,1'R,2R,2'R)-(((1,4-phenylenebis(methylene))bis(azanediyl))bis(carbonyl))bis(1,2,3,4-tetrahydronaphthalene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (76 mg, 0.057 mmol, 21.1% yield) as white solid. LCMS (2.5 min formic acid): Rt=1.80 min, m/z: 566.9 {[M−2Boc]=2]/2}$^+$.

Step 4: (4S,4'S,7S,7'S,9aS,9a'S)—N,N'-((1R,1'R,2R,2'R)-(((1,4-phenylenebis(methylene))bis(azanediyl))bis(carbonyl))bis(1,2,3,4-tetrahydronaphthalene-2,1-diyl))bis(8,8-dimethyl-4-((S)-2-(methylamino)propanamido)-5-oxooctahydropyrrolo[2,1-b][1,3]thiazepine-7-carboxamide) dihydrochloride To a solution of di-tert-butyl ((2S,2'S)-(((4S,4'S,7S,7'S,9aS,9a'S)-((((1R,1'R,2R,2'R)-(((1,4-phenylenebis(methylene))bis(azanediyl))bis(carbonyl))bis(1,2,3,4-tetrahydronaphthalene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (80 mg, 0.06 mmol) in dichloromethane (6 mL) was added hydrogen chloride (4 N in 1,4-dioxane, 1 mL). The mixture was stirred at room temperature overnight. The mixture was concentrated and dried under high vacuum to afford (4S,4'S,7S,7'S,9aS,9a'S)—N,N'-((1R,1'R,2R,2'R)-(((1,4-phenylenebis(methylene))bis(azanediyl))bis(carbonyl))bis(1,2,3,4-tetrahydronaphthalene-2,1-diyl))bis(8,8-dimethyl-4-((S)-2-(methylamino)propanamido)-5-oxooctahydropyrrolo[2,1-b][1,3]thiazepine-7-carboxamide) dihydrochloride (46.2 mg, 0.038 mmol, 60.5% yield) as white solid. $^1$H NMR (400 MHz, DMSO-$d_6$) δ ppm 9.24 (s, 2H), 8.86-8.85 (m, 2H), 8.78 (d, J=6.8 Hz, 2H), 8.36 (t, J=5.2 Hz, 2H), 7.94 (d, J=9.2 Hz, 2H), 7.31-7.29 (m, 2H), 7.22 (s, 4H), 7.14-7.12 (m, 4H), 7.09-7.06 (m, 3H), 5.48 (t, J=7.8 Hz, 2H), 5.43-5.30 (m, 2H), 4.72-4.67 (m, 2H), 4.38-4.33 (m, 2H), 4.14 (s, 2H), 4.08-4.03 (m, 2H), 3.91-3.86 (m, 2H), 3.21-3.15 (m, 2H), 2.96-2.87 (m, 4H), 2.82-2.68 (s, 4H), 2.47 (t, J=4.4 Hz, 6H), 2.21-2.16 (m, 2H), 2.09-1.99 (m, 6H), 2.00-1.96 (m, 2H), 1.75-1.70 (m, 2H), 1.38 (d, J=6.8 Hz, 6H), 1.03 (s, 6H), 1.00 (s, 6H). LCMS (2.5 min formic acid): Rt=1.453 min, m/z: 1133.7 (M+1)$^+$, 1155.6 (M+Na)$^+$.

Example 10

(4S,4'S,7S,7'S,9aS,9a'S)—N,N'-((1R,1'R,2R,2'R)-(((1,4-phenylenebis(methylene))bis(azanediyl))bis(carbonyl))bis(1,2,3,4-tetrahydronaphthalene-2,1-diyl))bis(8,8-dimethyl-4-((S)-2-(methylamino)propanethioamido)-5-oxooctahydropyrrolo[2,1-b][1,3]thiazepine-7-carboxamide)

Step 1: di-tert-butyl ((2S,2'S)-(((4S,4'S,7S,7'S,9aS,9a'S)-((((1R,1'R,2R,2'R)-(((1,4-phenylenebis(methylene))bis(azanediyl))bis(carbonyl))bis(1,2,3,4-tetrahydronaphthalene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate)

A solution of (1R,1'R,2R,2'R)—N,N'-(1,4-phenylenebis(methylene))bis(1-amino-1,2,3,4-tetrahydronaphthalene-2-carboxamide) dihydrochloride (Example 9, Step 2) (116 mg, 0.21 mmol), (4S,7S,9aS)-4-((S)-2-((tert-butoxycarbonyl)(methyl)amino)propanethioamido)-8,8-dimethyl-5-oxooctahydropyrrolo[2,1-b][1,3]thiazepine-7-carboxylic acid (Intermediate II) (201 mg, 0.44 mmol), 1-(3-dimethylaminopropyl)-3-ethylcarbodiimide methiodide (120 mg, 0.63 mmol), 1-hydroxybenzotriazole (113 mg, 0.84 mmol) and N,N-diisopropyl ethylamine (279 mg, 2.16 mmol) in dichloromethane (10 mL) was stirred at room temperature overnight. The reaction was quenched with water (30 mL) and extracted with dichloromethane (3×30 mL). The combined organic layers were washed with brine, dried, filtered and concentrated. The residue was purified by thin layer chromatography [ethyl acetate/petroleum ether (2/1 v/v)] to give impure product (110 mg) as yellow oil which was further purified by Prep-HPLC to give di-tert-butyl ((2S,2'S)-(((4S,4'S,7S,7'S,9aS,9a'S)-((((1R,1'R,2R,2'R)-(((1,4-phenylenebis(methylene))bis(azanediyl))bis(carbonyl))bis(1,2,3,4-tetrahydronaphthalene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate) (54 mg, 0.039 mmol, 18.9% yield) as white solid. LCMS (3.0 min formic acid): Rt=2.614 min, m/z: 1388 (M+Na)$^+$.

Step 2: (4S,4'S,7S,7'S,9aS,9a'S)—N,N'-((1R,1'R,2R,2'R)-(((1,4-phenylenebis(methylene))bis(azanediyl))bis(carbonyl))bis(1,2,3,4-tetrahydronaphthalene-2,1-diyl))bis(8,8-dimethyl-4-((S)-2-(methylamino)propanethioamido)-5-oxooctahydropyrrolo[2,1-b][1,3]thiazepine-7-carboxamide)

To a solution of di-tert-butyl ((2S,2'S)-(((4S,4'S,7S,7'S,9aS,9a'S)-((((1R,1'R,2R,2'R)-(((1,4-phenylenebis(methylene))bis(azanediyl))bis(carbonyl))bis(1,2,3,4-tetrahy-

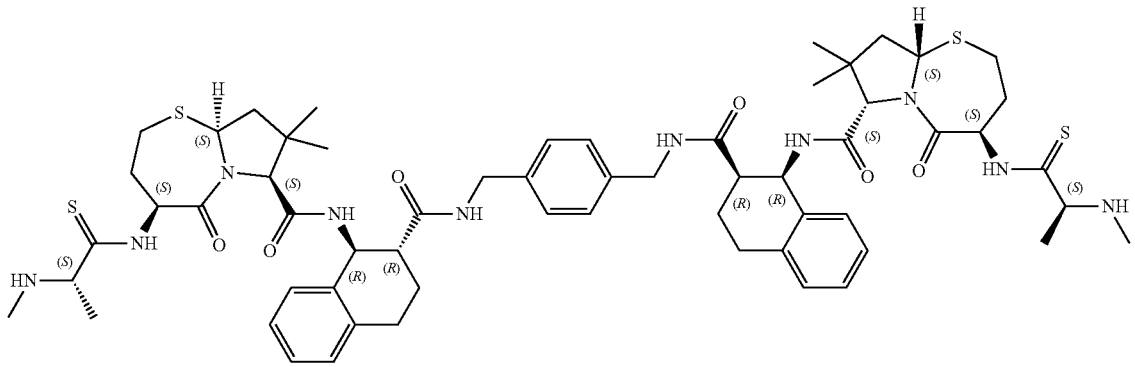

dronaphthalene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate) (54 mg, 0.04 mmol) in dichloromethane (5 mL) was added hydrogen chloride (4 N in 1,4-dioxane, 1 mL). The reaction was stirred at room temperature overnight. The solvent was removed under reduced pressure and diluted with water. The pH was adjusted to 8-9 with sodium bicarbonate and extracted with dichloromethane (3×10 mL). The combined organic layers were washed with brine, dried, filtered and concentrated under reduced pressure. The residue was purified by thin layer chromatography [dichloromethane/methanol (8/1 v/v)] to give (4S,4'S,7S,7'S,9aS,9a'S)—N,N'-((1R,1'R,2R,2'R)-(((1,4-phenylenebis(methylene))bis(azanediyl))bis(carbonyl))bis(1,2,3,4-tetrahydronaphthalene-2,1-diyl))bis(8,8-dimethyl-4-((S)-2-(methylamino)propanethioamido)-5-oxooctahydropyrrolo[2,1-b][1,3]thiazepine-7-carboxamide) (6 mg, 0.005 mmol, 13% yield) as white solid. $^1$H NMR (400 MHz, DMSO-$d_6$) δ ppm 8.43-8.37 (m, 2H), 7.85-7.82 (m, 2H), 7.33-7.27 (m, 2H), 7.20 (s, 4H), 7.15-7.13 (m, 4H), 7.08-7.06 (m, 2H), 5.51-5.46 (m, 2H), 5.40-5.37 (m, 2H), 5.10-5.06 (m, 2H), 4.40-4.34 (m, 2H), 4.16 (s, 2H), 4.04-4.00 (m, 2H), 3.49-3.42 (m, 2H), 3.22-3.14 (m, 2H), 2.98-2.91 (m, 4H), 2.79-2.69 (m, 4H), 2.42-2.31 (m, 2H), 2.27-2.20 (m, 2H), 2.16 (m, 6H), 2.07-1.98 (m, 4H), 1.74-1.65 (m, 2H), 1.22-1.21 (m, 6H), 1.07-1.06 (m, 6H), 1.03-1.02 (m, 6H). LCMS (2.5 min formic acid): Rt=1.52 min, 1164.7 (M+1)$^+$.

Example 11

(4S,7S,9aS)-8,8-dimethyl-4-[(2S)-2-(methylamino)propanamido]-5-oxo-N-[(1R,2R)-2-{[(1rs,4rs)-4-[(1R,2R)-1-[(4S,7S,9aS)-8,8-dimethyl-4-[(2S)-2-(methylamino)propanamido]-5-oxo-octahydropyrrolo[2,1-b][1,3]thiazepine-7-amido]-1,2,3,4-tetrahydronaphthalene-2-amido]cyclohexyl]carbamoyl}-1,2,3,4-tetrahydronaphthalen-1-yl]-octahydropyrrolo[2,1-b][1,3]thiazepine-7-carboxamide dihydrochloride Step 1: di-tert-butyl ((1R,1'R,2R,2'R)-((((1R,4R)-cyclohexane-1,4-diyl)bis(azanediyl))bis(carbonyl))bis(1,2,3,4-tetrahydronaphthalene-2,1-diyl))dicarbamate To a solution of (1R,2R)-1-((tert-butoxycarbonyl)amino)-1,2,3,4-tetrahydronaphthalene-2-carboxylic acid (250 mg, 0.858 mmol) and (1r,4r)-cyclohexane-1,4-diamine (49 mg, 0.429 mmol) in N,N-dimethylformamide (10 mL) at −10° C. was added N,N-diisopropylethylamine (221 mg, 1.716 mmol) and diethyl cyanophosphonate (210 mg, 1.287 mmol) slowly. The mixture was stirred for 20 min. The mixture was allowed to warm to room temperature and stirred for 3 h. The reaction was quenched with ice water (100 mL) to give a precipitate which was filtered to give di-tert-butyl ((1R,1'R,2R,2'R)-((((1R,4R)-cyclohexane-1,4-diyl)bis(azanediyl))bis(carbonyl))bis(1,2,3,4-tetrahydronaphthalene-2,1-diyl))dicarbamate (240 mg, 0.363 mmol, 84.6% yield) as orange solid. LCMS (2.5 min formic acid): Rt=1.724 min, m/z: 628.8 (M+Na)$^+$.

Step 2: (1R,1'R,2R,2'R)—N,N'-((1R,4R)-cyclohexane-1,4-diyl)bis(1-amino-1,2,3,4-tetrahydronaphthalene-2-carboxamide) dihydrochloride To a solution of di-tert-butyl ((1R,1'R,2R,2'R)-((((1R,4R)-cyclohexane-1,4-diyl)bis(azanediyl))bis(carbonyl))bis(1,2,3,4-tetrahydronaphthalene-2,1-diyl))dicarbamate (150 mg, 0.23 mmol) in dichloromethane (5 mL) was added 4 N hydrogen chloride in 1,4-dioxane (0.5 mL) slowly. The mixture was stirred at room temperature overnight. The mixture was concentrated under reduced pressure to give (1R,1'R,2R,2'R)—N,N'-((1R,4R)-cyclohexane-1,4-diyl)bis(1-amino-1,2,3,4-tetrahydronaphthalene-2-carboxamide) dihydrochloride (130 mg, crude) as yellow syrup. LCMS (2.5 min formic acid): Rt=1.122 min, m/z: 461.1 (M+1)$^+$.

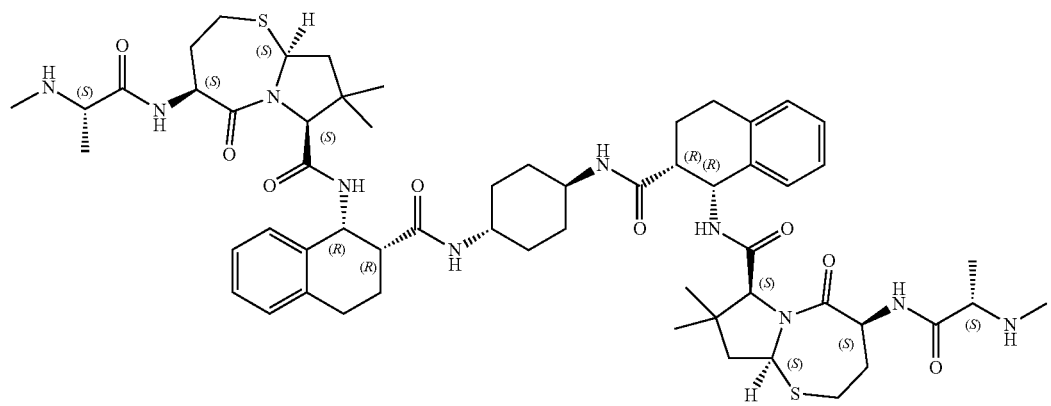

Step 3: di-tert-butyl ((2S,2'S)-(((4S,4'S,7S,7'S,9aS,9a'S)-((((1R,1'R,2R,2'R)-((((1R,4R)-cyclohexane-1,4-diyl)bis(azanediyl))bis(carbonyl))bis(1,2,3,4-tetrahydronaphthalene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate)

A solution of (1R,1'R,2R,2'R)—N,N'-((1R,4R)-cyclohexane-1,4-diyl)bis(1-amino-1,2,3,4-tetrahydronaphthalene-2-carboxamide) dihydrochloride (130 mg, 0.24 mmol), (4S,7S,9aS)-4-((S)-2-((tert-butoxycarbonyl)(methyl)amino)propanamido)-8,8-dimethyl-5-oxooctahydropyrrolo[2,1-b][1,3]thiazepine-7-carboxylic acid (Intermediate I) (216.2 mg, 0.49 mmol), 1-(3-dimethylaminopropyl)-3-ethylcarbodiimide methiodide (140.1 mg, 0.73 mmol), 1-hydroxybenzotriazole (131.7 mg, 0.97 mmol) and N,N-diisopropylethylamine (189 mg, 1.46 mmol) in dichloromethane (10 mL) was stirred at room temperature overnight. The reaction was quenched with water (50 mL) and extracted with dichloromethane (3×50 mL). The combined organic layers were washed with brine, dried, filtered and concentrated. The residue was purified by thin layer chromatography [ethyl acetate/petroleum ether (2/1 v/v)] to give crude product (170 mg) as yellow oil. This material was further purified by Prep-HPLC to afford di-tert-butyl ((2S,2'S)-(((4S,4'S,7S,7'S,9aS,9a'S)-((((1R,1'R,2R,2'R)-((((1R,4R)-cyclohexane-1,4-diyl)bis(azanediyl))bis(carbonyl))bis(1,2,3,4-tetrahydronaphthalene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (86 mg, 0.06 mmol, 26.8% yield) as white solid. LCMS (2.5 min formic acid): Rt=1.96 min, m/z: 555.9 {[M-2Boc]+2}/2$^+$.

Step 4: (4S,7S,9aS)-8,8-dimethyl-4-[(2S)-2-(methylamino)propanamido]-5-oxo-N-[(1R,2R)-2-{[(1rs,4rs)-4-[(1R,2R)-1-[(4S,7S,9aS)-8,8-dimethyl-4-[(2S)-2-(methylamino)propanamido]-5-oxo-octahydropyrrolo[2,1-b][1,3]thiazepine-7-amido]-1,2,3,4-tetrahydronaphthalene-2-amido]cyclohexyl]carbamoyl}-1,2,3,4-tetrahydronaphthalen-1-yl]-octahydropyrrolo[2,1-b][1,3]thiazepine-7-carboxamide dihydrochloride To a solution of di-tert-butyl ((2S,2'S)-(((4S,4'S,7S,7'S,9aS,9a'S)-((((1R,1'R,2R,2'R)-((((1R,4R)-cyclohexane-1,4-diyl)bis(azanediyl))bis(carbonyl))bis(1,2,3,4-tetrahydronaphthalene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (80 mg, 0.073 mmol) in dichloromethane (10 mL) was added hydrogen chloride (4 N in 1,4-dioxane, 1 mL). The reaction was stirred at room temperature overnight. The solvent was concentrated under reduced pressure and the solid was dried under high vacuum to give the title compound (62 mg, 0.052 mmol, 79.8% yield) as white solid. $^1$H NMR (400 MHz, DMSO-$d_6$) δ ppm 9.29 (s, 1H), 8.89-8.88 (m, 1H), 8.78 (d, J=6.8 Hz, 2H), 7.90 (d, J=9.2 Hz, 2H), 7.74 (d, J=7.6 Hz, 2H), 7.28-7.26 (m, 2H), 7.12-7.05 (m, 6H), 5.46 (t, J=7.6 Hz, 2H), 5.36-5.33 (m, 2H), 4.71-4.67 (m, 2H), 4.15 (s, 2H), 3.90 (s, 2H), 3.41-3.39 (m, 2H), 3.16 (t, J=11.8 Hz, 2H), 2.96-2.92 (m, 2H), 2.79-2.64 (m, 6H), 2.48 (s, 6H), 2.19-2.11 (m, 4H), 2.01-1.94 (m, 6H), 1.78-1.68 (m, 6H), 1.40 (d, J=6.8 Hz, 6H), 1.20-1.12 (m, 4H), 1.02 (s, 6H), 1.00 (s, 6H). LCMS (2.5 min formic acid): Rt=1.280 min, m/z: 1110.8 (M+1)$^+$.

Example 12

(4S,7S,9aS)-8,8-dimethyl-4-[(2S)-2-(methylamino)propanethioamido]-5-oxo-N-[(1R,2R)-2-{[(1rs,4rs)-4-[(1R,2R)-1-[(4S,7S,9aS)-8,8-dimethyl-4-[(2S)-2-(methylamino)propanethioamido]-5-oxo-octahydropyrrolo[2,1-b][1,3]thiazepine-7-amido]-1,2,3,4-tetrahydronaphthalene-2-amido]cyclohexyl]carbamoyl}-1,2,3,4-tetrahydronaphthalen-1-yl]-octahydropyrrolo[2,1-b][1,3]thiazepine-7-carboxamide dihydrochloride

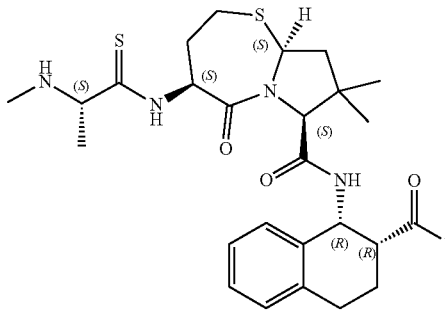
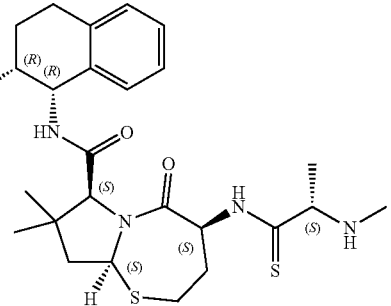

Step 1: di-tert-butyl ((2S,2'S)-(((4S,4'S,7S,7'S,9aS,9a'S)-((((1R,1'R,2R,2'R)-((((1R,4R)-cyclohexane-1,4-diyl)bis(azanediyl))bis(carbonyl))bis(1,2,3,4-tetrahydronaphthalene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate)

The mixture of (1R,1'R,2R,2'R)—N,N'-((1R,4R)-cyclohexane-1,4-diyl)bis(1-amino-1,2,3,4-tetrahydronaphthalene-2-carboxamide) dihydrochloride (Example 11, Step 2) (200 mg, 0.375 mmol), (4S,7S,9aS)-4-((S)-2-((tert-butoxycarbonyl)(methyl)amino)propanethioamido)-8,8-dimethyl-5-oxooctahydropyrrolo[2,1-b][1,3]thiazepine-7-carboxylic acid (Intermediate II) (413 mg, 0.901 mmol), N-(3-dimethylaminopropyl)-N'-ethylcarbodiimide hydrochloride (216 mg, 1.125 mmol), 1-hydroxybenzotriazole (203 mg, 1.5 mmol) and N,N-diisopropylethylamine (290 mg, 2.25 mmol) in dichloromethane (15 mL) was stirred at room temperature for 4 h. The reaction was poured into water (15 mL) and extracted with dichloromethane (2×10 mL). The combined organic phase was dried over anhydrous sodium sulfate, filtered and concentrated. The crude was then purified by prep-TLC [petroleum ether/ethyl acetate (1:2 v/v)] followed by prep-HPLC to afford di-tert-butyl ((2S,2'S)-(((4S,4'S,7S,7'S,9aS,9a'S)-((((1R,1'R,2R,2'R)-((((1R,4R)-cyclohexane-1,4-diyl)bis(azanediyl))bis(carbonyl))bis(1,2,3,4-tetrahydronaphthalene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate) (140 mg, 0.104 mmol, 28.0% yield) as beige solid. LCMS (2.5 min formic acid): Rt=2.115 min, m/z: 572.1 {[(M-2Boc)+2]/2}⁺.

Step 2: (4S,7S,9aS)-8,8-dimethyl-4-[(2S)-2-(methylamino)propanethioamido]-5-oxo-N-[(1R,2R)-2-{[(1rs,4rs)-4-[(1R,2R)-1-[(4S,7S,9aS)-8,8-dimethyl-4-[(2S)-2-(methylamino)propanethioamido]-5-oxo-octahydropyrrolo[2,1-b][1,3]thiazepine-7-amido]-1,2,3,4-tetrahydronaphthalene-2-amido]cyclohexyl]carbamoyl}-1,2,3,4-tetrahydronaphthalen-1-yl]-octahydropyrrolo[2,1-b][1,3]thiazepine-7-carboxamide dihydrochloride To a solution of di-tert-butyl ((2S,2'S)-(((4S,4'S,7S,7'S,9aS,9a'S)-((((1R,1'R,2R,2'R)-((((1R,4R)-cyclohexane-1,4-diyl)bis(azanediyl))bis(carbonyl))bis(1,2,3,4-tetrahydronaphthalene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate) (140 mg, 0.104 mmol) in dichloromethane (5 mL) was added 4 N hydrogen chloride in 1,4-dioxane (0.5 mL). The mixture was stirred at room temperature overnight. The solvent was removed under reduced pressure and dried under high vacuum to give the title compound (70 mg, 0.058 mmol, 55.3% yield) as white solid. ¹H NMR (400 MHz, DMSO-d₆) δ ppm 11.04-11.00 (m, 2H), 10.91 (s, 2H), 8.67 (s, 1H), 8.43 (s, 1H), 7.97 (t, J=8.4 Hz, 2H), 7.76-7.75 (m, 2H), 7.27-7.25 (m, 2H), 7.15-7.06 (m, 6H), 5.45-5.33 (m, 4H), 5.15-5.09 (m, 2H), 4.32 (s, 2H), 4.18 (d, J=9.2 Hz, 2H), 3.51-3.47 (m, 2H), 3.22-3.17 (m, 2H), 3.07-3.00 (m, 2H), 2.79-2.66 (m, 6H), 2.48 (s, 6H), 2.33-2.18 (m, 6H), 2.05-1.94 (m, 2H), 1.79-1.74 (m, 6H), 1.45 (s, 6H), 1.24-1.14 (m, 4H), 1.04-1.03 (m, 6H), 1.00 (m, 6H). LCMS (2.5 min formic acid): Rt=1.242 min, m/z: 1144.4 (M+1)⁺, 572.3 [(M+2)/2]⁺.

Example 13

(4S,4'S,7S,7'S,9aS,9a'S)—N,N'-((1S,1'S,2R,2'R)-(hexa-2,4-diyne-1,6-diylbis(oxy))bis(2,3-dihydro-1H-indene-2,1-diyl))bis(8,8-dimethyl-4-((S)-2-(methylamino)propanamido)-5-oxooctahydropyrrolo[2,1-b][1,3]thiazepine-7-carboxamide) dihydrochloride

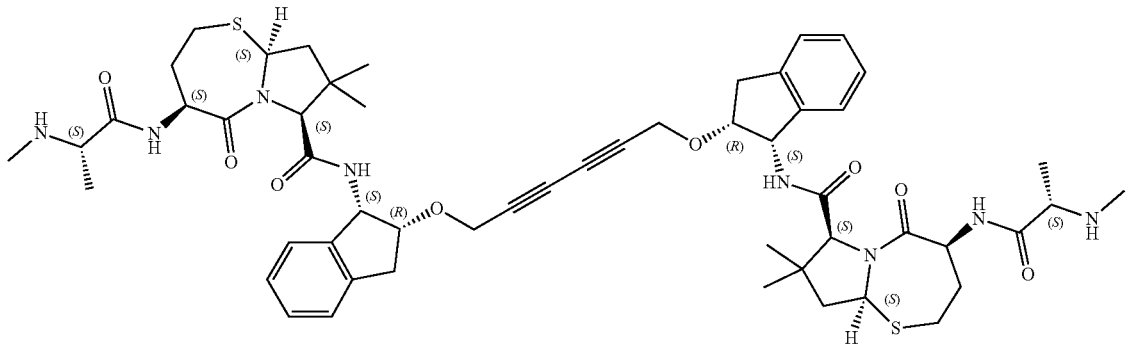

Step 1: (1S,2R)-2-(prop-2-yn-1-yloxy)-2,3-dihydro-1H-inden-1-amine

To a solution of (1S,2R)-1-amino-2,3-dihydro-1H-inden-2-ol (2 g, 13.4 mmol) in tetrahydrofuran (50 mL) at 0° C. was added portion wise sodium hydride (60%, dispersion in Paraffin Liquid) (0.59 g, 14.7 mmol). The mixture was allowed to warm to room temperature. 3-Bromoprop-1-yne (1.75 g, 14.7 mmol) was then added and the resulting mixture was heated to 70° C. It was stirred at 70° C. overnight. The mixture was quenched with ice water (50 mL) and extracted with ethyl acetate (3×30 mL). The combined organic layers were washed with brine (50 mL), dried over anhydrous sodium sulfate, filtered and concentrated. The crude was purified by silica gel chromatography [petroleum ether/ethyl acetate (3:2 v/v)] to afford (1S,2R)-2-(prop-2-yn-1-yloxy)-2,3-dihydro-1H-inden-1-amine (1.2 g, 6.4 mmol, 47.8% yield) as black oil. LCMS (ES, m/z): 187.1, 188.1 [M+H]⁺, retention time 0.942 min. ¹H NMR (400 MHz, DMSO-d₆) δ ppm 7.36-7.29 (m, 1H), 7.22-7.13 (m, 3H), 4.25 (dd, J=4.2, 2.4 Hz, 2H), 4.22-4.15 (m, 2H), 3.43 (t, J=2.4 Hz, 1H), 2.93 (qd, J=16.1, 3.5 Hz, 2H), 1.75 (s, 2H).

Step 2: tert-butyl ((S)-1-(((4S,7S,9aS)-8,8-dimethyl-5-oxo-7-(((1S,2R)-2-(prop-2-yn-1-yloxy)-2,3-dihydro-1H-inden-1-yl)carbamoyl)octahydropyrrolo[2,1-b][1,3]thiazepin-4-yl)amino)-1-oxopropan-2-yl)(methyl)carbamate To a solution of (4S,7S,9aS)-4-((S)-2-((tert-butoxycarbonyl)(methyl)amino)propanamido)-8,8-dimethyl-5-oxooctahydropyrrolo[2,1-b][1,3]thiazepine-7-carboxylic acid (260 mg, 0.587 mmol), 2-(7-azabenzotriazol-1-yl)-N,N,N',N'-tetramethyluronium hexafluorophosphate (305 mg, 0.801 mmol) and N,N-diisopropylethylamine (138 mg, 1.068 mmol) in 1,2-dichloroethane (10 mL) was added (1S,2R)-

2-(prop-2-yn-1-yloxy)-2,3-dihydro-1H-inden-1-amine (100 mg, 0.534 mmol). The mixture was stirred at 50° C. overnight. The solvent was removed under reduced pressure. The crude was purified by silica gel chromatography [petroleum ether/ethyl acetate (1:1 v/v)] and further purified by thin layer chromatography [ethyl acetate/petroleum ether (3/2 v/v)] to give tert-butyl ((S)-1-(((4S,7S,9aS)-8,8-dimethyl-5-oxo-7-(((1S,2R)-2-(prop-2-yn-1-yloxy)-2,3-dihydro-1H-inden-1-yl)carbamoyl)octahydropyrrolo[2,1-b][1,3]thiazepin-4-yl)amino)-1-oxopropan-2-yl)(methyl)carbamate (160 mg, 0.261 mmol, 48.9% yield). LCMS (2.5 min formic acid): Rt=1.662 min, m/z: 634.8 (M+Na)$^+$.

Step 3: di-tert-butyl ((2S,2'S)-(((4S,4'S,7S,7'S,9aS, 9a'S)-((((1S,1'S,2R,2'R)-(hexa-2,4-diyne-1,6-diylbis (oxy))bis(2,3-dihydro-1H-indene-2,1-diyl))bis (azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis (methylcarbamate)

a. To a solution of tert-butyl ((S)-1-(((4S,7S,9aS)-8,8-dimethyl-5-oxo-7-(((1S,2R)-2-(prop-2-yn-1-yloxy)-2,3-dihydro-1H-inden-1-yl)carbamoyl)octahydropyrrolo[2,1-b][1,3]thiazepin-4-yl)amino)-1-oxopropan-2-yl)(methyl) carbamate (160 mg, 0.261 mmol) and pyridine (124 mg, 1.566 mmol) in acetonitrile (7 mL) was added cupric acetate (57 mg, 0.313 mmol). The mixture was stirred at 85° C. for 1 h. The mixture was cooled, concentrated and diluted with ethyl acetate (15 mL). Aqueous ammonia (20 fold dilution, 15 mL) was added. The aqueous phase was extracted with ethyl acetate (2×10 mL). The combined organic layers were washed with brine (15 mL), dried over anhydrous sodium sulfate, filtered and concentrated. The crude was purified by thin layer chromatography [ethyl acetate/petroleum ether (2/1 v.v)] followed by Prep-HPLC to give di-tert-butyl ((2S,2'S)-(((4S,4'S,7S,7'S,9aS,9a'S)-((((1S,1'S,2R,2'R)-(hexa-2,4-diyne-1,6-diylbis(oxy))bis(2,3-dihydro-1H-indene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis (methylcarbamate) (80 mg, 0.065 mmol, 50.2% yield) as white solid. LCMS (2.5 min formic acid): Rt=1.853 min, m/z: 511.8 {[(M-2Boc)+2]/2}$^+$.

b. To a solution of tert-butyl ((S)-1-(((4S,7S,9aS)-8,8-dimethyl-5-oxo-7-(((1S,2R)-2-(prop-2-yn-1-yloxy)-2,3-dihydro-1H-inden-1-yl)carbamoyl)octahydropyrrolo[2,1-b][1,3]thiazepin-4-yl)amino)-1-oxopropan-2-yl)(methyl) carbamate (1.0 g, 1.63 mmol) and pyridine (775 mg, 9.79 mmol) in acetonitrile (20 mL) was added cupric acetate (366 mg, 1.96 mmol). The mixture was stirred at 85° C. for 1 h. The reaction mixture was cooled down, concentrated and diluted with ethyl acetate (100 mL). A solution of 20-fold ammonia (50 mL) was added. The water phase was extracted with ethyl acetate (2×50 mL). The organic layer was combined and washed with brine. Dried over anhydrous sodium sulfate and concentrated to get the crude. The residue was purified by chromatography on a silica gel column eluting with ethyl acetate/petroleum ether=1/1 to give crude product. Then the crude product was purified by Prep-HPLC to get di-tert-butyl ((2S,2'S)-(((4S,4'S,7S,7'S, 9aS,9a'S)-((((1S,1'S,2R,2'R)-(hexa-2,4-diyne-1,6-diylbis (oxy))bis(2,3-dihydro-1H-indene-2,1-diyl))bis(azanediyl)) bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (800 mg, 0.65 mmol, 80.2% yield) as a white solid. LCMS (ES, m/z): 1222.6, 512.2 [M/2-Boc+H]$^+$, retention time 1.735 min. $^1$H NMR (400 MHz, DMSO-d$_6$) δ ppm 7.96 (d, J=8.8 Hz, 2H), 7.77 (d, J=6.5 Hz, 2H), 7.24 (ddd, J=14.9, 8.9, 2.8 Hz, 8H), 5.48 (t, J=7.9 Hz, 2H), 5.38 (dd, J=8.7, 5.3 Hz, 2H), 4.67-4.62 (m, 2H), 4.30 (m, 6H), 4.23 (s, 2H), 3.15 (t, J=11.9 Hz, 2H), 3.03 (d, J=4.4 Hz, 2H), 2.88 (d, J=16.4 Hz, 2H), 2.73 (s, 6H), 2.26-2.17 (m, 2H), 2.16-2.05 (m, 6H), 1.76 (dt, J=23.3, 10.1 Hz, 4H), 1.40 (s, 18H), 1.24 (d, J=7.1 Hz, 6H), 1.07 (d, J=14.9 Hz, 12H).

Step 4: (4S,4'S,7S,7'S,9aS,9a'S)—N,N'-((1S,1'S,2R, 2'R)-(hexa-2,4-diyne-1,6-diylbis(oxy))bis(2,3-dihydro-1H-indene-2,1-diyl))bis(8,8-dimethyl-4-((S)-2-(methylamino)propanamido)-5-oxooctahydropyrrolo[2,1-b][1,3]thiazepine-7-carboxamide) dihydrochloride To a solution of di-tert-butyl ((2S,2'S)-(((4S,4'S,7S,7'S, 9aS,9a'S)-((((1S,1'S,2R,2'R)-(hexa-2,4-diyne-1,6-diylbis (oxy))bis(2,3-dihydro-1H-indene-2,1-diyl))bis(azanediyl)) bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (80 mg, 0.065 mmol) in dichloromethane (5 mL) was added 4 N hydrogen chloride in 1,4-dioxane (1.5 mL). The mixture was stirred at room temperature overnight. The solvent was removed under reduced pressure and the solid was dried under high vacuum to afford (4S,4'S,7S,7'S,9aS,9a'S)—N,N'-((1S,1'S, 2R,2'R)-(hexa-2,4-diyne-1,6-diylbis(oxy))bis(2,3-dihydro-1H-indene-2,1-diyl))bis(8,8-dimethyl-4-((S)-2-(methylamino)propanamido)-5-oxooctahydropyrrolo[2,1-b][1,3] thiazepine-7-carboxamide) dihydrochloride (55 mg, 0.050 mmol, 76.9% yield) as white solid. $^1$H NMR (400 MHz, DMSO-d$_6$) δ ppm 9.53-9.50 (m, 2H), 8.95-8.91 (m, 2H), 8.88 (d, J=7.2 Hz, 2H), 8.00 (d, J=8.8 Hz, 2H), 7.28-7.20 (m, 8H), 5.51 (t, J=7.8 Hz, 2H), 5.38 (dd, J=8.6, 5.4 Hz, 2H), 4.76-4.71 (m, 2H), 4.24-4.28 (m, 6H), 4.23 (s, 2H), 3.93-3.85 (m, 2H), 3.22-3.16 (m, 2H), 3.10-3.00 (m, 4H), 2.94-2.90 (m, 2H), 2.47 (t, J=5.2 Hz, 6H), 2.29-2.14 (m, 4H), 1.87-1.79 (m, 4H), 1.42 (d, J=6.8 Hz, 6H), 1.10 (s, 6H), 1.06 (s, 6H). LCMS (2.5 min formic acid): Rt=1.328 min, m/z: 512.0 [(M+2)/2]$^+$.

Example 14

(4S,7S,9aS)—N-((1S,2R)-2-((6-(((1S,2R)-1-((4S,7S, 9aS)-8,8-dimethyl-4-((S)-2-(methylamino)propanamido)-5-oxooctahydropyrrolo[2,1-b][1,3]thiazepine-7-carboxamido)-2,3-dihydro-1H-inden-2-yl)oxy) hexa-2,4-diyn-1-yl)oxy)-2,3-dihydro-1H-inden-1-yl)-8,8-dimethyl-4-((S)-2-(methylamino) propanethioamido)-5-oxooctahydropyrrolo[2,1-b][1, 3]thiazepine-7-carboxamide

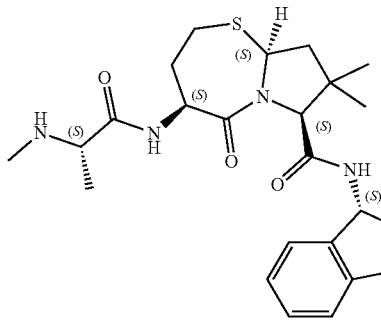
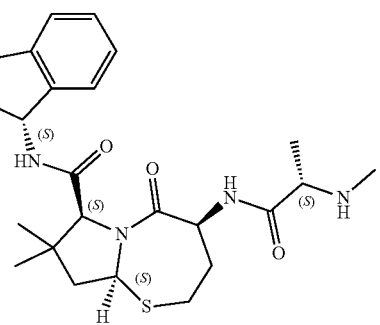

Step 1: tert-butyl ((S)-1-(((4S,7S,9aS)-8,8-dimethyl-5-oxo-7-(((1S,2R)-2-(prop-2-yn-1-yloxy)-2,3-dihydro-1H-inden-1-yl)carbamoyl)octahydropyrrolo[2,1-b][1,3]thiazepin-4-yl)amino)-1-thioxopropan-2-yl)(methyl)carbamate To a solution of (4S,7S,9aS)-4-((S)-2-((tert-butoxycarbonyl)(methyl)amino)propanethioamido)-8,8-dimethyl-5-oxooctahydropyrrolo[2,1-b][1,3]thiazepine-7-carboxylic acid (500 mg, 1.088 mmol), 2-(7-azabenzotriazol-1-yl)-N,N,N',N'-tetramethyluronium hexafluorophosphate (621 mg, 1.632 mmol) and N,N-diisopropylethylamine (309 mg, 2.393 mmol) in 1,2-dichloroethane (15 mL) was added (1S,2R)-2-(prop-2-yn-1-yloxy)-2,3-dihydro-1H-inden-1-amine (224 mg, 1.197 mmol). The mixture was stirred at 50° C. overnight. The mixture was concentrated and purified by silica gel chromatography [petroleum ether/ethyl acetate (3:2 v/v)] followed by prep-TLC [petroleum ether/ethyl acetate (2:3 v/v)] to afford tert-butyl ((S)-1-(((4S,7S,9aS)-8,8-dimethyl-5-oxo-7-(((1S,2R)-2-(prop-2-yn-1-yloxy)-2,3-dihydro-1H-inden-1-yl)carbamoyl)octahydropyrrolo[2,1-b][1,3]thiazepin-4-yl)amino)-1-thioxopropan-2-yl)(methyl)carbamate (400 mg, 0.636 mmol, 58.5% yield). LCMS (2.5 min formic acid): Rt=1.812 min, m/z: 650.8 (M+Na)+.

Step 2: tert-butyl ((S)-1-(((4S,7S,9aS)-7-(((1S,2R)-2-((6-(((1S,2R)-1-((4S,7S,9aS)-4-((S)-2-((tert-butoxycarbonyl)(methyl)amino)propanethioamido)-8,8-dimethyl-5-oxooctahydropyrrolo[2,1-b][1,3]thiazepine-7-carboxamido)-2,3-dihydro-1H-inden-2-yl)oxy)hexa-2,4-diyn-1-yl)oxy)-2,3-dihydro-1H-inden-1-yl)carbamoyl)-8,8-dimethyl-5-oxooctahydropyrrolo[2,1-b][1,3]thiazepin-4-yl)amino)-1-oxopropan-2-yl)(methyl)carbamate To a solution of tert-butyl ((S)-1-(((4S,7S,9aS)-8,8-dimethyl-5-oxo-7-(((1S,2R)-2-(prop-2-yn-1-yloxy)-2,3-dihydro-1H-inden-1-yl)carbamoyl)octahydropyrrolo[2,1-b][1,3]thiazepin-4-yl)amino)-1-oxopropan-2-yl)(methyl)carbamate (390 mg, 0.636 mmol), tert-butyl ((S)-1-(((4S,7S,9aS)-8,8-dimethyl-5-oxo-7-(((1S,2R)-2-(prop-2-yn-1-yloxy)-2,3-dihydro-1H-inden-1-yl)carbamoyl)octahydropyrrolo[2,1-b][1,3]thiazepin-4-yl)amino)-1-thioxopropan-2-yl)(methyl)carbamate (400 mg, 0.636 mmol) and pyridine (301 mg, 3.816 mmol) in acetonitrile (15 mL) was added cupric acetate (277 mg, 1.526 mmol). The mixture was stirred at 85° C. for 40 min. Upon cooling, the solvent was removed under reduced pressure. The crude was diluted with ethyl acetate (20 mL) and aqueous ammonia (20 fold dilution, 20 mL). The aqueous phase was extracted with ethyl acetate (2×15 mL). The combined organic layers were washed with brine (20 mL), dried over anhydrous sodium sulfate, filtered and concentrated. The crude was purified by prep-TLC [petroleum ether/ethyl acetate (2:3 v/v)] and prep-HPLC to give tert-butyl ((S)-1-(((4S,7S,9aS)-7-(((1S,2R)-2-((6-(((1S,2R)-1-((4S,7S,9aS)-4-((S)-2-((tert-butoxycarbonyl)(methyl)amino)propanethioamido)-8,8-dimethyl-5-oxooctahydropyrrolo[2,1-b][1,3]thiazepine-7-carboxamido)-2,3-dihydro-1H-inden-2-yl)oxy)hexa-2,4-diyn-1-yl)oxy)-2,3-dihydro-1H-inden-1-yl)carbamoyl)-8,8-dimethyl-5-oxooctahydropyrrolo[2,1-b][1,3]thiazepin-4-yl)amino)-1-oxopropan-2-yl)(methyl)carbamate (50 mg, 0.040 mmol, 6.29% yield) and di-tert-butyl ((2S,2'S)-(((4S,4'S,7S,7'S,9aS,9a'S)-((((1S,1'S,2R,2'R)-(hexa-2,4-diyne-1,6-diylbis(oxy))bis(2,3-dihydro-1H-indene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis (methylcarbamate) (30 mg, 0.024 mmol, 3.77% yield) both as white solids.

Step 3: (4S,7S,9aS)—N-((1S,2R)-2-((6-(((1S,2R)-1-((4S,7S,9aS)-8,8-dimethyl-4-((S)-2-(methylamino)propanamido)-5-oxooctahydropyrrolo[2,1-b][1,3]thiazepine-7-carboxamido)-2,3-dihydro-1H-inden-2-yl)oxy)hexa-2,4-diyn-1-yl)oxy)-2,3-dihydro-1H-inden-1-yl)-8,8-dimethyl-4-((S)-2-(methylamino)propanethioamido)-5-oxooctahydropyrrolo[2,1-b][1,3]thiazepine-7-carboxamide dihydrochloride To a solution of tert-butyl ((S)-1-(((4S,7S,9aS)-7-(((1S,2R)-2-((6-(((1S,2R)-1-((4S,7S,9aS)-4-((S)-2-((tert-butoxycarbonyl)(methyl)amino)propanethioamido)-8,8-dimethyl-5-oxooctahydropyrrolo[2,1-b][1,3]thiazepine-7-carboxamido)-2,3-dihydro-1H-inden-2-yl)oxy)hexa-2,4-diyn-1-yl)oxy)-2,3-dihydro-1H-inden-1-yl)carbamoyl)-8,8-dimethyl-5-oxooctahydropyrrolo[2,1-b][1,3]thiazepin-4-yl)amino)-1-oxopropan-2-yl)(methyl)carbamate (50 mg, 0.040 mmol) in dichloromethane (5 mL) was added 4 N hydrogen chloride in 1,4-dioxane (0.5 mL). The mixture was stirred at room temperature overnight. The mixture was concentrated and dried to give (4S,7S,9aS)—N-((1S,2R)-2-((6-(((1S,2R)-1-((4S,7S,9aS)-8,8-dimethyl-4-((S)-2-(methylamino)propanamido)-5-oxooctahydropyrrolo[2,1-b][1,3]thiazepine-7-carboxamido)-2,3-dihydro-1H-inden-2-yl)oxy)hexa-2,4-diyn-1-yl)oxy)-2,3-dihydro-1H-inden-1-yl)-8,8-dimethyl-4-((S)-2-(methylamino)propanethioamido)-5-oxooctahydropyrrolo[2,1-b][1,3]thiazepine-7-carboxamide dihydrochloride (20 mg, 0.018 mmol, 45% yield) as white solid. ¹H NMR (400 MHz, DMSO-d6) δ ppm 11.03-10.93 (m, 2H), 9.74-9.58 (m, 1H), 9.28 (s, 1H), 8.86-8.84 (m, 2H), 8.65-8.45 (m, 1H), 8.11-8.05 (m, 1H), 8.02-8.00 (m, 1H), 7.27-7.18 (m, 8H), 5.52-5.43 (m, 2H), 5.40-5.37 (m, 2H), 5.17 (q, J=6.4 Hz, 1H), 4.76-4.65 (m, 1H), 4.38-4.23 (m, 8H), 3.91-3.88 (m, 1H), 3.73-3.65 (m, 1H), 3.51-3.46 (m, 1H), 3.22-3.16 (m, 2H), 3.10-2.97 (m, 4H), 2.95-2.90 (m, 1H), 2.49 (s, 6H), 2.33-2.12 (m, 4H), 1.96-1.76 (m, 4H), 1.45 (d, J=6.4H, 3H), 1.41 (d, J=6.8H, 3H), 1.10-1.06 (m, 12H). LCMS (2.5 min formic acid): Rt=1.643 min, m/z: 520.0 [(M+2)/2]⁺.

Example 15

(4S,4'S,7S,7'S,9aS,9a'S)—N,N'-((1S,1'S,2R,2'R)-(hexa-2,4-diyne-1,6-diylbis(oxy))bis(2,3-dihydro-1H-indene-2,1-diyl))bis(8,8-dimethyl-4-((S)-2-(methylamino)propanethioamido)-5-oxooctahydropyrrolo[2,1-b][1,3]thiazepine-7-carboxamide)dihydrochloride

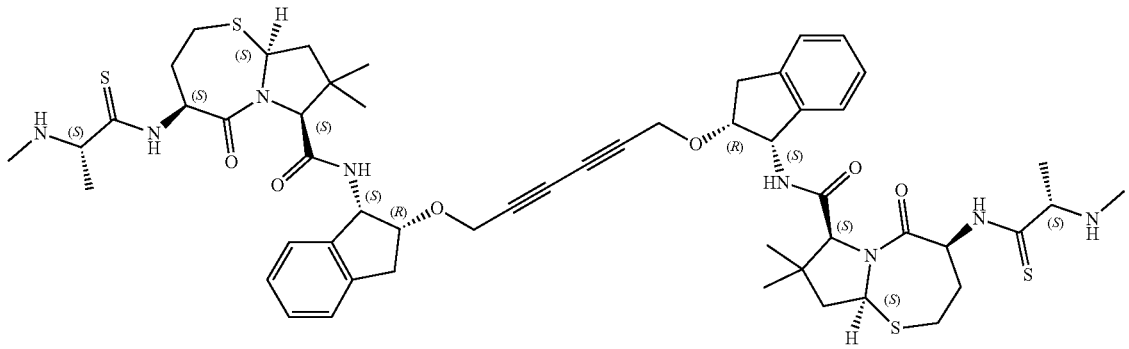

To a solution of di-tert-butyl ((2S,2'S)-(((4S,4'S,7S,7'S,9aS,9a'S)-((((1S,1'S,2R,2'R)-(hexa-2,4-diyne-1,6-diylbis(oxy))bis(2,3-dihydro-1H-indene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate) (Example 14, Step 2) (35 mg, 0.028 mmol) in dichloromethane (5 mL) was added 4 N hydrogen chloride in 1,4-dioxane (0.5 mL). The mixture was stirred at room temperature overnight. The solvent was removed under reduced pressure and dried under high vacuum to give (4S,4'S,7S,7'S,9aS,9a'S)—N,N'-((1S,1'S,2R,2'R)-(hexa-2,4-diyne-1,6-diylbis(oxy))bis(2,3-dihydro-1H-indene-2,1-diyl))bis(8,8-dimethyl-4-((S)-2-(methylamino)propanethioamido)-5-oxooctahydropyrrolo[2,1-b][1,3]thiazepine-7-carboxamide) dihydrochloride (12 mg, 0.011 mmol, 39.3% yield) as white solid. ¹H NMR (400 MHz, DMSO-d₆) δ ppm 11.00-10.91 (m, 2H), 9.66-9.51 (m, 2H), 8.62-8.44 (m, 2H), 8.08 (dd, J=13.9, 9.0 Hz, 2H), 7.28-7.18 (m, 8H), 5.46 (q, J=9.3 Hz, 2H), 5.38 (dd. J=8.6, 5.4 Hz, 2H), 5.17 (t, J=10.2 Hz, 2H), 4.38-4.26 (m, 10H), 3.23-3.17 (m, 2H), 3.06-2.99 (m, 6H), 2.50 (s, 6H), 2.33-2.17 (m, 4H), 1.95-1.84 (m, 4H), 1.44 (d, J=6.4H, 6H), 1.10 (s, 6H), 1.08 (s, 6H). LCMS (2.5 min formic acid): Rt=1.505 min, m/z: 1055.6 (M+1)⁺.

Example 16

(4S,4'S,7S,7'S,9aS,9a'S)—N,N'-((1S,1'S,2R,2'R)-(butane-1,4-diylbis(oxy))bis(2,3-dihydro-1H-indene-2,1-diyl))bis(8,8-dimethyl-4-((S)-2-(methylamino)propanamido)-5-oxooctahydropyrrolo[2,1-b][1,3]thiazepine-7-carboxamide)

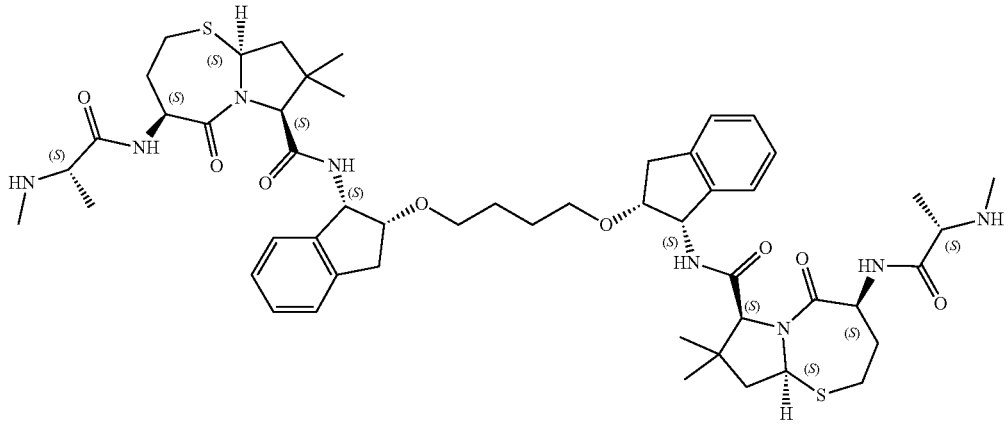

Step 1: (1S,2R)-1-isocyano-2-(prop-2-yn-1-yloxy)-2,3-dihydro-1H-indene

A suspension of (1S,2R)-2-(prop-2-yn-1-yloxy)-2,3-dihydro-1H-inden-1-amine (3.31 g, 17.68 mmol) and was heated in ethyl formate (28.8 mL, 354 mmol) at 70° C. for 21 h. Upon cooling, the solvent was removed under reduced pressure to give crude foramide (3.71 g). To s suspension of crude foramide in dichloromethane (DCM) (35 mL) at 0° C. was added Et$_3$N (12.32 mL, 88 mmol) followed by POCl$_3$ (2.471 mL, 26.5 mmol). After 2 hours, the crude was poured into a mixture of DCM (150 mL) and sat. aq. NaHCO$_3$ (60 mL). The aqueous phase was separated and extracted with DCM (50 mL). The combined organic layers were washed with brine (40 mL), dried (Na$_2$SO$_4$), filtered and concentrated. The crude was absorbed on Celite® and purified by silica gel chromatography [1-20% EtOAc in hexanes] to give (1S,2R)-1-isocyano-2-(prop-2-yn-1-yloxy)-2,3-dihydro-1H-indene, 0.15ETHYLACETATE (SOLVATE) (1.88 g, 8.93 mmol, 50.5% yield) as light yellow oil. $^1$H NMR (400 MHz, DMSO-d$_6$) δ ppm 2.99 (dd, J=16.4, 5.9 Hz, 1H), 3.11 (dd, J=16.0, 6.2 Hz, 1H), 3.53 (t, J=2.3 Hz, 1H), 4.26-4.38 (m, 2H), 4.44 (q, J=5.6 Hz, 1H), 5.34-5.45 (m, 1H), 7.28-7.38 (m, 3H), 7.44 (d, J=7.0 Hz, 1H); LCMS (ESI) m/z: 171.0 (M-(NC))$^+$.

Step 2: (4S,7S,9aS)-4-amino-8,8-dimethyl-5-oxo-N-((1S,2R)-2-(prop-2-yn-1-yloxy)-2,3-dihydro-1H-inden-1-yl)octahydropyrrolo[2,1-b][1,3]thiazepine-7-carboxamide and (4S,7R,9aS)-4-amino-8,8-dimethyl-5-oxo-N-((1S,2R)-2-(prop-2-yn-1-yloxy)-2,3-dihydro-1H-inden-1-yl)octahydropyrrolo[2,1-b][1,3]thiazepine-7-carboxamide A mixture of N-(tert-butoxycarbonyl)-S-trityl-L-homocysteine (2.05 g, 4.29 mmol), (1S,2R)-1-isocyano-2-(prop-2-yn-1-yloxy)-2,3-dihydro-1H-indene, 0.15ETHYLACETATE (SOLVATE) (0.903 g, 4.29 mmol), 4,4-dimethoxy-2,2-dimethylbutanal (1.2 g, 7.49 mmol) and ammonia, 7 M in MeOH (1.226 mL, 8.58 mmol) in trifluoroethanol (16 mL) was heated at 80° C. After 1 hour, the solvent was removed under reduced pressure. The crude was diluted with DCM (100 mL) and washed with 1 N NaOH (15 mL). The aqueous layer was separated and extracted with EtOAc (75 mL). The combined organic layers were washed with brine (30 mL), dried (MgSO$_4$), filtered and concentrated to give a foam. To this material was added dichloromethane (DCM) (20 mL) and TFA (4 mL, 51.9 mmol). The mixture was heated at 35-40° C. After 1 hour, TFA (2 mL) was added to mixture and heated for 1.5 hours. The mixture was allowed to stir at RT overnight. TFA (2 mL) was added and the mixture was heated at 50° C. for 1 hour. The crude was absorbed on Celite® and purified by C18 using an ISCO instrument [20-30% ACN gradient, 0.1% formic acid] to give 2 fractions. The lyophilized fractions were individually diluted with EtOAc (150 mL) and washed with sat. aq. NaHCO$_3$ (25 mL), dried (Na$_2$SO$_4$), filtered and concentrated. Two diastereoisomers were obtained-(4S,7S,9aS)-4-amino-8,8-dimethyl-5-oxo-N-((1S,2R)-2-(prop-2-yn-1-yloxy)-2,3-dihydro-1H-inden-1-yl)octahydropyrrolo[2,1-b][1,3]thiazepine-7-carboxamide (290.1 mg, 15.8% yield) and (4S,7R,9aS)-4-amino-8,8-dimethyl-5-oxo-N-((1S,2R)-2-(prop-2-yn-1-yloxy)-2,3-dihydro-1H-inden-1-yl)octahydropyrrolo[2,1-b][1,3]thiazepine-7-carboxamide (283.3 mg, 15.4%) both isolated as foam.

Data for 7S diastereosiomer: $^1$H NMR (400 MHz, DMSO-d$_6$) δ ppm 1.06 (s, 3H), 1.09 (s, 3H), 1.67-1.82 (m, 2H), 1.96-2.05 (m, 1H), 2.23 (dd, J=12.9, 7.4 Hz, 1H), 2.81 (dt, J=11.5, 2.6 Hz, 1H), 2.96-3.17 (m, 3H), 3.43 (t, J=2.3 Hz, 1H), 3.68 (d, J=9.8 Hz, 1H), 4.13 (t, J=2.5 Hz, 2H), 4.16-4.19 (m, 1H), 4.28-4.35 (m, 1H), 5.27-5.43 (m, 2H), 7.13-7.32 (m, 4H), 7.81 (d, J=8.6 Hz, 1H); LCMS(ESI) m/z: 428.3 (M+1)$^+$.

Data for 7R diastereosiomer: $^1$H NMR (400 MHz, DMSO-d$_6$) δ ppm 1.05 (s, 3H), 1.31 (s, 3H), 1.55-1.67 (m, 1H), 1.69 (d, J=13.3 Hz, 1H), 1.94 (br. s., 1H), 2.00-2.06 (m, 1H), 2.77 (dt, J=11.6, 2.8 Hz, 1H), 2.97 (dd, J=16.4, 3.1 Hz, 1H), 3.08 (dd, J=16.4, 5.5 Hz, 1H), 3.14-3.24 (m, 1H), 3.39 (t, J=2.1 Hz, 1H), 3.69 (d, J=9.8 Hz, 1H), 4.16-4.23 (m, 1H), 4.26-4.37 (m, 3H), 5.33 (dd, J=8.6, 5.5 Hz, 1H), 5.48 (d, J=9.0 Hz, 1H), 7.11-7.27 (m, 4H), 8.35 (d, J=9.0 Hz, 1H); LCMS(ESI) m/z: 428.7 (M+1)$^+$.

Step 3: tert-butyl ((S)-1-(((4S,7S,9aS)-8,8-dimethyl-5-oxo-7-(((1S,2R)-2-(prop-2-yn-1-yloxy)-2,3-dihydro-1H-inden-1-yl)carbamoyl)octahydropyrrolo[2,1-b][1,3]thiazepin-4-yl)amino)-1-oxopropan-2-yl)(methyl)carbamate To a solution of (4S,7S,9aS)-4-amino-8,8-dimethyl-5-oxo-N-((1S,2R)-2-(prop-2-yn-1-yloxy)-2,3-dihydro-1H-inden-1-yl)octahydropyrrolo[2,1-b][1,3]thiazepine-7-carboxamide (287 mg, 0.671 mmol) and Boc-N-Me-Ala-OH (205 mg, 1.007 mmol) in N,N-dimethylformamide (DMF) (3 mL) at 0° C. was added Hunig's base (0.586 mL, 3.36 mmol) followed by dropwise addition T3P, 50 wt % in EtOAc (0.699 mL, 1.175 mmol). After 45 min, the mixture was diluted with EtOAc (100 mL) and washed with sat. aq. NaHCO$_3$ (25 mL), then brine (25 mL), dried (Na$_2$SO$_4$), filtered and concentrated. The crude was absorbed on Celite® and purified by silica gel chromatography [20-80% EtOAc in hexanes] to give tert-butyl ((S)-1-(((4S,7S,9aS)-8,8-dimethyl-5-oxo-7-(((1S,2R)-2-(prop-2-yn-1-yloxy)-2,3-dihydro-1H-inden-1-yl)carbamoyl)octahydropyrrolo[2,1-b][1,3]thiazepin-4-yl)amino)-1-oxopropan-2-yl)(methyl)carbamate (314.5 mg, 0.513 mmol, 76% yield) as white solid. $^1$H NMR (400 MHz, CHLOROFORM-d) δ ppm 1.13 (s, 3H), 1.20 (s, 3H), 1.35 (d, J=7.0 Hz, 3H), 1.48 (s, 9H), 1.79-1.90 (m, 1H), 1.97-2.12 (m, 1H), 2.29 (dd, J=13.3, 7.0 Hz, 2H), 2.50 (br. s., 1H), 2.77-2.84 (m, 4H), 3.04-3.16 (m, 2H), 3.25-3.36 (m, 1H), 4.10 (dd, J=15.6, 2.3 Hz, 1H), 4.17 (dd, J=15.6, 2.3 Hz, 1H), 4.32 (s, 1H), 4.49 (q, J=5.1 Hz, 1H), 4.55 (dd, J=10.0, 6.1 Hz, 1H), 5.17 (dd, J=9.2, 7.6 Hz, 1H), 5.54 (dd, J=8.2, 5.9 Hz, 1H), 7.17-7.25 (m, 3H), 7.31 (d, J=6.2 Hz, 1H), 7.42 (d, J=8.6 Hz, 2H); LCMS(ESI) m/z: 613.4 (M+1)$^+$.

Step 4: tert-butyl ((S)-1-(((4S,7S,9aS)-7-(((1S,2R)-2-(allyloxy)-2,3-dihydro-1H-inden-1-yl)carbamoyl)-8,8-dimethyl-5-oxooctahydropyrrolo[2,1-b][1,3]thiazepin-4-yl)amino)-1-oxopropan-2-yl)(methyl)carbamate A suspension of tert-butyl ((S)-1-(((4S,7S,9aS)-8,8-dimethyl-5-oxo-7-(((1S,2R)-2-(prop-2-yn-1-yloxy)-2,3-dihydro-1H-inden-1-yl)carbamoyl)octahydropyrrolo[2,1-b][1,3]thiazepin-4-yl)amino)-1-oxopropan-2-yl)(methyl)carbamate (51.5 mg, 0.084 mmol) and Lindlar catalyst (12.8 mg, 6.01 µmol) was stirred under hydroen (1 atm) in MeOH (10 mL) for 2.5 hours. The suspension was filtered through 0.45 um disc and the filtrate was evaporated under reduced pressure to give tert-butyl ((S)-1-(((4S,7S,9aS)-7-(((1S,2R)-2-(allyloxy)-2,3-dihydro-1H-inden-1-yl)carbamoyl)-8,8-dimethyl-5-oxooctahydropyrrolo[2,1-b][1,3]thiazepin-4-yl)amino)-1-oxopropan-2-yl)(methyl)carbamate (51.4 mg, 0.071 mmol, 85% yield, 85% pure) as film. LCMS(ESI) m/z: 615.4, 617.6 (M+1) mixture of olefin and O-propyl (85:15 ratio by proton NMR).

Step 5: di-tert-butyl ((2S,2'S)-(((4S,4'S,7S,7'S,9aS,9a'S)-((((1S,1'S,2R,2'R)-(((E/Z)-but-2-ene-1,4-diyl)bis(oxy))bis(2,3-dihydro-1H-indene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate)

A mixture of tert-butyl ((S)-1-(((4S,7S,9aS)-7-(((1S,2R)-2-(allyloxy)-2,3-dihydro-1H-inden-1-yl)carbamoyl)-8,8-dimethyl-5-oxooctahydropyrrolo[2,1-b][1,3]thiazepin-4-yl) amino)-1-oxopropan-2-yl)(methyl)carbamate (51.4 mg, 0.084 mmol) and Grubbs Catalys™ 2nd generation (6.39 mg, 7.52 µmol) was stirred in dichloromethane (DCM) (350 µl) at RT under nitrogen. After 1 day, a second batch of Grubbs Catalyst™ 2nd generation (6.39 mg, 7.52 µmol) was added to the mixture. After 4 days, the crude mixture was purified by silica gel chromatography [20-100% EtOAc in hexanes] to give the adduct as a mixture of cis- and trans-isomers (10.9 mg, 21.8%). LCMS(ESI) m/z: 1199.7 (M-1).

Step 6: di-tert-butyl ((2S,2'S)-(((4S,4'S,7S,7'S,9aS,9a'S)-((((1S,1'S,2R,2'R)-(butane-1,4-diylbis(oxy))bis(2,3-dihydro-1H-indene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate)

A suspension of di-tert-butyl ((2S,2'S)-(((4S,4'S,7S,7'S,9aS,9a'S)-((((1S,1'S,2R,2'R)-(((E/Z)-but-2-ene-1,4-diyl)bis(oxy))bis(2,3-dihydro-1H-indene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (13 mg, 10.82 µmol) and palladium, 10 wt % on activated carbon, Degussa type E101 (1.151 mg, 1.082 µmol) was stirred under hydrogen (1 atm) in methanol (4 mL). After 1 day, the mixture was filtered through 0.45 um disc and re-subjected to hydrogenation condition under 30 psi in MeOH. A new batch of Pd/C was added and the mixture was stirred under hydrogen at 50 psi. After 4 days, the suspension was filtered through 0.45 um disc and the solvent was evaporated under reduced pressure. The crude was purified by C18 using an ISCO instrument [50-90% ACN gradient, 0.1% formic acid] to give di-tert-butyl ((2S,2'S)-(((4S,4'S,7S,7'S,9aS,9a'S)-((((1S,1'S,2R,2'R)-(butane-1,4-diylbis(oxy))bis(2,3-dihydro-1H-indene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (4.5 mg, 3.74 µmol, 34.6% yield) as white solid. $^1$H NMR (400 MHz, CHLOROFORM-d) b ppm 1.08 (s, 3H), 1.17 (s, 3H), 1.35 (d, J=7.0 Hz, 3H), 1.41-1.51 (m, 12H), 1.75-1.86 (m, 1H), 1.91 (dd, J=13.3, 9.4 Hz, 1H), 2.13-2.29 (m, 2H), 2.56-2.68 (m, 1H), 2.80 (s, 3H), 2.90-3.03 (m, 2H), 3.14 (t, J=12.7 Hz, 1H), 3.31-3.51 (m, 2H), 4.14 (q, J=4.3 Hz, 1H), 4.28 (s, 1H), 4.51 (dd, J=10.2, 5.9 Hz, 1H), 5.12 (t, J=8.4 Hz, 1H), 5.46 (dd, J=8.2, 5.9 Hz, 1H), 7.14-7.25 (m, 4H), 7.29 (d, J=7.0 Hz, 1H), 7.35 (d, J=4.3 Hz, 1H); LCMS(ESI) m/z: 502.4 {[(M-2Boc)+2]/2}$^+$.

Step 7: (4S,4'S,7S,7'S,9aS,9a'S)—N,N'-((1S,1'S,2R,2'R)-(butane-1,4-diylbis(oxy))bis(2,3-dihydro-1H-indene-2,1-diyl))bis(8,8-dimethyl-4-((S)-2-(methylamino)propanamido)-5-oxooctahydropyrrolo[2,1-b][1,3]thiazepine-7-carboxamide)

To a solution of di-tert-butyl ((2S,2'S)-(((4S,4'S,7S,7'S,9aS,9a'S)-((((1S,1'S,2R,2'R)-(butane-1,4-diylbis(oxy))bis(2,3-dihydro-1H-indene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (4.5 mg, 3.74 µmol) in dichloromethane (DCM) (1 mL) at RT was added hydrogen chloride (4 M in 1,4-dioxane) (0.2 mL, 0.800 mmol). After 5 h, the solvent was removed under reduced pressure. The crude was purified by C18 using an ISCO instrument [10-100% ACN gradient, 0.1% formic acid] to give (4S,4'S, 7S,7'S,9aS,9a'S)—N,N'-((1S,1'S,2R,2'R)-(butane-1,4-diyl-bis(oxy))bis(2,3-dihydro-1H-indene-2,1-diyl))bis(8,8-dimethyl-4-((S)-2-(methylamino)propanamido)-5-oxooctahydropyrrolo[2,1-b][1,3]thiazepine-7-carboxamide) (2.8 mg, 2.73 µmol, 73.1% yield) as white solid. ¹H NMR (400 MHz, CHLOROFORM-d) b ppm 1.11 (s, 3H), 1.17 (s, 3H), 1.29 (d, J=7.0 Hz, 3H), 1.53 (br. s., 2H), 1.79-1.98 (m, 2H), 2.16-2.32 (m, 2H), 2.43 (s, 3H), 2.72 (dd, J=14.8, 2.3 Hz, 1H), 2.99 (d, J=4.7 Hz, 2H), 3.14 (q, J=7.0 Hz, 1H), 3.24 (t, J=12.9 Hz, 1H), 3.33-3.43 (m, 1H), 3.50 (d, J=9.0 Hz, 1H), 4.18 (q, J=4.7 Hz, 1H), 4.30 (s, 1H), 4.59 (dd, J=10.1, 7.0 Hz, 1H), 5.17 (t, J=8.4 Hz, 1H), 5.45 (dd, J=8.4, 5.7 Hz, 1H), 7.15-7.25 (m, 3H), 7.29-7.39 (m, 2H), 8.34 (d, J=6.6 Hz, 1H); LCMS(ESI) m/z: 1003.5 (M+1)⁺.

Example 17

(4S,4'S,7S,7'S,9aS,9a'S)—N,N'-((1S,1'S,2R,2'R)-(butane-1,4-diylbis(oxy))bis(2,3-dihydro-1H-indene-2,1-diyl))bis(8,8-dimethyl-4-((S)-2-(methylamino)propanethioamido)-5-oxooctahydropyrrolo[2,1-b][1,3]thiazepine-7-carboxamide) dihydrochloride

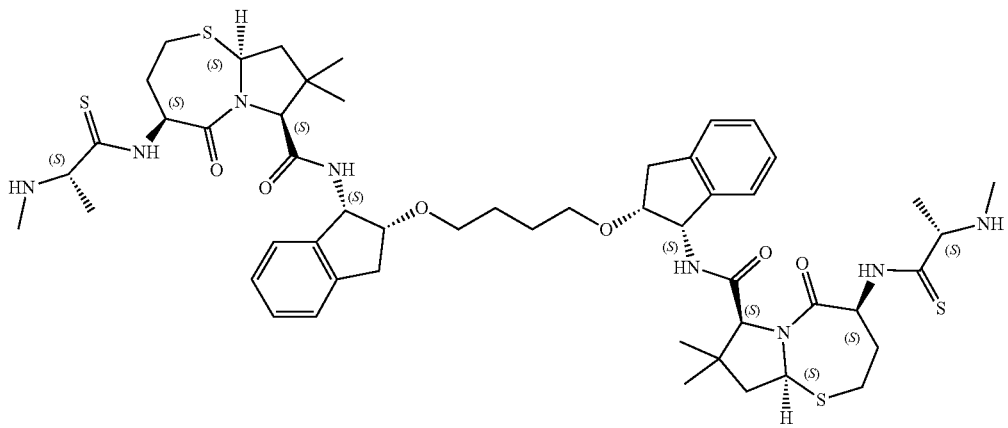

Step 1: butane-1,4-diyl bis(4-methylbenzenesulfonate)

To a solution of butane-1,4-diol (2 g, 22.19 mmol) and triethylamine (8.98 g, 48.82 mmol) in dichloromethane (100 mL) was added 4-dimethylaminopyridine (0.54 g, 4.44 mmol) followed by p-tosyl chloride (9.31 g, 48.82 mmol). The mixture was stirred at room temperature for 3 h. The mixture was concentrated. The crude was purified by silica gel chromatography [petroleum ether/ethyl acetate (3:1 v/v)] to afford butane-1,4-diyl bis(4-methylbenzenesulfonate) (4 g, 10.04 mmol, 45.2% yield) as white solid. LCMS (2.5 min formic acid): Rt=1.731 min, m/z: 420.8 (M+Na)⁺.

Step 2: (1S,1'S,2R,2'R)-2,2'-(butane-1,4-diylbis(oxy))bis(2,3-dihydro-1H-inden-1-amine)

To a solution of (1S,2R)-1-amino-2,3-dihydro-1H-inden-2-ol (749 mg, 5.02 mmol) in tetrahydrofuran (80 mL) at 0° C. was added portionwise sodium hydride (60%, dispersion in Paraffin Liquid) (221 mg, 5.52 mmol). The mixture was allowed to warm to room temperature. Butane-1,4-diyl bis(4-methylbenzenesulfonate) (1 g, 2.51 mmol) was then added. The resulting mixture was stirred at 70° C. overnight.

The reaction was quenched with ice water (50 mL) and extracted with ethyl acetate (3×30 mL). The combined organic layers were washed with brine (50 mL), dried over anhydrous sodium sulfate, filtered and concentrated. The crude was purified by silica gel chromatography [dichloromethane/methanol (10:1 v/v) to afford (1S,1'S,2R,2'R)-2,2'-(butane-1,4-diylbis(oxy))bis(2,3-dihydro-1H-inden-1-amine) (220 mg, 0.62 mmol, 24.7% yield) as brown solid. LCMS (2.5 min formic acid): Rt=1.206 min, m/z: (M+1)⁺.

Step 3: di-tert-butyl ((2S,2'S)-(((4S,4'S,7S,7'S,9aS,9a'S)-((((1S,1'S,2R,2'R)-(butane-1,4-diylbis(oxy))bis(2,3-dihydro-1H-indene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate)

To the mixture of (1S,1'S,2R,2'R)-2,2'-(butane-1,4-diylbis(oxy))bis(2,3-dihydro-1H-inden-1-amine) (130 mg, 0.369 mmol) and (4S,7S,9aS)-4-((S)-2-((tert-butoxycarbonyl)(methyl)amino)propanethioamido)-8,8-dimethyl-5-oxooctahydropyrrolo[2,1-b][1,3]thiazepine-7-carboxylic acid (Intermediate II) (373 mg, 0.812 mmol) in 1,2-dichloroethane (15 mL) was added N-ethoxycarbonyl-2-ethoxy-1,2-dihydroquinoline (274 mg, 1.107 mmol) and N,N-diisopropylethylamine (190 mg, 1.476 mmol). The resulting mixture was stirred at 50° C. overnight. The reaction was quenched with water (50 mL) and extracted with dichloromethane (3×50 mL). The combined organic layers were washed with brine, dried, filtered and concentrated. The residue was purified by thin layer chromatography [ethyl acetate/petroleum ether (1/1 v/v)] followed by Prep-HPLC to afford di-tert-butyl ((2S,2'S)-(((4S,4'S,7S,7'S,9aS,9a'S)-((((1S,1'S,2R,2'R)-(butane-1,4-diylbis(oxy))bis(2,3-dihydro-1H-indene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate) (60 mg, 0.049 mmol, 13.3% yield) as white solid. LCMS (2.5 min formic acid): Rt=2.154 min, m/z: 517.9 {[(M-2Boc)+2]/2}⁺.

Step 4: (4S,4'S,7S,7'S,9aS,9a'S)—N,N'-((1S,1'S,2R,2'R)-(butane-1,4-diylbis(oxy))bis(2,3-dihydro-1H-indene-2,1-diyl))bis(8,8-dimethyl-4-((S)-2-(methylamino)propanethioamido)-5-oxooctahydropyrrolo[2,1-b][1,3]thiazepine-7-carboxamide) dihydrochloride To a solution di-tert-butyl ((2S,2'S)-(((4S,4'S,7S,7'S,9aS,9a'S)-((((1S,1'S,2R,2'R)-(butane-1,4-diylbis(oxy))bis(2,3- dihydro-1H-indene-2,1-diyl))bis(azanediyl))bis(carbonyl)) bis(8,8-dimethyl-5-oxooctahydropyrrolo[2,1-b][1,3] thiazepine-7,4-diyl))bis(azanediyl))bis(1-thioxopropane-1,2-diyl))bis(methylcarbamate) (60 mg, 0.049 mmol) in dichloromethane (5 mL) was added 4 N hydrogen chloride in 1,4-dioxane (3 mL). The mixture was stirred at room temperature for 3 h. The solvent was concentrated under reduced pressure and the solid dried under high vacuum to give (4S,4'S,7S,7'S,9aS,9a'S)—N,N'-((1S,1'S,2R,2'R)-(butane-1,4-diylbis(oxy))bis(2,3-dihydro-1H-indene-2,1-diyl)) bis(8,8-dimethyl-4-((S)-2-(methylamino)propanethioamido)-5-oxooctahydropyrrolo[2,1-b][1,3]thiazepine-7-carboxamide) dihydrochloride (30 mg, 0.027 mmol, 57.7% yield) as white solid. $^1$H NMR (400 MHz, DMSO-d$_6$) δ ppm 11.01 (s, 1H), 10.93 (s, 1H), 9.63 (s, 1H), 9.48 (s, 1H), 8.64 (s, 2H), 8.47 (s, 2H), 7.98-7.93 (m, 2H), 7.24-7.20 (m, 8H), 5.46 (q, J=8.8 Hz, 2H), 5.35-5.32 (m, 2H), 5.19-5.14 (m, 2H), 4.28-4.26 (m, 4H), 4.10-4.09 (m, 2H), 3.73-3.65 (m, 2H), 3.51-3.47 (m, 2H), 3.39-3.38 (m, 2H), 3.20-3.14 (m, 2H), 2.96-2.95 (m, 4H), 2.50 (s, 6H), 2.27-2.13 (m, 4H), 1.94-1.82 (m, 4H), 1.45 (s, 10H), 1.07 (m, 12H). LCMS (2.5 min formic acid): Rt=1.408 min, m/z: 518.0 [(M+2)/2]$^+$.

Example 18

(4S,4'S,7S,7'S,9aS,9a'S)—N,N'-((1S,1'S,2R,2'R)-((oxybis(ethane-2,1-diyl))bis(oxy))bis(2,3-dihydro-1H-indene-2,1-diyl))bis(8,8-dimethyl-4-((S)-2-(methylamino)propanamido)-5-oxooctahydropyrrolo[2,1-b][1,3]thiazepine-7-carboxamide) dihydrochloride

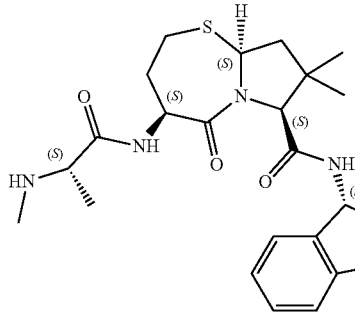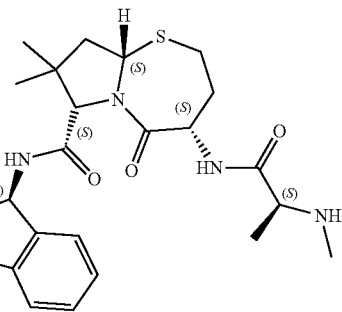

Step 1: (1S,1'S,2R,2'R)-2,2'-((oxybis(ethane-2,1-diyl))bis(oxy))bis(2,3-dihydro-1H-inden-1-amine)

To a solution of (1S,2R)-1-amino-2,3-dihydro-1H-inden-2-ol (800 mg, 5.36 mmol) in dry tetrahydrofuran (20 mL) was added slowly portionwise sodium hydride (60%, dispersion in Paraffin Liquid) (241 mg, 10.04 mmol) at 0° C. under nitrogen. The mixture was stirred at room temperature over 30 min and then oxybis(ethane-2,1-diyl) bis(4-methylbenzenesulfonate) (1.0 g, 2.44 mmol) was added. The mixture was heated to reflux and stirred for 5 h. The mixture was carefully quenched with water (150 mL) and extracted with ethyl acetate (3×50 mL). The combined organic layers were washed with brine, dried over anhydrous sodium sulfate, filtered and concentrated. The residue was purified by thin layer chromatography (dichloromethan/methanol (8:1 v/v)] to give (1S,1'S,2R,2'R)-2,2'-((oxybis(ethane-2,1-diyl))bis(oxy))bis(2,3-dihydro-1H-inden-1-amine) (410 mg, 1.11 mmol, 53% yield) as yellow oil. LCMS (2.5 min formic acid): Rt=1.107 min, m/z: 368.9 (M+1)$^+$.

Step 2: di-tert-butyl ((2S,2'S)-(((4S,4'S,7S,7'S,9aS,9a'S)-((((1S,1'S,2R,2'R)-((oxybis(ethane-2,1-diyl))bis(oxy))bis(2,3-dihydro-1H-indene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate)

To a solution of (1S,1'S,2R,2'R)-2,2'-((oxybis(ethane-2,1-diyl))bis(oxy))bis(2,3-dihydro-1H-inden-1-amine) (100 mg, 0.27 mmol), (4S,7S,9aS)-4-((S)-2-((tert-butoxycarbonyl) (methyl)amino)propanamido)-8,8-dimethyl-5-oxooctahydropyrrolo[2,1-b][1,3]thiazepine-7-carboxylic acid (Intermediate 1) (252.8 mg, 0.57 mmol), N-ethoxycarbonyl-2-ethoxy-1,2-dihydroquinoline (201.3 mg, 0.81 mmol) and N,N-diisopropyl-ethylamine (140.3 mg, 1.09 mmol) in 1,2-dichloroethane (6 mL) was stirred at 50° C. overnight. The solvent was removed under reduced pressure and the residue was purified by thin layer chromatography [ethyl acetate/petroleum ether (1/1 v/v)] to give the product (260 mg) as yellow oil. This material was further purified by Prep-HPLC to give di-tert-butyl ((2S,2'S)-(((4S,4'S,7S,7'S,9aS,9a'S)-((((1S,1'S,2R,2'R)-((oxybis(ethane-2,1-diyl))bis(oxy))bis(2,3-dihydro-1H-indene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (180 mg, 0.15 mmol, 54.4% yield) as white solid. LCMS (2.5 min formic acid): Rt=1.85 min, [½(M-Boc)+H]$^+$=509.9 {[(M-2Boc)+2]/2}.

Step 3: (4S,4'S,7S,7'S,9aS,9a'S)—N,N'-((1S,1'S,2R,2'R)-((oxybis(ethane-2,1-diyl))bis(oxy))bis(2,3-dihydro-1H-indene-2,1-diyl))bis(8,8-dimethyl-4-((S)-2-(methylamino)propanamido)-5-oxooctahydropyrrolo[2,1-b][1,3]thiazepine-7-carboxamide) dihydrochloride To a solution of di-tert-butyl ((2S,2'S)-(((4S,4'S,7S,7'S,9aS,9a'S)-((((1S,1'S,2R,2'R)-((oxybis(ethane-2,1-diyl))bis(oxy))bis(2,3-dihydro-1H-indene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (180 mg, 0.12 mmol) in dichloromethane (5 mL) was added hydrogen chloride (4 N in 1,4-dioxane, 1 mL). The reaction was stirred at room temperature overnight. The solvent was concentrated under reduced pressure and the solid dried under high vacuum to give (4S,4'S,7S,7'S,9aS,9a'S)—N,N'-((1S,1'S,2R,2'R)-((oxybis(ethane-2,1-diyl))bis(oxy))bis(2,3-dihydro-1H-indene-2,1-diyl))bis(8,8-dimethyl-4-((S)-2-(methylamino)propanamido)-5-oxooctahydropyrrolo[2,1-b][1,3]thiazepine-7-carboxamide) dihydrochloride (128.4 mg, 0.12 mmol, 80% yield) as white solid. $^1$H NMR (400 MHz, DMSO-d$_6$) δ ppm 9.56 (m, 2H), 8.95-8.90 (m, 4H), 7.89 (d, J=8.4 Hz, 2H), 7.23-7.20 (m, 8H), 5.51 (t, J=7.6 Hz, 2H), 5.34-5.30 (m, 2H), 4.73 (t, J=8.4 Hz, 2H), 4.22-4.18 (m, 4H), 3.91-3.89 (m, 2H), 3.54-3.53 (m, 4H), 3.46 (s, 4H), 3.19 (t, J=12.2 Hz, 2H), 2.98-2.90 (s, 6H), 2.46 (s, 6H), 2.24-2.14 (m, 4H), 1.86-1.77 (m, 4H), 1.42-1.40 (m, 6H), 1.06-1.05 (m, 12H). LCMS (2.5 min formic acid): Rt=1.318 min, m/z: 1018.7 (M+1)$^+$.

Example 19

(4S,4'S,7S,7'S,9aS,9a'S)—N,N'-((1S,1'S,2R,2'R)-((oxybis(ethane-2,1-diyl))bis(oxy))bis(2,3-dihydro-1H-indene-2,1-diyl))bis(8,8-dimethyl-4-((S)-2-(methylamino)propanethioamido)-5-oxooctahydropyrrolo[2,1-b][1,3]thiazepine-7-carboxamide) dihydrochloride

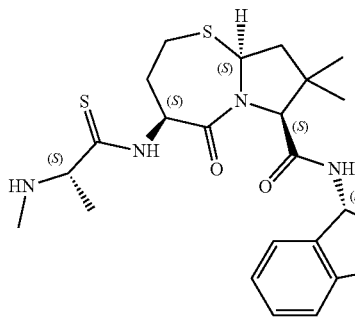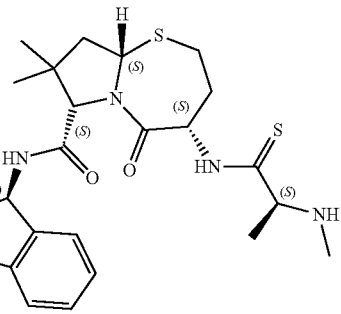

Step 1: di-tert-butyl ((2S,2'S)-(((4S,4'S,7S,7'S,9aS,9a'S)-(((( 1S,1'S,2R,2'R)-((oxybis(ethane-2,1-diyl))bis(oxy))bis(2,3-dihydro-1H-indene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate)

A solution of (1S,1'S,2R,2'R)-2,2'-((oxybis(ethane-2,1-diyl))bis(oxy))bis(2,3-dihydro-1H-inden-1-amine) (100 mg, 0.27 mmol), (4S,7S,9aS)-4-((S)-2-((tert-butoxycarbonyl)(methyl)amino)propanethioamido)-8,8-dimethyl-5-oxooctahydropyrrolo[2,1-b][1,3]thiazepine-7-carboxylic acid (Intermediate II) (262 mg, 0.57 mmol), N-ethoxycarbonyl-2-ethoxy-1,2-dihydroquinoline (201.3 mg, 0.81 mmol) and N,N-diisopropyl-ethylamine (140.3 mg, 1.09 mmol) in 1,2-dichloroethane (6 mL) was stirred at 50° C. overnight. The solvent was removed under reduced pressure and the crude was purified by thin layer chromatography [ethyl acetate/petroleum ether (1/1 v/v)] to give the product (200 mg) as yellow oil. This material was further purified by Prep-HPLC to give di-tert-butyl ((2S,2'S)-(((4S,4'S,7S,7'S,9aS,9a'S)- (((( 1S,1'S,2R,2'R)-((oxybis(ethane-2,1-diyl))bis(oxy))bis(2,3-dihydro-1H-indene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate) (150 mg, 0.13 mmol, 44.1% yield) as white solid. LCMS (2.5 min formic acid): Rt=2.11 min, m/z: 526.1 {[(M-2Boc)+2]/2}$^+$.

Step 2: (4S,4'S,7S,7'S,9aS,9a'S)—N,N'-((1S,1'S,2R,2'R)-((oxybis(ethane-2,1-diyl))bis(oxy))bis(2,3-dihydro-1H-indene-2,1-diyl))bis(8,8-dimethyl-4-((S)-2-(methylamino)propanethioamido)-5-oxooctahydropyrrolo[2,1-b][1,3]thiazepine-7-carboxamide) dihydrochloride To a solution of di-tert-butyl ((2S,2'S)-(((4S,4'S,7S,7'S,9aS,9a'S)-(((( 1S,1'S,2R,2'R)-((oxybis(ethane-2,1-diyl))bis(oxy))bis(2,3-dihydro-1H-indene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate) (150 mg, 0.122 mmol) in dichloromethane (5 mL) was added hydrogen chloride (4 N in 1,4-dioxane, 1 mL). The reaction was stirred at room temperature overnight. The solvent was concentrated under reduced pressure and the solid dried under high vacuum to afford (4S,4'S,7S,7'S,9aS,9a'S)—N,N'-((1S,1'S,2R,2'R)-((oxybis(ethane-2,1-diyl))bis(oxy))bis(2,3-dihydro-1H-indene-2,1-diyl))bis(8,8-dimethyl-4-((S)-2-(methylamino)propanethioamido)-5-oxooctahydropyrrolo[2,1-b][1,3]thiazepine-7-carboxamide) dihydrochloride (80.1 mg, 0.071 mmol, 60% yield) as white solid. $^1$H NMR (400 MHz, DMSO-d$_6$) δ ppm 11.06-10.93 (m, 2H), 9.76 (s, 1H), 9.58 (s, 1H), 8.65 (s, 1H), 8.45 (s, 1H), 7.98 (t, J=10.0 Hz, 2H), 7.23-7.20 (m, 8H), 5.46 (q, J=7.6 Hz, 2H), 5.34-5.31 (m, 2H), 5.19-5.13 (m, 2H), 4.30-4.25 (m, 4H), 4.18-4.17 (m, 2H), 3.54-3.53 (m, 4H), 3.47-3.46 (m, 4H), 3.20 (t, J=12.2 Hz, 2H), 3.00-2.98 (m, 6H), 2.50 (s, 6H), 2.33-2.21 (m, 4H), 1.96-1.82 (m, 4H), 1.45-1.43 (m, 6H), 1.07 (s, 12H). LCMS (2.5 min formic acid): Rt=1.404 min, m/z: 1072.7 (M+Na)$^+$.

Example 20

(4S,4'S,7S,7'S,9aS,9a'S)—N,N'-((1S,1'S,2R,2'R)-(hexane-1,6-diylbis(oxy))bis(2,3-dihydro-1H-indene-2,1-diyl))bis(8,8-dimethyl-4-((S)-2-(methylamino)propanamido)-5-oxooctahydropyrrolo[2,1-b][1,3]thiazepine-7-carboxamide)dihydrochloride

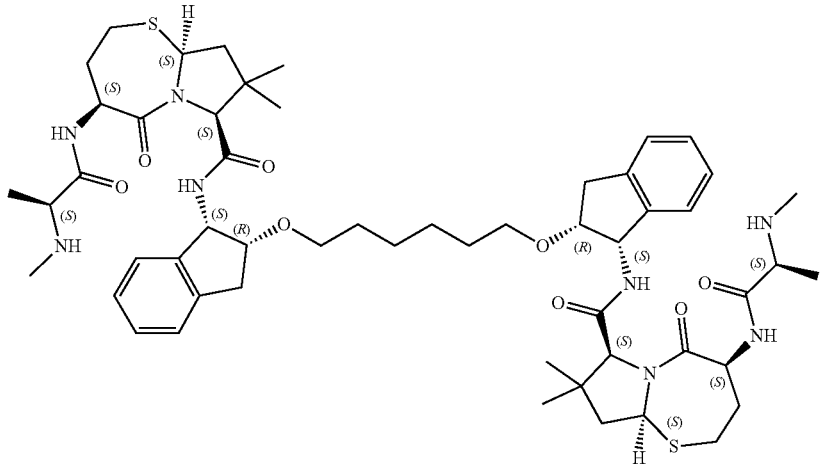

Step 1: (1S,1'S,2R,2'R)-2,2'-(hexane-1,6-diylbis(oxy))bis(2,3-dihydro-1H-inden-1-amine)

To a solution of (1S,2R)-1-amino-2,3-dihydro-1H-inden-2-ol (1.35 g, 9.10 mmol) in tetrahydrofuran (80 mL) at 0° C. was added portionwise sodium hydride (60%, dispersion in Paraffin Liquid) (428 mg, 10.70 mmol). The mixture was allowed to warm to room temperature. 1,6-dibromohexane (1 g, 4.12 mmol) was then added. The resulting mixture was stirred at 70° C. overnight. The mixture was quenched with ice water (50 mL) and extracted with ethyl acetate (3×30 mL). The combined organic layers were washed with brine (50 mL), dried over anhydrous sodium sulfate, filtered and concentrated. The crude was purified by silica gel chromatography [ethyl acetate/methanol (10:1 v/v)] to afford (170 mg, 0.45 mmol, 10.9% yield) as brown solid. LCMS (2.5 min formic acid): Rt=1.284 min, m/z: 381.0 (M+1)$^+$.

Step 2: di-tert-butyl ((2S,2'S)-(((4S,4'S,7S,7'S,9aS,9a'S)-((((1S,1'S,2R,2'R)-(hexane-1,6-diylbis(oxy))bis(2,3-dihydro-1H-indene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate)

To the mixture of (1S,1'S,2R,2'R)-2,2'-(hexane-1,6-diylbis(oxy))bis(2,3-dihydro-1H-inden-1-amine) (120 mg, 0.315 mmol) and (4S,7S,9aS)-4-((S)-2-((tert-butoxycarbonyl)(methyl)amino)propanamido)-8,8-dimethyl-5-oxooctahydropyrrolo[2,1-b][1,3]thiazepine-7-carboxylic acid (Intermediate I) (307 mg, 0.694 mmol) in 1,2-dichloroethane (8 mL) was added N-ethoxycarbonyl-2-ethoxy-1,2-dihydroquinoline (233 mg, 0.945 mmol) and N,N-diisopropylethylamine (162 mg, 1.26 mmol). The resulting mixture was stirred at 50° C. overnight. The solvent was removed under reduced pressure. The crude was purified by thin layer chromatography [ethyl acetate/petroleum ether (3/2 v/v)] followed by Prep-HPLC to give di-tert-butyl ((2S,2'S)-(((4S,4'S,7S,7'S,9aS,9a'S)-((((1S,1'S,2R,2'R)-(hexane-1,6-diylbis(oxy))bis(2,3-dihydro-1H-indene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (60 mg, 0.049 mmol, 15.6% yield) as colorless oil. LCMS (2.5 min formic acid): Rt=2.218 min, m/z: 515.9 {[(M-2Boc)+2]/2}$^+$.

Step 3: (4S,4'S,7S,7'S,9aS,9a'S)—N,N'-((1S,1'S,2R,2'R)-(hexane-1,6-diylbis(oxy))bis(2,3-dihydro-1H-indene-2,1-diyl))bis(8,8-dimethyl-4-((S)-2-(methylamino)propanamido)-5-oxooctahydropyrrolo[2,1-b][1,3]thiazepine-7-carboxamide) dihydrochloride To a solution of di-tert-butyl ((2S,2'S)-(((4S,4'S,7S,7'S,9aS,9a'S)-((((1S,1'S,2R,2'R)-(hexane-1,6-diylbis(oxy))bis(2,3-dihydro-1H-indene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (60 mg, 0.049 mmol) in methanol (5 mL) was added 4 N hydrogen chloride in 1,4-dioxane (4 mL). The mixture was stirred at room temperature for 2 h. The solvent was removed under reduced pressure and the solid dried under high vacuum to give (4S,4'S,7S,7'S,9aS,9a'S)—N,N'-((1S,1'S,2R,2'R)-(hexane-1,6-diylbis(oxy))bis(2,3-dihydro-1H-indene-2,1-diyl))bis(8,8-dimethyl-4-((S)-2-(methylamino)propanamido)-5-oxooctahydropyrrolo[2,1-b][1,3]thiazepine-7-carboxamide) dihydrochloride (30 mg, 0.027 mmol, 55.1% yield) as white solid. $^1$H NMR (400 MHz, DMSO-d$_6$) δ ppm 9.33 (s, 2H), 8.87-8.85 (m, 4H), 7.91 (d, J=8.4 Hz, 2H), 7.24-7.21 (m, 8H), 5.50 (t, J=7.8 Hz, 2H), 5.35-5.31 (m, 2H), 4.76-4.72 (m, 2H), 4.24 (s, 2H), 4.11-4.10 (m, 2H), 3.91-3.87 (m, 2H), 3.72-3.65 (m, 2H), 3.51-3.47 (m, 2H), 3.39-3.37 (m, 4H), 3.19 (t, J=12.4 Hz, 2H), 2.98-2.97 (m, 4H), 2.93-2.89 (m, 2H), 2.48 (s, 6H), 2.24-2.13 (m, 4H), 1.84-1.79 (m, 4H), 1.41-1.39 (m, 10H), 1.08 (m, 6H), 1.05 (m, 6H). LCMS (2.5 min formic acid): Rt=1.365 min, m/z: 1030.8 (M+1)$^+$.

Example 21

(4S,4'S,7S,7'S,9aS,9a'S)—N,N'-((1S,1'S,2R,2'R)-(hexane-1,6-diylbis(oxy))bis(2,3-dihydro-1H-indene-2,1-diyl))bis(8,8-dimethyl-4-((S)-2-(methylamino)propanethioamido)-5-oxooctahydropyrrolo[2,1-b][1,3]thiazepine-7-carboxamide)dihydrochloride

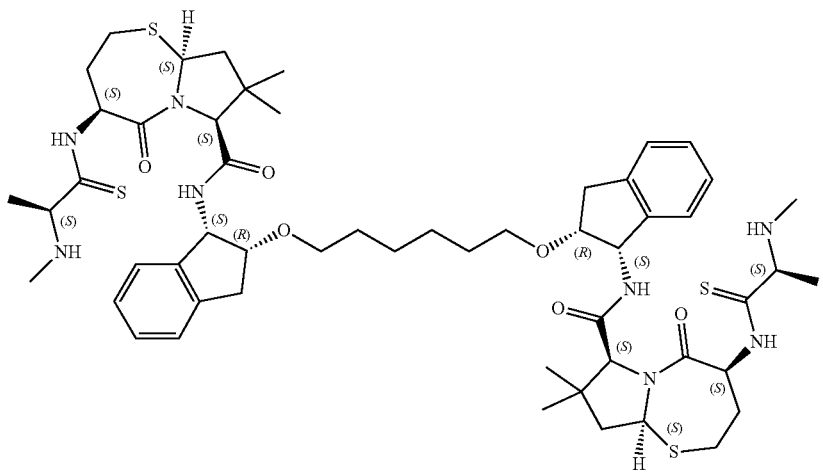

Step 1: di-tert-butyl ((2S,2'S)-(((4S,4'S,7S,7'S,9aS,9a'S)-((((1S,1'S,2R,2'R)-(hexane-1,6-diylbis(oxy))bis(2,3-dihydro-1H-indene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate)

To a mixture of (1S,1'S,2R,2'R)-2,2'-(hexane-1,6-diylbis(oxy)bis(2,3-dihydro-1H-inden-1-amine) (60 mg, 0.158 mmol) and (4S,7S,9aS)-4-((S)-2-((tert-butoxycarbonyl)(methyl)amino)propanethioamido)-8,8-dimethyl-5-oxooctahydropyrrolo[2,1-b][1,3]thiazepine-7-carboxylic acid (Intermediate II) (159 mg, 0.347 mmol) in 1,2-dichloroethane (5 mL) was added N-ethoxycarbonyl-2-ethoxy-1,2-dihydroquinoline (117 mg, 0.474 mmol) and N,N-diisopropylethylamine (81 mg, 0.632 mmol). The mixture was stirred at 50° C. overnight. The solvent was removed under reduced pressure. The crude was purified by thin layer chromatography [ethyl acetate/petroleum ether (1/1 v/v)] followed by Prep-HPLC to give di-tert-butyl ((2S,2'S)-(((4S,4'S,7S,7'S,9aS,9a'S)-((((1S,1'S,2R,2'R)-(hexane-1,6-diylbis(oxy))bis(2,3-dihydro-1H-indene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate) (30 mg, 0.024 mmol, 15.2% yield) as colorless oil. LCMS (2.5 min formic acid): Rt=2.218 min, m/z: 532.8 {[(M-2Boc)+2]/2}$^+$.

Step 2: (4S,4'S,7S,7'S,9aS,9a'S)—N,N'-((1S,1'S,2R,2'R)-(hexane-1,6-diylbis(oxy))bis(2,3-dihydro-1H-indene-2,1-diyl))bis(8,8-dimethyl-4-((S)-2-(methylamino)propanethioamido)-5-oxooctahydropyrrolo[2,1-b][1,3]thiazepine-7-carboxamide) dihydrochloride To a solution of di-tert-butyl ((2S,2'S)-(((4S,4'S,7S,7'S,9aS,9a'S)-((((1S,1'S,2R,2'R)-(hexane-1,6-diylbis(oxy))bis(2,3-dihydro-1H-indene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate) (30 mg, 0.024 mmol) in dichloromethane (5 mL) was added 4 N hydrogen chloride in 1,4-dioxane (2 mL). The mixture was stirred at room temperature overnight. The solvent was removed under reduced pressure and the solid dried under high vacuum to give (4S,4'S,7S,7'S,9aS,9a'S)—N,N'-((1S,1'S,2R,2'R)-(hexane-1,6-diylbis(oxy))bis(2,3-dihydro-1H-indene-2,1-diyl))bis(8,8-dimethyl-4-((S)-2-(methylamino)propanethioamido)-5-oxooctahydropyrrolo[2,1-b][1,3]thiazepine-7-carboxamide) dihydrochloride (13 mg, 0.011 mmol, 48.3% yield) as white solid. $^1$H NMR (400 MHz, DMSO-d$_6$) δ ppm 11.02 (d, J=6.4 Hz, 2H), 10.94 (d, J=6.4 Hz, 2H), 9.71 (s, 1H), 9.54 (s, 1H), 8.64 (s, 1H), 8.44 (s, 1H), 8.01-7.95 (m, 2H), 7.24-7.21 (m, 8H), 5.46 (q, J=8.0 Hz, 2H), 5.35-5.32 (m, 2H), 5.21-5.13 (m, 2H), 4.29-4.27 (m, 4H), 4.11-4.07 (m, 2H), 3.72-3.65 (m, 2H), 3.41-3.36 (m, 6H), 3.23-3.17 (m, 2H), 3.01-2.97 (m, 6H), 2.51 (s, 6H), 2.33-2.23 (m, 4H), 1.96-1.83 (m, 4H), 1.45-1.43 (m, 10H), 1.08 (m, 12H). LCMS (2.5 min formic acid): Rt=1.449 min, m/z: 532.0 [(M+2)/2]$^+$.

Example 22

(4S,4'S,7S,7'S,9aS,9a'S)—N,N'-((1S,1'S,2R,2'R)-((1,4-phenylenebis(methylene))bis(oxy))bis(2,3-dihydro-1H-indene-2,1-diyl))bis(8,8-dimethyl-4-((S)-2-(methylamino)propanamido)-5-oxooctahydropyrrolo[2,1-b][1,3]thiazepine-7-carboxamide)

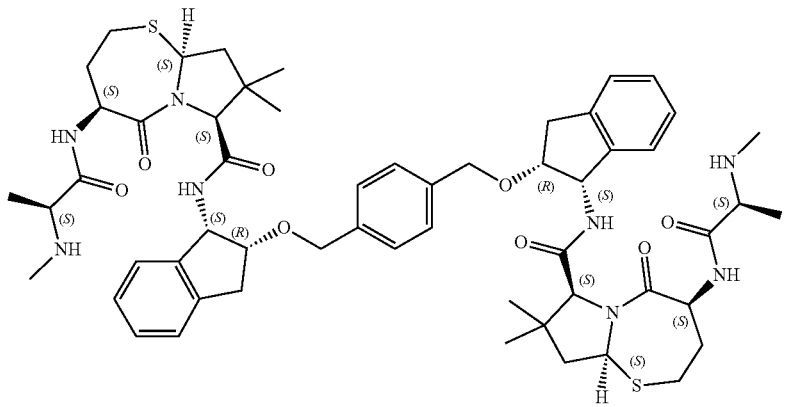

Step 1: (1S,1'S,2R,2'R)-2,2'-((1,4-phenylenebis(methylene))bis(oxy))bis(2,3-dihydro-1H-inden-1-amine)

To a solution of (1S,2R)-1-amino-2,3-dihydro-1H-inden-2-ol (800 mg, 5.36 mmol) in dry tetrahydrofuran (20 mL) at 0° C. was added slowly portionwise sodium hydride (60%, dispersion in Paraffin Liquid) (244 mg, 10.04 mmol) under nitrogen. The mixture was stirred at room temperature over 30 min followed by the addition of 1,4-bis(bromomethyl)benzene (644 mg, 2.43 mmol). The mixture was heated to reflux for 5 h. The mixture was carefully quenched with water (150 mL) and extracted with dichloromethane (3×50 mL). The combined organic layers were washed with brine, dried over anhydrous sodium sulfate, filtered and concentrate. The crude was purified by thin layer chromatography [dichloromethane/methanol (7:1 v/v)] to give (1S,1'S,2R,2'R)-2,2'-((1,4-phenylenebis(methylene))bis(oxy))bis(2,3-dihydro-1H-inden-1-amine) (200 mg, 0.53 mmol, 22% yield) as yellow oil. LCMS (2.5 min formic acid): Rt=1.208 min, m/z: 400.9 (M+1)$^+$.

Step 2: di-tert-butyl ((2S,2'S)-(((4S,4'S,7S,7'S,9aS,9a'S)-((((1S,1'S,2R,2'R)-((1,4-phenylenebis(methylene))bis(oxy))bis(2,3-dihydro-1H-indene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate)

A solution of (1S,1'S,2R,2'R)-2,2'-((1,4-phenylenebis(methylene))bis(oxy))bis(2,3-dihydro-1H-inden-1-amine) (80 mg, 0.21 mmol), (4S,7S,9aS)-4-((S)-2-((tert-butoxycarbonyl)(methyl)amino)propanamido)-8,8-dimethyl-5-oxooctahydropyrrolo[2,1-b][1,3]thiazepine-7-carboxylic acid (Intermediate 1) (198 mg, 0.45 mmol), N-ethoxycarbonyl-2-ethoxy-1,2-dihydroquinoline (157.6 mg, 0.64 mmol) and N,N-diisopropyl-ethylamine (110 mg, 0.85 mmol) in 1,2-dichloroethane (5 mL) was stirred at 50° C. overnight. The solvent was concentrated under reduced pressure. The crude was purified by thin layer chromatography [ethyl acetate/petroleum ether (1/1 v/v)] to give the product (110 mg) as yellow oil. This material was further purified by Prep-HPLC to give di-tert-butyl ((2S,2'S)-(((4S,4'S,7S,7'S,9aS,9a'S)-((((1S,1'S,2R,2'R)-((1,4-phenylenebis(methylene))bis(oxy))bis(2,3-dihydro-1H-indene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (68 mg, 0.045 mmol, 26.1% yield) as white solid. LCMS (2.5 min formic acid): Rt=1.86 min, m/z: 526.2 {[(M-2Boc)+2]/2}$^+$.

Step 3: (4S,4'S,7S,7'S,9aS,9a'S)—N,N'-((1S,1'S,2R,2'R)-((1,4-phenylenebis(methylene))bis(oxy))bis(2,3-dihydro-1H-indene-2,1-diyl))bis(8,8-dimethyl-4-((S)-2-(methylamino) propanamido)-5-oxooctahydropyrrolo[2,1-b][1,3]thiazepine-7-carboxamide)

To a solution of di-tert-butyl ((2S,2'S)-(((4S,4'S,7S,7'S,9aS,9a'S)-((((1S,1'S,2R,2'R)-((1,4-phenylenebis(methylene))bis(oxy))bis(2,3-dihydro-1H-indene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (68 mg, 0.055 mmol) in dichloromethane (5 mL) was added hydrogen chloride (4 N in 1,4-dioxane, 1 mL). The mixture was stirred at room temperature overnight. The solvent was removed under reduced pressure. The crude was diluted with water and the pH was adjusted 8-9 with sodium bicarbonate and extracted with dichloromethane (3×20 mL). The combined organic layers were washed with brine, dried, filtered and concentrated. The residue was purified by thin layer chromatography [dichloromethane/methanol (9/1 v/v)] to give (4S,4'S,7S,7'S,9aS,9a'S)—N,N'-((1S,1'S,2R,2'R)-((1,4-phenylenebis(methylene))bis(oxy))bis(2,3-dihydro-1H-indene-2,1-diyl))bis(8,8-dimethyl-4-((S)-2-(methylamino)propanamido)-5-oxooctahydropyrrolo[2,1-b][1,3]thiazepine-7-carboxamide) (38.8 mg, 0.037 mmol, 67.3% yield) as white solid. $^1$H NMR (400 MHz, DMSO-d$_6$) δ ppm 8.63-8.62 (m, 2H), 7.98 (d, J=9.2 Hz, 2H), 7.26-7.23 (m, 12H), 5.50 (t, J=7.8 Hz, 2H), 5.41-5.37 (m, 2H), 4.67-4.72 (m, 2H), 4.51 (s, 4H), 4.25-4.20 (m, 4H), 3.58-3.56 (m, 2H), 3.16-2.95 (m, 6H), 2.74-2.61 (s, 2H), 2.40 (s, 6H), 2.34-2.19 (m, 2H), 2.05-2.02 (m, 2H), 1.81-1.76 (m, 2H), 1.73-1.68 (m, 2H), 1.30 (d, J=6.4 Hz, 6H), 1.04 (m, 12H). LCMS (2.5 min formic acid): Rt=1.397 min, m/z: 1051.7 (M+1)$^+$.

Example 23

(4S,4'S,7S,7'S,9aS,9a'S)—N,N'-((1S,1'S,2R,2'R)-((1,4-phenylenebis(methylene))bis(oxy))bis(2,3-dihydro-1H-indene-2,1-diyl))bis(8,8-dimethyl-4-((S)-2-(methylamino)propanethioamido)-5-oxooctahydropyrrolo[2,1-b][1,3]thiazepine-7-carboxamide)

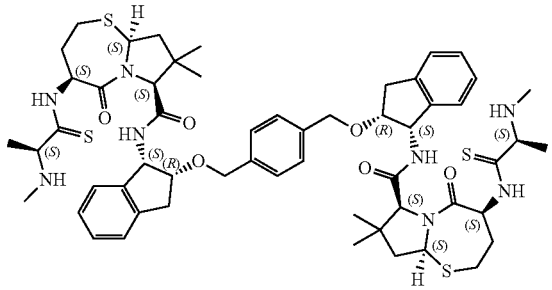

Step 1: tert-butyl ((S)-1-(((4S,7S,9aS)-7-(((1S,2R)-2-((4-(((((1S,2R)-1-((4S,7S,9aS)-4-((S)-2-((tert-butoxycarbonyl)(methyl)amino)propanethioamido)-8,8-dimethyl-5-oxooctahydropyrrolo[2,1-b][1,3]thiazepine-7-carbothioamido)-2,3-dihydro-1H-inden-2-yl)oxy)methyl)benzyl)oxy)-2,3-dihydro-1H-inden-1-yl)carbamoyl)-8,8-dimethyl-5-oxooctahydropyrrolo[2,1-b][1,3]thiazepin-4-yl)amino)-1-thioxopropan-2-yl)(methyl)carbamate A solution of (1S,1'S,2R,2'R)-2,2'-((1,4-phenylenebis(methylene))bis(oxy))bis(2,3-dihydro-1H-inden-1-amine) (80 mg, 0.21 mmol), (4S,7S,9aS)-4-((S)-2-((tert-butoxycarbonyl)(methyl)amino)propanethioamido)-8,8-dimethyl-5-oxooctahydropyrrolo[2,1-b][1,3]thiazepine-7-carboxylic acid (Intermediate II) (205.1 mg, 0.45 mmol), N-ethoxycarbonyl-2-ethoxy-1,2-dihydroquinoline (157.6 mg, 0.64 mmol) and N,N-diisopropyl-ethylamine (110 mg, 0.85 mmol) in 1,2-dichloroethane (5 mL) was stirred at 50° C. overnight. The solvent was removed under reduced pressure and the crude was purified by thin layer chromatography [ethyl acetate/petroleum ether (1/1 v/v)] to give the product (120 mg) as yellow oil. This material was further purified by Prep-HPLC to give tert-butyl ((S)-1-(((4S,7S,9aS)-7-(((1S,2R)-2-((4-(((((1S,2R)-1-((4S,7S,9aS)-4-((S)-2-((tert-butoxycarbonyl)(methyl)amino)propanethioamido)-8,8-dimethyl-5-oxooctahydropyrrolo[2,1-b][1,3]thiazepine-7-carbothioamido)-2,3-dihydro-1H-inden-2-yl)oxy)methyl)benzyl)oxy)-2,3-dihydro-1H-inden-1-yl)carbamoyl)-8,8-dimethyl-5-oxooctahydropyrrolo[2,1-b][1,3]thiazepin-4-yl)amino)-1-thioxopropan-2-yl)(methyl)carbamate (60 mg, 0.047 mmol, 22.4% yield) as white solid. LCMS (2.5 min formic acid): Rt=2.144 min, m/z: 541.9 {[(M-2Boc)+2]/2}$^+$.

Step 2: (4S,4'S,7S,7'S,9aS,9a'S)—N,N'-((1S,1'S,2R,2'R)-((1,4-phenylenebis(methylene))bis(oxy))bis(2,3-dihydro-1H-indene-2,1-diyl))bis(8,8-dimethyl-4-((S)-2-(methylamino)propanethioamido)-5-oxooctahydropyrrolo[2,1-b][1,3]thiazepine-7-carboxamide)

To a solution of di-tert-butyl ((2S,2'S)-(((4S,4'S,7S,7'S,9aS,9a'S)-(((1S,1'S,2R,2'R)-((1,4-phenylenebis(methylene))bis(oxy))bis(2,3-dihydro-1H-indene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate) (60 mg, 0.047 mmol) in dichloromethane (5 mL) was added hydrogen chloride (4 N in 1,4-dioxane, 1 mL). The reaction was stirred at room temperature overnight. The mixture was concentrated under reduced pressure. The crude was diluted with water and the pH was adjusted 8-9 with sodium bicarbonate and extracted with dichloromethane (3*20 mL). The combined organic layers were washed with brine, dried, filtered and concentrated. The residue was purified by thin layer chromatography [dichloromethane/methanol (10/1 v/v)] to give (4S,4'S,7S,7'S,9aS,9a'S)—N,N'-((1S,1'S,2R,2'R)-((1,4-phenylenebis(methylene))bis(oxy))bis(2,3-dihydro-1H-indene-2,1-diyl))bis(8,8-dimethyl-4-((S)-2-(methylamino)propanethioamido)-5-oxooctahydropyrrolo[2,1-b][1,3]thiazepine-7-carboxamide) (21.9 mg, 0.020 mmol, 42.6% yield) as white solid. $^1$H NMR (400 MHz, DMSO-d$_6$) δ ppm 7.98 (d, J=8.8 Hz, 2H), 7.24 (m, 12H), 5.51-5.46 (m, 2H), 5.42-5.39 (m, 2H), 5.11 (d, J=10.4 Hz, 2H), 4.51 (s, 4H), 4.29 (d, J=10.4 Hz, 2H), 4.24-4.21 (m, 2H), 3.31 (s, 4H), 3.17-3.09 (m, 2H), 3.05-2.97 (s, 4H), 2.79-2.73 (m, 2H), 2.26-2.26 (m, 10H), 1.81-1.73 (m, 2H), 1.68-1.66 (m, 2H), 1.29-1.28 (m, 6H), 1.06-1.05 (m, 12H). LCMS (2.5 min formic acid): Rt=1.443 min, m/z: 1083.7 (M+1)$^+$.

Example 24

(4S,4'S,7S,7'S,9aS,9a'S)—N,N'-((1S,1'S)-((1,4-phenylenebis(methylene))bis(azanediyl))bis(2-oxo-1-phenylethane-2,1-diyl))bis(8,8-dimethyl-4-((S)-2-(methylamino)propanamido)-5-oxooctahydropyrrolo[2,1-b][1,3]thiazepine-7-carboxamide)

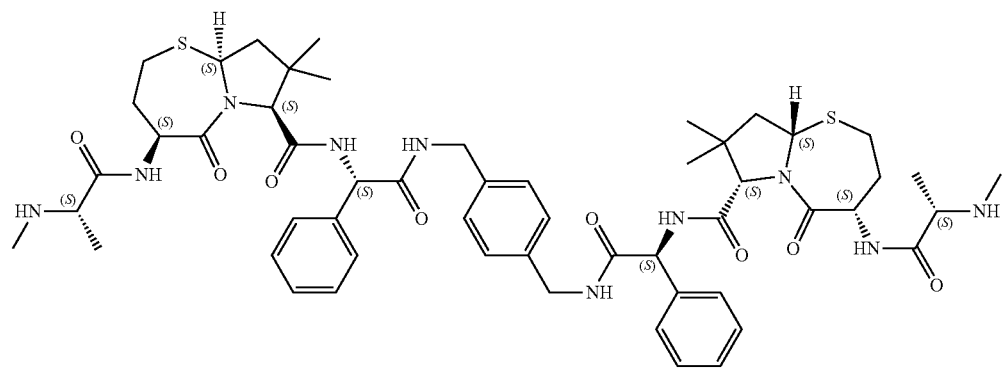

Step 1: (S)-2-((tert-butoxycarbonyl)amino)-2-phenylacetic Acid

To a solution of (S)-2-amino-2-phenylacetic acid (3.0 g, 19.8 mmol) in 1 M sodium hydroxide solution (28 mL) was added a solution of di-tert-butyl dicarbonate (4.75 g, 21.78 mmol) in tert-butyl alcohol (16 mL). The resulting suspension was stirred at room temperature for 1 h. The volatile solvent was removed under reduced pressure and the pH of the remaining solution was adjusted with citric acid to 3. The solid was filtered and dried to give (S)-2-((tert-butoxycarbonyl)amino)-2-phenylacetic acid (4.1 g, 16.3 mmol, 82% yield). LCMS (2.5 min formic acid): Rt=1.48 min, [M+H]$^+$=273.9.

Step 2: di-tert-butyl ((1S,1'S)-((1,4-phenylenebis(methylene))bis(azanediyl))bis(2-oxo-1-phenylethane-2,1-diyl))dicarbamate To a solution of (S)-2-((tert-butoxycarbonyl)amino)-2-phenylacetic acid (700 mg, 2.78 mmol) in N,N-dimethylformamide (15 mL) at −15° C. was added 1,4-phenylenedimethanamine (189 mg, 1.39 mmol) in N,N-dimethylformamide (5 mL). diethyl cyanophosphonate (680 mg, 4.17 mmol) and triethylamine (562 mg, 5.56 mmol) were then added successively. The mixture was stirred at room temperature overnight. The reaction was quenched with water (400 mL) to give a precipitate which was filtered and dried under high vacuum to give di-tert-butyl ((1S,1'S)-((1,4-phenylenebis(methylene))bis(azanediyl))bis(2-oxo-1-phenylethane-2,1-diyl))dicarbamate (1.1 g, 1.83 mmol, 59.6% yield) as white solid. LCMS (2.5 min formic acid): Rt=1.56 min, m/z: 502.7 [(M-Boc)+1]+.

Step 3: (2S,2'S)—N,N'-(1,4-phenylenebis(methylene))bis(2-amino-2-phenylacetamide) dihydrochloride To a solution of di-tert-butyl ((1S,1'S)-((1,4-phenylenebis(methylene))bis(azanediyl))bis(2-oxo-1-phenylethane-2,1-diyl))dicarbamate (1.1 g, 1.83 mmol) in dichloromethane (10 mL) was added hydrogen chloride (4 N in 1,4-dioxane, 2 mL) at room temperature. The reaction was stirred at room temperature overnight and the solvent was removed under reduced pressure to give (2S,2'S)—N,N'-(1,4-phenylenebis(methylene))bis(2-amino-2-phenylacetamide) dihydrochloride (810 mg, crude) as white solid. LCMS (2.5 min formic acid): Rt=0.38 min, m/z: 403.0 (M+1)$^+$.

Step 4: di-tert-butyl ((2S,2'S)-(((4S,4'S,7S,7'S,9aS,9a'S)-((((1S,1'S)-((1,4-phenylenebis(methylene))bis(azanediyl))bis(2-oxo-1-phenylethane-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate)

A solution of (2S,2'S)—N,N'-(1,4-phenylenebis(methylene))bis(2-amino-2-phenylacetamide) dihydrochloride (200 mg, 0.43 mmol), (4S,7S,9aS)-4-((S)-2-((tert-butoxycarbonyl)(methyl)amino)propanamido)-8,8-dimethyl-5-oxooctahydropyrrolo[2,1-b][1,3]thiazepine-7-carboxylic acid (379 mg, 0.86 mmol), 1-(3-dimethylaminopropyl)-3-ethylcarbodiimide methiodide (246 mg, 1.28 mmol), 1-hydroxybenzotriazole (231 mg, 1.71 mmol) and N,N-diisopropyl ethylamine (331 mg, 2.56 mmol) in dichloromethane (10 mL) was stirred at room temperature overnight. The reaction was quenched with water (50 mL) and extracted with dichloromethane (3×50 mL). The combined organic layers were washed with brine, dried, filtered and concentrated. The residue was purified by thin layer chromatography [ethyl acetate/petroleum ether (2/1 v/v)] to give crude product (96 mg) as yellow oil. This material was further purified by Prep-HPLC to afford di-tert-butyl ((2S,2'S)-(((4S,4'S,7S,7'S,9aS,9a'S)-((((1S,1'S)-((1,4-phenylenebis(methylene))bis(azanediyl))bis(2-oxo-1-phenylethane-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (67 mg, 0.053 mmol, 12.6% yield) as white solid. LCMS (3.0 min formic acid): Rt=2.55 min, m/z: 526.5 {[(M-2Boc)+2]/2}$^+$, 1153.4 (M-Boc+1)$^+$.

Step 5: (4S,4'S,7S,7'S,9aS,9a'S)—N,N'-((1S,1'S)-((1,4-phenylenebis(methylene))bis(azanediyl))bis(2-oxo-1-phenylethane-2,1-diyl))bis(8,8-dimethyl-4-((S)-2-(methylamino)propanamido)-5-oxooctahydropyrrolo[2,1-b][1,3]thiazepine-7-carboxamide)

To a solution of di-tert-butyl ((2S,2'S)-(((4S,4'S,7S,7'S,9aS,9a'S)-(((((1R,1'R,2R,2'R)-(((1,4-phenylenebis(methylene))bis(azanediyl))bis(carbonyl))bis(1,2,3,4-tetrahydronaphthalene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate) (67 mg, 0.05 mmol) in dichloromethane (10 mL) was added hydrogen chloride (4 N in 1,4-dioxane, 1 mL) at room temperature. The mixture was stirred at room temperature overnight. The solvent was removed under reduced pressure to give the crude product. The crude was diluted with water, the pH was adjusted to 8-9 with sodium bicarbonate and extracted with dichloromethane (3×20 mL). The combined organic layers were washed with brine, dried, filtered and concentrated. The residue was purified by thin layer chromatography [dichloromethane/methanol (8/1 v/v)] to give (4S,4'S,7S,7'S,9aS,9a'S)—N,N'-((1S,1'S)-((1,4-phenylenebis(methylene))bis(azanediyl))bis(2-oxo-1-phenylethane-2,1-diyl))bis(8,8-dimethyl-4-((S)-2-(methylamino)propanamido)-5-oxooctahydropyrrolo[2,1-b][1,3]thiazepine-7-carboxamide) (47.5 mg, 0.045 mmol, 84% yield) as white solid. $^1$H NMR (400 MHz, DMSO-d$_6$) δ ppm 8.79 (t, J=5.8 Hz, 2H), 8.52 (d, J=8.0 Hz, 2H), 8.21 (d, J=6.8 Hz, 2H), 7.46-7.44 (m, 4H), 7.38-7.29 (m, 6H), 6.96 (s, 4H), 5.55-5.50 (m, 4H), 4.69-4.65 (m, 2H), 4.23 (s, 6H), 3.22-3.16 (m, 2H), 2.96-2.88 (m, 4H), 2.22 (s, 8H), 2.14-2.09 (m, 2H), 1.84-1.71 (m, 4H), 1.12 (d, J=7.2 Hz, 6H), 1.05 (s, 6H), 0.90 (s, 6H). LCMS (2.5 min formic acid): Rt=1.248 min, m/z: 1052.7 (M+1)$^+$.

Example 25

(4S,4'S,7S,7'S,9aS,9a'S)—N,N'-((1S,1'S)-((1,4-phenylenebis(methylene))bis(azanediyl))bis(2-oxo-1-phenylethane-2,1-diyl))bis(8,8-dimethyl-4-((S)-2-(methylamino)propanethioamido)-5-oxooctahydropyrrolo[2,1-b][1,3]thiazepine-7-carboxamide) dihydrochloride

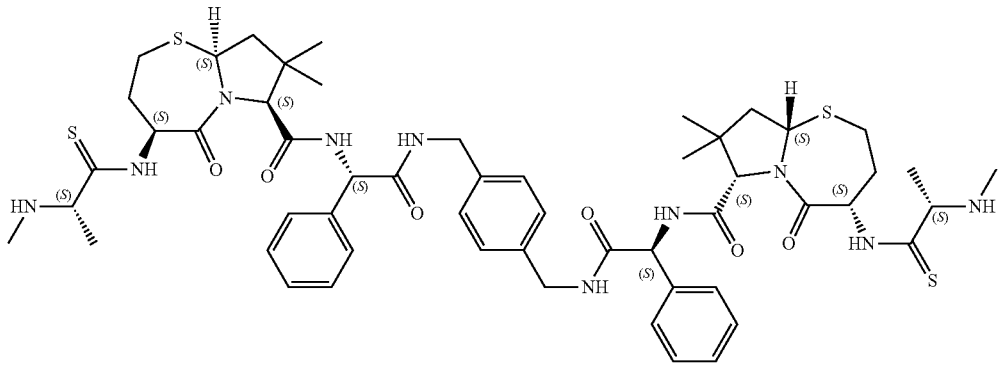

Step 1: di-tert-butyl ((2S,2'S)-(((4S,4'S,7S,7'S,9aS,9a'S)-((((1S,1'S)-((1,4-phenylenebis(methylene))bis(azanediyl))bis(2-oxo-1-phenylethane-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate)

A solution of (2S,2'S)—N,N'-(1,4-phenylenebis(methylene))bis(2-amino-2-phenylacetamide) dihydrochloride (200 mg, 0.42 mmol), (4S,7S,9aS)-4-((S)-2-((tert-butoxycarbonyl)(methyl)amino)propanethioamido)-8,8-dimethyl-5-oxooctahydropyrrolo[2,1-b][1,3]thiazepine-7-carboxylic acid (Intermediate II) (391 mg, 0.85 mmol), 1-(3-dimethylaminopropyl)-3-ethylcarbodiimide methiodide (243 mg, 1.27 mmol), 1-hydroxybenzotriazole (228 mg, 1.69 mmol) and N,N-diisopropyl ethylamine (327 mg, 2.53 mmol) in dichloromethane (10 mL) was stirred at room temperature overnight. The mixture was quenched with water (50 mL) and extracted with dichloromethane (3×50 mL). The combined organic layers were washed with brine, dried, filtered and concentrated. The residue was purified by thin layer chromatography [ethyl acetate/petroleum ether (2/1 v/v)] to give crude product (96 mg) as yellow oil. This material was further purified by Prep-HPLC to give di-tert-butyl ((2S,2'S)-(((4S,4'S,7S,7'S,9aS,9a'S)-((((1S,1'S)-((1,4-phenylenebis(methylene))bis(azanediyl))bis(2-oxo-1-phenylethane-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate) (63 mg, 0.049 mmol, 11.7% yield) as white solid. LCMS (3.0 min formic acid): Rt=2.76 min, m/z: 542.9 {[(M-2Boc)+2]/2}$^+$, 1185.6 (M-Boc+1)$^+$.

Step 2: (4S,4'S,7S,7'S,9aS,9a'S)—N,N'-((1S,1'S)-((1,4-phenylenebis(methylene))bis(azanediyl))bis(2-oxo-1-phenylethane-2,1-diyl))bis(8,8-dimethyl-4-((S)-2-(methylamino)propanethioamido)-5-oxooctahydropyrrolo[2,1-b][1,3]thiazepine-7-carboxamide) dihydrochloride To a solution of di-tert-butyl ((2S,2'S)-(((4S,4'S,7S,7'S,9aS,9a'S)-((((1R,1'R,2R,2'R)-(((1,4-phenylenebis(methylene))bis(azanediyl))bis(carbonyl))bis(1,2,3,4-tetrahydronaphthalene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate) (63 mg, 0.049 mmol) in dichloromethane (5 mL) was added hydrogen chloride (4 N in 1,4-dioxane, 1 mL). The reaction was stirred at room temperature overnight. The solvent was removed under reduced pressure and dried under high vacuum to give (4S,4'S,7S,7'S,9aS,9a'S)—N,N'-((1S,1'S)-((1,4-phenylenebis(methylene))bis(azanediyl))bis(2-oxo-1-phenylethane-2,1-diyl))bis(8,8-dimethyl-4-((S)-2-(methylamino)propanethioamido)-5-oxooctahydropyrrolo[2,1-b][1,3]thiazepine-7-carboxamide) dihydrochloride (33.2 mg, 0.029 mmol, 57.8% yield) as white solid. $^1$H NMR (400 MHz, DMSO-d$_6$) δ ppm 8.83 (t, J=6.0 Hz, 2H), 8.61 (d, J=6.4 Hz, 2H), 7.46-7.44 (m, 4H), 7.38-7.29 (m, 6H), 6.95 (s, 4H), 5.56-5.53 (m, 2H), 5.51-5.46 (m, 2H), 5.17-5.13 (m, 2H), 4.27-4.20 (m, 4H), 4.12-4.08 (m, 2H), 3.72-3.65 (m, 1H), 3.52-3.47 (m, 1H), 3.25-3.18 (m, 2H), 3.01-2.97 (m, 2H), 2.42 (d, J=4.8 Hz, 6H), 2.34-2.26 (m, 4H), 2.01-1.90 (m, 2H), 1.81-1.76 (m, 2H), 1.39 (d, J=5.4 Hz, 6H), 1.08 (s, 6H), 0.93 (s, 6H). LCMS (2.5 min formic acid): Rt=1.312 min, m/z: 1085.7 (M+1)$^+$.

Example 26

(4S,4'S,7S,7'S,9aS,9a'S)—N,N'-((1S,1'S)-piperazine-1,4-diylbis(2-oxo-1-phenylethane-2,1-diyl))bis(8,8-dimethyl-4-((S)-2-(methylamino)propanamido)-5-oxooctahydropyrrolo[2,1-b][1,3]thiazepine-7-carboxamide) dihydrochloride

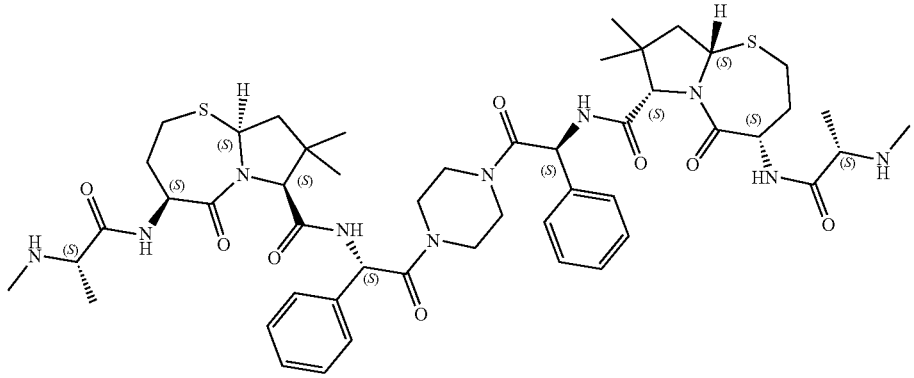

Step 1: di-tert-butyl ((1S,1'S)-piperazine-1,4-diylbis(2-oxo-1-phenylethane-2,1-diyl))dicarbamate To a solution of (S)-2-((tert-butoxycarbonyl)amino)-2-phenylacetic acid (500 mg, 2.1 mmol) in N,N-dimethylformamide (15 mL) at −15° C. was added piperazine (85.6 mg, 1.0 mmol) in N,N-dimethylformamide (5 mL), diethyl cyanophosphonate (488 mg, 3.0 mmol) and triethylamine (402.7 mg, 4.0 mmol) successively. The mixture was stirred at room temperature overnight. The mixture was poured into water (300 mL) to give a precipitate which was filtered and dried to afford di-tert-butyl ((1S,1'S)-piperazine-1,4-diylbis(2-oxo-1-phenylethane-2,1-diyl))dicarbamate (640 mg, 1.2 mmol, 58.2% yield) as white solid. LCMS (2.5 min formic acid): Rt=1.57 min, m/z: 575.8 (M+Na)$^+$.

Step 2: (2S,2'S)-1,1'-(piperazine-1,4-diyl)bis(2-amino-2-phenylethan-1-one) dihydrochloride To a solution of di-tert-butyl ((1S,1'S)-piperazine-1,4-diylbis(2-oxo-1-phenylethane-2,1-diyl))dicarbamate (200 mg, 0.32 mmol) in dichloromethane (10 mL) was added hydrogen chloride (4 N in 1,4-dioxane, 1 mL) at room temperature. The mixture was stirred at room temperature overnight. The mixture was concentrated under reduced pressure and dried under high vacuum to give crude (2S,2'S)-1,1'-(piperazine-1,4-diyl)bis(2-amino-2-phenylethan-1-one) dihydrochloride (150 mg) as white solid which was used for the next step without further purification. LCMS (2.5 min formic acid): Rt=0.39 min, m/z: 352.9 (M+1)$^+$.

Step 3: di-tert-butyl ((2S,2'S)-(((4S,4'S,7S,7'S,9aS,9a'S)-((((1S,1'S)-piperazine-1,4-diylbis(2-oxo-1-phenylethane-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate)

A solution of (2S,2'S)-1,1'-(piperazine-1,4-diyl)bis(2-amino-2-phenylethan-1-one) dihydrochloride (300 mg, 0.85 mmol), (4S,7S,9aS)-4-((S)-2-((tert-butoxycarbonyl)(methyl)amino)propanamido)-8,8-dimethyl-5-oxooctahydropyrrolo[2,1-b][1,3]thiazepine-7-carboxylic acid (750 mg, 1.69 mmol), 1-(3-dimethylaminopropyl)-3-ethylcarbodiimide methiodide (490 mg, 2.56 mmol), 1-hydroxybenzotriazole (460 mg, 3.40 mmol) and N,N-diisopropyl ethylamine (660 mg, 5.11 mmol) in dichloromethane (20 mL) was stirred at room temperature overnight. The reaction was quenched with water (100 mL) and extracted with dichloromethane (3×10 mL). The combined organic layers were washed with brine, dried, filtered and concentrated. The residue was purified by thin layer chromatography [ethyl acetate/petroleum ether (2/1 v/v)] to give crude product (170 mg) as yellow oil. This material was further purified by Prep-HPLC to afford di-tert-butyl ((2S,2'S)-(((4S,4'S,7S,7'S,9aS,9a'S)-((((1S,1'S)-piperazine-1,4-diylbis(2-oxo-1-phenylethane-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (80 mg, 0.067 mmol, 13.5% yield) as white solid. LCMS (2.5 min formic acid): Rt=1.73 min, m/z: 502.0 {[(M-2Boc)+2]/2}$^+$, [M-Boc+H]$^+$=1104.8 (M-Boc+1)$^+$.

Step 3: (4S,4'S,7S,7'S,9aS,9a'S)—N,N'-((1S,1'S)-piperazine-1,4-diylbis(2-oxo-1-phenylethane-2,1-diyl))bis(8,8-dimethyl-4-((S)-2-(methylamino)propanamido)-5-oxooctahydropyrrolo[2,1-b][1,3]thiazepine-7-carboxamide) dihydrochloride To a solution of di-tert-butyl ((2S,2'S)-(((4S,4'S,7S,7'S,9aS,9a'S)-((((1S,1'S)-piperazine-1,4-diylbis(2-oxo-1-phenylethane-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (80 mg, 0.067 mmol) in dichloromethane (5 mL) was added hydrogen chloride (4 N in 1,4-dioxane, 1 mL). The mixture was stirred at room temperature overnight. The solvent was removed under reduced pressure and dried under high vacuum to give (4S,4'S,7S,7'S,9aS,9a'S)—N,N'-((1S,1'S)-piperazine-1,4-diylbis(2-oxo-1-phenylethane-2,1-diyl))bis(8,8-dimethyl-4-((S)-2-(methylamino)propanamido)-5-oxooctahydropyrrolo[2,1-b][1,3]thiazepine-7-carboxamide) dihydrochloride (36 mg, 0.033 mmol, 49.3% yield) as white solid. $^1$H NMR (400 MHz, DMSO-d$_6$) δ ppm 8.56-8.51 (m, 2H), 8.47 (d, J=7.6 Hz, 2H), 7.37-7.33 (m, 10H), 5.88-5.81 (m, 2H), 5.50 (t, J=7.6 Hz, 2H), 4.68 (t, J=7.4 Hz, 2H), 4.10-4.08 (m, 2H), 3.55-3.37 (m, 4H), 3.25-3.13 (m, 6H), 2.97-2.90 (m, 4H), 2.32 (s, 6H), 2.18-2.13 (m, 4H), 1.97-1.87 (m, 2H), 1.57-1.49 (m, 2H), 1.24 (d, J=5.6 Hz, 6H), 1.00 (s, 6H), 0.81-0.78 (m, 6H). LCMS (2.5 min formic acid): Rt=1.368 min, m/z: 1003.8 (M+1)$^+$.

Example 27

(4S,4'S,7S,7'S,9aS,9a'S)—N,N'-((1S,1'S)-piperazine-1,4-diylbis(2-oxo-1-phenylethane-2,1-diyl))bis(8,8-dimethyl-4-((S)-2-(methylamino)propanethioamido)-5-oxooctahydropyrrolo[2,1-b][1,3]thiazepine-7-carboxamide) dihydrochloride

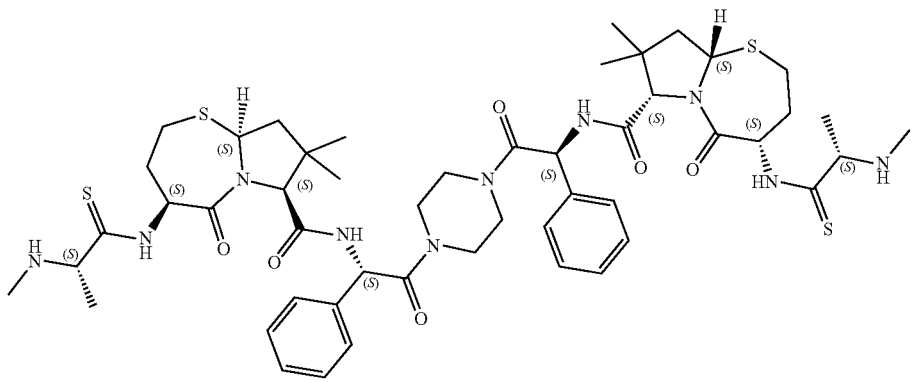

Step 1: di-tert-butyl ((2S,2'S)-(((4S,4'S,7S,7'S,9aS,9a'S)-(((((1S,1'S)-piperazine-1,4-diylbis(2-oxo-1-phenylethane-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate)

A solution of (2S,2'S)-1,1'-(piperazine-1,4-diyl)bis(2-amino-2-phenylethan-1-one) dihydrochloride (200 mg, 0.47 mmol), (4S,7S,9aS)-4-((S)-2-((tert-butoxycarbonyl)(methyl)amino)propanethioamido)-8,8-dimethyl-5-oxooctahydropyrrolo[2,1-b][1,3]thiazepine-7-carboxylic acid (Intermediate II) (432.2 mg, 0.94 mmol), 1-(3-dimethylaminopropyl)-3-ethylcarbodiimide methiodide (270.4 mg, 1.41 mmol), 1-hydroxybenzotriazole (254.1 mg, 1.88 mmol) and N,N-diisopropyl-ethylamine (364.5 mg, 2.82 mmol) in dichloromethane (10 mL) was stirred at room temperature overnight. The reaction was quenched with water (80 mL) and extracted with dichloromethane (3×80 mL). The combined organic layers were washed with brine, dried, filtered and concentrated. The residue was purified by thin layer chromatography [ethyl acetate/petroleum ether (2/1 v/v)] to give crude product (170 mg) as yellow oil. This material was further purified by Prep-HPLC to get the desired product (90 mg, 0.073 mmol, 15.5% yield) as white solid. LCMS (2.5 min formic acid): Rt=2.04 min, m/z: 641.0 [M+2Na]/2.

Step 2: (4S,4'S,7S,7'S,9aS,9a'S)—N,N'-((1S,1'S)-piperazine-1,4-diylbis(2-oxo-1-phenylethane-2,1-diyl))bis(8,8-dimethyl-4-((S)-2-(methylamino)propanethioamido)-5-oxooctahydropyrrolo[2,1-b][1,3]thiazepine-7-carboxamide) dihydrochloride To a solution of di-tert-butyl ((2S,2'S)-(((4S,4'S,7S,7'S,9aS,9a'S)-(((((1S,1'S)-piperazine-1,4-diylbis(2-oxo-1-phenylethane-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate) (90 mg, 0.073 mmol) in dichloromethane (5 mL) was added hydrogen chloride (4 N in 1,4-dioxane, 1 mL). The mixture was stirred at room temperature overnight. The mixture was concentrated under reduced pressure and dried under high vacuum to give (4S,4'S,7S,7'S,9aS,9a'S)—N,N'-((1S,1'S)-piperazine-1,4-diylbis(2-oxo-1-phenylethane-2,1-diyl))bis(8,8-dimethyl-4-((S)-2-(methylamino)propanethioamido)-5-oxooctahydropyrrolo[2,1-b][1,3]thiazepine-7-carboxamide) dihydrochloride (52.3 mg, 0.047 mmol, 64.2% yield) as white solid. $^1$H NMR (400 MHz, DMSO-$d_6$) δ ppm 8.53 (d, J=7.6 Hz, 2H), 7.41-7.34 (m, 12H), 5.89-5.82 (m, 2H), 5.49-5.43 (m, 2H), 5.14 (t, J=9.6 Hz, 2H), 4.17-4.09 (m, 4H), 3.57 (s, 2H), 3.41 (s, 2H), 3.23-3.07 (m, 5H), 3.01-2.96 (m, 3H), 2.44 (s, 6H), 2.33-2.26 (m, 2H), 2.20-2.17 (m, 2H), 2.08-1.99 (m, 2H), 1.60-1.57 (m, 2H), 1.40 (t, J=7.6 Hz, 6H), 1.02 (s, 6H), 0.86-0.82 (m, 6H). LCMS (2.5 min formic acid): Rt=1.341 min, m/z: 1035.7 (M+1)$^+$.

Example 28

(2S)—N-[(4S,7S,9aS)-8,8-dimethyl-5-oxo-7-{[(S)-phenyl({[(1rs,4rs)-4-[(2S)-2-{[(4S,7S,9aS)-8,8-dimethyl-4-[(2S)-2-(methylamino)propanamido]-5-oxo-octahydropyrrolo[2,1-b][1,3]thiazepin-7-yl]formamido}-2-phenylacetamido]cyclohexyl]carbamoyl})methyl]carbamoyl}-octahydropyrrolo[2,1-b][1,3]thiazepin-4-yl]-2-(methylamino)propanamide dihydrochloride

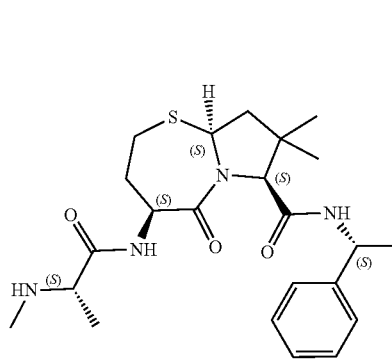
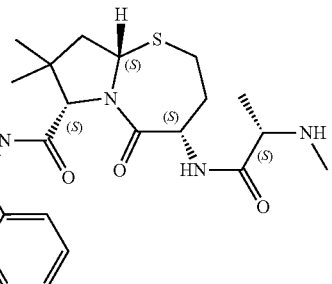

Step 1: di-tert-butyl ((1S,1'S)-(((1S,4S)-cyclohexane-1,4-diyl)bis(azanediyl))bis(2-oxo-1-phenylethane-2,1-diyl))dicarbamate To a solution of (S)-2-((tert-butoxycarbonyl)amino)-2-phenylacetic acid (600 mg, 2.1 mmol) in N,N-dimethylformamide (20 mL) at −15° C. was added (1r,4r)-cyclohexane-1,4-diamine (136.3 mg, 1.0 mmol), diethyl cyanophosphonate (584 mg, 3.0 mmol) and triethylamine (483 mg, 4.0 mmol) successively. The reaction was stirred at room temperature overnight. The mixture was poured into water (300 mL) to give a precipitate which was filtered and dried to give di-tert-butyl ((1S,1'S)-(((1S,4S)-cyclohexane-1,4-diyl)bis(azanediyl))bis(2-oxo-1-phenylethane-2,1-diyl))dicarbamate (640 mg, 1.1 mmol, 46.2% yield) as white solid. LCMS (2.5 min formic acid): Rt=1.61 min, m/z: 480.8 (M-Boc+1)⁺.

Step 2: (2S,2'S)—N,N'-((1S,4S)-cyclohexane-1,4-diyl)bis(2-amino-2-phenylacetamide) dihydrochloride To a solution of di-tert-butyl ((1S,1'S)-(((1S,4S)-cyclohexane-1,4-diyl)bis(azanediyl))bis(2-oxo-1-phenylethane-2,1-diyl))dicarbamate (460 mg, 0.32 mmol) in dichloromethane (10 mL) was added hydrogen chloride (4 N in 1,4-dioxane, 2 mL). The reaction was stirred at room temperature overnight. The solvent was removed under reduced pressure and dried under vacuum to give (2S,2'S)—N,N'-((1S,4S)-cyclohexane-1,4-diyl)bis(2-amino-2-phenylacetamide) dihydrochloride (crude 400 mg) as white solid. This material was used for the next step without further purification. LCMS (2.5 min formic acid): Rt=0.37 min, m/z: 381.0 (M+1).

Step 3: di-tert-butyl ((2S,2'S)-(((4S,4'S,7S,7'S,9aS,9a'S)-(((1S,1'S)-(((1R,4R)-cyclohexane-1,4-diyl)bis(azanediyl))bis(2-oxo-1-phenylethane-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate)

A solution of (2S,2'S)—N,N'-((1S,4S)-cyclohexane-1,4-diyl)bis(2-amino-2-phenylacetamide) dihydrochloride (200 mg, 0.44 mmol), (4S,7S,9aS)-4-((S)-2-((tert-butoxycarbonyl)(methyl)amino)propanamido)-8,8-dimethyl-5-oxooctahydropyrrolo[2,1-b][1,3]thiazepine-7-carboxylic acid (387 mg, 0.87 mmol), 1-(3-dimethylaminopropyl)-3-ethylcarbodiimide methiodide (239 mg, 1.25 mmol), 1-hydroxybenzotriazole (225 mg, 1.67 mmol) and N,N-diisopropyl ethylamine (323 mg, 2.50 mmol) in dichloromethane (10 mL) was stirred at room temperature overnight. The reaction was quenched with water (50 mL) and extracted with dichloromethane (3×50 mL). The combined organic layers were washed with brine, dried, filtered and concentrated. The residue was purified by thin layer chromatography [ethyl acetate/petroleum ether (2/1 v/v)] to give crude product (110 mg) as yellow oil. This material was further purified by Prep-HPLC to give di-tert-butyl di-tert-butyl ((2S,2'S)-(((4S,4'S,7S,7'S,9aS,9a'S)-((((1S,1'S)-(((1R,4R)-cyclohexane-1,4-diyl)bis(azanediyl))bis(2-oxo-1-phenylethane-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (61 mg, 0.049 mmol, 11.2% yield) as white solid. LCMS (2.5 min formic acid): Rt=1.68 min, m/z: 1130.7 (M-Boc+1)⁺.

Step 4: (2S)—N-[(4S,7S,9aS)-8,8-dimethyl-5-oxo-7-{[(S)-phenyl({[(1rs,4rs)-4-[(2S)-2-{[(4S,7S,9aS)-8,8-dimethyl-4-[(2S)-2-(methylamino)propanamido]-5-oxo-octahydropyrrolo[2,1-b][1,3]thiazepin-7-yl]formamido}-2-phenylacetamido]cyclohexyl]carbamoyl})methyl]carbamoyl}-octahydropyrrolo[2,1-b][1,3]thiazepin-4-yl]-2-(methylamino)propanamide dihydrochloride To a solution of di-tert-butyl ((2S,2'S)-(((4S,4'S,7S,7'S,9aS,9a'S)-((((1S,1'S)-(((1R,4R)-cyclohexane-1,4-diyl)bis(azanediyl))bis(2-oxo-1-phenylethane-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis (methylcarbamate) (61 mg, 0.05 mmol) in dichloromethane (5 mL) was added hydrogen chloride (4 N in 1,4-dioxane, 1 mL). The reaction was stirred at room temperature overnight. The solvent was concentrated under reduced pressure and dried under high vacuum to afford the title compound (36.6 mg, 0.033 mmol, 66.5% yield) as white solid. $^1$H NMR (400 MHz, DMSO-$d_6$) b ppm 9.25 (s, 2H), 8.91-8.82 (m, 4H), 8.49 (d, J=8.4 Hz, 2H), 8.23 (d, J=7.6 Hz, 2H), 7.42-7.40 (m, 4H), 7.35-7.31 (m, 4H), 7.28-7.24 (m, 2H), 5.52 (t, J=8.0 Hz, 2H), 5.46 (d, J=8.0 Hz, 2H), 4.75-4.70 (m, 2H), 4.19 (m, 2H), 3.87 (m, 2H), 3.72-3.65 (m, 1H), 3.50-3.39 (m, 3H), 3.25-3.19 (m, 2H), 2.96-2.92 (m, 2H), 2.48 (s, 6H), 2.24-2.13 (m, 4H), 1.92-1.69 (m, 6H), 1.58-1.56 (m, 2H), 1.39 (d, J=6.8 Hz, 6H), 1.04 (s, 6H), 0.94 (s, 6H). LCMS (2.5 min formic acid): Rt=1.404 min, m/z: 1031.7 (M+1)$^+$.

Example 29

(2S)-2-{[(4S,7S,9aS)-8,8-dimethyl-4-[(2S)-2-(methylamino)propanethioamido]-5-oxo-octahydropyrrolo[2,1-b][1,3]thiazepin-7-yl]formamido}-2-phenyl-N-[(1rs,4rs)-4-[(2S)-2-{[(4S,7S,9aS)-8,8-dimethyl-4-[(2S)-2-(methylamino)propanethioamido]-5-oxo-octahydropyrrolo[2,1-b][1,3]thiazepin-7-yl]formamido}-2-phenylacetamido]cyclohexyl]acetamide dihydrochloride

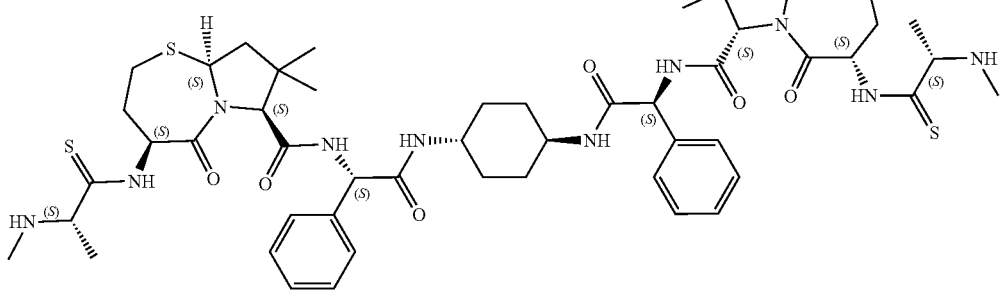

Step 1: di-tert-butyl ((2S,2'S)-(((4S,4'S,7S,7'S,9aS,9a'S)-((((1S,1'S)-(((1R,4R)-cyclohexane-1,4-diyl)bis(azanediyl))bis(2-oxo-1-phenylethane-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate)

A solution of (2S,2'S)—N,N'-((1S,4S)-cyclohexane-1,4-diyl)bis(2-amino-2-phenylacetamide) dihydrochloride (170 mg, 0.45 mmol), (4S,7S,9aS)-4-((S)-2-((tert-butoxycarbonyl)(methyl)amino)propanethioamido)-8,8-dimethyl-5-oxooctahydropyrrolo[2,1-b][1,3]thiazepine-7-carboxylic acid (Intermediate II) (362 mg, 0.79 mmol), 1-(3-dimethylaminopropyl)-3-ethylcarbodiimide methiodide (216 mg, 1.13 mmol), 1-hydroxybenzotriazole (203 mg, 1.5 mmol) and N,N-diisopropyl ethylamine (291 mg, 2.25 mmol) in dichloromethane (10 mL) was stirred at room temperature overnight. The reaction was quenched with water (50 mL) and extracted with dichloromethane (3×50 mL). The combined organic layers were washed with brine, dried, filtered and concentrated. The residue was purified by thin layer chromatography [ethyl acetate/petroleum ether (2/1 v/v)] to give the product (210 mg) as yellow oil. This material was further purified by Prep-HPLC to give di-tert-butyl ((2S,2'S)-(((4S,4'S,7S,7'S,9aS,9a'S)-((((1S,1'S)-(((1R,4R)-cyclohexane-1,4-diyl)bis(azanediyl))bis(2-oxo-1-phenylethane-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate) (127 mg, 1.0 mmol, 26.8% yield) as white solid. LCMS (2.5 min formic acid): Rt=2.182 min, m/z: 532.1 {[(M-2Boc)+2]/2}$^+$.

Step 2: (2S)-2-{[(4S,7S,9aS)-8,8-dimethyl-4-[(2S)-2-(methylamino)propanethioamido]-5-oxo-octahydropyrrolo[2,1-b][1,3]thiazepin-7-yl]formamido}-2-phenyl-N-[(1rs,4rs)-4-[(2S)-2-{[(4S,7S,9aS)-8,8-dimethyl-4-[(2S)-2-(methylamino)propanethioamido]-5-oxo-octahydropyrrolo[2,1-b][1,3]thiazepin-7-yl]formamido}-2-phenylacetamido]cyclohexyl]acetamide dihydrochloride To a solution of di-tert-butyl ((2S,2'S)-(((4S,4'S,7S,7'S,9aS,9a'S)-((((1S,1'S)-(((1R,4R)-cyclohexane-1,4-diyl)bis(azanediyl))bis(2-oxo-1-phenylethane-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate) (127 mg, 0.10 mmol) in dichloromethane (10 mL) was added hydrogen chloride (4 N in 1,4-dioxane, 1 mL). The reaction was stirred at room temperature overnight. The mixture was concentrated under reduced pressure and the solid dried under high vacuum to give the title compound (100 mg, 0.08 mmol, 87.4% yield) as white solid. $^1$H NMR (400 MHz, DMSO-$d_6$) b ppm 11.02-10.90 (m, 2H), 9.75 (s, 1H), 9.58 (s, 1H), 8.63-8.44 (m, 4H), 8.26 (d, J=7.6 Hz, 2H), 7.42-7.40 (m, 4H), 7.35-7.31 (m, 4H), 7.28-7.25 (m, 2H), 5.50-5.45 (m, 4H), 5.18-5.12 (m, 2H), 4.27-4.21 (m, 4H), 3.48-3.93 (m, 2H), 3.26-3.17 (m, 2H), 3.10-2.98 (m, 4H), 2.48 (s, 6H), 2.33-2.23 (m, 4H), 2.03-1.95 (m, 2H), 1.81-1.74 (m, 4H), 1.58 (d, J=7.2 Hz, 2H), 1.45-1.43 (m, 6H), 1.07 (s, 8H), 0.92 (s, 6H). LCMS (2.5 min formic acid): Rt=1.351 min, m/z: 1063.6 (M+1)$^+$.

Example 30

(4S,4'S,7S,7'S,9aS,9a'S)—N,N'-((1S,1'S)-(hexa-2,4-diyne-1,6-diylbis(azanediyl))bis(2-oxo-1-phenylethane-2,1-diyl))bis(8,8-dimethyl-4-((S)-2-(methylamino)propanamido)-5-oxooctahydropyrrolo[2,1-b][1,3]thiazepine-7-carboxamide) dihydrochloride

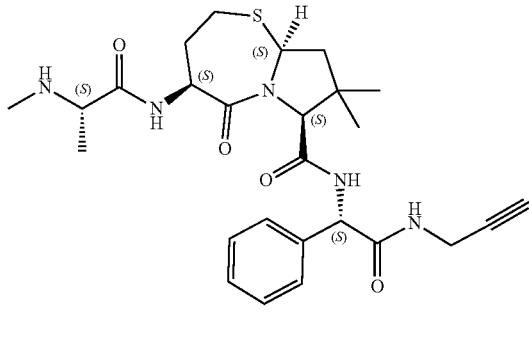
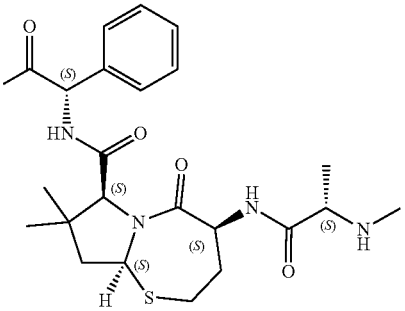

Step 1: tert-butyl (S)-(2-oxo-1-phenyl-2-(prop-2-yn-1-ylamino)ethyl)carbamate To a solution of (S)-2-((tert-butoxycarbonyl)amino)-2-phenylacetic acid (600 mg, 2.3 mmol) in dichloromethane (18 mL) was added prop-2-yn-1-amine (131.5 mg, 2.3 mmol), 2-(7-azabenzotriazol-1-yl)-N,N,N',N'-tetramethyluronium hexafluorophosphate (1.82 g, 4.8 mmol) and N,N-diisopropyl-ethylamin (925.8 mg, 7.2 mmol). The mixture was stirred at room temperature overnight. The mixture was quenched with water (300 mL) and extracted with dichloromethane (3×200 mL). The combined organic layers were washed with brine, dried over anhydrous sodium sulfate, filtered and concentrated. The residue was purified by thin layer chromatography [ethyl acetate/petroleum ether (1/3 v/v)] to give tert-butyl (S)-(2-oxo-1-phenyl-2-(prop-2-yn-1-ylamino)ethyl)carbamate (crude 300 mg) as yellow oil. LCMS (3.0 min formic acid): Rt=1.677 min, m/z: 289 (M+1)$^+$.

Step 2: (S)-2-amino-2-phenyl-N-(prop-2-yn-1-yl)acetamide hydrochloride

To a solution of tert-butyl (S)-(2-oxo-1-phenyl-2-(prop-2-yn-1-ylamino)ethyl)carbamate (300 mg, 1.04 mmol) in dichloromethane (12 mL) was added hydrogen chloride (4 N in 1,4-dioxane, 1 mL). The mixture was stirred at room temperature overnight. The solvent was removed under reduced pressure to give tert-butyl (S)-(2-oxo-1-phenyl-2-(prop-2-yn-1-ylamino)ethyl)carbamate (300 mg) as yellow solid which was used for the next step without further purification. LCMS (3.0 min formic acid): Rt=0.801 min, m/z: 189 (M+1)$^+$.

Step 3: tert-butyl ((S)-1-(((4S,7S,9aS)-8,8-dimethyl-5-oxo-7-(((S)-2-oxo-1-phenyl-2-(prop-2-yn-1-ylamino)ethyl)carbamoyl)octahydropyrrolo[2,1-b][1,3]thiazepin-4-yl)amino)-1-oxopropan-2-yl)(methyl)carbamate To a solution of (S)-2-amino-2-phenyl-N-(prop-2-yn-1-yl)acetamide hydrochloride (250 mg, 1.1 mmol) in 1,2-dichloroethane (15 mL) was added (4S,7S,9aS)-4-((S)-3-((tert-butoxycarbonyl)(methyl)amino)-2-oxobutyl)-8,8-dimethyl-5-oxooctahydropyrrolo[2,1-b][1,3]thiazepine-7-carboxylic acid (Intermediate I) (589 mg, 1.3 mmol), 2-(7-azabenzotriazol-1-yl)-N,N,N',N'-tetramethyluronium hexafluorophosphate (808 mg, 2.1 mmol) and N,N-diisopropyl ethylamine (412 mg, 3.2 mmol). The mixture was stirred at room temperature overnight. The reaction was quenched with water (300 mL) and extracted with dichloromethane (3×60 mL). The combined organic layers were washed with brine, dried over anhydrous sodium sulfate, filtered and concentrated. The residue was purified by thin layer chromatography [ethyl acetate/petroleum ether (2/1 v/v)] to give tert-butyl ((S)-1-(((4S,7S,9aS)-8,8-dimethyl-5-oxo-7-(((S)-2-oxo-1-phenyl-2-(prop-2-yn-1-ylamino)ethyl)carbamoyl)octahydropyrrolo[2,1-b][1,3]thiazepin-4-yl)amino)-1-oxopropan-2-yl)(methyl)carbamate (578 mg, 0.919 mmol, 83.5% yield) as yellow oil. LCMS (3.0 min formic acid): Rt=1.794 min, m/z: 636 (M+Na)$^+$.

Step 4: di-tert-butyl ((2S,2'S)-(((4S,4'S,7S,7'S,9aS,9a'S)-7,7'-((3S,14S)-4,13-dioxo-3,14-diphenyl-2,5,12,15-tetraazahexadeca-7,9-diyne-1,16-dioyl)bis(8,8-dimethyl-5-oxooctahydropyrrolo[2,1-b][1,3]thiazepine-7,4-diyl))bis(azanediyl))bis(1-oxopropane-2,1-diyl))bis(methylcarbamate)

A mixture of tert-butyl ((S)-1-(((4S,7S,9aS)-8,8-dimethyl-5-oxo-7-(((S)-2-oxo-1-phenyl-2-(prop-2-yn-1-ylamino)ethyl)carbamoyl)octahydropyrrolo[2,1-b][1,3]thiazepin-4-yl)amino)-1-oxopropan-2-yl)(methyl)carbamate (170 mg, 0.27 mmol) in acetonitrile (8 mL) and pyridine (131.6 mg, 1.62 mmol) was added copper(II) acetate (60.4 mg, 0.33 mmol). The resulting mixture was stirred at 85° C. for 1 h under nitrogen. The reaction was cooled to room temperature, quenched with water (50 mL) and extracted with dichloromethane (3×50 mL). The combined organic layers were washed with brine, dried over anhydrous sodium sulfate, filtered and concentrated. The residue was purified by thin layer chromatography [ethyl acetate/petroleum ether (2/1 v/v)] to give crude product (86 mg) as yellow oil. This material was further purified by Prep-HPLC to give di-tert-butyl ((2S,2'S)-(((4S,4'S,7S,7'S,9aS,9a'S)-7,7'-((3S,14S)-4,13-dioxo-3,14-diphenyl-2,5,12,15-tetraazahexadeca-7,9-diyne-1,16-dioyl)bis(8,8-dimethyl-5-oxooctahydropyrrolo[2,1-b][1,3]thiazepine-7,4-diyl))bis(azanediyl))bis(1-oxopropane-2,1-diyl))bis(methylcarbamate) (58 mg, 0.047 mmol, 17.1% yield) as white solid. LCMS (3.0 min formic acid): Rt=2.044 min, m/z: 1247 (M+Na)$^+$.

Step 5: (4S,4'S,7S,7'S,9aS,9a'S)—N,N'-((1S,1'S)-(hexa-2,4-diyne-1,6-diylbis(azanediyl))bis(2-oxo-1-phenylethane-2,1-diyl))bis(8,8-dimethyl-4-((S)-2-(methylamino)propanamido)-5-oxooctahydropyrrolo[2,1-b][1,3]thiazepine-7-carboxamide) dihydrochloride To a solution of di-tert-butyl ((2S,2'S)-(((4S,4'S,7S,7'S,9aS,9a'S)-7,7'-((3S,14S)-4,13-dioxo-3,14-diphenyl-2,5,12,15-tetraazahexadeca-7,9-diyne-1,16-dioyl)bis(8,8-dimethyl-5-oxooctahydropyrrolo[2,1-b][1,3]thiazepine-7,4-diyl))bis(azanediyl))bis(1-oxopropane-2,1-diyl))bis(methylcarbamate) (38 mg, 0.03 mmol) in dichloromethane (7 mL) was added hydrogen chloride (4 N in 1,4-dioxane, 1 mL). The reaction was stirred at room temperature for 4 h. The solvent was removed under reduced pressure and the product dried under high vacuum to give (4S,4'S,7S,7'S,9aS,9a'S)—N,N'-((1S,1'S)-(hexa-2,4-diyne-1,6-diylbis(azanediyl))bis(2-oxo-1-phenylethane-2,1-diyl))bis(8,8-dimethyl-4-((S)-2-(methylamino)propanamido)-5-oxooctahydropyrrolo[2,1-b][1,3]thiazepine-7-carboxamide) dihydrochloride (30 mg, 0.027 mmol, 88.3% yield) as white solid. $^1$H NMR (400 MHz, DMSO-$d_6$) δ ppm 9.08-8.81 (m, 8H), 8.52 (d, J=8.0 Hz, 2H), 7.42-7.40 (m, 3H), 7.37-7.28 (m, 5H), 5.54-5.47 (m, 4H), 4.76-4.71 (m, 2H), 4.19 (s, 2H), 4.0 (d, J=5.2 Hz, 4H), 3.89-3.84 (m, 2H), 3.25-3.18 (m, 2H), 2.97-2.91 (m, 2H), 2.49 (s, 6H), 2.24-2.19 (m, 2H), 2.17-2.12 (m, 2H), 1.93-1.83 (m, 2H), 1.75-1.70 (m, 2H), 1.38 (d, J=6.4 Hz, 6H), 1.05 (s, 6H), 0.91 (s, 6H). LCMS (2.5 min formic acid): Rt=1.309 min, m/z: 1025.7 (M+1)$^+$.

Example 31

(4S,7S,9aS)—N—((S)-2-((6-((S)-2-((4S,7S,9aS)-8,8-dimethyl-4-((S)-2-(methylamino)propanamido)-5-oxooctahydropyrrolo[2,1-b][1,3]thiazepine-7-carboxamido)-2-phenylacetamido)hexa-2,4-diyn-1-yl)amino)-2-oxo-1-phenylethyl)-8,8-dimethyl-4-((S)-2-(methylamino)propanethioamido)-5-oxooctahydropyrrolo[2,1-b][1,3]thiazepine-7-carboxamide dihydrochloride

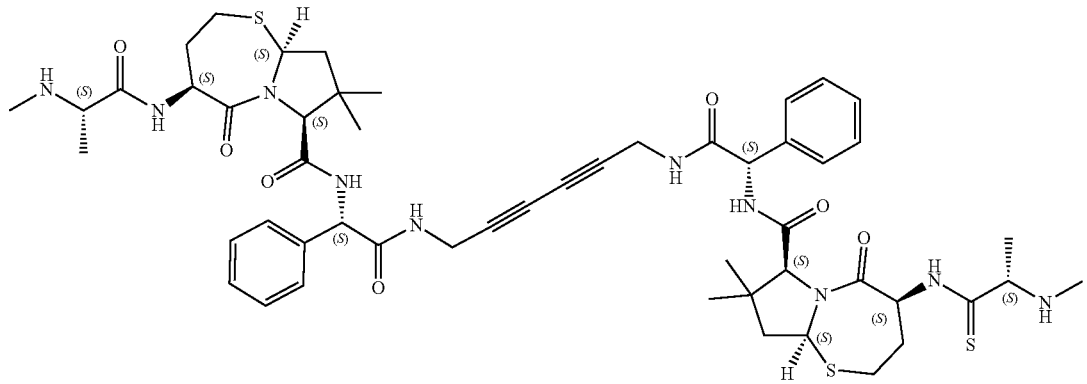

Step 1: tert-butyl ((S)-1-(((4S,7S,9aS)-8,8-dimethyl-5-oxo-7-(((S)-2-oxo-1-phenyl-2-(prop-2-yn-1-ylamino)ethyl)carbamoyl)octahydropyrrolo[2,1-b][1,3]thiazepin-4-yl)amino)-1-thioxopropan-2-yl)(methyl)carbamate To a solution of (S)-2-amino-2-phenyl-N-(prop-2-yn-1-yl)acetamide hydrochloride (216 mg, 0.96 mmol) in 1,2-dichloroethane (10 mL) was added (4S,7S,9aS)-4-((S)-3-((tert-butoxycarbonyl)(methyl)amino)-2-oxobutyl)-8,8-dimethyl-5-oxooctahydropyrrolo[2,1-b][1,3]thiazepine-7-carboxylic acid (527 mg, 1.15 mmol), 2-(7-azabenzotriazol-1-yl)-N,N,N',N'-tetramethyluronium hexafluorophosphate (700 mg, 1.84 mmol) and N,N-diisopropylethylamine (356 mg, 2.76 mmol). The mixture was stirred at room temperature overnight. The mixture was quenched with water (100 mL) and extracted with dichloromethane (3×100 mL). The combined organic layers were washed with brine, dried over anhydrous sodium sulfate, filtered and concentrated under vacuum. The residue was purified by thin layer chromatography [ethyl acetate/petroleum ether (2/1 v/v)] to give tert-butyl ((S)-1-(((4S,7S,9aS)-8,8-dimethyl-5-oxo-7-(((S)-2-oxo-1-phenyl-2-(prop-2-yn-1-ylamino)ethyl)carbamoyl)octahydropyrrolo[2,1-b][1,3]thiazepin-4-yl)amino)-1-thioxopropan-2-yl)(methyl)carbamate (500 mg, crude) as yellow oil. LCMS (3.0 min formic acid): Rt=2.004 min, m/z: 652 (M+Na)$^+$.

Step 2: tert-butyl ((S)-1-(((4S,7S,9aS)-7-(((S)-2-((6-((S)-2-((4S,7S,9aS)-4-((S)-2-((tert-butoxycarbonyl)(methyl)amino)propanethioamido)-8,8-dimethyl-5-oxooctahydropyrrolo[2,1-b][1,3]thiazepine-7-carboxamido)-2-phenylacetamido)hexa-2,4-diyn-1-yl)amino)-2-oxo-1-phenylethyl)carbamoyl)-8,8-dimethyl-5-oxooctahydropyrrolo[2,1-b][1,3]thiazepin-4-yl)amino)-1-oxopropan-2-yl)(methyl)carbamate and di-tert-butyl ((2S,2'S)-(((4S,4'S,7S,7'S,9aS,9a'S)-7,7'-((3S,14S)-4,13-dioxo-3,14-diphenyl-2,5,12,15-tetraazahexadeca-7,9-diyne-1,16-dioyl)bis(8,8-dimethyl-5-oxooctahydropyrrolo[2,1-b][1,3]thiazepine-7,4-diyl))bis(azanediyl))bis(1-thioxopropane-2,1-diyl))bis(methylcarbamate)

To a mixture of tert-butyl ((S)-1-(((4S,7S,9aS)-8,8-dimethyl-5-oxo-7-(((S)-2-oxo-1-phenyl-2-(prop-2-yn-1-ylamino)ethyl)carbamoyl)octahydropyrrolo[2,1-b][1,3]thiazepin-4-yl)amino)-1-oxopropan-2-yl)(methyl)carbamate (300 mg, 0.5 mmol) and tert-butyl ((S)-1-(((4S,7S,9aS)-8,8-dimethyl-5-oxo-7-(((S)-2-oxo-1-phenyl-2-(prop-2-yn-1-ylamino)ethyl)carbamoyl)octahydropyrrolo[2,1-b][1,3]thiazepin-4-yl)amino)-1-thioxopropan-2-yl)(methyl)carbamate (308 mg, 0.5 mmol) in acetonitrile (8 mL) and pyridine (232 mg, 2.9 mmol) was added copper(II) acetate (107 mg, 0.6 mmol). The mixture was heated to 85° C. and stirred for 1 h. The mixture was cooled to room temperature, diluted with water (50 mL) and extracted with dichloromethane (3×50 mL). The organic layer was combined, washed with brine, dried over anhydrous sodium sulfate, filtered and concentrated under vacuum. The residue was purified by thin layer chromatography [ethyl acetate/petroleum ether (2/1 v/v)] to give tert-butyl ((S)-1-(((4S,7S,9aS)-7-(((S)-2-((6-((S)-2-((4S,7S,9aS)-4-((S)-2-((tert-butoxycarbonyl)(methyl)amino)propanethioamido)-8,8-dimethyl-5-oxooctahydropyrrolo[2,1-b][1,3]thiazepine-7-carboxamido)-2-phenylacetamido)hexa-2,4-diyn-1-yl)amino)-2-oxo-1-phenylethyl)carbamoyl)-8,8-dimethyl-5-oxooctahydropyrrolo[2,1-b][1,3]thiazepin-4-yl)amino)-1-oxopropan-2-yl)(methyl)carbamate (20 mg, 0.016 mmol, 3.3% yield) [LCMS (3.0 min formic acid): Rt=2.100 min, m/z: 1263 (M+Na)$^+$] and di-tert-butyl ((2S,2'S)-(((4S,4'S,7S,7'S,9aS,9a'S)-7,7'-((3S,14S)-4,13-dioxo-3,14-diphenyl-2,5,12,15-tetraazahexadeca-7,9-diyne-1,16-dioyl)bis(8,8-dimethyl-5-oxooctahydropyrrolo[2,1-b][1,3]thiazepine-7,4-diyl))bis(azanediyl))bis(1-thioxopropane-2,1-diyl))bis(methylcarbamate) (8 mg, 0.006 mmol, 1.4% yield) [LCMS (3.0 min formic acid): Rt=2.367 min, m/z: 1279 (M+Na)$^+$] as white solids. The other diastereoisomer was not collected.

Step 3: (4S,7S,9aS)—N—((S)-2-((6-((S)-2-((4S,7S,9aS)-8,8-dimethyl-4-((S)-2-(methylamino)propanamido)-5-oxooctahydropyrrolo[2,1-b][1,3]thiazepine-7-carboxamido)-2-phenylacetamido)hexa-2,4-diyn-1-yl)amino)-2-oxo-1-phenylethyl)-8,8-dimethyl-4-((S)-2-(methylamino)propanethioamido)-5-oxooctahydropyrrolo[2,1-b][1,3]thiazepine-7-carboxamide dihydrochloride To a solution of tert-butyl ((S)-1-(((4S,7S,9aS)-7-(((S)-2-((6-((S)-2-((4S,7S,9aS)-4-((S)-2-((tert-butoxycarbonyl)(methyl)amino)propanethioamido)-8,8-dimethyl-5-oxooctahydropyrrolo[2,1-b][1,3]thiazepine-7-carboxamido)-2-phenylacetamido)hexa-2,4-diyn-1-yl)amino)-2-oxo-1-phenylethyl)carbamoyl)-8,8-dimethyl-5-oxooctahydropyrrolo[2,1-b][1,3]thiazepin-4-yl)amino)-1-oxopropan-2-yl)(methyl)carbamate (20 mg, 0.016 mmol) in dichloromethane (8 mL) was added hydrogen chloride (4 N in 1,4-dioxane, 0.5 mL). The reaction was stirred at room temperature for 4 h. The solvent was concentrated under reduced pressure and the solid was dried under high vacuum to give (4S,7S,9aS)—N—((S)-2-((6-((S)-2-((4S,7S,9aS)-8,8-dimethyl-4-((S)-2-(methylamino)propanamido)-5-oxooctahydropyrrolo[2,1-b][1,3]thiazepine-7-carboxamido)-2-phenylacetamido)hexa-2,4-diyn-1-yl)amino)-2-oxo-1-phenylethyl)-8,8-dimethyl-4-((S)-2-(methylamino)propanethioamido)-5-oxooctahydropyrrolo[2,1-b][1,3]thiazepine-7-carboxamide dihydrochloride (13 mg, 0.012 mmol, 72.2% yield) as white solid. $^1$H NMR (400 MHz, DMSO-d$_6$) δ ppm 8.84-8.81 (m, 3H), 8.57-8.48 (m, 4H), 8.27-8.24 (m, 2H), 7.43-7.30 (m, 11H), 5.53-5.46 (m, 5H), 5.12-5.09 (m, 1H), 4.69-4.64 (s, 2H), 4.26 (d, J=5.6 Hz, 1H), 4.21 (m, 1H), 4.00 (d, J=5.2 Hz, 4H), 3.24-3.16 (m, 3H), 3.01-2.88 (m, 4H), 2.23 (s, 3H), 2.16 (d, J=4.0 Hz, 2H), 1.83-1.69 (m, 6H), 1.24-1.20 (m, 6H), 1.05 (d, J=8.0 Hz, 6H), 0.92-0.90 (m, 6H). LCMS (2.5 min formic acid): Rt=1.425 min, m/z: 1040.6 (M+1)$^+$.

Example 32

(4S,4'S,7S,7'S,9aS,9a'S)—N,N'-((1S,1'S)-(hexa-2,4-diyne-1,6-diylbis(azanediyl))bis(2-oxo-1-phenylethane-2,1-diyl))bis(8,8-dimethyl-4-((S)-2-(methylamino)propanethioamido)-5-oxooctahydropyrrolo[2,1-b][1,3]thiazepine-7-carboxamide)dihydrochloride

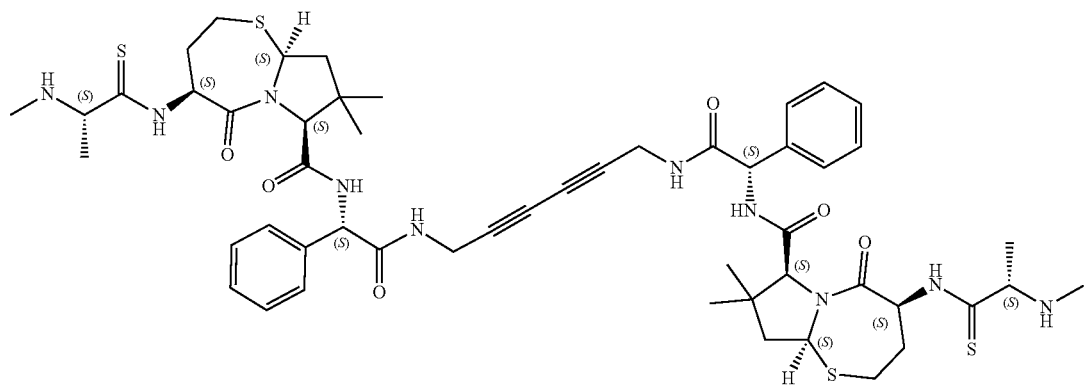

To a solution of di-tert-butyl ((2S,2'S)-(((4S,4'S,7S,7'S, 9aS,9a'S)-7,7'-((3S,14S)-4,13-dioxo-3,14-diphenyl-2,5,12, 15-tetraazahexadeca-7,9-diyne-1,16-dioyl)bis(8,8-dimethyl-5-oxooctahydropyrrolo[2,1-b][1,3]thiazepine-7,4-diyl))bis(azanediyl))bis(1-thioxopropane-2,1-diyl))bis (methylcarbamate) (Example 31, Step 2) (8 mg, 0.006 mmol) in dichloromethane (8 mL) was added hydrogen chloride (4 N in 1,4-dioxane, 0.5 mL). The reaction was stirred at room temperature for 4 h. The solvent was concentrated under reduced pressure and dried under high vacuum to give the title compound (2 mg, 0.002 mmol, 27.8% yield) as a white solid. $^1$H NMR (400 MHz, CD3OD-d$_4$) δ 7.47-7.46 (m, 4H), 7.40-7.34 (m, 6H), 5.58-5.53 (m, 2H), 5.50 (m, 2H), 5.28-5.25 (m, 2H), 4.23 (d, J=3.2 Hz, 2H), 4.03 (s, 4H), 3.79-3.71 (m, 2H), 3.47-3.41 (m, 2H), 3.05-3.00 (m, 2H), 2.44 (d, J=9.6 Hz, 6H), 2.39-2.34 (m, 2H), 2.28-2.21 (m, 2H), 1.83-1.77 (m, 2H), 1.62-1.55 (m, 2H), 1.31 (s, 6H), 1.61 (s, 6H), 0.96 (s, 6H). LCMS (2.5 min formic acid): Rt=1.546 min, m/z: 1056.6 (M+1)$^+$.

Example 33

(4S,4'S,7S,7'S,9aS,9a'S)—N,N'-((1S,1'S)-(hexa-2,4-diyne-1,6-diylbis(oxy))bis(1-phenylethane-2,1-diyl)) bis(8,8-dimethyl-4-((S)-2-(methylamino)propanamido)-5-oxooctahydropyrrolo[2,1-b][1,3]thiazepine-7-carboxamide) dihydrochloride Step 1: (S)-1-phenyl-2-(prop-2-yn-1-yloxy)ethan-1-amine To a solution of (S)-2-amino-2-phenylethan-1-ol (6 g, 43.7 mmol) in dry tetrahydrofuran (200 mL) at 0° C. was added sodium hydride (60%, dispersion in Paraffin Liquid) (1.9 g, 48.1 mmol). The mixture was stirred at 0° C. for 20 min. 3-Bromoprop-1-yne (5.72 g, 48.1 mmol) was then added. The mixture was heated at 70° C. overnight. Upon cooling, ice water (200 mL) was added to the mixture and the mixture was extracted with ethyl acetate (3×100 mL). The combined organic layers were washed with brine, dried over anhydrous sodium sulfate, filtered and concentrated. The crude was purified by silica gel chromatography [petroleum ether/ethyl acetate (1:1 v/v)] to afford (S)-1-phenyl-2-(prop-2-yn-1-yloxy)ethan-1-amine (2.5 g, 14.3 mmol, 32.65% yield) as orange oil. $^1$H NMR 1 (400 MHz, DMSO-d$_6$) δ ppm 7.44-7.14 (m, 5H), 4.18-4.12 (m, 2H), 4.08-4.00 (m, 1H), 3.55-3.47 (m, 1H), 3.44-3.37 (m, 2H), 1.84 (s, 2H).

Step 2: tert-butyl ((S)-1-(((4S,7S,9aS)-8,8-dimethyl-5-oxo-7-(((S)-1-phenyl-2-(prop-2-yn-1-yloxy)ethyl) carbamoyl)octahydropyrrolo[2,1-b][1,3]thiazepin-4-yl)amino)-1-oxopropan-2-yl)(methyl)carbamate To a solution of (S)-1-phenyl-2-(prop-2-yn-1-yloxy) ethan-1-amine (308 mg, 1.76 mmol) in dichloromethane (10 mL) was added (4S,7S,9aS)-4-((S)-2-((tert-butoxycarbonyl) (methyl)amino)propanamido)-8,8-dimethyl-5-oxooctahydropyrrolo[2,1-b][1,3]thiazepine-7-carboxylic acid (650 mg, 1.47 mmol), 2-(7-azabenzotriazol-1-yl)-N,N,N',N'-tetramethyluronium hexafluorophosphate (948 mg, 2.49 mmol) and N,N-diisopropyl-ethylamine (454 mg, 3.52 mmol) at room temperature. The mixture was stirred overnight. The reaction was quenched with water (300 mL), and extracted with dichloromethane (3×20 mL). The combined organic layers were washed with brine, dried, filtered and concentrated. The residue was purified by silica gel chromatography [ethyl acetate/petroleum ether (1/5 v/v)] to give tert-butyl ((S)-1-(((4S,7S,9aS)-8,8-dimethyl-5-oxo-7-(((S)-1-phenyl-2-(prop-2-yn-1-yloxy)ethyl)carbamoyl)octahydropyrrolo[2,1-b][1,3]thiazepin-4-yl)amino)-1-oxopropan-2-yl)(methyl)carbamate (194 mg, 0.32 mmol, 22.63% yield) as yellow oil. LCMS (3.0 min formic acid): Rt=1.70 min, m/z: 601 (M+1)$^+$.

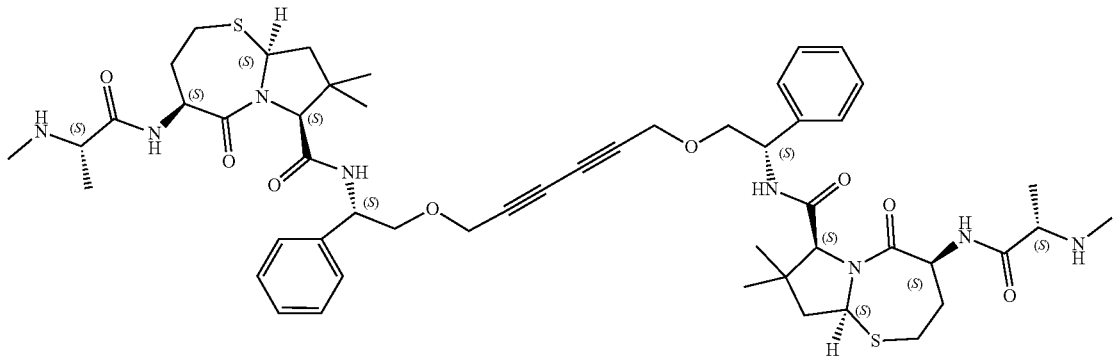

Step 3: di-tert-butyl ((2S,2'S)-(((4S,4'S,7S,7'S,9aS, 9a'S)-((3S,14S)-3,14-diphenyl-5,12-dioxa-2,15-diazahexadeca-7,9-diynedioyl)bis(8,8-dimethyl-5-oxooctahydropyrrolo[2,1-b][1,3]thiazepine-7,4-diyl))bis(azanediyl))bis(1-oxopropane-1,2-diyl))bis (methylcarbamate)

A mixture of tert-butyl ((S)-1-(((4S,7S,9aS)-8,8-dimethyl-5-oxo-7-(((S)-1-phenyl-2-(prop-2-yn-1-yloxy)ethyl) carbamoyl)octahydropyrrolo[2,1-b][1,3]thiazepin-4-yl) amino)-1-oxopropan-2-yl)(methyl)carbamate (194 mg, 0.32 mmol), copper(II) acetate (70.4 mg, 0.39 mmol) and pyridine (50.6 mg, 0.64 mmol) in acetonitrile (10 mL) was stirred at 85° C. for 1 h. Aqueous ammonia (20 fold dilution) was added to the mixture until it turned blue and the mixture was extracted with dichloromethane (3×30 mL). The combined organic layers were washed with brine, dried, filtered and concentrated. The residue was purified by thin layer chromatography [ethyl acetate/petroleum ether (2/1 v/v)] to give crude product (130 mg). This material was further purified by Prep-HPLC to afford di-tert-butyl ((2S,2'S)-

(((4S,4'S,7S,7'S,9aS,9a'S)-((3S,14S)-3,14-diphenyl-5,12-dioxa-2,15-diazahexadeca-7,9-diynedioyl)bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (70 mg, 0.058 mmol) as a white powder. LCMS (3.0 min formic acid): Rt=2.10 min, m/z: 1199.7 (M+1)$^+$.

Step 4: (4S,4'S,7S,7'S,9aS,9a'S)—N,N'-((1S,1'S)-(hexa-2,4-diyne-1,6-diylbis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide) dihydrochloride To a solution of di-tert-butyl ((2S,2'S)-(((4S,4'S,7S,7'S,9aS,9a'S)-((3S,14S)-3,14-diphenyl-5,12-dioxa-2,15-diazahexadeca-7,9-diynedioyl)bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (70 mg, 0.058 mmol) in dichloromethane (15 mL) was added hydrogen chloride (4 N in 1,4-dioxane, 1 mL). The reaction was stirred at room temperature overnight. The solvent was concentrated under reduced pressure and dried under high vacuum to give (4S,4'S,7S,7'S,9aS,9a'S)—N,N'-((1S,1'S)-(hexa-2,4-diyne-1,6-diylbis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide) dihydrochloride (50 mg, 0.047 mmol, 79.36% yield) as white solid. 1H NMR (400 MHz, DMSO-d$_6$) δ ppm 9.24 (s, 2H), 8.86 (d, J=6.4 Hz, 2H), 8.81 (d, J=7.2 Hz, 2H), 8.38 (d, J=8.0 Hz, 2H), 7.39-7.32 (m, 8H), 7.29-7.25 (m, 2H), 5.47 (t, J=8.0 Hz, 2H), 5.04 (q, J=6.8 Hz, 2H), 4.73-4.69 (m, 2H), 4.30 (s, 4H), 4.17 (s, 2H), 3.86 (q, J=6.9 Hz, 2H), 3.62 (d, J=6.0 Hz, 4H), 3.19-3.13 (m, 2H), 2.92-2.87 (m, 2H), 2.47 (s, 6H), 2.22-2.17 (m, 2H), 2.13-2.09 (m, 2H), 1.87 (dd, J=12.4, 8.8 Hz, 2H), 1.80-1.72 (m, 2H), 1.38 (d, J=6.8 Hz, 6H), 1.06 (s, 6H), 1.01 (s, 6H). LCMS (2.5 min formic acid): Rt=1.28 min, m/z: 999.7 (M+1)$^+$.

Example 34

(4S,7S,9aS)—N—((S)-2-((6-((S)-2-((4S,7S,9aS)-8,8-dimethyl-4-((S)-2-(methylamino)propanamido)-5-oxooctahydropyrrolo[2,1-b][1,3]thiazepine-7-carboxamido)-2-phenylethoxy)hexa-2,4-diyn-1-yl)oxy)-1-phenylethyl)-8,8-dimethyl-4-((S)-2-(methylamino)propanethioamido)-5-oxooctahydropyrrolo[2,1-b][1,3]thiazepine-7-carboxamide Step 1: tert-butyl ((S)-1-(((4S,7S,9aS)-8,8-dimethyl-5-oxo-7-(((S)-1-phenyl-2-(prop-2-yn-1-yloxy)ethyl)carbamoyl)octahydropyrrolo[2,1-b][1,3]thiazepin-4-yl)amino)-1-thioxopropan-2-yl)(methyl)carbamate To a solution of (4S,7S,9aS)-4-((S)-2-((tert-butoxycarbonyl)(methyl)amino)propanethioamido)-8,8-dimethyl-5-oxooctahydropyrrolo[2,1-b][1,3]thiazepine-7-carboxylic acid (500 mg, 1.088 mmol), 2-(7-azabenzotriazol-1-yl)-N,N,N',N'-tetramethyluronium hexafluorophosphate (624 mg, 1.64 mmol) and N,N-diisopropylethylamine (281 mg, 2.18 mmol) in 1,2-dichloroethane (15 mL) was added (S)-1-phenyl-2-(prop-2-yn-1-yloxy)ethan-1-amine (210 mg, 1.20 mmol). The mixture was stirred at room temperature overnight. The mixture was purified by silica gel chromatography [petroleum ether/ethyl acetate (2:1 v/v)] and prep-TLC [petroleum ether/ethyl acetate (1:1 v/v)] to give tert-butyl ((S)-1-(((4S,7S,9aS)-8,8-dimethyl-5-oxo-7-(((S)-1-phenyl-2-(prop-2-yn-1-yloxy)ethyl)carbamoyl)octahydropyrrolo[2,1-b][1,3]thiazepin-4-yl)amino)-1-thioxopropan-2-yl)(methyl)carbamate (400 mg, 0.65 mmol, 59.1% yield). LCMS (2.5 min formic acid): Rt=1.988 min, m/z: 638.8 (M+Na)$^+$.

Step 2: di-tert-butyl ((2S,2'S)-(((4S,4'S,7S,7'S,9aS,9a'S)-((3S,14S)-3,14-diphenyl-5,12-dioxa-2,15-diazahexadeca-7,9-diynedioyl)bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate)

tert-butyl ((S)-1-(((4S,7S,9aS)-7-(((S)-2-((6-((S)-2-((4S,7S,9aS)-4-((S)-2-((tert-butoxycarbonyl)(methyl)amino)propanethioamido)-8,8-dimethyl-5-oxooctahydropyrrolo[2,1-b][1,3]thiazepine-7-carboxamido)-2-phenylethoxy)hexa-2,4-diyn-1-yl)oxy)-1-phenylethyl)carbamoyl)-8,8-dimethyl-5-oxooctahydropyrrolo[2,1-b][1,3]thiazepin-4-yl)amino)-1-oxopropan-2-yl)(methyl)carbamate and di-tert-butyl ((2S,2'S)-(((4S,4'S,7S,7'S,9aS,9a'S)-((3S,14S)-3,14-diphenyl-5,12-dioxa-2,15-diazahexadeca-7,9-diynedioyl)bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate)

To a solution of tert-butyl ((S)-1-(((4S,7S,9aS)-8,8-dimethyl-5-oxo-7-(((1S,2R)-2-(prop-2-yn-1-yloxy)-2,3-di-

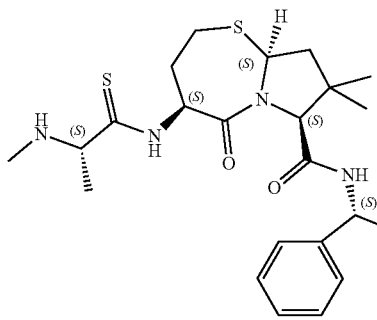
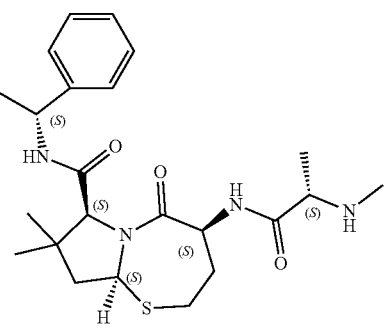

hydro-1H-inden-1-yl)carbamoyl)octahydropyrrolo[2,1-b] [1,3]thiazepin-4-yl)amino)-1-thioxopropan-2-yl)(methyl) carbamate (378 mg, 0.616 mmol tert-butyl ((S)-1-(((4S,7S, 9aS)-8,8-dimethyl-5-oxo-7-(((S)-1-phenyl-2-(prop-2-yn-1-yloxy)ethyl)carbamoyl)octahydropyrrolo[2,1-b][1,3] thiazepin-4-yl)amino)-1-oxopropan-2-yl)(methyl) carbamate (370 mg, 0.616 mmol) and pyridine (292 mg, 3.696 mmol) in acetonitrile (15 mL) was added copper(II) acetate (269 mg, 1.478 mmol). The mixture was stirred at 85° C. for 40 min. The reaction was concentrated and diluted with ethyl acetate (20 mL) and aqueous ammonia (20 fold dilution, 20 mL) was added. The water phase was separated and extracted with ethyl acetate (2×15 mL). The combined organic phase was washed with brine (20 mL), dried over anhydrous sodium sulfate, filtered and concentrated. The crude was purified by prep-TLC [petroleum ether/ethyl acetate (2:3 v/v)] and prep-HPLC to get the desired products di-tert-butyl ((2S,2'S)-(((4S,4'S,7S,7'S,9aS,9a'S)-((3S,14S)-3,14-diphenyl-5,12-dioxa-2,15-diazahexadeca-7,9-diynedioyl)bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (100 mg, 0.083 mmol, 13.5% yield) [LCMS (2.5 min formic acid): Rt=1.914 min, m/z: 499.8 {[(M-2Boc)+2]/2}⁺], tert-butyl ((S)-1-(((4S,7S,9aS)-7-(((S)-2-((6-((S)-2-((4S,7S,9aS)-4-((S)-2-((tert-butoxycarbonyl)(methyl)amino)propanethioamido)-8,8-dimethyl-5-oxooctahydropyrrolo[2,1-b][1,3]thiazepine-7-carboxamido)-2-phenylethoxy)hexa-2,4-diyn-1-yl)oxy)-1-phenylethyl)carbamoyl)-8,8-dimethyl-5-oxooctahydropyrrolo[2,1-b][1,3]thiazepin-4-yl)amino)-1-oxopropan-2-yl)(methyl)carbamate (66 mg, 0.054 mmol, 8.77% yield) [LCMS (2.5 min formic acid): Rt=2.042 min, m/z: 507.8 {[(M-2Boc)+2]/2}⁺] and di-tert-butyl ((2S,2'S)-(((4S,4'S,7S,7'S,9aS,9a'S)-((3S,14S)-3,14-diphenyl-5,12-dioxa-2,15-diazahexadeca-7,9-diynedioyl)bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate) (40 mg, 0.032 mmol, 5.19% yield) [LCMS (2.5 min formic acid): Rt=2.186 min, m/z: 516.1 {[(M-2Boc)+2]/2}⁺].

Step 3: (4S,7S,9aS)—N—((S)-2-((6-((S)-2-((4S,7S,9aS)-8,8-dimethyl-4-((S)-2-(methylamino)propanamido)-5-oxooctahydropyrrolo[2,1-b][1,3]thiazepine-7-carboxamido)-2-phenylethoxy)hexa-2,4-diyn-1-yl)oxy)-1-phenylethyl)-8,8-dimethyl-4-((S)-2-(methylamino)propanethioamido)-5-oxooctahydropyrrolo[2,1-b][1,3]thiazepine-7-carboxamide To a solution of tert-butyl ((S)-1-(((4S,7S,9aS)-7-(((S)-2-((6-((S)-2-((4S,7S,9aS)-4-((S)-2-((tert-butoxycarbonyl)(methyl)amino)propanethioamido)-8,8-dimethyl-5-oxooctahydropyrrolo[2,1-b][1,3]thiazepine-7-carboxamido)-2-phenylethoxy)hexa-2,4-diyn-1-yl)oxy)-1-phenylethyl)carbamoyl)-8,8-dimethyl-5-oxooctahydropyrrolo[2,1-b][1,3]thiazepin-4-yl)amino)-1-oxopropan-2-yl)(methyl)carbamate (60 mg, 0.049 mmol) in dichloromethane (5 mL) was added 4 N hydrogen chloride in 1,4-dioxane (1 mL). The mixture was stirred at room temperature overnight. The solvent was concentrated and the crude was purified by prep-TLC [dichloromethane/methanol (5:1 v/v)] to afford (4S,7S,9aS)—N—((S)-2-((6-((S)-2-((4S,7S,9aS)-8,8-dimethyl-4-((S)-2-(methylamino)propanamido)-5-oxooctahydropyrrolo[2,1-b][1,3]thiazepine-7-carboxamido)-2-phenylethoxy)hexa-2,4-diyn-1-yl)oxy)-1-phenylethyl)-8,8-dimethyl-4-((S)-2-(methylamino)propanethioamido)-5-oxooctahydropyrrolo[2,1-b][1,3]thiazepine-7-carboxamide (30 mg, 0.029 mmol, 59.2% yield) as white solid. ¹H NMR (400 MHz, DMSO-d₆) δ ppm 8.36-8.33 (m, 1H), 8.29 (d, J=8.0 Hz, 1H), 8.18 (d, J=6.8 Hz, 1H), 7.39-7.33 (m, 8H), 7.29-7.26 (m, 2H), 5.50-5.44 (m, 2H), 5.11-5.01 (m, 3H), 4.67-4.63 (m, 1H), 4.30 (s, 4H), 4.23-4.18 (m, 2H), 3.62 (d, J=6.0 Hz, 4H), 3.40-3.35 (m, 2H), 3.20-3.12 (m, 2H), 2.97-2.85 (m, 3H), 2.38-2.33 (m, 1H), 2.22 (s, 6H), 2.16-2.15 (m, 2H), 1.91-1.83 (m, 2H), 1.78-1.65 (m, 2H), 1.24 (s, 3H), 1.11 (d, J=6.8 Hz, 3H), 1.07 (d, J=8.4 Hz, 6H), 1.00 (d, J=6.8 Hz, 6H). LCMS (2.5 min formic acid): Rt=1.251 min, m/z: 1015.4 (M+1)⁺.

Example 35

(4S,4'S,7S,7'S,9aS,9a'S)—N,N'-((1S,1'S)-(hexa-2,4-diyne-1,6-diylbis(oxy))bis(1-phenylethane-2,1-diyl)) bis(8,8-dimethyl-4-((S)-2-(methylamino)propanethioamido)-5-oxooctahydropyrrolo[2,1-b][1,3] thiazepine-7-carboxamide)

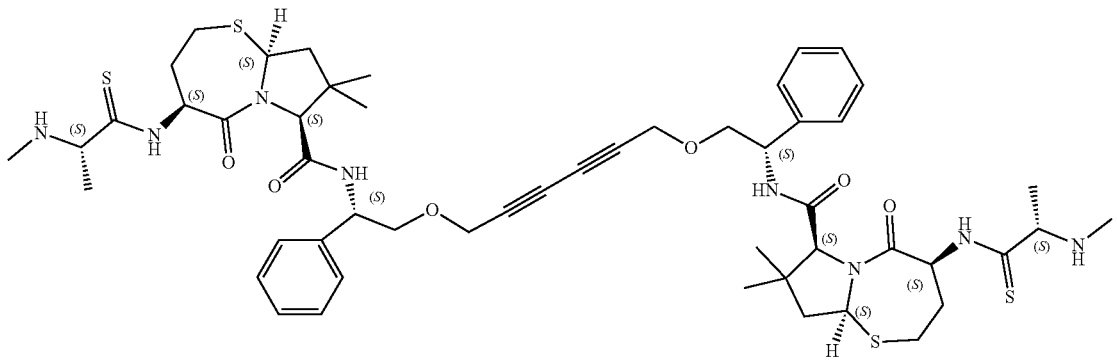

To a solution of di-tert-butyl ((2S,2'S)-(((4S,4'S,7S,7'S,9aS,9a'S)-((3S,14S)-3,14-diphenyl-5,12-dioxa-2,15-diazahexadeca-7,9-diynedioyl)bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate) (Example 34, Step 2) (40 mg, 0.032 mmol) in dichloromethane (5 mL) was added 4 N hydrogen chloride in 1,4-dioxane (1 mL).

The mixture was stirred at room temperature overnight. The solvent was concentrated and the crude was purified by prep-TLC (dichloromethane/methanol=5:1) to afford (4S,4'S,7S,7'S,9aS,9a'S)—N,N'-((1S,1'S)-(hexa-2,4-diyne-1,6-diylbis(oxy))bis(1-phenylethane-2,1-diyl))bis(8,8-dimethyl-4-((S)-2-(methylamino)propanethioamido)-5-oxooctahydropyrrolo[2,1-b][1,3]thiazepine-7-carboxamide) (19 mg, 0.018 mmol, 56.2% yield) as white solid. $^1$H NMR (400 MHz, DMSO-$d_6$) δ ppm 8.39-8.36 (m, 2H), 7.73-7.67 (m, 2H), 7.39-7.33 (m, 8H), 7.30-7.25 (m, 2H), 5.49-5.44 (m, 2H), 5.11-5.02 (m, 4H), 4.30 (m, 3H), 4.14 (dd, J=5.6, 3.6 Hz, 1H), 3.62 (d, J=6.0 Hz, 4H), 3.56 (s, 2H), 3.20-3.13 (m, 2H), 2.96-2.89 (m, 2H), 2.35-2.31 (m, 2H), 2.24-2.17 (m, 8H), 1.91-1.86 (m, 2H), 1.79-1.61 (m, 4H), 1.26-1.21 (m, 8H), 1.08 (s, 6H), 1.01 (s, 6H).

LCMS (2.5 min formic acid): Rt=1.314 min, m/z: 1031.4 (M+1)$^+$.

Example 36

(4S,4'S,7S,7'S,9aS,9a'S)—N,N'-((1S,1'S)-(butane-1,4-diylbis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide) dihydrochloride

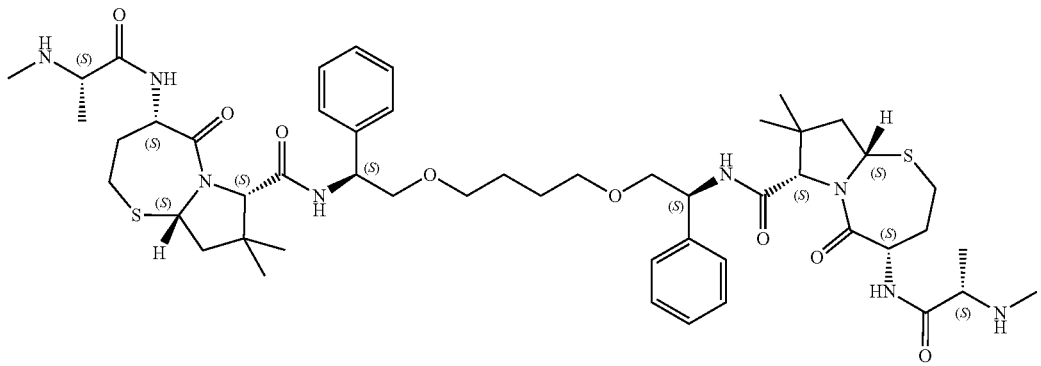

Step 1: (1S,1'S)-2,2'-(butane-1,4-diylbis(oxy))bis(1-phenylethan-1-amine)

To a solution of (S)-2-amino-2-phenylethan-1-ol (1 g, 7.29 mmol) in tetrahydrofuran (80 mL) at 0° C. was added sodium hydride (60%, dispersion in Paraffin Liquid) (321 mg, 8.02 mmol) slowly. The mixture was allowed to warm to room temperature. 1,4-Dibromobutane (787 mg, 3.65 mmol) was then added. The resulting mixture was heated to 70° C. and stirred overnight. Upon cooling, ice water (50 mL) was added and the mixture was extracted with ethyl acetate (3×30 mL). The combined organic layers were washed with brine (50 mL), dried over anhydrous sodium sulfate, filtered and concentrated. The crude was purified by thin layer chromatography [dichloromethane/methanol (10:1 v/v)] to give product (1S,1'S)-2,2'-(butane-1,4-diylbis(oxy))bis(1-phenylethan-1-amine) (190 mg, 0.58 mmol, 15.9% yield) as black oil. LCMS (2.5 min formic acid): Rt=1.162 min, m/z: 329.0 (M+1)$^+$.

Step 2: di-tert-butyl ((2S,2'S)-(((4S,4'S,7S,7'S,9aS,9a'S)-((3S,12S)-3,12-diphenyl-5,10-dioxa-2,13-diazatetradecanedioyl)bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate)

A mixture of (1S,1'S)-2,2'-(butane-1,4-diylbis(oxy))bis(1-phenylethan-1-amine) (90 mg, 0.274 mmol) and (4S,7S,9aS)-4-((S)-2-((tert-butoxycarbonyl)(methyl)amino)propanamido)-8,8-dimethyl-5-oxooctahydropyrrolo[2,1-b][1,3]thiazepine-7-carboxylic acid (Intermediate I) (267 mg, 0.603 mmol) in 1,2-dichloroethane (12 mL) was added N-ethoxycarbonyl-2-ethoxy-1,2-dihydroquinoline (203 mg, 0.822 mmol) and N,N-diisopropylethylamine (141 mg, 1.096 mmol). The mixture was stirred at 50° C. overnight. The solvent was removed under reduced pressure. The residue was purified by thin layer chromatography [ethyl acetate/petroleum ether (2/1 v/v)] followed by Prep-HPLC to give di-tert-butyl ((2S,2'S)-(((4S,4'S,7S,7'S,9aS,9a'S)-((3S,12S)-3,12-diphenyl-5,10-dioxa-2,13-diazatetradecanedioyl)bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (48 mg, 0.041 mmol, 14.6% yield) as white solid. LCMS (2.5 min formic acid): Rt=1.835 min, m/z: 489.9 {[(M-2Boc)+2]/2}$^+$.

Step 3: (4S,4'S,7S,7'S,9aS,9a'S)—N,N'-((1S,1'S)-(butane-1,4-diylbis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide) dihydrochloride To a solution of di-tert-butyl ((2S,2'S)-(((4S,4'S,7S,7'S,9aS,9a'S)-((3S,12S)-3,12-diphenyl-5,10-dioxa-2,13-diazatetradecanedioyl)bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (48 mg, 0.041 mmol) in dichloromethane (5 mL) was added 4 N hydrogen chloride in 1,4-dioxane (1 mL). The mixture was stirred at room temperature for 3 h. The mixture was concentrated and dried under high vacuum to afford (4S,4'S,7S,7'S,9aS,9a'S)—N,N'-((1S,1'S)-(butane-1,4-diylbis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide) dihydrochloride (34 mg, 0.032 mmol, 79.2% yield) as a white solid. $^1$H NMR (400 MHz, DMSO-$d_6$) δ ppm 9.34 (s, 1H), 8.62 (s, 1H), 8.81 (d, J=7.2 Hz, 2H), 8.34 (d, J=8.0 Hz, 2H), 7.37-7.30 (m, 8H), 7.27-7.23 (m, 2H), 5.47 (t, J=8.0 Hz, 2H), 4.99 (q, J=6.4 Hz, 2H), 4.71 (t, J=8.4 Hz, 2H), 4.17 (m, 2H), 3.88-3.84 (m, 2H), 3.49-3.48 (m, 4H), 3.41-3.29 (m, 4H), 3.16 (t, J=12.4 Hz, 2H), 2.90-2.87 (m, 2H), 2.46 (s, 6H), 2.22-2.19 (m, 2H), 2.12-2.10 (m, 2H), 1.89-1.84 (m, 2H), 1.79-1.70 (m, 2H), 1.42 (s, 4H), 1.39 (d, J=6.8 Hz, 6H), 1.06 (m, 6H), 1.00 (m, 6H). LCMS (2.5 min formic acid): Rt=1.323 min, m/z: 978.8 (M+1)$^+$.

Example 37

(4S,4'S,7S,7'S,9aS,9a'S)—N,N'-((1S,1'S)-(butane-1,4-diylbis(oxy))bis(1-phenylethane-2,1-diyl))bis(8,8-dimethyl-4-((S)-2-(methylamino)propanethioamido)-5-oxooctahydropyrrolo[2,1-b][1,3]thiazepine-7-carboxamide) dihydrochloride Step 1: di-tert-butyl ((2S,2'S)-(((4S,4'S,7S,7'S,9aS,9a'S)-((3S,12S)-3,12-diphenyl-5,10-dioxa-2,13-diazatetradecanedioyl)bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate)

To a mixture of (1S,1'S)-2,2'-(butane-1,4-diylbis(oxy))bis(1-phenylethan-1-amine) (100 mg, 0.304 mmol) and (4S,7S,9aS)-4-((S)-2-((tert-butoxycarbonyl)(methyl)amino)propanethioamido)-8,8-dimethyl-5-oxooctahydropyrrolo[2,1-b][1,3]thiazepine-7-carboxylic acid (Intermediate II) (308 mg, 0.670 mmol) in 1,2-dichloroethane (12 mL) was added N-ethoxycarbonyl-2-ethoxy-1,2-dihydroquinoline (226 mg, 0.912 mmol) and N,N-diisopropylethylamine (157 mg, 1.216 mmol). The mixture was stirred at 50° C. overnight. The solvent was removed under reduced pressure. The crude was purified by thin layer chromatography (ethyl acetate/Petroleum ether=1/1) followed by Prep-HPLC to give di-tert-butyl ((2S,2'S)-(((4S,4'S,7S,7'S,9aS,9a'S)-((3S,12S)-3,12-diphenyl-5,10-dioxa-2,13-diazatetradecanedioyl)bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate) (55 mg, 0.045 mmol, 14.8% yield) as colorless oil. LCMS (2.5 min formic acid): Rt=2.044 min, m/z: 506 {[(M-2Boc)+2]/2}$^+$.

Step 2: (4S,4'S,7S,7'S,9aS,9a'S)—N,N'-((1S,1'S)-(butane-1,4-diylbis(oxy))bis(1-phenylethane-2,1-diyl))bis(8,8-dimethyl-4-((S)-2-(methylamino)propanethioamido)-5-oxooctahydropyrrolo[2,1-b][1,3]thiazepine-7-carboxamide) dihydrochloride To a solution of di-tert-butyl ((2S,2'S)-(((4S,4'S,7S,7'S,9aS,9a'S)-((3S,12S)-3,12-diphenyl-5,10-dioxa-2,13-diazatetradecanedioyl)bis(8,8-dimethyl-5-oxooctahydropyrrolo[2,1-b][1,3]thiazepine-7,4-diyl))bis(azanediyl))bis(1-

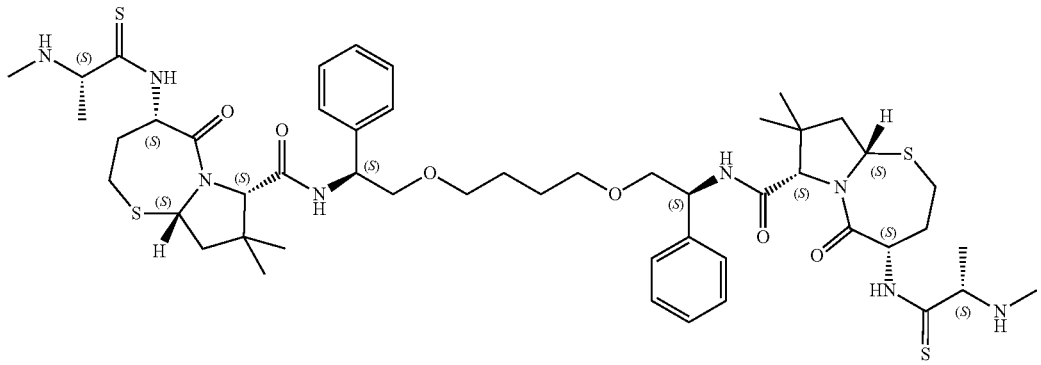

thioxopropane-1,2-diyl))bis(methylcarbamate) (55 mg, 0.045 mmol) in dichloromethane (5 mL) was added 4 N hydrogen chloride in 1,4-dioxane (1 mL). The mixture was stirred at room temperature for 2 h. The solvent was removed under reduced pressure and the product was dried under high vacuum to give (4S,4'S,7S,7'S,9aS,9a'S)—N,N'-((1S,1'S)-(butane-1,4-diylbis(oxy))bis(1-phenylethane-2,1-diyl))bis(8,8-dimethyl-4-((S)-2-(methylamino)propanethioamido)-5-oxooctahydropyrrolo[2,1-b][1,3]thiazepine-7-carboxamide) dihydrochloride (35 mg, 0.032 mmol, 71.4% yield) as white solid. $^1$H NMR (400 MHz, DMSO-$d_6$) δ ppm 10.96 (s, 1H), 10.89 (s, 1H), 9.71 (s, 1H), 9.55 (s, 1H), 8.61 (s, 1H), 8.40 (t, J=8.2 Hz, 2H), 7.37-7.30 (m, 8H), 7.27-7.23 (m, 2H), 5.42 (q, J=8.0 Hz, 2H), 5.16-5.11 (m, 2H), 5.02-4.98 (m, 2H), 4.26-4.23 (m, 2H), 4.21-4.20 (m, 2H), 3.49-3.48 (m, 4H), 3.33 (s, 4H), 3.19-3.13 (m, 2H), 2.96-2.92 (m, 2H), 2.48 (s, 6H), 2.24-2.21 (m, 4H), 1.93-1.88 (m, 4H), 1.43-1.42 (m, 6H), 1.08 (m, 6H), 1.02 (m, 6H). LCMS (2.5 min formic acid): Rt=1.326 min, m/z: 506.0 [(M+2)/2]$^+$.

Example 38

(4S,4'S,7S,7'S,9aS,9a'S)—N,N'-((1S,1'S)-((oxybis(ethane-2,1-diyl))bis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide)dihydrochloride

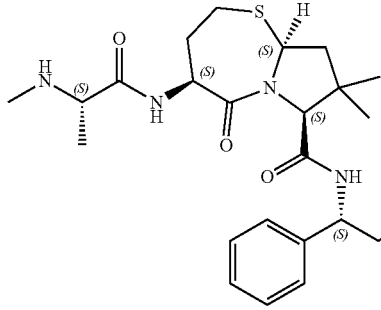
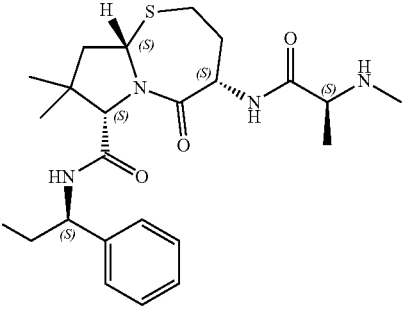

Step 1: oxybis(ethane-2,1-diyl) bis(4-methylbenzenesulfonate)

To a solution of 4-Tosyl chloride (11.86 g, 62.2 mmol) and 2,2'-oxybis(ethan-1-ol) (3.0 g, 28.30 mmol) in dichloromethane (200 mL) at 0° C. was added KOH (14.27 g, 25.4 mmol). The mixture was allowed to stir overnight. Ice-water (150 mL) was added to the mixture followed by extraction with dichloromethane (3×200 mL). The combined organic layers were dried over anhydrous magnesium sulfate, filtered and concentrated. The residue was crystallized from anhydrous methanol to give oxybis(ethane-2,1-diyl) bis(4-methylbenzenesulfonate) (9.3 g, 22.4 mmol, 79%) as a white solid. $^1$H NMR 1 (400 MHz, DMSO-$d_6$) δ ppm 7.78 (d, J=8.0 Hz, 4H), 7.47 (d, J=8.0 Hz, 4H), 4.07-4.05 (m, 4H), 3.53-3.51 (m, 4H), 2.42 (s, 6H); LCMS (2.5 min formic acid): Rt=1.675 min, m/z: 414.5 (M+1)$^+$, 436.8 (M+Na)$^+$.

Step 2: (1S,1'S)-2,2'-((oxybis(ethane-2,1-diyl))bis(oxy))bis(1-phenylethan-1-amine)

To a solution of (S)-2-amino-2-phenylethan-1-ol (364.1 mg, 2.65 mmol) in dry tetrahydrofuran (10 mL) at 0° C. was added portionwise a suspension of sodium hydride (60%, dispersion in Paraffin Liquid) (144.8 mg, 6.03 mmol) in dry tetrahydrofuran (10 mL) under nitrogen. The mixture was stirred at room temperature for 2 h. Oxybis(ethane-2,1-diyl) bis(4-methylbenzenesulfonate) (500 mg, 1.21 mmol) was added to the mixture and the mixture was stirred at room temperature for 12 h. The mixture was quenched with water (50 mL) and extracted with ethyl acetate (3×50 mL). The combined organic layers were washed with brine, dried, filtered and concentrated. The residue was purified by thin layer chromatography [ethyl acetate/petroleum ether (1/1 v/v)] to give (1S,1'S)-2,2'-((oxybis(ethane-2,1-diyl))bis(oxy))bis(1-phenylethan-1-amine) (260 mg, 0.76 mmol, 62% yield) as yellow oil. LCMS (2.5 min formic acid): Rt=1.085 min, m/z: 345.0 (M+1)$^+$.

Step 3: di-tert-butyl ((2S,2'S)-(((4S,4'S,7S,7'S,9aS,9a'S)-((3S,13S)-3,13-diphenyl-5,8,11-trioxa-2,14-diazapentadecanedioyl)bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate)

A solution of (1S,1'S)-2,2'-((oxybis(ethane-2,1-diyl))bis(oxy))bis(1-phenylethan-1-amine) (150 mg, 0.44 mmol), (4S,7S,9aS)-4-((S)-2-((tert-butoxycarbonyl)(methyl)amino)propanamido)-8,8-dimethyl-5-oxooctahydropyrrolo[2,1-b][1,3]thiazepine-7-carboxylic acid (405.6 mg, 0.91 mmol), N-ethoxycarbonyl-2-ethoxy-1,2-dihydroquinoline (323 mg, 1.31 mmol) and N,N-diisopropyl-ethylamine (225.1 mg, 1.74 mmol) in 1,2-dichloroethane (8 mL) was stirred at 50° C. overnight. The mixture was concentrated under reduced pressure and purified by thin layer chromatography [ethyl acetate/petroleum ether (2/1 v/v)] to give crude product (360 mg) as yellow oil. This material was further purified by prep-HPLC to give di-tert-butyl ((2S,2'S)-(((4S,4'S,7S,7'S,9aS,9a'S)-((3S,13S)-3,13-diphenyl-5,8,11-trioxa-2,14-diazapentadecanedioyl)bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (180 mg, 0.15 mmol, 33.5% yield) as white solid. LCMS (2.5 min formic acid): Rt=1.79 min, m/z: 498.1 {[(M-2Boc)+2]/2}$^+$.

Step 4: (4S,4'S,7S,7'S,9aS,9a'S)—N,N'-((1S,1'S)-((oxybis(ethane-2,1-diyl))bis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide) dihydrochloride To a solution of di-tert-butyl ((2S,2'S)-(((4S,4'S,7S,7'S,9aS,9a'S)-((3S,13S)-3,13-diphenyl-5,8,11-trioxa-2,14-diazapentadecanedioyl)bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (180 mg, 0.15 mmol) in dichloromethane (6 mL) was added hydrogen chloride (4 N in 1,4-dioxane, 2 mL) at room temperature. The reaction was stirred at room temperature overnight. The mixture was concentrated under reduced pressure and dried under high vacuum to give (4S,4'S,7S,7'S,9aS,9a'S)—N,N'-

((1S,1'S)-((oxybis(ethane-2,1-diyl))bis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide) dihydrochloride (130 mg, 0.131 mmol, 76% yield) as a white solid. ¹H NMR (400 MHz, DMSO-d₆) δ ppm 9.50 (s, 2H), 8.91 (s, 2H), 8.83 (d, J=6.4 Hz, 2H), 8.37 (d, J=7.6 Hz, 2H), 7.38-7.31 (m, 8H), 7.27-7.23 (m, 2H), 5.47 (t, J=7.8 Hz, 2H), 5.00 (q, J=7.2 Hz, 2H), 4.70 (t, J=8.8 Hz, 2H), 4.17 (s, 2H), 3.88-3.82 (m, 2H), 3.56-3.40 (m, 12H), 3.15 (t, J=12.2 Hz, 2H), 2.91-2.87 (m, 2H), 2.45 (s, 6H), 2.22-2.09 (m, 4H), 1.90-1.71 (m, 4H), 1.39 (d, J=6.8 Hz, 6H), 1.06 (m, 6H), 1.01 (m, 6H); LCMS (2.5 min formic acid): Rt=1.284 min, m/z: 995.8 (M+1)⁺.

Example 39

(4S,4'S,7S,7'S,9aS,9a'S)—N,N'-((1S,1'S)-((oxybis(ethane-2,1-diyl))bis(oxy))bis(1-phenylethane-2,1-diyl))bis(8,8-dimethyl-4-((S)-2-(methylamino)propanethioamido)-5-oxooctahydropyrrolo[2,1-b][1,3]thiazepine-7-carboxamide) dihydrochloride butyl ((2S,2'S)-(((4S,4'S,7S,7'S,9aS,9a'S)-((3S,13S)-3,13-diphenyl-5,8,11-trioxa-2,14-diazapentadecanedioyl)bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate) (100 mg, 0.082 mmol, 60% yield) as white solid. LCMS (2.5 min formic acid): Rt=2.02 min, m/z: 514.0 {[(M-2Boc)+2]/2}⁺.

Step 2: (4S,4'S,7S,7'S,9aS,9a'S)—N,N'-((1S,1'S)-((oxybis(ethane-2,1-diyl))bis(oxy))bis(1-phenylethane-2,1-diyl))bis(8,8-dimethyl-4-((S)-2-(methylamino)propanethioamido)-5-oxooctahydropyrrolo[2,1-b][1,3]thiazepine-7-carboxamide) dihydrochloride To a solution of di-tert-butyl ((2S,2'S)-(((4S,4'S,7S,7'S,9aS,9a'S)-((3S,13S)-3,13-diphenyl-5,8,11-trioxa-2,14-diazapentadecanedioyl)bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate) (100 mg,

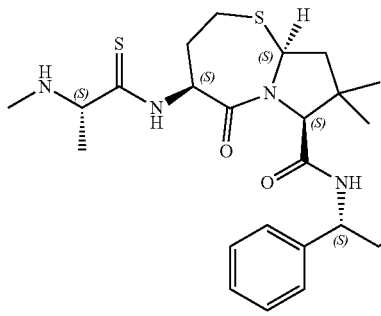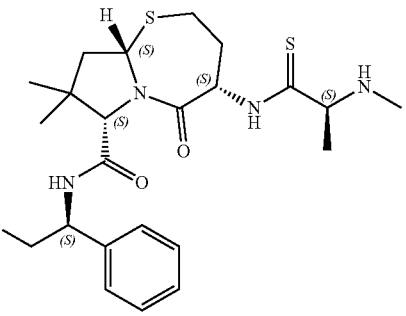

Step 1: di-tert-butyl ((2S,2'S)-(((4S,4'S,7S,7'S,9aS,9a'S)-((3S,13S)-3,13-diphenyl-5,8,11-trioxa-2,14-diazapentadecanedioyl)bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate)

A solution of (1S,1'S)-2,2'-((oxybis(ethane-2,1-diyl))bis(oxy))bis(1-phenylethan-1-amine) (50 mg, 0.15 mmol), (4S,7S,9aS)-4-((S)-2-((tert-butoxycarbonyl)(methyl)amino)propanethioamido)-8,8-dimethyl-5-oxooctahydropyrrolo[2,1-b][1,3]thiazepine-7-carboxylic acid (Intermediate II) (140.1 mg, 0.30 mmol), N-ethoxycarbonyl-2-ethoxy-1,2-dihydroquinoline (107.7 mg, 0.45 mmol) and N,N-diisopropylethylamine (75 mg, 0.60 mmol) in 1,2-dichloroethane (5 mL) was stirred at 50° C. overnight. The solvent was removed under reduced pressure. The residue was purified by thin layer chromatography [ethyl acetate/petroleum ether (1/1 v/v)] to give crude product (360 mg) as yellow oil. This material was further purified by Prep-HPLC to give di-tert- 0.082 mmol) in dichloromethane (5 mL) was added hydrogen chloride (4 N in 1,4-dioxane, 1 mL) at room temperature. The reaction was stirred at room temperature overnight. The solvent was removed under reduced pressure and dried under high vacuum to afford (4S,4'S,7S,7'S,9aS,9a'S)—N,N'-((1S,1'S)-((oxybis(ethane-2,1-diyl))bis(oxy))bis(1-phenylethane-2,1-diyl))bis(8,8-dimethyl-4-((S)-2-(methylamino)propanethioamido)-5-oxooctahydropyrrolo[2,1-b][1,3]thiazepine-7-carboxamide) dihydrochloride (50 mg, 0.05 mmol, 60% yield) as a white solid. ¹H NMR (400 MHz, DMSO-d₆) δ ppm 10.95 (d, J=6.4 Hz, 1H), 10.88 (d, J=6.4 Hz, 1H), 9.70 (s, 1H), 9.53 (s, 1H), 8.61 (s, 1H), 8.44-8.40 (m, 3H), 7.37-7.31 (m, 8H), 7.27-7.24 (m, 2H), 5.42 (q, J=8.0 Hz, 2H), 5.13 (q, J=7.6 Hz, 2H), 5.03-4.98 (m, 2H), 4.25-4.20 (m, 4H), 3.55-3.54 (m, 4H), 3.51-3.47 (m, 4H), 3.44 (s, 4H), 3.16 (t, J=12 Hz, 2H), 2.48 (s, 6H), 2.24-2.21 (m, 4H), 1.94-1.89 (m, 4H), 1.43 (d, J=6.4 Hz, 6H), 1.08 (m, 6H), 1.03 (m, 6H). LCMS (2.5 min formic acid): Rt=1.355 min, m/z: 1026.8 (M+1)⁺.

Example 40

(4S,4'S,7S,7'S,9aS,9a'S)—N,N'-((1S,1'S)-(hexane-1,6-diylbis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide) dihydrochloride

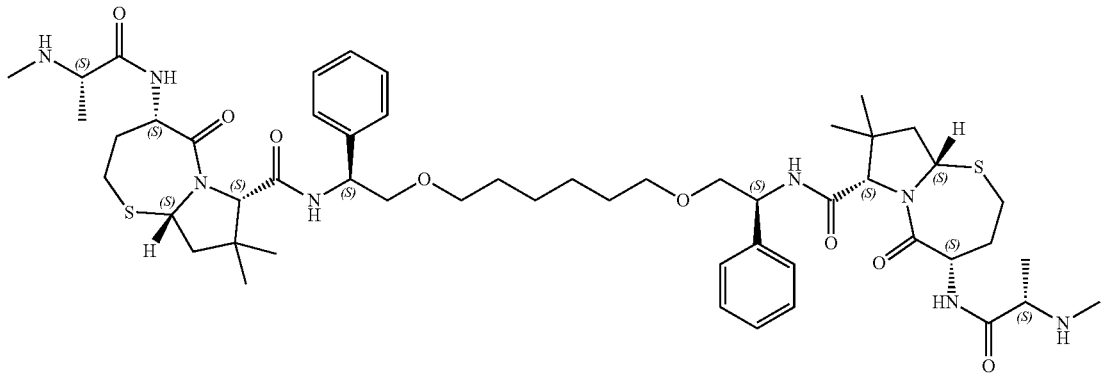

Step 1: (1S,1'S)-2,2'-(hexane-1,6-diylbis(oxy))bis(1-phenylethan-1-amine)

To a mixture of (S)-2-amino-2-phenylethan-1-ol (1.0 g, 7.20 mmol) in dry tetrahydrofuran (20 mL) at 0° C. was added slowly portionwise sodium hydride (60%, dispersion in Paraffin Liquid) (330 mg, 13.8 mmol) under nitrogen. The mixture was stirred at room temperature over 30 min and a solution of 1,6-dibromohexane (810 mg, 3.31 mmol) in dry tetrahydrofuran (10 mL) was added. The mixture was heated to reflux and stirred for another 5 h. Upon cooling, water (300 mL) was carefully added to the mixture followed by extracted with dichloromethane (3×100 mL). The combined organic layers were washed with brine, dried, filtered and concentrated. The residue was purified by thin layer chromatography (dichloromethane/methanol (7:1 v/v)] to give (1S,1'S)-2,2'-(hexane-1,6-diylbis(oxy))bis(1-phenylethan-1-amine) (410 mg, 1.15 mmol, 25.6% yield) as yellow oil. LCMS (2.5 min formic acid): Rt=1.24 min, m/z: 357.0 $(M+1)^+$.

Step 2: di-tert-butyl ((2S,2'S)-(((4S,4'S,7S,7'S,9aS,9a'S)-((3S,14S)-3,14-diphenyl-5,12-dioxa-2,15-diazahexadecanedioyl)bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate)

A solution of (1S,1'S)-2,2'-(hexane-1,6-diylbis(oxy))bis(1-phenylethan-1-amine) (90 mg, 0.25 mmol), (4S,7S,9aS)-4-((S)-2-((tert-butoxycarbonyl)(methyl)amino)propanamido)-8,8-dimethyl-5-oxooctahydropyrrolo[2,1-b][1,3]thiazepine-7-carboxylic acid (235.2 mg, 0.53 mmol), N-ethoxycarbonyl-2-ethoxy-1,2-dihydroquinoline (187.3 mg, 0.76 mmol) and N,N-diisopropyl-ethylamine (130.5 mg, 1.01 mmol) in 1,2-dichloroethane (5 mL) was stirred at 50° C. overnight. The solvent was removed under reduced pressure. The residue was purified by thin layer chromatography [ethyl acetate/petroleum ether (1:1 v/v)] to give crude product (120 mg) as yellow oil. This material was further purified by Prep-HPLC to give di-tert-butyl ((2S,2'S)-(((4S,4'S,7S,7'S,9aS,9a'S)-((3S,14S)-3,14-diphenyl-5,12-dioxa-2,15-diazahexadecanedioyl)bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (50 mg, 0.041 mmol, 16.4% yield) as a white solid. LCMS (2.5 min formic acid): Rt=1.89 min, m/z: 503.9 $\{[(M-2Boc)+2]/2\}^+$.

Step 3: (4S,4'S,7S,7'S,9aS,9a'S)—N,N'-((1S,1'S)-(hexane-1,6-diylbis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide) dihydrochloride To a solution of di-tert-butyl ((2S,2'S)-(((4S,4'S,7S,7'S,9aS,9a'S)-((3S,14S)-3,14-diphenyl-5,12-dioxa-2,15-diazahexadecanedioyl)bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (100 mg, 0.083 mmol) in dichloromethane (5 mL) was added hydrogen chloride (4 N in 1,4-dioxane, 1 mL). The mixture was stirred at room temperature overnight. The mixture was concentrated under reduced pressure and dried under high vacuum to give (4S,4'S,7S,7'S,9aS,9a'S)—N,N'-((1S,1'S)-(hexane-1,6-diylbis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide) dihydrochloride (41.9 mg, 0.038 mmol, 45.8% yield) as a white solid. $^1$H NMR (400 MHz, DMSO-$d_6$) δ ppm 9.34 (s, 2H), 8.88-8.86 (m, 2H), 8.82 (d, J=7.8 Hz, 2H), 8.36 (d, J=8.4 Hz, 2H), 7.38-7.31 (m, 8H), 7.27-7.23 (m, 2H), 5.47 (t, J=7.8 Hz, 2H), 5.48-5.02 (m, 2H), 4.73-4.68 (m, 2H), 4.17 (s, 2H), 3.88-3.83 (m, 2H), 3.72-3.65 (m, 2H), 3.51-3.47 (m, 6H), 3.32-3.28 (m, 4H), 3.19-3.13 (m, 2H), 2.90-2.87 (m, 2H), 2.46 (t, J=4.4H, 6H), 2.22-2.17 (m, 2H), 2.13-2.09 (m, 2H), 1.89-1.84 (m, 2H), 1.79-1.34 (m, 2H), 1.39-1.38 (m, 10H), 1.06 (s, 6H), 1.01 (m, 6H). LCMS (2.5 min formic acid): Rt=1.258 min, m/z: 1006.8 $(M+1)^+$.

Example 41

(4S,4'S,7S,7'S,9aS,9a'S)—N,N'-((1S,1'S)-(hexane-1,6-diylbis(oxy))bis(1-phenylethane-2,1-diyl))bis(8,8-dimethyl-4-((S)-2-(methylamino)propanethioamido)-5-oxooctahydropyrrolo[2,1-b][1,3]thiazepine-7-carboxamide) dihydrochloride

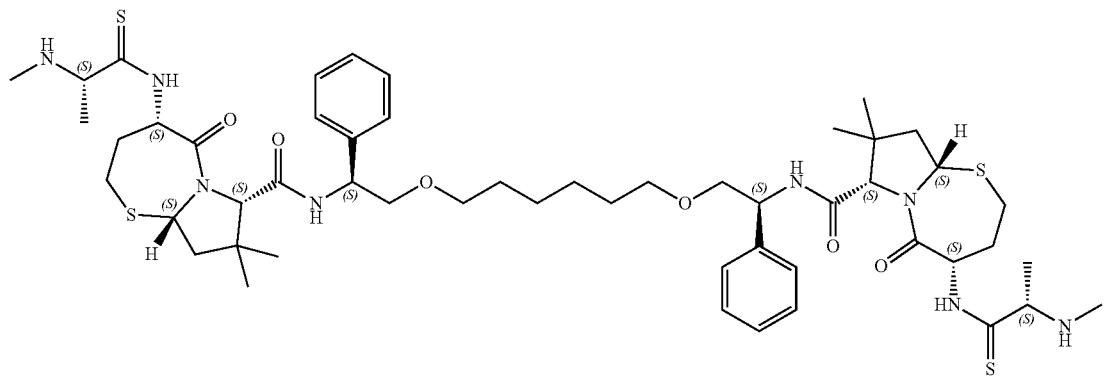

Step 1: di-tert-butyl ((2S,2'S)-(((4S,4'S,7S,7'S,9aS,9a'S)-((3S,14S)-3,14-diphenyl-5,12-dioxa-2,15-diazahexadecanedioyl)bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate)

A solution of (1S,1'S)-2,2'-(hexane-1,6-diylbis(oxy))bis(1-phenylethan-1-amine) (90 mg, 0.25 mmol), (4S,7S,9aS)-4-((S)-2-((tert-butoxycarbonyl)(methyl)amino)propanethioamido)-8,8-dimethyl-5-oxooctahydropyrrolo[2,1-b][1,3]thiazepine-7-carboxylic acid (243.7 mg, 0.53 mmol), N-ethoxycarbonyl-2-ethoxy-1,2-dihydroquinoline (187.3 mg, 0.76 mmol) and N,N-diisopropyl-ethylamine (130.5 mg, 1.01 mmol) in 1,2-dichloroethane (5 mL) was stirred at 50° C. overnight. The solvent was removed under reduced pressure. The residue was purified by thin layer chromatography [ethyl acetate/petroleum ether (1/1 v/v)] to give crude product (120 mg) as yellow oil. This material was further purified by Prep-HPLC to give di-tert-butyl ((2S,4'S,7S,7'S,9aS,9a'S)-((3S,14S)-3,14-diphenyl-5,12-dioxa-2,15-diazahexadecanedioyl)bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate) (130 mg, 0.104 mmol, 41.4% yield) as white solid. LCMS (2.5 min formic acid): Rt=2.094 min, m/z: 520.0 {[(M-2Boc)+2]/2}⁺.

Step 2: (4S,4'S,7S,7'S,9aS,9a'S)—N,N'-((1S,1'S)-(hexane-1,6-diylbis(oxy))bis(1-phenylethane-2,1-diyl))bis(8,8-dimethyl-4-((S)-2-(methylamino)propanethioamido)-5-oxooctahydropyrrolo[2,1-b][1,3]thiazepine-7-carboxamide) dihydrochloride To a solution of di-tert-butyl ((2S,2'S)-(((4S,4'S,7S,7'S,9aS,9a'S)-((3S,14S)-3,14-diphenyl-5,12-dioxa-2,15-diazahexadecanedioyl)bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate) (130 mg, 0.10 mmol) in dichloromethane (5 mL) was added hydrogen chloride (4 N in 1,4-dioxane, 1 mL). The reaction was stirred at room temperature overnight. The mixture was concentrated under reduced pressure and dried under high vacuum to give (4S,4'S,7S,7'S,9aS,9a'S)—N,N'-((1S,1'S)-(hexane-1,6-diylbis(oxy))bis(1-phenylethane-2,1-diyl))bis(8,8-dimethyl-4-((S)-2-(methylamino)propanethioamido)-5-oxooctahydropyrrolo[2,1-b][1,3]thiazepine-7-carboxamide) dihydrochloride (78.4 mg, 0.07 mmol, 70.0% yield) as a white solid. $^1$H NMR (400 MHz, DMSO-$d_6$) δ ppm 10.96-10.88 (m, 2H), 9.62 (s, 2H), 8.61 (s, 1H), 8.42 (t, J=8.4 Hz, 3H), 7.37-7.31 (m, 8H), 7.27-7.23 (m, 2H), 5.42 (q, J=8.0 Hz, 2H), 5.17-5.10 (m, 2H), 5.03-4.98 (m, 2H), 4.24-4.20 (m, 4H), 3.57 (s, 2H), 3.54-3.47 (m, 4H), 3.40-3.38 (m, 2H), 3.32-3.28 (m, 4H), 3.19-3.13 (m, 2H), 2.96-2.93 (m, 2H), 2.48-2.47 (m, 6H), 2.24-2.21 (m, 4H), 1.94-1.81 (m, 4H), 1.44-1.42 (m, 10H), 1.09 (s, 6H), 1.03 (m, 6H). LCMS (2.5 min formic acid): Rt=1.300 min, m/z: 1038.7 (M+1)⁺.

Example 42

(4S,4'S,7S,7'S,9aS,9a'S)—N,N'-((1S,1'S)-((1,4-phenylenebis(methylene))bis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide) dihydrochloride

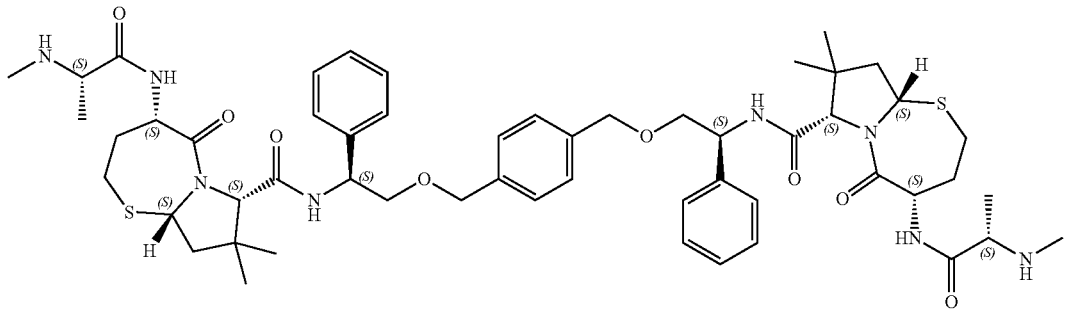

Step 1: (1S,1'S)-2,2'-((1,4-phenylenebis(methylene))bis(oxy))bis(1-phenylethan-1-amine)

To a solution of (S)-2-amino-2-phenylethan-1-ol (2.2 g, 16.0 mmol) in dry tetrahydrofuran (30 mL) was added sodium hydride (60%, dispersion in Paraffin Liquid) (760 mg, 31.6 mmol). After 30 minutes, 1,4-bis-bromomethylbenzene (2.0 g, 7.6 mmol) was added. The mixture was stirred at room temperature overnight. The mixture was quenched with ice water (50 mL) and extracted with ethyl acetate (3×60 mL). The combined organic layers were washed with brine, dried (Na$_2$SO$_4$), filtered and concentrated. The crude was purified by silica gel chromatography (dichloromethane/methanol (20:1 v/v)] to afford (1S,1'S)-2,2'-((1,4-phenylenebis(methylene))bis(oxy))bis(1-phenylethan-1-amine) (1.2 g, 3.2 mmol, 31% yield) as yellow oil. LCMS (2.5 min formic acid): Rt=1.14 min, m/z: 377.0 (M+1)$^+$.

Step 2: tert-butyl di-tert-butyl ((2S,2'S)-(((4S,4'S,7S,7'S,9aS,9a'S)-(((((1S,1'S)-((1,4-phenylenebis(methylene))bis(oxy))bis(1-phenylethane-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate)

A solution of (1S,1'S)-2,2'-((1,4-phenylenebis(methylene))bis(oxy))bis(1-phenylethan-1-amine) (100 mg, 0.266 mmol), (4S,7S,9aS)-4-((S)-2-((tert-butoxycarbonyl)(methyl)amino)propanamido)-8,8-dimethyl-5-oxooctahydropyrrolo[2,1-b][1,3]thiazepine-7-carboxylic acid (247.5 mg, 0.56 mmol), N-ethoxycarbonyl-2-ethoxy-1,2-dihydroquinoline (197.1 mg, 0.80 mmol) and N,N-diisopropylethylamine (137.3 mg, 0.29 mmol) in 1,2-dichloroethane (6 mL) was stirred at 50° C. overnight. The mixture was concentrated under reduced pressure and purified by thin layer chromatography [ethyl acetate/petroleum ether (2:1 v/v)] to give crude product (200 mg) as yellow oil. This material was further purified by Prep-HPLC to give tert-butyl di-tert-butyl ((2S,2'S)-(((4S,4'S,7S,7'S,9aS,9a'S)-(((((1S,1'S)-((1,4-phenylenebis(methylene))bis(oxy))bis(1-phenylethane-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (160 mg, 0.130 mmol, 49.1% yield) as white solid. LCMS (2.5 min formic acid): Rt=1.86 min, m/z: 514.1 {[(M-2Boc)+2]/2}$^+$.

Step 3: (4S,4'S,7S,7'S,9aS,9a'S)—N,N'-((1S,1'S)-((1,4-phenylenebis(methylene))bis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide) dihydrochloride To a solution of di-tert-butyl ((2S,2'S)-(((4S,4'S,7S,7'S,9aS,9a'S)-(((((1S,1'S)-((1,4-phenylenebis(methylene))bis(oxy))bis(1-phenylethane-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (160 mg, 0.13 mmol) in dichloromethane (15 mL) was added hydrogen chloride (4 N in 1,4-dioxane, 1 mL). The reaction was stirred at room temperature overnight. The mixture was concentrated under reduced pressure and dried under high vacuum to give (4S,4'S,7S,7'S,9aS,9a'S)—N,N'-((1S,1'S)-((1,4-phenylenebis(methylene))bis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide) dihydrochloride (110 mg, 0.11 mmol, 78% yield) as white solid. $^1$H NMR (400 MHz, DMSO-d$_6$) δ ppm 9.39 (s, 2H), 8.88-8.86 (m, 2H), 8.81 (d, J=6.8 Hz, 2H), 8.42 (d, J=8.0 Hz, 2H), 7.39-7.32 (m, 8H), 7.28-7.25 (m, 2H), 7.20 (s, 4H), 5.47 (t, J=7.6 Hz, 2H), 5.08 (q, J=6.0 Hz, 2H), 4.70 (t, J=9.0 Hz, 2H), 4.49-4.43 (m, 4H), 4.18 (s, 2H), 3.86 (s, 2H), 3.72-3.63 (m, 2H), 3.55-3.47 (m, 2H), 3.13 (t, J=12.2 Hz, 2H), 2.82-2.78 (m, 2H), 2.46 (s, 6H), 2.21-2.16 (m, 2H), 2.09-2.06 (m, 2H), 1.88-1.83 (m, 2H), 1.77-1.68 (m, 2H), 1.39 (d, J=6.8 Hz, 6H), 1.05 (m, 6H), 0.97 (m, 6H). LCMS (2.5 min formic acid): Rt=1.334 min, m/z: 1027.8 (M+1)$^+$.

Example 43

(4S,4'S,7S,7'S,9aS,9a'S)—N,N'-((1S,1'S)-((1,4-phenylenebis(methylene))bis(oxy))bis(1-phenylethane-2,1-diyl))bis(8,8-dimethyl-4-((S)-2-(methylamino)propanethioamido)-5-oxooctahydropyrrolo[2,1-b][1,3]thiazepine-7-carboxamide) dihydrochloride

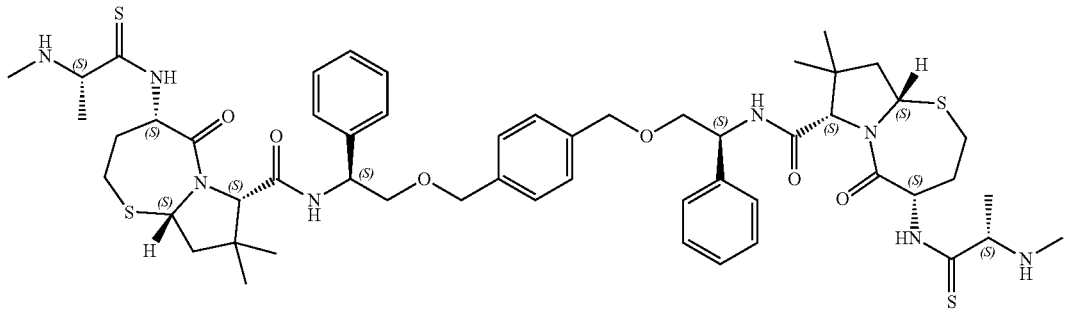

Step 1: di-tert-butyl ((2S,2'S)-(((4S,4'S,7S,7'S,9aS,9a'S)-((((1S,1'S)-((1,4-phenylenebis(methylene))bis(oxy))bis(1-phenylethane-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate)

To a solution of (1S,1'S)-2,2'-((1,4-phenylenebis(methylene))bis(oxy))bis(1-phenylethan-1-amine) (100 mg, 0.266 mmol), (4S,7S,9aS)-4-((S)-2-((tert-butoxycarbonyl)(methyl)amino)propanethioamido)-8,8-dimethyl-5-oxooctahydropyrrolo[2,1-b][1,3]thiazepine-7-carboxylic acid (Intermediate II) (256.4 mg, 0.56 mmol), N-ethoxycarbonyl-2-ethoxy-1,2-dihydroquinoline (197.1 mg, 0.80 mmol) and N,N-diisopropyl-ethylamine (137.3 mg, 0.29 mmol) in 1,2-dichloroethane (6 mL) was stirred at 50° C. overnight. The mixture was concentrated and purified by thin layer chromatography [ethyl acetate/petroleum ether (1:1 v/v)] to give crude product (200 mg) as yellow oil. This material was further purified by Prep-HPLC to give di-tert-butyl ((2S,2'S)-(((4S,4'S,7S,7'S,9aS,9a'S)-((((1S,1'S)-((1,4-phenylenebis(methylene))bis(oxy))bis(1-phenylethane-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate) (100 mg, 0.08 mmol, 30% yield) as white solid. LCMS (2.5 min formic acid): Rt=2.08 min, m/z: 530.6 {[(M-2Boc)+2]/2}$^+$.

Step 2: (4S,4'S,7S,7'S,9aS,9a'S)—N,N'-((1S,1'S)-((1,4-phenylenebis(methylene))bis(oxy))bis(1-phenylethane-2,1-diyl))bis(8,8-dimethyl-4-((S)-2-(methylamino)propanethioamido)-5-oxooctahydropyrrolo[2,1-b][1,3]thiazepine-7-carboxamide) dihydrochloride To a solution of di-tert-butyl ((2S,2'S)-(((4S,4'S,7S,7'S,9aS,9a'S)-((((1S,1'S)-((1,4-phenylenebis(methylene))bis(oxy))bis(1-phenylethane-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-thioxopropane-1,2-diyl))bis(methylcarbamate) (100 mg, 0.08 mmol) in dichloromethane (5 mL) was added hydrogen chloride (4 N in 1,4-dioxane, 1 mL) at room temperature. The reaction was stirred at room temperature overnight. The mixture was concentrated under reduced pressure and dried under high vacuum to afford (4S,4'S,7S,7'S,9aS,9a'S)—N,N'-((1S,1'S)-((1,4-phenylenebis(methylene))bis(oxy))bis(1-phenylethane-2,1-diyl))bis(8,8-dimethyl-4-((S)-2-(methylamino)propanethioamido)-5-oxooctahydropyrrolo[2,1-b][1,3]thiazepine-7-carboxamide) dihydrochloride (53 mg, 0.05 mmol, 63% yield) as white solid. $^1$H NMR (400 MHz, DMSO-$d_6$) δ ppm 10.97 (d, J=6.0 Hz, 1H), 10.89 (d, J=6.0 Hz, 1H), 9.74 (s, 1H), 9.57 (s, 1H), 8.62 (s, 1H), 8.49-8.45 (m, 3H), 7.39-7.32 (m, 8H), 7.28-7.25 (m, 2H), 7.20 (s, 4H), 5.42 (q, J=7.6 Hz, 2H), 5.16-5.06 (m, 4H), 4.49-4.43 (m, 4H), 4.27-4.21 (m, 4H), 3.65-3.59 (m, 2H), 3.42-3.38 (m, 2H), 3.14 (t, J=12 Hz, 2H), 2.89-2.86 (m, 2H), 2.48-2.47 (m, 6H), 2.24-2.18 (m, 4H), 1.92-1.76 (m, 4H), 1.43 (d, J=6.4 Hz, 6H), 1.07 (m, 6H), 0.99 (m, 6H). LCMS (2.5 min formic acid): Rt=1.397 min, m/z: 1058.7 (M+1)$^+$.

Examples 44-55

Examples 44-55 were prepared similarly to other compounds disclosed herein. The compounds were found to have characterizing data as set forth below.

Example 44

(4S,7S,9aS)—N-[(1R,2R)-2-({[4-({[(1R,2R)-1-[(4S,7S,9aS)-8,8-dimethyl-4-[(2S)-2-(methylamino)propanethioamido]-5-oxo-octahydropyrrolo[2,1-b][1,3]thiazepine-7-amido]-2,3-dihydro-1H-inden-2-yl]formamido}methyl)phenyl]methyl}carbamoyl)-2,3-dihydro-1H-inden-1-yl]-8,8-dimethyl-4-[(2S)-2-(methylamino)propanethioamido]-5-oxo-octahydropyrrolo[2,1-b][1,3]thiazepine-7-carboxamide

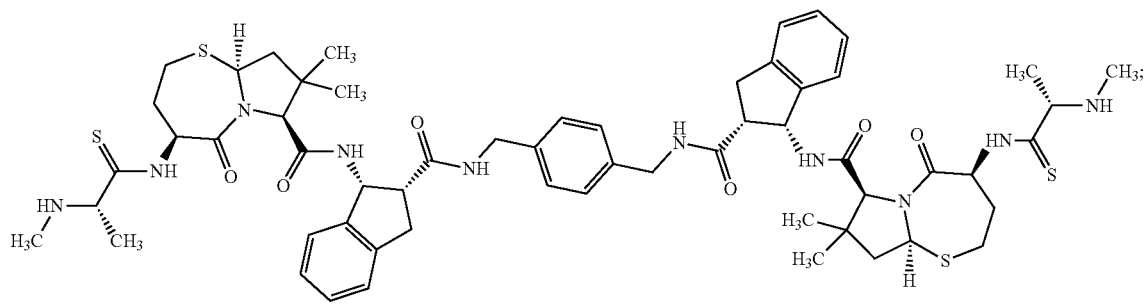 [SMILES: CN[C@@H](C)C(=S)N[C@H]1CCS[C@H]2CC(C)(C)[C@@H](C(=O)N[C@H]3c4ccccc4C[C@H]3C(=O)NCc3ccc(CNC(=O)[C@@H]4Cc5ccccc5[C@@H]4NC(=O)[C@H]4N5C(=O)[C@@H](NC(=S)[C@H](C)NC)CCS[C@H]5CC4(C)C)cc3)N2C1=O]

LCMS (ES, m/z): 1137.6 [M+H]⁺, retention time 1.265 min.

¹H NMR (400 MHz, DMSO-d₆): δ ppm 10.90 (d, J=34.6 Hz, 2H), 9.81-9.43 (m, 2H), 8.62 (s, 1H), 8.52-8.36 (m, 3H), 7.94 (dd, J=16.9, 9.3 Hz, 2H), 7.34-7.12 (m, 12H), 5.67 (t, J=8.6 Hz, 2H), 5.45 (q, J=8.3 Hz, 2H), 5.20-5.05 (m, 2H), 4.43 (d, J=14.8 Hz, 2H), 4.30 (s, 2H), 4.13 (d, J=13.3 Hz, 2H), 3.95 (dd, J=15.1, 4.3 Hz, 2H), 3.48-3.39 (m, 2H), 3.28-3.16 (m, 4H), 3.11-3.01 (m, 2H), 3.01-2.91 (m, 2H), 2.48 (s, 6H), 2.39-2.16 (m, 6H), 1.83-1.65 (m, 2H), 1.43 (d, J=6.0 Hz, 6H), 1.19-0.90 (m, 12H).

Example 45

(4S,7S,9aS)—N-[(1R,2R)-2-({[4-({[(1R,2R)-1-[(4S,7S,9aS)-8,8-dimethyl-4-[(2S)-2-(methylamino)propanamido]-5-oxo-octahydropyrrolo[2,1-b][1,3]thiazepine-7-amido]-2,3-dihydro-1H-inden-2-yl]formamido}methyl)phenyl]methyl}carbamoyl)-2,3-dihydro-1H-inden-1-yl]-8,8-dimethyl-4-[(2S)-2-(methylamino)propanamido]-5-oxo-octahydropyrrolo[2,1-b][1,3]thiazepine-7-carboxamide

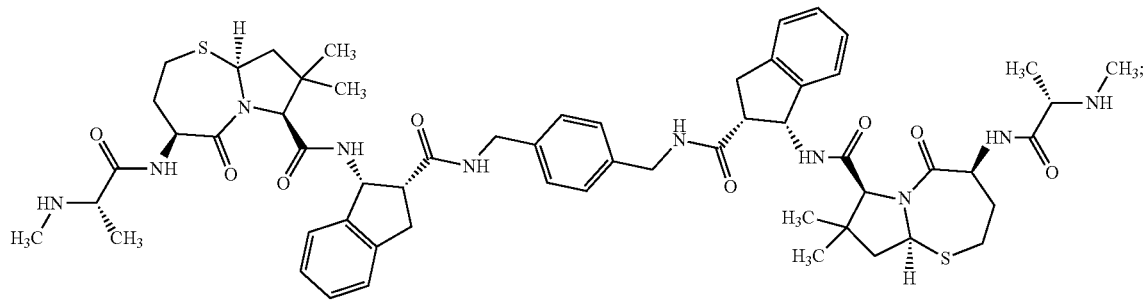 [SMILES: CN[C@@H](C)C(=O)N[C@H]1CCS[C@H]2CC(C)(C)[C@@H](C(=O)N[C@H]3c4ccccc4C[C@H]3C(=O)NCc3ccc(CNC(=O)[C@@H]4Cc5ccccc5[C@@H]4NC(=O)[C@H]4N5C(=O)[C@@H](NC(=O)[C@H](C)NC)CCS[C@H]5CC4(C)C)cc3)N2C1=O]

LCMS (ES, m/z): 1105.7 [M+H]⁺, retention time 1.268 min.

¹H NMR (400 MHz, DMSO-d₆): δ ppm 9.07 (s, 2H), 8.92-8.72 (m, 4H), 8.48-8.38 (m, 2H), 7.88 (d, J=8.9 Hz, 2H), 7.41-6.98 (m, 12H), 5.71-5.62 (m, 2H), 5.57-5.43 (m, 2H), 4.76-4.65 (m, 2H), 4.44 (dd, J=14.7, 6.7 Hz, 2H), 4.11 (s, 2H), 4.00-3.91 (m, 2H), 3.91-3.82 (m, 2H), 3.47-3.41 (m, 2H), 3.25-3.12 (m, 4H), 3.05 (dd, J=16.2, 8.6 Hz, 2H), 2.90 (d, J=13.0 Hz, 2H), 2.50-2.42 (m, 6H), 2.28-2.15 (m, 4H), 2.13-2.02 (m, 2H), 1.76-1.63 (m, 2H), 1.43-1.32 (m, 6H), 0.98 (s, 12H).

Example 46

(4S,7S,9aS)—N-[(1R,2R)-2-{4-[(1R,2R)-1-[(4S,7S,9aS)-8,8-dimethyl-4-[(2S)-2-(methylamino)propanamido]-5-oxo-octahydropyrrolo[2,1-b][1,3]thiazepine-7-amido]-2,3-dihydro-1H-indene-2-carbonyl]piperazine-1-carbonyl}-2,3-dihydro-1H-inden-1-yl]-8,8-dimethyl-4-[(2S)-2-(methylamino)propanamido]-5-oxo-octahydropyrrolo[2,1-b][1,3]thiazepine-7-carboxamide

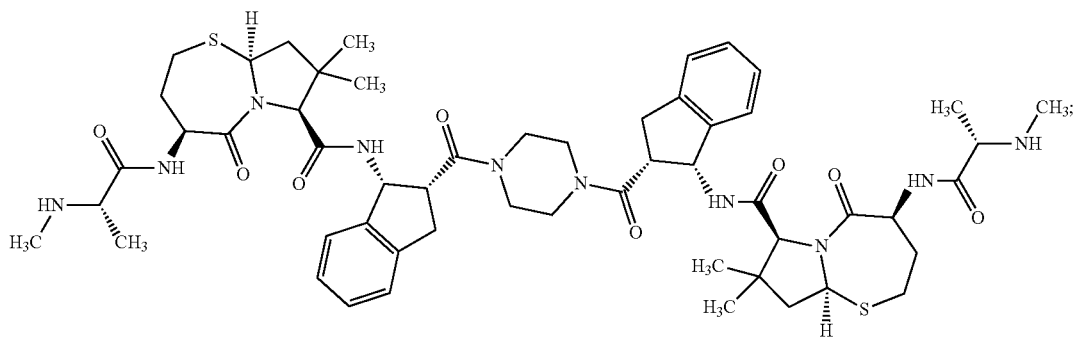 [SMILES: CN[C@@H](C)C(=O)N[C@H]1CCS[C@H]2CC(C)(C)[C@@H](C(=O)N[C@H]3c4ccccc4C[C@H]3C(=O)N3CCN(C(=O)[C@@H]4Cc5ccccc5[C@@H]4NC(=O)[C@H]4N5C(=O)[C@@H](NC(=O)[C@H](C)NC)CCS[C@H]5CC4(C)C)CC3)N2C1=O]

LCMS (ES, m/z): 1055.3 [M+H]⁺, retention time 1.185 min.

¹H NMR (400 MHz, DMSO-d₆): δ ppm 9.66-9.32 (m, 2H), 9.06-8.71 (m, 4H), 7.98-7.85 (m, 1H), 7.67 (d, J=9.5 Hz, 1H), 7.38-7.11 (m, 8H), 5.78-5.59 (m, 2H), 5.55-5.40 (m, 2H), 4.72-4.58 (m, 2H), 4.09-3.80 (m, 6H), 3.77-3.47 (m, 10H), 3.46-3.32 (m, 4H), 3.29-3.12 (m, 2H), 3.02-2.77 (m, 4H), 2.50-2.43 (m, 6H), 2.28-2.09 (m, 4H), 1.46-1.37 (m, 6H), 1.07-0.83 (m, 12H).

Example 47

(4S,7S,9aS)-N-[(1R,2R)-2-{4-[(1R,2R)-1-[(4S,7S,9aS)-8,8-dimethyl-4-[(2S)-2-(methylamino)propanethioamido]-5-oxo-octahydropyrrolo[2,1-b][1,3]thiazepine-7-amido]-2,3-dihydro-1H-indene-2-carbonyl]piperazine-1-carbonyl}-2,3-dihydro-1H-inden-1-yl]-8,8-dimethyl-4-[(2S)-2-(methylamino)propanethioamido]-5-oxo-octahydropyrrolo[2,1-b][1,3]thiazepine-7-carboxamide

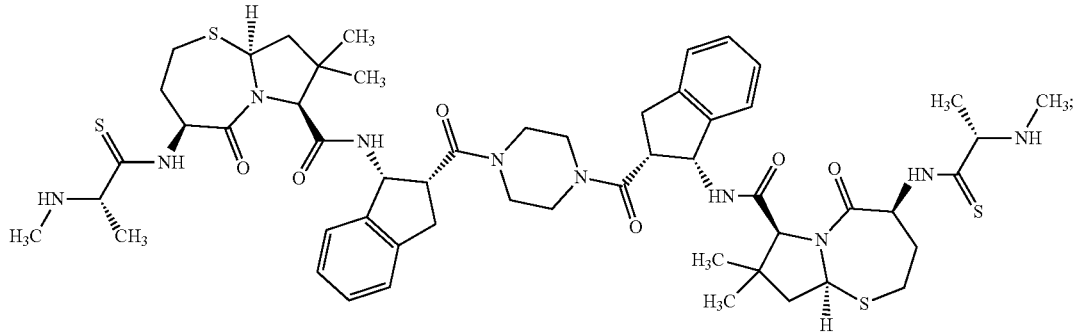

LCMS (ES, m/z): 1086.6 [M+H]⁺, retention time 1.337 min.

¹H NMR (400 MHz, DMSO-d₆): δ ppm 11.37-10.79 (m, 2H), 9.95-9.38 (m, 2H), 8.80-8.22 (m, 2H), 7.97 (dd, J=28.6, 9.8 Hz, 1H), 7.72 (d, J=9.4 Hz, 1H), 7.38-7.09 (m, 8H), 5.79-5.59 (m, 2H), 5.44 (dd, J=16.3, 8.2 Hz, 2H), 5.22-4.91 (m, 2H), 4.71-4.31 (m, 2H), 4.15-3.79 (m, 4H), 3.80-3.38 (m, 10H), 3.33-3.12 (m, 4H), 3.04-2.83 (m, 4H), 2.51-2.49 (m, 6H), 2.37-2.00 (m, 6H), 1.48-1.38 (m, 6H), 1.01 (d, J=9.6 Hz, 12H).

Example 48

(4S,7S,9aS)-N-[(1S,2R)-2-[(8-{[(1S,2R)-1-[(4S,7S,9aS)-8,8-dimethyl-4-[(2S)-2-(methylamino)propanamido]-5-oxo-octahydropyrrolo[2,1-b][1,3]thiazepine-7-amido]-2,3-dihydro-1H-inden-2-yl]oxy}octyl)oxy]-2,3-dihydro-1H-inden-1-yl]-8,8-dimethyl-4-[(2S)-2-(methylamino)propanamido]-5-oxo-octahydropyrrolo[2,1-b][1,3]thiazepine-7-carboxamide

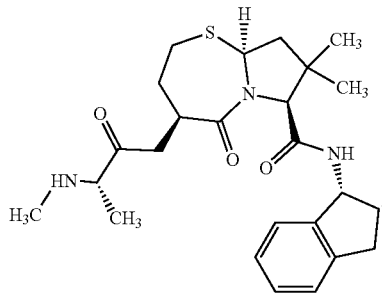
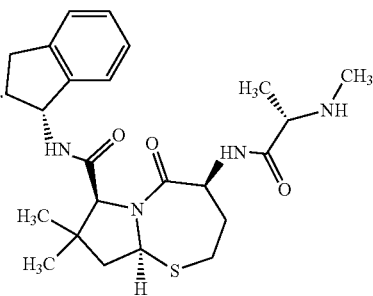

LCMS (ES, m/z): 1059.7 [M+H]⁺, retention time 1.348 min.

¹H NMR (400 MHz, DMSO-d₆) d ppm δ 9.50 (s, 2H), 8.93 (s, 2H), 8.87 (d, J=6.6 Hz, 2H), 7.91 (d, J=8.7 Hz, 2H), 7.27-7.19 (m, 8H), 5.51 (t, J=7.9 Hz, 2H), 5.33 (dd, J=8.6, 5.4 Hz, 2H), 4.78-4.70 (m, 2H), 4.24 (s, 2H), 4.11 (dd, J=9.3, 4.1 Hz, 2H), 3.89 (dd, J=10.5, 6.1 Hz, 2H), 3.44-3.38 (m, 4H), 3.20 (t, J=11.8 Hz, 2H), 2.98 (d, J=3.7 Hz, 4H), 2.95-2.85 (m, 2H), 2.47 (s, 6H), 2.27-2.11 (m, 4H), 1.89-1.76 (m, 4H), 1.47-1.36 (m, 10H), 1.24-1.17 (m, 8H), 1.08 (s, 6H), 1.06 (s, 6H).

Example 49

(4S,7S,9aS)—N-[(1R,2R)-2-[(6-{[(1R,2R)-1-[(4S,7S,9aS)-8,8-dimethyl-4-[(2S)-2-(methylamino)propanamido]-5-oxo-octahydropyrrolo[2,1-b][1,3]thiazepine-7-amido]-2,3-dihydro-1H-inden-2-yl]formamido}hexa-2,4-diyn-1-yl)carbamoyl]-2,3-dihydro-1H-inden-1-yl]-8,8-dimethyl-4-[(2S)-2-(methylamino)propanamido]-5-oxo-octahydropyrrolo[2,1-b][1,3]thiazepine-7-carboxamide

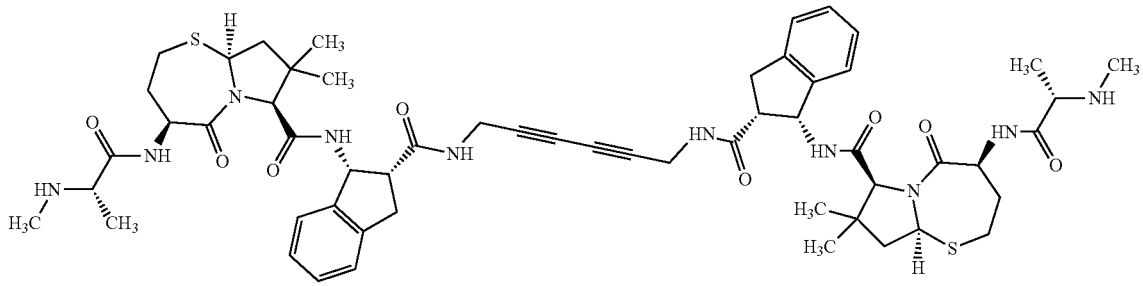

LCMS (ES, m/z): 1105.7 [M+H]+, retention time 1.370 min.
¹H NMR (400 MHz, DMSO-$d_6$) d ppm δ 9.05 (s, 2H), 8.77 (d, J=7.0 Hz, 4H), 8.45 (s, 2H), 7.87 (d, J=9.3 Hz, 2H), 7.29 (d, J=8.2 Hz, 2H), 7.17-7.05 (m, 6H), 5.46 (t, J=8.0 Hz, 2H), 5.37 (dd, J=9.1, 5.4 Hz, 2H), 4.72-4.63 (m, 2H), 4.12-4.01 (m, 4H), 3.89 (dd, J=12.1, 6.5 Hz, 2H), 3.82 (d, J=4.3 Hz, 1H), 3.77 (d, J=4.8 Hz, 1H), 3.65 (s, 1H), 3.57 (s, 1H), 3.21-3.11 (m, 2H), 2.96-2.88 (m, 2H), 2.87-2.80 (m, 2H), 2.78-2.64 (m, 4H), 2.18 (dd, J=12.9, 7.3 Hz, 2H), 2.12-1.90 (m, 8H), 1.77-1.67 (m, 2H), 1.37 (d, J=6.8 Hz, 6H), 1.24 (s, 4H), 0.99 (d, J=13.7 Hz, 12H).

Example 50

(4S,7S,9aS)-N-[(1S)-2-[2-(4-{[(2S)-2-{[(4S,7S,9aS)-8,8-dimethyl-4-[(2S)-2-(methylamino)propanamido]-5-oxo-octahydropyrrolo[2,1-b][1,3]thiazepin-7-yl]formamido}-2-phenylethoxy]methyl}-1H-1,2,3-triazol-1-yl)ethoxy]-1-phenylethyl]-8,8-dimethyl-4-[(2S)-2-(methylamino)propanamido]-5-oxo-octahydropyrrolo[2,1-b][1,3]thiazepine-7-carboxamide

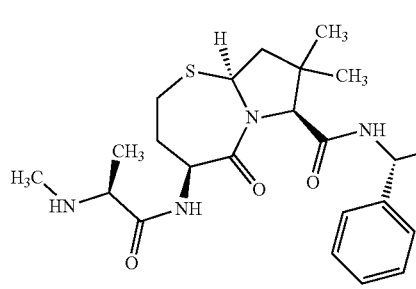
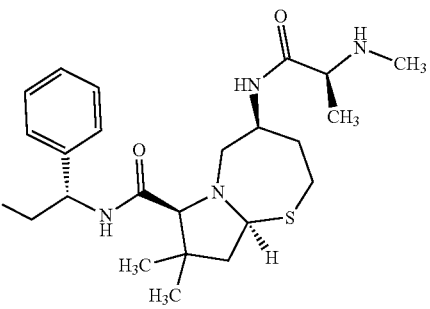

LCMS (ES, m/z): 1032.7 [M+H]+, retention time 1.224 min.
¹H NMR (400 MHz, DMSO-$d_6$) δ ppm 9.74-9.45 (m, 2H), 8.92 (d, J=5.8 Hz, 2H), 8.85 (d, J=7.0 Hz, 2H), 8.39 (d, J=8.0 Hz, 2H), 7.79 (s, 1H), 7.42-7.15 (m, 10H), 5.46 (t, J=7.5 Hz, 2H), 5.01 (td, J=14.0, 6.5 Hz, 2H), 4.73-4.65 (m, 2H), 4.49-4.45 (m, 4H), 4.17 (d, J=3.4 Hz, 2H), 3.92-3.81 (m, 2H), 3.87 (t, J=4.7 Hz, 2H), 3.63-3.50 (m, 4H), 3.23-3.06 (m, 2H), 2.95-2.80 (m, 2H), 2.45 (t, J=5.0 Hz, 6H), 2.26-2.03 (m, 4H), 1.92-1.66 (m, 4H), 1.39 (d, J=6.8 Hz, 6H), 1.04 (s, 6H), 0.96 (s, 6H).

Example 51

(4S,7S,9aS)-N-[(1S,2R)-2-[3-(3-{[(1S,2R)-1-[(4S,7S,9aS)-8,8-dimethyl-4-[(2S)-2-(methylamino)propanamido]-5-oxo-octahydropyrrolo[2,1-b][1,3]thiazepine-7-amido]-2,3-dihydro-1H-inden-2-yl]oxy}propoxy)propoxy]-2,3-dihydro-1H-inden-1-yl]-8,8-dimethyl-4-[(2S)-2-(methylamino)propanamido]-5-oxo-octahydropyrrolo[2,1-b][1,3]thiazepine-7-carboxamide

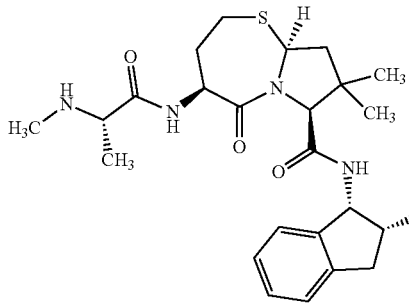
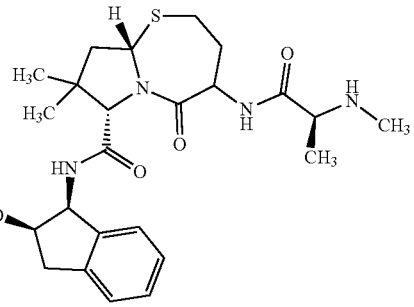

LCMS (ES, m/z): 1047.7 [M+H]⁺, retention time 1.147 min.

¹H NMR (400 MHz, DMSO-d₆) d ppm δ 9.47 (s, 2H), 8.99-8.81 (m, 4H), 7.91 (d, J=8.7 Hz, 2H), 7.28-7.18 (m, 8H), 5.51 (t, J=7.9 Hz, 2H), 5.34 (dd, J=8.6, 5.4 Hz, 2H), 4.74 (dd, J=9.9, 7.7 Hz, 2H), 4.24 (s, 2H), 4.12 (dd, J=9.1, 4.0 Hz, 2H), 3.89 (dd, J=11.1, 6.4 Hz, 2H), 3.52-3.39 (m, 6H), 3.32-3.30 (m, 2H), 3.25-3.15 (m, 2H), 2.98 (d, J=3.5 Hz, 4H), 2.95-2.87 (m, 2H), 2.47 (s, 6H), 2.30-2.10 (m, 4H), 1.88-1.75 (m, 4H), 1.73-1.58 (m, 4H), 1.41 (d, J=6.9 Hz, 6H), 1.07 (d, J=9.5 Hz, 12H).

Example 52

(4S,7S,9aS)-N-[(1S)-2-[2-(4-{[(2S)-2-{[(4S,7S,9aS)-8,8-dimethyl-4-[(2S)-2-(methylamino)propanethioamido]-5-oxo-octahydropyrrolo[2,1-b][1,3]thiazepin-7-yl]formamido}-2-phenylethoxy]methyl}-1H-1,2,3-triazol-1-yl)ethoxy]-1-phenylethyl]-8,8-dimethyl-4-[(2S)-2-(methylamino)propanethioamido]-5-oxo-octahydropyrrolo[2,1-b][1,3]thiazepine-7-carboxamide

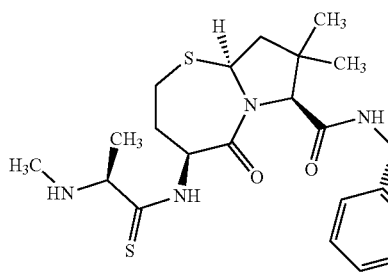
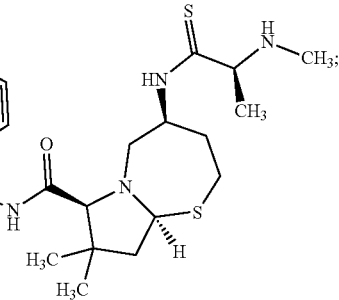

LCMS (ES, m/z): 1064.6 [M+H]⁺, retention time 1.267 min.

¹H NMR (400 MHz, DMSO-d₆) d ppm δ 11.02-10.87 (m, 2H), 9.65 (d, J=70.2 Hz, 2H), 8.62 (s, 1H), 8.43 (t, J=7.0 Hz, 3H), 7.78 (s, 1H), 7.37-7.23 (m, 10H), 5.42 (q, J=7.6 Hz, 2H), 5.17-5.07 (m, 2H), 5.07-4.95 (m, 2H), 4.53-4.42 (m, 4H), 4.30-4.16 (m, 4H), 3.61-3.54 (m, 4H), 3.21-3.09 (m, 2H), 2.99-2.88 (m, 2H), 2.49-2.44 (m, 6H), 2.29-2.14 (m, 4H), 1.95-1.77 (m, 4H), 1.43 (d, J=6.3 Hz, 6H), 1.24 (s, 2H), 1.07 (s, 6H), 0.98 (s, 6H).

Example 53

(4S,7S,9aS)-N-[(1S)-2-[3-(4-{[(2S)-2-{[(4S,7S,9aS)-8,8-dimethyl-4-[(2S)-2-(methylamino)propanethioamido]-5-oxo-octahydropyrrolo[2,1-b][1,3]thiazepin-7-yl]formamido}-2-phenylethoxy]methyl}-1H-1,2,3-triazol-1-yl)propoxy]-1-phenylethyl]-8,8-dimethyl-4-[(2S)-2-(methylamino)propanethioamido]-5-oxo-octahydropyrrolo[2,1-b][1,3]thiazepine-7-carboxamide

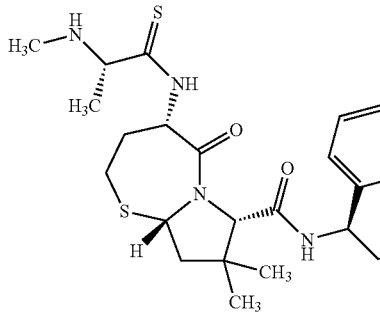
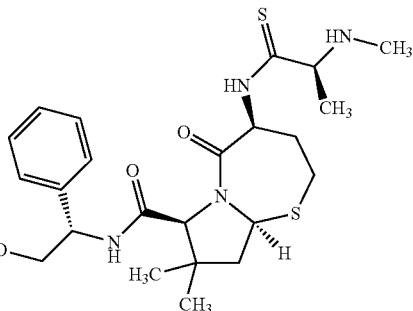

LCMS (ES, m/z): 1079.7 [M+H]⁺, retention time 1.148 min.

¹H NMR (400 MHz, DMSO-d$_6$): d ppm δ 10.99 (d, J=3.8 Hz, 1H), 10.90 (d, J=6.0 Hz, 1H),9.75 (s, 1H), 9.57 (s, 1H), 8.63 (s, 1H), 8.51-8.31 (m, 3H), 7.88 (s, 1H), 7.40-7.23 (m, 10H), 5.49-5.35 (m, 2H), 5.13 (dd, J=16.0, 9.1 Hz, 2H), 5.07-4.98 (m, 2H), 4.50 (s, 2H), 4.36-4.15 (m, 6H), 3.61-3.55 (m, 4H), 3.39-3.28 (m, 2H), 3.21-3.10 (m, 2H), 3.01-2.88 (m, 2H), 2.49-2.40 (m, 6H), 2.30-2.14 (m, 4H), 2.02-1.81 (m, 6H), 1.43 (d, J=6.4 Hz, 6H), 1.11-1.04 (m, 6H), 1.03 (s, 3H), 0.96 (s, 3H).

Example 54

(4S,7S,9aS)-8,8-dimethyl-4-[(2S)-2-(methylamino)propanethioamido]-5-oxo-N-[(1R,2R)-2-{[(1rs,4rs)-4-[(1R,2R)-1-[(4S,7S,9aS)-8,8-dimethyl-4-[(2S)-2-(methylamino)propanethioamido]-5-oxo-octahydropyrrolo[2,1-b][1,3]thiazepine-7-amido]-2,3-dihydro-1H-indene-2-amido]cyclohexyl]carbamoyl}-2,3-dihydro-1H-inden-1-yl]-octahydropyrrolo[2,1-b][1,3]thiazepine-7-carboxamide

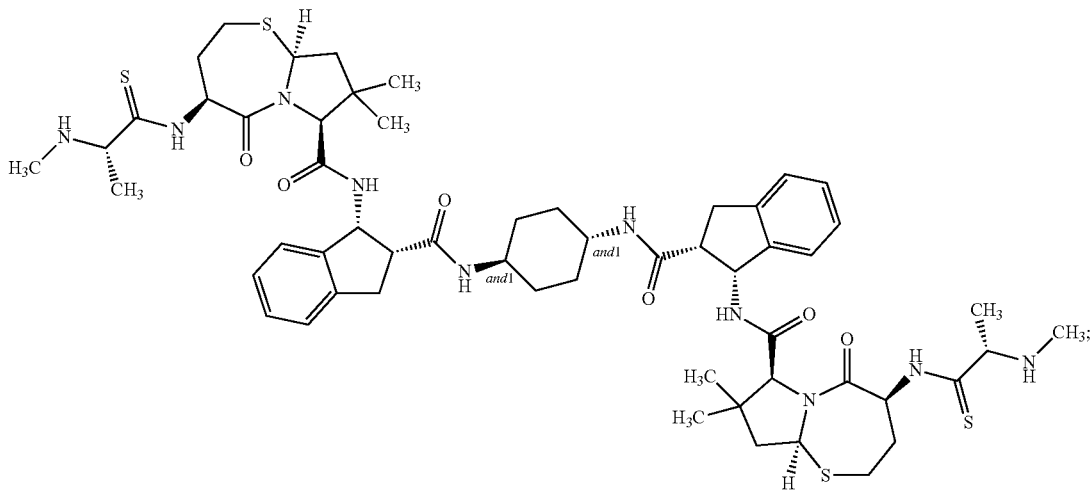 [SMILES: CN[C@@H](C)C(=S)N[C@H]1CCS[C@H]2CC(C)(C)[C@@H](C(=O)N[C@H]3c4ccccc4C[C@H]3C(=O)N[C@H]3CC[C@H](NC(=O)[C@@H]4Cc5ccccc5[C@@H]4NC(=O)[C@H]4N5C(=O)[C@@H](NC(=S)[C@H](C)NC)CCS[C@H]5CC4(C)C)CC3)N2C1=O]

LCMS (ES, m/z): 1115.6 [M+H]⁺, retention time 1.136 min.

¹H NMR (400 MHz, DMSO-d$_6$): d ppm δ 11.00-10.80 (m, 2H), 9.56 (s, 1H), 9.41 (s, 1H), 8.64 (s, 1H), 8.46 (s, 1H), 8.00-7.82 (m, 4H), 7.45-7.12 (m, 8H), 5.60 (t, J=16.0 Hz, 2H), 5.50-5.37 (m, 2H), 5.17-5.07 (m, 2H), 4.41-4.26 (m, 2H), 4.14 (d, J=8.0 Hz, 2H), 3.75-3.65 (m, 2H), 3.35-3.27 (m, 2H), 3.25-3.07 (m, 4H), 3.05-2.91 (m, 4H), 2.50 (s, 6H), 2.30-2.02 (m, 6H), 1.85-1.67 (m, 6H), 1.44 (d, J=4.0 Hz, 6H), 1.25-1.10 (m, 4H), 1.03 (d, J=8.0 Hz, 12H).

Example 55

(4S,7S,9aS)-8,8-dimethyl-4-[(2S)-2-(methylamino)
propanamido]-5-oxo-N-[(1R,2R)-2-{[(1rs,4rs)-4-
[(1R,2R)-1-[(4S,7S,9aS)-8,8-dimethyl-4-[(2S)-2-
(methylamino)propanamido]-5-oxo-
octahydropyrrolo[2,1-b][1,3]thiazepine-7-amido]-2,
3-dihydro-1H-indene-2-amido]cyclohexyl]
carbamoyl}-2,3-dihydro-1H-inden-1-yl]-
octahydropyrrolo[2,1-b][1,3]thiazepine-7-
carboxamide

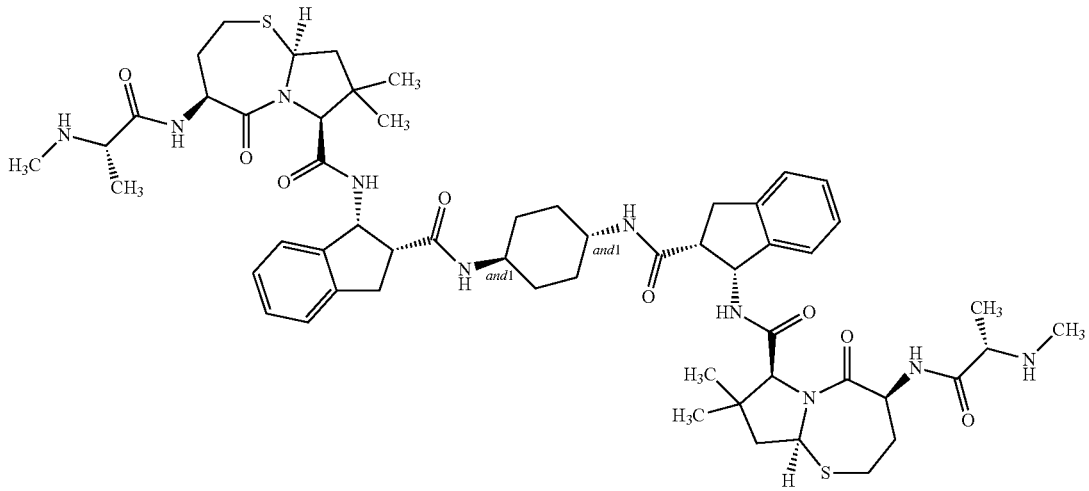

LCMS (ES, m/z): 1083.7 [M+H]$^+$, retention time 1.091 min.

$^1$H NMR (400 MHz, DMSO-d): d ppm δ 9.17 (s, 2H), 8.92 (s, 2H), 8.75 (d, J=4.0 Hz, 2H), 7.90 (s, 2H), 7.84 (d, J=8.0 Hz, 2H), 7.30-7.05 (m, 8H), 5.60 (t, J=16.0 Hz, 2H), 5.48 (t, J=16.0 Hz, 2H), 4.75-4.60 (m, 2H), 4.11 (s, 2H), 3.98-3.85 (m, 2H), 3.38-3.28 (m, 2H), 3.24-3.10 (m, 4H), 3.07-2.97 (m, 2H), 2.95-2.85 (m, 2H), 2.50-2.43 (m, 6H), 2.25-2.00 (m, 6H), 1.87-1.73 (m, 4H), 1.73-1.62 (m, 2H), 1.40 (d, J=8.0 Hz, 6H), 1.25-1.17 (m, 2H), 1.17-1.10 (m, 2H), 1.02 (s, 12H).

Example 56

(4S,4'S,7S,7'S,9aS,9a'S)—N,N'-((1S,1'S)-((naphtha-
lene-2,7-diylbis(methylene))bis(oxy))bis(1-phenyle-
thane-2,1-diyl))bis(8,8-dimethyl-4-((S)-2-(methyl-
amino)propanamido)-5-oxooctahydropyrrolo[2,1-b]
[1,3]thiazepine-7-carboxamide)

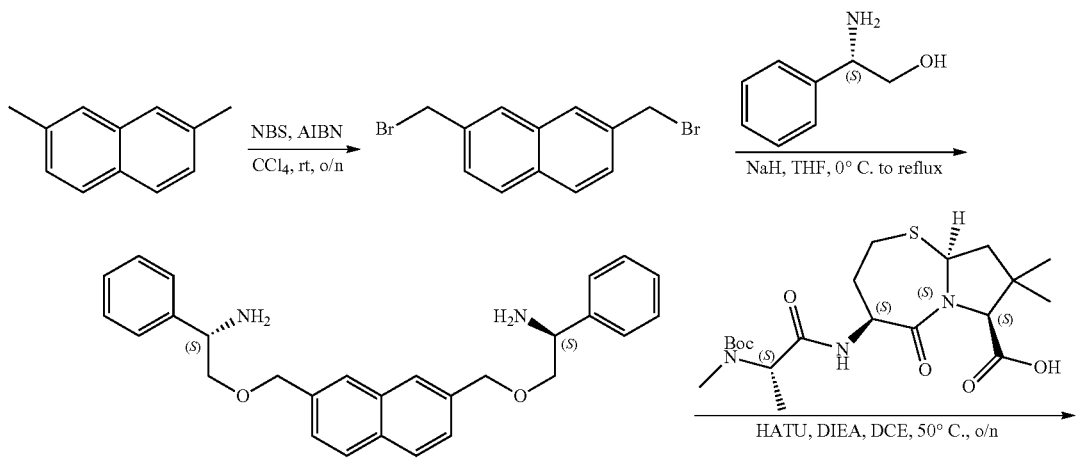

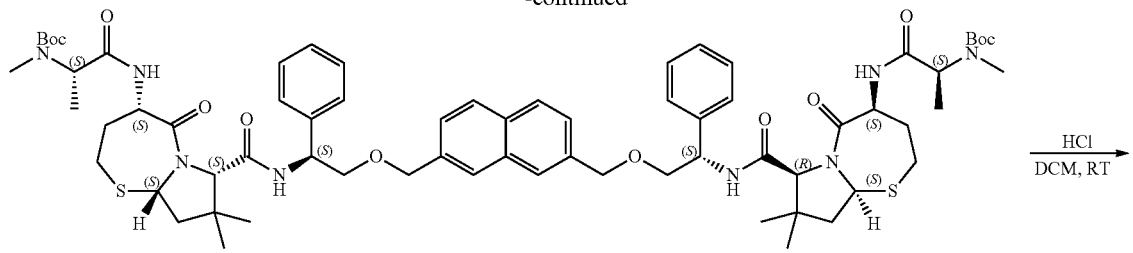

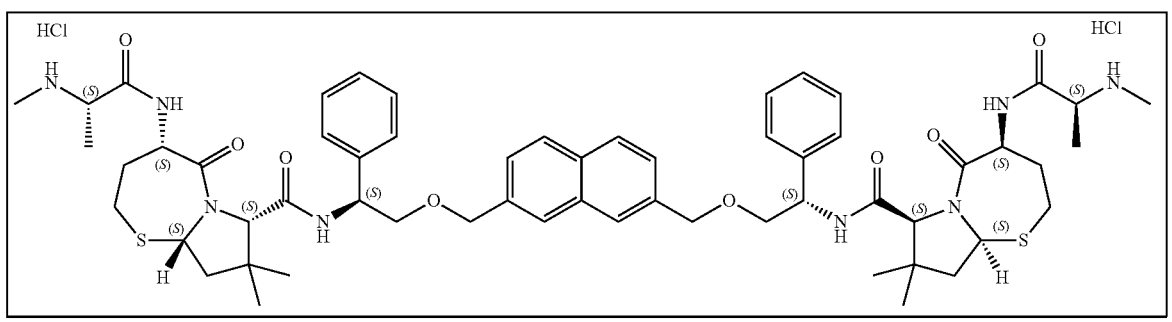

Synthesis of 2,7-bis(bromomethyl)naphthalene

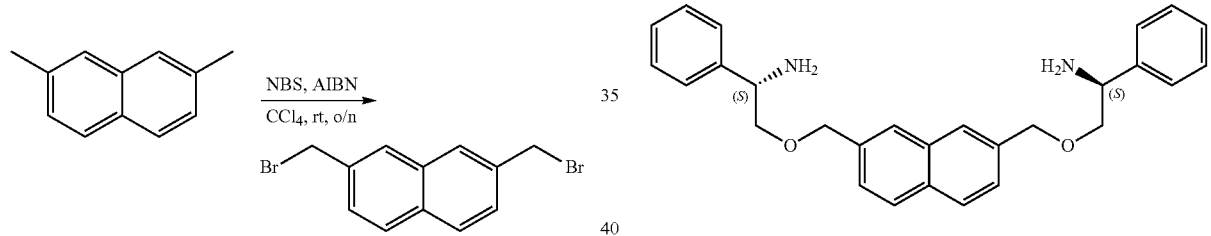

To a solution of 2,7-dimethylnaphthalene (1 g, 6.40 mmol) and 1-bromopyrrolidine-2,5-dione (2.5 g, 14.08 mmol) in perchloromethane (40 mL) was added 2,2'-Azobis-(2-methylpropanenitrile) (105 mg, 0.64 mmol). The mixture was stirred at 80° C. overnight. The insoluble solid was removed by filtration through a celite pad. The filtrate was washed with saturated sodium bicarbonate solution (20 mL), dried over anhydrous sodium sulfate, filtered and concentrated to get the crude. It was purified by column chromatography on silica gel (petroleum ether/ethyl acetate=100:1) to afford 2,7-bis(bromomethyl)naphthalene (600 mg, 1.91 mmol, 29.9% yield) as a white solid.

Synthesis of (1S,1'S)-2,2'-((naphthalene-2,7-diylbis (methylene))bis(oxy))bis(1-phenylethan-1-amine)

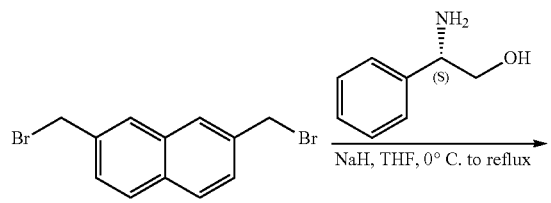

To a solution of (S)-2-amino-2-phenylethan-1-ol (585 mg, 3.92 mmol) in tetrahydrofuran (20 mL) at 0° C. was added portion wise sodium hydrogen (60%, dispersion in Paraffin Liquid) (171 g, 4.27 mmol). The mixture was warmed to room temperature naturally. Then 2,7-bis(bromomethyl) naphthalene (560 mg, 1.78 mmol) was dropped and the resulting mixture was heated to 70° C. It was stirred at 70° C. overnight. The reaction mixture was quenched ice water (30 mL) and extracted with ethyl acetate (3×20 mL). The organic layers were combined, washed with brine (20 mL), dried over anhydrous sodium sulfate, filtered and concentrated to get the crude. It was purified by column chromatography on silica gel (dichloromethane/methanol=15:1) to afford (1S,1'S)-2,2'-((naphthalene-2,7-diylbis(methylene)) bis(oxy))bis(1-phenylethan-1-amine) (200 mg, 0.469 mmol, 26.3% yield) as a black oil.

LCMS (ES, m/z): 426.8 [M+H]$^+$, retention time 1.047 min.

Synthesis of tert-butyl((S)-1-(((4S,7R,9aS)-7-(((S)-2-((7-(((S)-2-((4S,7S,9aS)-4-((S)-2-((tert-butoxycarbonyl)(methyl)amino)propanamido)-8,8-dimethyl-5-oxooctahydropyrrolo[2,1-b][1,3]thiazepine-7-carboxamido)-2-phenylethoxy)methyl)naphthalen-2-yl)methoxy)-1-phenylethyl)carbamoyl)-8,8-dimethyl-5-oxooctahydropyrrolo[2,1-b][1,3]thiazepin-4-yl)amino)-1-oxopropan-2-yl)(methyl)carbamate

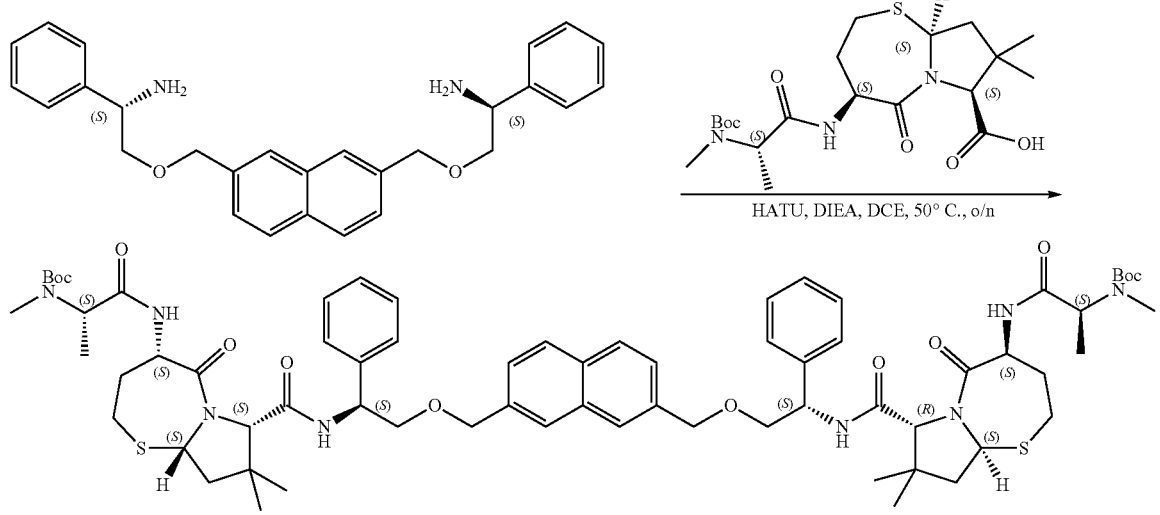

To a solution of (4S,7S,9aS)-4-((S)-2-((tert-butoxycarbonyl)(methyl)amino)propanamido)-8,8-dimethyl-5-oxooctahydropyrrolo[2,1-b][1,3]thiazepine-7-carboxylic acid (499 mg, 1.13 mmol), ethyl 2-ethoxyquinoline-1(2H)-carboxylate (325 mg, 1.31 mmol) and N,N-diisopropylethylamine (243 mg, 1.88 mmol) in 1,2-dichloroethane (10 mL) was added (1S,1'S)-2,2'-((naphthalene-2,7-diylbis(methylene))bis(oxy))bis(1-phenylethan-1-amine) (200 mg, 0.47 mmol). The mixture was stirred at 50° C. overnight. The reaction was concentrated to get the crude. It was purified by column chromatography on silica gel (petroleum ether/ethyl acetate=1:4) to give crude product. Then the crude product was purified by prep-HPLC to get product (110 mg, 0.086 mmol, 18.3% yield) as a white solid.

LCMS (ES, m/z): 539.3 [M/2-Boc+H]$^+$, retention time 1.770 min.

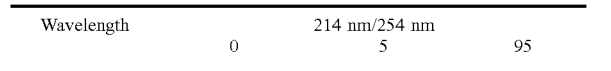

| Instrument Column | Combi Flash WelFlash® C18-I Spherical C18, 20-40 μm Size 120 g |  |  |
|---|---|---|---|
| Flow Rate |  | 20 mL/min |  |
| Gradient Method | Time (min) | ACN | H$_2$O |
|  | 5 | 5 | 95 |
|  | 50 | 45 | 55 |
|  | 60 | 45 | 55 |
|  | 90 | 100 | 0 |

Synthesis of (4S,4'S,7S,7'S,9aS,9a'S)—N,N'-((1S,1'S)-((naphthalene-2,7-diylbis(methylene))bis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide)

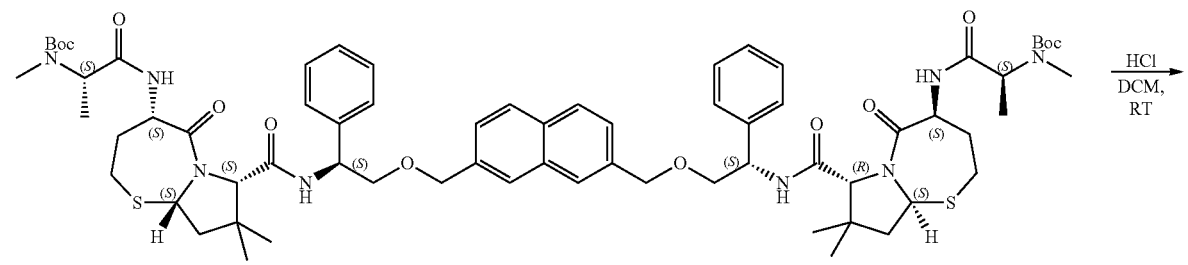

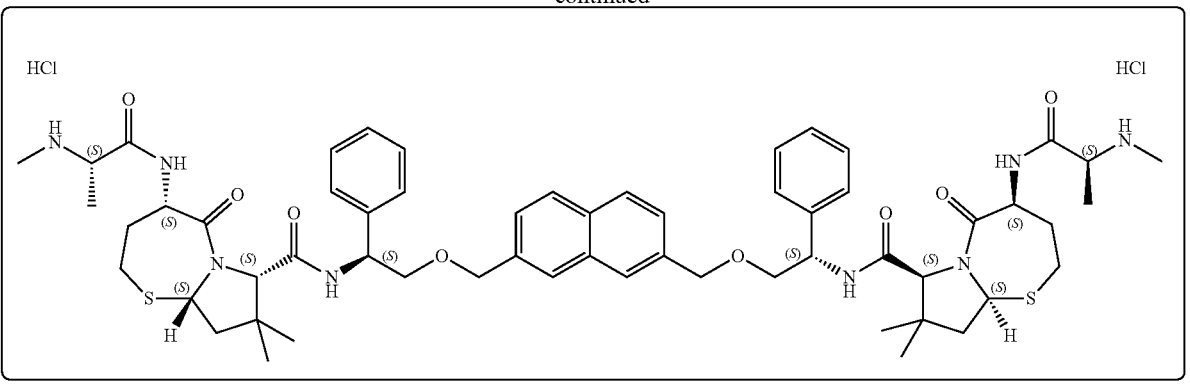

To a solution of tert-butyl ((S)-1-(((4S,7R,9aS)-7-(((S)-2-((7-(((S)-2-((4S,7S,9aS)-4-((S)-2-((tert-butoxycarbonyl)(methyl)amino)propanamido)-8,8-dimethyl-5-oxooctahydropyrrolo[2,1-b][1,3]thiazepine-7-carboxamido)-2-phenylethoxy)methyl)naphthalen-2-yl)methoxy)-1-phenylethyl)carbamoyl)-8,8-dimethyl-5-oxooctahydropyrrolo[2,1-b][1,3]thiazepin-4-yl)amino)-1-oxopropan-2-yl)(methyl)carbamate (110 mg, 0.086 mmol) in dichloromethane (5 mL) was added 4 N hydrochloric acid/dioxane (0.5 mL). The mixture was stirred at room temperature overnight. The reaction mixture was concentrated to get the desired product (90 mg, 0.078 mmol, 90.9% yield) as a white solid. The compound was further lyophilized to remove solvent residue.

LCMS (ES, m/z): 1077.4 [M+H]$^+$, retention time 1.253 min.

$^1$H NMR (400 MHz, DMSO-d$_6$) δ ppm 9.48 (s, 2H), 9.01-8.77 (m, 4H), 8.47 (d, J=8.1 Hz, 2H), 7.85 (d, J=8.4 Hz, 2H), 7.68 (s, 2H), 7.45-7.33 (m, 10H), 7.31-7.25 (m, 2H), 5.46 (t, J=7.9 Hz, 2H), 5.14 (dd, J=13.1, 6.6 Hz, 2H), 4.74-4.59 (m, 6H), 4.20 (s, 2H), 3.85 (s, 2H), 3.72-3.60 (m, 4H), 3.13 (t, J=12.3 Hz, 2H), 2.84-2.73 (m, 2H), 2.45 (s, 6H), 2.18 (dd, J=12.6, 7.0 Hz, 2H), 2.11-2.02 (m, 2H), 1.87 (dd, J=12.5, 9.0 Hz, 2H), 1.73 (dd, J=22.6, 11.5 Hz, 2H), 1.40 (d, J=6.9 Hz, 6H), 1.05 (s, 6H), 0.99 (s, 6H).

Example 57

(4S,4'S,7S,7'S,9aS,9a'S)—N,N'-((1S,1'S,2R,2'R)-(decane-1,10-diylbis(oxy))bis(2,3-dihydro-1H-indene-2,1-diyl))bis(8,8-dimethyl-4-((S)-2-(methylamino)propanamido)-5-oxooctahydropyrrolo[2,1-b][1,3]thiazepine-7-carboxamide) dihydrochloride

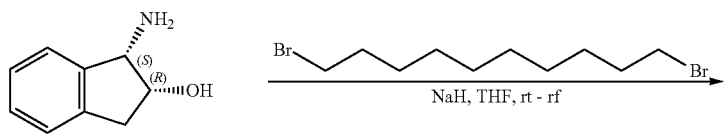

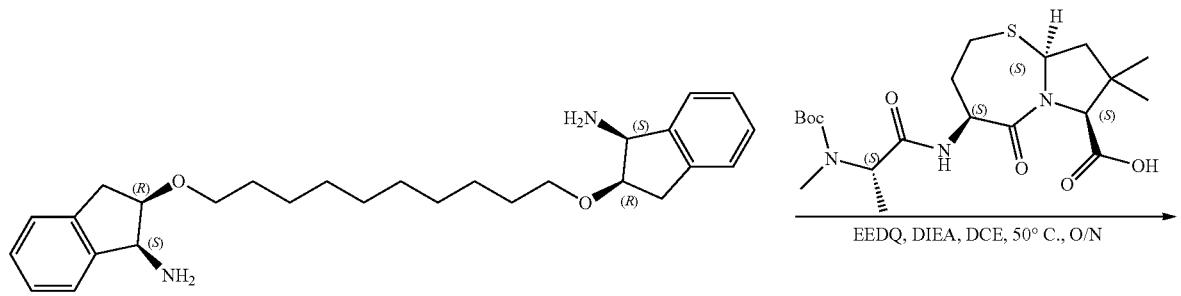

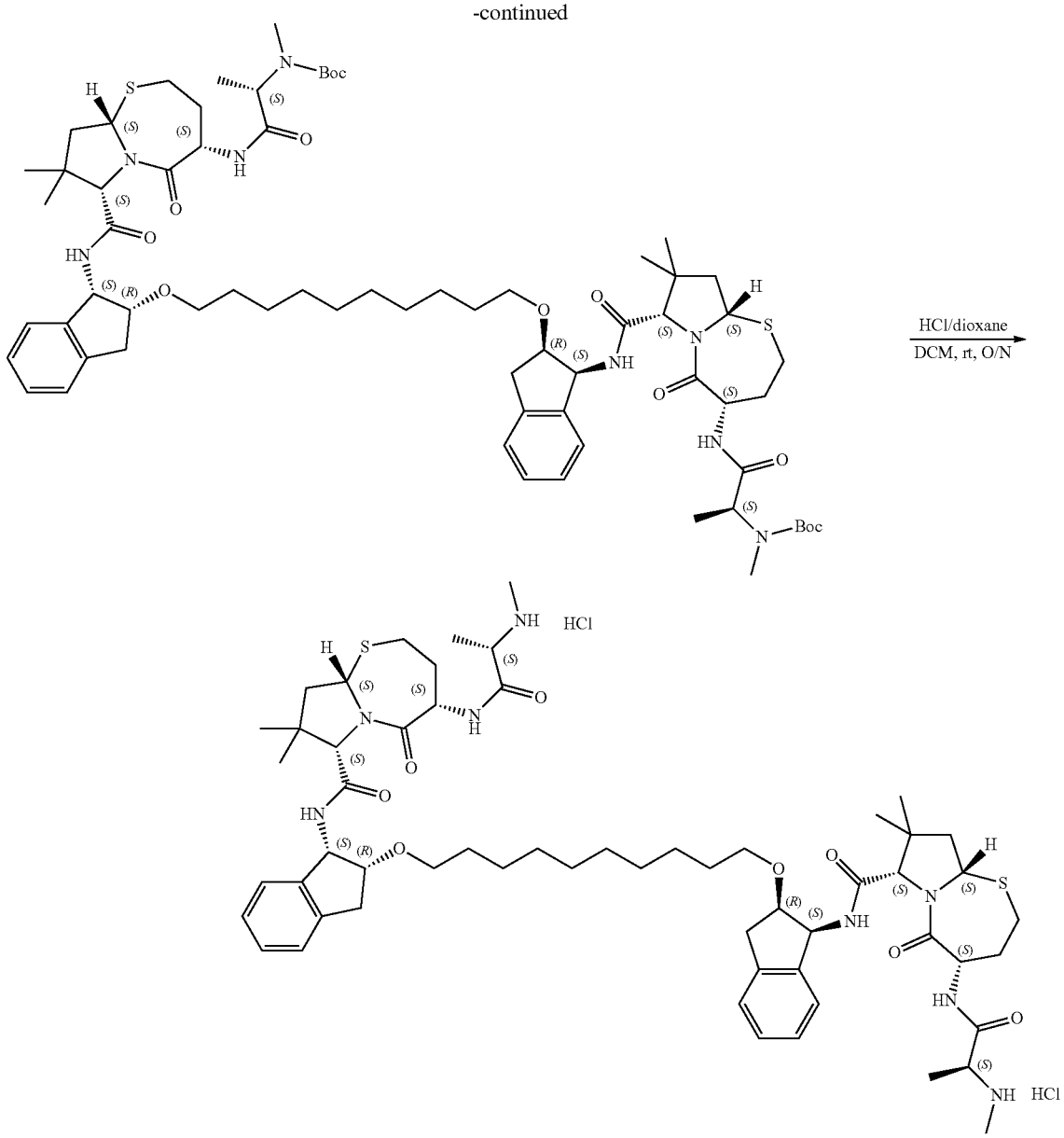

Synthesis of (1S,1'S,2R,2'R)-2,2'-(decane-1,10-diyl-bis(oxy))bis(2,3-dihydro-1H-inden-1-amine)

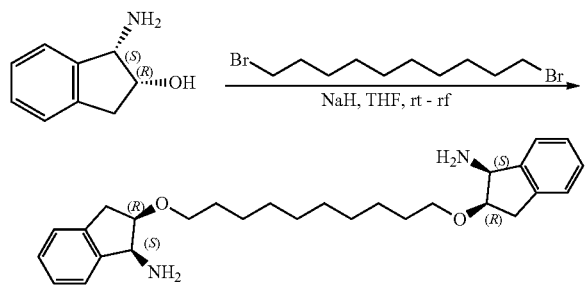

To a solution of (1S,2R)-1-amino-2,3-dihydro-1H-inden-2-ol (1 g, 6.71 mmol) in tetrahydrofuran (60 mL) at 0° C. was added portion wise sodium hydrogen (60%, dispersion in Paraffin Liquid) (293 mg, 7.32 mmol). The mixture was warmed to room temperature naturally. Then 1,10-dibromo-decane (1.0 g, 3.05 mmol) was added. The resulting mixture was stirred at 70° C. overnight. The reaction mixture was quenched with ice water (30 mL) and extracted with ethyl acetate (3×30 mL). The organic layer was combined, washed with brine (50 mL), dried over anhydrous sodium sulfate, filtered and concentrated to get the crude. It was purified by Combi-Flash eluting with dichloromethane/methanol=20:1 and thin layer chromatography developed with ethyl acetate/petroleum ether=3/1 to afford the desired product (100 mg, 0.23 mmol, 7.5% yield) as a dark oil.

LCMS (ES, m/z): 437.0 [M+H]$^+$, retention time 1.117 min.

Synthesis of di-tert-butyl ((2S,2'S)-(((4S,4'S,7S,7'S,9aS,9a'S)-((((1S,1'S,2R,2'R)-(decane-1,10-diylbis(oxy))bis(2,3-dihydro-1H-indene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate)

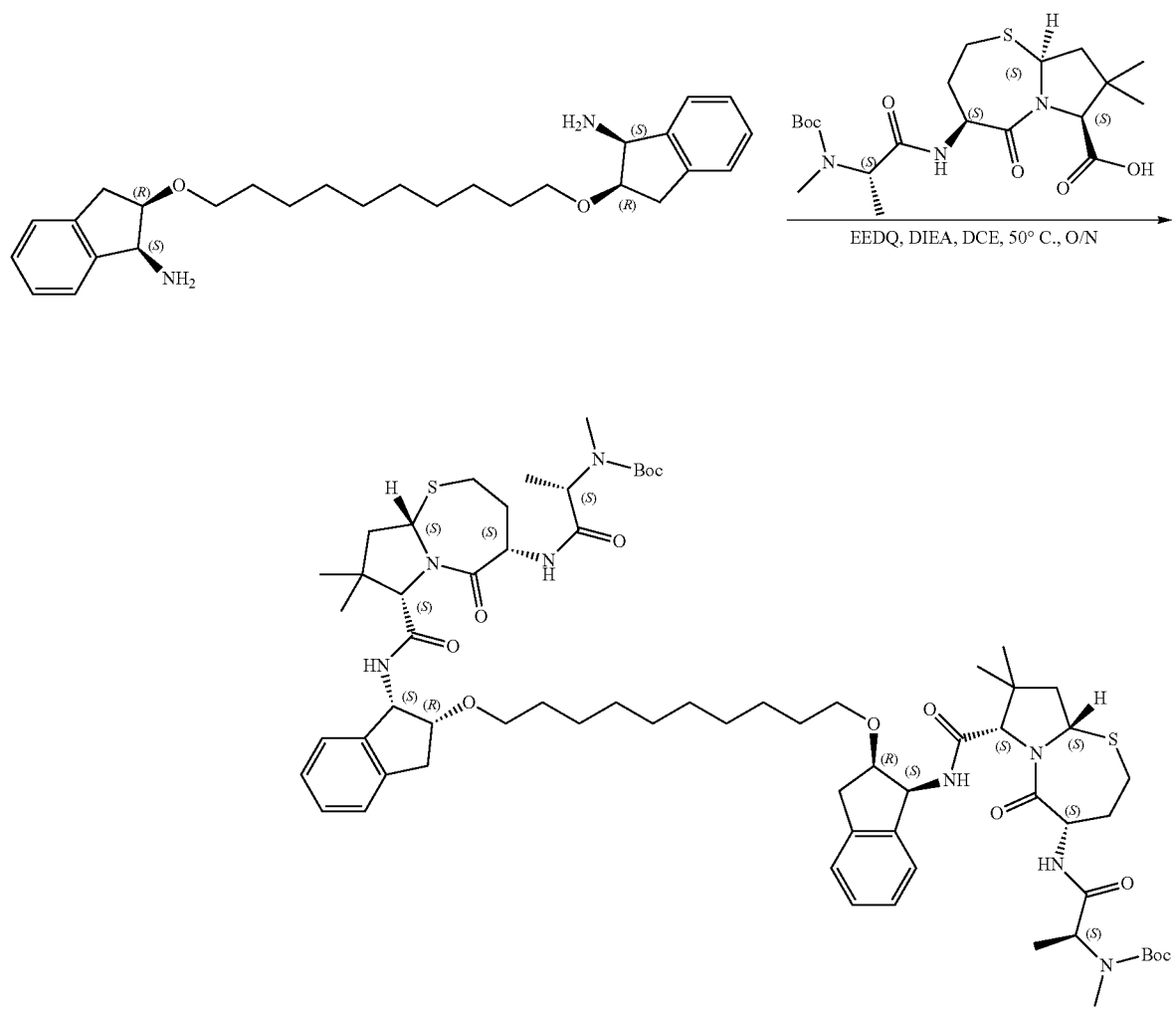

A mixture of (1S,1'S,2R,2'R)-2,2'-(decane-1,10-diylbis(oxy))bis(2,3-dihydro-1H-inden-1-amine) (100 mg, 0.229 mmol) and (4S,7S,9aS)-4-((S)-2-((tert-butoxycarbonyl)(methyl)amino)propanamido)-8,8-dimethyl-5-oxooctahydropyrrolo[2,1-b][1,3]thiazepine-7-carboxylic acid (220 mg, 0.505 mmol) in 1,2-dichloroethane (8 mL) was added N-Ethoxycarbonyl-2-ethoxy-1,2-dihydroquinoline (170 mg, 0.687 mmol) and N,N-Diisopropylethylamine (118 mg, 0.916 mmol). The resulting mixture was stirred at 50° C. overnight. The reaction mixture was concentrated to get the crude. It was purified by thin layer chromatography developed with ethyl acetate/petroleum ether=2/1 to give crude product. Then the crude product was purified by Prep-HPLC to get product (100 mg, 0.077 mmol, 33.9% yield) as a beige solid.

LCMS (ES, m/z): 543.6 [M/2-Boc+H]$^+$, retention time 2.072 min.

| Wavelength | 214 nm | |
|---|---|---|
| Instrument | Waters 2545 | |
| Column | Gemini 5 u C18 150 × 21.2 mm | |
| Flow Rate | 20 mL/min | |
| Gradient Method | Time (min) | can | H$_2$O |
| | 0 | 5 | 95 |
| | 10 | 50 | 50 |
| | 60 | 100 | 0 |
| | 100 | 100 | 0 |

Synthesis of (4S,4'S,7S,7'S,9aS,9a'S)—N,N'-((1S,1'S,2R,2'R)-(decane-1,10-diylbis(oxy))bis(2,3-dihydro-1H-indene-2,1-diyl))bis(8,8-dimethyl-4-((S)-2-(methylamino)propanamido)-5-oxooctahydropyrrolo[2,1-b][1,3]thiazepine-7-carboxamide) dihydrochloride

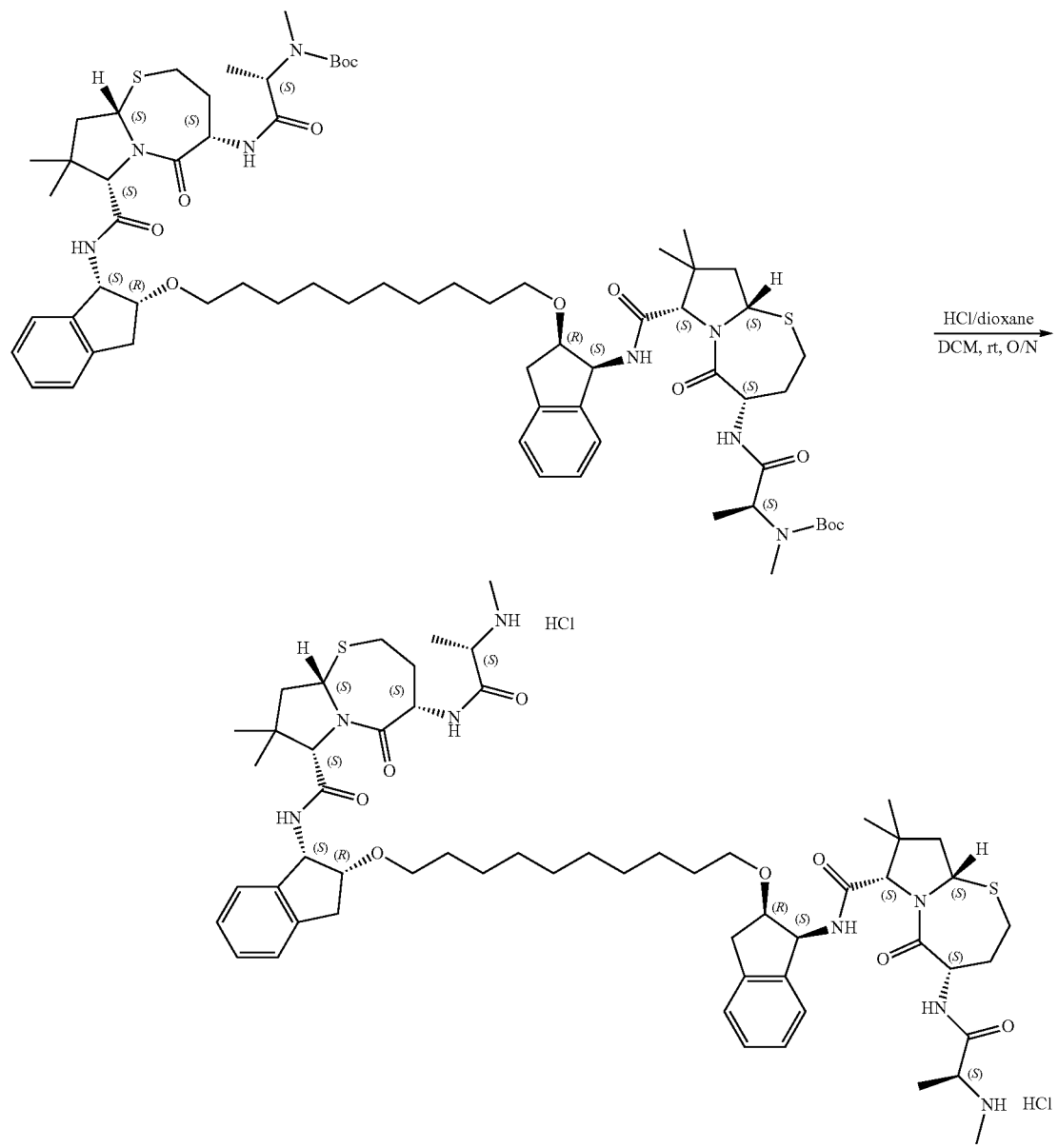

To a solution of di-tert-butyl ((2S,2'S)-(((4S,4'S,7S,7'S,9aS,9a'S)-((((1S,1'S,2R,2'R)-(decane-1,10-diylbis(oxy))bis(2,3-dihydro-1H-indene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (100 mg, 0.078 mmol) in dichloromethane (5 mL) was added 4 N hydrochloric acid in dioxane (0.7 mL). The mixture was stirred at room temperature overnight. The reaction was concentrated to get the desired product (62 mg, 0.053 mmol, 67.9% yield) as a white solid.

LCMS (ES, m/z): 1087.8 [M-2HCl+H]$^+$ (Calc M-2HCl+H=1087.6), retention time 1.254 min.

$^1$H NMR (400 MHz, DMSO) δ ppm 9.43 (s, 2H), 8.99-8.76 (m, 4H), 7.90 (d, J=8.7 Hz, 2H), 7.34-7.09 (m, 8H), 5.51 (t, J=7.7 Hz, 2H), 5.34 (dd, J=8.3, 5.5 Hz, 2H), 4.82-4.67 (m, 2H), 4.24 (s, 2H), 4.12 (dd, J=8.4, 3.7 Hz, 2H), 3.89 (dd, J=11.0, 6.0 Hz, 2H), 3.42-3.36 (m, 4H), 3.20 (t, J=12.1 Hz, 2H), 2.98 (d, J=3.2 Hz, 4H), 2.95-2.86 (m, 2H), 2.50-2.44 (m, 6H), 2.29-2.09 (m, 4H), 1.90-1.74 (m, 4H), 1.54-1.35 (m, 10H), 1.28-1.15 (m, 12H), 1.09 (s, 6H), 1.06 (s, 6H).

Example 58
(4S,4'S,7S,7'S,9aS,9a'S)—N,N'-((1S,1'S)-(octane-1,8-diylbis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide) dihydrochloride
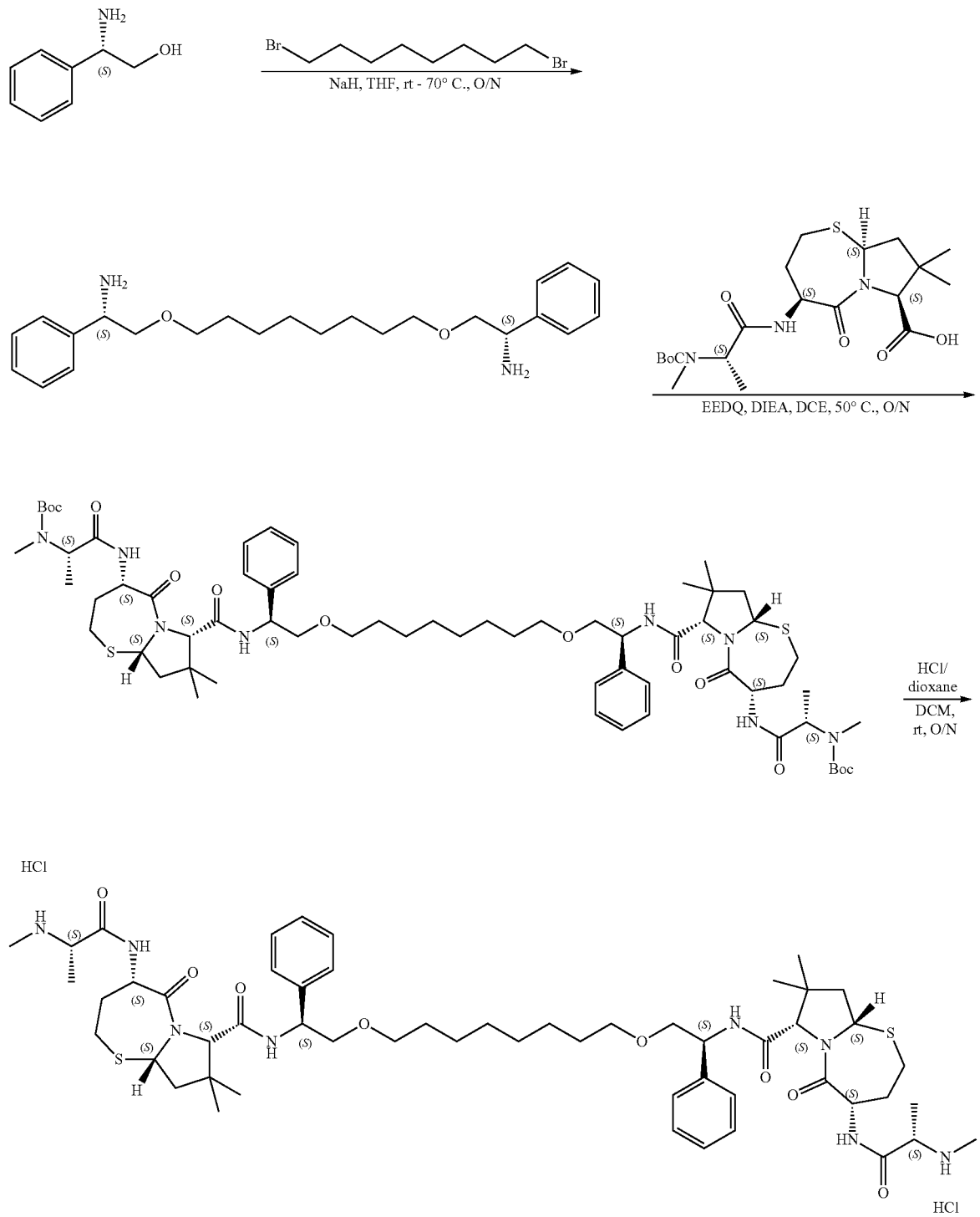

Synthesis of (1S,1'S)-2,2'-(octane-1,8-diylbis(oxy)bis(1-phenylethan-1-amine)

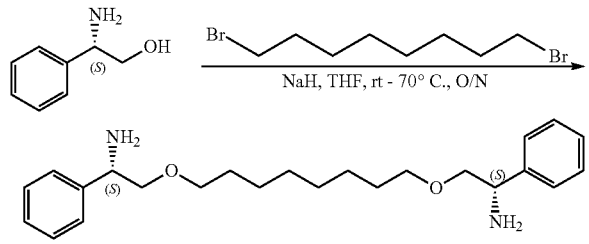

To a solution of (S)-2-amino-2-phenylethan-1-ol (1 g, 7.29 mmol) in tetrahydrofuran (60 mL) at 0° C. was added portion wise sodium hydrogen (60%, dispersion in Paraffin Liquid) (318 mg, 7.94 mmol). The mixture was warmed to room temperature naturally. Then 1,8-dibromooctane (901 mg, 3.31 mmol) was added. The resulting mixture was stirred at 70° C. overnight. The reaction mixture was quenched with ice water (30 mL) and extracted with ethyl acetate (3×30 mL). The organic layer was combined, washed with brine (50 mL), dried over anhydrous sodium sulfate, filtered and concentrated to get the crude. It was purified by Combi-Flash eluting with dichloromethane/methanol=25:1 and thin layer chromatography developed with ethyl acetate/petroleum ether=3/1 to afford the desired product (400 mg, 1.04 mmol, 31.4% yield) as a yellow oil.

LCMS (ES, m/z): 385.0 [M+H]$^+$, retention time 1.037 min.

Synthesis of di-tert-butyl((2S,2'S)-(((4S,4'S,7S,7'S,9aS,9a'S)-((3S,16S)-3,16-diphenyl-5,14-dioxa-2,17-diazaoctadecanedioyl)bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate)

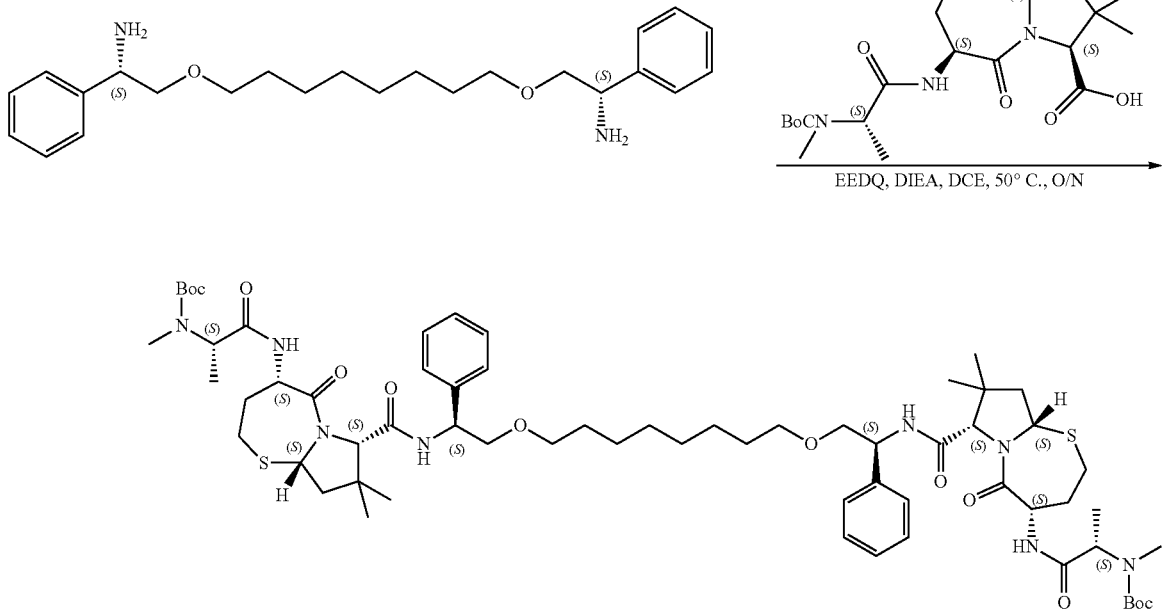

A mixture of (1S,1'S)-2,2'-(octane-1,8-diylbis(oxy))bis(1-phenylethan-1-amine) (100 mg, 0.26 mmol) and (4S,7S,9aS)-4-((S)-2-((tert-butoxycarbonyl)(methyl)amino)propanamido)-8,8-dimethyl-5-oxooctahydropyrrolo[2,1-b][1,3]thiazepine-7-carboxylic acid (252 mg, 0.57 mmol) in 1,2-dichloroethane (10 mL) was added N-Ethoxycarbonyl-2-ethoxy-1,2-dihydroquinoline (193 mg, 0.78 mmol) and N,N-Diisopropylethylamine (134 mg, 1.04 mmol). The resulting mixture was stirred at 50° C. overnight. The reaction mixture was concentrated to get the crude. It was purified by thin layer chromatography developed with ethyl acetate/petroleum ether=3/1 to give crude product. Then the crude product was purified by Prep-HPLC to get product (100 mg, 0.081 mmol, 31.2% yield) as a white solid.

LCMS (ES, m/z): 517.8 [1/2M-Boc+H]$^+$, retention time 1.859 min.

| | | | |
|---|---|---|---|
| Wavelength | 214 nm | | |
| Instrument | Waters 2545 | | |
| Column | Gemini 5 u C18 150 × 21.2 mm | | |
| Flow Rate | 20 mL/min | | |
| Gradient Method | Time (min) | can | H₂O |
| | 0 | 5 | 95 |
| | 10 | 45 | 55 |
| | 65 | 100 | 0 |
| | 100 | 100 | 0 |

Synthesis of (4S,4'S,7S,7'S,9aS,9a'S)—N,N'-((1S,1'S)-(octane-1,8-diylbis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide) dihydrochloride

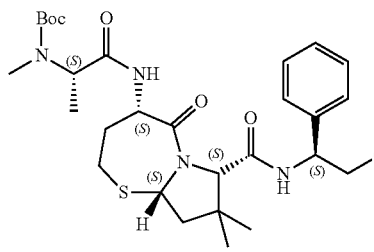
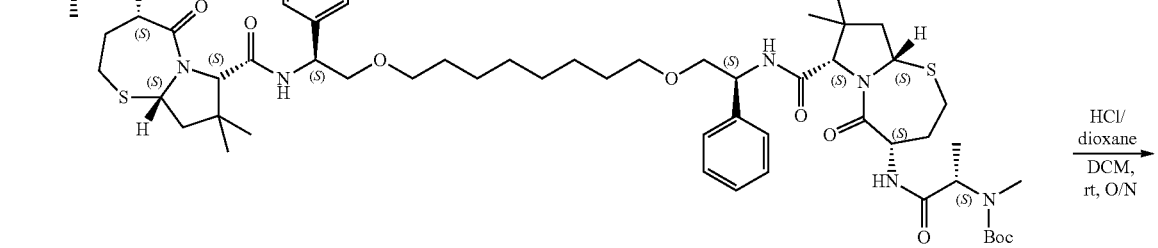
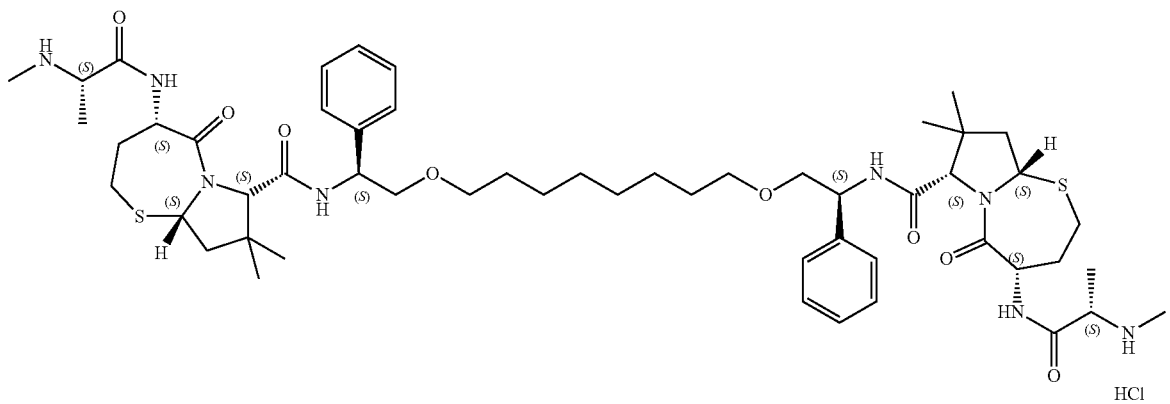

To a solution of di-tert-butyl ((2S,2'S)-(((4S,4'S,7S,7'S,9aS,9a'S)-((3S,16S)-3,16-diphenyl-5,14-dioxa-2,17-diazaoctadecanedioyl)bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (100 mg, 0.081 mmol) in dichloromethane (5 mL) was added 4 N hydrochloric acid in dioxane (0.7 mL). The mixture was stirred at room temperature overnight. The reaction was concentrated to get the desired product (60 mg, 0.054 mmol, 66.7% yield) as a white solid. LCMS (ES, m/z): 1035.7 [M-2HCl+H]⁺ (Calc M-2HCl+H=1035.6), retention time 1.211 min.
$^1$H NMR (400 MHz, DMSO) δ ppm 9.45 (s, 2H), 8.89 (d, J=6.1 Hz, 2H), 8.82 (d, J=7.0 Hz, 2H), 8.37 (d, J=8.1 Hz, 2H), 7.40-7.30 (m, 8H), 7.28-7.21 (m, 2H), 5.46 (t, J=7.8 Hz, 2H), 5.00 (dd, J=13.4, 6.6 Hz, 2H), 4.75-4.65 (m, 2H), 4.17 (s, 2H), 3.85 (d, J=5.6 Hz, 2H), 3.55-3.47 (m, 4H), 3.39-3.33 (m, 4H), 3.16 (t, J=12.0 Hz, 2H), 2.94-2.82 (m, 2H), 2.45 (s, 6H), 2.19 (dd, J=12.6, 7.0 Hz, 2H), 2.14-2.06 (m, 2H), 1.87 (dd, J=12.4, 8.8 Hz, 2H), 1.75 (dd, J=22.3, 11.4 Hz, 2H), 1.47-1.35 (m, 10H), 1.24-1.16 (m, 8H), 1.06 (s, 6H), 1.01 (s, 6H).

Example 59
(4S,4'S,7S,7'S,9aS,9a'S)—N,N'-((1S,1'S,2R,2'R)-(dodecane-1,12-diylbis(oxy))bis(2,3-dihydro-1H-indene-2,1-diyl))bis(8,8-dimethyl-4-((S)-2-(methylamino)propanamido)-5-oxooctahydropyrrolo[2,1-b][1,3]thiazepine-7-carboxamide)dihydrochloride
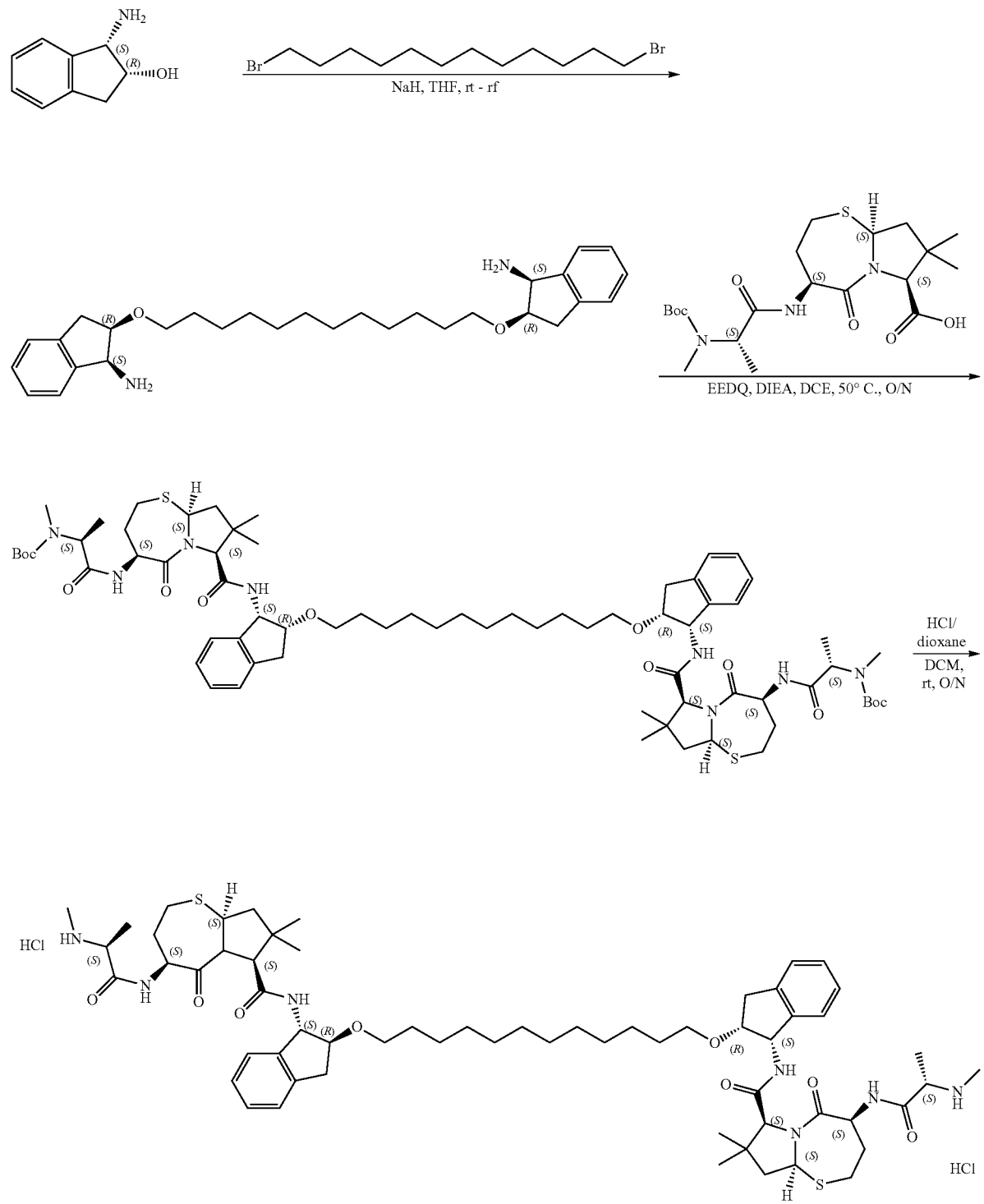

Synthesis of (1S,1'S,2R,2'R)-2,2'-(dodecane-1,12-diylbis (oxy))bis(2,3-dihydro-1H-inden-1-amine)

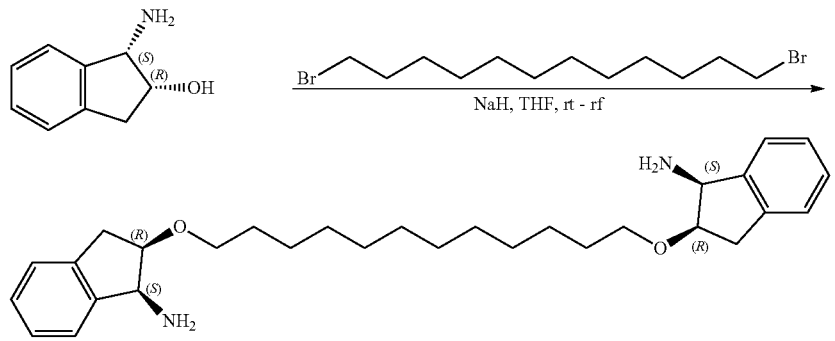

To a solution of (1S,2R)-1-amino-2,3-dihydro-1H-inden-2-ol (1 g, 5.70 mmol) in tetrahydrofuran (60 mL) at 0° C. was added portion wise sodium hydrogen (60%, dispersion in Paraffin Liquid) (249 mg, 6.22 mmol). The mixture was warmed to room temperature naturally. Then 1,12-dibromododecane (0.85 g, 2.59 mmol) was added. The resulting mixture was stirred at 70° C. overnight. The reaction mixture was quenched with ice water (30 mL) and extracted with ethyl acetate (3×30 mL). The organic layer was combined, washed with brine (50 mL), dried over anhydrous sodium sulfate, filtered and concentrated to get the crude. It was purified by thin layer chromatography developed with ethyl acetate/petroleum ether=3/1 to afford the desired product (160 mg, 0.34 mmol, 13.3% yield) as a dark oil.

LCMS (ES, m/z): 465.0 [M+H]$^+$, retention time 1.149 min.

Synthesis of di-tert-butyl((2S,2'S)-(((4S,4'S,7S,7'S,9aS,9a'S)-((((1S,1'S,2R,2'R)-(dodecane-1,12-diylbis (oxy))bis(2,3-dihydro-1H-indene-2,1-diyl))bis (azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis (methylcarbamate)

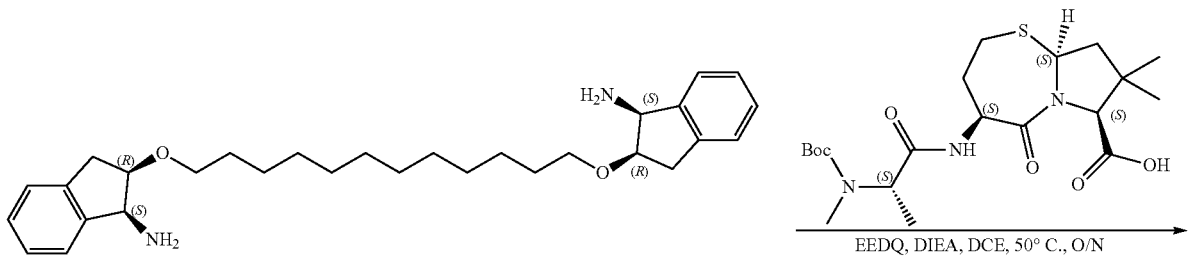

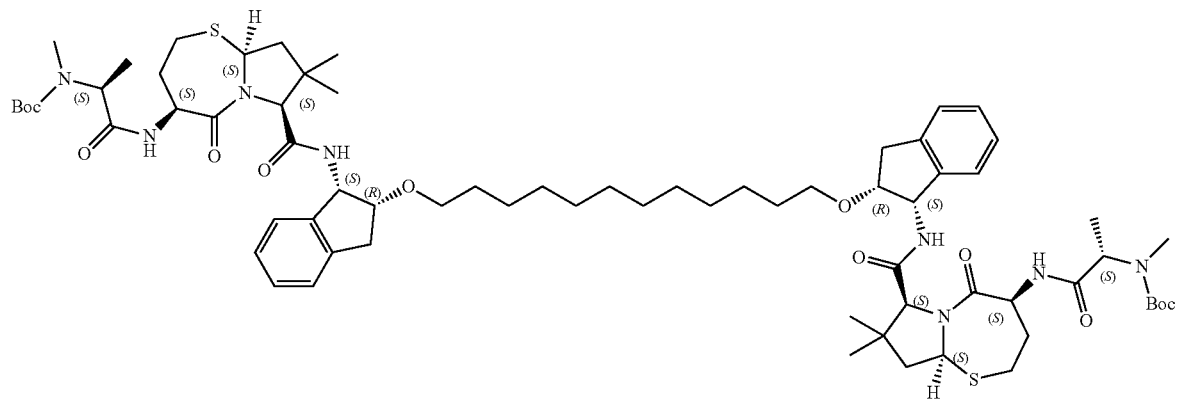

A mixture of (1S,1'S,2R,2'R)-2,2'-(dodecane-1,12-diylbis(oxy))bis(2,3-dihydro-1H-inden-1-amine) (110 mg, 0.237 mmol) and (4S,7S,9aS)-4-((S)-2-((tert-butoxycarbonyl)(methyl)amino)propanamido)-8,8-dimethyl-5-oxooctahydropyrrolo[2,1-b][1,3]thiazepine-7-carboxylic acid (231 mg, 0.521 mmol) in 1,2-dichloroethane (8 mL) was added N-Ethoxycarbonyl-2-ethoxy-1,2-dihydroquinoline (176 mg, 0.711 mmol) and N,N-Diisopropylethylamine (122 mg, 0.948 mmol). The resulting mixture was stirred at 50° C. overnight. The reaction mixture was concentrated to get the crude. It was purified by thin layer chromatography developed with ethyl acetate/petroleum ether=3/1 to give crude product. Then the crude product was purified by Prep-HPLC to get product (105 mg, 0.080 mmol, 33.7% yield) as a beige solid.

LCMS (ES, m/z): 557.9 [1/2M-Boc+H]$^+$, retention time 2.312 min.

| Wavelength | 214 nm |
|---|---|
| Instrument | Waters 2545 |
| Column | Gemini 5 u C18 150 × 21.2 mm |
| Flow Rate | 20 mL/min |

| Gradient Method | Time (min) | CAN | H$_2$O |
|---|---|---|---|
| | 0 | 5 | 95 |
| | 10 | 55 | 45 |
| | 55 | 100 | 0 |
| | 100 | 100 | 0 |

Synthesis of (4S,4'S,7S,7'S,9aS,9a'S)—N,N'-((1S,1'S,2R,2'R)-(dodecane-1,12-diylbis(oxy))bis(2,3-dihydro-1H-indene-2,1-diyl))bis(8,8-dimethyl-4-((S)-2-(methylamino)propanamido)-5-oxooctahydropyrrolo[2,1-b][1,3]thiazepine-7-carboxamide) dihydrochloride

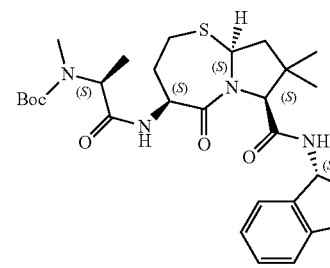
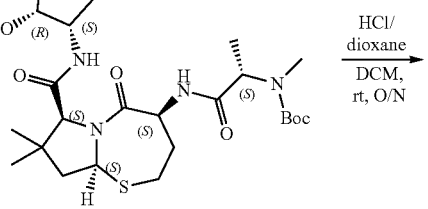
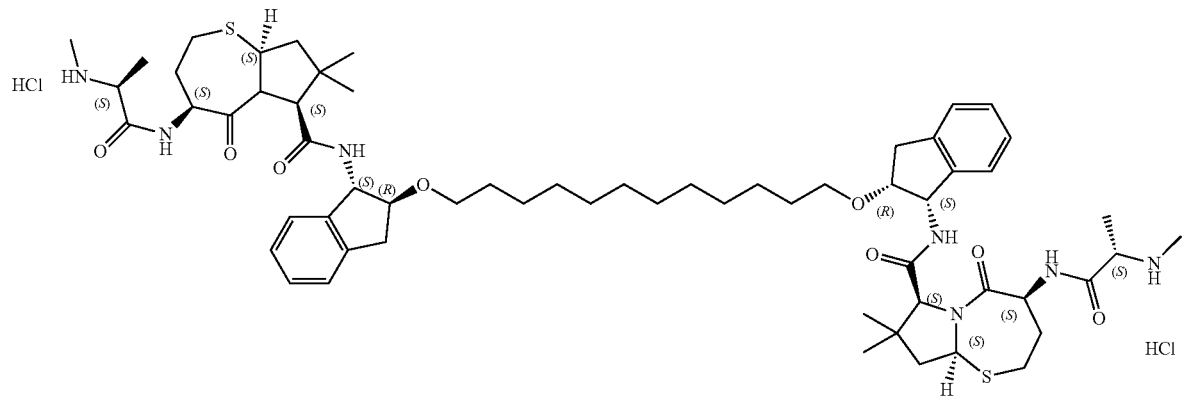

To a solution of di-tert-butyl ((2S,2'S)-(((4S,4'S,7S,7'S,9aS,9a'S)-((((1S,1'S,2R,2'R)-(dodecane-1,12-diylbis(oxy))bis(2,3-dihydro-1H-indene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (105 mg, 0.080 mmol) in dichloromethane (5 mL) was added 4 N hydrochloric acid in dioxane (0.7 mL). The mixture was stirred at room temperature overnight. The reaction was concentrated to get the desired product (65 mg, 0.055 mmol, 68.6% yield) as a white solid.

LCMS (ES, m/z): 558.0 [1/2M-HCl+H]$^+$, retention time 1.448 min.

285
¹H NMR (400 MHz, DMSO) δ ppm 9.45 (s, 2H), 9.03-8.77 (m, 4H), 7.90 (d, J=8.7 Hz, 2H), 7.29-7.14 (m, 8H), 5.51 (t, J=7.8 Hz, 2H), 5.34 (dd, J=8.4, 5.5 Hz, 2H), 4.78-4.69 (m, 2H), 4.24 (s, 2H), 4.11 (dd, J=8.8, 4.0 Hz, 2H), 3.89 (dd, J=12.9, 6.1 Hz, 2H), 3.47-3.36 (m, 4H), 3.20 (t, J=12.5 Hz, 2H), 2.98 (d, J=3.3 Hz, 4H), 2.95-2.86 (m, 2H), 2.47 (s, 6H), 2.26-2.07 (m, 4H), 1.90-1.73 (m, 4H), 1.49-1.36 (m, 10H), 1.25-1.17 (s, 16H), 1.08 (s, 6H), 1.06 (s, 6H).
286
Example 60
(4S,4'S,7S,7'S,9aS,9a'S)—N,N'-((1S,1'S)-(decane-1,10-diylbis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide) dihydrochloride
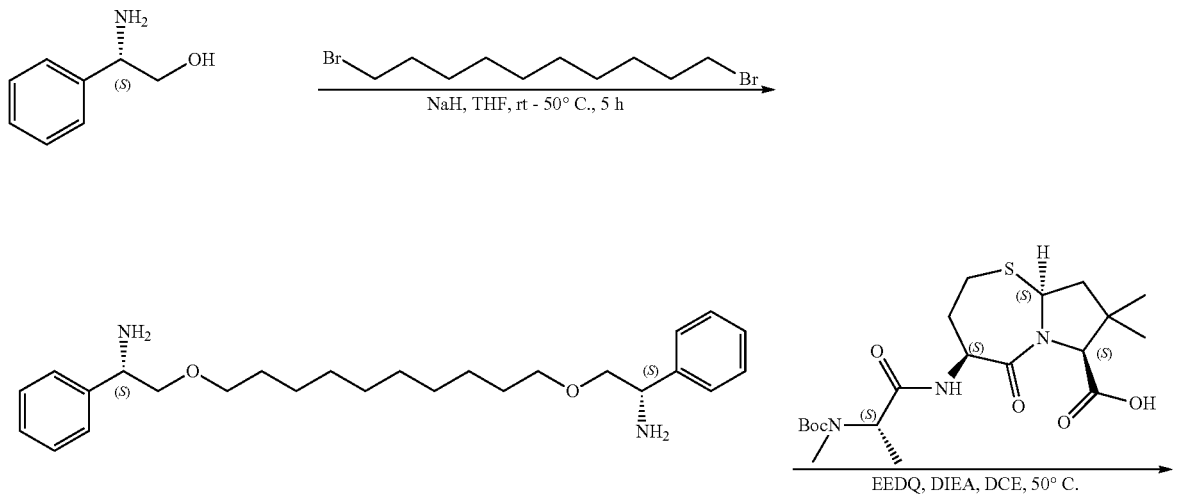
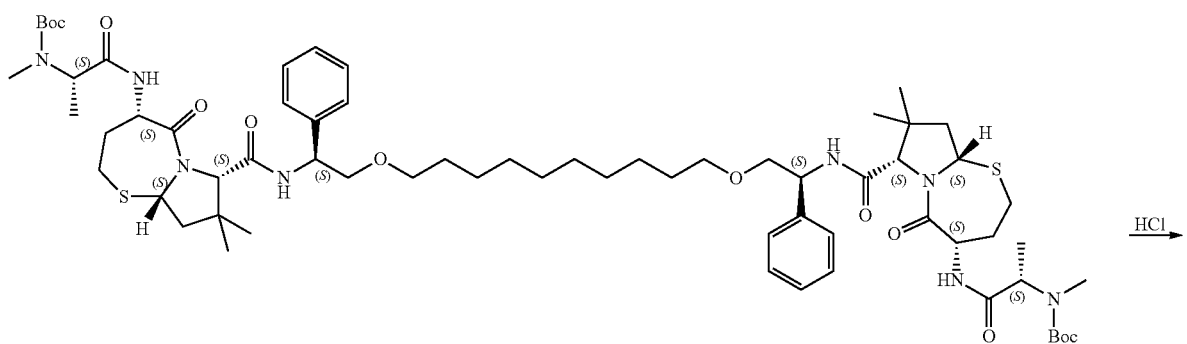
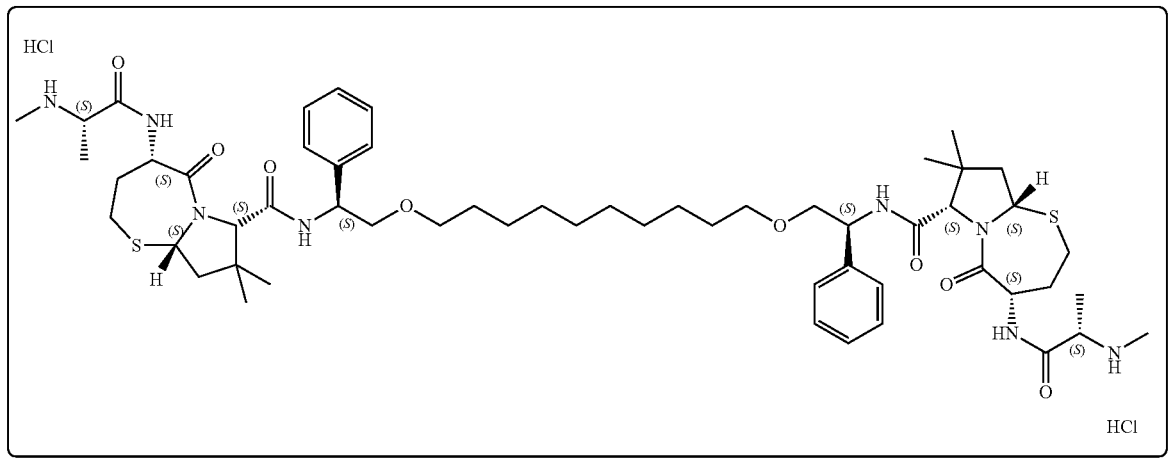

Synthesis of (1,1S)-2,2-(decane-1,1-diylbis(oxy))bis(1-phenylethan-1-amine)

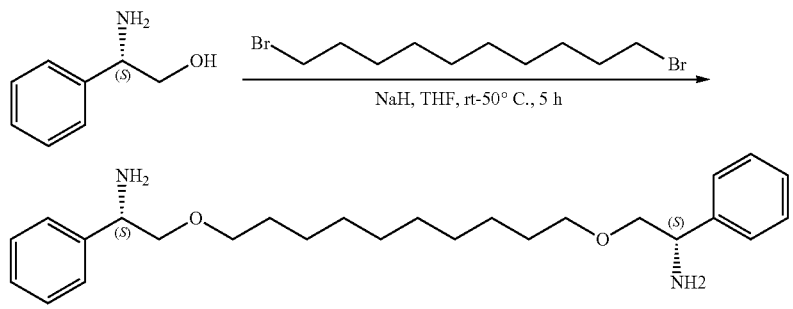

To a solution of (S)-2-amino-2-phenylethan-1-ol (2.1 g, 15.4 mmol) in tetrahydrofuran (40 mL) was added sodium hydride (0.672 g, 16.8 mmol) in batches at 0° C. The mixture was stirred at room temperature for 40 min. Then 1,10-dibromodecane (2.1 g, 7 mmol) was added and the mixture was stirred at room temperature for 10 min and heated to 50° C. for 3h. The reaction was quenched by the addition of water (100 mL). Then it was extracted with ethyl acetate (3*100 mL). The combined organic layers were washed with brine, dried over anhydrous sodium sulfate and concentrated in vacuo to get the crude. It was purified by column chromatography on silica gel (dichloromethane/methanol=15:1) and TLC (petroleum ether/ethyl acetate=1:3) to afford (1S,1'S)-2,2'-(decane-1,10-diylbis(oxy))bis(1-phenylethan-1-amine)(0.5 g, 1.21 mmol, 7.9% yield) as a yellow oil.

LCMS (ES, m/z): 413.0 [M+H]$^+$, retention time 1.073 min.

Synthesis of di-tert-butyl((2S,2'S)-(((4S,4'S,7S,7'S,9aS,9a'S)-((3S,18S)-3,18-diphenyl-5,16-dioxa-2,19-diazaicosanedioyl)bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate)

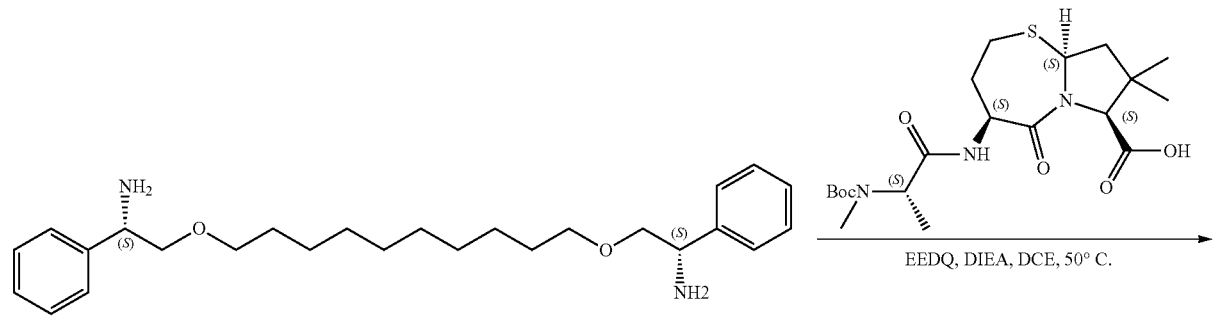

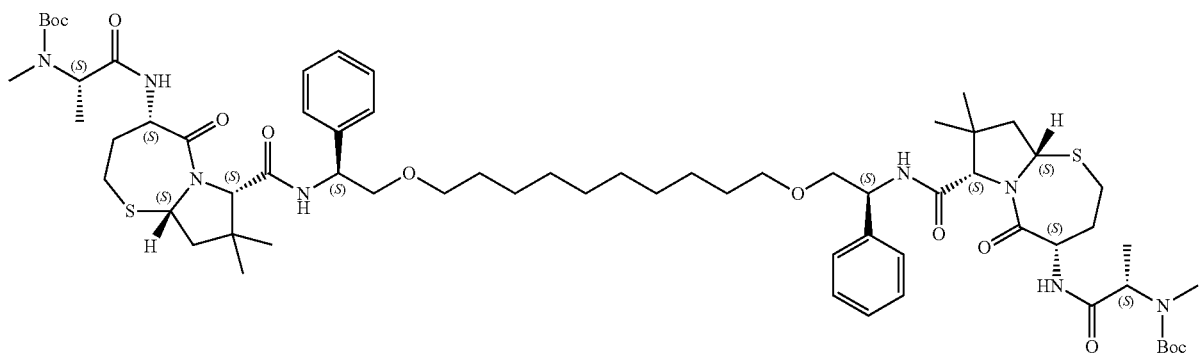

289

To a solution of (1S,1'S)-2,2'-(decane-1,10-diylbis(oxy))bis(1-phenylethan-1-amine) (150 mg, 0.364 mmol) and (4S,7S,9aS)-4-((S)-2-((tert-butoxycarbonyl)(methyl)amino)propanamido)-8,8-dimethyl-5-oxooctahydropyrrolo[2,1-b][1,3]thiazepine-7-carboxylic acid (355 mg, 0.800 mmol) in 1,2-dichloroethane (10 mL) was added 2-ethoxy-1-ethoxy-

290

Synthesis of (4S,4'S,7S,7'S,9aS,9a'S)—N,N'-((1S,1'S)-(decane-1,10-diylbis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide) dihydrochloride

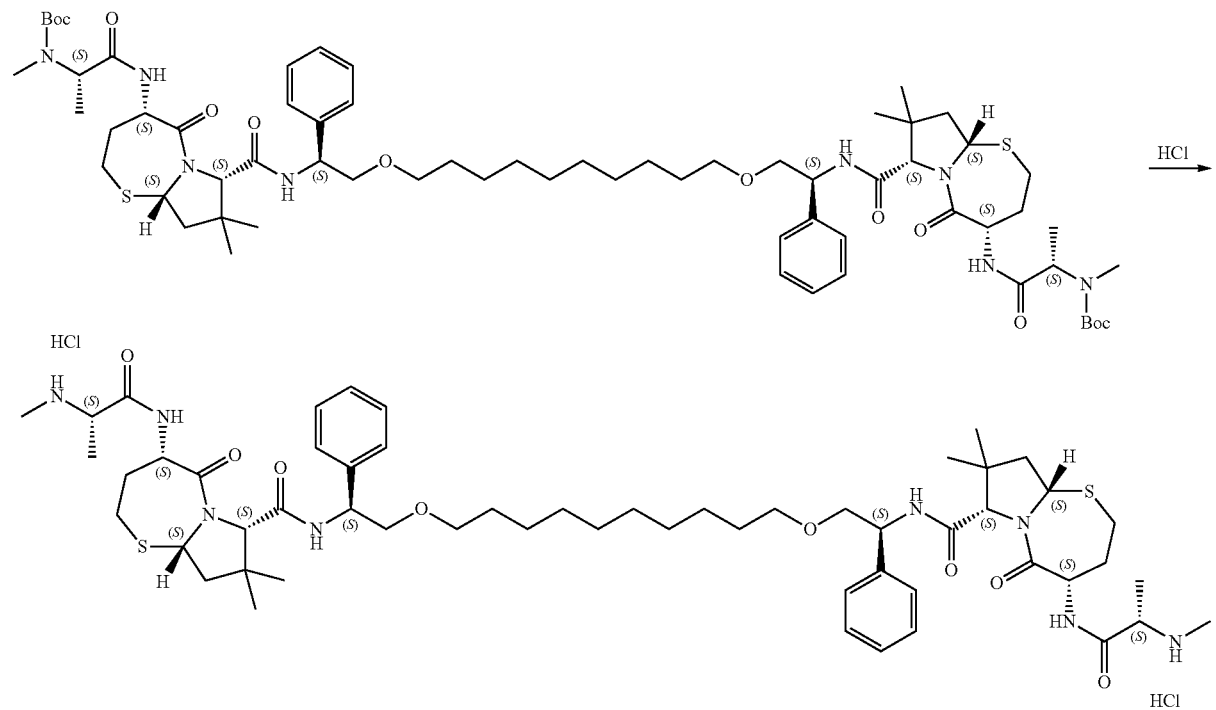

carbonyl-1,2-dihydroquinoline (270 mg, 1.091 mmol) and N,N-diisopropylethylamine (188 mg, 1.454 mmol). The resulting mixture was stirred at room temperature overnight. At which time it was diluted with water (10 mL), then it was extracted with dichloromethane (3*20 ml). The organic layers were combined, washed with brine, dried over anhydrous sodium sulfate and concentrated to get the crude. It was purified by prep-TLC (petroleum ether/ethyl acetate=1:3) to get crude product. Then the crude product was further purified by prep-HPLC to get di-tert-butyl ((2S,2'S)-(((4S,4'S,7S,7'S,9aS,9a'S)-((3S,18S)-3,18-diphenyl-5,16-dioxa-2,19-diazaicosanedioyl)bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (70 mg, 0.055 mmol, 15.2% yield) as a brown solid.

LCMS (ES, m/z): 532.1 [1/2M-Boc+H]$^+$, retention time 1.994 min.

| Wavelength | 214 nm/254 nm | | |
|---|---|---|---|
| Instrument | Combi Flash | | |
| Column | WelFlash ® C18-I Spherical C18, 20-40 μm Size 120 g | | |
| Flow Rate | 20 mL/min | | |
| Gradient Method | Time (min) | can | H$_2$O |
| | 0 | 5 | 95 |
| | 5 | 5 | 95 |
| | 50 | 45 | 55 |
| | 60 | 45 | 55 |
| | 90 | 100 | 0 |

To a solution of di-tert-butyl ((2S,2'S)-(((4S,4'S,7S,7'S,9aS,9a'S)-((3S,18S)-3,18-diphenyl-5,16-dioxa-2,19-diazaicosanedioyl)bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (70 mg, 0.055 mmol) in dichloromethane (5 ml) was added 4M hydrochloric acid (0.7 mL) in dioxane. The resulting mixture was stirred for 4h at room temperature. At which time it was concentrated to get (4S,4'S,7S,7'S,9aS,9a'S)—N,N'-((1S,1'S)-(decane-1,10-diylbis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide) dihydrochloride (60 mg, 0.053 mmol, 96.0% yield) as a light yellow solid.

LCMS (ES, m/z): 1062.8 [M-2HCl+H]$^+$ (Calc M-2HCl+H=1063.6), retention time 1.213 min.

$^1$H NMR (400 MHz, DMSO-d6): δ ppm 9.42 (s, 2H), 8.99-8.77 (m, 4H), 8.38 (d, J=8.0 Hz, 2H), 7.43-7.21 (m, 10H), 5.56-5.42 (t, 2H), 5.05-4.98 (t, 2H), 4.79-4.65 (t, 2H), 4.19 (s, 2H), 3.87 (s, 2H), 3.57-3.46 (t, 4H), 3.42-3.35 (m, 4H), 3.23-3.11 (t, 2H), 2.90 (d, J=12.0 Hz, 2H), 2.47 (m, 6H), 2.26-2.17 (m, 2H), 2.16-2.07 (m, 2H), 1.93-1.83 (dd, J=12.0, 8.0 Hz, 2H), 1.83-1.70 (m, 2H), 1.50-1.35 (m, 10H), 1.21 (d, J=16.0 Hz, 12H), 1.06 (d, J=20.0 Hz, 12H).

Example 61
(4S,4'S,7S,7'S,9aS,9a'S)—N,N'-((1S,1'S)-(dodecane-1,12-diylbis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide)dihydrochloride
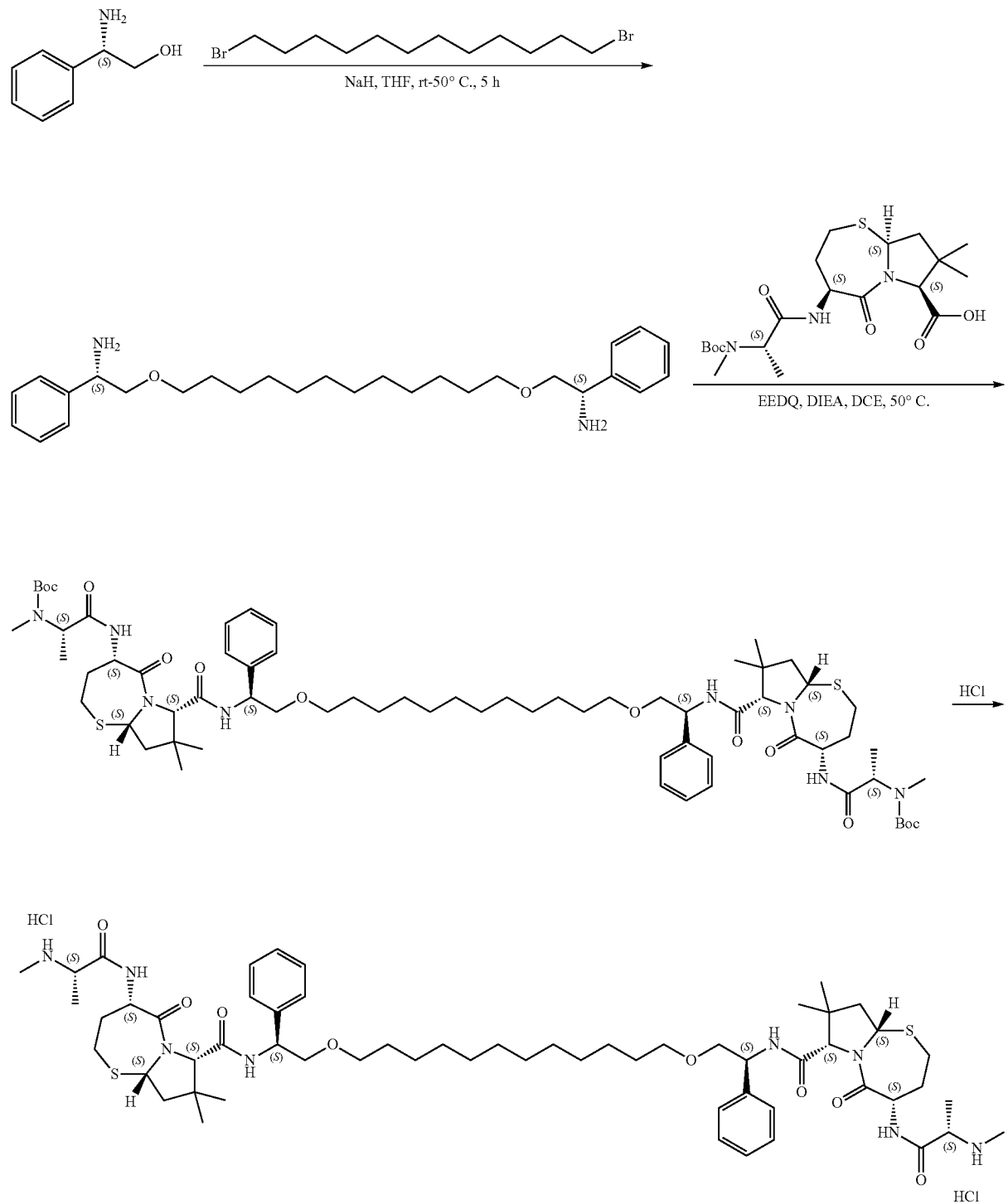

Synthesis of (1S,1'S)-2,2'-(dodecane-1,12-diylbis(oxy))bis(1-phenylethan-1-amine)

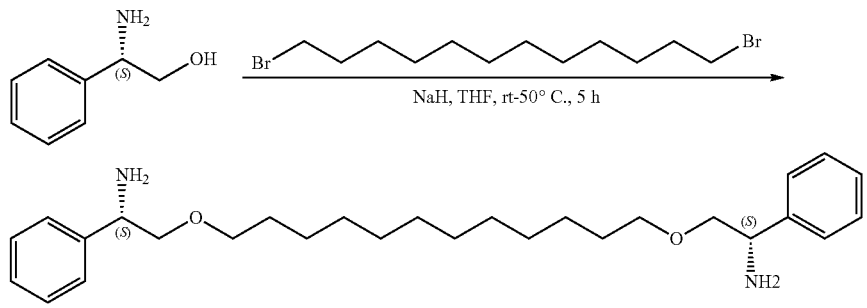

To a solution of (S)-2-amino-2-phenylethan-1-ol (0.920 g, 6.71 mmol) in tetrahydrofuran (50 mL) was added sodium hydride (0.293 g, 7.31 mmol) in batches at 0° C. The mixture was stirred at room temperature for 40 min. Then 1,12-dibromododecane (1 g, 3.05 mmol) was added and the mixture was stirred at room temperature for 10 min and heated to 50° C. for 3h. At which time the reaction was quenched by the addition of water (50 mL). Then it was extracted with ethyl acetate (3*50 mL). Combined the organic layers were washed with brine, dried over anhydrous sodium sulfate and concentrated in vacuo to get the crude. It was purified by column chromatography on silica gel (dichloromethane/methanol=15:1) and prep-TLC (petroleum ether/ethyl acetate=1:3) to afford (1S,1'S)-2,2'-(dodecane-1,12-diylbis(oxy))bis(1-phenylethan-1-amine) (70 mg, 0.159 mmol, 5.2% yield) as a brown oil. LCMS (ES, m/z): 441.0 [M+H]$^+$, retention time 1.162 min.

Synthesis of di-tert-butyl ((2S,2'S)-(((4S,4'S,7S,7'S,9aS,9a'S)-((3S,20S)-3,20-diphenyl-5,18-dioxa-2,21-diazadocosanedioyl)bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate)

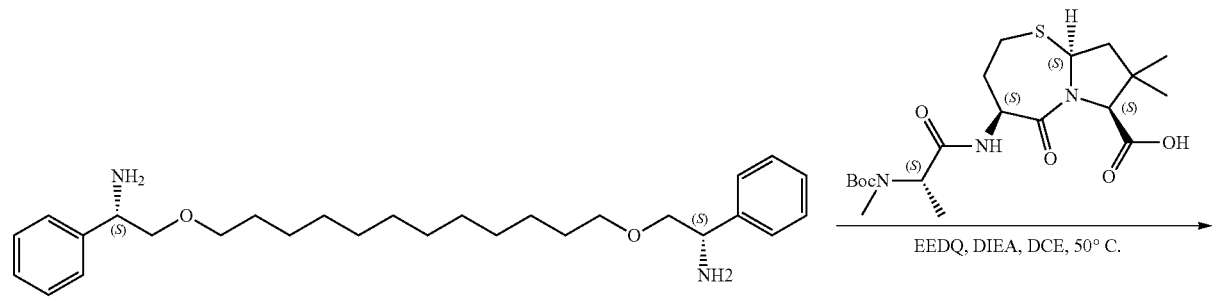

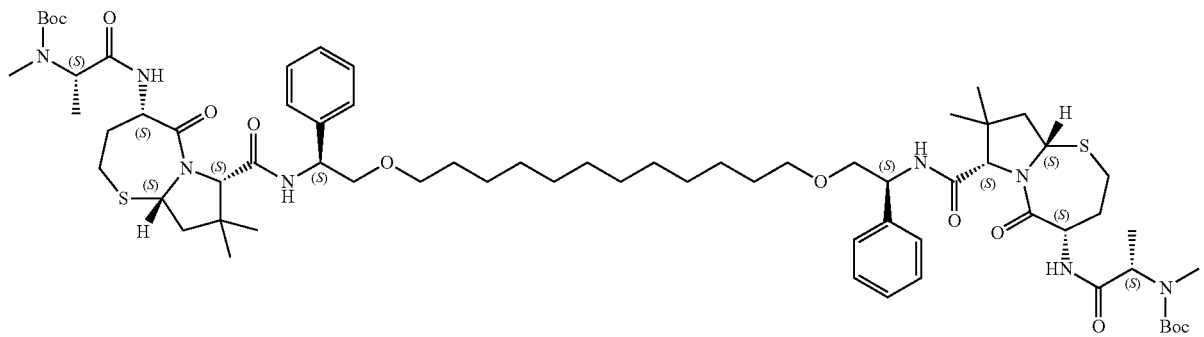

To a solution of (1S,1'S)-2,2'-(dodecane-1,12-diylbis(oxy))bis(1-phenylethan-1-amine) (70 mg, 0.159 mmol) and (4S,7S,9aS)-4-((S)-2-((tert-butoxycarbonyl)(methyl)amino)propanamido)-8,8-dimethyl-5-oxooctahydropyrrolo[2,1-b][1,3]thiazepine-7-carboxylic acid (211.4 mg, 0.477 mmol) in 1,2-dichloroethane (5 mL) was added 2-ethoxy-1-ethoxycarbonyl-1,2-dihydroquinoline (157 mg, 0.635 mmol) and N,N-diisopropylethylamine (123 mg, 0.953 mmol). The resulting mixture was stirred at 50° C. overnight. At which time it was diluted with water (10 mL), then it was extracted with dichloromethane (3*20 ml). The organic layers were combined, washed with brine, dried over anhydrous sodium sulfate and concentrated to get the crude. It was purified by prep-TLC (petroleum ether/ethyl acetate=1:3) to get crude product. Then the crude product was purified by prep-HPLC to get di-tert-butyl ((2S,2'S)-(((4S,4'S,7S,7'S,9aS,9a'S)-((3S,20S)-3,20-diphenyl-5,18-dioxa-2,21-diazadocosanedioyl)bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (20 mg, 0.016 mmol, 9.7% yield) as a brown solid.

LCMS (ES, m/z): 546.1 [1/2M-Boc+H]+, retention time 2.192 min.

| Wavelength | 214 nm/254 nm | |
|---|---|---|
| Instrument | Combi Flash | |
| Column | WelFlash ® C18-I Spherical C18, 20-40 μm Size 120 g | |
| Flow Rate | 20 mL/min | |
| Gradient Method | Time (min) | ACN | H₂O |
| | 0 | 5 | 95 |
| | 5 | 5 | 95 |
| | 50 | 45 | 55 |
| | 60 | 45 | 55 |
| | 90 | 100 | 0 |

Synthesis of (4S,4'S,7S,7'S,9aS,9a'S)—N,N'-((1S,1'S)-(dodecane-1,12-diylbis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide)dihydrochloride

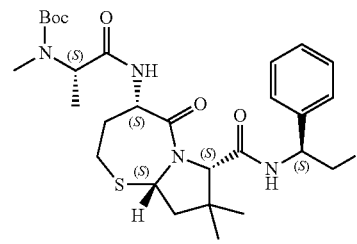
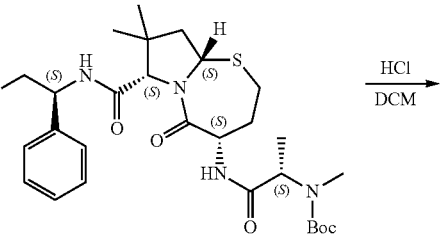
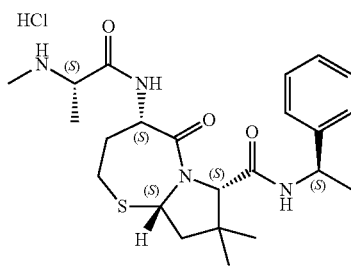
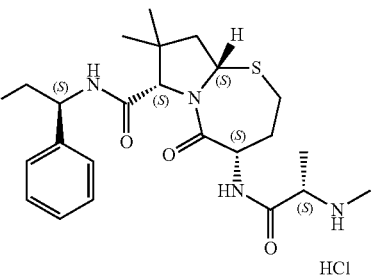

To a solution of di-tert-butyl ((2S,2'S)-(((4S,4'S,7S,7'S,9aS,9a'S)-((3S,20S)-3,20-diphenyl-5,18-dioxa-2,21-diazadocosanedioyl)bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (20 mg, 0.016 mmol) in dichloromethane (5 ml) was added 4M hydrochloric acid (0.5 mL) in dioxane. The resulting mixture was stirred for 4h at room temperature. At which time it was concentrated to get (4S,4'S,7S,7'S,9aS,9a'S)—N,N'-((1S,1'S)-(dodecane-1,12-diylbis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide) dihydrochloride (11 mg, 0.009 mmol, 60.9% yield) as a white solid.

LCMS (ES, m/z): 546.1 [M/2-HCl+H]+ (Calc M/2-HCl+H=546.3), retention time 1.397 min.

1H NMR (400 MHz, MeOD-d6): δ ppm 8.36 (d, J=8.0 Hz, 2H), 7.39 (d, J=8.0 Hz, 4H), 7.34-7.27 (t, 4H), 7.27-7.21 (t, 2H), 5.51-5.43 (t, 2H), 5.12-5.05 (dd, J=4.0, 4.0 Hz, 2H), 4.75 (d, J=8.0 Hz, 2H), 4.22 (s, 2H), 3.89 (d, J=8.0 Hz, 2H), 3.66-3.59 (m, 4H), 3.50-3.43 (m, 2H), 3.40-3.33 (m, 2H), 2.96-2.87 (m, 2H), 2.67 (d, J=4.0 Hz, 6H), 2.38-2.29 (m, 2H), 2.29-2.20 (d, J=16.0 Hz, 2H), 2.06-1.99 (d, J=12.0 Hz, 2H), 1.99-1.91 (m, 2H), 1.57-1.46 (m, 10H), 1.26 (s, 18H), 1.15 (s, 6H), 1.04 (s, 6H).
Example 62
(4S,4'S,7S,7'S,9aS,9a'S)—N,N'-((1S,1'S)-((naphthalene-2,6-diylbis(methylene))bis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide)
Synthesis of (1S,1S)-2,2-((naphthalene-2,6-diylbis(methylene))bis(oxy))bis(1-phenylethan-1-amine)
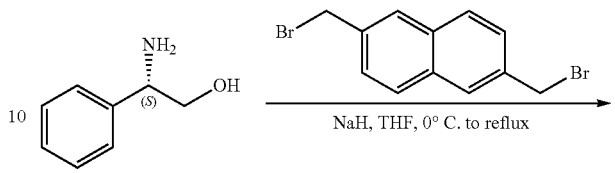
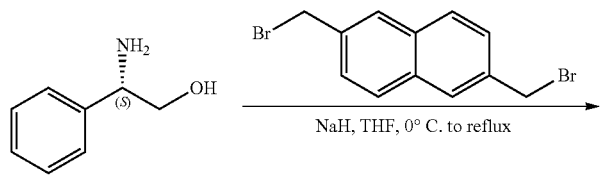
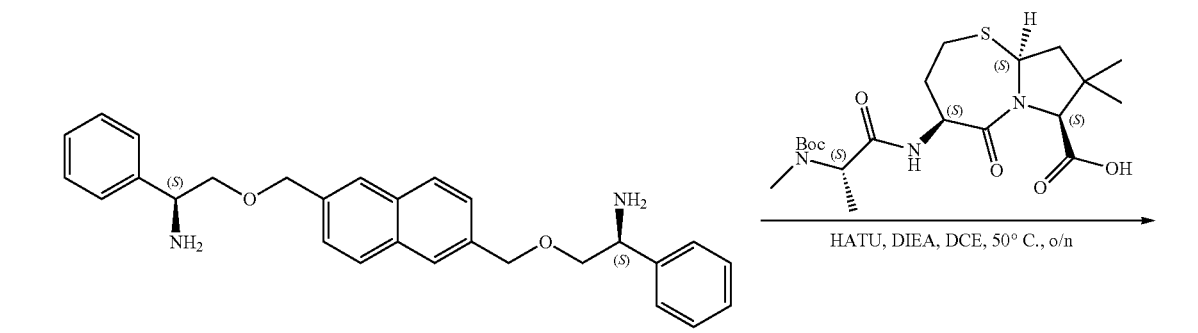
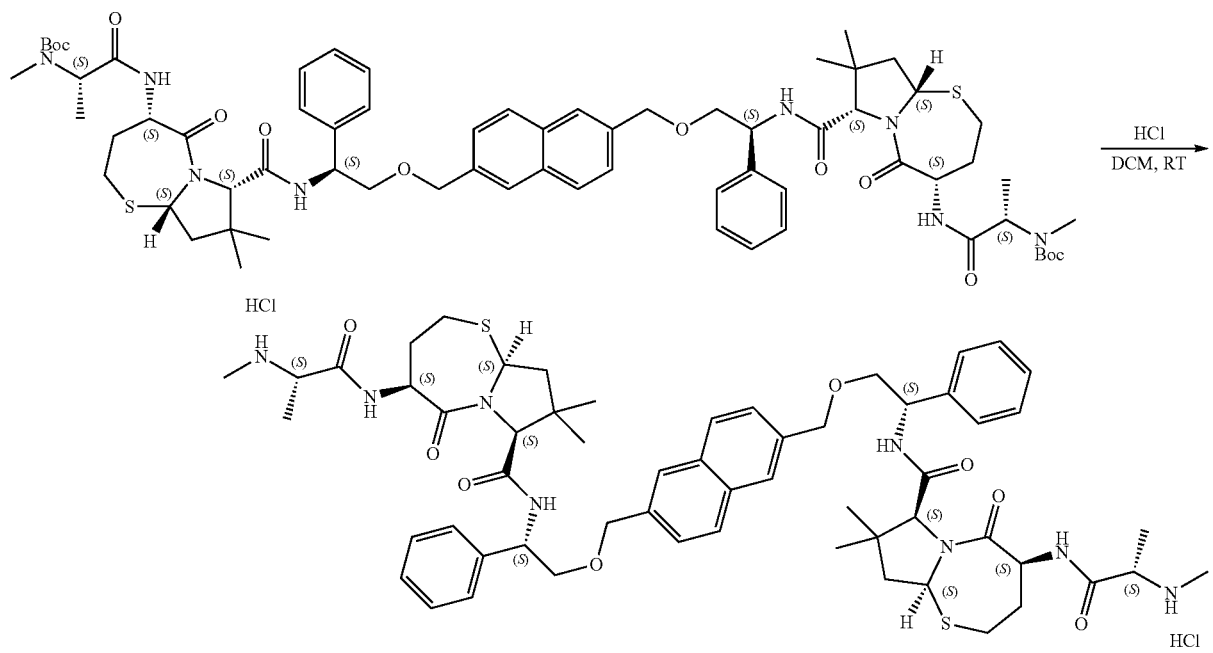

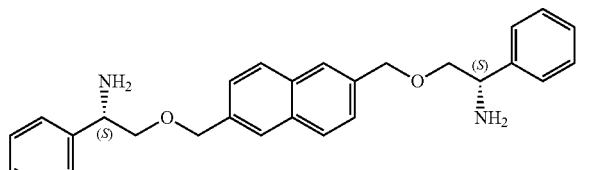

To a solution of (S)-2-amino-2-phenylethan-1-ol (480 mg, 3.5 mmol) in tetrahydrofuran (20 mL) at 0° C. was added portion wise sodium hydrogen (60%, dispersion in Paraffin Liquid) (166 g, 4.1 mmol). The mixture was warmed to room temperature naturally. Then 2,6-bis(bromomethyl)naphthalene (500 mg, 1.6 mmol) was dropped and the resulting mixture was heated to 70° C. It was stirred at 70° C. overnight. The reaction mixture was quenched ice water (30 mL) and extracted with ethyl acetate (3×20 mL). The organic layers were combined, washed with brine (20 mL), dried over anhydrous sodium sulfate, filtered and concentrated to get the crude. It was purified by column chromatography on silica gel (dichloromethane/methanol=15:1) to afford (1S,1'S)-2,2'-((naphthalene-2,6-diylbis(methylene))bis(oxy))bis(1-phenylethan-1-amine) (400 mg, 0.938 mmol, 58.9% yield) as a black oil.

LCMS (ES, m/z): 427.2 [M+H]$^+$, retention time 1.037 min.

Synthesis of di-tert-butyl((2S,2'S)-(((4S,4'S,7S,7'S,9aS,9a'S)-(((((1S,1'S)-((naphthalene-2,6-diylbis(methylene))bis(oxy))bis(1-phenylethane-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate)

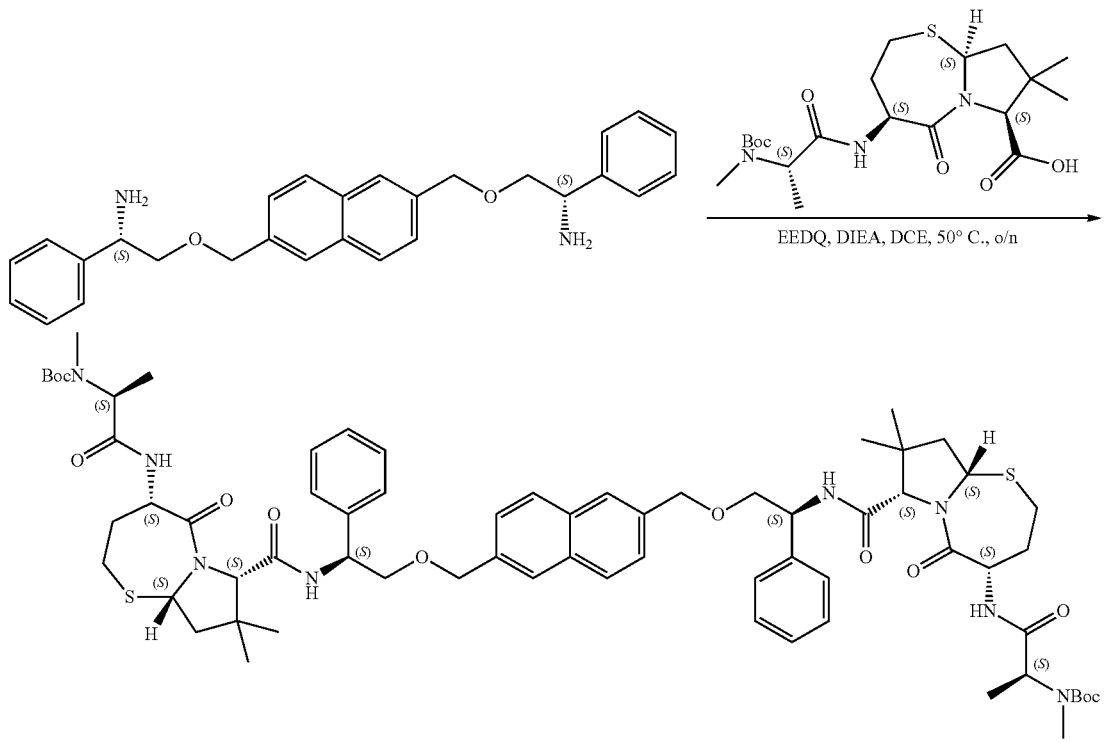

To a solution of (4S,7S,9aS)-4-((S)-2-((tert-butoxycarbonyl)(methyl)amino)propanamido)-8,8-dimethyl-5-oxooctahydropyrrolo[2,1-b][1,3]thiazepine-7-carboxylic acid (259 mg, 0.59 mmol), ethyl 2-ethoxyquinoline-1(2H)-carboxylate (162 mg, 0.66 mmol) and N,N-diisopropylethylamine (121 mg, 0.94 mmol) in 1,2-dichloroethane (5 mL) was added (1S,1'S)-2,2'-((naphthalene-2,6-diylbis(methylene))bis(oxy))bis(1-phenylethan-1-amine) (100 mg, 0.23 mmol). The mixture was stirred at 50° C. overnight. The reaction was concentrated to get the crude. It was purified by column chromatography on silica gel (petroleum ether/ethyl acetate=1:4) to give crude product. Then the crude product was purified by prep-HPLC to get product (100 mg, 0.078 mmol, 33.4% yield) as a white solid.

LCMS (ES, m/z): 539.3 [M/2-Boc+H]$^+$, retention time 1.778 min.

| | |
|---|---|
| Wavelength | 214 nm/254 nm |
| Instrument | Combi Flash |
| Column | WelFlash ® C18-I Spherical C18, 20-40 μm Size 120 g |
| Flow Rate | 20 mL/min |

| Gradient Method | Time (min) | ACN | H₂O |
|---|---|---|---|
| | 0 | 5 | 95 |
| | 5 | 5 | 95 |
| | 50 | 45 | 55 |
| | 60 | 45 | 55 |
| | 90 | 100 | 0 |

Synthesis of (4S,4'S,7S,7'S,9aS,9a'S)—N,N'-((1S,1'S)-((naphthalene-2,6-diylbis(methylene))bis(oxy))bis(1-phenylethane-2,1-diyl))bis(8,8-dimethyl-4-((S)-2-(methylamino)propanamido)-5-oxooctahydropyrrolo[2,1-b][1,3]thiazepine-7-carboxamide)

perature overnight. The reaction mixture was concentrated to get the desired product (20 mg, 0.017 mmol, 24.2% yield) as a white solid. The compound was further lyophilized to remove solvent residue.

LCMS (ES, m/z): 1077.7 [M-2HCl+H]⁺, retention time 1.426 min.

$^1$H NMR (400 MHz, DMSO-d$_6$) δ ppm 9.30 (s, 2H), 8.91-8.77 (m, 4H), 8.45 (d, J=8.2 Hz, 2H), 7.82-7.72 (m, 4H), 7.45-7.32 (m, 10H), 7.28 (t, J=7.2 Hz, 2H), 5.46 (t, J=7.9 Hz, 2H), 5.13 (dd, J=13.3, 6.6 Hz, 2H), 4.74-4.59 (m, 6H), 4.20 (s, 2H), 3.90-3.80 (m, 2H), 3.72-3.61 (m, 4H), 3.13 (t, J=12.4 Hz, 2H), 2.83-2.73 (m, 2H), 2.49-3.42 (m, 6H), 2.18 (dd, J=12.5, 6.8 Hz, 2H), 2.10-2.02 (m, 2H), 1.86 (dd, J=12.7, 8.8 Hz, 2H), 1.73 (dd, J=22.5, 11.2 Hz, 2H), 1.40-1.33 (m, 6H), 1.05 (s, 6H), 0.98 (s, 6H).

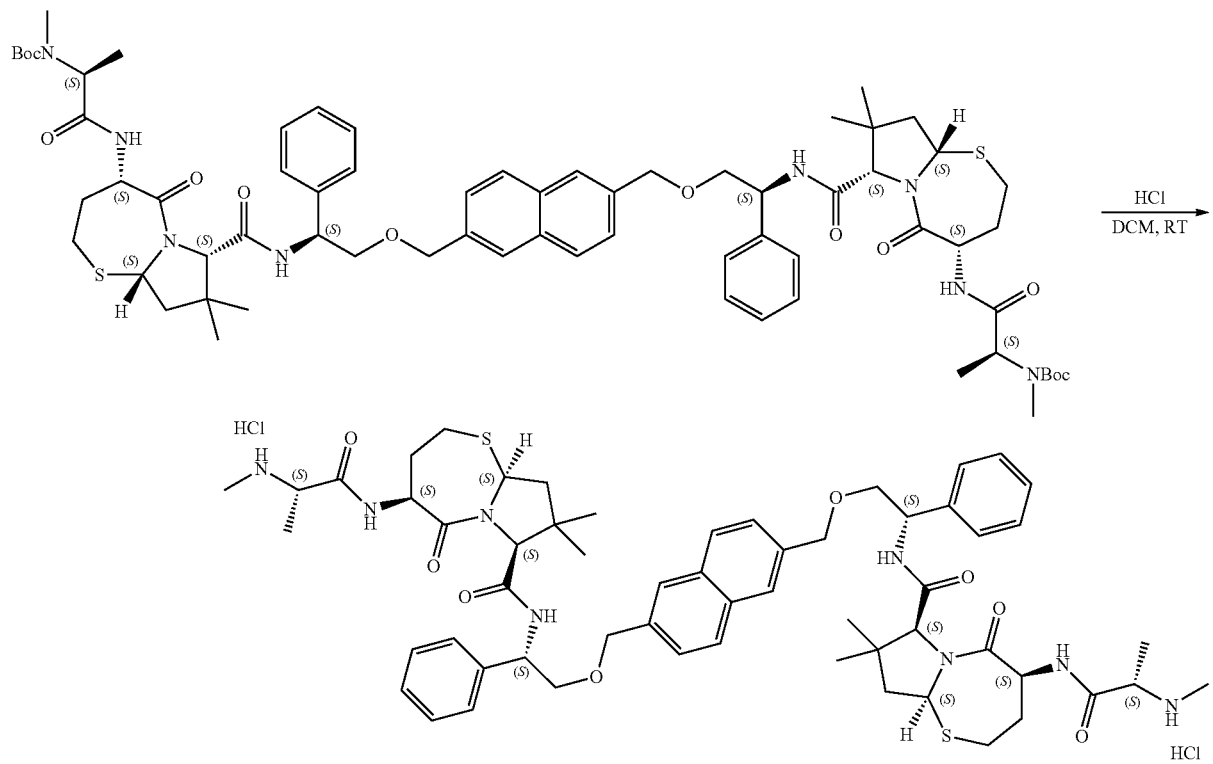

To a solution of di-tert-butyl ((2S,2'S)-(((4S,4'S,7S,7'S,9aS,9a'S)-((((1S,1'S)-((naphthalene-2,6-diylbis(methylene))bis(oxy))bis(1-phenylethane-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (92 mg, 0.072 mmol) in dichloromethane (5 mL) was added 4 N hydrochloric acid/dioxane (0.5 mL). The mixture was stirred at room tem- Example 63

(4S,4'S,7S,7'S,9aS,9a'S)—N,N'-((1S,1'S,2R,2'R)-(octane-1,8-diylbis(oxy))bis(2,3-dihydro-1H-indene-2,1-diyl))bis(8,8-dimethyl-4-((S)-2-(methylamino)propanamido)-5-oxooctahydropyrrolo[2,1-b][1,3]thiazepine-7-carboxamide) dihydrochloride

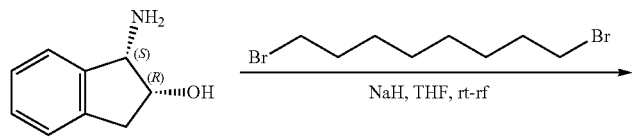

303                                                                 304
-continued
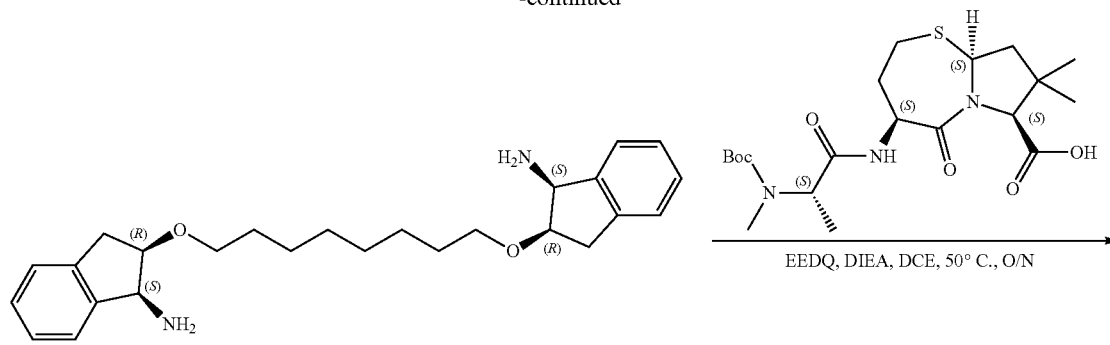
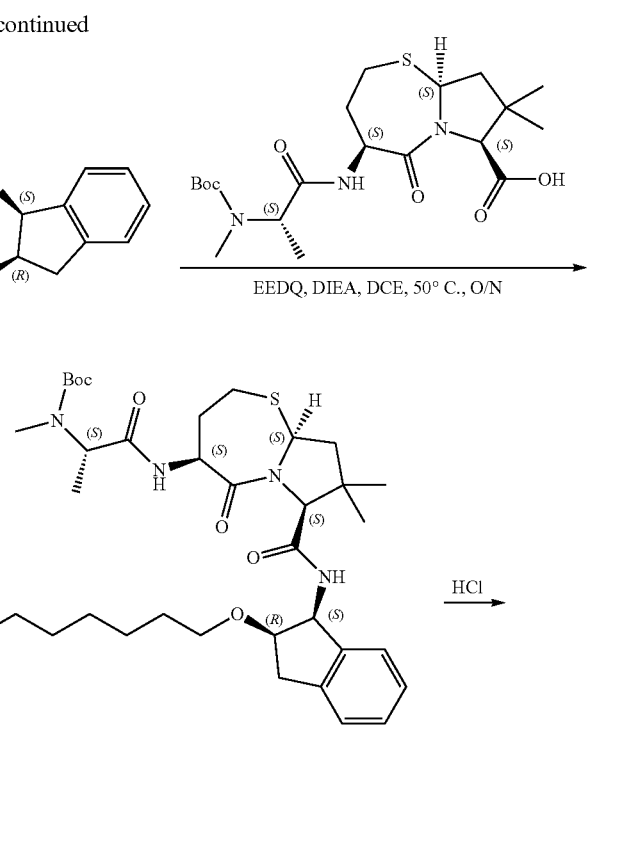
Synthesis of (1S,1'S,2R,2'R)-2,2'-(octane-1,8-diylbis(oxy))bis (2,3-dihydro-1H-inden-1-amine)
-continued
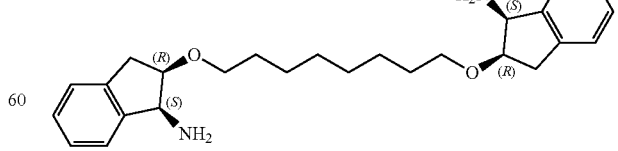
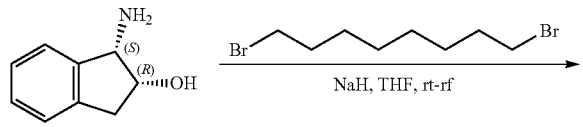
To a solution of (1S,2R)-1-amino-2,3-dihydro-1H-inden-2-ol (1.21 g, 8.09 mmol) in tetrahydrofuran (50 mL) at 0° C. was added portion wise sodium hydrogen (60%, dispersion in Paraffin Liquid) (380 mg, 9.57 mmol). The mixture was warmed to room temperature naturally. Then 1,8-dibromooctane (1.0 g, 3.68 mmol) was added. The resulting mixture was stirred at 70° C. overnight. The reaction mixture was quenched with ice water (30 mL) and extracted with ethyl acetate (3×30 mL). The organic layer was combined, washed with brine (50 mL), dried over anhydrous sodium sulfate, filtered and concentrated to get the crude. It was purified by Combi-Flash eluting with dichloromethane/methanol=10:1 and thin layer chromatography developed with ethyl dichloromethane/methanol=10/1 to afford the desired product (170 mg, 0.42 mmol, 11.4% yield) as a dark oil.

Synthesis of di-tert-butyl ((2S,2'S)-(((4S,4'S,7S,7'S,9aS,9a'S)-((((1S,1'S,2R,2'R)-(octane-1,8-diylbis(oxy))bis(2,3-dihydro-1H-indene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate)

(1S,1'S,2R,2'R)-2,2'-(octane-1,8-diylbis(oxy))bis(2,3-dihydro-1H-inden-1-amine) (150 mg, 0.367 mmol) and ((4S,7S,9aS)-4-((S)-2-((tert-butoxycarbonyl)(methyl)amino)propanamido)-8,8-dimethyl-5-oxooctahydropyrrolo[2,1-b][1,3]thiazepine-7-carboxylic acid (358 mg, 0.808 mmol) in 1,2-dichloroethane (10 mL) was added N-Ethoxycarbonyl-2-ethoxy-1,2-dihydroquinoline (272 mg, 1.101 mmol) and N,N-Diisopropylethylamine (189 mg, 1.468 mmol). The resulting mixture was stirred at 50° C. overnight. The reaction mixture was concentrated to get the crude. It was purified by thin layer chromatography developed with ethyl acetate/petroleum ether=3/1 to give crude product. Then the crude product was purified by Prep-HPLC to get product (150 mg, 0.119 mmol, 32.4% yield) as a beige solid.

LCMS (ES, m/z): 529.9 [1/2M-Boc+H]$^+$, retention time 2.027 min.

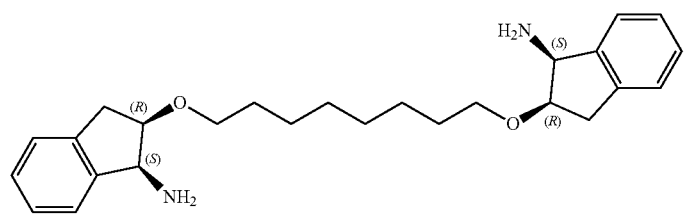
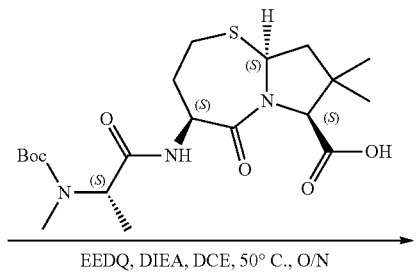
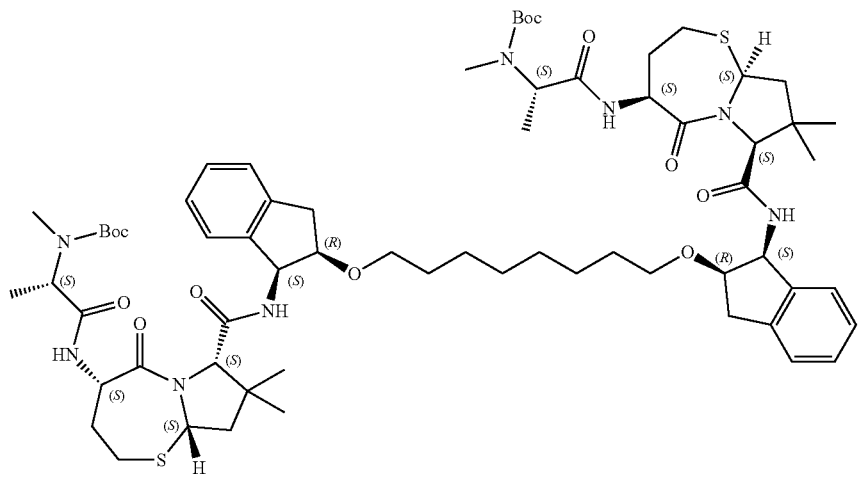

| | | | |
|---|---|---|---|
| Wavelength | 214 nm | | |
| Instrument | Waters 2545 | | |
| Column | Gemini 5 u C18 150 × 21.2 mm | | |
| Flow Rate | 20 mL/min | | |
| Gradient Method | Time (min) | ACN | H₂O |
| | 0 | 5 | 95 |
| | 10 | 50 | 50 |
| | 60 | 100 | 0 |
| | 100 | 100 | 0 |

Synthesis of (4S,4'S,7S,7'S,9aS,9a'S)—N,N'-((1S,1'S,2R,2'R)-(octane-1,8-diylbis(oxy))bis(2,3-dihydro-1H-indene-2,1-diyl))bis(8,8-dimethyl-4-((S)-2-(methylamino)propanamido)-5-oxooctahydropyrrolo[2,1-b][1,3]thiazepine-7-carboxamide) dihydrochloride perature overnight. The reaction was concentrated to get the desired product (85 mg, 0.075 mmol, 63.1% yield) as a white solid.

LCMS (ES, m/z): 1058.8 [M-2HCl+H]$^+$ (Calc M-2HCl+H=1059.6), retention time 1.348 min.

$^1$H NMR (400 MHz, DMSO) δ ppm 9.50 (s, 2H), 8.93 (s, 2H), 8.87 (d, J=6.6 Hz, 2H), 7.91 (d, J=8.7 Hz, 2H), 7.27-7.19 (m, 8H), 5.51 (t, J=7.9 Hz, 2H), 5.33 (dd, J=8.6, 5.4 Hz, 2H), 4.78-4.70 (m, 2H), 4.24 (s, 2H), 4.11 (dd, J=9.3, 4.1 Hz, 2H), 3.89 (dd, J=10.5, 6.1 Hz, 2H), 3.44-3.38 (m, 4H), 3.20 (t, J=11.8 Hz, 2H), 2.98 (d, J=3.7 Hz, 4H), 2.95-2.85 (m, 2H), 2.47 (s, 6H), 2.27-2.11 (m, 4H), 1.89-1.76 (m, 4H), 1.47-1.36 (m, 10H), 1.24-1.17 (m, 8H), 1.08 (s, 6H), 1.06 (s, 6H).

Jurkat Latency Reversal Assay

Jurkat HIV-luciferase clones were maintained in RPMI medium 1640 (Gibco by Life Technologies) containing 10%

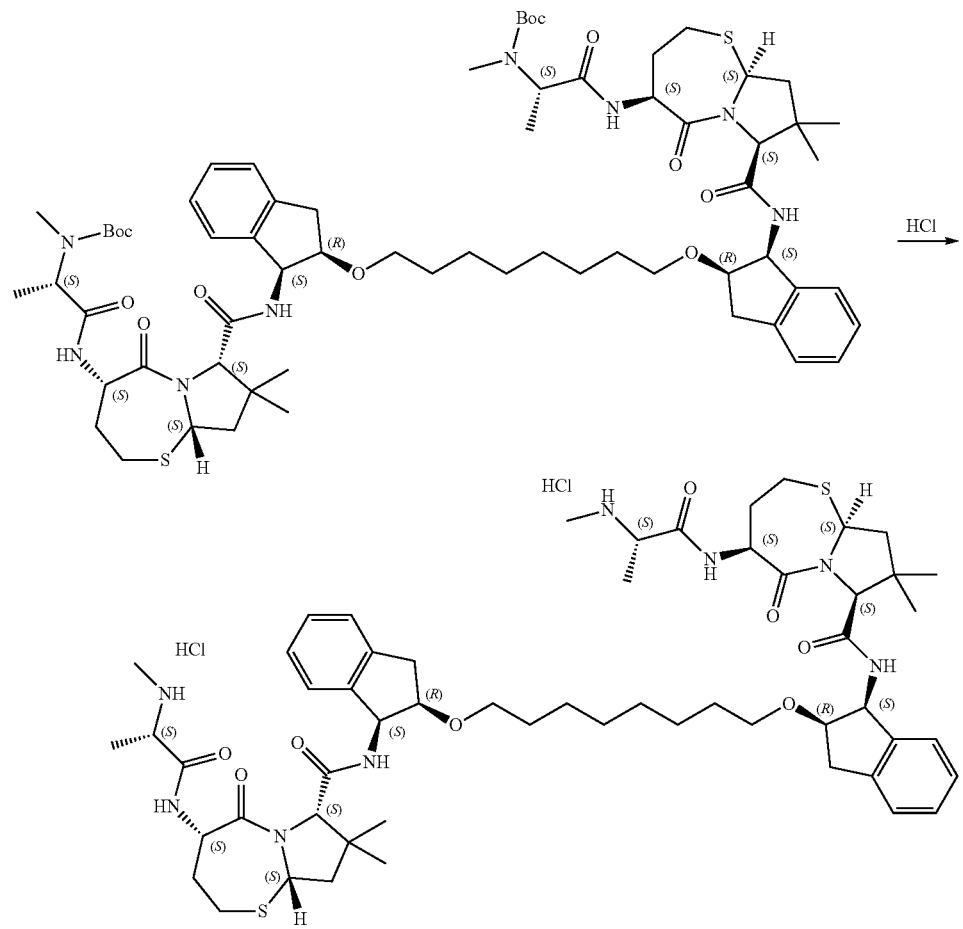

To a solution of di-tert-butyl ((2S,2'S)-(((4S,4'S,7S,7'S,9aS,9a'S)-((((1S,1'S,2R,2'R)-(octane-1,8-diylbis(oxy))bis(2,3-dihydro-1H-indene-2,1-diyl))bis(azanediyl))bis(carbonyl))bis(8,8-dimethyl-5-oxooctahydropyrrolo[2,1-b][1,3]thiazepine-7,4-diyl))bis(azanediyl))bis(1-oxopropane-1,2-diyl))bis(methylcarbamate) (150 mg, 0.119 mmol) in dichloromethane (5 mL) was added 4 N hydrochloric acid in dioxane (0.5 mL). The mixture was stirred at room tem- (vol/vol) fetal bovine serum (SAFC/Sigma-Aldrich) and 25 units/mL penicillin, 25 units/mL streptomycin (Gibco by Life Technologies), and were split 1:4 every 3 to 4 days to maintain a cell density of ~0.3 to 1 million cells/mL. The Jurkat clones were maintained with the addition of 500 nM EFV in the medium. Three Jurkat cell clones (C16, I15, and N6), each harboring one or two integrated HIV proviruses expressing the luciferase reporter gene, were added at equal amounts for a total of 5,000 cells per well to 384-well plates containing compound titrations. Dose-response testing was performed on compounds dissolved in dimethyl sulfoxide (DMSO, Fisher Scientific, Merelbeke, Belgium) dispensed in duplicate serial 3-fold, 14-point titrations using a D300e Digital Droplet Dispenser (Hewlett-Packard) to give final assay concentrations of 10 µM to 2.1 pM in 50 µL of medium at 0.5% DMSO (vol/vol) final concentration. Cells and compound were incubated at 37° C. for 48 hours, unless otherwise indicated, followed by the addition of 20 µL of Steady-Glo® Luciferase (Promega). Luminescence resulting from the induction of the virally expressed luciferase was measured using an EnVision 2102 Multilabel Plate Reader (Perkin Elmer). Dose-response relationships were analyzed with GraphPad PRISM 6 using a four-parameter logistic regression model to calculate the concentration of compound that gives half-maximal response ($EC_{50}$) and the maximal percent activation compared to the vehicle control.

Results from the above assay are set forth in Table 3.

TABLE 3

| Example No. | EC50 (nM) |
|---|---|
| 1 | 47.0 |
| 2 | 585.1 |
| 3 | 80.5 |
| 4 | 387.2 |
| 5 | 53.6 |
| 6 | 7051 |
| 7 | 141.5 |
| 8 | 2.4 |
| 9 | 90.3 |
| 10 | 43.4 |
| 11 | 324.0 |
| 12 | 6.8 |
| 13 | 9.3 |
| 14 | 8.4 |
| 15 | 15.3 |
| 16 | 10.1 |
| 17 | 20.7 |
| 18 | 22.3 |
| 19 | 9.4 |
| 20 | 11.9 |
| 21 | 13.0 |
| 22 | 8.8 |
| 23 | 55.5 |
| 24 | 47.9 |
| 25 | 61.8 |
| 26 | 69.1 |
| 27 | 52.2 |
| 28 | 53.7 |
| 29 | 89.5 |
| 30 | 65.4 |
| 31 | 25.8 |
| 32 | 165.5 |
| 33 | 5.5 |
| 34 | 36.3 |
| 35 | 9.0 |
| 36 | 9.5 |
| 37 | 10.9 |
| 38 | 50.7 |
| 39 | 51.8 |
| 40 | 6.1 |
| 41 | 51.6 |
| 42 | 6.8 |
| 43 | 43.4 |
| 44 | 20.4 |
| 45 | 183.1 |
| 46 | 127.2 |
| 47 | 1.2 |
| 48 | 11.6 |
| 49 | 466.4 |
| 50 | 95.9 |
| 51 | 24.0 |
| 52 | 243.3 |
| 53 | 178.0 |
| 54 | 32.0 |
| 55 | 429.2 |
| 56 | 2.9 |
| 57 | 8.5 |
| 58 | 4.5 |
| 59 | 13.3 |
| 60 | 3.5 |
| 61 | 11.8 |
| 62 | 4.2 |
| 63 | 11.6 |

Pharmacokinetic Data

Rodent pharmacokinetic (PK) data of several SMAC mimetic compounds of Formula I was compared with that of SMACm AZD5582 PK data (FIG. 1). As can be seen in FIG. 1, the plasma drug concentration versus time curves for the compounds of Formula I demonstrate a PK relationship comparable to that of AZD5582.

NFkB2 Gene Induction $5 \times 10^5$ normal donor CD4 T cells were treated for 24h with serial dilutions of compounds starting at 1.0 µM at 6 fold, 7 places. Total RNA was isolated using the RNEasy Mini kit (Qiagen) per the manufacturer's instructions. The following TaqMan primer probe sets were sourced from Applied Biosystems: Hs00174517_m1 (NFKB2) and Hs02800695 (HPRT1). TaqMan-based real-time PCR (Fast Virus 1-Step Master Mix, Applied Biosystems) was used to amplify host genes of interest. Gene expression was normalized to HPRT1 and comparative threshold cycle (CT) method (ΔΔCT) was used for relative fold change of gene expression as compared to untreated cells. The data was analyzed by QuantStudio3 Real-Time PCR System. Results are provided in Table 4.

p100/p52 WB Line

Cell Culture and Treatment

Cell cultures were set up to evaluate several SMACm compounds. Frozen PBMC cells from healthy donors were thawed and plated in 2 ml deepwell plates at $2 \times 10^6$ cells/ml. Serial dilutions of each compound was carried out as a 7 fold 1:6 dilution with the starting final dose of 1000 nM. Cells were then combined with compound and place at 37° for 24 hrs. The following day cells were pelleted and placed at −80 until lysis.

Harvest of Whole Cell Lysis

In preparation for cell lysis, the frozen cell pellets and an aliquot of NP40 Cell Lysis Buffer (Invitrogen, Part #FNN0021), as well as an aliquot of 10× Protease Inhibitor Cocktail (Sigma, Part #P-2714) are thawed on ice. Once thawed, the complete lysis buffer is prepared by adding 10% final volume PI cocktail to the NP40 buffer and then adding in sufficient volume of 0.1 M PMSF (Sigma, Part #93482) and 1 M DTT (Sigma, Part #43816) to create a final concentration of 1 mM each in the complete lysis buffer.

Cell lysis is then carried out by resuspending each cell pellet in 30 μL per 10^6 cells then incubating on ice for 30 minutes with vigorous vortexing every 10 minutes. The lysed cells are then centrifuged at 13K RPM for 10 minutes at 4° C. in a refrigerated microcentrifuge. The supernatants (lysates) are then transferred into new microcentrifuge tubes and either stored at −80° or utilized immediately for protein concentration and Western blot analysis.

Bradford Microplate Procedure

Protein concentration for each lysate is determined using a detergent compatible Bradford assay (Pierce, Part #23246) following the manufacturer's microplate instructions.

Protein Separation and Immunodetection

Capillary Western analysis were performed using the ProteinSimple Jess System. A total of 1 ug of cell lysate was prepared according to the provided protocol supplied by ProteinSimple. The primary antibody for p100/p52 (Cell, Signaling #3017) is diluted 1:10 for use in the Jess system. The 12-230 kDa Jess Seperation Module capillary cartridges Separation Module (SM-W004) is used in conjunction with the Anti-Rabbit Secondary NIR conjugate (043-819). The Separation module includes prefilled plates that the samples, primary and secondary antibodies, as well as protein normalization reagent and diluents are loaded onto to perform separation and detection. Once the assay has run, the data is then analyzed utilizing the Compass software provided by ProteinSimple.

Immunoblot Analysis

Alternatively to capillary electrophoresis, traditional immunoblot assays were carried out, 10 μg of cell lysate was loaded per well into 4-20% Tris-Glycine SDS-PAGE gels. Protein from the SDS-PAGE gels were transferred to Turbo Midi PVDF Transfer Packs (BioRad) using the "Mixed MW" protocol for one Midi Format Gel (constant 2.5 A up to 25V, for 7 minutes) of the Trans-Blot Turbo Transfer System (Bio-Rad) with premade Trans-Blot per the manufacturer's instructions. After transfer, PVDF membranes were blocked in 5% bovine serum albumin (BSA) in 1×TBS (BioRad) with 0.1% Tween-20 for 1 hour at room temperature with gentle rocking. Primary antibodies were added and incubated overnight at 4° C. (anti-p100/p52, Cell Signaling Technology #3017, 1:1000; anti-Actin-HRP conjugate, Abcam #49900, 1:30,000). Following primary staining, the membrane washed three times with 1× Tris Buffered Saline (TBS)+0.1% TWEEN® 20 for 10 minutes each wash. After washing, the membrane was incubated in 5% BSA in 1×TBS+0.1% TWEEN® 20 with the appropriate secondary antibody for 2 hours at room temperature. Following secondary stain the membrane was washed twice for 10 minutes with 1×TBS+0.1% TWEEN® 20 followed by a 10-minute wash with 1×TBS. The membrane was then patted dry with filter paper and an image was captured of the undeveloped membrane on the ChemiDoc MP Imaging System using Image Lab software (BioRad). Sufficient ECL reagent (GE Healthcare) was used to cover the membrane and a series of images were taken starting with 0.001 second and doubling to tripling the exposure time until the luminescence from the developed membrane saturated the image. The developed membrane was then washed three times with 1×TBS for 5 minutes to remove the residual ECL reagent and then stored at 4° C. in sufficient 1×TBS to submerse the entire membrane. Densitometry of images of the developed membrane were then carried out using the Image Lab software. Some membranes were stripped for one minute with One Minute Plus Western Blot Stripping Buffer (GM Biosciences) and then washed three times for 10 minutes with 1×TBS. The stripped membranes were then blocked in 5% BSA in 1×TBS+0.1% TWEEN® 20 for an hour and reprobed overnight with a new primary antibody. Results of the p100/p52 WB line assay are provided in Table 4.

Cell Associated HIV RNA (caRNA)

During the productive phase of the viral life cycle, HIV produces a large number of differentially spliced transcripts collectively termed cell-associated HIV RNA (ca-HIV RNA) within some cells that are infected. In HIV-infected individuals on suppressive antiretroviral therapy (ART), changes in the levels of caHIV RNA is an accepted surrogate measure of the efficacy of HIV latency reversal.

To measure ca-HIVRNA, peripheral blood mononuclear cells (PBMCs) are isolated from leukocytes obtained by continuous-flow leukapheresis. Total $CD4^+$ T cells were isolated from PBMCs by negative selection using the EasySep Human $CD4^+$ T cell Enrichment kit (StemCell, Vancouver, Canada) per the manufacturer's recommendations. Resting $CD4^+$ T cells are isolated by negative selection with an immunomagnetic column as described previously (25) and either cryopreserved immediately or maintained for two days in IMDM medium (Gibco), 10% FBS, 2 μg/mL IL-2 (Peprotech), and antiretrovirals to prevent viral expansion.

For SMACm treatment, three to five replicates of $2-5\times10^6$ $CD4^+$ T cells were treated for 48 hours at 37° C. in 1 mL of RPMI medium 1640, 10% FBS, 10 μg/mL of enfuvirtide (Sigma), and 200 nM rilpivirine. 10 nM phorbol 12-myristate 13-acetate (PMA; Sigma) with 1 μM ionomycin (Sigma) was used as a positive control for LRA activation and 0.2% DMSO vehicle was used as a negative control. Following treatment, cells were lysed and RNA and DNA were co-extracted using an AllPrep 96 RNA/DNA kit (Qiagen, Valencia, Calif.) per the manufacturer's instructions, adjusting the volume of lysis buffer to 0.6 mL, adding an on-column DNase I treatment (Qiagen) and eluting RNA in 50 μL of water.

RT-qPCR was performed in triplicate for each of three replicate wells using TaqMan Fast Virus 1-step RT-qPCR Master Mix (Applied Biosciences) with 5 μL isolated RNA and 900 nM of HIV capsid primers HIV-gag (5'-ATCAAGCAGCTATGCAAATGTT-3' (SEQ ID NO: 1)) and gag reverse (5'-CTGAAGGGTACTAGTAGTTCCTGCTATGTC-3' (SEQ ID NO: 2)) and 250 nM of FAM/ZEN/IABFQ HIV gag probe (5'-ACCATCAATGAG- GAAGCTGCAGAATGGGA-3' (SEQ ID NO: 3)). Samples were amplified and data was collected using a QuantStudio™ 3 Real-Time PCR system (Applied Biosystems) with the following cycling conditions: one cycle at 50° C. for 5 minutes (reverse transcription), one cycle at 95° C. for 20 seconds (reverse transcriptase inactivation), and 50 cycles at 95° C. for 3 seconds and 60° C. for 20 seconds (denaturation and annealing/extension).

HIV absolute HIV gag RNA copies per reaction were determined using an HIV gag gBlock qPCR standard corresponding to the DNA sequence of the qPCR product (5'-ATCAAGCAGCCATGCAAATGTTAAAAGAGAC-CATCAATGAGGAAGCTGCAGAATGGGAT AGATTG-CATCCAGTGCATGCAGGGCCTATTGCACCAGGCCA-GATGAGAGAACCAAGGG GAAGTGACATAGCAGGAACTACTAGTACCCTTCAG-3' (SEQ ID NO: 4); Integrated DNA Technologies), and copies were normalized to cell counts as determined by bright field microscopy. RT-qPCR efficiency was required to be between 90% to 110%. Assay values with a positive signal that were less than the lower limit of detection (LLOD) of seven HIV gag copies per reaction were adjusted to the LLOD. Analysis was performed using QuantStudio™ Design and Analysis Software (Applied Biosystems) and the R software package (described in detail below).

Shown in Table 4 are data comparing the Jurkat EC50, p100/p52 WB assay, NFkB2 gene induction assay and caRNA assay data of several SMAC mimetics disclosed herein with competitor mimetics.

Compounds of the present invention (namely Examples 33, 13, 42, 40 and 20), are potent dimeric SMACm which are able to activate the ncNF-kB pathway and induce HIV expression. These molecules efficiently deplete cIAP1 and cIAP2, lead to cleavage of p100 to release p52, activate the ncNF-kB pathway and induce HIV expression. Moreover, these have properties that engage the ncNF-kB pathway in vivo. In particular, Examples 13 and are believed to possess the best combination of unexpected and surprising properties.

TABLE 4

Summary of SMAC mimetics disclosed herein with other mimetics

|  | AZD-5582 | Birinapant | SBI-0637142 | Formula F US20190135861A1 | Ex. 33 | Ex. 13 | Ex. 42 | Ex. 40 | Ex. 20 |
| --- | --- | --- | --- | --- | --- | --- | --- | --- | --- |
| Jurkat EC50 (nM) | 8 | 200 | 1 | ~1000 | 5.5 | 9.3 | 6.8 | 6.1 | 11.9 |
| p100/p52 Western Blot (WB)EC50 (nM) | 63 | 1000 | 100-1000 | >1000 | 158 | 12.6 | 3.1 | 1 | 3.1 |
| NFkB2 gene induction EC50 (nM) | 28 | >1000 | 18000 | Not tested | 46 | 73 | 3.6 | 11 | 75 |
| caRNA Lowest efficacious concentration observed | 10 | >1000 | >1000 | Not tested | 10 | 10 | 10 | 10 | 10 |

"Ex" means Example wherein:

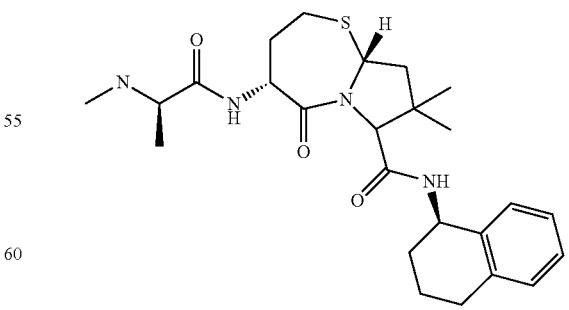

SBI-0637142
Sanford-Burnham

-continued

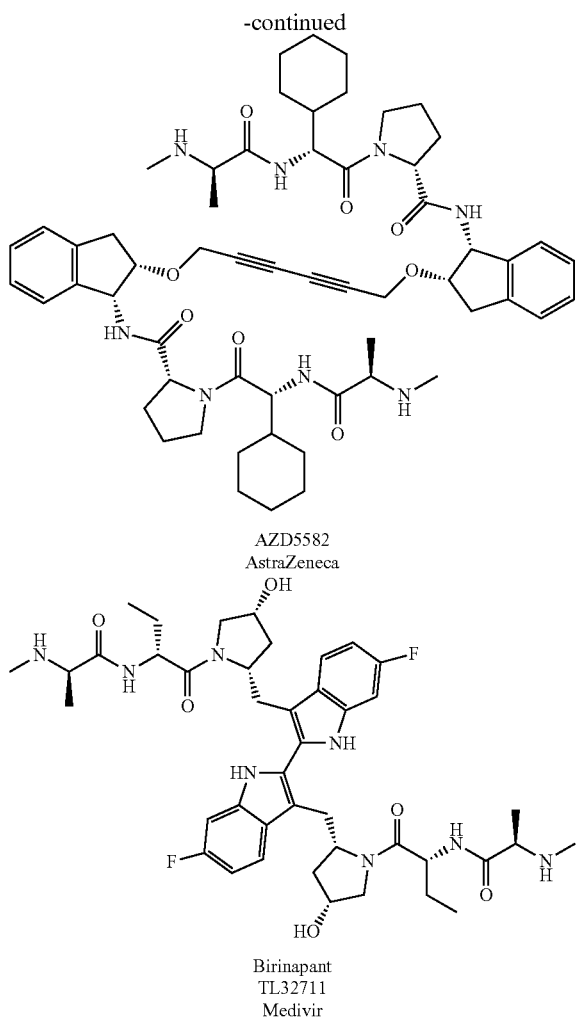

AZD5582
AstraZeneca

Birinapant
TL32711
Medivir and SBI-described dimer Formula F:

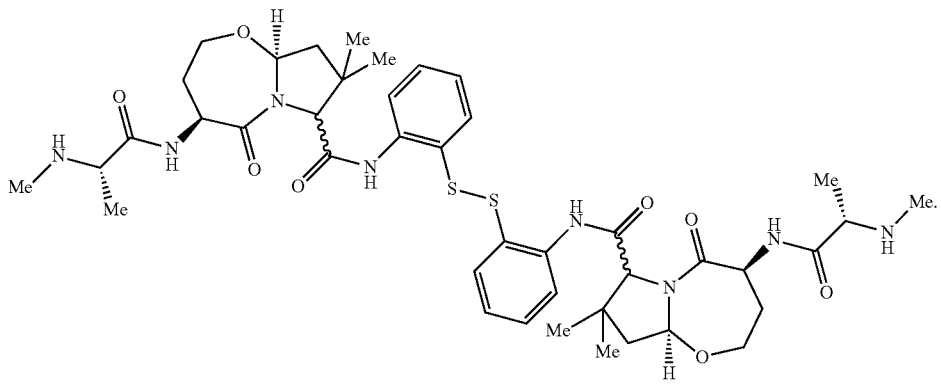 [SMILES: CN[C@@H](C)C(=O)N[C@H]1CCO[C@H]2CC(C)(C)C(C(=O)Nc3ccccc3SSc3ccccc3NC(=O)C3N4C(=O)[C@@H](NC(=O)[C@H](C)NC)CCO[C@H]4CC3(C)C)N2C1=O]

Cytotoxicity

Cell viability of Jurkat cells was determined using the CellTiter-Glo® Luminescent Cell Viability Assay (Promega), a homogeneous method to determine the ATP levels in a culture well, which corresponds to the presence of metabolically active cells in culture. Cells were cultured as indicated elsewhere for the Jurkat assays. For assessment of SMACm-mediated toxicity in the context of TNFa 10 ng/mL TNFa (R&D Systems) was added to the culture A proportion of cells was removed and 30 µL of Promega CellTiter-Glo® reagent was added to each well containing cells and luminescence was measured using a Perkin Elmer EnVision plate reader. Dose-response relationships were analyzed with GraphPad PRISM 6 using a four-parameter model logistic regression model to calculate the concentration of compound that reduces cell viability by 50% when compared to untreated controls ($CC_{50}$).

Efforts have been made to ensure accuracy with respect to numbers used (e.g. amounts, temperature, etc.) but some experimental errors and deviations should be accounted for.

One skilled in the art will recognize many methods and materials similar or equivalent to those described herein, which could be used in the practicing the subject matter described herein. The present disclosure is in no way limited to just the methods and materials described.

Unless defined otherwise, technical and scientific terms used herein have the same meaning as commonly understood by one of ordinary skill in the art to which this subject matter belongs, and are consistent with: Singleton et al (1994) Dictionary of Microbiology and Molecular Biology, 2nd Ed., J. Wiley & Sons, New York, N.Y.; and Janeway, C., Travers, P., Walport, M., Shlomchik (2001) Immunobiology, 5th Ed., Garland Publishing, New York.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

As used herein, the term "about," when referring to a value is meant to encompass variations of, in some embodiments ±50%, in some embodiments 20%, in some embodiments 10%, in some embodiments 5%, in some embodiments 1%, in some embodiments ±0.5%, and in some embodiments ±0.1% from the specified amount, as such variations are appropriate to perform the disclosed methods or employ the disclosed compositions.

Where a range of values is provided, it is understood that each intervening value, to the tenth of the unit of the lower limit, unless the context clearly dictates otherwise, between the upper and lower limit of the range and any other stated or intervening value in that stated range, is encompassed. The upper and lower limits of these small ranges which may independently be included in the smaller rangers is also encompassed, subject to any specifically excluded limit in the stated range. Where the stated range includes one or both of the limits, ranges excluding either or both of those included limits are also included.

Many modifications and other embodiments set forth herein will come to mind to one skilled in the art to which this subject matter pertains having the benefit of the teachings presented in the foregoing descriptions and the associated drawings. Therefore, it is to be understood that the subject matter is not to be limited to the specific embodiments disclosed and that modifications and other embodiments are intended to be included within the scope of the appended claims. Although specific terms are employed herein, they are used in a generic and descriptive sense only and not for purposes of limitation

What is claimed is:

1. A compound represented by the Formula (I):

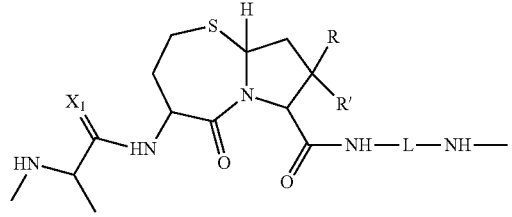

(I)

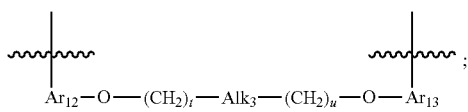

or a pharmaceutically acceptable salt or stereoisomer thereof, wherein:

R, R', R" and R'" are each independently selected from H and CH$_3$;

X$_1$ and X$_2$ are each independently selected from the group consisting of O and S; and L is a linker represented by the formula:

Ar$_{12}$—O—(CH$_2$)$_t$—Alk$_3$—(CH$_2$)$_u$—O—Ar$_{13}$ wherein:

Ar$_{12}$ and Ar$_{13}$ are each independently selected from (C$_6$-C$_{14}$)aryl;

Alk$_3$ is selected from:

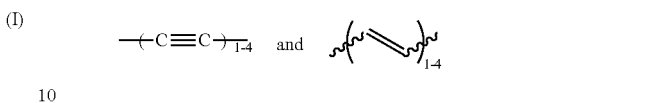

and t and u are each independently selected from 1 to 12.

2. The compound according to claim 1, wherein t and u are independently selected from 1 to 6.

3. The compound according to claim 2, wherein t and u are independently selected from 1 to 4.

4. The compound according to claim 1, wherein Alk$_3$ is:

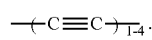

5. The compound according to claim 4, wherein Alk$_3$ is:

6. The compound according to claim 1, wherein Ar$_{12}$ and Ar$_{13}$ are each Independently C$_{6-9}$ aryl.

7. The compound according to claim 6, wherein Ar$_{12}$ and Ar$_{13}$ are each C$_9$ aryl.

8. A pharmaceutical composition comprising a compound according to claim 1, or a pharmaceutically acceptable salt or stereoisomer thereof, and a pharmaceutically acceptable excipient.

9. The composition according to claim 8, wherein said composition is adapted for parenteral administration.

10. A method of depleting latent HIV infected cells comprising administering to a subject a compound of claim 1 or a pharmaceutically acceptable salt or stereoisomer thereof.

11. A method of treating an HIV infection in a subject comprising administering to the subject a compound of claim 1 or a pharmaceutically acceptable salt or stereoisomer thereof.

12. A compound represented by the Formula (I):

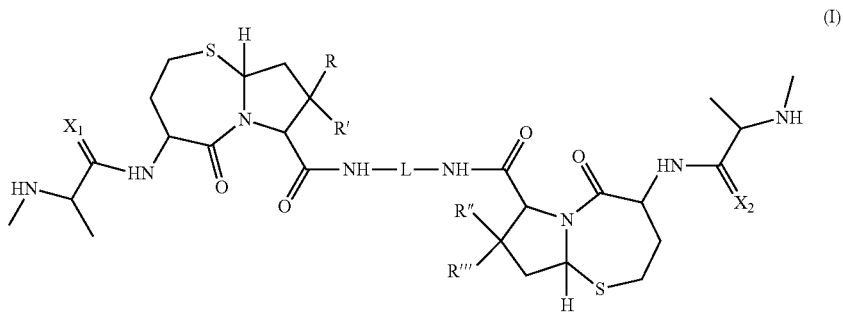

(I)

or a pharmaceutically acceptable salt or stereoisomer thereof, wherein:

R, R', R" and R'" are each independently selected from H and $CH_3$;

$X_1$ and $X_2$ are each independently selected from the group consisting of O and S; and L is a linker represented by the formula:

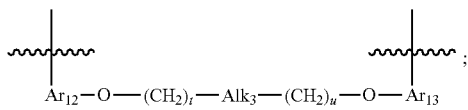

wherein:

$Ar_{12}$ and $Ar_{13}$ are each independently selected from ($C_6$-$C_9$)aryl;

$Alk_3$ is selected from:

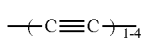

and t and u are each independently selected from 1 to 6.

13. The compound according to claim 12, wherein $Alk_3$ is:

14. The compound according to claim 12, wherein $Ar_{12}$ and $Ar_{13}$ are each $C_9$ aryl.

15. A pharmaceutical composition comprising a compound according to claim 12, or a pharmaceutically acceptable salt or stereoisomer thereof, and a pharmaceutically acceptable excipient.

16. The composition according to claim 15, wherein said composition is adapted for parenteral administration.

17. A method of depleting latent HIV infected cells comprising administering to a subject a compound of claim 12 or a pharmaceutically acceptable salt or stereoisomer thereof.

18. A method of treating an HIV infection in a subject comprising administering to the subject a compound of claim 12 or a pharmaceutically acceptable salt or stereoisomer thereof.

19. A combination comprising a compound according to claim 1, a pharmaceutically acceptable salt or stereoisomer thereof and one or more pharmaceutical agents active against HIV.

20. A method of treating an HIV infection in a subject comprising administering to the subject a combination of claim 19.

21. A method of depleting latent HIV infected cells comprising administering to a subject a combination of claim 19.

22. A combination comprising a compound having the structure:

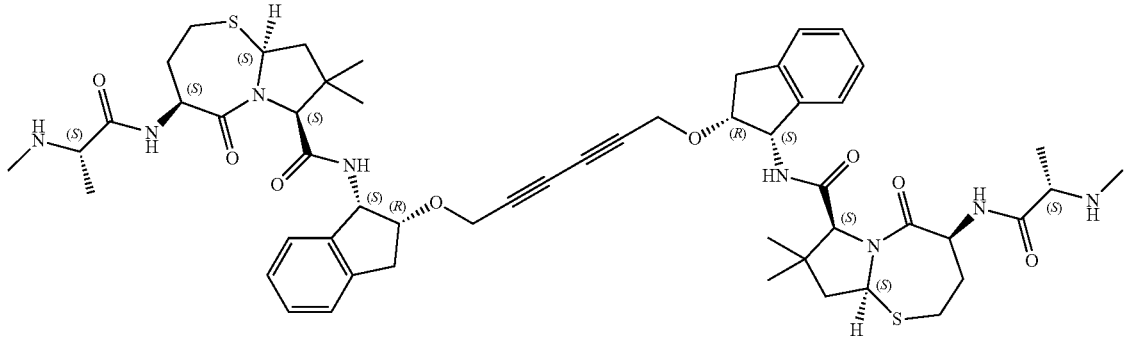

or a pharmaceutically acceptable salt thereof and one or more pharmaceutical agents active against HIV.

23. A method of treating an HIV infection in a subject comprising administering to the subject a combination of claim 22.

24. A method of depleting latent HIV infected cells comprising administering to a subject a combination of claim 22.

* * * * *